US012697332B2

(12) United States Patent
Wei et al.

(10) Patent No.: US 12,697,332 B2
(45) Date of Patent: *Aug. 4, 2026

(54) ALPHA PROTEIN KINASE 1 INHIBITORS FOR USE IN TREATING KAWASAKI DISEASE

(71) Applicant: Shanghai Yao Yuan Biotechnology Co., Ltd., Shanghai (CN)

(72) Inventors: Yuning Wei, Shanghai (CN); Danyang Liu, Shanghai (CN); Cong Xu, Shanghai (CN); Lawrence S. Melvin, Jr., Shanghai (CN); Xiong Wei, Shanghai (CN); Tongruei Raymond Li, Shanghai (CN); Jieqing Fan, Shanghai (CN); Yanfang Pan, Shanghai (CN); Huaixin Dang, Shanghai (CN); Henri Lichenstein, Shanghai (CN); Tian Xu, Shanghai (CN)

(73) Assignee: Shanghai Yao Yuan Biotechnology Co., Ltd., Shanghai (CN)

( * ) Notice: Subject to any disclaimer, the term of this patent is extended or adjusted under 35 U.S.C. 154(b) by 461 days.

This patent is subject to a terminal disclaimer.

(21) Appl. No.: 18/287,158

(22) PCT Filed: Apr. 19, 2022

(86) PCT No.: PCT/CN2022/087450

§ 371 (c)(1),
(2) Date: Oct. 16, 2023

(87) PCT Pub. No.: WO2022/222888

PCT Pub. Date: Oct. 27, 2022

(65) Prior Publication Data

US 2024/0226094 A1 Jul. 11, 2024

(30) Foreign Application Priority Data

Apr. 19, 2021 (WO) ................ PCT/CN2021/088106

(51) Int. Cl.
*A61K 31/496* (2006.01)
*A61K 31/426* (2006.01)
(Continued)

(52) U.S. Cl.
CPC .......... *A61K 31/496* (2013.01); *A61K 31/426* (2013.01); *A61K 31/427* (2013.01); *A61P 9/00* (2018.01)

(58) Field of Classification Search
CPC .................................................... A61K 31/426
See application file for complete search history.

(56) References Cited

U.S. PATENT DOCUMENTS 3,591,600 A 7/1971 Fancher
6,410,533 B1 6/2002 Hirth et al.
(Continued)

FOREIGN PATENT DOCUMENTS

RU 2017139515 A 5/2019
WO 2008057862 A2 5/2008
(Continued)

OTHER PUBLICATIONS

CAS RN 2162783-43-7 STN Registry, 2017, 5 pages.
(Continued)

*Primary Examiner* — Andrew D Kosar
*Assistant Examiner* — John D McAnany
(74) *Attorney, Agent, or Firm* — Mintz Levin Cohn Ferris Glovsky and Popeo, P.C.

(57) ABSTRACT

Provided herein are methods for inhibiting ALPK1 kinase activity using a compound of Formula I, and compositions and methods for therapy, for example in treating Kawasaki Disease.

20 Claims, 8 Drawing Sheets

(51) Int. Cl.
*A61K 31/427* (2006.01)
*A61P 9/00* (2006.01)

(56) References Cited

U.S. PATENT DOCUMENTS

| | | | |
|---|---|---|---|
| 2024/0109853 | A1 | 4/2024 | Liu et al. |
| 2024/0116885 | A1 | 4/2024 | Liu et al. |
| 2024/0216362 | A1 | 7/2024 | Wei et al. |
| 2025/0163008 | A1 | 5/2025 | Liu et al. |
| 2025/0241908 | A1 | 7/2025 | Dang et al. |

FOREIGN PATENT DOCUMENTS

| | | | | |
|---|---|---|---|---|
| WO | 2009002933 | A1 | 12/2008 | |
| WO | 2013131018 | A1 | 9/2013 | |
| WO | 2019007362 | A1 | 1/2019 | |
| WO | 2019046668 | A1 | 3/2019 | |
| WO | WO-2020176863 | A1 * | 9/2020 | ........... C07D 417/14 |
| WO | 2022063152 | A1 | 3/2022 | |
| WO | 2022063153 | A1 | 3/2022 | |
| WO | 2022222888 | A1 | 10/2022 | |
| WO | 2022222890 | A1 | 10/2022 | |

OTHER PUBLICATIONS

CAS RN 2484862-72-6 STN Registry, 2020, 6 pages.
CAS RN 850402-11-8 STN Registry, 2005, 5 pages.
Chemical Abstracts Registry No. 1045395-82-1, indexed in the Registry file on STN CAS Online Sep. 1, 2008, 4 pages.
Chemical Abstracts Registry No. 1045399-69-6, indexed in the Registry file on STN CAS Online Sep. 1, 2008, 4 pages.
European Search Report Issued in Patent Application No. 21871521.7, mailed on Oct. 10, 2024, 12 pages.
First Office Action issued in Saudi Arabia Patent Application No. 523440146, mailed on Feb. 28, 2024, 5 pages.
Office Action Issued in Japanese Patent Application No. 2023-518941, mailed on May 2, 2025, 10 pages.
Office Action Issued in Russian Patent Application No. 2023110054, mailed on Dec. 17, 2024, 69 pages.
Office Action Issued in Saudi Arabia Patent Application No. 523440146, mailed on Oct. 29, 2024, 9 pages.
RN: 2484862-72-6, STN Registry, May 13, 2005, 3 pages.
RN: 2637370-96-6, STN Registry, Apr. 23, 2021 and RN: 2144340-55-4, STN Registry, Nov. 20, 2017, STN Registry, 1 page.
Aghekyan et al. (2004) "Synthesis of 4-[1-(3,4-dimethoxyphenyl)cyclopentyl]- and 4-[4-(3,4-dimethoxyphenyl)-4-tetrahydropyran-4-yl]-2-aminothiazoles", American Chemical Journal, 57(3):85-89 (10 pages).
Barrett et al. (2013) "NCBI GEO: Archive for Functional Genomics Data Sets-update", Nucleic Acids Res., 41(Database issue):D991-995.
Berge et al. (1977) "Pharmaceutical Salts", Journal of Pharmaceutical Sciences, 66(1):19 pages.
Bezençon et al. (2017) "Discovery of a Potent, Selective T-type Calcium Channel Blocker as a Drug Candidate for the Treatment of Generalized Epilepsies", Journal of Medicinal Chemistry, 60(23):9769-9789 (65 pages).
Bolstad et al. (2003) "A Comparison of Normalization Methods for High Density Oligonucleotide Array Data Based on Variance and Bias", Bioinformatics, 19(2):185-193.
Broderick et al. (2011) "Recurrent Fever Syndromes in Patients after Recovery from Kawasaki Syndrome", Pediatrics, 127(2):e489-e493.
Chaudhary et al. (2019) "Biomarkers for Kawasaki Disease: Clinical Utility and the Challenges Ahead", Frontiers in Pediatrics, 7(242):10 pages.
Chen et al. (Jan. 2019) "ALPK1 Expression is Associated with Lymph Node Metastasis and Tumor Growth in Oral Squamous Cell Carcinoma Patients", The American Journal of Pathology, 189(1):190-199.
Database Registry, "CAS Registry No. 424798-58-3", Chemical Abstracts Services, Jun. 3, 2002, 1 page.
Dietz et al. (2017) "Dissecting Kawasaki Disease: A State-of-the-art Review", European Journal of Pediatrics, 176(8):995-1009 (15 pages).
Du et al. (2008) "Lumi: A Pipeline for Processing Illumina Microarray", Bioinformatics, 24(13):1547-1548.
Dunning et al. (2007) "Beadarray: R Classes and Methods for Illumina Bead-based Data", Bioinformatics, 23(16):2183-2184.
Elakabawi et al. (2020) "Kawasaki Disease: Global Burden and Genetic Background", Cardiology Research, 11(1):9-14.
Fujimaki et al. (Jan. 2014) "Association of Genetic Variants of the α-kinase 1 Gene with Myocardial Infarction in Community-dwelling Individuals", Biomedical Reports, 2(1):127-131.
Hoang et al. (2014) "Global Gene Expression Profiling Identifies New Therapeutic Targets in Acute Kawasaki Disease", Genome Medicine, 6(11):541 (13 pages).
Inoue et al. (2012) "Synthesis and SAR study of new thiazole derivatives as vascular adhesion protein-1 (VAP-1) inhibitors for the treatment of diabetic macular edema", Bioorganic & Medicinal Chemistry, 21(5):1219-1233 (47 pages).
Kummerer, Klaus (Nov. 2010) "Pharmaceuticals in the Environment", Annual Review of Environment and Resources, (35):57-75.
Lee et al. (May 12, 2016) "ALPK1 Phosphorylates Myosin IIA Modulating TNF-Alpha Trafficking in Gout Flares", Scientific Reports, 6(1):25740 (12 pages).
Lin et al. (2016) "TIFA as a Crucial Mediator for NLRP3 Inflammasome", Proceedings of the National Academy of Sciences, 113(52):15078-15083.
Lo, Mindy S. (2020) "A Framework for Understanding Kawasaki Disease Pathogenesis", Journal of Clinical Immunology, 214:108385 (7 pages).
McCrindle et al. (2017) "Diagnosis, Treatment, and Long-Term Management of Kawasaki Disease: A Scientific Statement for Health Professionals from the American Heart Association", Circulation, 135(17):e927-e999 (73 pages).
Milivojevic et al. (Feb. 21, 2017) "ALPK1 controls TIFA/TRAF6-Dependent Innate Immunity Against Heptose-1,7-Bisphosphate of Gram-Negative Bacteria", PLOS Pathogens, e1006224, 13(2):28 pages.
Ninomiya et al. (2013) "Development of Kawasaki Disease in a Patient with PFAPA", Pediatrics International, 55(6):801-802.
Park et al. (Feb. 1, 2005) "Non-peptidic small molecule inhibitors of XIAP", Bioorganic & Medicinal Chemistry Letters, 15(3):771-775.
International Search Report & Written Opinion Issued in PCT Application No. PCT/CN2021/119801, mailed on Dec. 21, 2021, 12 pages.
Rahmati et al. (2020) "Gene Expression Analysis in Kawasaki Disease; Bioinformatics and Experimental Approach", Informatics in Medicine Unlocked, 20(100423): 9 pages.
Ryazanov et al. (Jan. 28, 1999) "Alpha-kinases: A New Class of Protein Kinases with a Novel Catalytic Domain", Current Biology, 9(2):R43-R45.
Ryazanov et al. (May 13, 1997) "Identification of a New Class of Protein Kinases Represented by Eukaryotic Elongation Factor-2 Kinase", Proceedings of the National Academy of Sciences, 94(10):4884-4889.
Schmid et al. (2010) "Comparison of normalization methods for Illumina BeadChip HumanHT-12 v3", BMC Genomics, 11:349 (17 pages).
Straub, Christopher S. (2011) "Targeting IAPs as an Approach to Anti-Cancer Therapy", Current Topics in Medicinal Chemistry, 11(3):291-316.
Sundel et al. (2003) "Corticosteroids in the Initial Treatment of Kawasaki Disease: Report of a Randomized Trial", The Journal of Pediatrics, 142(6):611-616.
Yamada et al. (2015) "Association of Genetic Variants with Coronary Artery Disease and Ischemic Stroke in a Longitudinal Population-based Genetic Epidemiological Study", Biomedical Reports, 3(3):413-419.

(56) References Cited

OTHER PUBLICATIONS

Zhou et al. (2018) "Alpha-Kinase 1 is a Cytosolic Innate Immune Receptor for Bacterial ADP-Heptose", Nature, 561:122-126 (23 pages).
Zimmermann et al. (Sep. 5, 2017) "ALPK1- and TIFA-Dependent Innate Immune Response Triggered by the Helicobacter pylori Type IV Secretion System", Cell Reports, 20(10):2384-2395.
International Search Report & Written Opinion Issued in PCT Application No. PCT/CN2022/087450, mailed on Jul. 19, 2022, 16 pages.

* cited by examiner

ALPHA PROTEIN KINASE 1 INHIBITORS FOR USE IN TREATING KAWASAKI DISEASE

CROSS-REFERENCE

This is a 371 application of PCT/CN2022/087450, filed Apr. 18, 2022, and claims the benefit of PCT/CN2021/088106, filed Apr. 19, 2021. These PCT applications are incorporated by reference in their entireties.

FIELD OF THE INVENTION

The present invention relates to methods for inhibiting ALPK1 kinase activity using a compound of Formula 1, and related compositions and methods for therapy.

BACKGROUND OF THE INVENTION

Alpha-kinases display little sequence similarity to conventional protein kinases. A total of six alpha kinase members have been identified. These include alpha-protein kinase 1 (ALPK1). ALPK2, ALPK3, elongated factor-2 kinase (eEF2K), and transient receptor potential cation channel M6 and M7 (TRPM6 and TRPM7). See Ryazanov et al., *Curr Biol* 9:R43-45 (1999) and Ryazanov et al., *Proc Natl Acad Sci USA* 94:4884-4889 (1997).

ALPK1 is an intracytoplasmic serine threonine protein kinase that plays an important role in activating the innate immune response to bacteria via TRAF-interacting protein with forkhead-associated domain (TIFA) dependent proinflammatory nuclear factor-kappa-B (NFkB) signaling. See Zimmermann et al. *Cell Rep.* 20:2384-2395 (2017); Milivojevic et al., *PLoS Pathog.* 13:E1006224-E 1006224 (2017); and Zhou et al., *Nature* 561:122-126 (2018). TIFA can also be activated in vascular endothelial cells by oxidative and inflammatory stresses, leading to nucleotide oligomerization domain-like receptor family pyrin domain-containing protein 3 (NLRP3) inflammasome activation; see Lin et al, *Proc Natl Acad Sci USA* 113: 15078-15083 (2016)

Inappropriate activation of ALPK1 signaling has been implicated in diseases and disorders associated with excessive or inappropriate inflammation. For example, ALPK1 has been implicated in monosodium urate monohydrate (MSU)-induced inflammation and gout. Lee et al. *Sci. Rep.* 6:25740-25740(2016). Elevated ALPK1 expression has also been associated with lymph node metastasis and tumor growth in oral squamous cell carcinoma. Chen et al., *Am. J Pathol* 189:190-199 (2019).

SUMMARY OF THE INVENTION

The disclosure provides methods for inhibiting ALPK1 kinase activity in a target tissue and methods of treating a disease, disorder, or condition characterized by excessive or inappropriate ALPK1-dependent proinflammatory signaling, such as Kawasaki disease, in a subject in need of such treatment. The methods comprise administering to the subject a compound of Formula I and subembodiments of Formula I described herein.

In some aspects, the methods comprise administering to the subject a compound having a structure of Formula I Formula I

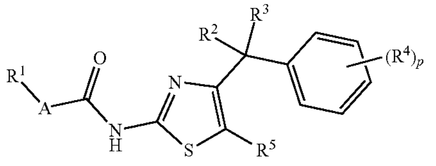

wherein A, p, $R^1$, $R^2$, $R^3$, $R^4$ and $R^5$ are as defined herein

In some embodiments, compounds of Formula I are represented by Formula IA

Formula IA

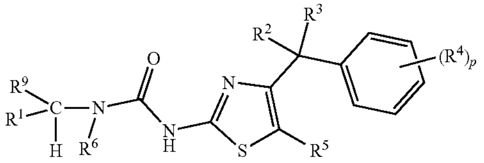

wherein p, $R^1$, $R^2$, R3, $R^4$,$R^5$, $R^6$, and $R^9$ are as defined herein.

In some embodiments, compounds of Formula I are represented by Formula IA-1

Formula IA-1

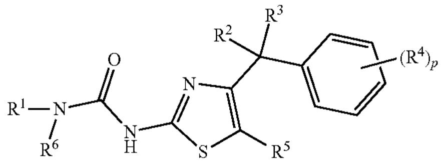

wherein p, $R^1$, $R^2$, $R^3$, $R^4$, $R^5$, $R^6$, and $R^9$ are as defined herein.

In some embodiments, compounds of Formula I are represented by Formula IB

Formula IB

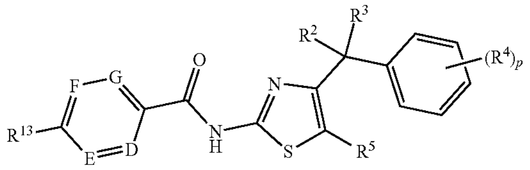

wherein p, $R^2$, $R^3$, $R^4$, $R^5$, $R^3$, D, E, F, and G are as defined herein.

In some embodiments, compounds of Formula I are represented by Formula IB-1

Formula IB-1

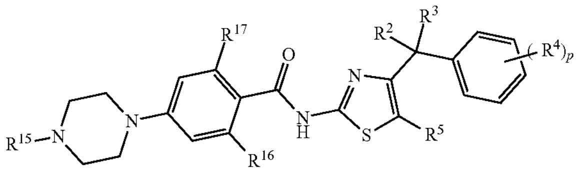

wherein p, $R^2$, $R^3$, $R^4$, $R^5$, $R^{15}$, $R^{16}$, and $R^{17}$ are as defined herein.

In some embodiments, compounds of Formula I are represented by Formula IC

Formula IC

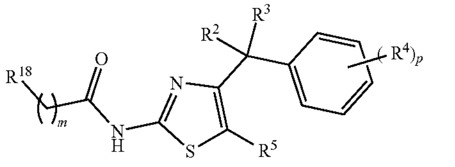

wherein p, m, $R^2$, $R^3$, $R^4$, $R^5$, $R^{18}$ are as defined herein.

In embodiments, the disclosure provides a method for inhibiting ALPK1 kinase activity in a cell or tissue of a subject in need of such therapy, the method comprising administering to the subject a compound of Formula I, IA, IB, or IC, or a subembodiment thereof, as described herein.

In embodiments, the disclosure provides a method for inhibiting or reducing inflammation in a target tissue of a subject in need of such treatment, the method comprising administering to the subject a compound of Formula I, IA, IB, or IC, or a subembodiment thereof, as described herein.

In embodiments, the disclosure provides a method for treating a disease, disorder, or condition characterized by excessive or inappropriate ALPK1-dependent proinflammatory signaling in a subject in need of such therapy, the method comprising administering to the subject a compound of Formula I, IA, IB, or IC, or a subembodiment thereof, as described herein.

In embodiments, the disease is Kawasaki disease.

In embodiments, the subject in need of such therapy or treatment is a subject carrying one or more genetic mutations in ALPK1. In embodiments, the subject carrying one or more genetic mutations in ALPK1 is a human subject diagnosed with Kawasaki disease carrying one or both of the ALPK1 SNPs defined by rs2074380 and rs2074381. In embodiments, the subject in need of such therapy or treatment is a subject diagnosed with Kawasaki disease and Periodic Fever, Aphthous Stomatitis, Pharyngitis, and Adenitis" ("PFAPA").

DETAILED DESCRIPTION

Figure 1:
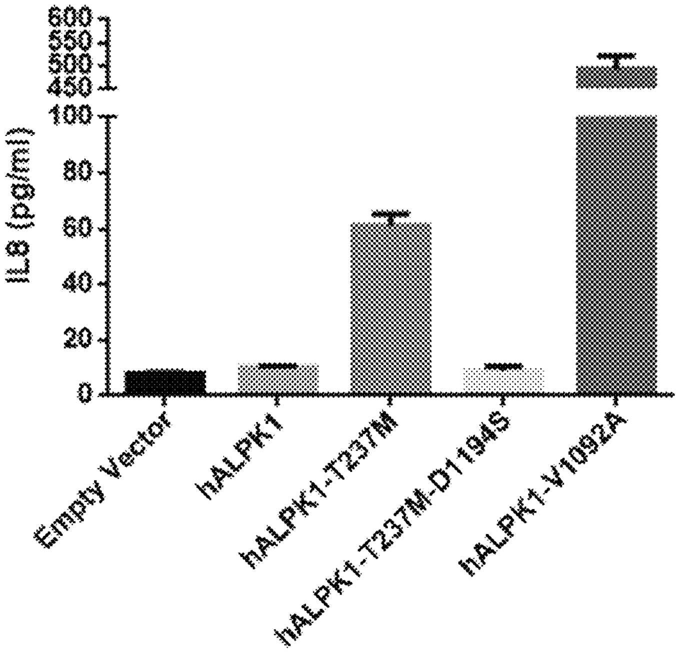
FIG. 1: Bar graph showing IL-8 secretion (pg/ml) in HEK293 cells transiently transfected with empty vector, or expression vectors encoding human ALPK1 (hALPK1), an activating mutation in hALPK1 (T237M, V1092A) or an activating mutation combined with a kinase dead mutation in ALPK1 (hALPK1-T237M-D1194S).

The disclosure provides compounds that are inhibitors of ALPK1, compositions comprising same, and methods for their use in therapy.

The term "ALPK1" is used herein to refer interchangeably to isoform I (Q96QP1-1) or the alternative splice variant isoform 2 (Q96QP1-2) of the human sequence identified by UniProtKB-Q96QP1 (ALPK1_HUMAN).

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-4}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

As used herein, "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. In some embodiments, an alkenyl group has 1 double bond. Alkenyl groups can be substituted or unsubstituted.

As used herein, "alkynyl" refers to a straight chain or branched hydrocarbon having at least 2 carbon atoms and at least one triple bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkynyl groups can have any suitable number of triple bonds, including, but not limited to, 1, 2, 3, 4, 5 or more. In some embodiments, an alkynyl group has 1 triple bond. Alkynyl groups can be substituted or unsubstituted.

As used herein, the term "alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of $-(CH_2)n$-, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups can be substituted or unsubstituted. In some embodiments, alkylene groups are substituted with 1-2 substituents. As a non-limiting example, suitable substituents include halogen and hydroxyl.

As used herein, the term "alkoxy" or "alkoxy" refers to an alkyl group having an oxygen atom that connects the alkyl group to the point of attachment: alkyl-O—. As for alkyl group, alkoxyl groups can have any suitable number of carbon atoms, such as C1-6. Alkoxyl groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be substituted or unsubstituted.

As used herein, the term "alkenyloxy" or "alkenyloxyl" refers to an alkenyl group, as defined above, having an oxygen atom that connects the alkenyl group to the point of attachment: alkenyl-O—. Alkenyloxyl groups can have any suitable number of carbon atoms, such as C1-6. Alkenyloxyl groups can be further substituted with a variety of substituents described within. Alkenyloxyl groups can be substituted or unsubstituted.

"Aminoalkyl" means a linear monovalent hydrocarbon radical of one to six carbon atoms or a branched monovalent hydrocarbon radical of three to six carbons substituted with —NR'R" where R' and R" are independently hydrogen, alkyl, haloalkyl, or hydroxyalkyl, each as defined herein, e.g., aminomethyl, aminoethyl, methylaminomethyl, and the like.

As used herein, the term "halogen" or "halo" refers to fluorine, chlorine, bromine and iodine.

As used herein, the term "haloalkyl" refers to alkyl, as defined above, where some or all of the hydrogen atoms are replaced with halogen atoms. As for alkyl group, haloalkyl groups can have any suitable number of carbon atoms, such as $C_{1-6}$. For example, haloalkyl includes trifluoromethyl, fluoromethyl, etc.

As used herein, the term "haloalkoxyl" or "haloalkoxy" refers to an alkoxyl group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, or more halogens.

As used herein, the term "deuteroalkyl" means an alkyl radical as defined above wherein one to six hydrogen atoms in the alkyl radical are replaced by deuterium, e.g., $—CH_2D$, $—CHD_2$, $—CD_3$, $—CH_2CD_3$, and the like.

As used herein, the term "hydroxyalkyl" refers to an alkyl radical wherein at least one of the hydrogen atoms of the alkyl radical is replaced by OH. Examples of hydroxyalkyl include, but are not limited to, hydroxy-methyl, 2-hydroxy-ethyl, 2-hydroxy-propyl, 3-hydroxy-propyl and 4-hydroxy-butyl.

As used herein, the term "oxo" refers to an oxygen atom connected to the point of attachment by a double bond (=O).

As used herein, the term "aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

As used herein, the term "heteroaryl" refers to a monocyclic or fused bicyclic aromatic ring assembly containing 5 to 12 ring atoms, where from 1 to 5 of the ring atoms am a heteroatom such as N, O or S. Additional heteroatoms can also be useful, including, but not limited to, B, Al, Si and P. The heteroatoms can also be oxidized, such as, but not limited to, —S(O)— and $—S(O)_2—$. Heteroaryl groups can include any number of ring atoms, such as, 3 to 6, 4 to 6, 5 to 6, 3 to 8, 4 to 8, 5 to 8, 6to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, I to 5, 2 to 3, 2 to 4, 2 to 5, 3 to 4, or 3 to 5. Heteroaryl groups can have from 5 to 9 ring members and from 1 to 4 heteroatoms, or from 5 to 9 ring members and from 1 to 3 heteroatoms, or from 5 to 6 ring members and from 1 to 4 heteroatoms, or from 5 to 6 ring members and from I to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), purine. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

As used herein, "cycloalkyl" refers to a saturated ring assembly containing from 3 to 10 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$. Cycloalkyl rings can be saturated or unsaturated, when unsaturated cycloalkyl rings can have one or two double bonds. Cycloalkyl rings include, for example, cyclopropyl, cyclobutyl, cyclopentyl, cyclohexyl, and cyclooctyl. Cycloalkyl groups can be substituted or unsubstituted.

As used herein, the term "heterocyclyl" or "heterocyclic" refers to a heterocyclic group that is saturated or partially saturated and is a monocyclic or a polycyclic ring; which has 3 to 16, most preferably 5 to 10 and most preferably 1 or 4 ring atoms; wherein one or more, preferably one to four, especially one or two ring atoms are a heteroatom selected from oxygen, nitrogen and sulfur (the remaining ring atoms therefore being carbon). The term heterocyclyl excludes heteroaryl. The heterocyclic group can be attached to the rest of the molecule through a heteroatom, selected from oxygen, nitrogen and sulfur, or a carbon atom. The heterocyclyl can include fused or bridged rings as well as spirocyclic rings. Examples of heterocyclyl include dihydrofuranyl, dioxolanyl, dioxanyl, dithianyl, piperazinyl, pyrrolidine, dihydropyranyl, oxathiolanyl, dithiolane, oxathianyl, thiomorpholino, oxiranyl, aziridinyl, oxetanyl, oxepanyl, azetidinyl, tetrahydrofuranyl, tetrahydrothiophenyl, pyrrolidinyl, tetrahydropyranyl, piperidinyl, morpholino, piperazinyl, azepinyl, oxapinyl, oxazepanyl, oxathianyl, thiepanyl, azepanyl, dioxepanyl, and diazepanyl.

As used herein, "spiroheterocyclyl" refers to a specific bicyclic heterocyclic group wherein the 2 ring systems are connected through a single carbon atom. For example, the term"spiroheterocyclyl" can refer to a 6-10 spiro heterocyclyl. Examples of include, but not limited to, 6,9-diazaspiro [4.5]decane, 2-oxa-6,9-diazaspiro[4.5]decane, 2-Oxa-6-azaspiro[3.4]octane, 6-azaspiro[3.4]octane, 2,6-diazaspiro [3.4]octane, 1,6-diazaspiro[3.4]octane, 2,8-diazaspiro[4.5] decane,2,7-diazaspiro[4.4]nonane, 1-thia-8-azaspiro[4.5] decane 1,1-dioxide, I-oxa-7-azaspiro[4.4]nonane and 1-oxa-9-azaspiro[5.5]undecane.

As used herein. "bridged heterocyclyl" refers to a C3 cycloalkyl ring or a 3- to 6-membered heterocyclyl ring, as defined above, where two non-adjacent ring vertices ("bridgehead atoms") of the cycloalkyl ring or the heterocyclyl ring are linked to form an additional cyclic moiety (a "bridge"). The bridge comprises 1 to 4 ring vertices, not including the bridgehead atoms. Examples include, but not limited to, 2,5-diazabicyclo[2.2.l]heptane, 3,6-diazabicyclo [3.1.1]heptane, 3,8-diazabicyclo[3.2.1]octane, 2,5-diazabicyclo[2.2.2]octane, 3,9-diazabicyclo[3.3.1]nonane, 2-thia-5-azabicyclo[2.2.1]heptane 2,2-dioxide, 2-azabicyclo[2.2.1] hept-5-ene, 3-oxa-8-azabicyclo[3.2.1]octane, 3-oxa-6-azabicyclo[3.1.1]heptane, 6-oxa-3-azabicyclo[3.1.1]heptane and 2-oxa-5-azabicyclo[2.2.1]heptane.

The term "bicyclic heterocyclyl" refers to a heterocyclic group as defined above where the two ring systems are connected through two adjacent ring vertices (e.g., a fused ring system). Typical "bicyclic heterocyclyl" rings include 6 to 11 ring members having 1 to 4 heteroatom ring vertices selected from N, O, and S (the remaining ring atoms therefore being carbon). Examples include, but not limited to, benzodioxolyl, benzimidazolyl, benzisoxazolyl, benzofurazanyl, benzopyranyl, benzothiopyranyl, benzofuryl, benzothiazolyl, benzothienyl, benzotriazolyl, benzoxazolyl, chromanyl, cinnolinyl dihydrobcnzofuryl, dihydroisobenzofuranyl, dihydrobenzothienyl, dihydrobenzothiopyranyl, dihydrobenzothiopyranyl sulfone, indolinyl, indolyl, isochromanyl, isoindolinyl, isoquinolinyl, isothiazolidinyl, naphthyridinyl, pyrazolopyridinyl, quinazolinyl, quinolinyl, quinoxalinyl, tetrahydroisoquinolinyl, tetrahydroquinolinyl.

As used herein, "saturated or unsaturated" refers to a cyclic system where two of the atoms in the group may be bound to one another by a single bond, a double bond, or a triple bond. Saturated moieties are those having only single bonds, where moieties having multiple bonds (e.g., at least one double bond or at least one triple bond are referred to as unsaturated.

When needed, any definition herein may be used in combination with any other definition to describe a composite structural group. By convention, the trailing element of any such definition is that which attaches to the parent moiety. For example, the composite group cycloalkoxyl means that a cycloalkyl group is attached to the parent molecule through an oxyl group.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science.* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

Certain compounds of the present invention possess asymmetric carbon atoms (optical centers) or double bonds; the racemates, diastereomer, geometric isomers, regioisomers and individual isomers (e.g., separate enantiomers) are all intended to be encompassed within the scope of the present invention. In some embodiments, the compounds of the present invention are a particular enantiomer, anomer, or diastereomer substantially free of other forms.

As used herein, the term "substantially free" refers to an amount of 10% or less of another isomeric form, preferably 8%, 5%, 4%, 3%, 2%, 1%, 0.5%, or less of another form. In some embodiments, the isomer is a stereoisomer.

DETAILED DESCRIPTION OF THE EMBODIMENTS

The disclosure provides methods for inhibiting ALPK1 kinase activity in a target tissue as well as methods of treating a disease, disorder, or condition characterized by excessive or inappropriate ALPK1-dependent proinflammatory signaling, such as Kawasaki disease, in a subject in need of such treatment, the methods comprising administering to the subject a compound represented by formula (I) and, or pharmaceutically acceptable salts thereof.

The compounds are represented by formula I

Formula I

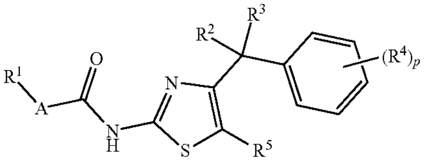

wherein A, p, $R^1$, $R^2$, $R^3$, $R^4$ and $R^5$ are as defined herein:

A is selected from a bond, azetidinyl, —O—, —$N(R^6)$—, —$CH_2$—$N(R^6)$—, —$CHR^9$—$N(R^6)$—, wherein $R^6$ is selected from H, —OH, optionally substituted $C_1$-$C_6$ alkyl, optionally substituted $C_1$-$C_6$ haloalkyl, optionally substituted $C_1$-$C_6$ alkenyl, optionally substituted $C_1$-$C_6$ hydroxyalkyl, optionally substituted $C_1$-$C_6$ aminoalkyl, optionally substituted $C_1$-$C_6$ alkoxyl, optionally substituted saturated or unsaturated $C_3$-$C_6$ cycloalkyl, and optionally substituted saturated or unsaturated $C_3$-$C_6$ cycloalkoxyl, wherein the optionally substituted $R^6$ moieties comprise 0-3 substituents independently selected from halo, —OH, —COOH, —$NH_2$, =O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, and $C_1$-$C_6$ alkoxyl;

$R^9$ is selected from optionally substituted $C_1$-$C_6$ alkyl, $C_1$-$C_6$ haloalkyl, optionally substituted saturated or unsaturated $C_3$-$C_6$ cycloalkyl, optionally substituted saturated or unsaturated $C_3$-$C_6$ cycloalkoxyl, wherein optionally substituted $R^9$ moieties comprise 0-2 substituents independently selected from halo, —OH, —COOH, —$NH_2$, =O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, $C_1$-$C_6$ haloalkoxyl, saturated or unsaturated $C_3$-$C_6$ cycloalkyl, saturated or unsaturated $C_3$-$C_6$ cycloalkoxyl, —CH-1$R^{7f}R^{8f}$, —$OR^{7f}$, —OC(O)($R^{7f}$), —C(O)($R^{7f}$), —C(O)N($R^{7f}R^{8f}$), —C(O)O($R^{7f}$), —$S(O)_2$($R^{7f}$), —S(O)ON($R^{7f}R^{8f}$) and —N($R^{7f}R^{8f}$) wherein each $R^{7f}$ and $R^{8f}$ are independently selected from H, C7-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, $C_1$-$C_6$ haloalkoxyl, saturated or unsaturated $C_3$-$C_6$ cycloalkyl, and saturated or unsaturated $C_3$-$C_6$ cycloalkoxy;

$R^1$ is selected from H, optionally substituted $C_1$-$C_6$ alkyl, optionally substituted $C_1$-$C_6$ alkenyl, optionally substituted $C_1$-$C_6$ hydroxyalkyl, optionally substituted $C_1$-$C_6$ haloalkyl, optionally substituted $C_1$-$C_6$haloalkoxyl, optionally substituted $C_1$-$C_6$ aminoalkyl, optionally substituted $C_1$-$C_6$ alkoxyl, optionally substituted saturated or unsaturated $C_3$-$C_6$ cycloalkyl, optionally substituted saturated or unsaturated $C_3$-$C_6$ cycloalkoxyl, optionally substituted mono or bicyclic aryl, optionally substituted 5-10 membered heteroaryl containing 1-4 heteroatom ring vertices selected from N, O, and S; optionally substituted saturated or unsaturated 3-7 membered heterocyclyl containing 1-2 heteroatom ring vertices selected from N, O, and S; optionally substituted saturated or unsaturated 7-8 membered bridged heterocyclyl containing 1-2 heteroatom ring vertices selected from N, O, and S; optionally substituted saturated or unsaturated 7-11 membered spiroheterocyclyl containing 1-2 heteroatom ring vertices selected from N, O, and S; and optionally substituted saturated or unsaturated 6-11 membered bicyclic heterocyclyl containing 1-2 heteroatom ring vertices selected from N, O, and S;

wherein optionally substituted $R^1$ moieties comprise 0-4 substituents independently selected from halo, —OH, —COOH, —$NH_2$, =O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, $C_1$-$C_6$ haloalkoxyl, —$R^{7a}$, —$X^1$—$R^{7a}$, $CHR^{7a}R^{8a}$, —$OR^{7a}$, —O—$X^1$—$R^{7a}$, —$X^1$—O—$X^1$—$R^{7a}$, —OC(O)($R^{7a}$), —O—$X^1$—C(O)($R^{7a}$), —C(O)($R^{7a}$), —C(O)N($R^{7a}R^{8a}$), —$NR^{7a}$(CO)$R^{8a}$, —C(O)O($R^{7a}$), $S(O)_2R^{7a}$, —$S(O)_2$N($R^{7a}R^{8a}$), —N($R^{7a}R^{8a}$), saturated or unsaturated $C_3$-$C_6$ cycloalkyl, saturated or unsaturated $C_3$-$C_6$ cycloalkoxyl, saturated or unsaturated 3-7 membered heterocyclyl containing 1-2 heteroatom ring vertices selected from N, O, and S, mono or bicyclic aryl, 5-10 membered heteroaryl containing 1-4 heteroatom ring vertices selected from N, O, and S, saturated or unsaturated 7-8 membered bridged heterocyclyl containing 1-2 heteroatom ring vertices selected from N, O, and S, saturated or unsaturated 7-11 membered spiroheterocyclyl containing 1-2 heteroatom ring vertices selected from N, O, and S, and 6-11 membered bicyclic heterocyclyl containing 1-2 heteroatom ring vertices selected from N, O, and S; wherein each X is independently $C_{1-6}$ alkylene;

each $R^{7a}$ and $R^{8a}$ are independently selected from H, $C_1$-$C_6$ alkyl, saturated or unsaturated $C_3$-$C_6$ cycloalkyl, saturated or unsaturated $C_3$-$C_6$ cycloalkoxyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, $C_1$-$C_6$haloalkoxyl, saturated or unsaturated C3-$C_6$ cycloalkyl, saturated or unsaturated $C_3$-$C_6$ cycloalkoxyl, aryl, saturated or unsaturated $C_3$-$C_6$ cycloalkyl, saturated or unsaturated $C_3$-$C_6$ cycloalkoxyl, saturated or unsaturated 3-7 membered heterocyclyl containing 1-2 heteroatom ring vertices selected from N, O, and S, wherein the aryl and 3-7 membered heterocyclyl groups are substituted with 0-3 substituents selected from halo, —OH, —COOH, —$NH_2$, =O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl; and the $C_3$-$C_6$ cycloalkyl, $C_3$-$C_6$ cycloalkoxyl, 3-7 membered heterocyclyl, the mono or bicyclic aryl, the 5-10 membered heteroaryl, the saturated or unsaturated 7-8 membered bridged heterocyclyl, the saturated or unsaturated 7-11 membered spiroheterocyclyl, and the 6-11 membered bicyclic heterocyclyl are each independently substituted with 0 to 3 moieties selected from halo, —OH, —COOH, —$NH_2$, =O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, saturated or unsaturated $C_1$-$C_6$ cycloalkoxyl, —$CHR^{7b}R^{8b}$, —$OR^{7b}$, —OC(O)($R^{7b}$), —C(O)($R^{7b}$), —C(O)N($R^{7b}R^{8b}$), —$NR^{7b}(CO)R^{8b}$, —$C(O)O(R^{7b})$, —$S(O)_2N(R^{7b}R^{8b})$ and —$N(R^{7b}R^{8b})$, wherein each $R^{7b}$ and $R^{8b}$ are independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated C3-$C_6$ cycloalkyl, and saturated or unsaturated $C_3$-$C_6$ cycloalkoxyl; or $R^1$ and $R^6$ combine to form a 3-6 membered heterocycloalkyl substituted with 0-3 moieties independently selected from the group consisting of halo, —OH, —COOH, —$NH_2$, =O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, and $C_1$-$C_6$ alkoxyl;

$R^5$ is selected from H, deuterium, halo, $C_1$-$C_6$ alkyl, $C_1$-$C_6$ deuteroalkyl, and $C_1$-$C_6$ haloalkyl;

$R^2$ and $R^3$ are each independently selected from H, OH, $C_1$-$C_6$ alkyl and $C_2$-$C_6$ alkynyl, wherein $C_1$-$C_6$ alkyl and $C_2$-$C_6$ alkynyl are each substituted with 0-3 moieties independently selected from halo, —OH, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, saturated or unsaturated $C_3$-$C_6$ cycloalkoxyl, —$OC(O)(R^{7c})$, —$C(O)(R^{7c})$, $C(O)O(R^{7c})$, $S(O)_2N(R^{7c}R^{8c})$, and $N(R^{7c}R^{8c})$, wherein each $R^{7c}$ and $R^{8c}$ are independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, $C_1$-$C_6$ haloalkoxy, saturated or unsaturated $C_3$-$C_6$ cycloalkyl, and saturated or unsaturated $C_3$-$C_6$ cycloalkoxyl;

provided that $R^2$ and $R^3$ are not both H; or $R^2$ and $R^3$ combine to form a $C_3$-$C_6$ cycloalkyl ring or a 3-7 membered heterocyclyl containing 1-2 heteroatom ring vertices independently selected from N, O, and S, wherein the ring formed can be optionally substituted with 1-2 substituents independently selected from $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, halo, —OH, =O, —CN, $OC(O)(R^{7d})$, —$C(O)(R^{7d})$, $C(O)O(R^{7d})$, $S(O)_2N(R^{7d}R^{8d})$ and $N(R^{7d}R^{8d})$, wherein each $R^{7d}$ and $R^{8d}$ are independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl;

each $R^4$ is independently selected from halo, —OH, —$NH_2$, CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, saturated or unsaturated $C_3$-$C_6$ cycloalkoxyl, $CHR^{7e}R^{8e}$, $OR^{7e}$, $OC(O)(R^{7e})$, $C(O)(R^{7e})$, $C(O)N(R^{7e}R^{8e})$, $C(O)O(R^{7e})$, $S(O)_2N(R^{7e}R^{8e})$ and $N(R^{7e}R^{8e})$ wherein each $R^{7c}$ and $R^{8c}$ are independently selected from H, $C_1$-$C_6$ alkyl, $C_1$-$C_6$ alkenyl, $C_1$-$C_6$ hydroxyalkl, $C_1$-$C_6$ haloalkyl, $C_1$-$C_6$ aminoalkyl, $C_1$-$C_6$ alkoxyl, saturated or unsaturated $C_3$-$C_6$ cycloalkyl, saturated or unsaturated $C_3$-$C_6$ cycloalkoxyl, and the subscript p is 0, 1, 2 or 3.

In some embodiments, A in Formula I is a bond.

In some embodiments, A in Formula I is azetidinyl.

In some embodiments, A in Formula I is —O—.

In some embodiments, A in Formula I is —$N(R^6)$—.

In some embodiments, A in Formula I is —$CH_2$—$N(R^6)$—.

In some embodiments, A in Formula I is —$CHR^9$—$N(R^6)$—.

In some embodiments, the compound of formula I is represented by the compound of formula IA, formula IA-1, formula IA-2 and/or a stereoisomer, a stable isotope, or a pharmaceutically acceptable salt thereof Formula IA

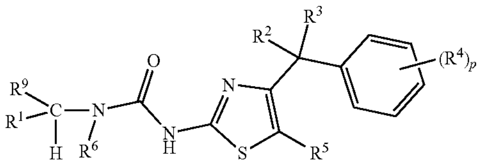

Formula IA-1

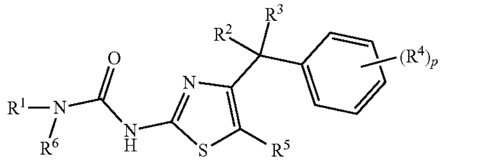

Formula IA-2

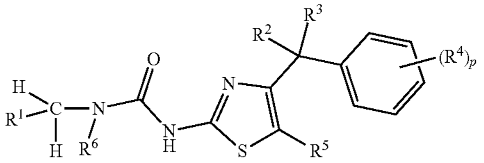

wherein p, $R^1$, $R^2$, $R^3$, $R^4$, $R^5$, $R^6$, and R are as defined above.

In some embodiments $R^6$ in formula I, 1A, 1A-1, 1A-2 is H, $C_1$-$C_6$ alkyl or $C_1$-$C_6$ hydroxyalkyl.

In some embodiments $R^9$ in formula I and 1A is $CH_3$ or $CH_2OH$.

In some embodiments $R^9$ in formula I and 1A is saturated $C_3$-$C_6$ cycloalkyl.

In some embodiments $R^1$ in formula I, 1A, 1A-1, 1A-2 is selected from H and optionally substituted $C_1$-$C_6$ alkyl, wherein optionally substituted $C_1$-$C_6$ alkyl comprises 0-4 substituents independently selected from halo, —OH, —COOH, —$NH_2$, =O, —CN, $C_1$-$C_6$ alkenyl, $C_1$-$C_6$ hydroxyalkyl, $C_1$-$C_6$ alkoxyl, $C_1$-$C_6$ haloalkoxyl, saturated or unsaturated $C_3$-$C_6$ cycloalkyl, saturated or unsaturated $C_3$-$C_6$ cycloalkoxyl, —$CHR^{7a}R^{8a}$, —$OR^{7a}$, —$C(O)(R^{7a})$, —$C(O)(R^{7a})$, —$C(O)N(R^{7a}R^{8a})$, —$C(O)O(R^{7a})$, —$S(O)_2R^{7a}$, —$S(O)_2N(R^{7a}R^{8a})$ and —$N(R^{7a}R^{8a})$, wherein each $R^{7a}$ and $R^{8a}$ are independently selected from H, $C_1$-$C_6$ alkyl, $C_1$-$C_6$ alkenyl, $C_1$-$C_6$ hydroxyalkyl $C_1$-$C_6$ haloalkyl, $C_1$-$C_6$ aminoalkyl, $C_1$-$C_6$ alkoxyl, $C_1$-$C_6$ haloalkoxyl, saturated or unsaturated $C_3$-$C_6$ cycloalkyl, and saturated or unsaturated $C_3$-$C_6$ cycloalkoxyl.

In some embodiments $R^1$ in formula I, 1A, 1A-1, 1A-2 is optionally substituted saturated or unsaturated $C_3$-$C_6$ cycloalkyl, wherein optionally substituted $C_3$-$C_6$ cycloalkyl comprises 0-4 substituents independently selected from halo, —OH, —COOH, —$NH_2$, =O, —CN, $C_1$-$C_6$ alkenyl, $C_1$-$C_6$ hydroxyalkyl, $C_1$-$C_6$ alkoxyl, and $C_1$-$C_6$haloalkoxyl.

In some embodiments R in formula I, 1A, 1A-1, 1A-2 combines with $R^6$ to form a 3-6 membered heterocycloalkyl substituted with 0-3 moieties independently selected from the group consisting of halo, —OH, —COOH, —$NH_2$, =O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, and $C_1$-$C_6$ alkoxyl.

In some embodiments $R^1$ in formula I, 1A, 1A-1, 1A-2 is $C_1$-$C_6$ alkyl substituted with 0-4 substituents independently selected from —OH, $C_1$-$C_6$ hydroxyalkyl, $C_1$-$C_6$ alkoxyl, —OC(O)($R^{7a}$), —$S(O)_2N(R^{7a}R^{8a})$ and —$N(R^{7a}R^{8a})$, wherein each $R^{7a}$ and $R^{8a}$ are independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl.

In some embodiments $R^1$ in formula I, 1A, 1A-1, 1A-2 is $C_1$-$C_6$ alkyl substituted with 0-2 substituents independently selected from —OH, $C_1$-$C_6$ hydroxyalkyl, and —$S(O)_2N(R^{7a}R^{8a})$, wherein each $R^{7a}$ and $R^{8a}$ are independently selected from H, and $C_1$-$C_6$ alkyl.

In some embodiments $R^1$ in formula I, 1A, 1A-1, 1A-2 is optionally substituted $C_1$-$C_6$ hydroxyalkyl.

In some embodiments $R^1$ in formula I, 1A, 1A-1, 1A-2 is a 5-10 membered heteroaryl containing 1-4 heteroatom ring vertices selected from N, O, and S, the 5-10 membered bicyclic heteroaryl is substituted with 0 to 3 moieties selected from halo, —OH, —COOH, —$NH_2$, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, 3-7 membered heterocyclyl containing 1-2 heteroatom ring vertices selected from N, O, and S, saturated or unsaturated $C_3$-$C_6$ cycloalkyl, saturated or unsaturated $C_3$-$C_6$ cycloalkoxyl, —$CHR^{7b}R^{8b}$, —$OR^{7b}$, —OC(O)($R^{7b}$), —C(O)($R^{7b}$), —C(O)N($R^{7b}R^{8b}$), —C(O)O($R^{7b}$), —$S(O)_2N(R^{7b}R^{8b})$ and —$N(R^{7b}R^{8b})$, wherein each $R^{7b}$ and $R^{8b}$ are independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl.

In some embodiments $R^1$ in formula I, 1A, 1A-1, 1A-2 is pyridinyl substituted with 0 to 3 moieties selected from halo, —OH, —COOH, —$NH_2$, —CN, $C_1$-$C_6$ alkyl, $C_1$-$C_6$ alkenyl, 3-7 membered heterocyclyl containing 1-2 heteroatom ring vertices selected from N, O, and S, wherein the 3-7 membered heterocyclyl is substituted with 0-3 substituents selected from halo, —OH, —COOH, —$NH_2$, —CN, $C_1$-$C_6$ alkyl, $C_1$-$C_6$ alkenyl, $C_1$-$C_6$ haloalkyl.

In some embodiments $R^1$ in formula I, 1A, 1A-1, 1 A-2 is a saturated or unsaturated 7-8 membered bridged heterocyclyl containing 1-2 heteroatom ring vertices selected from N, O, and S, wherein the 7-8 membered bridged heterocyclyl is substituted with 0-3 moieties selected from halo, —OH, —COOH, —$NH_2$, =O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, saturated or unsaturated $C_3$-$C_6$ cycloalkoxyl, —$CHR^{7b}R^{8b}$, —$OR^{7b}$, —OC(O)($R^{7b}$), —C(O)($R^{7b}$), —C(O)N($R^{7b}R^{8b}$), —C(O)O($R^{7b}$), —$S(O)_2N(R^{7b}R^{8b})$ and —$N(R^{7b}R^{8b})$, wherein each $R^{7b}$ and $R^{8b}$ are independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl.

In some embodiments $R^1$ in formula I, IA, IA-i, 1A-2 is a saturated or unsaturated 7-11 membered spiroheterocyclyl containing 1-2 heteroatom ring vertices selected from N, O, and S, wherein the 7-11 membered spiroheterocyclyl is substituted with 0-3 moieties selected from halo, —OH, —COOH, —$NH_2$, =O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, saturated or unsaturated $C_3$-$C_6$ cycloalkoxyl, —$CHR^{7b}R^{8b}$, $OR^{7b}$, —OC(O)($R^{7b}$), —C(O)($R^{7b}$), —C(O)N($R^{7b}R^{8b}$), —C(O)O($R^{7b}$), —$S(O)_2N(R^{7b}R^{8b})$ and —$N(R^{7b}R^{8b})$, wherein each $R^{7b}$ and $R^{8b}$ are independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl.

In some embodiments, $R^1$ in formula 1, 1A, 1A-1, 1A-2 is aryl substituted with 0-3 substituents selected from halo, a 3-7 membered heterocyclyl containing 1-2 heteroatom ring vertices selected from N, O, and S; a 7-8 membered bridged heterocyclyl containing 1-2 heteroatom ring vertices selected from N, O, and S; and a saturated or unsaturated 7-11 membered spiroheterocyclyl containing 1-2 heteroatom ring vertices selected from N, O, and S, wherein the 3-7 membered heterocyclyl, the 7-8 membered bridged heterocyclyl, and the 7-11 membered spiroheterocyclyl are substituted with from 0 to 3 moieties selected from halo, —OH, —COOH, —$NH_2$, =O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, saturated or unsaturated $C_3$-$C_6$ cycloalkoxyl, —$CHR^{7b}R^{8b}$, —$OR^{7b}$, —OC(O)($R^{7b}$), —C(O)($R^{7b}$), —C(O)N($R^{7b}R^{8b}$), —C(O)O($R^{7b}$), —$S(O)_2R^{7b}$, —$S(O)_2N(R^{7b}R^{8b})$ and —$N(R^{7b}R^{8b})$, wherein each $R^{7b}$ and $R^{8b}$ are independently selected from H. $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl In some embodiments $R^1$ in formula I, 1A, 1A-1, 1A-2 is aryl substituted with 0-3 moieties selected from halo —OH, —COOH, —$NH_2$, =O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, and a 3-7 membered heterocyclyl containing 1-2 heteroatom ring vertices selected from N, O, and S, the 3-7 membered heterocyclyl is substituted with 0-3 moieties selected from halo, —OH, —COOH, —$NH_2$, =O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_1$-$C_6$ cycloalkyl, saturated or unsaturated $C_1$-$C_6$ cycloalkoxyl, —$CR^{7b}R^{9b}$, —$OR^{7b}$, —OC(O)($R^{7b}$), —C(O)($R^{7b}$), —C(O)N($R^{7b}R^{8b}$), —C(O)O($R^{7b}$), —$S(O)_2N(R^{7b}R^{8b})$ and —$N(R^{7b}R^{8b})$, wherein each $R^{7b}$ and $R^{8b}$ are independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl.

In some embodiments $R^1$ in formula I, 1A, 1A-1, 1A-2 is aryl substituted with 0-3 moieties selected from halo and a 3-7 membered heterocyclyl containing 1-2 heteroatom ring vertices selected from N, O, and S, wherein the 3-7 membered heterocyclyl is further substituted with 0-3 moieties selected from —OH, —COOH, —$NH_2$, =O, —CN, and —$C_1$-$C_6$ alkyl.

In some embodiments, the compound of formula I is represented by the compound of Formula IB and/or a stereoisomer, a stable isotope, or a pharmaceutically acceptable salt thereof Formula IB

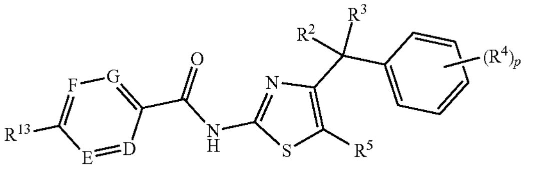

wherein p, $R^2$, $R^3$, $R^4$ and $R^5$ are as defined above; and

D is $CR^{10}$ or N;

E is $CR^{14}$ or N;

F is $CR^{12}$ or N;

G is $CR^{11}$ or N;

provided that no more than three of D, E, F, and i are N;

$R^{10}$, $R^{11}$, $R^{12}$, $R^{13}$ and $R^{14}$, when present, are each independently selected from H, halo, —OH, —COOH, —$NH_2$, =O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, $C_1$-$C_6$ haloalkoxyl, —$R^{7a}$, —$X^1$—$R^{7a}$, $X^1$—O—$X^1$—R—$^{7a}$, —$CHR^{7a}R^{8a}$, —$OR^{7a}$, —O—$X^1$—$R^{7a}$, —OC(O)($R^{7a}$), —O—$X^1$—C(O)($R^{7a}$), —C(O)($R^{7a}$), —C(O)N($R^{7a}R^{8a}$), —C(O)O($R^{7a}$), $S(O)_2R^{7a}$, —$S(O)_2N(R^{7a}R^{8a})$, —N($R^{7a}R^{8a}$), saturated or unsaturated $C_3$-$C_6$ cycloalkyl, saturated or unsaturated $C_1$-$C_6$ cycloalkoxyl, saturated or unsaturated 3-7 membered heterocyclyl containing 1-2 heteroatom ring vertices selected from N, O, and S; mono or bicyclic aryl, a 9-10 membered bicyclic heteroaryl containing 1-4 heteroatom ring vertices selected from N, O, and S; saturated or unsaturated 7-8 membered bridged heterocyclyl containing 1-2 heteroatom ring vertices selected from N, O, and S; and saturated or unsaturated 7-11 membered spiroheterocyclyl containing 1-2 heteroatom ring vertices selected from N, O, and S; 6-11 membered bicyclic heterocyclyl containing 1-2 heteroatom ring vertices selected from N, O, and S; wherein each $X^1$ is independently $C_{1-6}$ alkylene;

each $R^{7a}$ and $R^{8a}$ are independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl; and the 3-7 membered heterocyclyl, the mono or bicyclic aryl, the 9-10 membered bicyclic heteroaryl, the 7-8 membered bridged heterocyclyl, the 7-11 membered spiroheterocycly, and the 6-11 membered bicyclic heterocyclyl are each independently substituted with 0 to 2 moieties selected from halo, —OH, —COOH, —$NH_2$, =O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, saturated or unsaturated $C_3$-$C_6$ cycloalkoxyl, —$CHR^{7g}R^{8g}$, —$OR^{7g}$, —OC(O)($R^{7g}$), —C(O)($R^{7g}$), —C(O)N($R^{7g}R^{8g}$), —$NR^{7g}$(CO)$R^{8g}$, —C(O)O($R^{7g}$), —$S(O)_2N(R^{7g}R^{8g})$ and —N($R^{7g}R^{8g}$), wherein each $R^{7g}$ and $R^{8g}$ are each independently selected from H, $C_1$-$C_6$ alkyl, $C_1$-$C_6$ alkenyl, $C_1$-$C_6$ hydroxyalkyl. $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl;

In some embodiments, D, E, F and G in Formula IB are $CR^{10}$, $CR^{14}$, $CR^{12}$, and $CR^{11}$, respectively.

In some embodiments, F and G in Formula IB are $CR^{14}$ and $CR^{11}$, respectively, E is N or $CR^{14}$ and D is N or $CR^{10}$.

In some embodiments, $R^{10}$ and $R^{11}$ in Formula IB are each H, $R^{12}$ and $R^{14}$ are each independently selected from halo, —OH, —COOH, —$NH_2$, =O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, saturated or unsaturated $C_3$-$C_6$ cycloalkoxyl, —$CHR^{7b}R^{8b}$, —$OR^{7b}$, —OC(O)($R^{7b}$), —C(O)($R^{7b}$), —C(O)N($R^{7b}R^{8b}$), —C(O)O($R^{7b}$), —$S(O)_2N(R^{7b}R^{8b})$ and —N($R^{7b}R^{8b}$), wherein $R^{7b}$ and $R^{8b}$ are each independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl; —$R^{13}$ is 3-7 membered heterocyclyl containing 1-2 heteroatom ring vertices selected from N, O, and S, saturated or unsaturated 7-8 membered bridged heterocyclyl containing 1-2 heteroatom ring vertices selected from N, O, and S, saturated or unsaturated 7-11 membered spiroheterocyclyl containing 1-2 heteroatom ring vertices selected from N, O, and S, wherein the 3-7 membered heterocyclyl, the 7-8 membered bridged heterocyclyl, and the 7-11 membered spiroheterocyclyl are optionally substituted with 0-2 moieties independently selected from halo, —OH, —COOH, —$NH_2$, =O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_1$-$C_6$ cycloalkyl, saturated or unsaturated $C_3$-$C_6$ cycloalkoxyl.

In some embodiments, $R^{12}$ and $R^{14}$ in Formula IB are H, $R^{10}$ and $R^{11}$ are each independently selected from halo, —OH, —COOH, —$NH_2$, =O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, saturated or unsaturated $C_3$-$C_6$ cycloalkoxyl, —$CHR^{7b}R^{8b}$, —$OR^{7b}$, —OC(O)($R^{7b}$), —C(O)($R^{7b}$), —C(O)N($R^{7b}R^{8b}$), —C(O)O($R^{7b}$), —$S(O)_2N(R^{7b}R^{8b})$ and —N($R^{7b}R^{8b}$), wherein $R^{7b}$, and $R^{8b}$ are each independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl; $R^3$ is 3-7 membered heterocyclyl containing 1-2 heteroatom ring vertices selected from N, O, and S, saturated or unsaturated 7-8 membered bridged heterocyclyl containing 1-$^2$ heteroatom ring vertices selected from N, O, and S, saturated or unsaturated 7-11 membered spiroheterocyclyl containing 1-2 heteroatom ring vertices selected from N, O, and S, wherein the 3-7 membered heterocyclyl, the 7-8 membered bridged heterocyclyl, and the 7-11 membered spiroheterocyclyl are optionally substituted with 0-2 moieties independently selected from halo, —OH, —COOH, —$NH_2$, =O, —CN, $C_1$-$C_6$ alkyl, $C_1$-$C_6$ alkenyl, $C_1$-$C_6$ hydroxyalkyl, $C_3$-$C_6$ haloalkyl, $C_1$-$C_6$ aminoalkyl, $C_1$-$C_6$ alkoxyl, saturated or unsaturated $C_3$-$C_6$ cycloalkyl, saturated or unsaturated $C_3$-$C_6$ cycloalkoxyl.

In some embodiments, $R^{10}$, $R^{11}$, $R^{12}$ and $R^{14}$ in Formula IB are all H; $R^{13}$ is saturated or unsaturated $C_3$-$C_6$ cycloalkyl, 3-7 membered heterocyclyl containing 1-2 heteroatom ring vertices selected from N, O, and S, saturated or unsaturated 7-8 membered bridged heterocyclyl containing 1-2 heteroatom ring vertices selected from N, O, and S, saturated or unsaturated 7-11 membered spiroheterocyclyl containing 1-2 heteroatom ring vertices selected from N, O, and S, wherein the 3-7 membered heterocyclyl, the 7-8 membered bridged heterocyclyl, and the 7-1I membered spiroheterocyclyl are optionally substituted with 0-2 moieties independently selected from halo, —OH, —COOH, —$NH_2$, ═O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, saturated or unsaturated $C_1$-$C_6$ cycloalkoxyl.

In some embodiments, $R^{10}$, $R^{11}$, $R^{12}$ and $R^{14}$ in Formula IB are each H; $R^{13}$ is 3-7 membered heterocyclyl containing 1-2 heteroatom ring vertices selected from N, O, and S w substituted with 0-2 moieties independently selected from halo, —OH, —COOH, —$NH_2$, ═O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ Cycloalkyl, and saturated or unsaturated $C_3$-$C_6$ cycloalkoxyl.

In some embodiments, $R^{1O}$, $R^{11}$, $R^{12}$ and $R^{14}$ in Formula IB are each H; $R^{13}$ is optionally substituted saturated or unsaturated 7-8 membered bridged heterocyclyl containing 1-2 heteroatom ring vertices selected from N, O, and S substituted with 0-2 substituents selected from —OH, —COOH, —$NH_2$, ═O, —CN, and —$C_1$-$C_6$ alkyl.

In some embodiments, the compound of formula IB is represented by the compound of formula IB-1 or IB-2, and/or a stereoisomer, a stable isotope, or a pharmaceutically acceptable salt thereof Formula IB-1

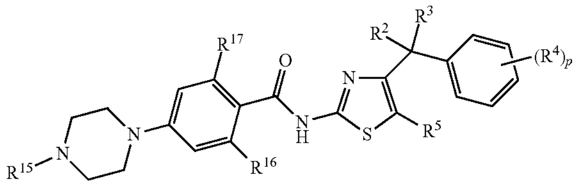

Formula IB-2

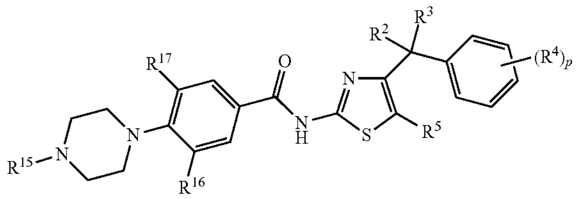

wherein p, $R^2$, $R^3$, $R^4$ and $R^5$ are as defined above; and $R^6$ and $R^{17}$ are each independently selected from halo and $C_1$-$C_6$ alkyl;

$R^{15}$ is selected from —OH, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, $C_1$-$C_6$ haloalkoxyl, saturated or unsaturated $C_3$-$C_6$ cycloalkyl, saturated or unsaturated $C_3$-$C_6$ cycloalkoxyl, —$CHR^{7b}R^{8b}$, —C(O)($R^{7b}$), —C(O)N($R^{7b}R^{8b}$), —C(O)O(R($^6$), —S(O)$_2R^{7b}$ and —S(O)N($R^{7b}R^{8b}$), wherein each $R^{7b}$ and $R^{8b}$ are independently selected from H, $C_1$-$C_6$ alkyl, $C_1$-$C_6$ alkenyl, $C_3$-$C_6$ hydroxyalkyl, $C_1$-$C_6$ haloalkyl, $C_1$-$C_6$, aminoalkyl, $C_1$-$C_6$ alkoxyl, saturated or unsaturated $C_3$-$C_6$ cycloalkyl, and saturated or unsaturated $C_3$-$C_6$ cycloalkoxyl.

In some embodiments, $R^{15}$ in formula IB-1 or IB-2 is selected from $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, $C_1$-$C_6$ haloalkoxyl; saturated or unsaturated $C_3$-$C_6$ cycloalkyl, saturated or unsaturated $C_3$-$C_6$ cycloalkoxyl, —$CHR^{7b}R^{8b}$, wherein each $R^{7b}$ and $R^{8b}$ are independently selected from II, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl.

In some embodiments, $R^{15}$ in formula IB-1 or IB-2 is $C_1$-$C_6$ alkyl.

In some embodiments, both $R^2$ and $R^3$ in formula IB-1 or IB-2 are methyl groups.

In some embodiments, $R^2$ and $R^3$ in formula IB-1 or IB-2 are each independently a methyl or an ethynyl group.

In some embodiments, IB-1 is represented by Formula IB-1-a, or Formula IB-2-a (IB-1-a)

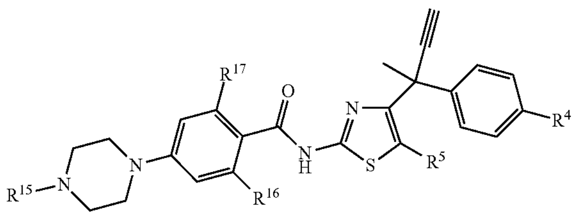

(IB-2-a)

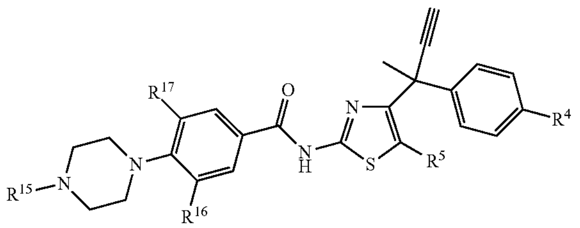

or a pharmaceutically acceptable salt thereof

In some embodiments, IB-1 is represented by Formula IB-1-b, or Formula IB-2-b (IB-1-b)

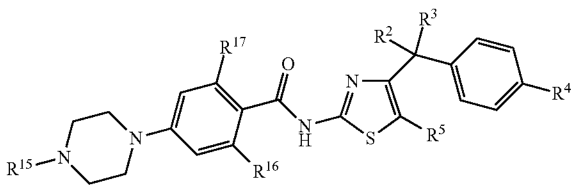

-continued (IB-2-b)

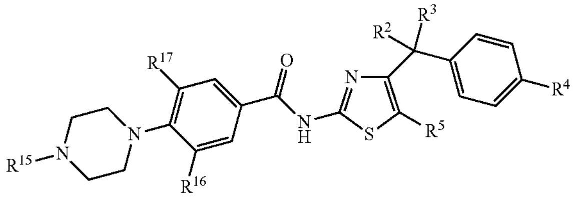

or a pharmaceutically acceptable salt thereof, wherein $R^4$ is halo.

In some embodiments, IB-1 is represented by Formula (IB-1-c), or Formula IB-2-c (IB-1-c)

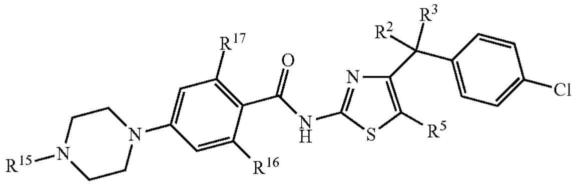

(IB-2-c)

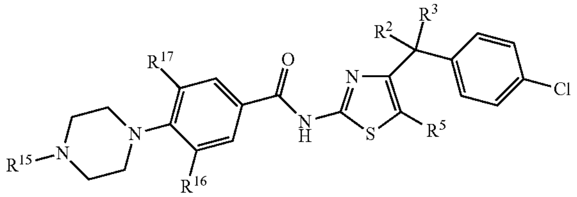

or a pharmaceutically acceptable salt thereof

In some embodiments, $R^5$ in formula IB-1 or IB-2 is H or methyl.

The present invention discloses novel heterocyclic compounds as inhibitors of ALPK1. The compounds are represented by formula IC Formula IC

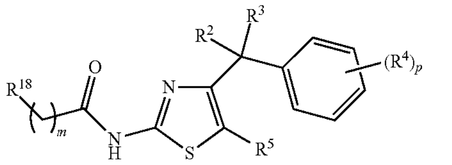

wherein $R^2$, $R^3$, $R^4$ and $R^5$ are as defined above formula I; and m is an integer from 0-6;

$R^{18}$ is selected from H, halo, —OH, —COOH, —$NH_2$, —CN, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, $C_1$-$C_6$ haloalkoxyl, —$R^{7a}$, —$X^1$—$R^{7a}$, $CHR^{7a}R^{8a}$, —$OR^{7a}$, —O—$X^1$—$R^{7a}$, $X^1$—O—$X^1$—$R^{7a}$, —OC(O)($R^{7a}$), —O—$X^1$—C(O)($R^{7a}$), —C(O)($R^{7a}$), —C(O)N($R^{7a}R^{8a}$), —$NR^{7a}$(CO)$R^{8a}$, C(O)O($R^{7a}$), $S(O)_2R^{7a}$, —$S(O)_2N(R^{7a}R^{8a})$, —N($R^{7a}R^{8a}$), saturated or unsaturated $C_3$-$C_6$ cycloalkyl, saturated or unsaturated $C_3$-$C_6$ cycloalkoxyl, saturated or unsaturated 3-7 membered heterocyclyl containing 1-2 heteroatom ring vertices selected from N, O, and S, mono or bicyclic aryl, 9-10 membered bicyclic heteroaryl containing 1-4 heteroatom ring vertices selected from N, O, and S, saturated or unsaturated 7-8 membered bridged heterocyclyl containing 1-2 heteroatom ring vertices selected from N, O, and S, saturated or unsaturated 7-11 membered spiroheterocyclyl containing 1-2 heteroatom ring vertices selected from N, O, and S, and 6-11 membered bicyclic heterocyclyl containing 1-2 heteroatom ring vertices selected from N, O, and S; wherein each $X^1$ is independently $C_{1-6}$ alkylene;

each $R^{7a}$ and $R^{8a}$ are independently selected from H, $C_1$-$C_6$ alkyl, saturated or unsaturated $C_3$-$C_6$ cycloalkyl, saturated or unsaturated $C_3$-$C_6$ cycloalkoxyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, $C_1$-$C_{16}$haloalkoxyl, saturated or unsaturated $C_3$-$C_6$ cycloalkyl, saturated or unsaturated $C_3$-$C_6$ cycloalkoxyl, aryl, saturated or unsaturated $C_3$-$C_6$ cycloalkyl, saturated or unsaturated C:3-$C_6$ cycloalkoxyl, saturated or unsaturated 3-7 membered heterocyclyl containing 1-2 heteroatom ring vertices selected from N, O, and S, wherein the aryl and 3-7 membered heterocyclyl groups are substituted with 0-3 substituents selected from halo, —OH, —COOH, —NH, ═O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl; and the $C_3$-$C_6$ cycloalkyl, $C_3$-$C_6$ cycloalkoxyl, 3-7 membered heterocyclyl, the mono or bicyclic aryl, the 9-10 membered bicyclic heteroaryl, the saturated or unsaturated 7-8 membered bridged heterocyclyl, the saturated or unsaturated 7-11 membered spiroheterocycly, and the 6-11 membered bicyclic heterocyclyl are each independently substituted with 0 to 3 moieties selected from halo, —OH, —COOH, —$NH_2$, ═0, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, saturated or unsaturated $C_3$-$C_6$ cycloalkoxyl, —$CHR^{7b}R^{8b}$, —$OR^{7b}$, —OC(O)($R^{7b}$), —C(O)($R^{7b}$), —C(O)N($R^{7b}R^{8b}$), —$NR^{7b}$(CO)$R^{8b}$, —C(O)O($R^{7b}$), —$S(O)_2N(R^{7b}R^{8b})$ and —N($R^{7b}R^{8b}$), wherein each $R^{7b}$ and $R^{8a}$ are independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl;

In some embodiments, in in formula IC is 1;

In some embodiments, $R^{18}$ in formula IC is H.

In some embodiments, $R^2$ and $R^3$ in each of the formulas described herein are both $C_1$-$C_6$ alkyl groups;

In some embodiments, $R^2$ is methyl and $R^3$ is $CH_2OMe$ in each of the formulas described herein.

In some embodiments, $R^2$ and $R^3$ are each methyl in each of the formulas described herein.

In some embodiments, $R^2$ is methyl and $R^3$ is ethynyl in each of the formulas described herein.

In some embodiments, in each of the formulas described herein, the subscript p is 1, and $R^4$ is attached to the phenyl ring as shown below:

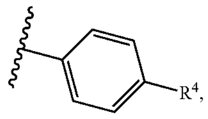

wherein the wavy line represents the point of attachment to the remainder of the formula.

In some embodiments, in each of the formulas described herein, the subscript p is 1, and $R^4$ is halo attached to the phenyl ring as shown below:

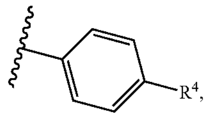

wherein the wavy line represents the point of attachment to the remainder of the formula.

In some embodiments, in each of the formulas described herein, the subscript p is 1, and $R^4$ is chloro attached to the phenyl ring as shown below:

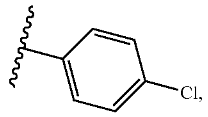

wherein the wavy line represents the point of attachment to the remainder of the formula.

In some embodiments, in each of the formulas described herein, the subscript p is 1, and $R^4$ is methoxy attached to the phenyl ring as shown below:

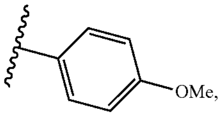 [SMILES: *c1ccc(OC)cc1]

wherein the wavy line represents the point of attachment to the remainder of the formula.

In some embodiments, $R^5$ in each of the formulas described herein is H.

In some embodiments, $R^5$ in each of the formulas described herein is deuterium.

In some embodiments, $R^5$ in each of the formulas described herein is $C_1$-$C_6$ deuteroalkyl. In some embodiments, $R^5$ in each of the formulas described herein is selected from the group consisting of $—CH_2D$, $—CHD_2$, and $—CD_3$.

In some embodiments, the carbon atom attached to $R^2$ and $R^3$ in each of the formulas described herein is chiral. In such embodiments, it is understood that $R^2$ and $R^3$ are not the same. In some embodiments, the carbon atom attached to $R^2$ and $R^3$ in each of the formulas described herein is the S isomer, referring to the absolute stereochemistry at this carbon atom. In some embodiments, the carbon atom attached to $R^2$ and R in each of the formulas described herein is the R isomer, referring to the absolute stereochemistry at this carbon atom. In some embodiments, $R^2$ is methyl and $R^3$ is ethynyl.

In some embodiments, the compound of Formula I is selected from

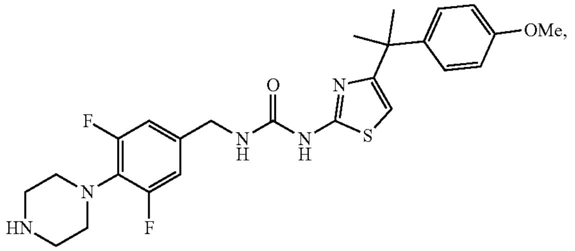

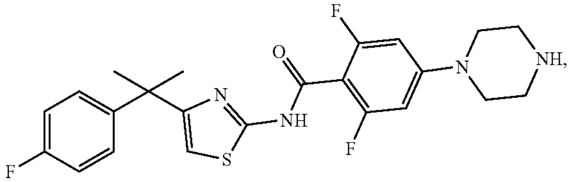

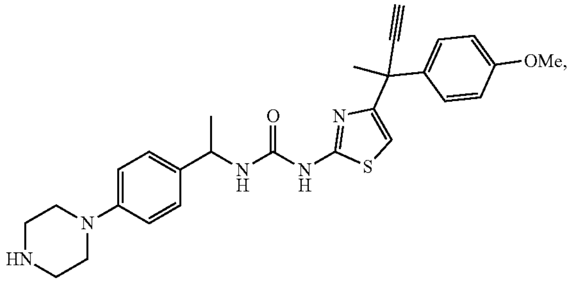

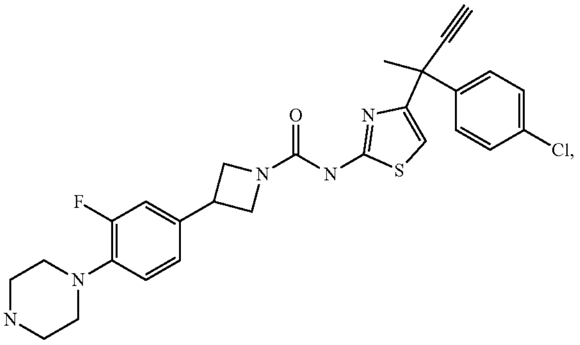

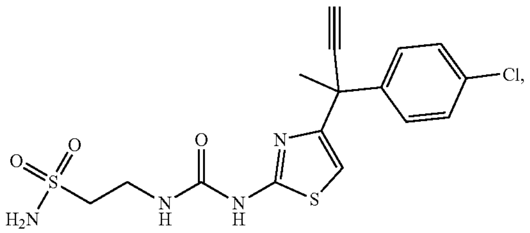

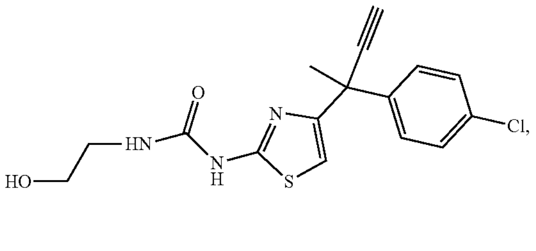

-continued
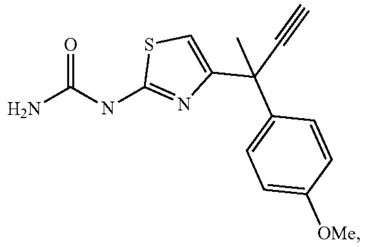
,
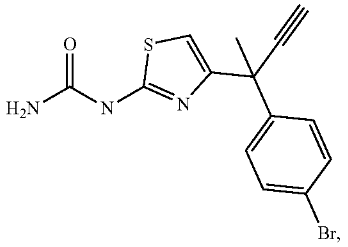
,
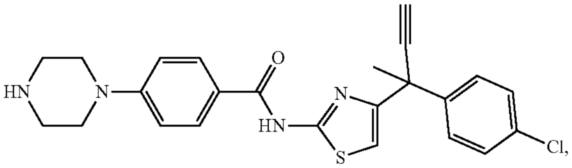
,
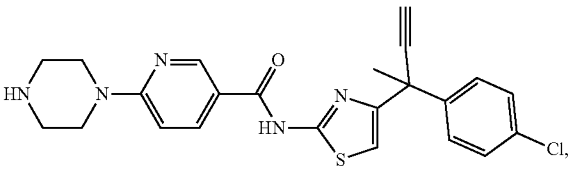
,
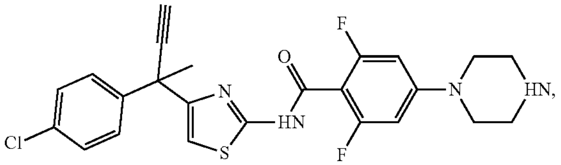
,
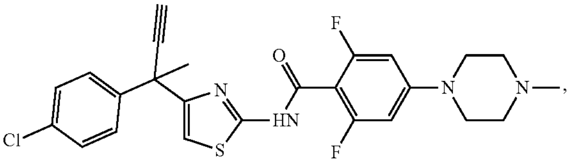
,
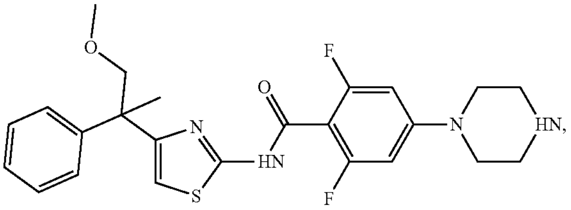
,
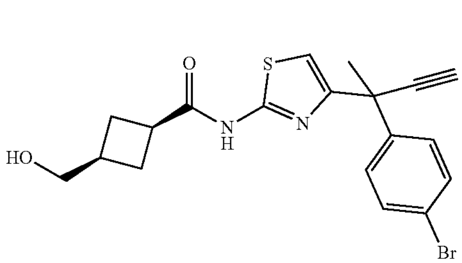
-continued
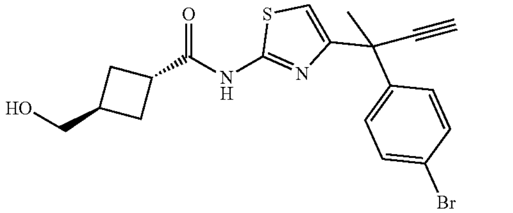
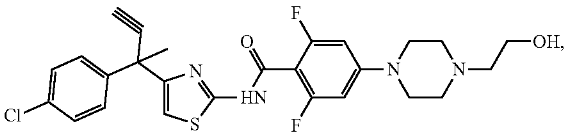
,
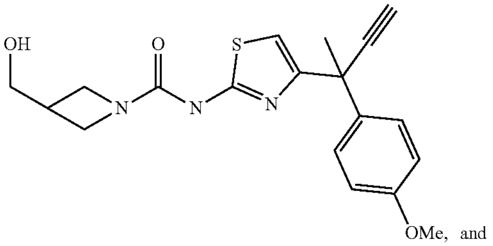
, and
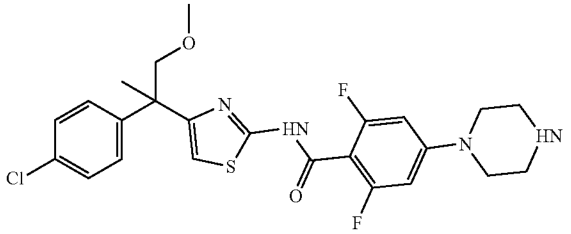
In some embodiments, the compound of Formula I is selected from
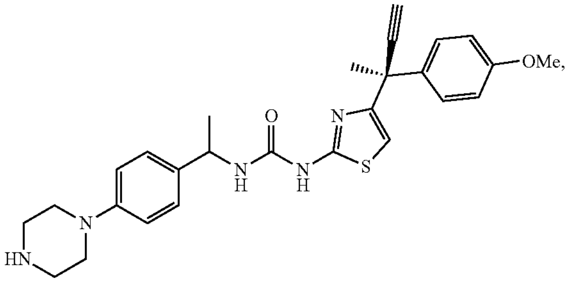
,
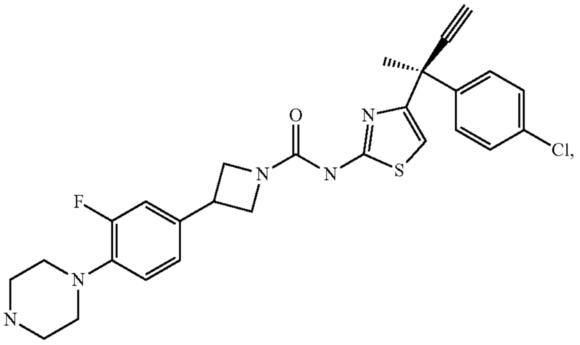
, -continued

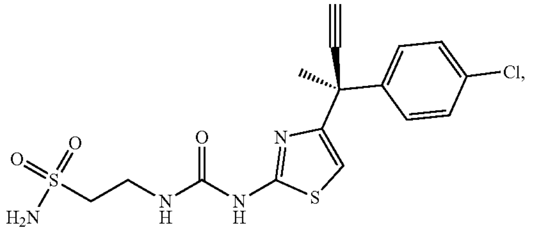
,

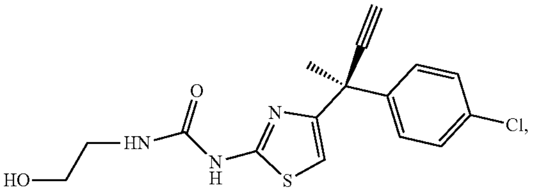
,

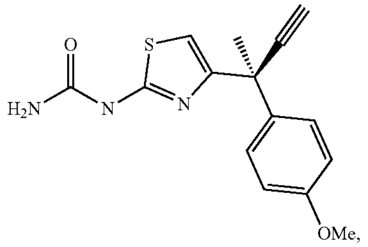
,

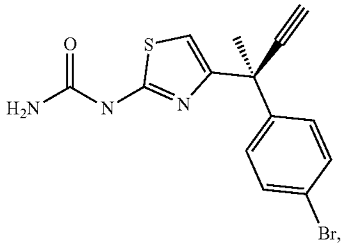
,

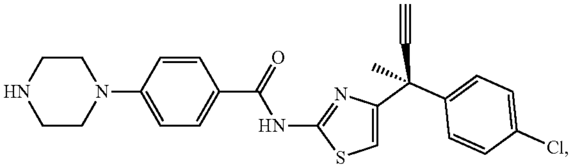
,

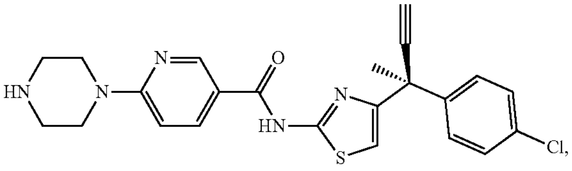
,

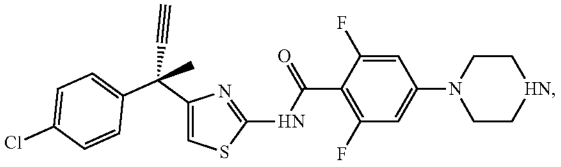
,

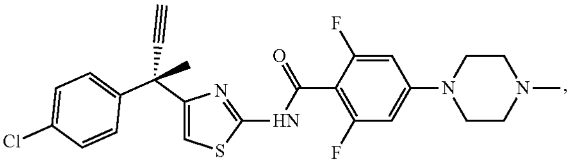
,

-continued

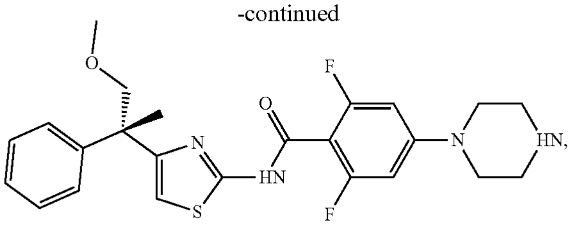
,

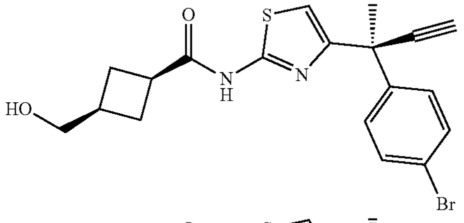

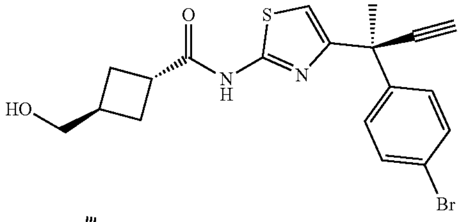

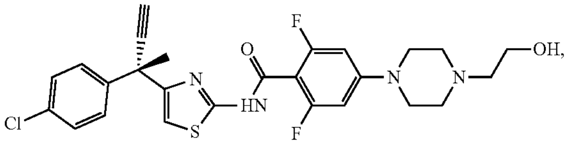
,

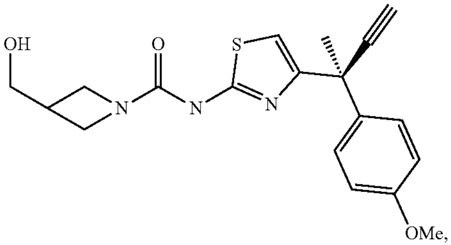
, and

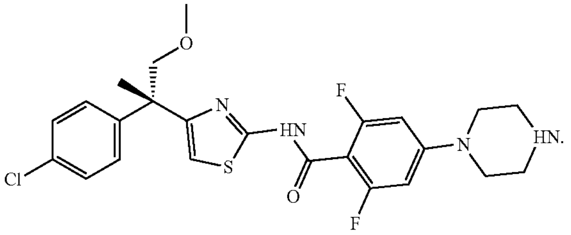
.

In some embodiments, the compound is selected from the examples provided herein.

Preparation of Compounds of Formula I and Exemplary Compounds

Analytical Details

NMR: Measurements were performed on a Bruker Ultra-shield™ 400 (400 MHz) spectrometer using or not tetramethylsilane (TMS) as an internal standard. Chemical shifts (6) are reported ppm downfield from TMS, spectra splitting pattern are designated as single (s), doublet (d), triplet(t), quartet (q), multiplet, unresolved or overlapping signals (in), broad signal (br). Deuterated solvent are given in parentheses and have a chemical shifts of dimethyl sulfoxide (δ2.50 ppm), chloroform (δ 7.26 ppm), methanol (δ3.31 ppm), or other solvent as indicated in NMR spectral data.

LC-MS: Shimadzu20A-2010MS

Detection: SPD-M20A

Column: MERCK, RP-18e 25-2 mm;

Wavelength: UV 220 nm, 254 nm

Column temperature: 50° C.; MS ionization: ESI

Mobile Phase: 1.5ML/4LTFA in water (solvent A) and 0.75ML/4LTFA in acetonitrile (solvent B),using the elution gradient 5%-95% (solvent B) over 0.7 minutes and holding at 95/o for 0.4 minutes at a flow rate of 1.5 ml/mi;

Flash Column Chromatography System

System: CombiFlash Rf+

Column: Santai Technologies, Inc, SEPAFLASH®

Samples were typically adsorbed on isolute

HPLC Separation Conditions

System: TRILUTION LC 4.0

Detection: Gilson 159 UV-VIS

Condition 1: Column: Phenomenex Gemini-NX 80*40 mm*3 um

Eluent A: water (0.05% NH3H2O+10 mM $NH_4$HCO3)

Eluent B: CH3CN

Begin B: 20-45%, End B: 80-20%, Gradient Time (min): 8

Condition 2: Column: Xtimate C18 10μ 250 mm*50 mm;

Eluent A: water (0.04% NH3H2O+10 mM $NH_4$HCO3).

Eluent B: CH3CN 50%-80%; Gradient Time (min): 8

SFC Chiral Separation Conditions

Mobile phase: [0.1% $NH_3H_2O$ ETOH]; B %:30%-30%, 35%-35% or 45-45%

Column: DAICEL CHRALCEL OJ-H (250 mm*30 mm, 5 um);

Mobile phase: [0.1% $NH_3H_2O$ ETOH];B %:30%-30%, 40%-40%;

Column: DAICEL CHRALPAK AD (250 mm*30 mm, 10 um);

Mobile phase: [0.1o.% $NH_3H_2O$ ETOH]; B %:35%-35%;

Column: DAICEL CHITRALPAK AS (250 mm*30 mm, 10 um);

Mobile phase: [0.i % $NH_3H_2O$ ETOH]; B %:35%-35%

All starting materials, building blocks, reagents, acids, bases, dehydrating agents, solvents, and catalysts utilized to synthesis the compounds of the present invention are either commercially available or can be produced by organic synthesis methods known to one of ordinary skill in the art.

Below is the abbreviation table for chemistry:

| | |
|---|---|
| Ac | Acetyl |
| ACN | Acetonitrile |
| Cbz | Benzoxycarbonyl |
| CDI | N,N-Carbonyldiimidazole |
| Com. | Compound |
| DCM | Dichloromethane |
| DIEA | N,N-Diisopropylethylamine |
| DMAP | 4-Dimethylaminopyridine |
| DMF | N,N-Dimethylformamide |
| DMP | Dess-Martin Periodinane |
| DMSO | Dimethyl sulfoxide |
| EA | Ethyl Acetate |
| EDCI | 1-Ethyl-3-(3-dimethylaminopropyl)carbodiimide |
| ESI | Electron Spray Ionization |
| Et | Ethyl |
| HATU | 2-(7-Azabenzotriazol-1-yl)-N,N,N',N'-tetramethyluronium hexafluorophosphate |
| HBTU | O-Benzotriazole-N,N,N',N'-tetramethyl-uronium-hexafluorophosphate |
| HOBt | 1-Hydroxybenzotriazole |
| HPLC | High Performance Liquid Chromatography |
| Int | Intermediate |
| LCMS | Liquid Chromatography-Mass Spectrometry |

-continued

| | |
|---|---|
| LiHMDS | Bis(trimethylsilyl)amine lithium salt |
| Me | Methyl |
| MS | Mass Spectrometry |
| Ms | Methanesulfonyl |
| NMR | Nuclear Magnetic Resonance |
| $Pd_2(dba)_3$ | Tris(dibenzylideneacetone)dipalladium |
| PE | Petroleum Ether |
| PyBOP | Benzotriazol-1-yl-oxytripyrrolidinophosphonium hexafluorophosphate |
| RT | Room Temperature |
| TBAF | Tetrabutylammonium fluoride |
| TBDPS | t-butyldiphenylsilyl |
| TBME | tert-Butyl Methyl Ether |
| t-Bu | tert-butyl |
| TEA | Triethylamine |
| TFA | Trifluoroacetic Acid |
| THF | Tetrahydrofuran |
| TLC | Thin Layer Chromatography |
| TMS | Tetramethylsilane |
| Ts | p-Toluenesulfonyl |
| X-phos | (2-(2,4,6-triisopropylphenethyl)phenyl)dicyclohexylphosphine |

Reaction Scheme 1

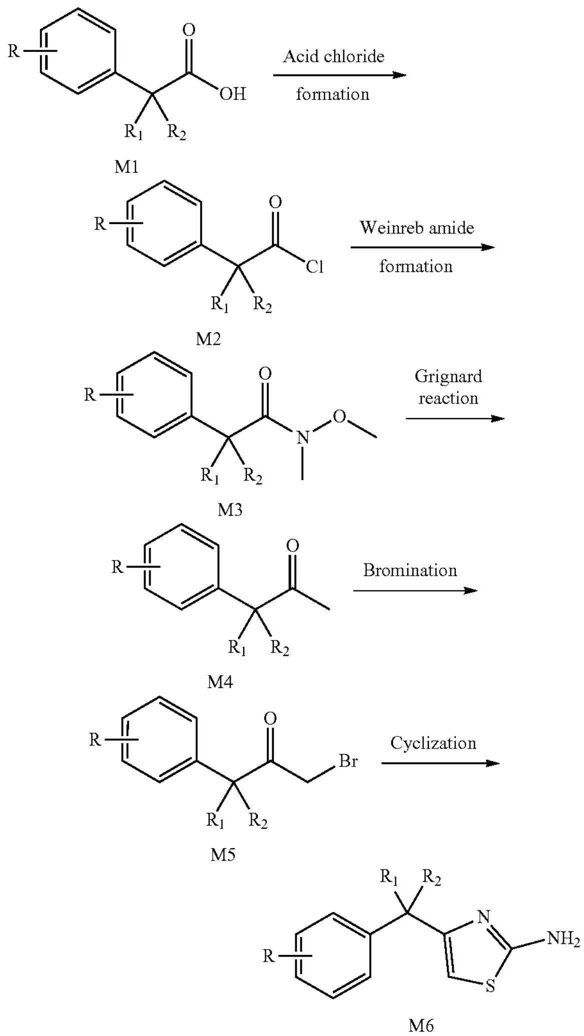

Appropriately substituted compound M1 wherein R are suitable 1-3 groups like halo or $C_1$-$C_6$ alkyl, etc, and $R_1$ and $R_2$ are suitable groups like independently selected from H, $C_1$-$C_6$ alkyl and $C_2$-$C_6$ alkynyl, converted to acid chloride with $SOCl_2$ or $(COCl)_2$ under heating or room temperature. Weinreb amide was formed by the reaction of N,O-dimethylhydroxylamine hydrochloride with the acid chloride at 0° C. Grignard reagent in THF was added to the Weinreb amide at 0° C. to give the ketone, which was converted to M5 by bromination. The cyclization with thiourea under basic condition gave the intermediate M6.

Example 1

Preparation of 4-2-(4-bromophenyl)propan-2-yl) thiazol-2-amine (Intermediate 1)

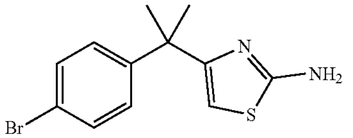 [SMILES: CC(C)(c1ccc(Br)cc1)c1csc(N)n1]

Step 1. Preparation of compound 2-(4-bromophenyl)-2-methylpropanoyl chloride

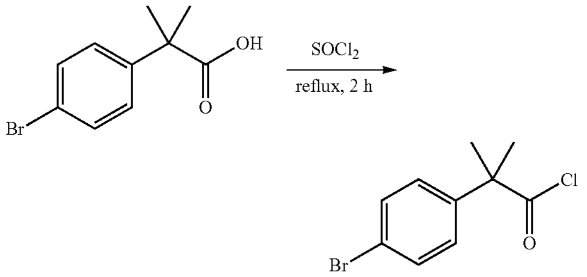

Compound 2-(4-bromophenyl)-2-methylpropanoic acid (100 g, 411 mmol, 1.0 eq) in $SOCl_2$ (175 mL, 6 eq) was warmed to reflux for 2 h. Then the solution was cooled to RT, the mixture was concentrated under reduced pressure to get dry acid chloride (yellow oil) which was used in next step without further purification.

Step 2. Preparation of compound 2-(4-bromophenyl)-N-methoxy-N,2-dimethylpropanamide

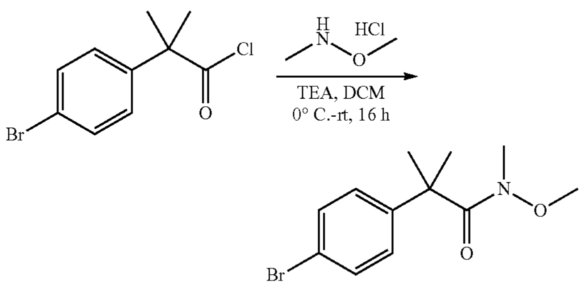

The solution of compound N,O-dimethylhydroxylamine HCl salt (48.2 g, 49 mmol, 1.2 eq) in DCM (300 mL) was cooled to 0° C. Then to the mixture was added crude acid chloride obtained from step 1 above (1.0 eq) in DCM (200 mL) and TEA (114 mL, 2 eq), and the mixture was stirred at RT overnight. The reaction mixture was quenched with 1-120 (200 mL). The mixture was extracted with DCM (200 mL×3), the combined organic layers were washed with water (200 mL×3), brine (200 mL×3), dried over $Na_2SO_4$, filtered and concentrated to give a residue. The desired compound (108 g, pure) was obtained as a pale yellow oil which was used in next step without further purification.

$^1H$ NMR (400 MHz, $CDCl_3$) δ 7.42 (d, J=8.8 Hz, 2H), 7.12 (d, J=8.8 Hz, 2H), 3.08 (s, 3H), 2.71 (s, 3H), 1.49 (s, 61H).

Step 3. Preparation of compound 3-(4-bromophenyl)-3-methylbutan-2-one

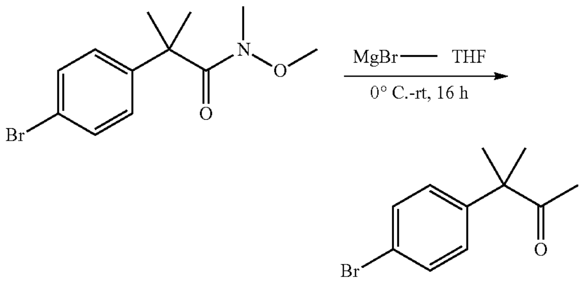

The solution of compound obtained from step 2 above (54 g, 189 mmol, 1 eq) in dry THF (500 mL) was cooled to 0° C. $CH_3MgBr$ (3 M in THF, 253 mL, 757.8 mmol, 4 eq) was added dropwise. The mixture was stirred at RT overnight. The reaction mixture was quenched with sat. $NH_4Cl$ (200 mL) and extracted with EA (300 mL×2). The combined organic layers were washed with brine (300 mL×2), dried over $Na_2SO_4$, filtered and concentrated to give a residue. The desired compound (90.4 g, pure) was obtained as a pale yellow oil which was used into the next step without further purification.

$^1H$ NMR (400 MHz, $CDCl_3$) 7.45 (d, J=8.4 Hz, 2H), 7.11 (d, J=8.4 Hz, 2H), 1.90 (s, 3H), 1.44 (s, 6H).

Step 4. Preparation of compound 1-bromo-3-(4-bromophenyl)-3-methylbutan-2-one

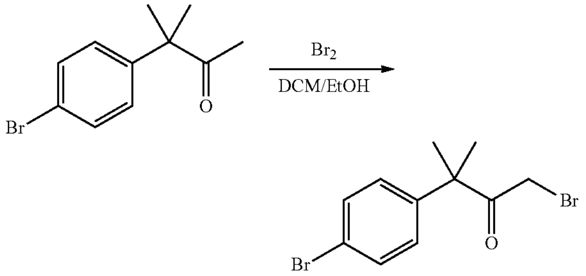

To the solution of compound obtained from step 3 above (46 g, 191 mmol, I eq) in DCM/EtOH (250 mL/250 mL) was added $Br_2$ (14.7 mL, 286 mmol, 1.5 eq) drop wise. The mixture was stirred at RT for 3.5 h. The reaction mixture was quenched with sat.$Na_2SO_3$ (150 mL). The mixture was extracted with DCM (300 mL×2) and the combined organic layers were washed with brine (300 mL×2), dried over $Na_2SO_4$, filtered and concentrated to give a residue. The desired compound (118.8 g, crude) was obtained as a white solid which was used into the next step without further purification.

$^1H$ NMR (400 MHz, $CDCl_3$) δ 7.48 (d, J=8.4 Hz, 2H), 7.11 (d, J=8.4 Hz, 2H), 3.82 (s, 2H), 1.52 (s, 61H).

Step 5. Preparation of 4-(2-(4-bromophenyl)propan-2-yl)thiazol-2-amine

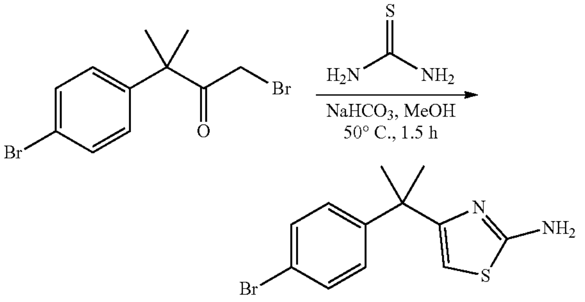

To the solution of compound obtained from step 4 above (50 g, 156 mmol, 1 eq) in MeOH (500 mL) was added thiourea (14.3 g, 188 mmol, 1.2 eq). The mixture was stirred at 50° C. for 1.5 h. The mixture was concentrated under reduced pressure. The mixture was extracted with EA (300 mL×2), the combined organic layers were washed with brine (300 mL×2), dried over $Na_2SO_4$, filtered and concentrated to give a residue, the residue was purified by PE/EA=10:1 on silica gel chromatography to give pure desired compound (34 g, white solid).

$^1H$ NMR (400 MHz, DMSO) δ 7.39 (d, J:8.0 Hz, 2H), 7.14 (d, J=8.0 Hz, 2H), 6.78 (s, 2H), 6.22 (s, 1H), 1.50 (s, 6H). MS (ESI) m/z $(M+H)^+$=297.0.

4-1-(4-bromophenyl)cyclopentyl)thiazol-2-anine (Intermediate 2)

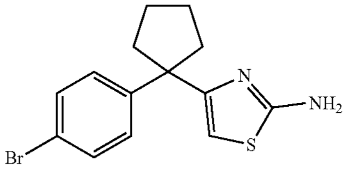 [SMILES: Nc1nc(C2(c3ccc(Br)cc3)CCCC2)cs1]

Step 1. Preparation of compound ethyl 1-(4-bromophenyl)cyclopentane-1-carboxylate

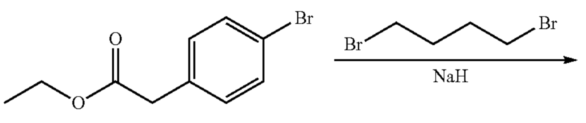

-continued

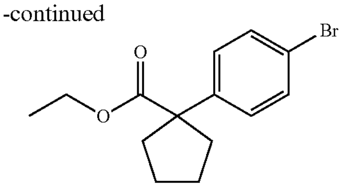

To a solution of compound ethyl 2-(4-bromophenyl) acetate (10 g, 41.3 mmol) in DMF (50 mL), NaH (8.3 g, 207 mmol) was added slowly at 0° C. and then the reaction was stirred at RT for 30 min. 1,4-dibromobutane (8.8 g, 41.3 mmol) was added slowly at RT. The mixture was stirred at RT overnight. The reaction mixture was concentrated to give a residue. The residue was purified by flash silica gel chromatography (PE:EA=1:0 to 5: 1). The title compound (7.8 g, yield: 63.8%) was obtained.

MIS (ESI) m/z $(M+H)^+$=297.0

Step 2. Preparation of compound 1-(4-bromophenyl)cyclopentane-1-carboxylic acid

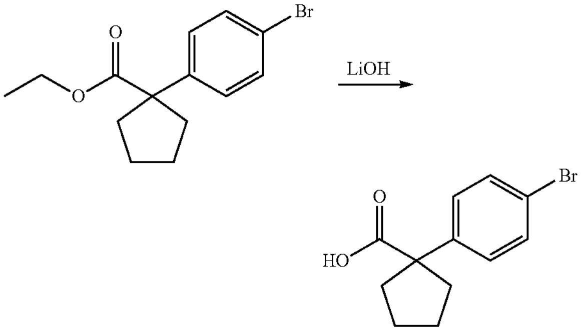

To a solution of compound ethyl 1-(4-bromophenyl) Cyclopentane-1-carboxylate (7.8 g, 26.3 mmol) in THF (25 mL) were added NaOH (3.2 g, 79 mmol) and $H_2O$ (5 mL) and the reaction was stirred at 40° C. overnight. After cooling down, the PH value of the reaction solution was adjusted to 6. The reaction mixture was concentrated to give a residue. The residue was purified by flash silica gel chromatography (PE:EA=1:0 to 1:2). The desired compound (5.6 g, yield: 79.4%) was obtained.

MS (ESI) m/z $(M+H)^+$==269.0

The synthesis of following steps was similar as described in intermediate 1.

4-(2-(5-bromopyridin-2-yl)propan-2-yl)thiazol-2-amine (Intermediate 3)

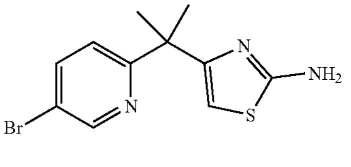 [SMILES: CC(C)(c1ccc(Br)cn1)c1csc(N)n1]

Step 1. Preparation of compound methyl 2-(5-bromopyridin-2-yl)-2-methylpropanoate

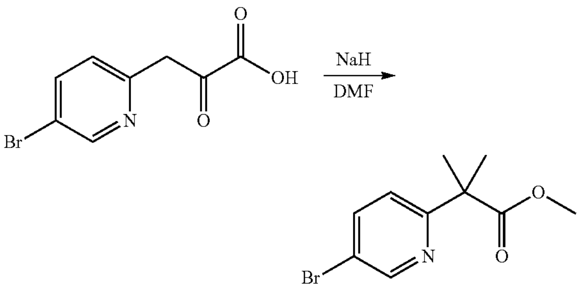

To a solution of 3-(5-bromopyridin-2-yl)-2-oxopropanoic acid (2 g, 9.26 mmol, 1.0 eq) in DMF (20 mL) was added NaH (1.3 g, 32.4 mmol, 3.5eq) at 0UC. The resulting mixture was stirred for 20 min at 0° C. The mixture was added $CH_3I$ (2 mL, 3.5 eq) at 0° C. and stirred for 6 h. The reaction mixture was quenched with water (50 mL), extracted with EA (25 mL×2) and washed with brine (10 mL×2), then dried over $Na_2SO_4$, filtered and evaporated to dryness. The resulting residue was purified by column chromatography on a silica gel to obtain the desired compound (1.95 g, yield: 93%).

Step 2. Preparation of compound 2-(5-bromopyridin-2-yl)-2-methylpropanoic acid

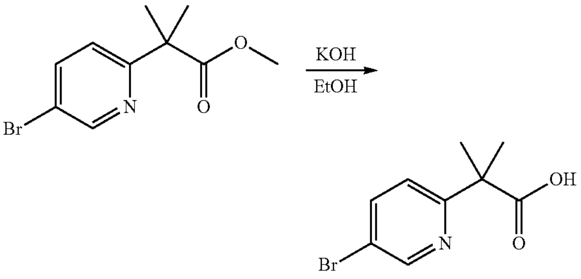

A mixture of 2-(5-bromopyridin-2-yl)-2-methylpropanoate (1.95 g, 7.56 mmol, 1.0eq) and KOH (1.9 mL, 2M in $H_2O$, 3.0 eq) was heated to reflux for 1 h. The reaction was cooled to $R^1$ and quenched with 0.1M HCl, extracted with EA, washed by brine, dried over $Na_2SO_4$, filtered and evaporated to dryness to obtain the desired compound (1.82 g, yield: 98%).

The next few steps are similar as described for intermediate 1.

The following examples were synthesized analogous to the procedure of intermediate 1 using the appropriate starting materials and thiourea:

TABLE 1

| Com. ID | Structure | Name | HNMR | LCMS ([M + H]$^+$ =) |
|---|---|---|---|---|
| Intermediate 4 | 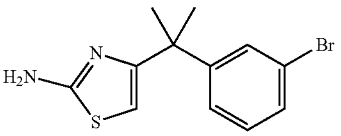 [SMILES: CC(C)(c1cccc(Br)c1)c1csc(N)n1] | 4-(2-(3-bromophenyl)propan-2-yl)thiazol-2-amine | 1H NMR (400MHZ, CDCl3) δ 7.67 (t, J = 1.88 Hz, 1 H), 7.43 (d, J = 7.78 Hz, 1 H), 7.33-7.39 (m, 1 H), 7.14-7.22 (m, 1 H), 6.48 (s, 1 H), 4.87 (br s, 2 H), 2.57 (s, 1 H), 1.91 (s, 3 H). MS (ESI) m/z (M + H)+ = 309.0. | 297.0 |
| Intermediate 5 | 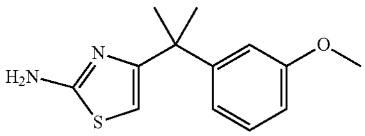 [SMILES: COc1cccc(C(C)(C)c2csc(N)n2)c1] | 4-(2-(3-methoxyphenyl)propan-2-yl)thiazol-2-amine | | 249.1 |
| Intermediate 6 | 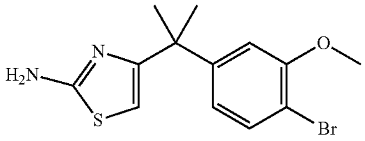 [SMILES: COc1cc(C(C)(C)c2csc(N)n2)ccc1Br] | 4-(2-(4-bromo-3-methoxyphenyl)propan-2-yl)thiazol-2-amine | | 327.0 |
| Intermediate 7 | 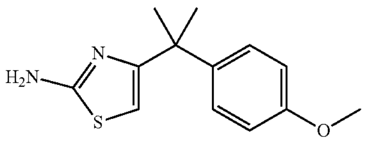 [SMILES: COc1ccc(C(C)(C)c2csc(N)n2)cc1] | 4-(2-(4-methoxyphenyl)propan-2-yl)thiazol-2-amine | | 249.1 |
| Intermediate 8 | 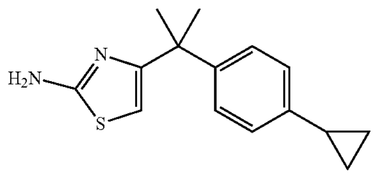 [SMILES: CC(C)(c1ccc(C2CC2)cc1)c1csc(N)n1] | 4-(2-(4-cyclopropylphenyl)propan-2-yl)thiazol-2-amine | | 259.1 |

TABLE 1-continued

| Com. ID | Structure | Name | HNMR | LCMS ([M + H]$^+$ =) |
|---|---|---|---|---|
| Intermediate 9 | 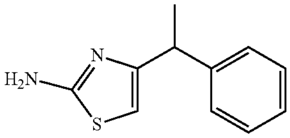 | 4-(1-phenylethyl)thiazol-2-amine | | 205.0 |
| Intermediate 10 | 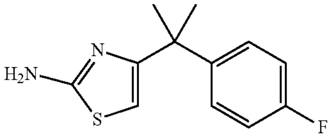 [SMILES: CC(C)(c1ccc(F)cc1)c1csc(N)n1] | 4-(2-(4-fluorophenyl)propan-2-yl)thiazol-2-amine | | 237.0 |
| Intermediate 11 | 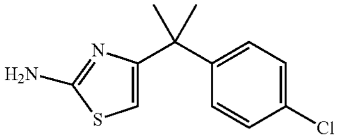 [SMILES: CC(C)(c1ccc(Cl)cc1)c1csc(N)n1] | 4-(2-(4-chlorophenyl)propan-2-yl)thiazol-2-amine | | 253.0 |
| Intermediate 12 | 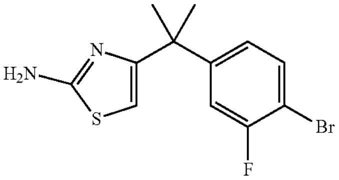 [SMILES: CC(C)(c1ccc(Br)c(F)c1)c1csc(N)n1] | 4-(2-(4-bromo-3-fluorophenyl)propan-2-yl)thiazol-2-amine | | 314.9 |
| Intermediate 13 | 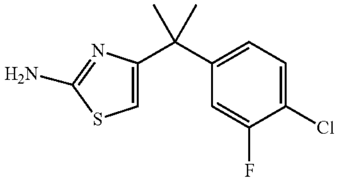 | 4-(2-(4-chloro-3-fluorophenyl)propan-2-yl)thiazol-2-amine | | 271.0 |
| Intermediate 14 | 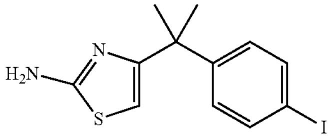 [SMILES: CC(C)(c1ccc(I)cc1)c1csc(N)n1] | 4-(2-(4-iodophenyl)propan-2-yl)thiazol-2-amine | | 344.9 |
| Intermediate 15 | 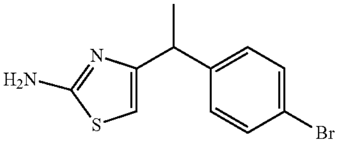 | 4-(1-(4-bromophenyl)ethyl)thiazol-2-amine | | 282.9 |
| Intermediate 16 | 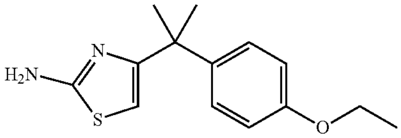 [SMILES: CCOc1ccc(C(C)(C)c2csc(N)n2)cc1] | 4-(2-(4-ethoxyphenyl)propan-2-yl)thiazol-2-amine | | 263.1 |
| Intermediate 17 | 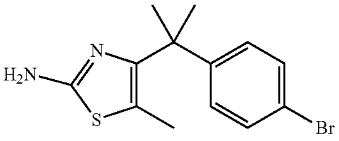 [SMILES: Cc1sc(N)nc1C(C)(C)c1ccc(Br)cc1] | 4-(2-(4-bromophenyl)propan-2-yl)-5-methylthiazol-2-amine | | 311.0 |

TABLE 1-continued

| Com. ID | Structure | Name | HNMR | LCMS ([M + H]$^+$ =) |
|---|---|---|---|---|
| Intermediate 18 | 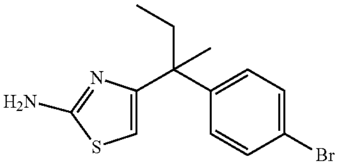 [SMILES: CCC(C)(c1ccc(Br)cc1)c1csc(N)n1] | 4-(2-(4-bromophenyl)butan-2-yl)thiazol-2-amine | | 311.0 |
| Intermediate 19 | 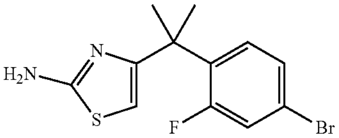 [SMILES: CC(C)(c1csc(N)n1)c1ccc(Br)cc1F] | 4-(2-(4-bromo-2-fluorophenyl)propan-2-yl)thiazol-2-amine | | 315.0 |
| Intermediate 20 | 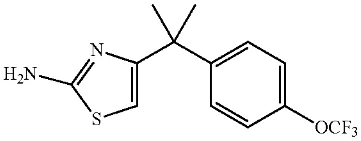 [SMILES: CC(C)(c1ccc(OC(F)(F)F)cc1)c1csc(N)n1] | 4-(2-(4-(trifluoromethoxy)phenyl) propan-2-yl)thiazol-2-amine | | 303.0 |
| Intermediate 21 | 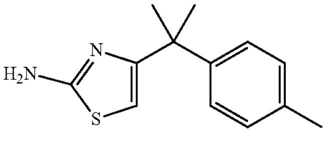 [SMILES: Cc1ccc(C(C)(C)c2csc(N)n2)cc1] | 4-(2-(p-tolyl)propan-2-yl)thiazol-2-amine | | 233.1 |
| Intermediate 22 | 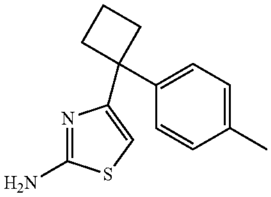 | 4-(1-(4-bromophenyl)cyclobutyl) thiazol-2-amine | 1H NMR (400MHz, CDCl3) δ 7.45-7.41 (m, 2H), 7.22-7.17 (m, 2H), 6.05 (s, 1H), 4.88 (s, 2H), 2.74-2.65 (m, 2H), 2.62-2.51 (m, 2H), 2.20-2.04 (m, 1H), 1.97-1.85 (m, 1H). MS (ESI) m/z (M + H)+ = 311.0. | 309.0 |
| Intermediate 23 | 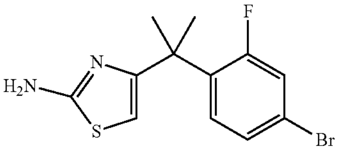 [SMILES: CC(C)(c1csc(N)n1)c1ccc(Br)cc1F] | 4-(2-(4-bromo-2-fluorophenyl)propan-2-yl)thiazol-2-amine | | 314.9 |
| Intermediate 24 | 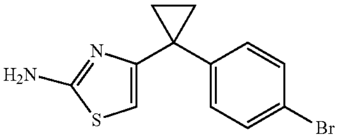 [SMILES: Nc1nc(C2(c3ccc(Br)cc3)CC2)cs1] | 4-(1-(4-bromophenyl)cyclopropyl) thiazol-2-amine | | 294.9 |
| Intermediate 25 | 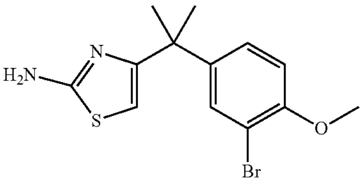 [SMILES: COc1ccc(C(C)(C)c2csc(N)n2)cc1Br] | 4-(2-(3-bromo-4-methoxyphenyl)propan-2-yl)thiazol-2-amine | | 327.0 |
| Intermediate 26 | 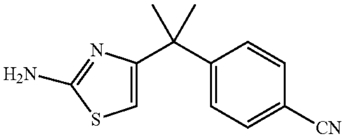 [SMILES: CC(C)(c1ccc(C#N)cc1)c1csc(N)n1] | 4-(2-(2-aminothiazol-4-yl)propan-2-yl)benzonitrile | | 244.1 |

Reaction Scheme 2

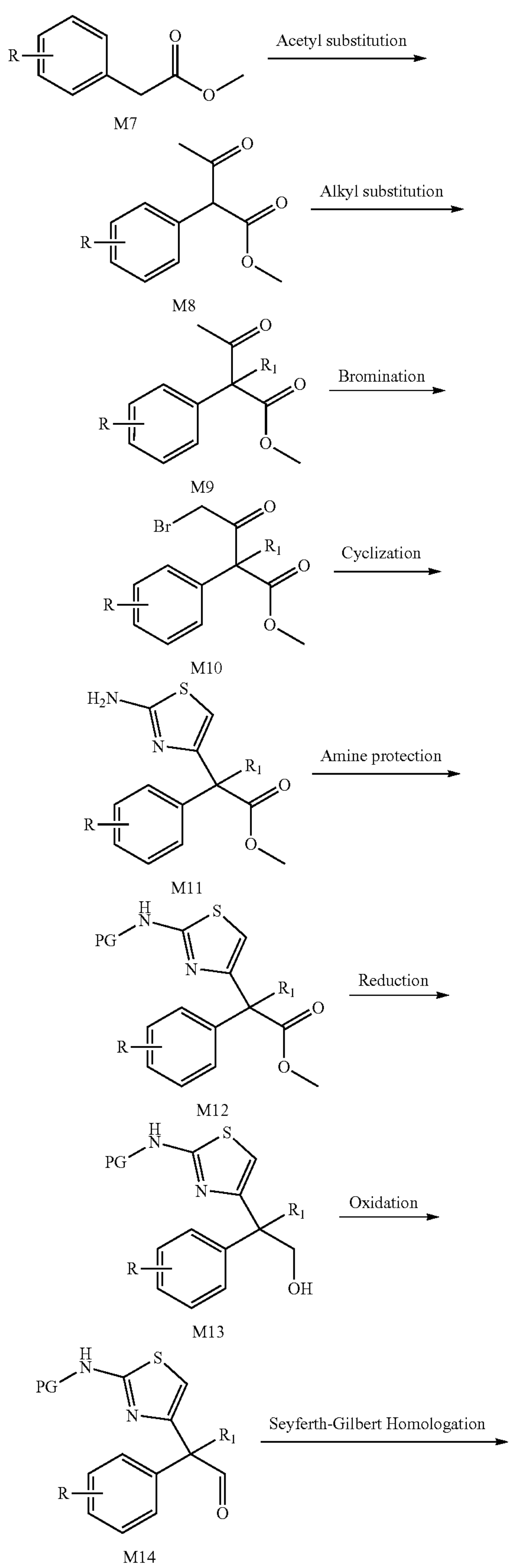

M7 M8 M9 M10 M11 M12 M13 M14

-continued

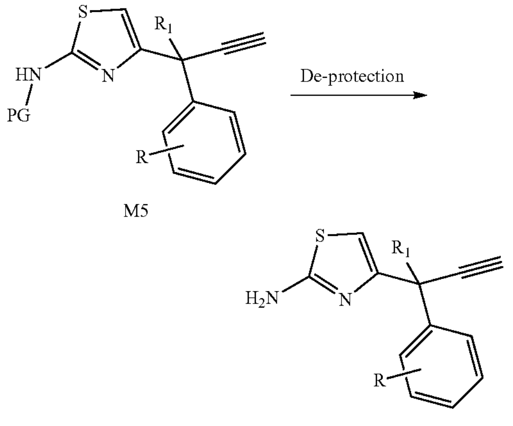

M5 M16

Appropriately substituted compound M7 wherein R was suitable 1-3 groups like halo or $C_1$—C % alkyl, etc, was acetylated with lithium base at lower than −60° C. condition. M9 was obtained by alkyl substitution like $C_1$-$C_6$ alkyl group, of M8 under base condition at 50-70° C. After bromination, M10 was obtained. The cyclization of MIO with thiourea under base condition gave the thiazole intermediate M11. An appropriate protection group was introduced to protect amine. The reduction of ester into alcohol was performed by $LiBH_4$ at 0° C. yielding M13, which was oxidized to the corresponding aldehyde by using Dess-Martin Periodinane (DMP) reagent. The alkynylthiazole amine intermediate M15 was obtained by Seyferth-Gilbert Homologation with treating M14 with 1-diazo-1-dimethoxyphosphoryl-propan-2-one under base condition at RT. The final de-protection gave the intermediate M16.

Example 2

Preparation of 4-(2-(4-chlorophenyl)but-3-In-2-yl) thiazol-2-amine (Intermediate 27)

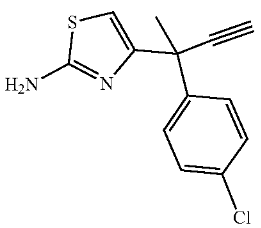 [SMILES: C#CC(C)(C1=CCSC(N)=N1)c1ccc(Cl)cc1]

Step 1. Preparation of compound methyl 2-(4-chlorophenyl)-3-oxobutanoate

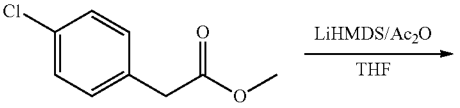

-continued

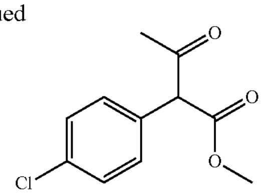

To a solution of compound methyl 2-(4-chlorophenyl) acetate (10 g, 54.2 mmol, 8.77 mL) in THF (80 mL) was added dropwise LiHMDS (IM, 65.0 mL) at −78° C. The mixture was stirred at −78° C. for 20 min. Then acetyl acetate (5.53 g, 54.17 mmol, 5.07 mL) was added at −78° C. The mixture was warmed to 0° C. and stirred for 2 h at 0° C. The mixture was quenched with sat. $NH_4Cl$ (200 mL) and extracted with EA (100 mL×3). The combined organic layers were washed with brine (200 mL), dried over anhydrous $Na_2SO_4$, filtered and concentrated to give a residue. The residue was purified by flash silica gel chromatography (PE:EA=1:0 to 5: 1). The desired compound (7.47 g, yield: 60.9%) was obtained as a pale yellow oil.

MS (ESI) m/z $(M+H)^+$=227.1.

Step 2. Preparation of compound methyl 2-(4-chlorophenyl)-2-methyl-3-oxobutanoate

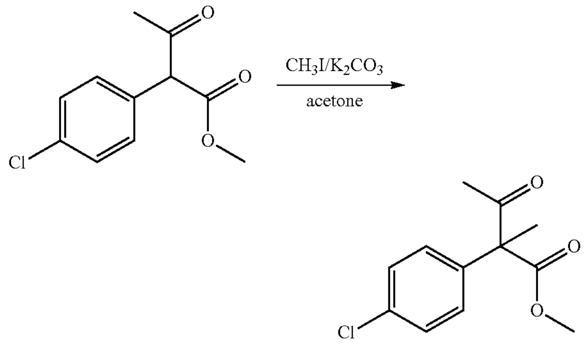

To a solution of compound obtained from step 1 above (7.47 g, 33.0 mmol) and $K_2CO_3$ (22.8 g, 165 mmol) in acetone (60 mL) was added iodomethane (13.10 g, 92.28 mmol, 5.74 mL). The mixture was stirred at 70° C. for 16 h. The mixture was filtered and the filtrate was concentrated to give a residue. The desired compound (7.79 g, yield: 98.2%) was obtained as a pale yellow oil which was used into the next step without further purification.

MS (ESI) m/z $(M+H)^+$=241.1.

Step 3. Preparation of compound methyl 4-bromo-2-(4-chlorophenyl)-2-methyl-3-oxobutanoate

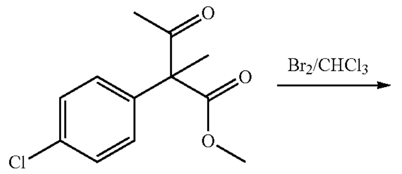

-continued

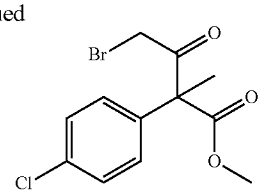

To a solution of compound obtained from step 2 above (7.79 g, 32.4 mmol) in $CHCl_3$ (80 mL) was added $Br_2$ (4.66 g, 29.1 mmol, 1.50 mL). The mixture was stirred at 75° C. for 16 h. The reaction mixture was adjust to PH=6-7 with NaOH (1 N), and then washed with $H_2O$ (100 mL), brined (100 mL), dried over anhydrous $Na_2SO_4$, filtered and concentrated to give a residue. The desired compound (9.91 g, yield: 95.8%) was obtained as a pale brown oil, which was used into the next step without further purification.

MS (ESI) m/z $(M+H)^+$=319.0.

Step 4. Preparation of compound methyl 2-(2-aminothiazol-4-yl)-2-(4-chlorophenyl)propanoate

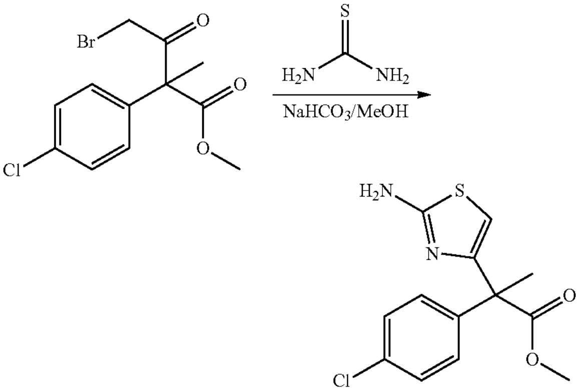

To a solution of compound obtained from step 3 above (9.91 g, 31.0 mmol) and thiourea (2.83 g, 37.2 mmol) in MeOH (60 mL) was added $NaHCO_3$ (3.13 g, 37.2 mmol, 1.45 mL). The mixture was stirred at 50° C. for 1 h. The reaction mixture was concentrated to give a residue. The precipitate was triturated in 120 (100 mL) and collected by filtration. The desired compound (8.49 g, yield: 92.3%) was obtained as a brown solid.

MS (ESI) m/z $(M+H)^+$=297.0.

Step 5. Preparation of compound methyl 2-(2-acetamidothiazol-4-yl)-2-(4-chlorophenyl)propanoate

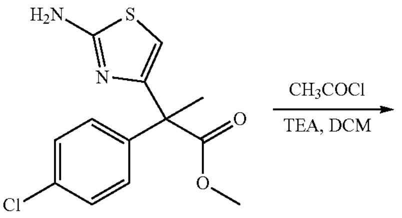

-continued

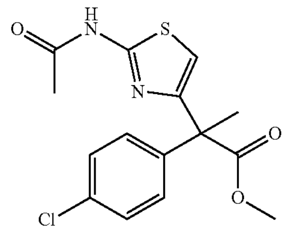

To a solution of compound obtained from step 4 above (3 g, 10.1 mmol) and TEA (1.53 g, 15.2 mmol 2.11 mL) in DCM (60 mL) was added acetyl chloride (794 mg, 10.11 mmol, 721 uL) at 0° C. The mixture was stirred at 25° C. for 1.5 h. The second batch of acetyl chloride (794 mg, 10.1 mmol, 721 uL) and TEA (1.53 g, 15.2 mmol, 211 mL) was added at 0° C., the mixture was stirred at 25° C. for 1 h. The third batch of acetyl chloride (793.5 mg, 10.11 mmol, 721.38 uL) and TEA (1.53 g, 15.16 mmol, 2.11 mL) was added at 0° C., the mixture was stirred at 25° C. for 1.5 h. The reaction mixture was quenched with $H_2O$ (3 mL) and then added anhydrous $Na_2SO_4$, filtered and concentrated to give a residue. The residue was purified by flash silica gel chromatography (PE:EA=1:0 to 2:1). The desired compound (1.4 g, yield: 32.6/$_0$) was obtained as a pale yellow solid.

MS (ESI) m/z $(M+H)^+$=339.1.

Step 6. Preparation of compound N-(4-(2-(4-chlorophenyl)-1-hydroxypropan-2-yl)thiazol-2-yl)acetamide

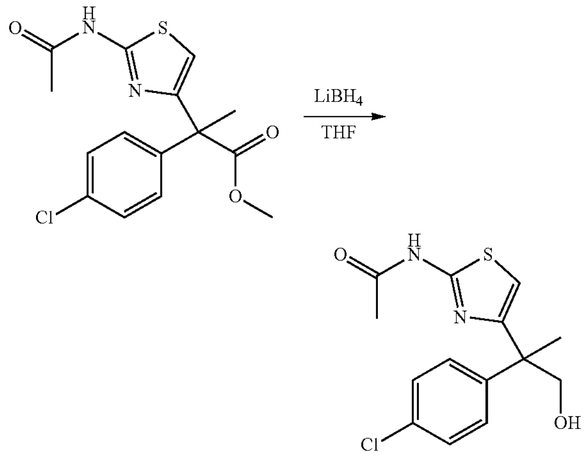

To a solution of compound obtained from step 5 above (1.4 g, 4.13 mmol) in THF (50 mL) was added partly $LiBH_4$ (450 mg, 20.66 mmol). The mixture was stirred at 25° C. for 16 h. The reaction mixture was quenched with sat. $NH_4Cl$ (40 mL) and then extracted with EA (30 mL×3), the combined organic layer was washed with brine (60 mL), dried over anhydrous $Na_2SO_4$, filtered and concentrated to give a residue. The residue was purified by flash silica gel chromatography (PE:EA=1:0 to 2: 3). The desired compound (970 mg, yield: 73.4%) was obtained as a pale yellow solid.

MS (ESI) m/z $(M+H)^+$=311 0.1.

Step 7. Preparation of compound N-(4-(2-(4-chlorophenyl)-1-oxopropan-2-yl)thiazol-2-yl)acetamide

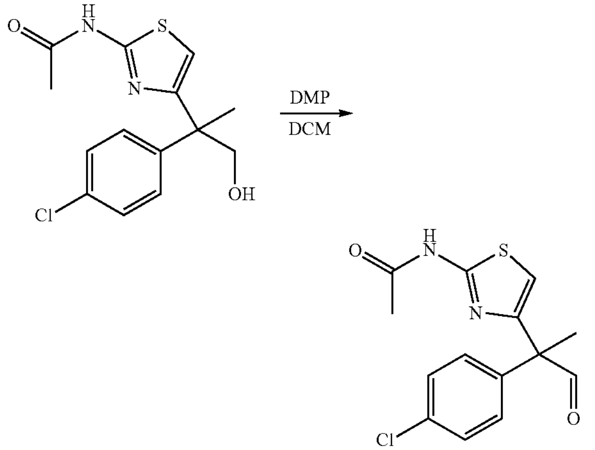

To a solution of compound obtained from step 6 above (970 mg, 3.12 mmol) in DCM (30 mL) was added partly DMP (1.72 g, 4.06 mmol) in DCM (20 mL). The mixture was stirred at 25° C. for 2 h. DMP (1.72 g, 4.06 mmol) in DCM (20 mL) was added and the mixture was stirred at 25° C. for 1 h. DMP (1.06 g, 2.50 mmol) in DCM (20 mL) was added and the mixture was stirred at 25° C. for 2 h. The reaction mixture was diluted with DCM (40 mL), quenched with sat. $Na_2S_2O_3$/sat. $NaHCO_3$(1/1, 200 mL), the organic layer was separated and the aqueous layer was extracted with DCM (60 mL), the combined organic layers were washed with sat. $Na_2S_2O_3$/sat. $NaHCO_3$ (1/1, 100 mL), water (200 mL×2), brine (200 ml×2), dried over anhydrous $Na_2SO_4$, filtered and concentrated to give a residue. The desired compound (1.03 g, crude) was obtained as a yellow solid which was used into the next step without further purification.

Step 8. Preparation of compound N-(4-(2-(4-chlorophenyl)but-3-v-2-yl)thiazol-2-yl)acetamide

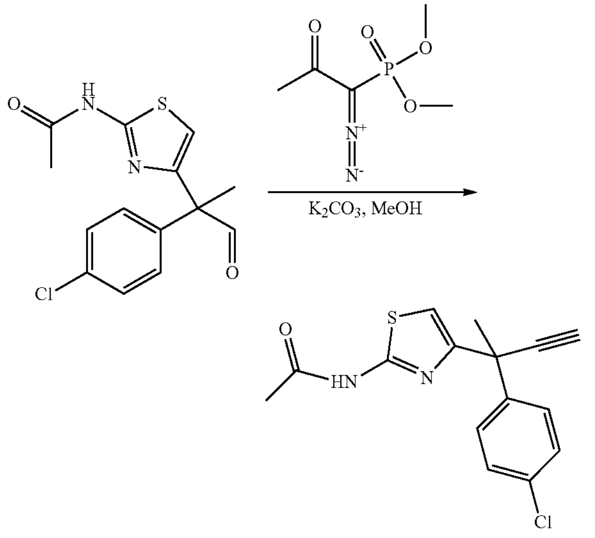

To a solution of compound obtained from step 7 above (1.03 g, 3.34 mmol) and 1-diazo-1-dimethoxyphosphoryl-propan-2-one (961 mg, 5.00 mmol) in MeOH (40 mL) was added $K_2CO_3$ (922 mg, 6.67 mmol). The mixture was stirred at 25° C. for 12 h. The reaction mixture was concentrated to give a residue. The residue was purified by flash silica gel chromatography (PE:EA=1:0 to 1: 1). The residue was purified by prep-HPLC (column: Venusil ASB Phenyl 150×30 mm×5 um; mobile phase: [water (0.05% HCl)-ACN]; B %:55%-85%, 9 mi). The desired compound (219 mg, yield: 21.54%) was obtained as a white solid.

1H NMR (400 MHz, $CDC_3$) δ 9.98 (br s, 1H), 7.45 (d, J=8.5 Hz, 2H), 7.30 (d, J=8.5 Hz, 2H) 6.88 (s, 1H), 2.63 (s, 1H), 2.25 (s, 3H), 1.99 (s, 3H). MS (ESI) m/z $(M+H)^+$=305.1.

Step 9. Preparation of compound 4-(2-(4-chloro-phenyl)but-3-yn-2-yl)thiazol-2-amine

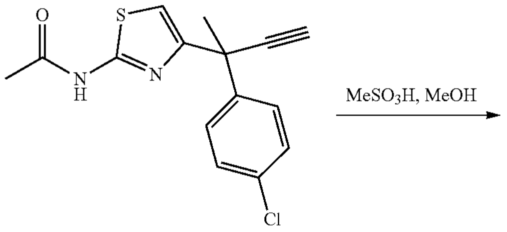

-continued

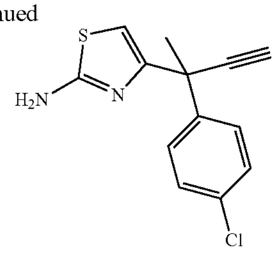

To a solution of compound obtained from step 8 above (180 mg, 591 umol) in MeOH (10 mL) was added methanesulfonic acid (284 mg, 2.95 mmol, 210 μL). The mixture was stirred at 80° C. for 16 h. The reaction mixture was adjusted pH=7 with solid $NaHCO_3$ and concentrated to give a residue. The residue was purified by flash silica gel chromatography (PE:EA=1:0 to 2:1). The desired compound (137 mg, yield: 88.3%) was obtained as a pale yellow solid.

$^1$H NMR (400 MHz, $CDCl_3$) δ 7.39-7.32 (m, 2H), 7.20-7.16 (m, 2H), 6.35 (s, 1H), 4.90 (br s, 2H), 2.46 (s, 1H), 1.82 (s, 3H). MS (ESI) m/z $(M+H)^+$=263.0.

The following examples were synthesized analogous to the procedure of example 2 (intermediate 27) using the appropriate starting materials and thiourea:

TABLE 2

| Com. ID | Structure | Name | HNMR | LCMS |
|---|---|---|---|---|
| Intermediate 28 | 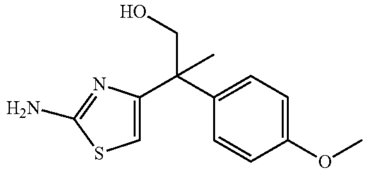 [SMILES: COc1ccc(C(C)(CO)c2csc(N)n2)cc1] | 2-(2-aminothiazol-4-yl)-2-(4-methoxyphenyl)propan-1-ol | | 265.1 |
| Intermediate 29 | 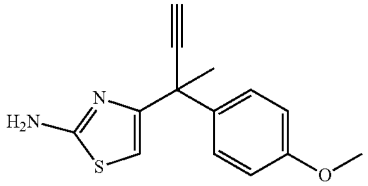 [SMILES: C#CC(C)(c1ccc(OC)cc1)c1csc(N)n1] | 4-(2-(4-methoxyphenyl)but-3-yn-2-yl)thiazol-2-amine | | 259.1 |
| Intermediate 30 | 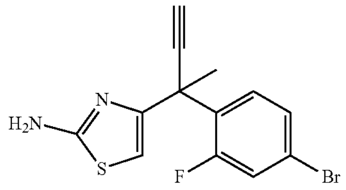 [SMILES: C#CC(C)(c1csc(N)n1)c1ccc(Br)cc1F] | 4-(2-(4-bromo-2-fluorophenyl)but-3-yn-2-yl)thiazol-2-amine | 1H NMR (400 MHz, DMSO-d6) δ 7.52-7.46 (m, 1H), 7.45-7.39 (m, 2H), 6.93 (s, 2H), 6.42 (s, 1H), 3.44 (s, 1H), 1.84 (s, 3H). 19F NMR (376 MHz, DMSO-d6) δ −107.657 | 324.9 |
| Intermediate 31 | 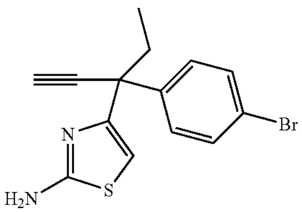 [SMILES: C#CC(CC)(c1ccc(Br)cc1)c1csc(N)n1] | 4-(3-(4-bromophenyl)pent-1-yn-3-yl)thiazol-2-amine | 1H NMR (400MHz, DMSO-d) δ = 7.60-7.58 (m, 2 H), 7.43-7.39 (m, 2 H), 6.74 (s, 1 H), 3.77 (s, 1 H), 2.32-2.23 (m, 1 H), 2.18-2.11 (m, 1 H), 0.83 (t, J = 7.2 Hz, 3 H) | 321.0 |

TABLE 2-continued

| Com. ID | Structure | Name | HNMR | LCMS |
|---|---|---|---|---|
| Intermediate 32 | 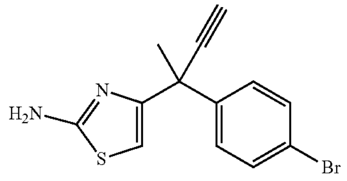 [SMILES: C#CC(C)(c1ccc(Br)cc1)c1csc(N)n1] | 4-(2-(4-bromophenyl)but-3-yn-2-yl)thiazol-2-amine | | 306.9 |

Example 3

4-(2-(4-bromophenyl-1-methoxypropan-2-yl) thiazol-2-amine (Intermediate 33)

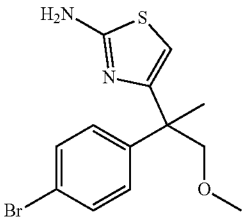 [SMILES: COCC(C)(c1ccc(Br)cc1)c1csc(N)n1]

Step 1. Preparation of compound N-(4-(2-(4-bromophenyl)-1-methoxypropan-2-yl)thiazol-2-yl)acetamide

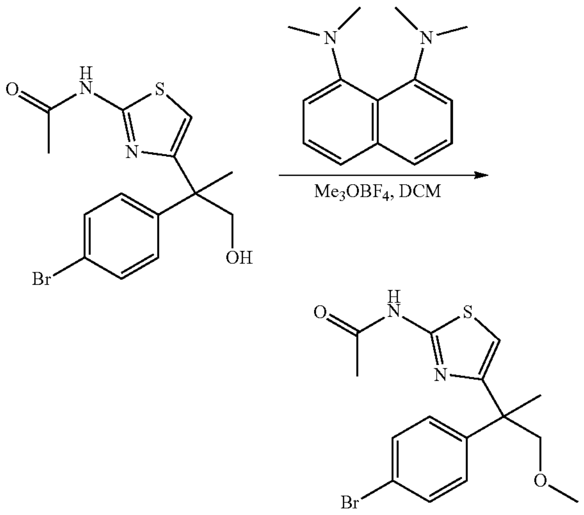

To a solution of N-(4-(2-(4-bromophenyl)-1-hydroxypropan-2-yl)thiazol-2-yl) acetamide (200 mg, 563 μmol, synthesized in the similar method described in intermediate 46) and N1,N1,N8,N8-tetramethylnaphthalene-1,8-diamine (603 mg, 2.81 mmol) in DCM (10 mL) was added trimethyloxonium; tetrafluoroborate (416 mg, 2.8 mmol) at 0° C. The mixture was stirred at 25° C. for 16 h. The reaction mixture was diluted with DCM (10 mL), quenched with $NH_3H_2O$ (10 mL), washed with $H_2O$ (30 mL), HCl (1 N, 20 mL), sat. $NaHCO_3$ (20 mL) and brine (40 mL), dried over anhydrous $Na_2SO_4$, filtered and concentrated to give a residue. The residue was purified by flash silica gel chromatography (PE:EA=1:0 to 1:1). The desired compound (41 mg, yield: 19.72%) was obtained as a white solid.

$^1$H NMR (400 MHz, $CDCl_3$) δ 8.69 (br s, 1H), 7.39 (d, J=8.5 Hz, 2H), 7.10 (d, J=8.5 Hz, 2H), 6.69 (s, 1H), 3.80 (s, 2H), 3.34 (s, 3H), 2.20 (s, 3H), 1.68 (s, 3H). MS (EST) m/z $(M+H)^+$=371.0.

Step 2. Preparation of compound 4-(2-(4-bromophenyl)-1-methoxypropan-2-yl) thiazol-2-amine

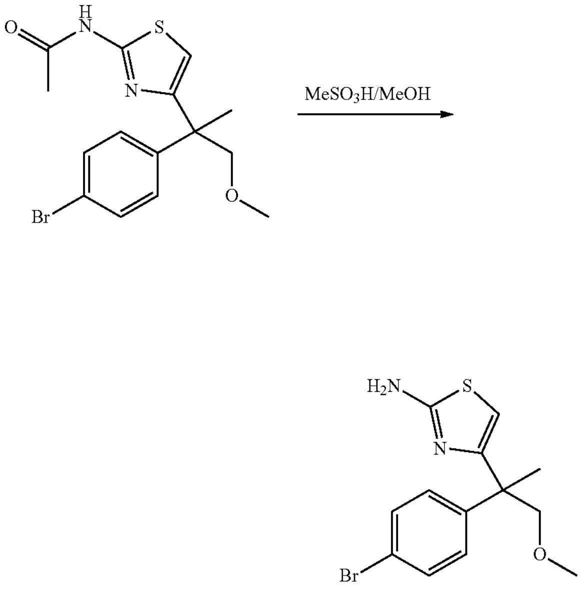

The synthesis is similar as described in intermediate 44. The desired compound (20 mg, yield: 90.3%) was obtained as a white solid.

$^1$H NMR (400 MHz, $CDCl_3$) δ 7.42-7.36 (m, 2H), 7.18-7.13 (m, 2H), 6.22 (s, 1H), 483 (br s, 2H), 3.84-3.73 (m, 2H), 3.34 (s, 3H), 1.65 (s, 3H). MS (ESI) m/z $(M+H)^+$=327.0.

The following intermediates were synthesized analogous to the procedure of example 3 (intermediate 33) using the appropriate starting materials and thiourea:

TABLE 3

| Com. ID | Structure | Name | HNMR | LCMS |
|---|---|---|---|---|
| Intermediate 34 | 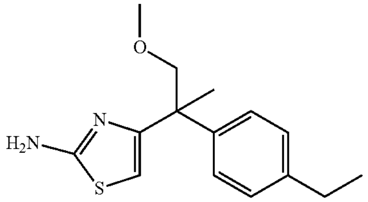 [SMILES: CCc1ccc(C(C)(COC)c2csc(N)n2)cc1] | 4-(1-methoxy-2-(4-methoxyphenyl)propan-2-yl)thiazol-2-amine | | 279.1 |
| Intermediate 35 | 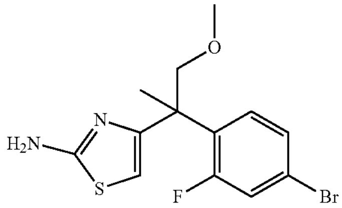 [SMILES: COCC(C)(c1csc(N)n1)c1ccc(Br)cc1F] | 4-(2-(4-bromo-2-fluorophenyl)-1-methoxypropan-2-yl)thiazol-2-amine | | 345.0 |
| Intermediate 36 | 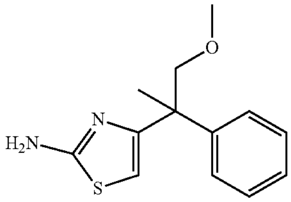 [SMILES: COCC(C)(c1ccccc1)c1csc(N)n1] | 4-(1-methoxy-2-phenylpropan-2-yl)thiazol-2-amine | | 248.1 |
| Intermediate 37 | 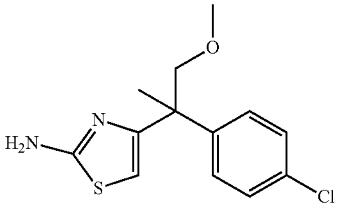 [SMILES: COCC(C)(c1ccc(Cl)cc1)c1csc(N)n1] | 4-(2-(4-chlorophenyl)-1-methoxypropan-2-yl)thiazol-2-amine | | 282.1 |

Example 4

1-(2-aminothiazol-4-yl)-1-(4-bromophenyl)ethan-1-ol (Intermediate 38)

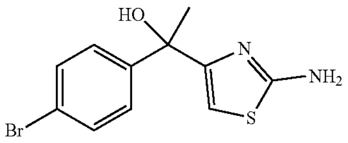 [SMILES: CC(O)(c1ccc(Br)cc1)c1csc(N)n1]

Step 1. Preparation of compound 1-(4-bromophenyl)propane-1,2-dione

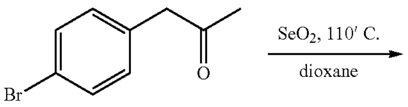

-continued

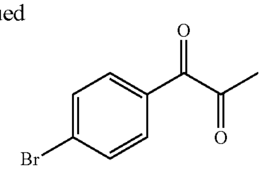

To a solution of compound 1-(4-bromophenyl)propan-2-one (2.0 g, 9.4 mmol, 1.0 eq) in dioxane (20 mL) was added $SeO_2$ (3.12 g, 28.1 mmol, 3.0 eq). The mixture was stirred at 110° C. for 4 h. After cooling down, the reaction mixture was concentrated to give a residue. The residue was purified by flash silica gel chromatography (PE:EA=96%:4%). The desired compound (960 mg, yield: 45%) was obtained as a yellow oil.

Step 2. Preparation of compound 3-bromo-1-(4-bromophenyl)propane-1,2-dione

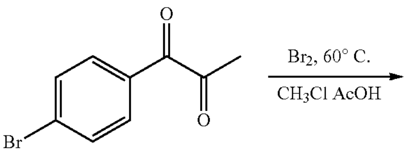

-continued

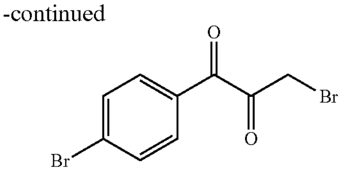

To a solution of compound obtained from step 1 above (960 mg, 4.23 mmol, 1.0 eq) in $CH_3Cl$ (20 mL) was added $Br_2$ (1.05 g, 6.34 mmol, 1.5 eq) and AcOH (3 drops). The mixture was stirred at 60° C. for 16 h. The reaction mixture was quenched by sat.$Na_2SO_3$ (aq) (20 mL), extracted with DCM (20 mL×2) and washed with brine (15 mL), then dried over $Na_2SO_4$, filtered and evaporated to dryness. The residue was purified by flash silica gel chromatography (PE:EA:=94%:6%). The desired compound (800 mug, yield: 740) was obtained as a yellow oil.

Step 3. Preparation of compound (2-aminothiazol-4-yl)(4-bromophenyl)methanone

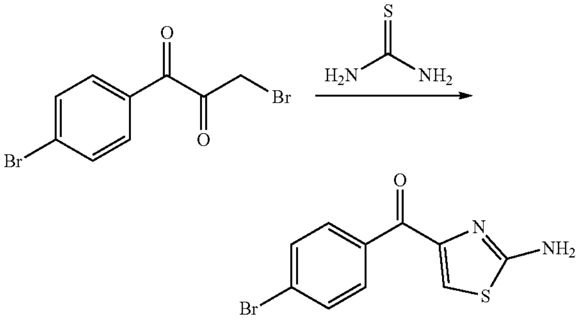

To a solution of compound obtained from step 2 above (800 mg, 2.62 mmol, 1.0 eq) in MeOH (8 mL) was added thiourea (200 mg, 2.62 mmol, 1.0 eq) and $NaHCO_3$. The mixture was stirred at 50° C. for 1.5 h. The mixture was concentrated under reduced pressure, extracted with EA (15 mL×2), the combined organic layers were washed with brine (10 mL×2), dried over $Na_2SO_4$, filtered and concentrated to give a residue, which was purified by flash silica gel chromatography (PE:EA=3:1) to get the desired group (680 mg, yield: 90%).

$^1$H NMR (400 MHz, $CD_3OD$) δ 7.95 (d, J=8.5 Hz, 2H), 7.85 (s, 1H), 764 (d, J=8.6 Hz, 2H), 7.26 (d, J=8.6 Hz, 2H), 6.99 (d, J=8.6 Hz, 2H), 4.35 (s, 2H), 3.36 (s, 4H), 3.34 (s, 4H).

Step 4 Preparation of compound 1-(2-aminothiazol-4-yl)-1-(4-bromophenyl)ethan-1-ol

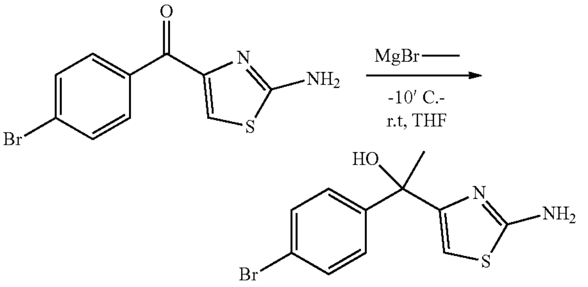

The solution of compound (2-aminothiazol-4-yl)(4-bromophenyl)methanone (200 mg, 0.71 mmol, 1.0 eq) in dry THF (4 mL) was cooled to 0° C., and was added $CH_3MgBr$ (3 M in THE, 1.6 mL, 4.9 mmol, 7.0 eq) dropwise. The mixture was stirred at RT overnight. The reaction mixture was quenched with sat. $NH_4Cl$ (200 mL). The mixture was extracted with EA (20 mL×2), the combined organic layers were washed with brine (110 mL×2), dried over $Na_2SO_4$, filtered and concentrated to give a residue. The resulting residue was purified by Prep-TLC to give the desired compound (40 mg, yield: 20%).

$^1$H NMR (400 MHz, DMSO) δ 7.45-7.38 (m, 2H), 7.22 (t, J=7.5 Hz, 2H), 7.12 (t, J:=7.3 Hz, 1H), 6.77 (s, 2H), 6.30 (s, 1H), 5.37 (s, 1H), 1.67 (s, 3H).

MS (ESI) m/z (M+H)+=221.0

General Method I

To a solution of thiazole amines (1 eq) and in appropriate organic solvent like DMF was added NaH (1.2-1.5 eqiv.) at 0-10° C., the resulting mixture was stirred for 5-30 mins. The mixture was added activated amine by CDI and stirred for 4-16 hours. Once the reaction was completed, the resulting suspension was diluted with organic solvent and washed with brine and then dried. After filtration and evaporation, the resulting residue was purified by trituration/Prep-TLC/chromatography/Prep-HPLC to give the product.

Example 5

Preparation of tert-butyl 4-(4-((3-(4-(2-(4-chloro-3-fluorophenyl)propan-2-yl)thiazol-2-yl)ureido)methyl)phenyl)piperazine-1-carboxylate

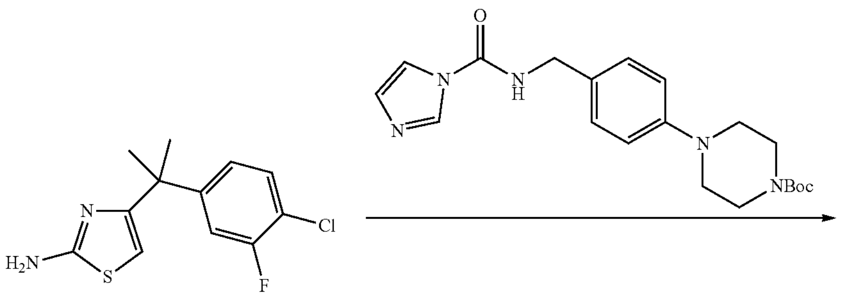

-continued

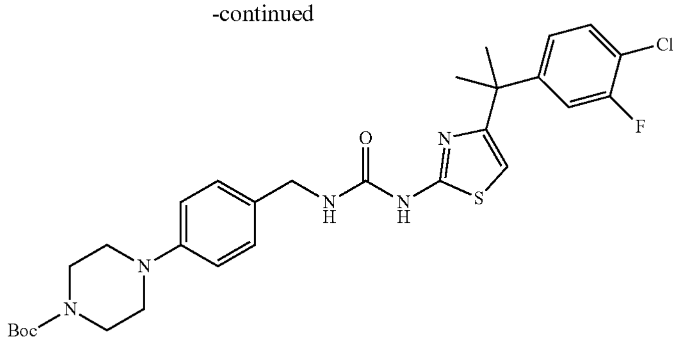

To a solution of 4-(2-(4-chloro-3-fluorophenyl)propan-2-yl)thiazol-2-amine (40 mg, 0.15 mmol, 1 eq) and in DMF (5 mL) was added NaH (7 mg, 0.3 mmol, 2 eq) at 10° C. The resulting mixture was stirred for 5 min. The mixture was added tert-butyl 4-(4-((1H-imidazole-1-carboxamido) methyl)phenyl)piperazine-1-carboxylate (58 mg, 0.15 mmol, 1 eq), and stirred overnight. The reaction was quenched with water, extracted with EA and combined organic layers were washed with brine then dried ($Na_2SO_4$), filtered and evaporated to dryness. The resulting residue was purified by Prep-TLC (PE:EA=3:1) to give the title compound 35 mg (0.06 mmol) with the yield 40%. MS (ESI) m/z $(M+H)^+$=588.2

General Method II

To a solution of amine fragment (1 eq) and pyridine in appropriate solvent like dry DCM was added phenyl carbonochloridate (2 eq) below 20° C. slowly. The mixture was stirred at RT for 4-6 h. Once the reaction was completed, the resulting reaction was diluted with organic solvent and washed with brine and then dried. After filtration and evaporation, the resulting residue was purified by trituration/Prep-TLC/chromatography/Prep-HPLC to give the product.

Example 6

Preparation of tert-butyl 4-(5-((3-(4-(2-(4-bromophenyl)propan-2-yl)thiazol-2-yl) ureido)methyl) pyrimidin-2-yl)piperazine-1-carboxylate

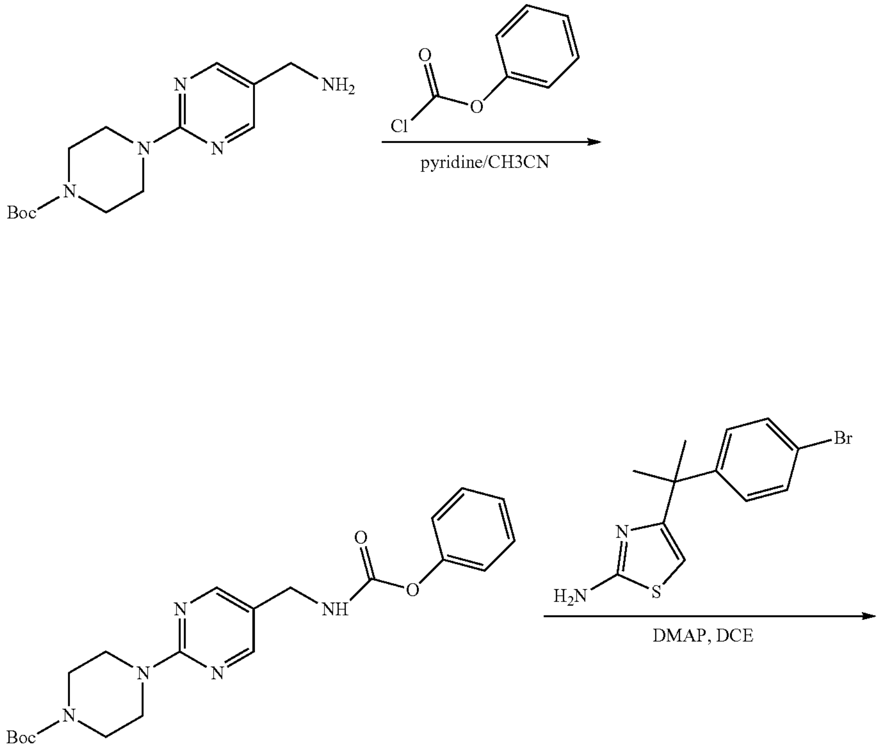

-continued

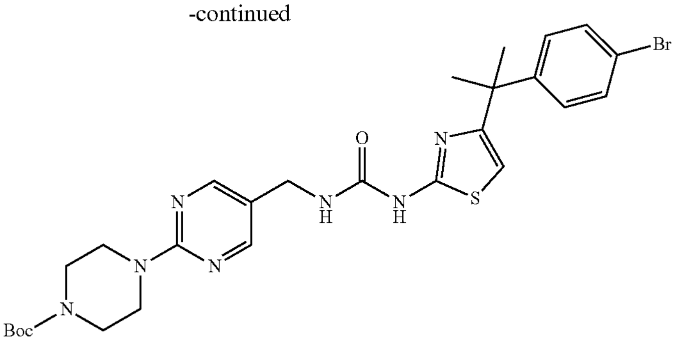

Phenyl carbonochloridate (336 mg, 2.2 mmol, 269.0 μL) was added to the mixture of tert-butyl 4-(5-(aminomethyl) pyrimidin-2-yl)piperazine-1-carboxylate (600 mg, 2.1 mmol), pyridine (194 mg, 2.5 mmol, 198 L) in $CH_3CN$ (15 mL) at −20° C. After addition, the mixture was allowed to warm to 25° C. and stirred at 25° C. for 0.25 h. The solvent was removed under vacuum. The residue was triturated with ice water (15 mL). White solid was precipitated from the mixture. The mixture was filtered and the solid was collected, dried under vacuum. Tert-butyl 4-(5-(((phenoxycarbonyl)amino)methyl)pyrimidin-2-yl)piperazine-1-carboxylate (420 mg, yield: 38.2%) was obtained as a white solid. MS (ESI) m/z $(M+H)^+$=414.2.

To the mixture of tert-butyl 4-(5-(((phenoxycarbonyl) amino)methyl)pyrimidin-2-yl) piperazine-1-carboxylate (139 mg, 336 μmol) and 4-(2-(4-bromophenyl) propan-2-yl)thiazol-2-amine (50 mg, 168 μmol) in DCE (10 mL) was added DMAP (41.0 mg, 337.0 μmol, 2 eq). The mixture was stirred at 85-C for 16 h. The mixture was concentrated under vacuum. The residue was purified by prep-TLC ($SiO_2$, DCM:MeOH=13:1) and further purified by prep-TLC ($SiO_2$, DCM:MeOH=12:1). The desired compound (60 mg, yield: 57.7%) was obtained as a white solid.

$^1H$ NMR (400 MHz, MeOD) δ 8.32 (s, 2H), 7.40-7.38 (m, 2H), 7.17-7.14 (m, 2H), 6.71 (s, 1H), 4.23 (s, 2H), 3.82-3.80 (m, 4H), 3.50 (br, 4H), 3.32 (s, 6H). MS (ESI) m/z $(M+H)^+$=616.2.

General Method III

To a solution of substituted thiazol-2-amine and hunig base or pyridine in appropriate solvent like DCM or $CH_3CN$, or DCM/water was added phenyl carbonochloridate (2 eq) at 0° C.-RT slowly. The mixture was stirred 2-4 h at RT and the resulting reaction was diluted with organic solvent and washed with brine and then dried. After filtration and evaporation, the resulting residue was purified by chromatography to give the substituted thiazol-2-amine carbamate.

The mixture of the substituted thiazol-2-amine carbamate, amine and DMAP in appropriate solvent like THF was heated to reflux for 1-2 h. After cooling down, the resulting reaction evaporated and diluted with appropriate organic solvent like EA and washed with brine and then dried. After filtration and evaporation, the resulting residue was purified by trituration/Prep-TLC/chromatography/Prep-HPLC to give the product.

Example 7

Preparation of 1-(4-(4-((tert-butyldimethylsilyl)oxy) piperidin-1-yl)benzyl)-3-(4-(2-(4-methoxyphenyl) propan-2-yl)thiazol-2-yl)urea

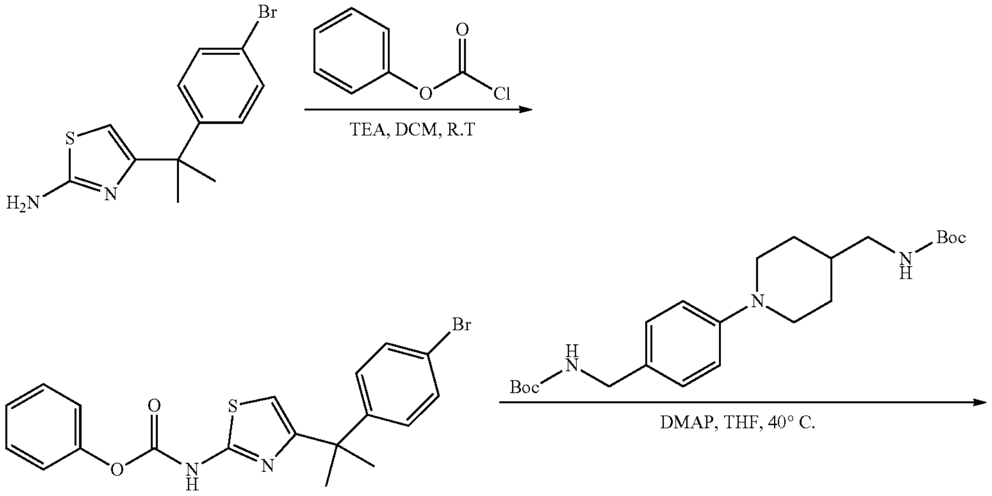

-continued

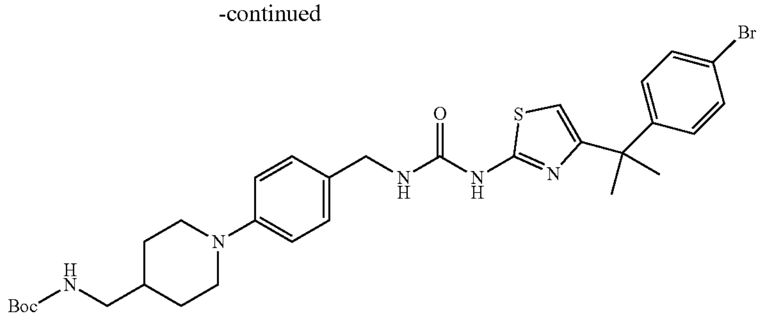

To a solution of 4-(2-(4-bromophenyl)propan-2-yl)thiazol-2-amine (100 mg, 0.34 mmol, 1 eq) and triethylamine in dry DCM (5 mL) was added phenyl carbonochloridate (106 mg, 0.68 mmol, 2 eq) at 0° C.-RT slowly and the mixture was stirred for 4 h at RT. Quenched by brine, extracted with EA, the combined organic layers were washed with brine, dried over $Na_2SO_4$, filtered and concentrated to give a residue, which was purified by column chromatography on a silica gel to afford phenyl (4-(2-(4-bromophenyl)propan-2-yl)thiazol-2-yl)carbamate (112 mg).

The mixture of phenyl (4-(2-(4-bromophenyl)propan-2-yl)thiazol-2-yl)carbamate (112 mg), 0.27 mmol, 1 eq), tert-butyl ((1-(4-(aminomethyl)phenyl)piperidin-4-yl)methyl) carbamate (24 mg, 0.27 mmol, 1 eq) and DMAP (52 mg, 0.4 mmol, 1.5 eq) in THF (5 mL) was heated to reflux for 1 hour. Cooled down to RT, the reaction mixture was participated between $H_2O$ (15 mL) and EA (10 mL×2), the combined organic layers were washed with brine (10 mL), dried over $Na_2SO_4$, filtered and concentrated. The residue was purified by column chromatography on a silica gel to afford tert-butyl ((1-(4-((3-(4-(2-(4-bromophenyl)propan-2-yl)thiazol-2-yl)ureido)methyl)phenyl)piperidin-4-yl)methyl)carbamate (42 mg) as a white powder.

General Method IV

The mixture of amine and isocyanate-alkanes in THF was stirred at RT overnight. Once the reaction was completed, the resulting suspension was diluted with organic solvent and washed with brine and then dried. After filtration and evaporation, the resulting residue was purified by trituration/Prep-TLC/Prep-HPLC to give the product.

Example 8

Preparation of 1-ethyl-3-(4-(2-(4-methoxyphenyl)propan-2-yl)thiazol-2-yl)urea

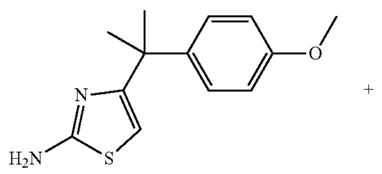

-continued

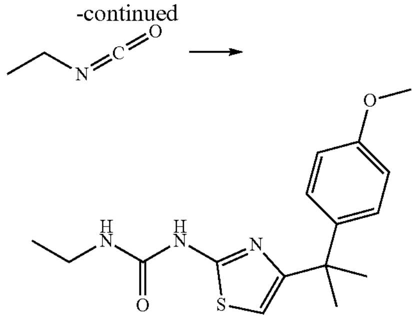

To a solution of 4-(2-(4-methoxyphenyl)propan-2-yl)thiophen-2-amine (200 mg, 0.67 mmol) in THF (5 mL) was added isocyanatoethane (48 mg, 0.67 mmol) and TEA (136 mg, 1.34 mmol). The resulting mixture was stirred at RT overnight. The mixture was concentrated at 45° C. with reduce pressure to remove THF. The resulting suspension was diluted with EtOAc and washed with brine and then dried ($Na_2SO_4$), filtered and evaporated to dryness. The resulting residue was purified by Prep-TLC to give the desired compound (164 mg, yield: 65.4%) as a pale yellow solid. MS (ESI) m/z $(M+H)^+$=367,1.

De-BOC General Method

The Boc compounds were dissolved in HCl/MeOH, the reaction mixture was stirred for 1-2 h at RT. The solution was concentrated to dryness to give the final compound.

Example 9

Preparation of compound 1-(4-(2-(4-bromophenyl)propan-2-yl)thiazol-2-yl)-3-((6-(piperazin-1-yl)pyridin-3-yl)methyl)urea hydrochloride

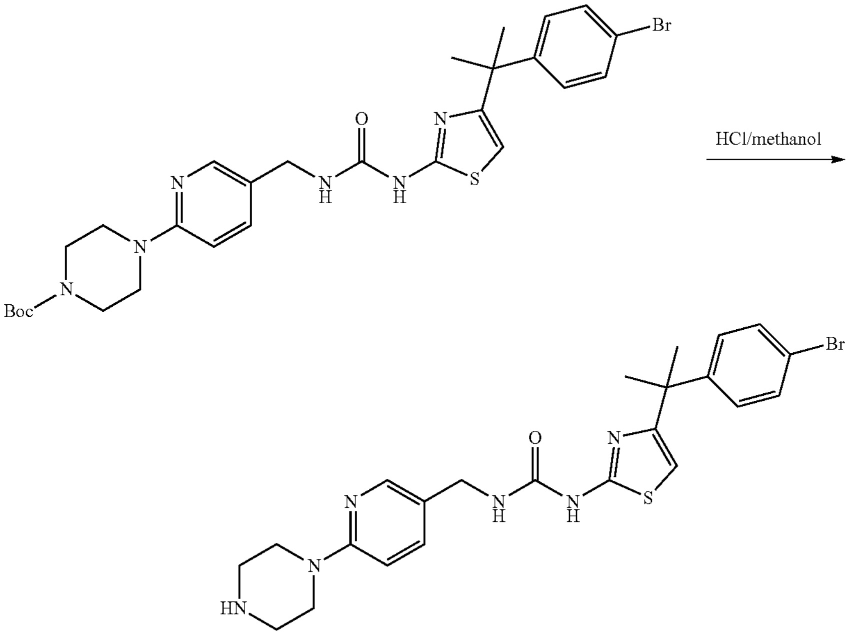

To a solution of tert-butyl 4-(5-((3-(4-(2-(4-bromophenyl)propan-2-yl)thiazol-2-yl)ureido)methyl)pyridin-2-yl)piperazine-1-carboxylate (70.0 mg, 113.71 μmol) in MeOH (2 mL) was added HCl/MeOH (4 M, 2 mL). The mixture was stirred at 25° C. for 1 hr. The mixture was concentrated in vacuum. The desired compound (47.0 mg, yield: 74.1%, HCl) was obtained as a white solid.

$^1$H NMR (400 MHz, DMSO-d %) δ 10.90 (br s, 1H), 9.66 (br s, 2H), 8.05-7.92 (i, 2H), 7.48-7.28 (m, 4H), 7.21-7.10 (m, 2H), 6.75 (s, 1H), 4.30-4.20 (m, 2H), 404-3.92 (m, 4H), 3.24 (br s, 4H), 1.57 (s, 61H). MS (ESI) m/z $(M+H)^+$=517.2.

The following examples were synthesized analogous to the procedure of example 5, 6, 7, 8 and 9 using the appropriate intermediates and the corresponding fragments:

TABLE 4
| Com. ID | Structure | Name | HNMR | LCMS | Kinase assay IC50 nM. | NFkB assay IC50 μM |
|---|---|---|---|---|---|---|
| A001 | 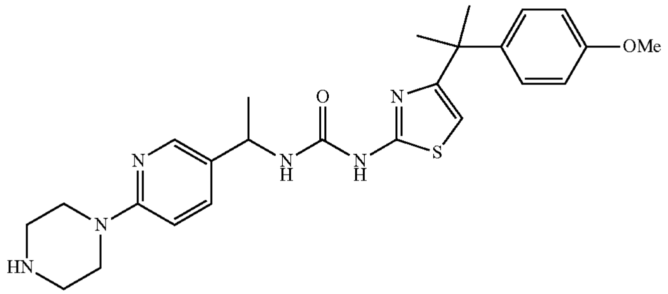 [SMILES: COc1ccc(C(C)(C)c2csc(NC(=O)NC(C)c3ccc(N4CCNCC4)nc3)n2)cc1] | 1-(4-(2-(4-methoxyphenyl) propan-2-yl)thiazol-2-yl)-3-(1-(6-(piperazin-1-yl)pyridin-3-yl)ethyl)urea | | $[M + H]^+ = 481$ | 58 | 0.67 |
| A002 | 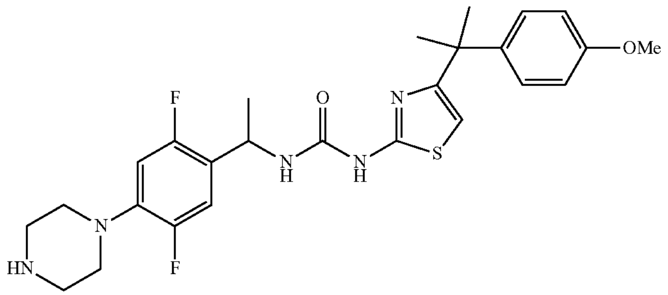 [SMILES: COc1ccc(C(C)(C)c2csc(NC(=O)NC(C)c3cc(F)c(N4CCNCC4)cc3F)n2)cc1] | 1-(1-(2,5-difluoro-4-(piperazin-1-yl)phenyl)ethyl)-3-(4-(2-(4-methoxyphenyl) propan-2-yl)thiazol-2-yl)urea | | $[M + H]^+ = 516$ | 63 | 0.70 |
| A003 | 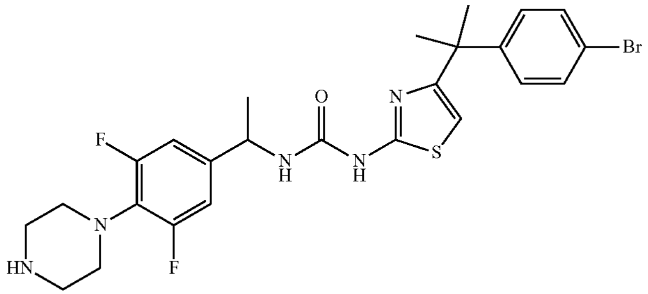 [SMILES: CC(NC(=O)Nc1nc(C(C)(C)c2ccc(Br)cc2)cs1)c1cc(F)c(N2CCNCC2)c(F)c1] | 1-(4-(2-(4-bromophenyl)propan-2-yl)thiazol-2-yl)-3-(1-(3,5-difluoro-4-(piperazin-1-yl)phenyl)ethyl)urea | | $[M + H]^+ = 564$ | 45 | 1.20 |

TABLE 4-continued
| Com. ID | Structure | Name | HNMR | LCMS | Kinase assay IC50 nM. | NFkB assay IC50 μM |
|---|---|---|---|---|---|---|
| A004 | 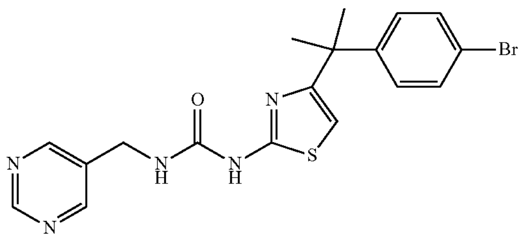 [SMILES: CC(C)(c1ccc(Br)cc1)c1csc(NC(=O)NCc2cncnc2)n1] | 1-(4-(2-(4-bromophenyl)propan-2-yl) thiazol-2-yl)-3-(pyrimidin-5-ylmethyl)urea | | $[M + H]^+ = 432$ | 240 | 2.03 |
| A005 | 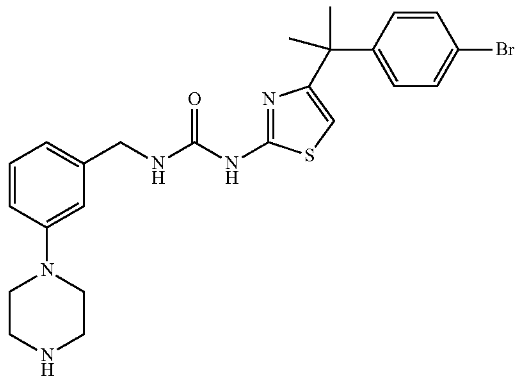 [SMILES: CC(C)(c1ccc(Br)cc1)c1csc(NC(=O)NCc2cccc(N3CCNCC3)c2)n1] | 1-(4-(2-(4-bromophenyl)propan-2-yl)thiazol-2-yl)-3-(3-(piperazin-1-yl)benzyl)urea | | $[M + H]^+ = 514$ | 97 | 3.15 |

TABLE 4-continued
| Com. ID | Structure | Name | HNMR | LCMS | Kinase assay IC50 nM. | NFkB assay IC50 µM |
|---|---|---|---|---|---|---|
| A006 | 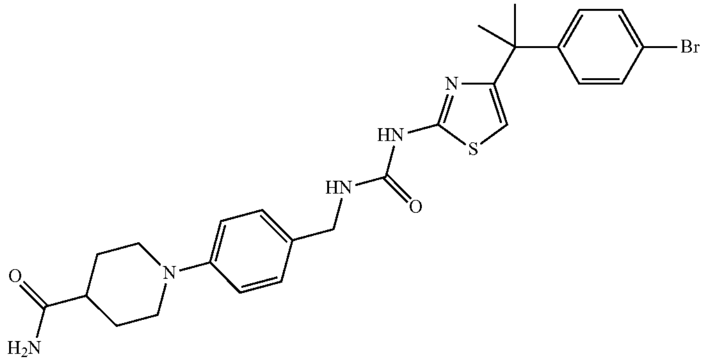 [SMILES: CC(C)(c1ccc(Br)cc1)c1csc(NC(=O)NCc2ccc(N3CCC(C(N)=O)CC3)cc2)n1] | 1-(4-((3-(4-(2-(4-bromophenyl)propan-2-yl)thiazol-2-yl)ureido)methyl) phenyl)piperidine-4-carboxamide | | $[M + H]^+ = 556$ | 104 | |
| A007 | 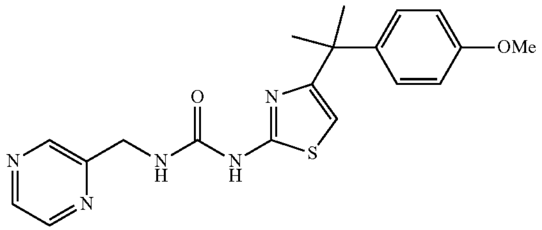 [SMILES: COc1ccc(C(C)(C)c2csc(NC(=O)NCc3cnccn3)n2)cc1] | 1-(4-(2-(4-methoxyphenyl) propan-2-yl)thiazol-2-yl)-3-(pyrazin-2-ylmethyl)urea | | $[M + H]^+ = 384$ | 91 | 5.58 |
| A008 | 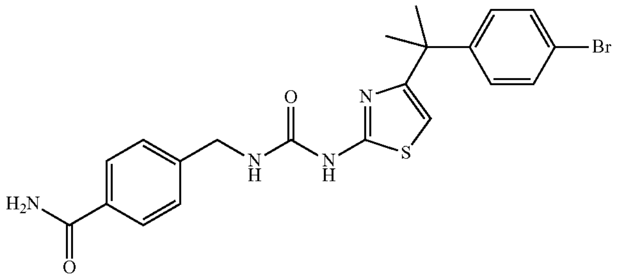 [SMILES: CC(C)(c1ccc(Br)cc1)c1csc(NC(=O)NCc2ccc(C(N)=O)cc2)n1] | 4-((3-(4-(2-(4-bromophenyl)propan-2-yl)thiazol-2-yl)ureido)methyl) benzamide | | $[M + H]^+ = 473$ | 8 | 0.70 |

TABLE 4-continued
| Com. ID | Structure | Name | HNMR | LCMS | Kinase assay IC50 nM. | NFkB assay IC50 µM |
|---|---|---|---|---|---|---|
| A009 | 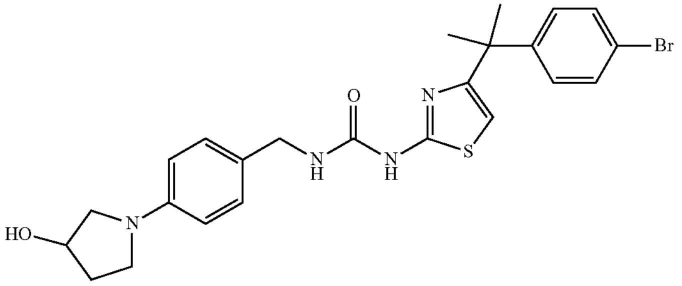 [SMILES: CC(C)(c1ccc(Br)cc1)c1csc(NC(=O)NCc2ccc(N3CCC(O)C3)cc2)n1] | 1-(4-(2-(4-bromophenyl)propan-2-yl)thiazol-2-yl)-3-(4-(3-hydroxypyrrolidin-1-yl)benzyl)urea | | $[M + H]^+ = 515$ | 154 | 3.15 |
| A010 | 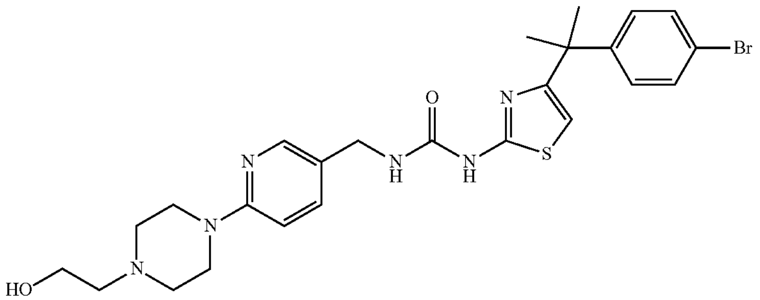 [SMILES: CC(C)(c1ccc(Br)cc1)c1csc(NC(=O)NCc2ccc(N3CCN(CCO)CC3)nc2)n1] | 1-(4-(2-(4-bromophenyl)propan-2-yl)thiazol-2-yl)-3-((6-(4-(2-hydroxyethyl)piperazin-1-yl)pyridin-3-yl)methyl)urea | | $[M + H]^+ = 559$ | 200 | 3.95 |
| A011 | 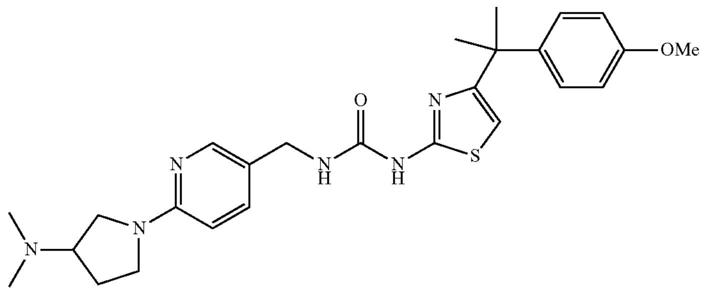 [SMILES: COc1ccc(C(C)(C)c2csc(NC(=O)NCc3ccc(N4CCC(N(C)C)C4)nc3)n2)cc1] | 1-((6-(3-(dimethylamino)pyrrolidin-1-yl)pyridin-3-yl)methyl)-3-(4-(2-(4-methoxyphenyl)propan-2-yl)thiazol-2-yl)urea | | $[M + H]^+ = 495$ | 49 | 1.37 |

TABLE 4-continued
| Com. ID | Structure | Name | HNMR | LCMS | Kinase assay IC50 nM. | NFkB assay IC50 μM |
|---|---|---|---|---|---|---|
| A012 | 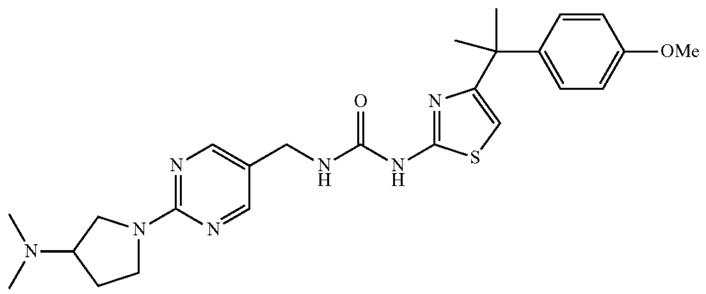 [SMILES: COc1ccc(C(C)(C)c2csc(NC(=O)NCc3cnc(N4CCC(N(C)C)C4)nc3)n2)cc1] | 1-((2-(3-(dimethylamino)pyrrolidin-1-yl)pyrimidin-5-yl)methyl)-3-(4-(2-(4-methoxyphenyl)propan-2-yl)thiazol-2-yl)urea | | $[M + H]^+ = 496$ | 40 | 2.21 |
| A013 | 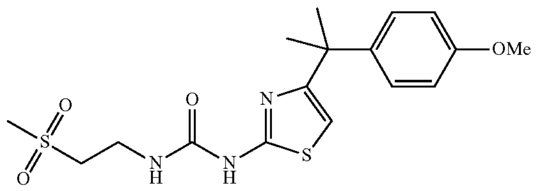 [SMILES: COc1ccc(C(C)(C)c2csc(NC(=O)NCCS(C)(=O)=O)n2)cc1] | 1-(4-(2-(4-methoxyphenyl)propan-2-yl)thiazol-2-yl)-3-(2-(methylsulfonyl)ethyl)urea | | $[M + H]^+ = 398$ | 316 | 2.97 |
| A014 | 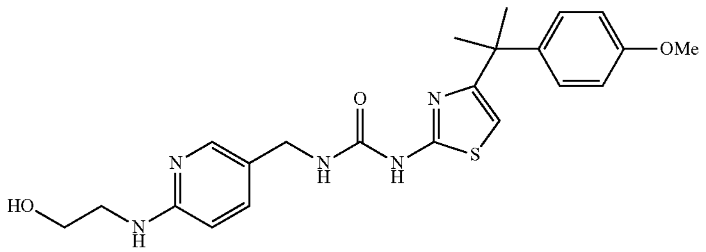 [SMILES: COc1ccc(C(C)(C)c2csc(NC(=O)NCc3ccc(NCCO)nc3)n2)cc1] | 1-((6-((2-hydroxyethyl)amino)pyridin-3-yl)methyl)-3-(4-(2-(4-methoxyphenyl)propan-2-yl)thiazol-2-yl)urea | | $[M + H]^+ = 442$ | 160 | 0.88 |

TABLE 4-continued
| Com. ID | Structure | Name | HNMR | LCMS | Kinase assay IC50 nM. | NFkB assay IC50 μM |
|---|---|---|---|---|---|---|
| A015 | 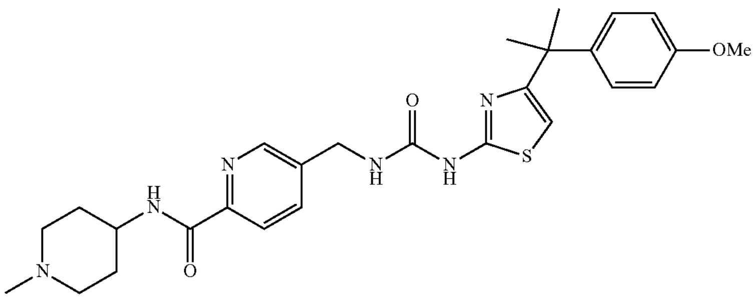 [SMILES: COc1ccc(C(C)(C)c2csc(NC(=O)NCc3ccc(C(=O)NC4CCN(C)CC4)nc3)n2)cc1] | 5-((3-(4-(2-(4-methoxyphenyl)propan-2-yl)thiazol-2-yl)ureido)methyl)-N-(1-methylpiperidin-4-yl)picolinamide | | $[M + H]^+ = 523$ | 24 | 0.88 |
| A016 | 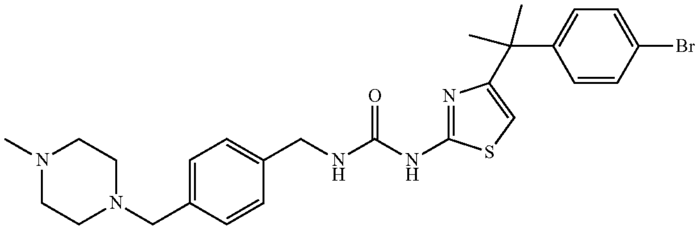 [SMILES: CN1CCN(Cc2ccc(CNC(=O)Nc3nc(C(C)(C)c4ccc(Br)cc4)cs3)cc2)CC1] | 1-(4-(2-(4-bromophenyl)propan-2-yl)thiazol-2-yl)-3-(4-((4-methylpiperazin-1-yl)methyl)benzyl)urea | | $[M + H]^+ = 542$ | 27 | 2.34 |
| A017 | 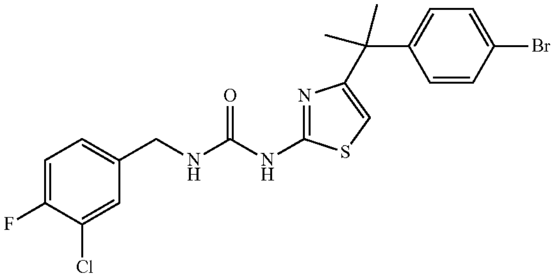 [SMILES: CC(C)(c1ccc(Br)cc1)c1csc(NC(=O)NCc2ccc(F)c(Cl)c2)n1] | 1-(4-(2-(4-bromophenyl)propan-2-yl)thiazol-2-yl)-3-(3-chloro-4-fluorobenzyl)urea | | $[M + H]^+ = 482$ | 204 | 0.97 |

TABLE 4-continued
| Com. ID | Structure | Name | HNMR | LCMS | Kinase assay IC50 nM. | NFkB assay IC50 µM |
|---|---|---|---|---|---|---|
| A018 | 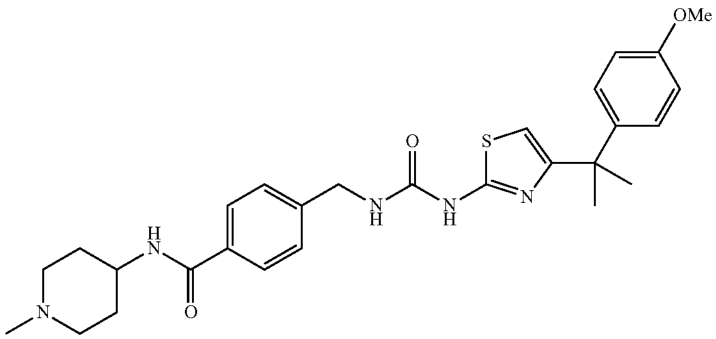 [SMILES: COc1ccc(C(C)(C)c2csc(NC(=O)NCc3ccc(C(=O)NC4CCN(C)CC4)cc3)n2)cc1] | 4-((3-(4-(2-(4-methoxyphenyl) propan-2-yl)thiazol-2-yl)ureido)methyl)-N-(1-methylpiperidin-4-yl)benzamide | | $[M + H]^+ = 522$ | 29 | 1.28 |
| A019 | 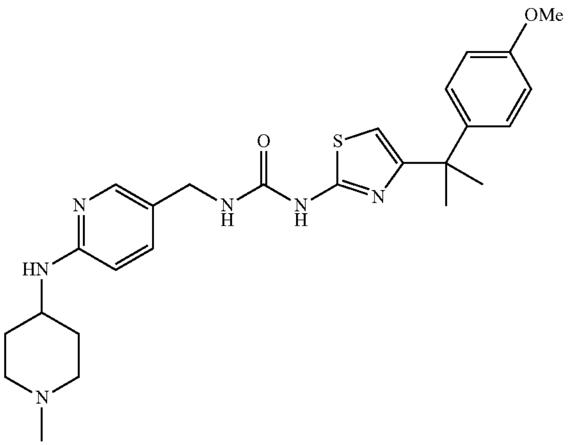 [SMILES: COc1ccc(C(C)(C)c2csc(NC(=O)NCc3ccc(NC4CCN(C)CC4)nc3)n2)cc1] | 1-(4-(2-(4-methoxyphenyl) propan-2-yl)thiazol-2-yl)-3-((6-((1-methylpiperidin-4-yl)amino)pyridin-3-yl)methyl)urea | | $[M + H]^+ = 495$ | 32 | 1.29 |

TABLE 4-continued

| Com. ID | Structure | Name | HNMR | LCMS | Kinase assay IC50 nM. | NFkB assay IC50 μM |
|---|---|---|---|---|---|---|
| A020 | 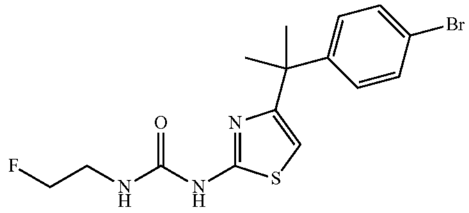 [SMILES: CC(C)(c1ccc(Br)cc1)c1csc(NC(=O)NCCF)n1] | 1-(4-(2-(4-bromophenyl)propan-2-yl)thiazol-2-yl)-3-(2-fluoroethyl)urea | $^1$H NMR (400 MHz, cdcl3) δ 7.40-7.35 (m, 2H), 7.15-7.10 (m, 2H), 6.42 (s, 1H), 4.54-4.49 (m, 1H), 4.41-4.37 (m, 1H), 3.55 (ddd, J = 28.1, 10.0, 5.2 Hz, 2H), 1.63 (s, 6H). | $[M + H]^+$ = 386 | 144 | 6.79 |
| A021 | 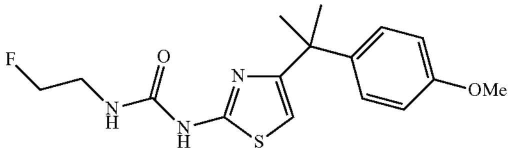 [SMILES: COc1ccc(C(C)(C)c2csc(NC(=O)NCCF)n2)cc1] | 1-(2-fluoroethyl)-3-(4-(2-(4-methoxyphenyl)propan-2-yl)thiazol-2-yl)urea | $^1$H NMR (400 MHz, dmso) δ 10.53 (s, 1H), 7.12-7.00 (m, 2H), 6.83-6.68 (m, 2H), 6.60 (s, 1H), 6.48 (s, 1H), 4.40 (dt, J = 47.5, 5.0 Hz, 2H), 3.72-3.58 (m, 3H), 3.37 (ddd, J = 26.8, 10.6, 5.2 Hz, 2H), 1.60-1.46 (m, 6H). | $[M + H]^+$ = 338 | 104 | 1.39 |
| A022 | 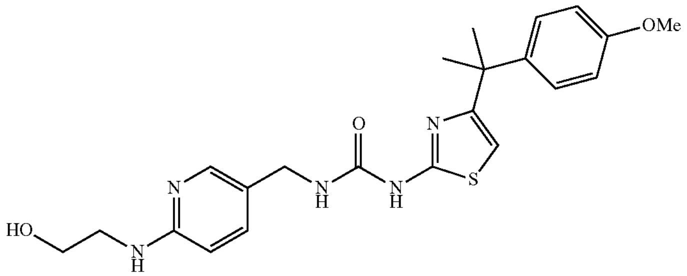 [SMILES: COc1ccc(C(C)(C)c2csc(NC(=O)NCc3ccc(NCCO)nc3)n2)cc1] | 1-((6-((2-hydroxyethyl)amino)pyridin-3-yl)methyl)-3-(4-(2-(4-methoxyphenyl)propan-2-yl)thiazol-2-yl)urea | $^1$H NMR (400 MHz, MeOD) δ 7.85 (dd, J = 9.3, 1.9 Hz, 1H), 7.75 (s, 1H), 7.20-7.15 (m, 2H), 7.08 (d, J = 9.3 Hz, 1H), 6.87-6.81 (m, 2H), 6.78 (s, 1H), 4.31 (s, 2H), 3.85-3.78 (m, 2H), 3.78-3.73 (m, 3H), 3.55-3.48 (m, 2H), 1.67 (s, 6H). | $[M + H]^+$ = 442 | 232 | 0.96 |

TABLE 4-continued

| Com. ID | Structure | Name | HNMR | LCMS | Kinase assay IC50 nM. | NFkB assay IC50 µM |
|---|---|---|---|---|---|---|
| A023 | 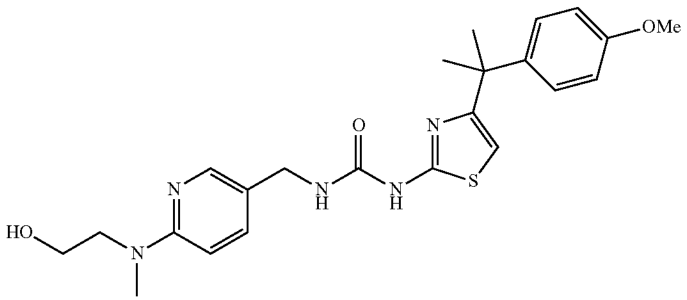 [SMILES: COc1ccc(C(C)(C)c2csc(NC(=O)NCc3ccc(N(C)CCO)nc3)n2)cc1] | 1-((6-((2-hydroxyetbyl)(methyl)amino)pyridin-3-yl)methyl)-3-(4-(2-(4-methoxyphenyl)propan-2-yl)thiazol-2-yl)urea | $^1$H NMR (400 MHz, MeOD) δ 7.94 (dd, J = 9.5, 2.1 Hz, 1H), 7.84 (d, J = 1.6 Hz, 1H), 7.31 (d, J = 9.5 Hz, 1H), 7.21-7.16 (m, 2H), 6.88-6.85 (m, 1H), 6.85 (d, J = 2.1 Hz, 1H), 6.84 (s, 1H), 4.35 (s, 2H), 3.85 (t, J = 4.8 Hz, 2H), 3.80-3.77 (m, 2H), 3.77 (s, 3H), 3.29 (s, 3H), 1.68 (s, 6H). | $[M + H]^+ = 456$ | 229 | 1.32 |
| A024 | 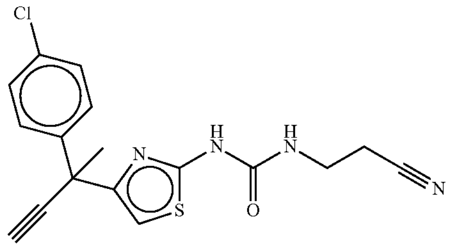 | 1-(4-(2-(4-chlorophenyl)but-3-yn-2-yl)thiazol-2-yl)-3-(2-cyanoethyl)urea | $^1$H NMR (400 MHz, (CD3)2SO) δ 7.40 (d, 2H), 7.25 (m, 2H), 6.75 (s, 1H), 3.47 (m, 2H), 2.55 (m, 3H), 1.92 (s, 3H). | $[M + H]^+ = 359$ | 13 | 1.25 |
| A025 | 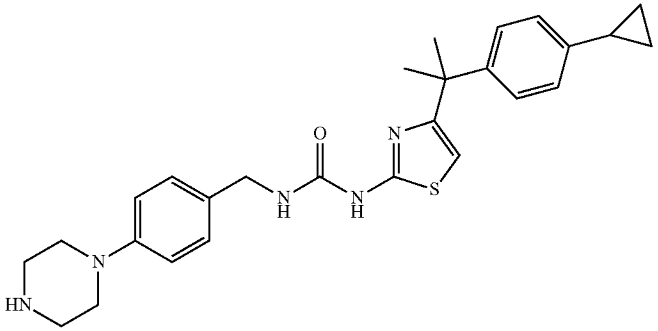 [SMILES: CC(C)(c1ccc(C2CC2)cc1)c1csc(NC(=O)NCc2ccc(N3CCNCC3)cc2)n1] | 1-(4-(2-(4-cyclopropylphenyl)propan-2-yl)thiazol-2-yl)-3-(4-(piperazin-1-yl)benzyl)urea | | $[M + H]^+ = 476$ | 334 | 8.58 |

TABLE 4-continued
| Com. ID | Structure | Name | HNMR | LCMS | Kinase assay IC50 nM. | NFkB assay IC50 μM |
|---|---|---|---|---|---|---|
| A026 | 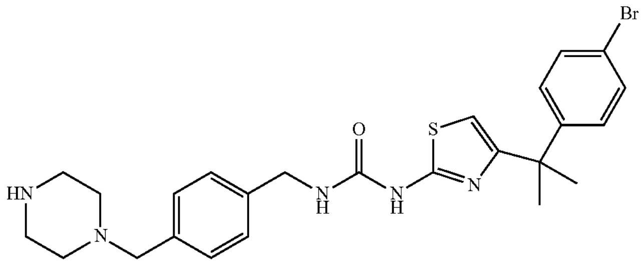 [SMILES: CC(C)(c1ccc(Br)cc1)c1csc(NC(=O)NCc2ccc(CN3CCNCC3)cc2)n1] | 1-(4-(2-(4-bromophenyl)propan-2-yl)thiazol-2-yl)-3-(4-(piperazin-1-ylmethyl)benzyl)urea | | $[M + H]^+ = 528$ | 117 | 1.25 |
| A027 | 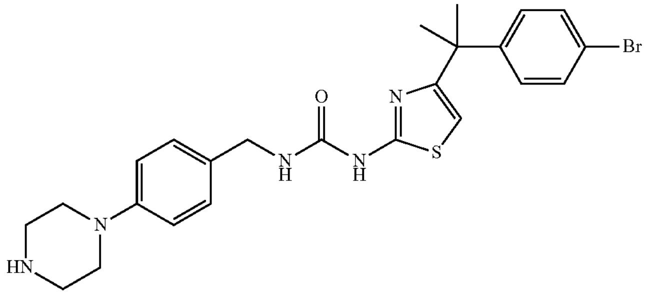 [SMILES: CC(C)(c1ccc(Br)cc1)c1csc(NC(=O)NCc2ccc(N3CCNCC3)cc2)n1] | 1-(4-(2-(4-bromophenyl)propan-2-yl)thiazol-2-yl)-3-(4-(piperazin-1-yl)benzyl)urea | | $[M + H]^+ = 514$ | 46 | 1.45 |
| A028 | 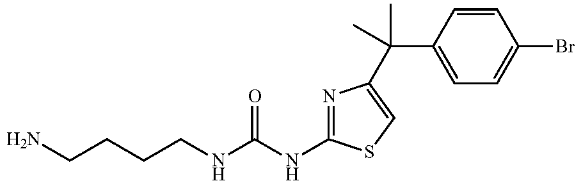 [SMILES: CC(C)(c1ccc(Br)cc1)c1csc(NC(=O)NCCCCN)n1] | 1-(4-aminobutyl)-3-(4-(2-(4-bromophenyl)propan-2-yl)thiazol-2-yl)urea | | $[M + H]^+ = 411$ | 53 | 2.56 |

TABLE 4-continued
| Com. ID | Structure | Name | HNMR | LCMS | Kinase assay IC50 nM. | NFkB assay IC50 μM |
|---|---|---|---|---|---|---|
| A029 | 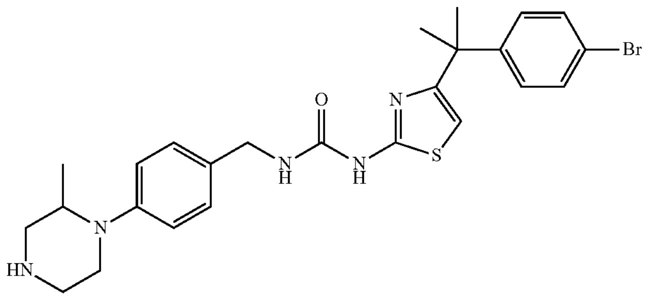 [SMILES: CC1CNCCN1c1ccc(CNC(=O)Nc2nc(C(C)(C)c3ccc(Br)cc3)cs2)cc1] | 1-(4-(2-(4-bromophenyl)propan-2-yl)thiazol-2-yl)-3-(4-(2-methylpiperazin-1-yl)benzyl)urea | | $[M + H]^+ = 528$ | 73 | |
| A030 | 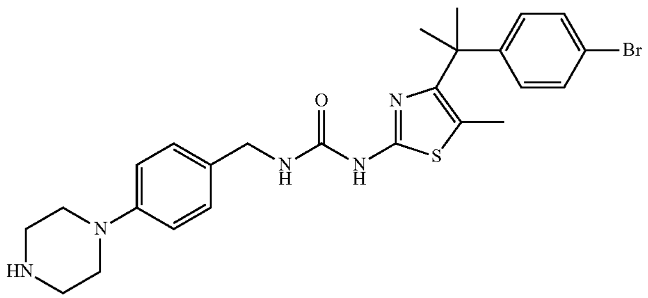 [SMILES: Cc1sc(NC(=O)NCc2ccc(N3CCNCC3)cc2)nc1C(C)(C)c1ccc(Br)cc1] | 1-(4-(2-(4-bromophenyl)propan-2-yl)-5-methylthiazol-2-yl)-3-(4-(piperazin-1-yl)benzyl)urea | | $[M + H]^+ = 528$ | 232 | 4.11 |
| A031 | 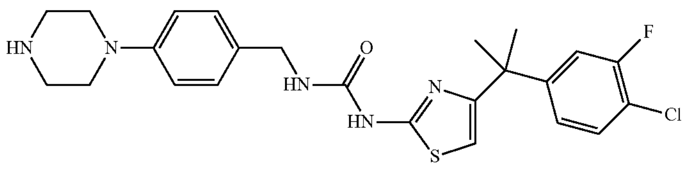 [SMILES: CC(C)(c1ccc(Cl)c(F)c1)c1csc(NC(=O)NCc2ccc(N3CCNCC3)cc2)n1] | 1-(4-(2-(4-chloro-3-fluorophenyl)propan-2-yl)thiazol-2-yl)-3-(4-(piperazin-1-yl)benzyl)urea | | $[M + H]^+ = 488$ | 345 | 1.45 |

TABLE 4-continued
| Com. ID | Structure | Name | HNMR | LCMS | Kinase assay IC50 nM. | NFkB assay IC50 µM |
|---|---|---|---|---|---|---|
| A032 | 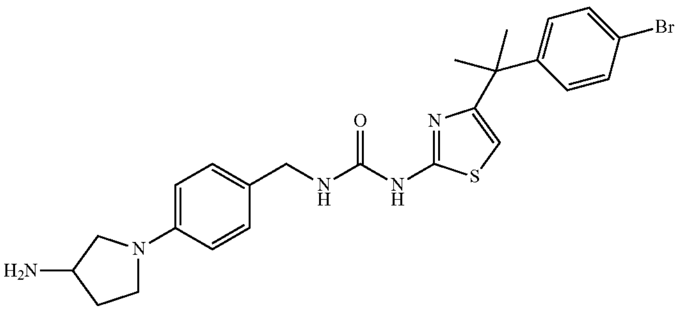 [SMILES: CC(C)(c1ccc(Br)cc1)c1csc(NC(=O)NCc2ccc(N3CCC(N)C3)cc2)n1] | 1-(4-(3-aminopyrrolidin-1-yl)benzyl)-3-(4-(2-(4-bromophenyl)propan-2-yl)thiazol-2-yl)urea | | $[M + H]^+ = 514$ | 291 | 0.58 |
| A033 | 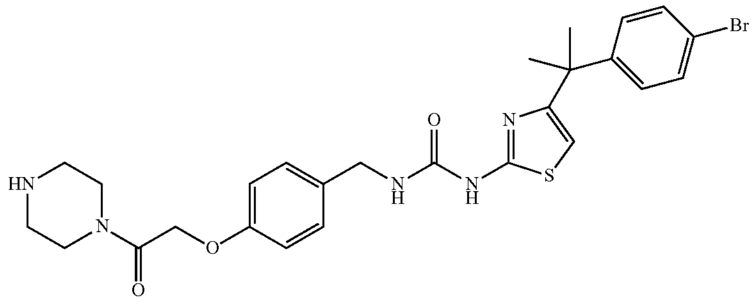 [SMILES: CC(C)(c1ccc(Br)cc1)c1csc(NC(=O)NCc2ccc(OCC(=O)N3CCNCC3)cc2)n1] | 1-(4-(2-(4-bromophenyl)propan-2-yl)thiazol-2-yl)-3-(4-(2-oxo-2-(piperazin-1-yl)ethoxy)benzyl)urea | | $[M + H]^+ = 572$ | 80 | 3.19 |
| A034 | 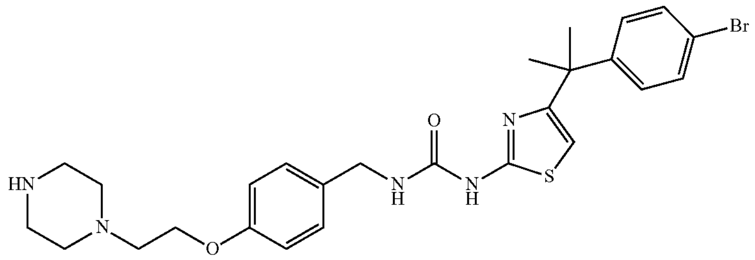 [SMILES: CC(C)(c1ccc(Br)cc1)c1csc(NC(=O)NCc2ccc(OCCN3CCNCC3)cc2)n1] | 1-(4-(2-(4-bromophenyl)propan-2-yl)thiazol-2-yl)-3-(4-(2-(piperazin-1-yl)ethoxy )benzyl)urea | | $[M + H]^+ = 558$ | 114 | 0.73 |

TABLE 4-continued
| Com. ID | Structure | Name | HNMR | LCMS | Kinase assay IC50 nM. | NFkB assay IC50 μM |
|---|---|---|---|---|---|---|
| A035 | 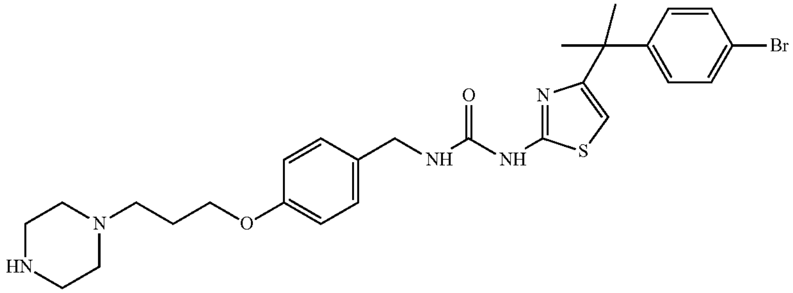 [SMILES: CC(C)(c1ccc(Br)cc1)c1csc(NC(=O)NCc2ccc(OCCCN3CCNCC3)cc2)n1] | 1-(4-(2-(4-bromophenyl)propan-2-yl)thiazol-2-yl)-3-(4-(3-(piperazin-1-yl)propoxy)benzyl)urea | | $[M + H]^+ = 572$ | 52 | 2.03 |
| A036 | 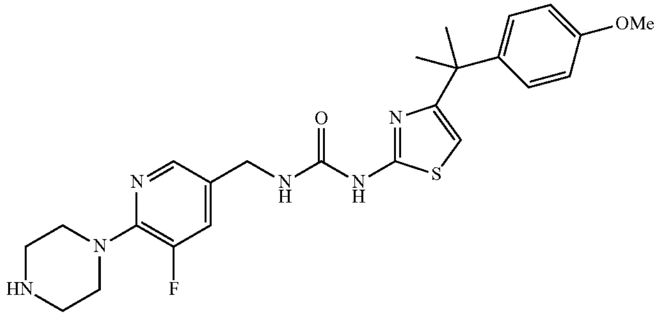 [SMILES: COc1ccc(C(C)(C)c2csc(NC(=O)NCc3cnc(N4CCNCC4)c(F)c3)n2)cc1] | 1-((5-fluoro-6-(piperazin-1-yl)pyridin-3-yl)methyl)-3-(4-(2-(4-methoxyphenyl)propan-2-yl)thiazol-2-yl)urea | | $[M + H]^+ = 485$ | 24 | 0.62 |
| A037 | 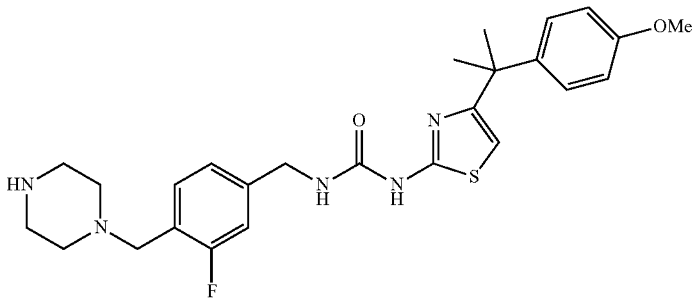 [SMILES: COc1ccc(C(C)(C)c2csc(NC(=O)NCc3ccc(CN4CCNCC4)c(F)c3)n2)cc1] | 1-(3-fluoro-4-(piperazin-1-ylmethyl)benzyl)-3-(4-(2-(4-methoxyphenyl)propan-2-yl)thiazol-2-yl)urea | | $[M + H]^+ = 498$ | 57 | 2.51 |

TABLE 4-continued
| Com. ID | Structure | Name | HNMR | LCMS | Kinase assay IC50 nM. | NFkB assay IC50 μM |
|---|---|---|---|---|---|---|
| A038 | 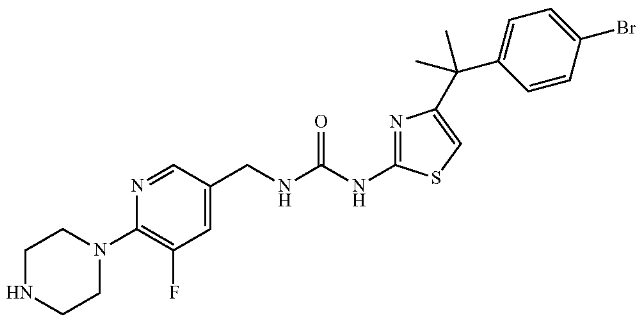 [SMILES: CC(C)(c1ccc(Br)cc1)c1csc(NC(=O)NCc2cnc(N3CCNCC3)c(F)c2)n1] | 1-(4-(2-(4-bromophenyl)propan-2-yl)thiazol-2-yl)-3-((5-fluoro-6-(piperazin-1-yl)pyridin-3-yl)methyl)urea | | $[M + H]^+ = 533$ | 30 | 1.66 |
| A039 | 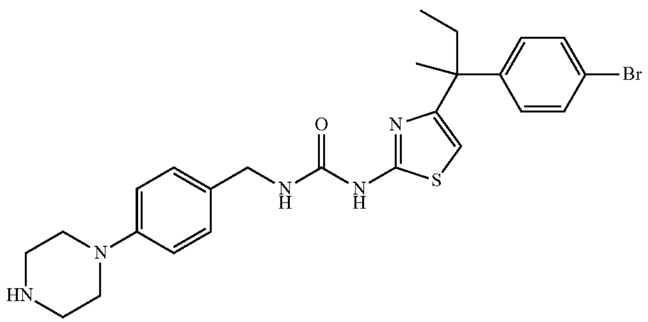 [SMILES: CCC(C)(c1ccc(Br)cc1)c1csc(NC(=O)NCc2ccc(N3CCNCC3)cc2)n1] | 1-(4-(2-(4-bromophenyl)butan-2-yl)thiazol-2-yl)-3-(4-(piperazin-1-yl)benzyl)urea | | $[M + H]^+ = 528$ | 189 | 0.711 |
| A040 | 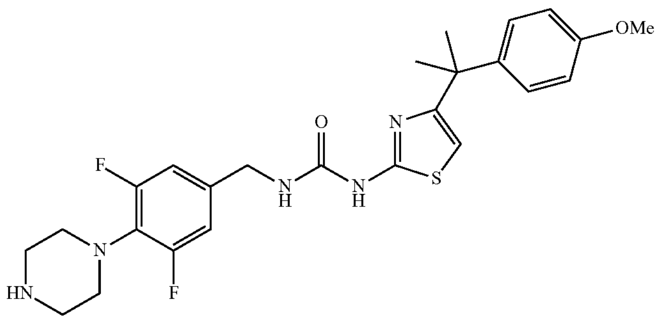 [SMILES: COc1ccc(C(C)(C)c2csc(NC(=O)NCc3cc(F)c(N4CCNCC4)c(F)c3)n2)cc1] | 1-(3,5-difluoro-4-(piperazin-1-yl)benzyl)-3-(4-(2-(4-methoxyphenyl)propan-2-yl)thiazol-2-yl)urea | | $[M + H]^+ = 502$ | 45 | 0.50 |

TABLE 4-continued
| Com. ID | Structure | Name | HNMR | LCMS | Kinase assay IC50 nM. | NFkB assay IC50 μM |
|---|---|---|---|---|---|---|
| A041 | 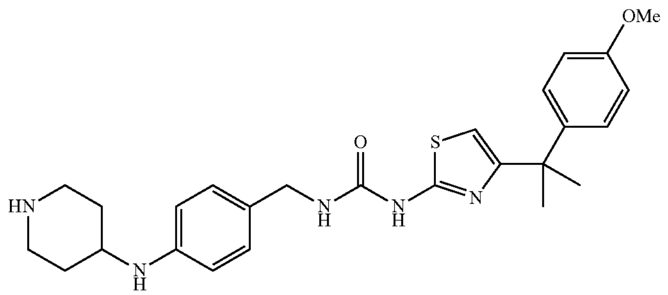 [SMILES: COc1ccc(C(C)(C)c2csc(NC(=O)NCc3ccc(NC4CCNCC4)cc3)n2)cc1] | 1-(4-(2-(4-methoxyphenyl)propan-2-yl)thiazol-2-yl)-3-(4-(piperidin-4-ylamino)benzyl)urea | | $[M + H]^+ = 480$ | 23 | 1.86 |
| A042 | 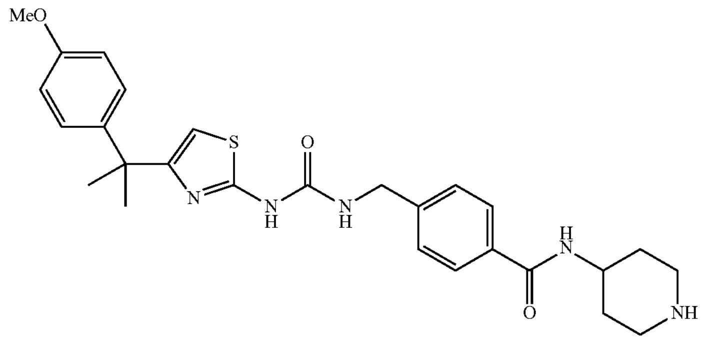 [SMILES: COc1ccc(C(C)(C)c2csc(NC(=O)NCc3ccc(C(=O)NC4CCNCC4)cc3)n2)cc1] | 4-((3-(4-(2-(4-methoxyphenyl)propan-2-yl)thiazol-2-yl)ureido)methyl)-N-(piperidin-4-yl)benzamide | | $[M + H]^+ = 508$ | 15 | |
| A043 | 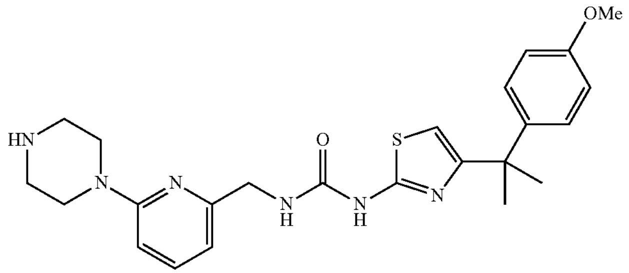 [SMILES: COc1ccc(C(C)(C)c2csc(NC(=O)NCc3cccc(N4CCNCC4)n3)n2)cc1] | 1-(4-(2-(4-methoxyphenyl)propan-2-yl)thiazol-2-yl)-3-((6-(piperazin-1-yl)pyridin-2-yl)methyl)urea | | $[M + H]^+ = 467$ | 165 | |

TABLE 4-continued

| Com. ID | Structure | Name | HNMR | LCMS | Kinase assay IC50 nM. | NFkB assay IC50 μM |
|---|---|---|---|---|---|---|
| A044 | 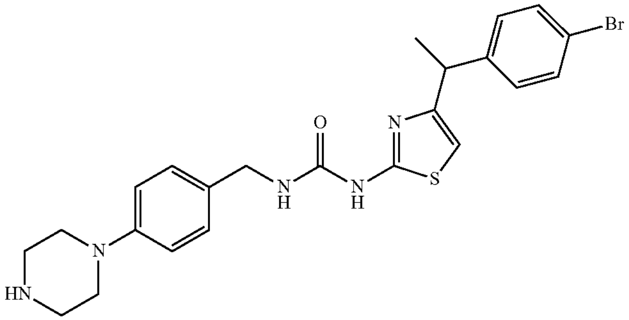 | 1-(4-(1-(4-bromophenyl)ethyl) thiazol-2-yl)-3-(4-(piperazin-1-yl)benzyl)urea | $^1$H NMR (400 MHz, cd3od) δ 7.45 (d, J = 6.9 Hz, 2H), 7.22 (s, 2H), 7.14 (s, 2H), 6.97 (s, 3H), 4.32 (s, 2H), 4.18 (s, 1H), 3.37 (s, 4H), 3.33 (s, 4H), 1.59 (s, 3H). | $[M + H]^+ = 500$ | 147 | 1.11 |
| A045 | 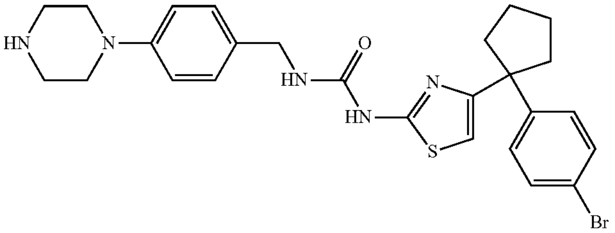 [SMILES: O=C(NCc1ccc(N2CCNCC2)cc1)Nc1nc(C2(c3ccc(Br)cc3)CCCC2)cs1] | 1-(4-(1-(4-bromophenyl) cyclopentyl)thiazol-2-yl)-3-(4-(piperazin-1-yl)benzyl)urea | $^1$H NMR (400 MHz, dmso) δ 9.28 (s, 1H), 7.39 (d, J = 8.3 Hz, 1H), 7.19 (d, J = 8.5 Hz, 2H), 7.13 (d, J = 8.3 Hz, 2H), 6.93 (d, J = 8.5 Hz, 2H), 6.76 (s, 1H), 4.18 (d, J = 4.4 Hz, 2H), 3.31 (s, 4H), 3.16 (s, 4H), 2.41 (d, J = 12.9 Hz, 2H), 1.95 (s, 2H), 1.59 (d, J = 9.0 Hz, 4H). | $[M + H]^+ = 540$ | 24 | 1.07 |
| A046 | 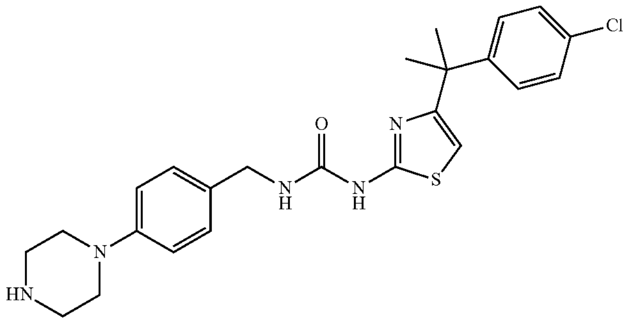 [SMILES: CC(C)(c1ccc(Cl)cc1)c1csc(NC(=O)NCc2ccc(N3CCNCC3)cc2)n1] | 1-(4-(2-(4-chlorophenyl)propan-2-yl)thiazol-2-yl)-3-(4-(piperazin-1-yl)benzyl)urea | $^1$H NMR (400 MHz, dmso) δ 8.99 (s, 1H), 7.26 (d, J = 8.5 Hz, 2H), 7.17 (d, J = 8.4 Hz, 2H), 7.12 (d, J = 8.2 Hz, 2H), 6.91 (d, J = 8.7 Hz, 3H), 6.70 (s, 1H), 4.17 (d, J = 5.8 Hz, 2H), 3.28 (s, 4H), 3.17 (s, 4H), 1.54 (s, 6H). | $[M + H]^+ = 470$ | 79 | 1.06 |

TABLE 4-continued

| Com. ID | Structure | Name | HNMR | LCMS | Kinase assay IC50 nM. | NFkB assay IC50 μM |
|---|---|---|---|---|---|---|
| A047 | 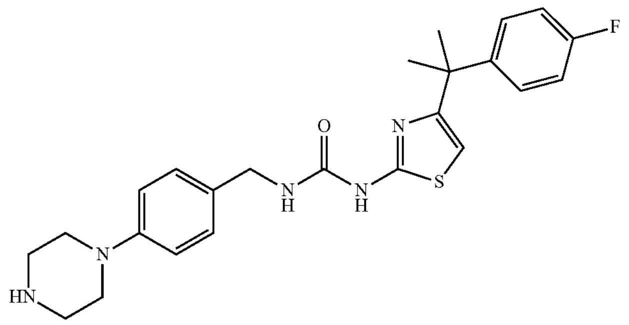 [SMILES: CC(C)(c1ccc(F)cc1)c1csc(NC(=O)NCc2ccc(N3CCNCC3)cc2)n1] | 1-(4-(2-(4-fluorophenyl)propan-2-yl)thiazol-2-yl)-3-(4-(piperazin-1-yl)benzyl)urea | $^1$H NMR (400 MHz, dmso) δ 7.18 (dd, J = 8.1, 5.7 Hz, 2H), 7.12 (d, J = 8.2 Hz, 2H), 7.01 (t, J = 8.6 Hz, 2H), 6.89 (d, J = 8.1 Hz, 2H), 6.84 (s, 1H), 6.66 (s, 1H), 4.17 (d, J = 5.6 Hz, 2H), 3.24 (d, J = 5.3 Hz, 4H), 3.13 (d, J = 5.0 Hz, 4H), 1.54 (s, 6H). | $[M + H]^+ = 454$ | 167 | 2.10 |
| A048 | 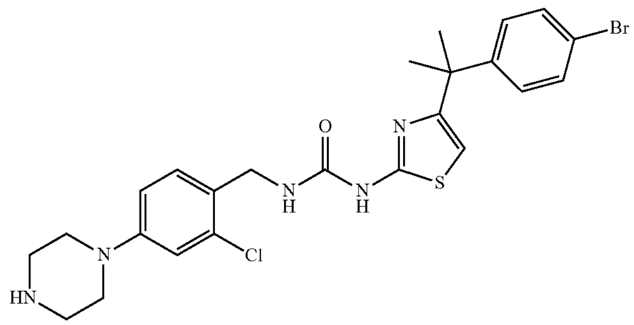 [SMILES: CC(C)(c1ccc(Br)cc1)c1csc(NC(=O)NCc2ccc(N3CCNCC3)cc2Cl)n1] | 1-(4-(2-(4-bromophenyl)propan-2-yl)thiazol-2-yl)-3-(2-chloro-4-(piperazin-1-yl)benzyl)urea | $^1$H NMR (400 MHz, dmso) δ 9.24 (s, 1H), 7.39 (d, J = 8.6 Hz, 2H), 7.19 (d, J = 8.6 Hz, 1H), 7.12 (d, J = 8.6 Hz, 3H), 7.01 (d, J = 2.3 Hz, 1H), 6.90 (dd, J = 8.7, 2.3 Hz, 1H), 6.70 (s, 1H), 4.25 (d, J = 5.7 Hz, 2H), 3.43-3.28 (m, 4H), 3.13 (s, 4H), 1.54 (s, 6H). | $[M + H]^+ = 548$ | 138 | 1.53 |
| A049 | 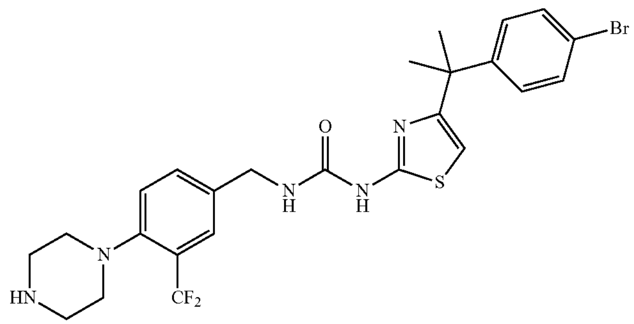 | 1-(4-(2-(4-bromophenyl)propan-2-yl)thiazol-2-yl)-3-(4-(piperazin-1-yl)-3-(trifluoromethyl) benzyl)urea | $^1$H NMR (400 MHz, dmso) δ 9.11 (s, 2H), 7.54 (d, J = 9.0 Hz, 2H), 7.46 (d, J = 8.1 Hz, 1H), 7.38 (d, J = 8.5 Hz, 2H), 7.19 (s, 1H), 7.11 (d, J = 8.5 Hz, 2H), 6.70 (s, 1H), 4.30 (d, J = 5.7 Hz, 2H), 3.10 (d, J = 17.0 Hz, SH), 3.01 (d, J = 3.9 Hz, SH), 1.56 (d, J = 22.5 Hz, 8H). | $[M + H]^+ = 582$ | 119 | 0.8 |

TABLE 4-continued
| Com. ID | Structure | Name | HNMR | LCMS | Kinase assay IC50 nM. | NFkB assay IC50 μM |
|---|---|---|---|---|---|---|
| A050 | 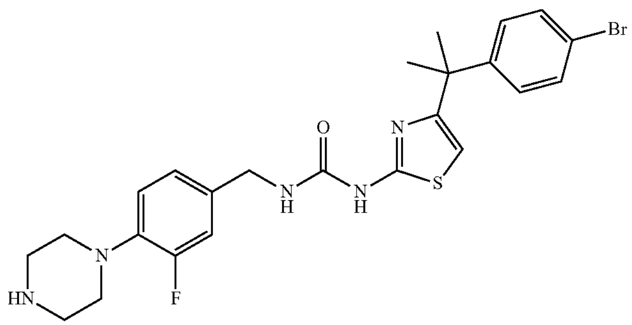 [SMILES: CC(C)(c1ccc(Br)cc1)c1csc(NC(=O)NCc2ccc(N3CCNCC3)c(F)c2)n1] | 1-(4-(2-(4-bromophenyl)propan-2-yl)thiazol-2-yl)-3-(3-fluoro-4-(piperazin-1-yl)benzyl)urea | $^1$H NMR (400 MHz, dmso) δ 9.31 (s, 1H), 7.31 (d, J = 44.6 Hz, 3H), 7.04 (d, J = 44.4 Hz, 5H), 6.68 (s, 1H), 4.18 (s, 2H), 3.15 (s, 8H), 1.51 (s, 6H). | $[M + H]^+ = 532$ | 26 | 1.21 |
| A051 | 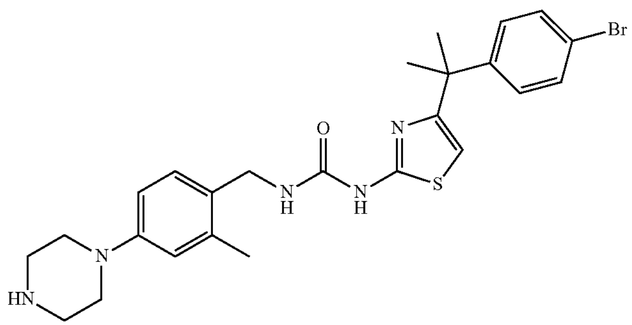 [SMILES: Cc1cc(N2CCNCC2)ccc1CNC(=O)Nc1nc(C(C)(C)c2ccc(Br)cc2)cs1] | 1-(4-(2-(4-bromophenyl)propan-2-yl)thiazol-2-yl)-3-(2-methyl-4-(piperazin-1-yl)benzyl)urea | $^1$H NMR (400 MHz, dmso) δ 10.54-10.45 (m, 1H), 9.02 (s, 1H), 7.39 (d, J = 8.6 Hz, 2H), 7.11 (d, J = 8.6 Hz, 2H), 7.05 (d, J = 8.5 Hz, 1H), 6.78 (s, 2H), 6.74 (d, J = 8.5 Hz, 1H), 6.70 (s, 1H), 4.17 (d, J = 5.4 Hz, 2H), 3.28 (d, J = 5.5 Hz, 4H), 3.16 (s, 4H), 2.20 (s, 3H), 1.54 (s. 6H). | $[M + H]^+ = 528$ | 125 | 0.29 |

TABLE 4-continued
| Com. ID | Structure | Name | HNMR | LCMS | Kinase assay IC50 nM. | NFkB assay IC50 µM |
|---|---|---|---|---|---|---|
| A052 | 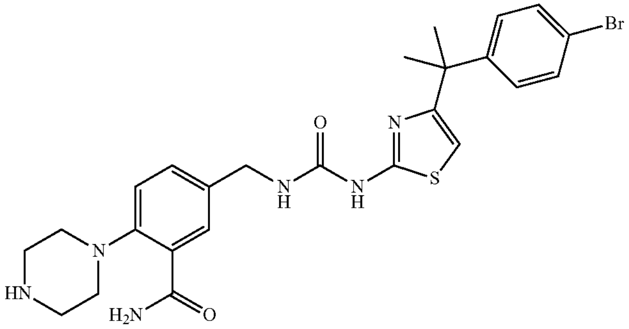 [SMILES: CC(C)(c1ccc(Br)cc1)c1csc(NC(=O)NCc2ccc(N3CCNCC3)c(C(N)=O)c2)n1] | 5-((3-(4-(2-(4-bromophenyl)propan-2-yl)thiazol-2-yl)ureido)methyl)-2-(piperazin-1-yl)benzamide | $^1$H NMR (400 MHz, dmso) δ 9.35 (s, 1H), 8.04 (s, 1H), 7.54-7.32 (m, 3H), 7.23 (d, J = 29.5 Hz, 2H), 7.09 (d, J = 19.3 Hz, 3H), 6.70 (s, 1H), 3.13 (d, J = 46.5 Hz, 8H), 2.66 (d, J = 17.4 Hz, 2H), 1.53 (s, 6H). | $[M + H]^+ = 557$ | 24 | 1.96 |
| A053 | 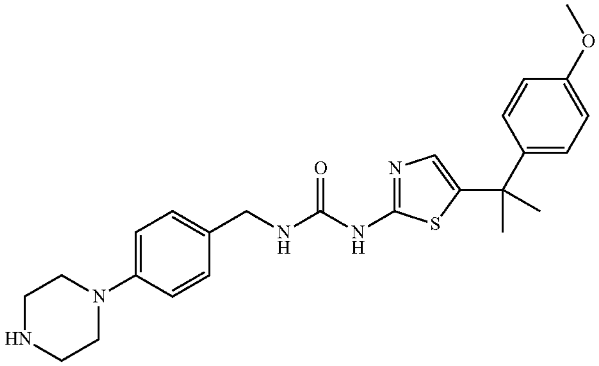 [SMILES: COc1ccc(C(C)(C)c2cnc(NC(=O)NCc3ccc(N4CCNCC4)cc3)s2)cc1] | 1-(4-(2-(4-methoxyphenyl)propan-2-yl)thiazol-2-yl)-3-(4-(piperazin-1-yl)benzyl)urea | $^1$H NMR (400 MHz, dmso) δ 9.15 (s, 1H), 7.09 (d, J = 18.4 Hz, 4H), 6.90 (s, 2H), 6.75 (s, 2H), 6.61 (s, 1H), 4.17 (s, 2H), 3.65 (s, 3H), 3.28 (s, 4H), 3.15 (s, 4H), 1.52 (s, 6H). | $[M + H]^+ = 466$ | 43 | 0.76 |

TABLE 4-continued
| Com. ID | Structure | Name | HNMR | LCMS | Kinase assay IC50 nM. | NFkB assay IC50 μM |
|---|---|---|---|---|---|---|
| A054 | 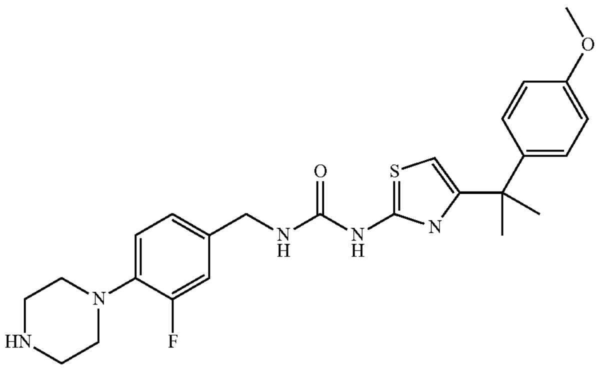 | 1-(3-fluoro-4-(piperazin-1-yl)benzyl)-3-(4-(2-(4-methoxyphenyl)propan-2-yl)thiazol-2-yl)urea | $^1$H NMR (400 MHz, cd3od) δ 10.12 (s, 2H), 8.12 (s, 1H), 7.81 (d, J = 23.1 Hz, 5H), 7.53 (s, 2H), 7.39 (s, 1H), 4.97 (s, 2H), 4.43 (s, 3H), 3.93 (s, 8H), 2.29 (s. 6H). | $[M + H]^+ = 484$ | 30 | 0.88 |
| A055 | 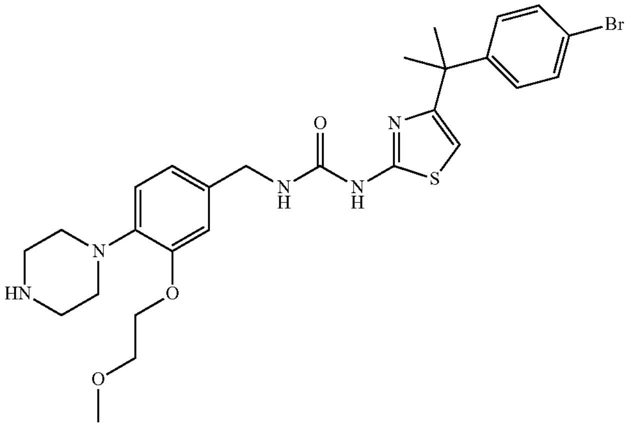 [SMILES: COCCOc1cc(CNC(=O)Nc2nc(C(C)(C)c3ccc(Br)cc3)cs2)ccc1N1CCNCC1] | 1-(4-(2-(4-bromophenyl)propan-2-yl)thiazol-2-yl)-3-(3-(2-methoxyethoxy)-4-(piperazin-1-yl)benzyl)urea | $^1$H NMR (400 MHz, cd3od) δ 7.48 (d. J = 8.4 Hz, 2H), 7.19 (d, J = 7.1 Hz, 2H), 7.11 (s, 1H), 7.00 (s, 2H), 6.93 (s, 1H), 4.38 (s, 2H), 4.19 (s, 4H), 3.77 (s, 4H), 3.43 (s, 4H), 3.40 (s, 3H), 1.69 (s, 6H). | $[M + H]^+ = 588$ | 182 | 4.70 |

TABLE 4-continued

| Com. ID | Structure | Name | HNMR | LCMS | Kinase assay IC50 nM. | NFkB assay IC50 μM |
|---|---|---|---|---|---|---|
| A056 | 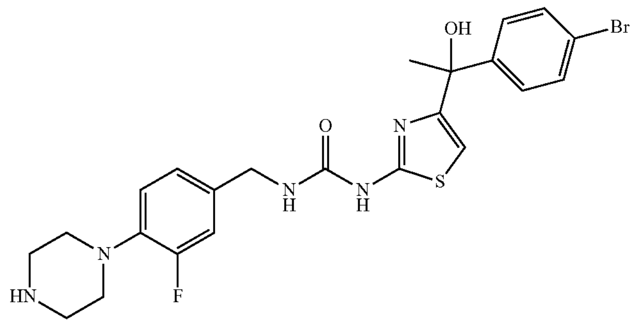 [SMILES: CC(O)(c1ccc(Br)cc1)c1csc(NC(=O)NCc2ccc(N3CCNCC3)c(F)c2)n1] | 1-(4-(1-(4-bromophenyl)-1-hydroxyethyl)thiazol-2-yl)-3-(3-fluoro-4-(piperazin-1-yl)benzyl)urea | $^1$H NMR (400 MHz, cd3od) δ 7.46 (d, J = 8.4 Hz, 2H), 7.38 (d, J = 8.5 Hz, 2H), 7.04 (t, J = 9.9 Hz, 4H), 4.36 (d, J = 6.7 Hz, 2H), 3.29 (s, 8H), 1.84 (d, J = 13.6 Hz, 3H). | $[M + H]^+ = 534$ | 176 | 1.06 |
| A057 | 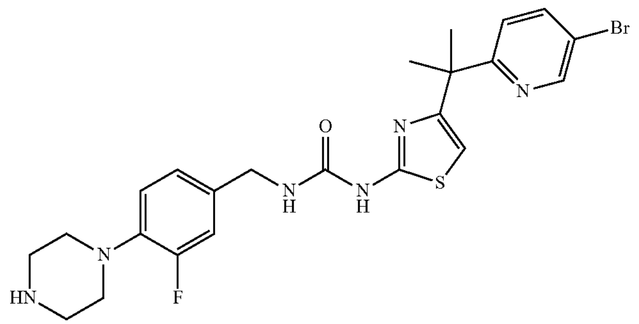 [SMILES: CC(C)(c1ccc(Br)cn1)c1csc(NC(=O)NCc2ccc(N3CCNCC3)c(F)c2)n1] | 1-(4-(2-(5-bromopyridin-2-yl)propan-2-yl)thiazol-2-yl)-3-(3-fluoro-4-(piperazin-1-yl)benzyl)urea | $^1$H NMR (400 MHz, cd3od) δ 8.48 (d, J = 2.3 Hz, 1H), 7.80-7.73 (m, 1H), 7.08 (d, J = 8.4 Hz, 1H), 7.01 (d, J = 4.2 Hz, 2H), 6.99 (s, 1H), 6.73 (s, 1H), 4.30 (s, 2H), 3.25 (s, 4H), 3.23 (s, 4H), 1.64 (s, 6H). | $[M + H]^+ = 533$ | 246 | |
| A058 | 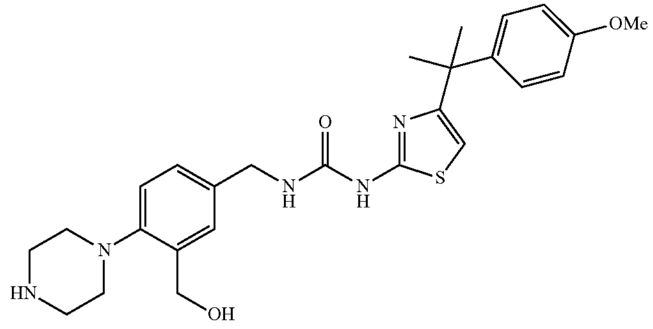 [SMILES: COc1ccc(C(C)(C)c2csc(NC(=O)NCc3ccc(N4CCNCC4)c(CO)c3)n2)cc1] | 1-(3-(hydroxymethyl)-4-(piperazin-1-yl)benzyl)-3-(4-(2-(4-methoxyphenyl)propan-2-yl)thiazol-2-yl)urea | $^1$H NMR (400 MHz, cd3od) δ 7.41 (d, J = 4.2 Hz, 2H), 7.21 (s. 1H), 7.15 (d, J = 6.7 Hz, 1H), 7.12 (d, J = 5.9 Hz, 2H), 6.88 (s, 1H), 6.85 (s, 1H), 6.82 (d, J = 5.7 Hz, 2H), 4.67 (s, 2H), 4.38 (s, 2H), 3.74 (s, 3H), 3.25-3.22 (m, 4H), 3.17-3.11 (m, 4H), 1.63 (s, 6H). | $[M + H]^+ = 496$ | 130 | 3.10 |

TABLE 4-continued

| Com. ID | Structure | Name | HNMR | LCMS | Kinase assay IC50 nM. | NFkB assay IC50 μM |
|---|---|---|---|---|---|---|
| A059 | 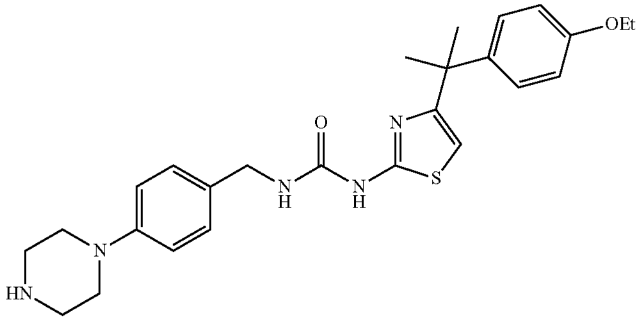 [SMILES: CCOc1ccc(C(C)(C)c2csc(NC(=O)NCc3ccc(N4CCNCC4)cc3)n2)cc1] | 1-(4-(2-(4-ethoxyphenyl)propan-2-yl)thiazol-2-yl)-3-(4-(piperazin-1-yl)benzyl)urea | $^1$H NMR (400 MHz, cd3od) δ 7.17 (t, J = 5.9 Hz, 2H), 7.09 (dd, J = 9.4, 2.7 Hz, 2H), 6.96 (d, J = 8.7 Hz, 2H), 6.78-6.73 (m, 2H), 6.58 (s, 1H), 4.28 (s, 2H), 3.96 (q, J = 7.0 Hz, 2H), 3.34 (d. J = 3.6 Hz, 4H), 3.33 (s, 4H), 1.57 (s, 6H), 1.37-1.29 (m, 3H). | $[M + H]^+ = 480$ | 269 | |
| A060 | 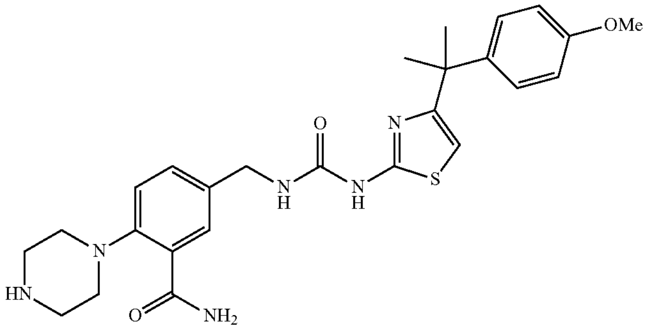 [SMILES: COc1ccc(C(C)(C)c2csc(NC(=O)NCc3ccc(N4CCNCC4)c(C(N)=O)c3)n2)cc1] | 5-((3-(4-(2-(4-methoxyphenyl) propan-2-yl)thiazol-2-yl)ureido)methyl)-2-(piperazin-1-yl)benzamide | $^1$H NMR (400 MHz, dmso) δ 9.35 (s, 2H), 8.05 (s, 1H), 7.53 (d, J = 2.0 Hz, 1H), 7.48 (s, 1H), 7.30 (d, J = 10.1 Hz, 2H), 7.08 (t, J = 8.0 Hz, 3H), 6.78 (d, J = 8.8 Hz, 2H), 6.65 (s, 1H), 4.24 (d, J = 5.2 Hz, 2H), 3.66 (s, 3H), 3.20 (s, 4H), 3.08 (s, 4H), 1.54 (s, 6H). | $[M + H]^+ = 509$ | 8 | 4.80 |
| A061 | 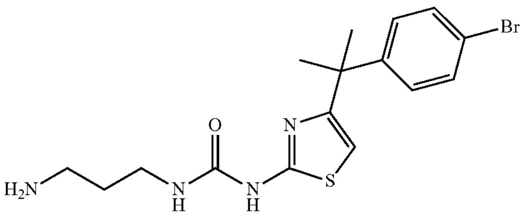 [SMILES: CC(C)(c1ccc(Br)cc1)c1csc(NC(=O)NCCCN)n1] | 1-(3-aminopropyl)-3-(4-(2-(4-bromophenyl)propan-2-yl)thiazol-2-yl)urea | $^1$H NMR (400 MHz, dmso) δ 8.08 (s, 3H), 7.49 (s, 1H), 7.40 (d. J = 8.2 Hz, 2H), 7.11 (d, J = 8.2 Hz, 2H), 6.78 (s, 1H), 4.82 (s, 5H), 2.73 (s, 2H), 1.70 (s, 2H), 1.53 (s, 6H). | $[M + H]^+ = 397$ | 195 | 1.99 |

TABLE 4-continued

| Com. ID | Structure | Name | HNMR | LCMS | Kinase assay IC50 nM. | NFkB assay IC50 μM |
|---|---|---|---|---|---|---|
| A062 | 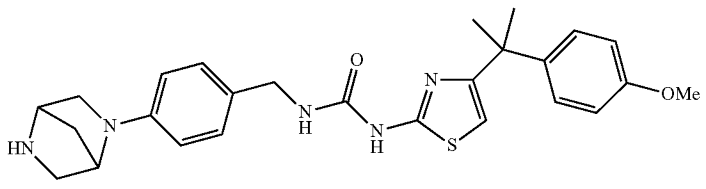 [SMILES: COc1ccc(C(C)(C)c2csc(NC(=O)NCc3ccc(N4CC5CC4CN5)cc3)n2)cc1] | 1-(4-(2,5-diazabicyclo[2.2.1]heptan-2-yl)benzyl)-3-(4-(2-(4-methoxyphenyl)propan-2-yl)thiazol-2-yl)urea | $^1$H NMR (400 MHz, cd3od) δ 7.22-7.15 (m, 4H), 7.09 (s, 1H), 6.89 (d, J = 8.8 Hz, 2H), 6.64 (d, J = 8.5 Hz, 2H), 4.62 (s, 1H), 4.46 (s, 1H), 4.30 (s, 2H), 3.75 (s, 3H), 3.69 (dd, J = 10.7, 2.2 Hz, 1H), 3.31-3.27 (m, 3H), 2.25 (d, J = 11.0 Hz, 1H), 2.04 (d, J = 11.2 Hz, 1H), 1.68 (s. 6H). | $[M + H]^+$ = 478 | 60 | 1.33 |
| A063 | 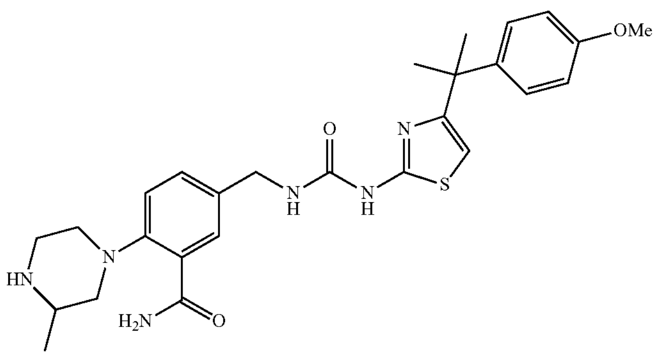 [SMILES: COc1ccc(C(C)(C)c2csc(NC(=O)NCc3ccc(N4CCNC(C)C4)c(C(N)=O)c3)n2)cc1] | 5-((3-(4-(2-(4-methoxyphenyl)propan-2-yl)thiazol-2-yl)ureido)methyl)-2-(3-methylpiperazin-1-yl)benzamide | $^1$H NMR (400 MHz, MeOD) δ 7.70 (d, J = 2.0 Hz, 1H), 7.50 (dd, J = 8.3, 2.0 Hz, 1H), 7.28 (d, J = 8.3 Hz, 1H), 7.23 (s, 1H), 7.20 (s, 1H), 7.14 (s, 1H), 6.93 (d, J = 8.8 Hz, 2H), 4.47 (s, 2H), 3.79 (s, 3H), 3.56-3.48 (m, 1H), 3.46-3.41 (m, 1H), 3.38 (d, J = 11.9 Hz, 1H), 3.17 (d, J = 12.7 Hz, 1H), 3.00 (d, J = 13.9 Hz, 1H), 2.97-2.91 (m, 1H), 2.90-2.84 (m, 1H), 1.72 (s, 6H), 1.40 (d, J = 6.6 Hz, 3H). | $[M + H]^+$ = 523 | 29 | 2.91 |
| A064 | 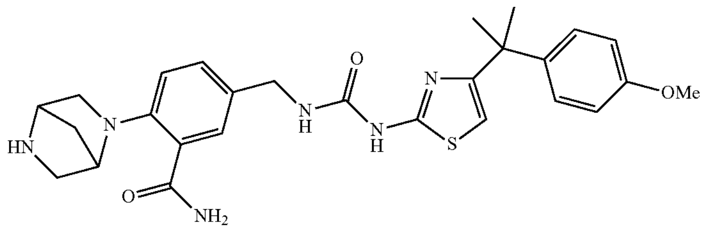 [SMILES: COc1ccc(C(C)(C)c2csc(NC(=O)NCc3ccc(N4CC5CC4CN5)c(C(N)=O)c3)n2)cc1] | 2-(2,5-diazabicyclo[2.2.1]heptan-2-yl)-5-((3-(4-(2-(4-methoxyphenyl)propan-2-yl)thiazol-2-yl)ureido)methyl)benzamide | $^1$H NMR (400 MHz, DMSO) δ 10.70 (s, 1H), 9.72 (s, 1H), 8.89 (s, 1H), 7.68 (s, 1H), 7.37 (s, 1H), 7.23 (d, J = 1.9 Hz, 1H), 7.18 (dd, J = 8.5, 1.9 Hz, 1H), 7.13 (d, J = 8.8 Hz, 2H), 6.80 (dd, J = 14.2, 8.7 Hz, 3H), 6.68 (d. J = 1.1 Hz, 1H), 5.44 (s, 5H), 4.48 (s, 1H), 4.35 (s, 1H), 4.22 (d, J = 5.1 Hz, 2H), 3.71 (s, 3H), 3.17 (s, 1H), 3.11 (d, J = 10.7 Hz, 1H), 2.04 (d, J = 10.5 Hz, 1H), 1.95-1.89 (m, 1H), 1.58 (s, 6H). | $[M + H]^+$ = 521 | 41 | 19.73 |

TABLE 4-continued

| Com. ID | Structure | Name | HNMR | LCMS | Kinase assay IC50 nM. | NFkB assay IC50 μM |
|---|---|---|---|---|---|---|
| A065 | 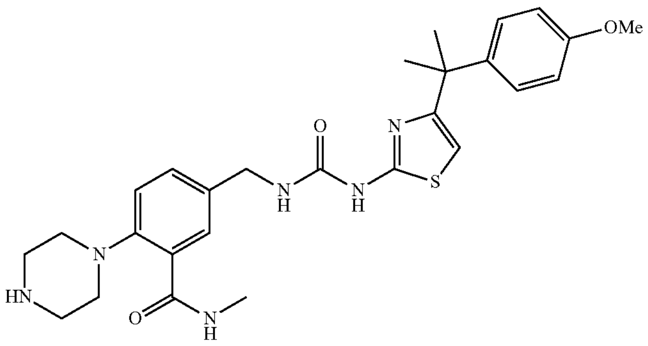 [SMILES: CNC(=O)c1cc(CNC(=O)Nc2nc(C(C)(C)c3ccc(OC)cc3)cs2)ccc1N1CCNCC1] | 5-((3-(4-(2-(4-methoxyphenyl)propan-2-yl)thiazol-2-yl)ureido)methyl)-N-methyl-2-(piperazin-1-yl)benzamide | $^1$H NMR (400 MHz, dmso) δ 9.42 (s, 1H), 8.45 (s, 1H), 7.51 (d, J = 28.5 Hz, 2H), 7.28 (d, J = 8.0 Hz, 1H), 7.07 (t, J = 10.0 Hz, 3H), 6.78 (d, J = 8.4 Hz, 2H), 6.67 (s, 1H), 4.23 (s, 2H), 3.66 (s, 3H), 3.18 (s, 4H), 3.06 (s, 4H), 2.77 (d, J = 3.7 Hz, 3H), 2.46 (s, 1H), 1.54 (s, 6H). | $[M + H]^+ = 523$ | 30 | 4.44 |
| A066 | 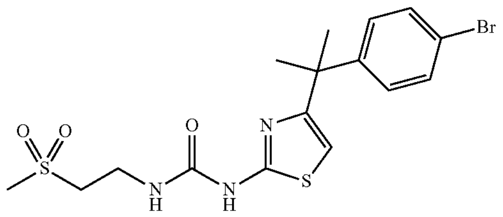 [SMILES: CC(C)(c1ccc(Br)cc1)c1csc(NC(=O)NCCS(C)(=O)=O)n1] | 1-(4-(2-(4-bromophenyl)propan-2-yl)thiazol-2-yl)-3-(2-(methylsulfonyl)ethyl)urea | | $[M + H]^+ = 446$ | 126 | 10.50 |
| A067 | 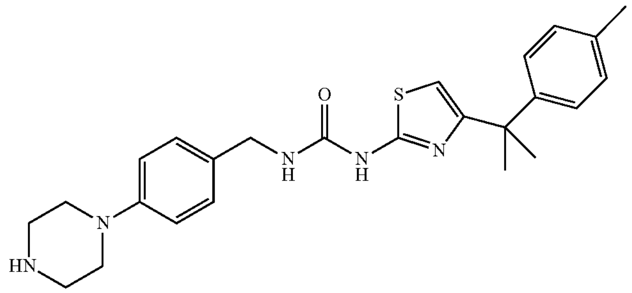 | 1-(4-(2-(4-iodophenyl)propan-2-yl)thiazol-2-yl)-3-(4-(piperazin-1-yl)benzyl)urea | | $[M + H]^+ = 562$ | 28 | 1.11 |

TABLE 4-continued
| Com. ID | Structure | Name | HNMR | LCMS | Kinase assay IC50 nM. | NFkB assay IC50 μM |
|---|---|---|---|---|---|---|
| A068 | 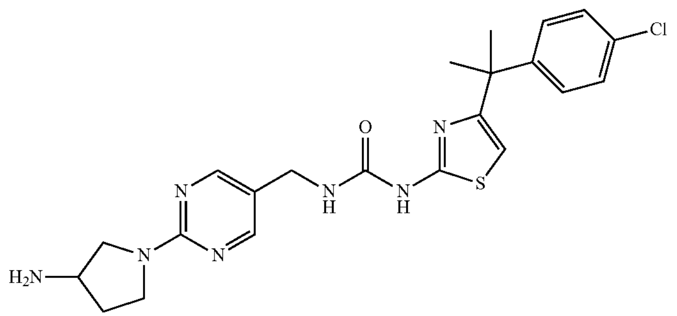 [SMILES: CC(C)(c1ccc(Cl)cc1)c1csc(NC(=O)NCc2cnc(N3CCC(N)C3)nc2)n1] | 1-((2-(3-aminopyrrolidin-1-yl)pyrimidin-5-yl)methyl)-3-(4-(2-(4-chlorophenyl)propan-2-yl)thiazol-2-yl)urea | | $[M + H]^+ = 472$ | 269 | |
| A069 | 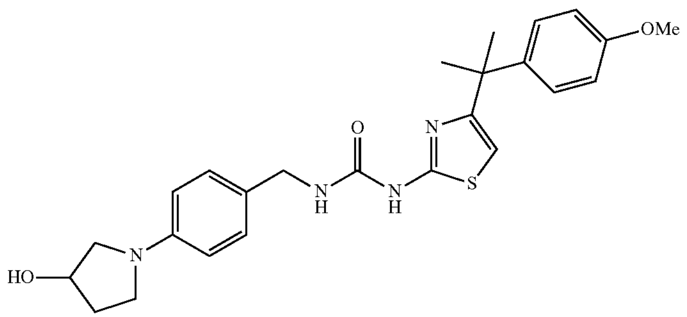 [SMILES: COc1ccc(C(C)(C)c2csc(NC(=O)NCc3ccc(N4CCC(O)C4)cc3)n2)cc1] | 1-(4-(3-hydroxypyrrolidin-1-yl)benzyl)-3-(4-(2-(4-methoxyphenyl)propan-2-yl)thiazol-2-yl)urea | | $[M + H]^+ = 467$ | 269 | |
| A070 | 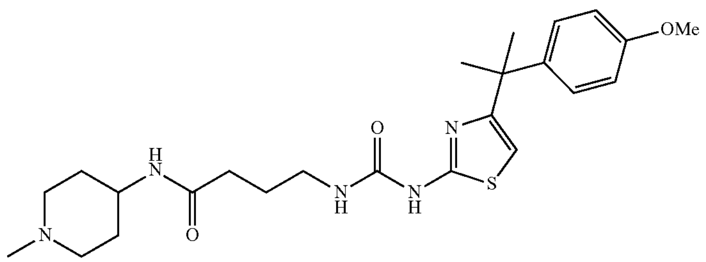 [SMILES: COc1ccc(C(C)(C)c2csc(NC(=O)NCCCC(=O)NC3CCN(C)CC3)n2)cc1] | 4-(3-(4-(2-(4-methoxyphenyl)propan-2-yl)thiazol-2-yl)ureido)-N-(1-methylpiperidin-4-yl)butanamide | | $[M + H]^+ = 474$ | 140 | 16.91 |

TABLE 4-continued
| Com. ID | Structure | Name | HNMR | LCMS | Kinase assay IC50 nM. | NFkB assay IC50 µM |
|---|---|---|---|---|---|---|
| A071 | 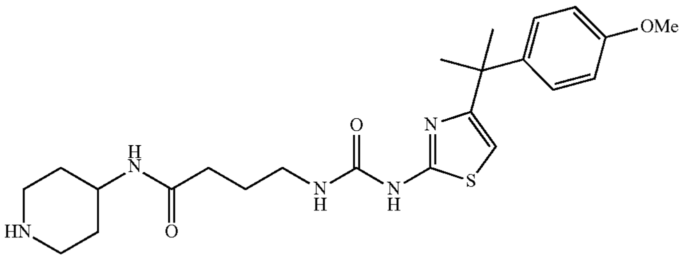 [SMILES: COc1ccc(C(C)(C)c2csc(NC(=O)NCCCC(=O)NC3CCNCC3)n2)cc1] | 4-(3-(4-(2-(4-methoxyphenyl) propan-2-yl)thiazol-2-yl)ureido)-N-(piperidin-4-yl)butanamide | | $[M + H]^+ = 460$ | 64 | |
| A072 | 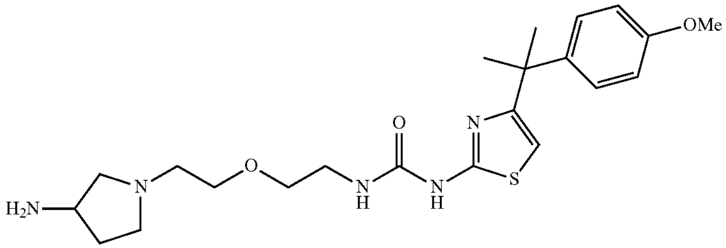 [SMILES: COc1ccc(C(C)(C)c2csc(NC(=O)NCCOCCN3CCC(N)C3)n2)cc1] | 1-(2-(2-(3-aminopyrrolidin-1-yl)ethoxy)ethyl)-3-(4-(2-(4-methoxyphenyl) propan-2-yl)thiazol-2-yl)urea | | $[M + H]^+ = 448$ | 143 | 1.45 |
| A073 | 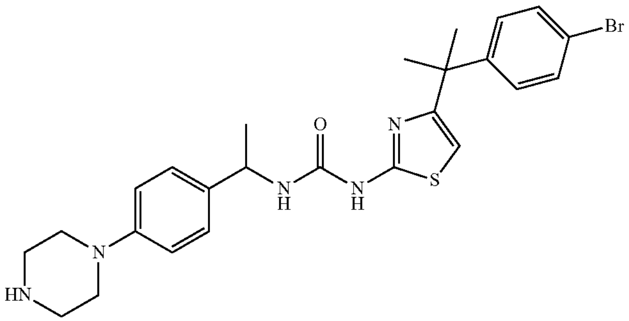 [SMILES: CC(NC(=O)Nc1nc(C(C)(C)c2ccc(Br)cc2)cs1)c1ccc(N2CCNCC2)cc1] | 1-(4-(2-(4-bromophenyl)propan-2-yl)thiazol-2-yl)-3-(1-(4-(piperazin-1-yl)phenyl)ethyl)urea | | $[M + H]^+ = 528$ | 85 | 2.79 |

TABLE 4-continued
| Com. ID | Structure | Name | HNMR | LCMS | Kinase assay IC50 nM. | NFkB assay IC50 μM |
|---|---|---|---|---|---|---|
| A074 | 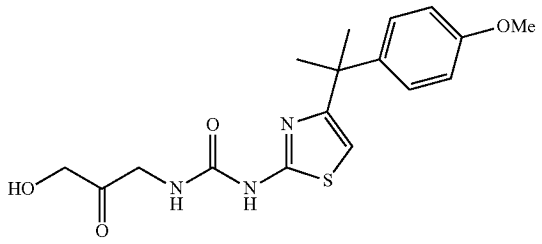 [SMILES: COc1ccc(C(C)(C)c2csc(NC(=O)NCC(=O)CO)n2)cc1] | 1-(3-hydroxy-2-oxopropyl)-3-(4-(2-(4-methoxyphenyl) propan-2-yl)thiazol-2-yl)urea | | $[M + H]^+ = 364$ | 61 | |
| A075 | 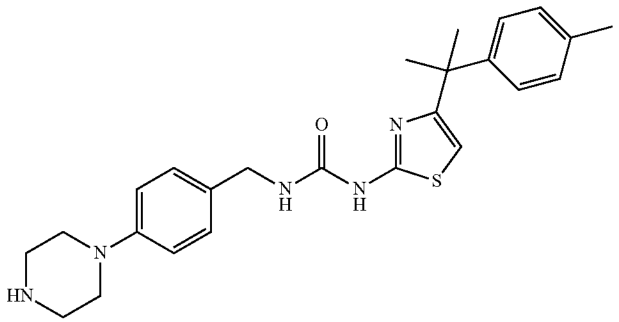 [SMILES: Cc1ccc(C(C)(C)c2csc(NC(=O)NCc3ccc(N4CCNCC4)cc3)n2)cc1] | 1-(4-(piperazin-1-yl)benzyl)-3-(4-(2-(p-tolyl)propan-2-yl)thiazol-2-yl)urea | | $[M + H]^+ = 450$ | 25 | 0.267 |
| A076 | 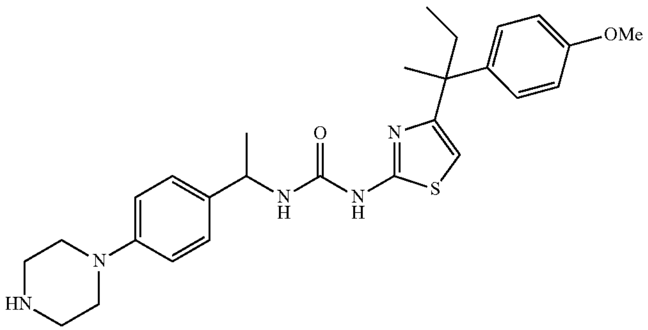 [SMILES: CCC(C)(c1ccc(OC)cc1)c1csc(NC(=O)NC(C)c2ccc(N3CCNCC3)cc2)n1] | 1-(4-(2-(4-methoxyphenyl)butan-2-yl)thiazol-2-yl)-3-(1-(4-(piperazin-1-yl)phenyl)ethyl)urea | | $[M + H]^+ = 494$ | 147 | 4.48 |

TABLE 4-continued

| Com. ID | Structure | Name | HNMR | LCMS | Kinase assay IC50 nM. | NFkB assay IC50 μM |
|---|---|---|---|---|---|---|
| A077 | 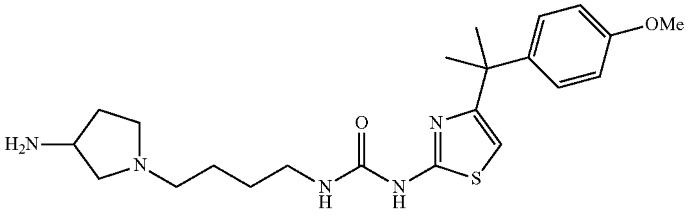 [SMILES: COc1ccc(C(C)(C)c2csc(NC(=O)NCCCCN3CCC(N)C3)n2)cc1] | 1-(4-(3-aminopyrrolidin-1-yl)butyl)-3-(4-(2-(4-methoxyphenyl)propan-2-yl)thiazol-2-yl)urea | | $[M + H]^+ = 432$ | 180 | 2.97 |
| A078 | 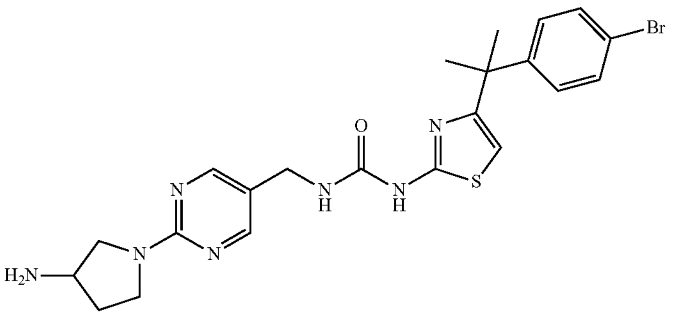 [SMILES: CC(C)(c1ccc(Br)cc1)c1csc(NC(=O)NCc2cnc(N3CCC(N)C3)nc2)n1] | 1-((2-(3-aminopyrrolidin-1-yl)pyrimidin-5-yl)methyl)-3-(4-(2-(4-bromophenyl)propan-2-yl)thiazol-2-yl)urea | $^1H$ NMR (400 MHz, DMSO) δ 8.46 (br, 5H), 7.39 (d, J = 8.8 Hz, 2H), 7.32 (s, 1H), 7.10 (d, J = 8.8 Hz, 2H), 6.73 (s, 1H), 4.15 (s, 2H), 3.70-3.59 (m, 5H), 2.30-2.27 (m, 1H), 2.16-2.13 (m, 1H), 1.53 (s, 6H). | $[M + H]^+ = 516.1$ | 8 | |
| A079 | 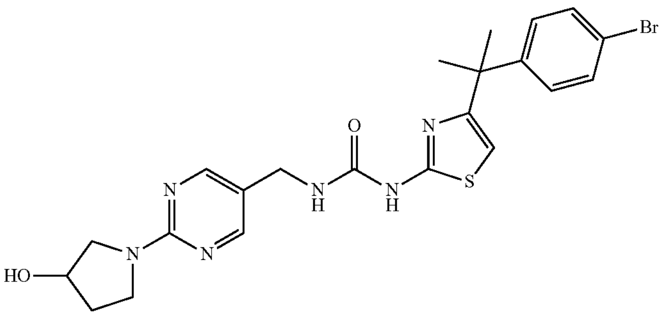 [SMILES: CC(C)(c1ccc(Br)cc1)c1csc(NC(=O)NCc2cnc(N3CCC(O)C3)nc2)n1] | 1-(4-(2-(4-bromophenyl)propan-2-yl)thiazol-2-yl)-3-((2-(3-hydroxypyrrolidin-1-yl)pyrimidin-5-yl)methyl)urea | $^1H$ NMR (400 MHz, CDCl3) δ 8.13 (s, 2H), 7.34 (d, J = 8.4 Hz, 2H), 7.05 (d, J = 8.4 Hz, 2H), 6.48 (s, 1H), 4.49 (br s, 1H), 4.07 (br d, J = 4.0 Hz, 2H), 3.85-3.50 (m, 4H), 2.22-1.92 (m, 3H), 1.59 (s, 6H), 1.26 (s, 1H). | $[M + H]^+ = 519.2$ | 170 | 1.68 |

TABLE 4-continued

| Com. ID | Structure | Name | HNMR | LCMS | Kinase assay IC50 nM. | NFkB assay IC50 µM |
|---|---|---|---|---|---|---|
| A080 | 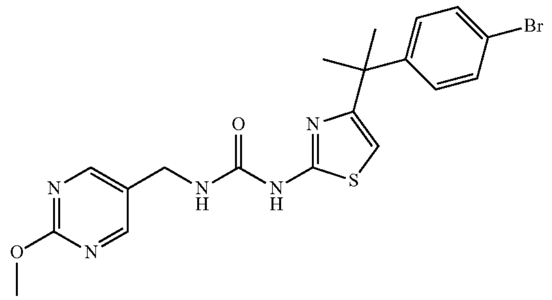 [SMILES: COc1ncc(CNC(=O)Nc2nc(C(C)(C)c3ccc(Br)cc3)cs2)cn1] | 1-(4-(2-(4-bromophenyl)propan-2-yl)thiazol-2-yl)-3-((2-methoxypyrimidin-5-yl)methyl)urea | $^1$H NMR (400 MHz, DMSO-$d_6$) δ 10.72 (s, 1H), 8.49 (s, 2H), 7.39 (d, J = 8.56 Hz, 2H), 7.14-7.07 (m, 2H), 6.85-6.79 (m, 1H), 6.70 (s, 1H), 4.20 (s, 2H), 3.82-3.87 (m, 3H), 1.53 (s, 6H). | $[M + H]^+$ = 461.9 | 172 | 13.30 |
| A081 | 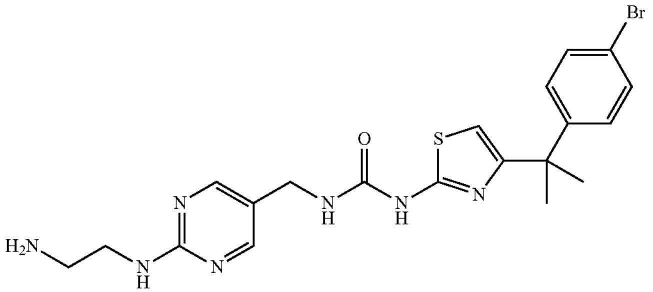 [SMILES: CC(C)(c1ccc(Br)cc1)c1csc(NC(=O)NCc2cnc(NCCN)nc2)n1] | 1-((2-((2-aminoethyl)amino) pyrimidin-5-yl)methyl)-3-(4-(2-(4-bromophenyl)propan-2-yl)thiazol-2-yl)urea | $^1$H NMR (400 MHz, DMSO-$d_6$) δ 8.44 (s, 2H), 8.06 (br s, 3H), 7.43 (d, J = 8.56 Hz, 2H), 7.24 (br s, 1H), 7.14 (d, J = 8.56 Hz, 2H), 6.75 (s, 1H), 4.17 (br d, J = 5.38 Hz, 2H), 3.52-3.65 (m, 2H), 2.88-3.04 (m, 2H), 1.57 (s, 6H). | $[M + H]^+$ = 492.1 | 17 | 1.84 |
| A082 | 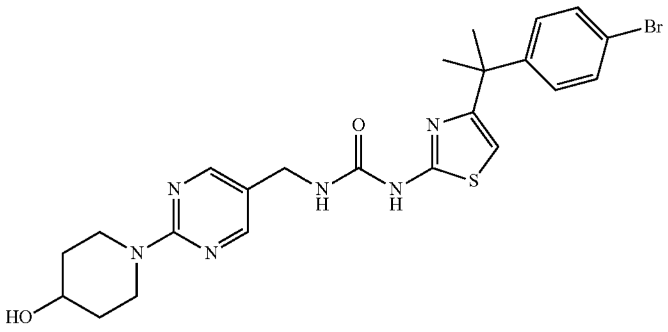 [SMILES: CC(C)(c1ccc(Br)cc1)c1csc(NC(=O)NCc2cnc(N3CCC(O)CC3)nc2)n1] | 1-(4-(2-(4-bromophenyl)propan-2-yl)thiazol-2-yl)-3-((2-(4-hydroxypiperidin-1-yl)pyrimidin-5-yl)methyl)urea | $^1$H NMR (400 MHz, DMSO-$d_6$) δ 10.65 (s, 1H), 8.27 (s, 2H), 7.42 (d, J = 8.6 Hz, 2H), 7.14 (d, J = 8.8 Hz, 2H), 6.77-6.67 (m, 2H), 4.74-4.68 (m, 1H), 4.27-4.19 (m, 2H), 4.12-4.06 (m, 2H), 3.75-3.66 (m, 1H), 3.26-3.18 (m, 2H), 1.79-1.71 (m, 2H), 1.57 (s, 6H), 1.31-1.24 (m, 2H). | $[M + H]^+$ = 533.0 | 125 | 6.15 |

TABLE 4-continued

| Com. ID | Structure | Name | HNMR | LCMS | Kinase assay IC50 nM. | NFkB assay IC50 µM |
|---|---|---|---|---|---|---|
| A083 | 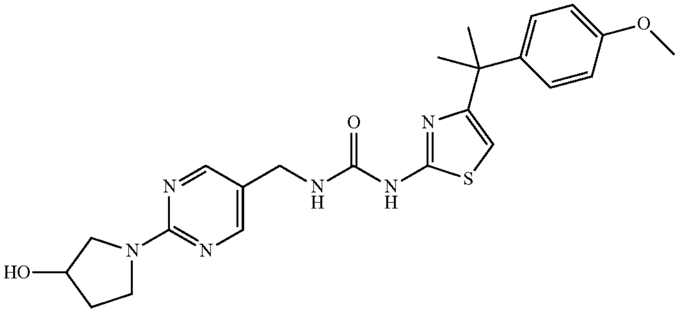 [SMILES: COc1ccc(C(C)(C)c2csc(NC(=O)NCc3cnc(N4CCC(O)C4)nc3)n2)cc1] | 1-((2-(3-hydroxypyrrolidin-1-yl)pyrimidin-5-yl)methyl)-3-(4-(2-(4-methoxyphenyl)propan-2-yl)thiazol-2-yl)urea | $^1$H NMR (400 MHz, $CDCl_3$) δ 8.16 (s, 2H), 7.15-7.03 (m, 2H), 6.79-6.77 (m, 1H), 6.83-6.72 (m, 1H), 6.46-6.38 (m, 1H), 4.55-4.49 (m, 1H), 4.15-4.06 (m, 2H), 3.77 (s, 3H), 3.71-3.59 (m, 4H), 2.13-2.02 (m, 2H), 1.58 (s, 6H) | $[M + H]^+$ = 469.2 | 111 | 0.68 |
| A084 | 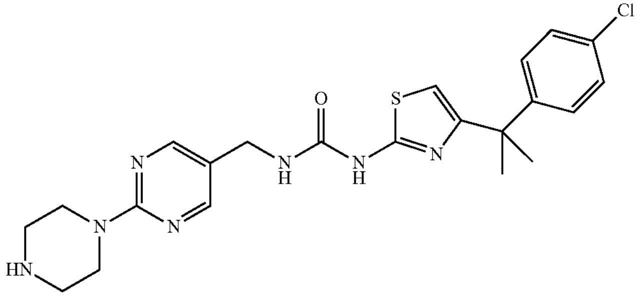 [SMILES: CC(C)(c1ccc(Cl)cc1)c1csc(NC(=O)NCc2cnc(N3CCNCC3)nc2)n1] | 1-(4-(2-(4-chlorophenyl)propan-2-yl)thiazol-2-yl)-3-((2-(piperazin-1-yl)pyrimidin-5-yl)methyl)urea | $^1$H NMR (400 MHz, dmso) δ 9.17 (s, 1H), 8.34 (s, 2H), 7.25 (d. J = 8.0 Hz, 2H), 7.16 (d, J = 8.0 Hz, 2H), 7.02 (s. 1H), 6.69 (s, 1H), 4.11 (s, 2H), 3.90 (s, 4H), 3.09 (s, 4H), 1.53 (s, 6H). | $[M + H]^+$ = 472 | 22 | 0.34 |
| A085 | 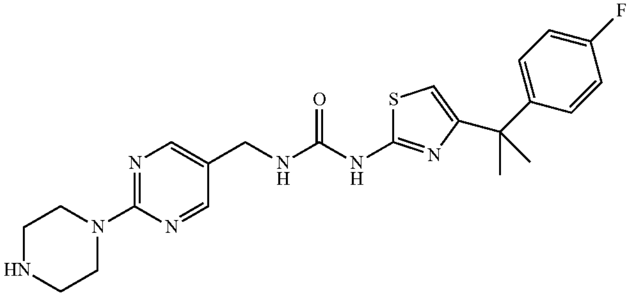 [SMILES: CC(C)(c1ccc(F)cc1)c1csc(NC(=O)NCc2cnc(N3CCNCC3)nc2)n1] | 1-(4-(2-(4-fluorophenyl)propan-2-yl)thiazol-2-yl)-3-((2-(piperazin-1-yl)pyrimidin-5-yl)methyl)urea | $^1$H NMR (400 MHz, dmso) δ 9.34 (s, 1H), 8.35 (s, 1H), 7.22 (d, J = 40.8 Hz, 2H), 7.01 (s, 2H), 6.69 (s, 1H), 4.11 (s, 2H), 3.91 (s, 4H), 3.08 (s, 4H), 1.54 (s, 6H). | $[M + H]^+$ = 456 | 85 | 0.49 |

TABLE 4-continued

| Com. ID | Structure | Name | HNMR | LCMS | Kinase assay IC50 nM. | NFkB assay IC50 µM |
|---|---|---|---|---|---|---|
| A086 | 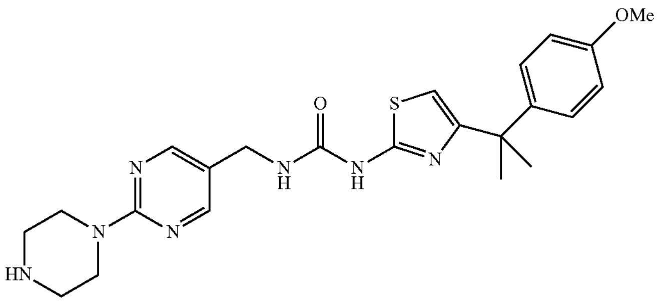 [SMILES: COc1ccc(C(C)(C)c2csc(NC(=O)NCc3cnc(N4CCNCC4)nc3)n2)cc1] | 1-(4-(2-(4-methoxyphenyl)propan-2-yl)thiazol-2-yl)-3-((2-(piperazin-1-yl)pyrimidin-5-yl)methyl)urea | $^{1}$H NMR (400 MHz, cd3od) δ 8.47 (s, 2H), 7.17 (s, 2H), 7.09 (s, 1H), 6.88 (s, 2H), 4.32 (s, 2H), 4.09 (s, 3H), 3.74 (s, 4H), 3.32 (d. J = 5.5 Hz, 4H), 1.67 (s, 6H). | $[M + H]^+$ = 468 | 16 | 0.39 |
| A087 | 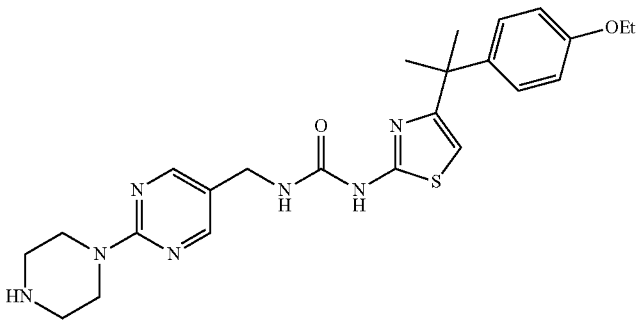 [SMILES: CCOc1ccc(C(C)(C)c2csc(NC(=O)NCc3cnc(N4CCNCC4)nc3)n2)cc1] | 1-(4-(2-(4-ethoxyphenyl)propan-2-yl)thiazol-2-yl)-3-((2-(piperazin-1-yl)pyrimidin-5-yl)methyl)urea | $^{1}$H NMR (400 MHz, cd3od) δ 8.57 (s, 2H), 7.15 (d, J = 8.2 Hz, 2H), 7.11 (s, 1H), 6.87 (d, J = 8.2 Hz, 2H), 4.37 (s, 2H), 4.14 (s, 4H), 3.99 (q, J = 6.9 Hz, 2H), 3.34 (d, J = 12.6 Hz, 4H), 1.68 (s, 6H), 1.34 (t, J = 6.9 Hz, 3H) | $[M + H]^+$ = 482 | 89 | 1.74 |
| A088 | 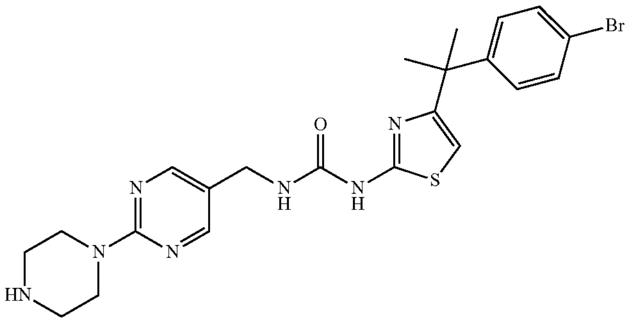 [SMILES: CC(C)(c1ccc(Br)cc1)c1csc(NC(=O)NCc2cnc(N3CCNCC3)nc2)n1] | 1-(4-(2-(4-bromophenyl)propan-2-yl)thiazol-2-yl)-3-((2-(piperazin-1-yl)pyrimidin-5-yl)methyl)urea compound with methane (1:1) | $^{1}$H NMR (400 MHz, MeOD) δ 8.51 (s, 2H), 7.53-7.51 (m, 2H), 7.24-7.22 (m, 2H), 7.15 (s, 1H), 4.36 (s, 2H), 4.14-4.12 (m, 4H), 3.34-3.33 (m, 4H), 1.73 (s, 6H). | $[M + H]^+$ = 518.0 | 13 | 1.45 |

TABLE 4-continued

| Com. ID | Structure | Name | HNMR | LCMS | Kinase assay IC50 nM. | NFkB assay IC50 μM |
|---|---|---|---|---|---|---|
| A089 | 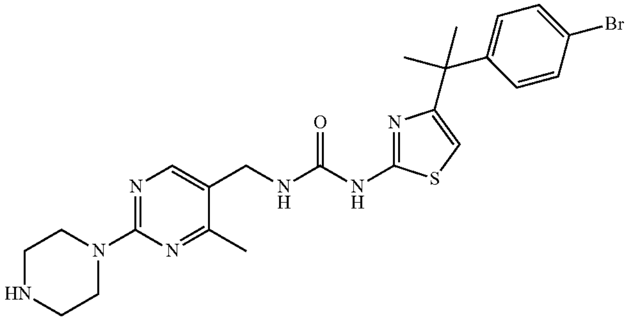 [SMILES: Cc1nc(N2CCNCC2)ncc1CNC(=O)Nc1nc(C(C)(C)c2ccc(Br)cc2)cs1] | 1-(4-(2-(4-bromophenyl)propan-2-yl)thiazol-2-yl)-3-((4-methyl-2-(piperazin-1-yl)pyrimidin-5-yl)methyl)urea | $^1$H NMR (400 MHz, DMSO-d6) δ 10.70 (br s, 1H), 9.37 (br s, 2H), 8.21 (s, 1H), 7.42 (d, J = 8.3 Hz, 2H), 7.34-7.26 (m.1H), 7.14 (d, J = 8.6 Hz, 2H), 6.75 (s, 1H), 4.20 (br d, J = 5.1 Hz, 2H), 4.01-3.91 (m, 4H), 3.12 (br s, 4H), 2.37 (s, 3H), 1.57 (s, 6H) | $[M + H]^+ = 532$ | 26 | 1.19 |
| A090 | 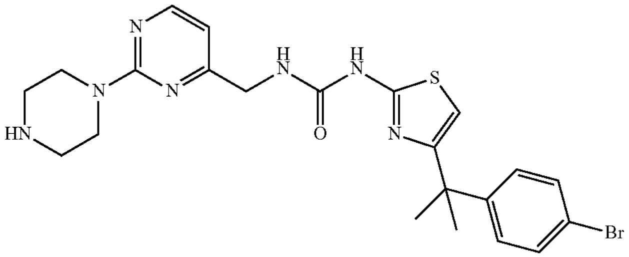 [SMILES: CC(C)(c1ccc(Br)cc1)c1csc(NC(=O)NCc2ccnc(N3CCNCC3)n2)n1] | 1-(4-(2-(4-bromophenyl)propan-2-yl)thiazol-2-yl)-3-((2-(piperazin-1-yl)pyrimidin-4-yl)methyl)urea | $^1$H NMR (400 MHz, DMSO-d6)) 9.45 (br s, 2H), 8.35 (d, J = 5.1 Hz, 1H), 7.41-7.47 (m, 3H). 7.24-7.34 (m, 2H), 7.11-7.21 (m, 3H), 6.75 (s, 1H), 6.67 (d, J = 5.1 Hz, 1H), 4.28 (br s, 1H), 4.27 (br s, 1H), 4.05 (s, 1H), 3.05 (s. 1H), 1.58 ppm (s, 6H) | | 178 | 1.11 |
| A091 | 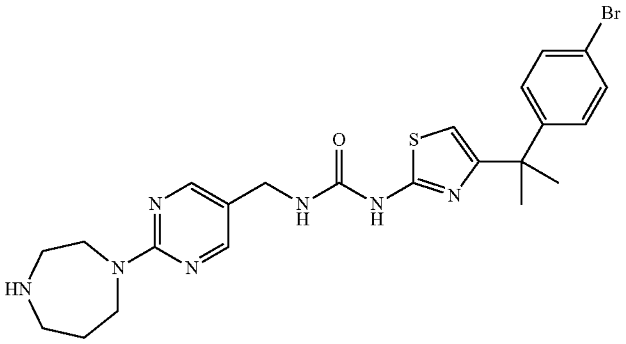 [SMILES: CC(C)(c1ccc(Br)cc1)c1csc(NC(=O)NCc2cnc(N3CCCNCC3)nc2)n1] | 1-((2-(1,4-diazepan-1-yl)pyrimidin-5-yl)methyl)-3-(4-(2-(4-bromophenyl)propan-2-yl)thiazol-2-yl)urea | $^1$H NMR (400 MHz, DMSO-d6) δ 9.24 (br s, 2H), 8.31 (d, J = 5.0 Hz, 1H), 7.45 (s, 1H), 7.42 (d, J = 3.3 Hz, 2H), 7.29 (s, 1H), 7.17 (d, J = 1.8 Hz, 2H), 7.15-7.14 (m, 1H), 6.74 (s, 1H), 6.64 (d, J = 5.0 Hz, 1H), 4.28 (br d, J = 5.3 Hz, 2H), 4.01 (br s, 2H), 3.20 (br s, 2H), 3.16-3.08 (m, 2H), 2.09-2.01 (m, 2H), 1.58 (s, 6H), 1.26-1.19 (m, 2H). | $[M + H]^+ = 530.0$ | 135 | 3.45 |

TABLE 4-continued
| Com. ID | Structure | Name | HNMR | LCMS | Kinase assay IC50 nM. | NFkB assay IC50 μM |
|---|---|---|---|---|---|---|
| A092 | 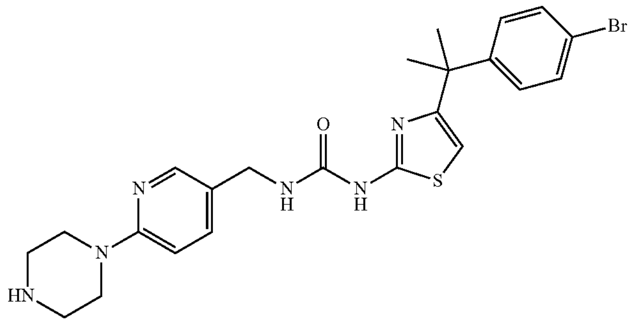 [SMILES: CC(C)(c1ccc(Br)cc1)c1csc(NC(=O)NCc2ccc(N3CCNCC3)nc2)n1] | 1-(4-(2-(4-bromophenyl)propan-2-yl)thiazol-2-yl)-3-((6-(piperazin-1-yl)pyridin-3-yl)methyl)urea | $^1$H NMR (400 MHz, DMSO-d6) ¿ 10.90 (br s, 1H), 9.66 (br s, 2H), 8.05-7.92 (m, 2H), 7.48-7.28 (m, 4H), 7.21-7.10 (m, 2H), 6.75 (s, 1H), 4.30-4.20 (m, 2H), 4.04-3.92 (m, 4H), 3.24 (br s, 4H), 1.57 (s, 6H) | $[M + H]^+$ = 517.2 | 20 | 0.57 |
| A093 | 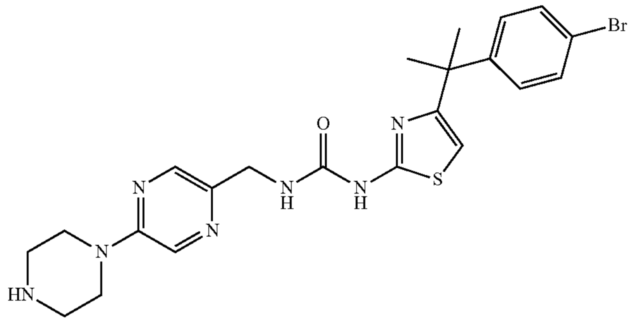 [SMILES: CC(C)(c1ccc(Br)cc1)c1csc(NC(=O)NCc2cnc(N3CCNCC3)cn2)n1] | 1-(4-(2-(4-bromophenyl)propan-2-yl)thiazol-2-yl)-3-((5-(piperazin-1-yl)pyrazin-2-yl)methyl)urea | $^1$H NMR (400 MHz, DMSO-d6) δ 9.26 (s, 2H), 8.30 (s, 1H), 8.07 (s, 2H), 7.41-7.36 (m, 2H), 7.13-7.11 (m, 3H), 6.72 (s, 1H), 4.29-4.28 (m, 2H), 3.76-3.74 (m, 4H), 3.16-3.14 (m, 4H), 1.54 (s, 6H). | $[M + H]^+$ = 516.1 | 9 | 0.32 |

TABLE 4-continued

| Com. ID | Structure | Name | HNMR | LCMS | Kinase assay IC50 nM. | NFkB assay IC50 µM |
|---|---|---|---|---|---|---|
| A094 | 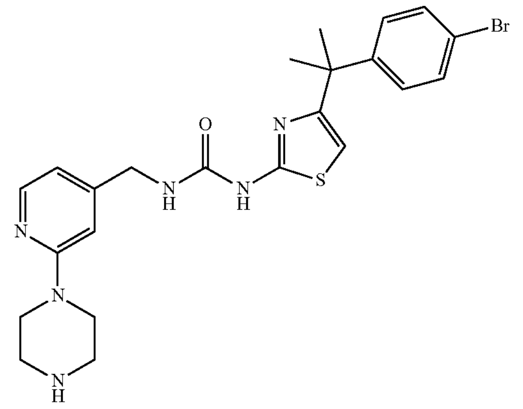 | 1-(4-(2-(4-bromophenyl)propan-2-yl)thiazol-2-yl)-3-((6-(piperazin-1-yl)pyrimidin-4-yl)methyl)urea | $^1$H NMR (400 MHz, DMSO-$d_6$) δ 11.05 (br s, 1H), 9.70 (br s, 2H), 8.86 (s, 1H), 7.48-7.43 (m, 2H), 7.39-7.33 (m, 1H), 7.21-7.14 (m, 3H), 6.78 (s, 1H), 4.45 (br d, J = 6.0 Hz, 2H), 4.11 (br s, 4H), 3.25 (br s, 4H), 1.59 (s, 6H). | $[M + H]^+$ = 518.2 | 73 | 1.29 |
| A095 | 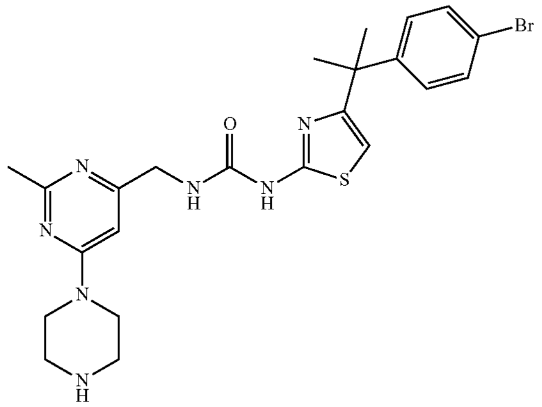 [SMILES: Cc1nc(CNC(=O)Nc2nc(C(C)(C)c3ccc(Br)cc3)cs2)cc(N2CCNCC2)n1] | 1-(4-(2-(4-bromophenyl)propan-2-yl)thiazol-2-yl)-3-((2-methyl-6-(piperazin-1-yl)pyrimidin-4-yl)methyl)urea | $^1$H NMR (400 MHz, DMSO) δ 7.40 (d, J = 8.4 Hz, 2H), 7.13 (d. J = 8.8 Hz, 2H), 6.87 (s, 1H), 6.70 (s, 1H), 6.43 (s, 1H), 4.12 (s, 2H), 3.46-3.39 (m, 4H), 2.69-2.67 (m, 4H), 2.30 (s, 3H), 1.55 (s, 6H). | $[M + H]^+$ = 532.1 | 32 | |

TABLE 4-continued

| Com. ID | Structure | Name | HNMR | LCMS | Kinase assay IC50 nM. | NFkB assay IC50 μM |
|---|---|---|---|---|---|---|
| A096 | 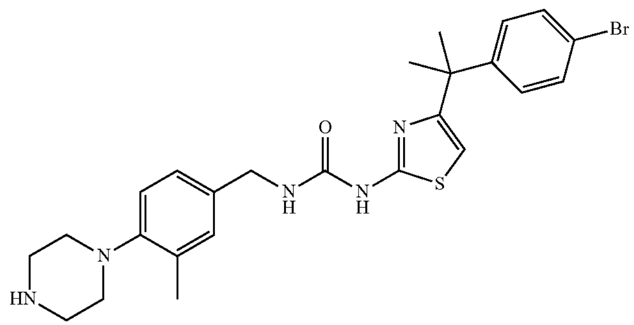 [SMILES: Cc1cc(CNC(=O)Nc2nc(C(C)(C)c3ccc(Br)cc3)cs2)ccc1N1CCNCC1] | 1-(4-(2-(4-bromophenyl)propan-2-yl)thiazol-2-yl)-3-(3-methy 1-4-(piperazin-1-yl)benzyl)urea | $^1$H NMR (400 MHz, DMSO-$d_6$) δ 10.61 (br s, 1H), 9.04 (br s, 2H), 7.40 (d, J = 8.8 Hz, 2H), 7.12 (d, J = 8.8 Hz, 2H), 7.07-6.99 (m, 2H), 6.95 (br d, J = 7.6 Hz. 2H), 6.71 (s, 1H), 4.18 (br d, J = 5.6 Hz, 2H), 3.17 (br s, 4H), 2.97 (br d, J = 4.4 Hz, 4H), 2.19 (s, 3H), 1.54 (s, 6H). | $[M + Na]^+$ = 552.0 | 69 | 1.43 |
| A097 | 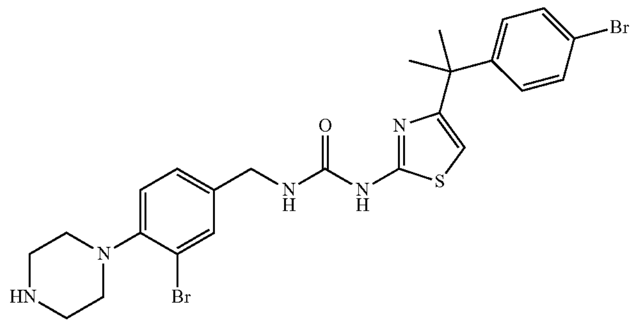 [SMILES: CC(C)(c1ccc(Br)cc1)c1csc(NC(=O)NCc2ccc(N3CCNCC3)c(Br)c2)n1] | 1-(3-bromo-4-(piperazin-1-yl)benzyl)-3-(4-(2-(4-bromophenyl)propan-2-yl)thiazol-2-yl)urea | $^1$H NMR (400 MHz, $CDCl_3$) δ 9.18 (brs, 2H), 7.43 (d, J = 8.4 Hz, 2H), 7.57-7.29 (m, 1H), 7.18-7.13 (m, 4H), 6.75 (s, 1H), 4.24 (s, 2H), 3.23-3.14 (m, 8H), 1.58 (s, 6H). | $[M + H]^+$ = 593.03 | 87 | 1.42 |
| A098 | 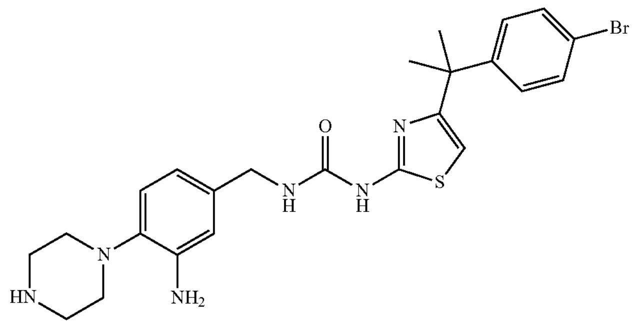 [SMILES: CC(C)(c1ccc(Br)cc1)c1csc(NC(=O)NCc2ccc(N3CCNCC3)c(N)c2)n1] | 1-(3-amino-4-(piperazin-1-yl)benzyl)-3-(4-(2-(4-bromophenyl)propan-2-yl)thiazol-2-yl)urea | $^1$H NMR (400 MHz, DMSO) δ 10.76 (br, 1H), 9.22 (br, 2H), 7.42-7.39 (m, 2H), 7.26-7.12 (m, 6H), 6.71 (s, 1H), 4.26-4.25 (m, 2H), 3.24-3.22 (m, 4H), 3.03-3.02 (m, 4H), 1.55 (s, 6H). | $[M + H]^+$ = 530.9 | 31 | 1.07 |

TABLE 4-continued
| Com. ID | Structure | Name | HNMR | LCMS | Kinase assay IC50 nM. | NFkB assay IC50 μM |
|---|---|---|---|---|---|---|
| A099 | 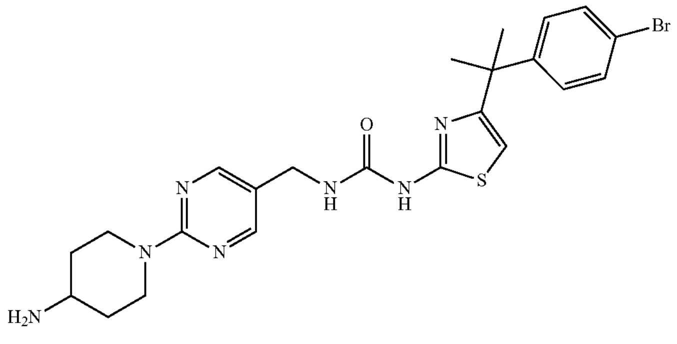 [SMILES: CC(C)(c1ccc(Br)cc1)c1csc(NC(=O)NCc2cnc(N3CCC(N)CC3)nc2)n1] | 1-((2-(4-aminopiperidin-1-yl)pyrimidin-5-yl)methyl)-3-(4-(2-(4-bromophenyl)propan-2-yl)thiazol-2-yl)urea | $^1$H NMR (400 MHz, DMSO-d6) δ 10.94-10.50 (m, 1H), 8.34 (s, 2H), 8.25-7.95 (m, 3H), 7.42 (d, J = 8.5 Hz, 2H), 7.19-6.92 (m, 3H), 6.74 (s, 1H), 4.71-4.54 (m, 2H), 4.19-4.05 (m, 2H), 3.38-3.24 (m, 1H), 3.04-2.87 (m, 2H), 2.03-1.90 (m, 2H), 1.57 (s, 6H), 1.49-1.35 (m, 2H). | $[M + H]^+ = 532.0$ | 13 | 0.45 |
| A100 | 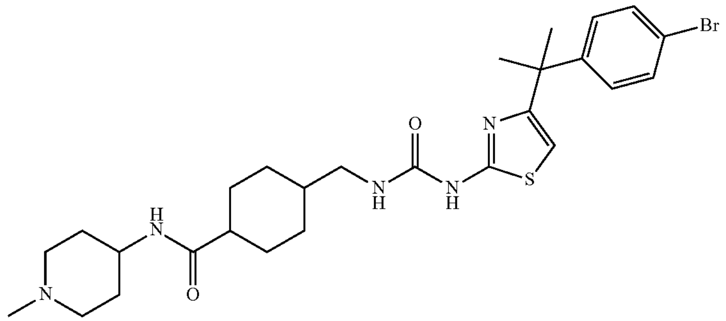 [SMILES: CN1CCC(NC(=O)C2CCC(CNC(=O)Nc3nc(C(C)(C)c4ccc(Br)cc4)cs3)CC2)CC1] | 4-((3-(4-(2-(4-bromophenyl)propan-2-yl)thiazol-2-yl)ureido)methyl)-N-(1-methylpiperidin-4-yl)cyclohexane-1-carboxamide | | $[M + H]^+ = 576$ | 72 | 1.37 |

TABLE 4-continued
| Com. ID | Structure | Name | HNMR | LCMS | Kinase assay IC50 nM. | NFkB assay IC50 µM |
|---|---|---|---|---|---|---|
| A101 | 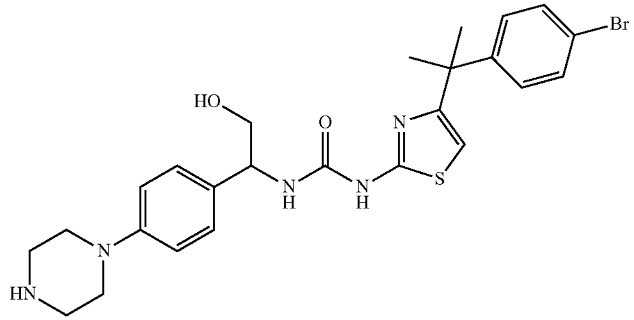 [SMILES: CC(C)(c1ccc(Br)cc1)c1csc(NC(=O)NC(CO)c2ccc(N3CCNCC3)cc2)n1] | 1-(4-(2-(4-bromophenyl)propan-2-yl)thiazol-2-yl)-3-(2-hydroxy-1-(4-(piperazin-1-yl)phenyl)ethyl)urea | | $[M + H]^+ = 544$ | 50 | 1.65 |
| A102 | 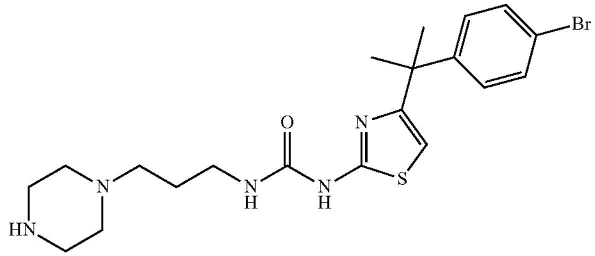 [SMILES: CC(C)(c1ccc(Br)cc1)c1csc(NC(=O)NCCCN2CCNCC2)n1] | 1-(4-(2-(4-bromophenyl)propan-2-yl)thiazol-2-yl)-3-(3-(piperazin-1-yl)propyl)urea | | $[M + H]^+ = 466$ | 90 | 0.71 |
| A103 | 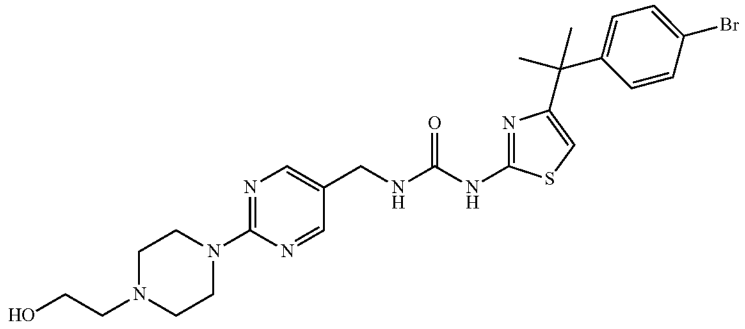 [SMILES: CC(C)(c1ccc(Br)cc1)c1csc(NC(=O)NCc2cnc(N3CCN(CCO)CC3)nc2)n1] | 1-(4-(2-(4-bromophenyl)propan-2-yl)thiazol-2-yl)-3-((2-(4-(2-hydroxyethyl)piperazin-1-yl)pyrimidin-5-yl)methyl)urea | | $[M + H]^+ = 560$ | 97 | 6.2 |

TABLE 4-continued
| Com. ID | Structure | Name | HNMR | LCMS | Kinase assay IC50 nM. | NFkB assay IC50 µM |
|---|---|---|---|---|---|---|
| A104 | 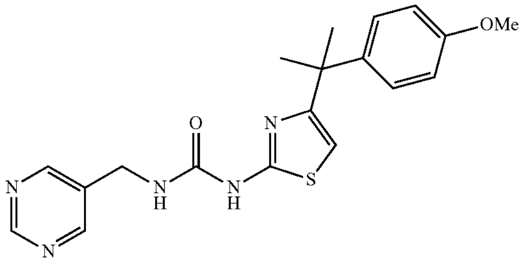 [SMILES: COc1ccc(C(C)(C)c2csc(NC(=O)NCc3cncnc3)n2)cc1] | 1-(4-(2-(4-methoxyphenyl)propan-2-yl)thiazol-2-yl)-3-(pyrimidin-5-ylmethyl)urea | | $[M + H]^+ = 384$ | 223 | 1.69 |
| A105 | 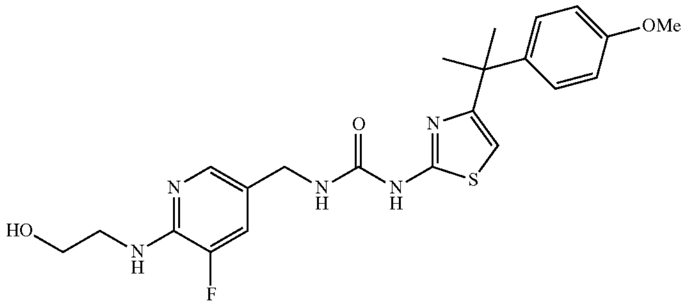 [SMILES: COc1ccc(C(C)(C)c2csc(NC(=O)NCc3cnc(NCCO)c(F)c3)n2)cc1] | 1-((5-fluoro-6-((2-hydroxyethyl)amino)pyridin-3-yl)methyl)-3-(4-(2-(4-methoxyphenyl)propan-2-yl)thiazol-2-yl)urea | | $[M + H]^+ = 460$ | 144 | 1.02 |
| A106 | 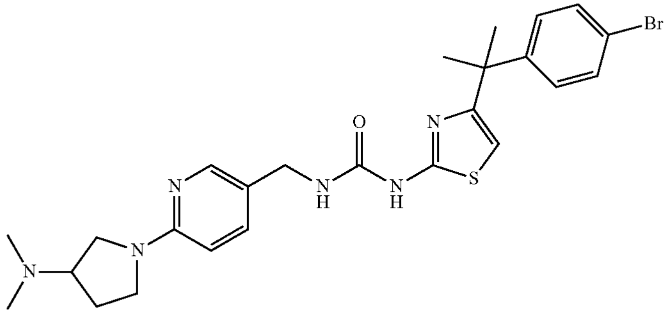 [SMILES: CN(C)C1CCN(c2ccc(CNC(=O)Nc3nc(C(C)(C)c4ccc(Br)cc4)cs3)cn2)C1] | 1-(4-(2-(4-bromophenyl)propan-2-yl)thiazol-2-yl)-3-((6-(3-(dimethylamino)pyrrolidin-1-yl)pyridin-3-yl)methyl)urea | | $[M + H]^+ = 543$ | 48 | 6.72 |

TABLE 4-continued
| Com. ID | Structure | Name | HNMR | LCMS | Kinase assay IC50 nM. | NFkB assay IC50 μM |
|---|---|---|---|---|---|---|
| A107 | 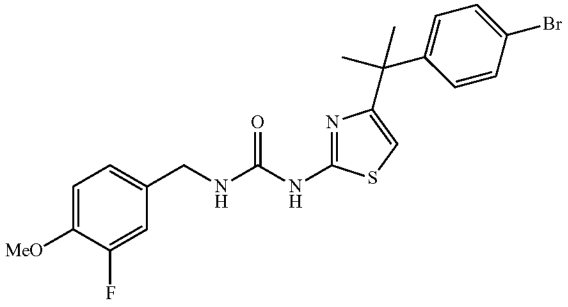 [SMILES: COc1ccc(CNC(=O)Nc2nc(C(C)(C)c3ccc(Br)cc3)cs2)cc1F] | 1-(4-(2-(4-bromophenyl)propan-2-yl) thiazol-2-yl)-3-(3-fluoro-4-methoxybenzyl)urea | | $[M + H]^+ = 478$ | 216 | |
| A108 | 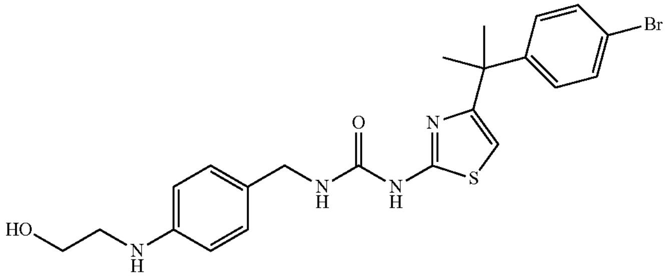 [SMILES: CC(C)(c1ccc(Br)cc1)c1csc(NC(=O)NCc2ccc(NCCO)cc2)n1] | 1-(4-(2-(4-bromophenyl)propan-2-yl)thiazol-2-yl)-3-(4-((2-hydroxyethyl)amino) benzyl)urea | | $[M + H]^+ = 489$ | 244 | 0.82 |
| A109 | 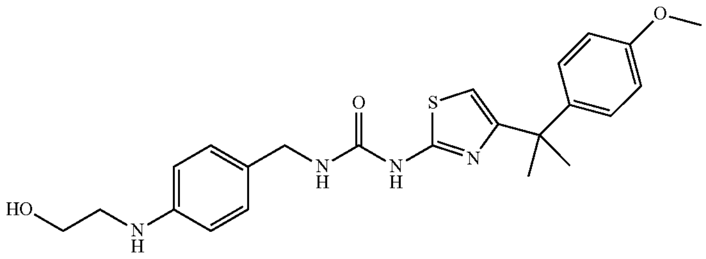 [SMILES: COc1ccc(C(C)(C)c2csc(NC(=O)NCc3ccc(NCCO)cc3)n2)cc1] | 1-(4-((2-hydroxyethyl)amino) benzyl)-3-(4-(2-(4-methoxyphenyl) propan-2-yl)thiazol-2-yl)urea | | $[M + H]^+ = 441$ | 146 | |

TABLE 4-continued
| Com. ID | Structure | Name | HNMR | LCMS | Kinase assay IC50 nM. | NFkB assay IC50 μM |
|---|---|---|---|---|---|---|
| A110 | 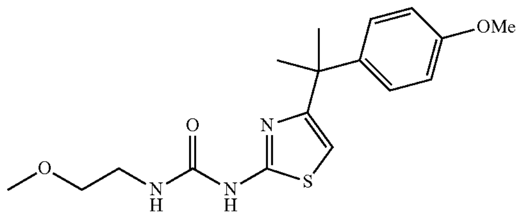 [SMILES: COCCNC(=O)Nc1nc(C(C)(C)c2ccc(OC)cc2)cs1] | 1-(2-methoxyethyl)-3-(4-(2-(4-methoxyphenyl)propan-2-yl)thiazol-2-yl)urea | | $[M + H]^+ = 350$ | 193 | 0.94 |
| A111 | 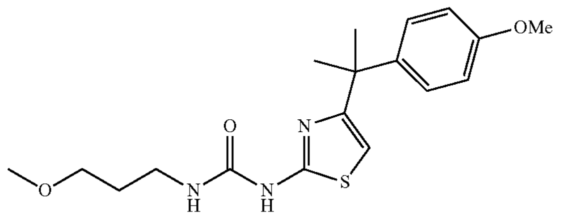 [SMILES: COCCCNC(=O)Nc1nc(C(C)(C)c2ccc(OC)cc2)cs1] | 1-(4-(2-(4-methoxyphenyl)propan-2-yl)thiazol-2-yl)-3-(3-methoxypropyl)urea | | $[M + H]^+ = 364$ | 127 | 1.24 |
| A112 | 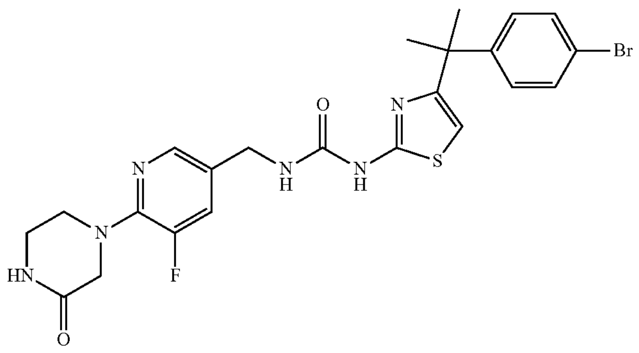 [SMILES: CC(C)(c1ccc(Br)cc1)c1csc(NC(=O)NCc2cnc(N3CCNC(=O)C3)c(F)c2)n1] | 1-(4-(2-(4-bromophenyl)propan-2-yl)thiazol-2-yl)-3-((5-fluoro-6-(3-oxopiperazin-1-yl)pyridin-3-yl)methyl)urea | | $[M + H]^+ = 547$ | 334 | |

TABLE 4-continued
| Com. ID | Structure | Name | HNMR | LCMS | Kinase assay IC50 nM. | NFkB assay IC50 μM |
|---|---|---|---|---|---|---|
| A113 | 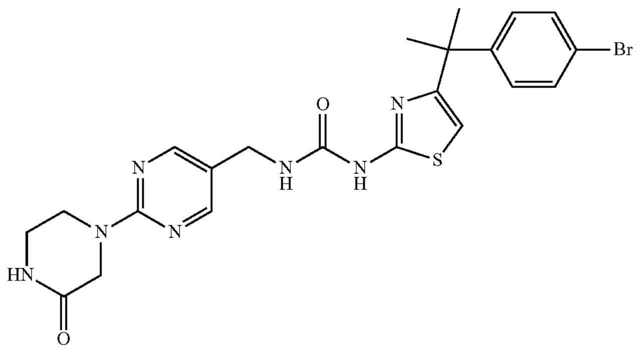 [SMILES: CC(C)(c1ccc(Br)cc1)c1csc(NC(=O)NCc2cnc(N3CCNC(=O)C3)nc2)n1] | 1-(4-(2-(4-bromophenyl)propan-2-yl)thiazol-2-yl)-3-((2-(3-oxopiperazin-1-yl)pyrimidin-5-yl)methyl)urea | | $[M + H]^+ = 530$ | 126 | |
| A114 | 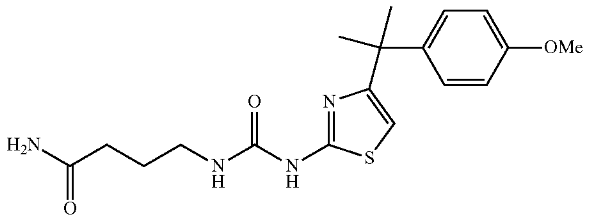 [SMILES: COc1ccc(C(C)(C)c2csc(NC(=O)NCCCC(N)=O)n2)cc1] | 4-(3-(4-(2-(4-methoxyphenyl) propan-2-yl)thiazol-2-yl)ureido)butanamide | | $[M + H]^+ = 377$ | 260 | |

TABLE 4-continued
| Com. ID | Structure | Name | HNMR | LCMS | Kinase assay IC50 nM. | NFkB assay IC50 µM |
|---|---|---|---|---|---|---|
| A115 | 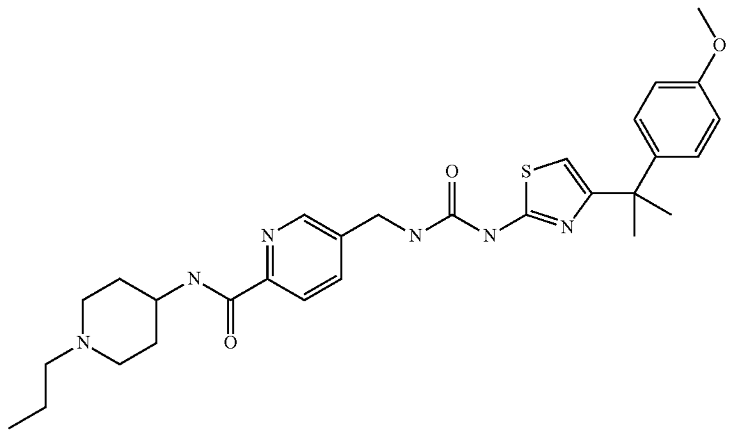 [SMILES: CCCN1CCC(NC(=O)c2ccc(CNC(=O)Nc3nc(C(C)(C)c4ccc(OC)cc4)cs3)cn2)CC1] | 5-((3-(4-(2-(4-methoxyphenyl) propan-2-yl)thiazol-2-yl)ureido)methyl)-N-(1-propylpiperidin-4-yl)picolinamide | | $[M + H]^+ = 551$ | 19 | 0.83 |
| A116 | 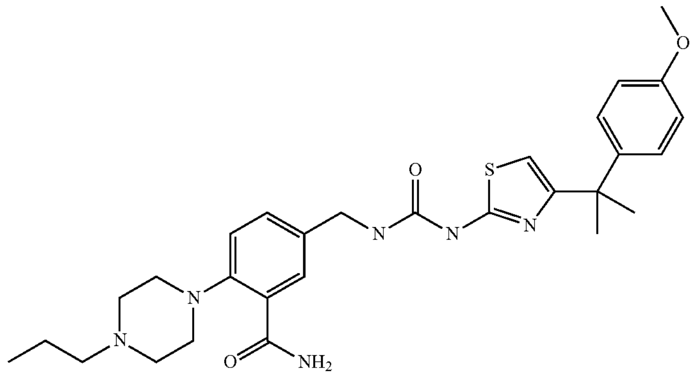 [SMILES: CCCN1CCN(c2ccc(CNC(=O)Nc3nc(C(C)(C)c4ccc(OC)cc4)cs3)cc2C(N)=O)CC1] | 5-((3-(4-(2-(4-methoxyphenyl) propan-2-yl)thiazol-2-yl)ureido)methyl)-2-(4-propylpiperazin-1-yl)benzamide | | $[M + H]^+ = 551$ | 72 | 0.72 |

TABLE 4-continued
| Com. ID | Structure | Name | HNMR | LCMS | Kinase assay IC50 nM. | NFkB assay IC50 µM |
|---|---|---|---|---|---|---|
| A117 | 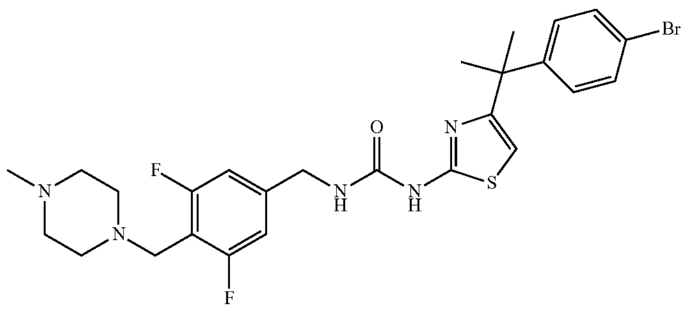 [SMILES: CN1CCN(Cc2c(F)cc(CNC(=O)Nc3nc(C(C)(C)c4ccc(Br)cc4)cs3)cc2F)CC1] | 1-(4-(2-(4-bromophenyl)propan-2-yl)thiazol-2-yl)-3-(3,5-difluoro-4-((4-methy lpiperazin-1-yl)methyl)benzyl)urea | | [M + H]$^+$ = 578 | 67 | 5.03 |
| A118 | 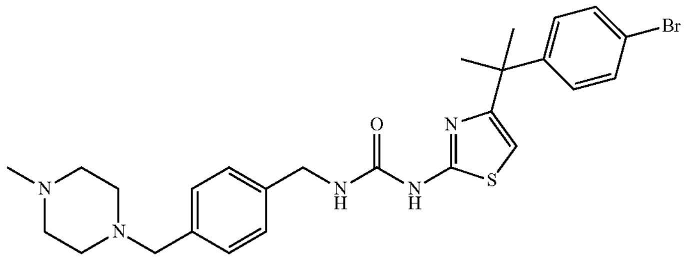 | 1-(4-(2-(4-bromophenyl)propan-2-yl)thiazol-2-yl)-3-(1-(4-((4-methylpiperazin-1-yl)methyl)phenyl) ethyl)urea | | [M + H]$^+$ = 556 | 227 | 4.38 |
| A119 | 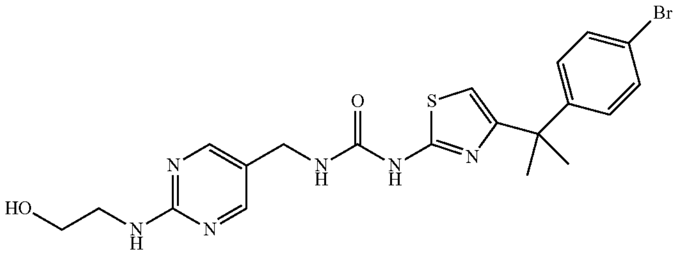 [SMILES: CC(C)(c1ccc(Br)cc1)c1csc(NC(=O)NCc2cnc(NCCO)nc2)n1] | 1-(4-(2-(4-bromophenyl)propan-2-yl)thiazol-2-yl)-3-((2-((2-hydroxyethyl)amino) pyrimidin-5-yl)methyl)urea | | [M + H]$^+$ = 491 | 36 | 4.43 |

TABLE 4-continued
| Com. ID | Structure | Name | HNMR | LCMS | Kinase assay IC50 nM. | NFkB assay IC50 μM |
|---|---|---|---|---|---|---|
| A120 | 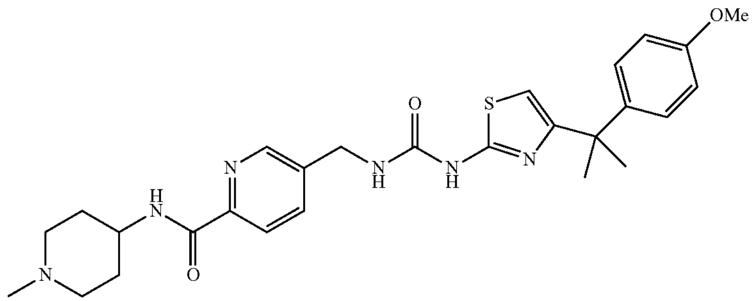 [SMILES: COc1ccc(C(C)(C)c2csc(NC(=O)NCc3ccc(C(=O)NC4CCN(C)CC4)nc3)n2)cc1] | 5-((3-(4-(2-(4-methoxyphenyl)propan-2-yl)thiazol-2-yl)ureido)methyl)-N-(1-methylpiperidin-4-yl)picolinamide | | $[M + H]^+ = 523$ | 53 | 0.99 |
| A121 | 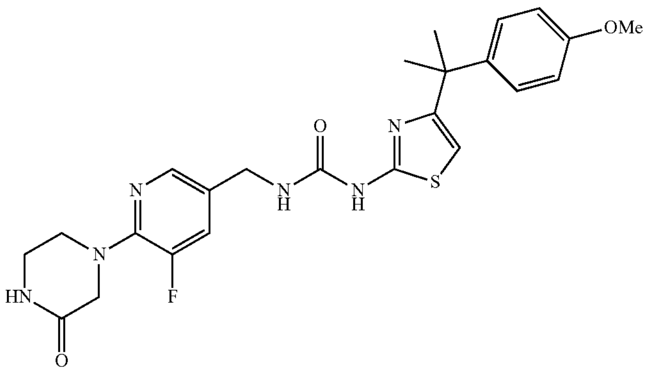 [SMILES: COc1ccc(C(C)(C)c2csc(NC(=O)NCc3cnc(N4CCNC(=O)C4)c(F)c3)n2)cc1] | 1-((5-fluoro-6-(3-oxopiperazin-1-yl)pyridin-3-yl)methyl)-3-(4-(2-(4-methoxyphenyl)propan-2-yl)thiazol-2-yl)urea | | $[M + H]^+ = 499$ | 209 | 2.02 |
| A122 | 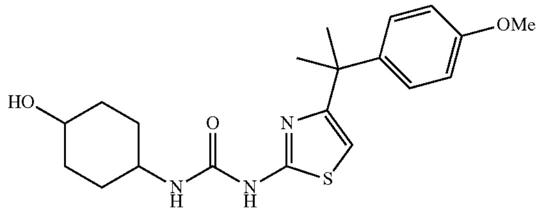 [SMILES: COc1ccc(C(C)(C)c2csc(NC(=O)NC3CCC(O)CC3)n2)cc1] | 1-(4-hydroxycyclohexyl)-3-(4-(2-(4-methoxyphenyl)propan-2-yl)thiazol-2-yl)urea | | $[M + H]^+ = 390$ | 219 | 1.70 |

TABLE 4-continued

| Com. ID | Structure | Name | HNMR | LCMS | Kinase assay IC50 nM. | NFkB assay IC50 μM |
|---|---|---|---|---|---|---|
| A123 | 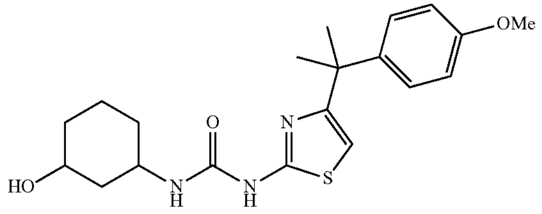 [SMILES: COc1ccc(C(C)(C)c2csc(NC(=O)NC3CCCC(O)C3)n2)cc1] | 1-(3-hydroxycyclohexyl)-3-(4-(2-(4-methoxyphenyl)propan-2-yl)thiazol-2-yl)urea | | $[M + H]^+ = 390$ | 354 | 2.40 |
| A124 | 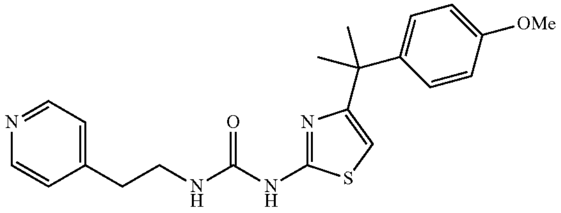 [SMILES: COc1ccc(C(C)(C)c2csc(NC(=O)NCCc3ccncc3)n2)cc1] | 1-(4-(2-(4-methoxyphenyl)propan-2-yl)thiazol-2-yl)-3-(2-(pyridin-4-yl)ethyl)urea | | $[M + H]^+ = 397$ | 165 | 1.05 |
| A125 | 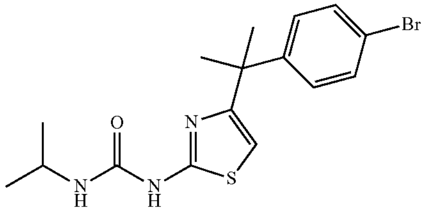 [SMILES: CC(C)NC(=O)Nc1nc(C(C)(C)c2ccc(Br)cc2)cs1] | 1-(4-(2-(4-bromophenyl)propan-2-yl)thiazol-2-yl)-3-isopropylurea | $^1H$ NMR (400 MHz, $CDCl_3$) δ 8.57 (br s, 1H), 7.39 (d, J = 8.8 Hz, 2H), 7.13 (d, J = 8.4 Hz, 2H), 6.43 (s, 1H), 3.96-3.82 (m, 1H), 1.64 (s, 6H), 1.10 (d, J = 6.4 Hz, 2H). | $[M + H]^+ = 382.1$ | 28 | 2.80 |
| A126 | 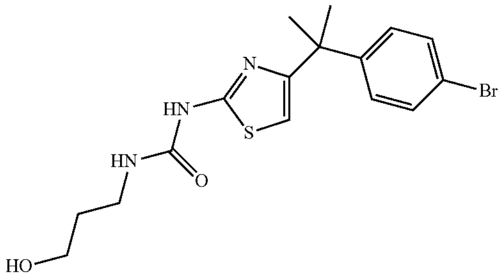 [SMILES: CC(C)(c1ccc(Br)cc1)c1csc(NC(=O)NCCCO)n1] | 1-(4-(2-(4-bromophenyl)propan-2-yl)thiazol-2-yl)-3-(3-hydroxypropyl)urea | $^1H$ NMR (400 MHz, $CDCl_3$) δ 7.30-7.26 (m, 2H), 7.15-7.10 (m, 2H), 6.47 (s, 1H), 3.60-3.55 (m, 2H), 3.45-3.30 (m, 2H), 1.63 (s, 6H), 1.40-1.30 (m, 2H). | $[M + H]^+ = 398.1$ | 88 | 2.96 |

TABLE 4-continued

| Com. ID | Structure | Name | HNMR | LCMS | Kinase assay IC50 nM. | NFkB assay IC50 μM |
|---|---|---|---|---|---|---|
| A127 | 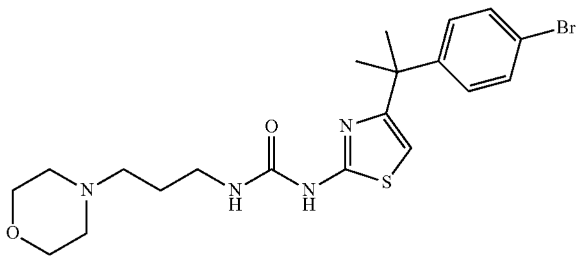 [SMILES: CC(C)(c1ccc(Br)cc1)c1csc(NC(=O)NCCCN2CCOCC2)n1] | 1-(4-(2-(4-bromophenyl)propan-2-yl)thiazol-2-yl)-3-(3-morpholinopropyl) urea | $^1$H NMR (400 MHz, DMSO-d6) δ 10.50 (br s, 1H), 7.40 (d, J = 8.56 Hz, 2H), 7.12 (d, J = 8.56 Hz, 2H), 6.68 (s, 1H), 6.29 (br s, 1H), 3.53 (t, J = 4.52 Hz, 4H), 3.09 (q, J = 6.60 Hz, 2H), 2.27 (br s, 4H), 2.22 (t, J = 6.97 Hz, 2H) 1.54 (s, 6H), 1.53-1.47 (m, 2H), | $[M + H]^+$ = 467.1 | 113 | 0.94 |
| A128 | 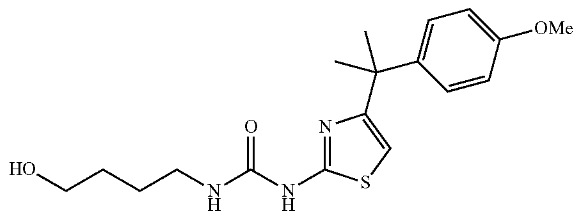 [SMILES: COc1ccc(C(C)(C)c2csc(NC(=O)NCCCCO)n2)cc1] | 1-(4-hydroxybutyl)-3-(4-(2-(4-methoxyphenyl) propan-2-yl)thiazol-2-yl)urea | | $[M + H]^+$ = 364.1 | 146 | 0.53 |
| A129 | 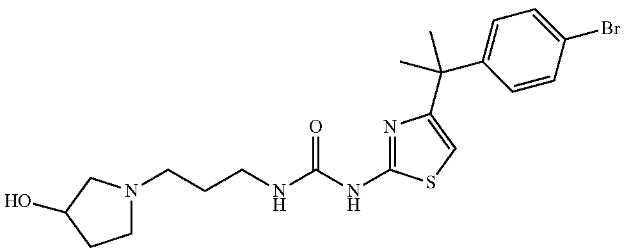 [SMILES: CC(C)(c1ccc(Br)cc1)c1csc(NC(=O)NCCCN2CCC(O)C2)n1] | 1-(4-(2-(4-bromophenyl)propan-2-yl)thiazol-2-yl)-3-(3-(3-hydroxypyrrolidin-1-yl)propyl)urea | $^1$H NMR (400 MHz, $CDCl_3$) δ 7.40-7.34 (m, 2H), 7.40-7.34 (m, 2H), 7.08 (d, J = 8.78 Hz, 2H), 6.56 (br s, 1H), 5.00-4.84 (m, 1H), 4.12-4.00 (m, 1H), 3.46-3.19 (m, 3H), 3.01--2.74 (m, 3H), 2.40-2.21 (m, 1H), 2.00-1.82 (m, 2H), 1.64-1.51 (m, 6H), 1.36-1.20 (m, 2H). | $[M + H]^+$ = 467.2 | 40 | 0.51 |

TABLE 4-continued

| Com. ID | Structure | Name | HNMR | LCMS | Kinase assay IC50 nM. | NFkB assay IC50 μM |
|---|---|---|---|---|---|---|
| A130 | 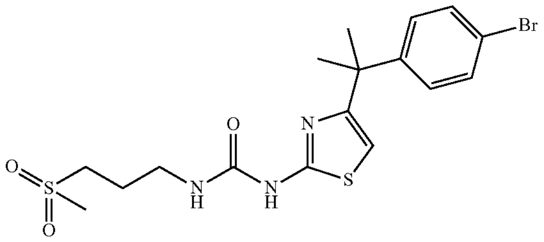 [SMILES: CC(C)(c1ccc(Br)cc1)c1csc(NC(=O)NCCCS(C)(=O)=O)n1] | 1-(4-(2-(4-bromophenyl)propan-2-yl)thiazol-2-yl)-3-(3-(methylsulfonyl) propyl)urea | $^1$H NMR (400 MHz, CDCl3) δ 7.38 (d, J = 8.07 Hz, 2H), 7.10 (d, J = 8.31 Hz, 2H), 6.47 (s, 1H), 3.38 (q, J = 6.11 Hz, 2H), 2.99 (br t, J = 7.58 Hz, 2H), 2.86 (s, 3H), 2.03-1.95 (m, 2H), 1.62 (s, 6H). | $[M + H]^+$ = 462.1 | 293 | 1.10 |
| A131 | 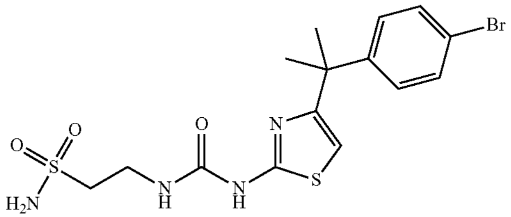 [SMILES: CC(C)(c1ccc(Br)cc1)c1csc(NC(=O)NCCS(N)(=O)=O)n1] | 2-(3-(4-(2-(4-bromophenyl)propan-2-yl)thiazol-2-yl)ureido) ethanesulfonamide | $^1$H NMR (400 MHz, METHANOL-d4) δ 7.38 (d, J = 8.31 Hz, 2H), 7.16 (d, J = 8.56 Hz, 2H), 6.66 (s, 1H), 3.67 (t, J = 6.48 Hz, 2H), 3.26 (t, J = 6.36 Hz, 2H), 1.63 (s, 6H) | $[M + H]^+$ = 447.0 | 219 | 0.94 |
| A132 | 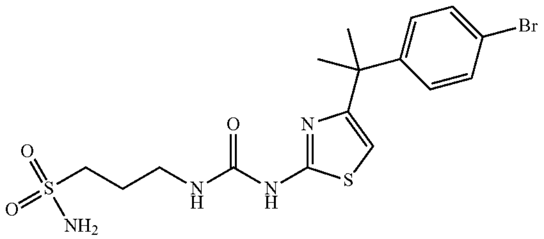 [SMILES: CC(C)(c1ccc(Br)cc1)c1csc(NC(=O)NCCCS(N)(=O)=O)n1] | 3-(3-(4-(2-(4-bromophenyl)propan-2-yl)thiazol-2-yl)ureido)propane-1-sulfonamide | $^1$H NMR (400 MHz, $CDCl_3$) δ 7.43-7.35 (m, 2H), 7.13-7.03 (m, 2H), 6.53 (s, 1H) 5.56-5.31 (m, 1H), 3.34 (d, J = 5.77 Hz, 2H), 3.03 (s, 2H), 1.99-1.89 (m, 2H), 1.61 (s, 6H). | $[M + H]^+$ = 463.1 | 80 | 4.56 |
| A133 | 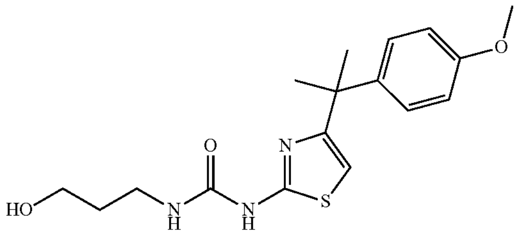 [SMILES: COc1ccc(C(C)(C)c2csc(NC(=O)NCCCO)n2)cc1] | 1-(3-hydroxypropyl)-3-(4-(2-(4-methoxyphenyl) propan-2-yl)thiazol-2-yl)urea | | $[M + H]^+$ = 350.2 | 57 | 0.60 |

TABLE 4-continued

| Com. ID | Structure | Name | HNMR | LCMS | Kinase assay IC50 nM. | NFkB assay IC50 μM |
|---|---|---|---|---|---|---|
| A134 | 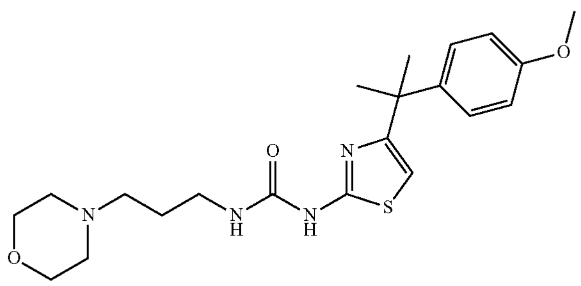 [SMILES: COc1ccc(C(C)(C)c2csc(NC(=O)NCCCN3CCOCC3)n2)cc1] | 1-(4-(2-(4-methoxyphenyl)propan-2-yl)thiazol-2-yl)-3-(3-morpholinopropyl)urea | $^1$H NMR (400 MHz, DMSO-d6) 6 10.46 (br s, 1H), 7.11-7.05 (m, 2H), 6.77 (d, J = 9.05 Hz, 2H), 6.59 (s, 1H), 6.32 (br s, 1H), 3.66 (s, 3H), 3.53 (br t, J = 4.52 Hz, 4H), 3.12-3.06 (m, 2H), 2.27 (br s, 4H), 2.22 (t, J = 6.97 Hz, 2H), 1.59-1.49 (m, 8H), | $[M + H]^+ = 419.2$ | 152 | 5.11 |
| A135 | 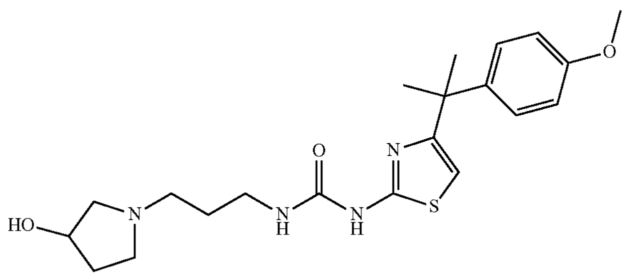 [SMILES: COc1ccc(C(C)(C)c2csc(NC(=O)NCCCN3CCC(O)C3)n2)cc1] | 1-(3-(3-hydroxypyrrolidin-1-yl)propyl)-3-(4-(2-(4-methoxyphenyl)propan-2-yl)thiazol-2-yl)urea | $^1$H NMR (400 MHz, $CDCl_3$) δ 7.08 (d, J = 8.8 Hz, 2H), 6.77 (d. J = 8.8 Hz, 2H), 6.69 (s, 1H), 6.60 (s, 1H), 5.40 (s, 1H), 4.34 (s, 1H), 3.66 (s, 3H), 3.11 (s, 3H), 3.03 (s, 3H), 1.77 (s, 2H), 1.53 (s, 6H), 1.35-1.15 (m, 2H), 0.95-0.85 (m, 2H). | $[M + H]^+ = 419.2$ | 112 | 1.24 |
| A136 | 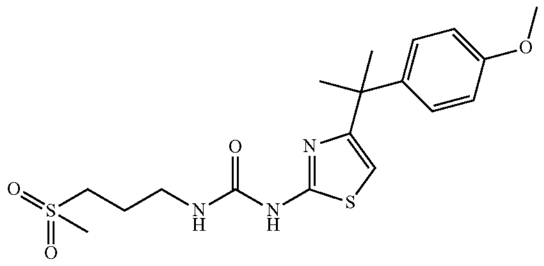 [SMILES: COc1ccc(C(C)(C)c2csc(NC(=O)NCCCS(C)(=O)=O)n2)cc1] | 1-(4-(2-(4-methoxyphenyl)propan-2-yl)thiazol-2-yl)-3-(3-(methylsulfonyl)propyl)urea | $^1$H NMR (400 MHz, MeOD) δ 7.17 (d, J = 8.8 Hz, 2H), 6.82 (d, J = 8.8 Hz, 2H), 6.43 (s, 3H), 3.78 (s, 3H), 3.42-3.38 (m, 2H), 3.00-2.97 (m, 2H), 2.86 (s, 3H), 2.05-1.98 (m, 2H), 1.64 (s, 3H) | $[M + H]^+ = 412.2$ | 209 | 0.64 |

TABLE 4-continued

| Com. ID | Structure | Name | HNMR | LCMS | Kinase assay IC50 nM. | NFkB assay IC50 μM |
|---|---|---|---|---|---|---|
| A137 | 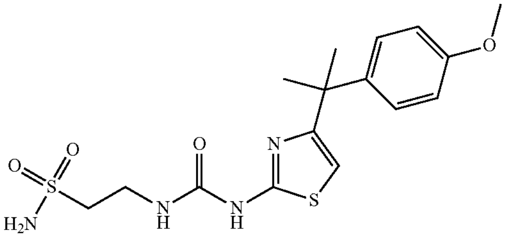 [SMILES: COc1ccc(C(C)(C)c2csc(NC(=O)NCCS(N)(=O)=O)n2)cc1] | 2-(3-(4-(2-(4-methoxyphenyl) propan-2-yl)thiazol-2-yl)ureido) ethanesulfonamide | $^1$H NMR (400 MHz, MeOD) δ 7.18 (d, J = 8.8 Hz, 2H), 7.25 (d, J = 8.4 Hz, 2H), 6.61 (s, 1H), 3.77 (s, 3H), 3.72-3.66 (m, 2H), 3.30-3.25 (m, 2H), 1.65 (s, 6H). | $[M + H]^+ = 399.2$ | 42 | 1.96 |
| A138 | 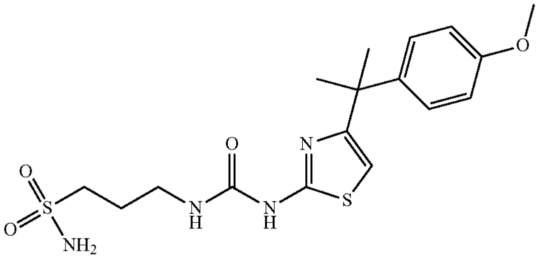 [SMILES: COc1ccc(C(C)(C)c2csc(NC(=O)NCCCS(N)(=O)=O)n2)cc1] | 3-(3-(4-(2-(4-methoxyphenyl) propan-2-yl)thiazol-2-yl)ureido)propane-1-sulfonamide | $^1$H NMR (400 MHz, MeOD) δ 7.17 (d, J = 8.8 Hz, 2H), 6.83 (d, J = 8.0 Hz, 2H), 6.63 (s, 1H), 3.77 (s, 3H), 3.39-3.35 (m, 2H), 3.15-3.02 (m, 2H), 2.12-2.00 (m, 2H), 1.65 (s, 6H). | $[M + H]^+ = 413.2$ | 97 | 2.38 |
| A139 | 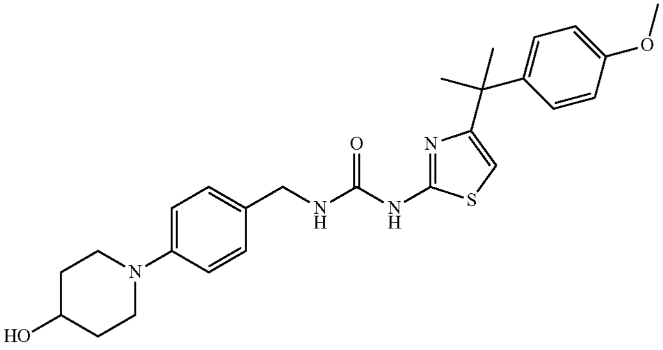 [SMILES: COc1ccc(C(C)(C)c2csc(NC(=O)NCc3ccc(N4CCC(O)CC4)cc3)n2)cc1] | 1-(4-(4-hydroxypiperidin-1-yl)benzyl)-3-(4-(2-(4-methoxyphenyl) propan-2-yl)thiazol-2-yl)urea | $^1$H NMR (400 MHz, DMSO-d6) δ 10.48 (s, 1H), 7.09 (dd, J = 12.59, 8.68 Hz, 4H), 6.87 (d, J = 8.56 Hz, 2H), 6.79 (d, J = 9.05 Hz, 2H), 6.68 (br s, 1H), 6.63 (s, 1H), 4.67 (d, J = 4.16 Hz, 1H), 4.17 (d, J = 5.87 Hz, 2H), 3.69 (s, 3H), 3.59 (td, J = 8.80, 4.40 Hz, 1H), 3.51-3.44 (m, 2H), 2.83-2.72 (m, 2H), 1.82-1.73 (m, 2H), 1.56 (s, 6H), 1.52-1.34 (m, 2H). | $[M + H]^+ = 481.2$ | 261 | 1.35 |

TABLE 4-continued

| Com. ID | Structure | Name | HNMR | LCMS | Kinase assay IC50 nM. | NFkB assay IC50 µM |
|---|---|---|---|---|---|---|
| A140 | 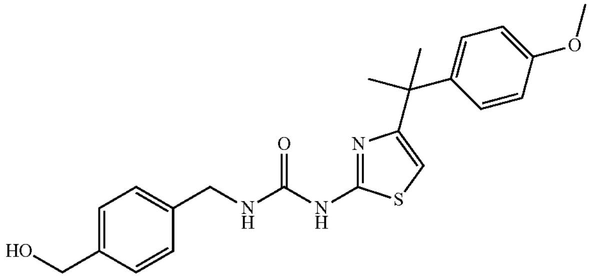 [SMILES: COc1ccc(C(C)(C)c2csc(NC(=O)NCc3ccc(CO)cc3)n2)cc1] | 1-(4-(hydroxymethyl)benzyl)-3-(4-(2-(4-methoxyphenyl)propan-2-yl)thiazol-2-yl)urea | $^1$H NMR (400 MHz, $CDCl_3$) δ 7.25-7.22 (m, 2H), 7.18-7.10 (m, 4H), 6.83-6.73 (m, 2H), 6.45 (s, 1H), 4.57 (s, 2H), 4.31-4.29 (m, 2H), 3.76 (s, 3H), 1.59 (s, 6H). | $[M + H]^+ = 412.2$ | 131 | 5.52 |
| A141 | 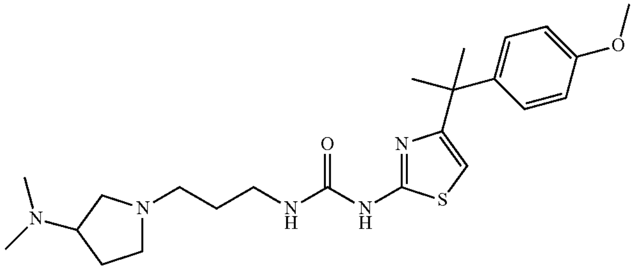 | 1-(3-(3-(dimethylamino)pyrrolidin-1-yl)propyl)-3-(4-(2-(4-methoxyphenyl)propan-2-yl)thiazol-2-yl)urea | $^1$H NMR (400 MHz, DMSO-d6) δ 10.43 (s, 1H) 7.08 (d, J = 8.82 Hz, 2H) 6.77 (d, J = 8.82 Hz. 2H) 6.58 (s, 1H) 6.36 (s, 1H) 3.66 (s, 3H) 3.08 (q, J = 6.39 Hz, 2H) 2.57-2.70 (m, 2H) 2.50-2.56 (m, 1H) 2.23-2.40 (m, 3H) 2.19 (t, J = 7.06 Hz, 1H) 2.05 (s, 6H) 1.73-1.84 (m, 1H) 1.44-1.60 (m, 9H) | $[M + H]^+ = 446.3$ | 228 | 4.22 |
| A142 | 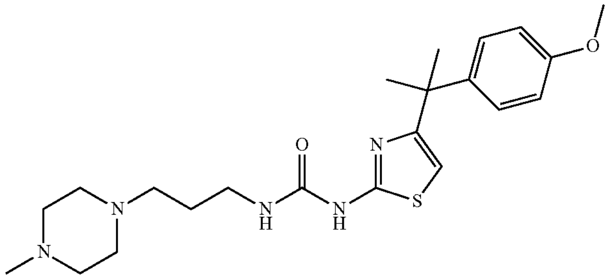 | 1-(4-(2-(4-methoxyphenyl)propan-2-yl)thiazol-2-yl)-3-(3-(4-methylpiperazin-1-yl)propyl)urea | $^1$H NMR (400 MHz, DMSO) δ 10.49 (br, 1H), 7.14-7.12 (m, 2H), 6.83-6.80 (m, 2H), 6.63 (s, 1H), 6.34 (br, 1H), 3.73 (s, 3H), 3.14-3.09 (m, 2H), 2.53 (s, 3H), 2.40-2.29 (m, 9H), 2.21 (s, 3H), 1.57-1.52 (m, 8H) | $[M + H]^+ = 432.3$ | 180 | 1.33 |

TABLE 4-continued

| Com. ID | Structure | Name | HNMR | LCMS | Kinase assay IC50 nM. | NFkB assay IC50 µM |
|---|---|---|---|---|---|---|
| A143 | 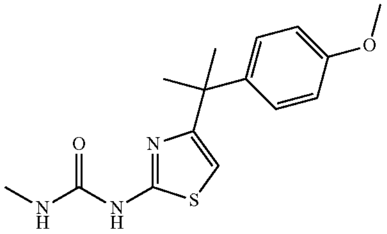 | 1-(4-(2-(4-methoxyphenyl)propan-2-yl)thiazol-2-yl)-3-methylurea | $^1$H NMR (400 MHz, MeOD) δ 7.17 (d, J = 9.2 Hz, 2H), 7.25 (d. J = 8.8 Hz, 2H), 6.60 (s, 1H), 3.77 (s, 3H), 2.78 (s, 3H), 1.64 (s, 6H). | $[M + H]^+$ = 306.2 | 53 | |
| A144 | 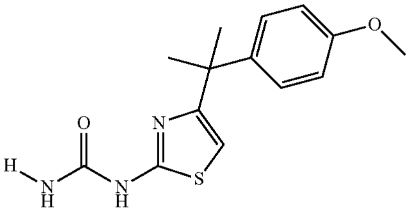 | 1-hydroxy-3-(4-(2-(4-methoxyphenyl)propan-2-yl)thiazol-2-yl)urea | $^1$H NMR (400 MHz, DMSO-d6) δ 9.26-8.43 (m, 2H), 7.12-7.04 (m, 2H), 6.80-6.74 (m, 2H), 6.67 (s, 1H), 3.66 (s, 3H), 1.54 (s. 6H). | $[M + H]^+$ = 308.1 | 154 | 1.75 |
| A145 | 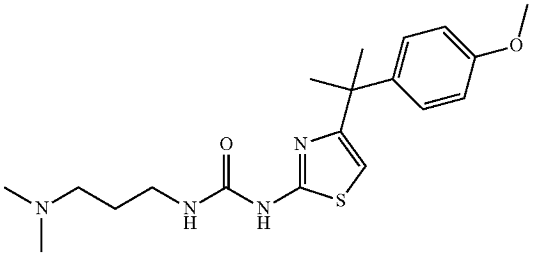 | 1-(3-(dimethylamino)propyl)-3-(4-(2-(4-methoxyphenyl)propan-2-yl)thiazol-2-yl)urea | $^1$H NMR (400 MHz, CD3OD) δ 7.14 (d, J = 8.82 Hz, 2H), 6.80 (d, J = 9.04 Hz, 2H), 6.59 (s, 1H), 3.74 (s, 3H), 3.22 (t, J = 6.84 Hz, 2H), 2.35-2.30 (m, 2H), 2.21 (s, 6H), 1.71-1.64 (m, 2H). 1.62 (s, 6H). | $[M + H]^+$ = 377.2 | 216 | 4.49 |

TABLE 4-continued

| Com. ID | Structure | Name | HNMR | LCMS | Kinase assay IC50 nM. | NFkB assay IC50 μM |
|---|---|---|---|---|---|---|
| A146 | 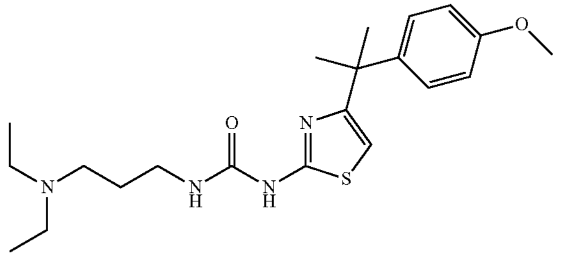 [SMILES: CCN(CC)CCCNC(=O)Nc1nc(C(C)(C)c2ccc(OC)cc2)cs1] | 1-(3-(diethylamino)propyl)-3-(4-(2-(4-methoxyphenyl)propan-2-yl)thiazol-2-yl)urea | $^1$H NMR (400 MHz, MeOD) δ 7.14 (d, J = 8.8 Hz, 2H), 6.80 (d, J = 8.8 Hz, 2H), 6.59 (s, 1H), 3.74 (s, 3H), 3.21 (br t, J = 6.7 Hz, 2H), 2.68-2.24 (m, 6H), 1.97-1.39 (m, 8H), 1.03 (t, J = 7.2 Hz, 6H). | $[M + H]^+ = 405.2$ | 124 | 3.07 |
| A147 | 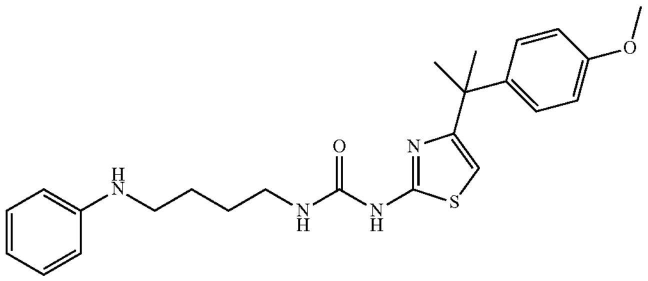 [SMILES: COc1ccc(C(C)(C)c2csc(NC(=O)NCCCCNc3ccccc3)n2)cc1] | 1-(4-(2-(4-methoxyphenyl)propan-2-yl)thiazol-2-yl)-3-(4-(phenylamino)butyl)urea | $^1$H NMR (400 MHz, MeOD) δ 7.13 (d, J = 8.82 Hz, 2H), 7.09-7.04 (m, 3H), 6.79 (d, J = 8.82 Hz, 2H), 6.62-6.55 (m, 4H), 3.72 (s, 3H), 3.25-3.19 (m, 2H), 3.06 (br t, J = 6.50 Hz, 2H), 1.61 (s, 6H), 1.59-1.54 (m, 4H) | $[M + H]^+ = 439.3$ | 235 | 1.91 |
| A148 | 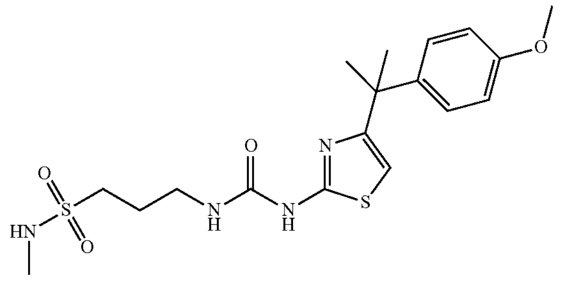 [SMILES: CNS(=O)(=O)CCCNC(=O)Nc1nc(C(C)(C)c2ccc(OC)cc2)cs1] | 3-(3-(4-(2-(4-methoxyphenyl)propan-2-yl)thiazol-2-yl)ureido)-N-methylpropane-1-sulfonamide | $^1$H NMR (400 MHz, CDCl3) δ 7.16-7.14 (m, 2H), 6.84-6.82 (m, 2H), 6.46 (s, 1H), 3.78 (s, 3H), 3.38-3.34 (m, 2H), 2.97-2.93 (m, 2H), 2.68-2.67 (m, 3H), 1.96-1.89 (m, 2H), 1.63 (s, 6H). | $[M + H]^+ = 427.0$ | 45 | 0.85 |

TABLE 4-continued

| Com. ID | Structure | Name | HNMR | LCMS | Kinase assay IC50 nM. | NFkB assay IC50 μM |
|---|---|---|---|---|---|---|
| A149 | 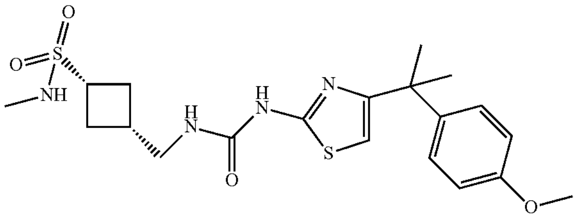 | rac-(1s,3s)-3-((3-(4-(2-(4-methoxyphenyl) propan-2-yl)thiazol-2-yl)ureido)methyl)-N-methylcyclobutane-1-sulfonamide | $^1$H NMR (400 MHz, CDCl3) δ 8.67 (br s, 1H), 7.13-7.11 (m, 2H), 6.82-6.80 (m, 2H), 6.41 (s, 1H), 4.85 (br s, 1H), 3.77 (s, 3H), 3.67-3.60 (m, 1H), 3.27-3.24 (m, 2H), 2.64-2.63 (m, 3H), 2.41-2.37 (m, 1H), 2.25-2.17 (m, 2H), 2.10-2.05 (m, 2H), 1.61 (s, 6H) . | $[M + H]^+ = 453.2$ | 155 | 9.40 |
| A150 | 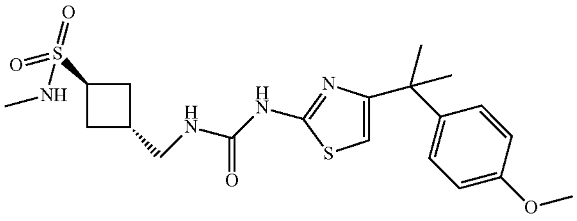 | rac-(11,3r)-3-((3-(4-(2-(4-methoxyphenyl) propan-2-yl)thiazol-2-yl)urcido)methyl)-N-methylcyclobutane-1-sulfonamide | $^1$H NMR (400 MHz, CDCl3) δ 9.06 (br s, 1H), 7.12-7.09 (m, 2H), 6.82-6.79 (m, 2H), 6.44 (s, 1H), 4.94 (br s, 1H), 3.77 (s, 3H), 3.75-3.64 (m, 1H), 3.31-3.28 (m, 2H), 2.68-2.67 (m, 3H), 2.51-2.47 (m, 1H), 2.43-2.36 (m, 2H), 1.99-1.91 (m, 2H), 1.60 (s, 6H) . | $[M + H]^+ = 453.2$ | 25 | 1.41 |
| A151 | 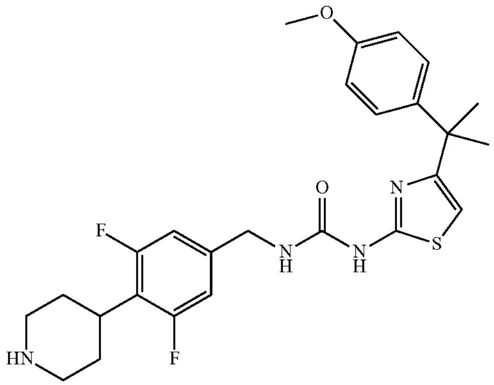 [SMILES: COc1ccc(C(C)(C)c2csc(NC(=O)NCc3cc(F)c(C4CCNCC4)c(F)c3)n2)cc1] | 1-(3,5-difluoro-4-(piperidin-4-yl)benzyl)-3-(4-(2-(4-methoxyphenyl) propan-2-yl)thiazol-2-yl)urea hydrochloride | $^1$H NMR (400 MHz, DMSO-d6) δ 10.72 (br, 1H), 9.10-8.70 (m, 2H), 7.09-7.07 (m, 2H), 6.95-6.93 (m, 2H), 6.78-6.76 (m, 2H), 6.62 (s, 1H), 4.22-4.20 (m, 2H), 3.66 (s, 3H), 3.30-3.25 (m, 4H), 3.20-3.14 (m, 4H), 1.53 (s, 6H). | $[M + H]^+ = 502.1$ | 43 | 0.95 |

TABLE 4-continued

| Com. ID | Structure | Name | HNMR | LCMS | Kinase assay IC50 nM. | NFkB assay IC50 µM |
|---|---|---|---|---|---|---|
| A152 | 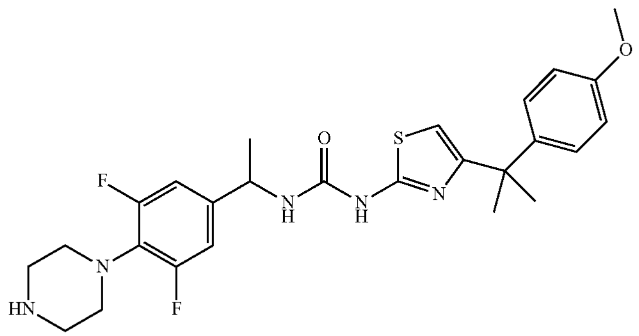 [SMILES: COc1ccc(C(C)(C)c2csc(NC(=O)NC(C)c3cc(F)c(N4CCNCC4)c(F)c3)n2)cc1] | 1-(1-(3,5-difluoro-4-(piperazin-1-yl)phenyl)ethyl)-3-(4-(2-(4-methoxyphenyl)propan-2-yl)thiazol-2-yl)urea | $^1$H NMR (400 MHz, DMSO-$d_6$) δ 10.74 (br s, 2H), 7.27 (s, 1H), 7.13-7.10 (m, 2H), 6.99-6.97 (m, 2H), 6.82-6.79 (m, 2H), 6.68 (s, 1H), 4.26-4.24 (m, 2H), 3.70 (s, 3H), 3.47-3.40 (m, 4H), 3.28-3.25 (m, 2H), 3.16-3.08 (m, 2H), 2.80-2.79 (m, 3H), 1.57 (s, 6H) . | $[M + H]^+$ = 516.1 | 55 | 0.35 |
| A153 | 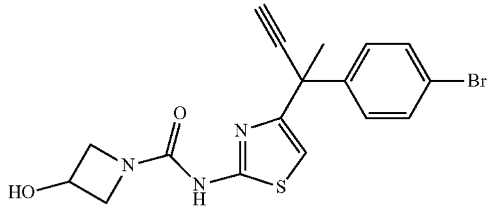 [SMILES: C#CC(C)(c1ccc(Br)cc1)c1csc(NC(=O)N2CC(O)C2)n1] | N-(4-(2-(4-bromophenyl)but-3-yn-2-yl)thiazol-2-yl)-3-hydroxyazetidine-1-carboxamide | $^1$H NMR (400 MHz, CDCl3) δ 7.84 (br, 1H), 7.44 (d, J = 8.4 Hz, 2H), 7.34 (d, J = 8.8 Hz, 2H), 7.28 (s, 1H), 6.80 (s, 1H), 4.72-4.68 (m, 1H), 4.29-4.25 (m, 2H), 3.95-3.91 (m, 2H), 2.58 (s, 1H), 1.93 (s, 3H). | $[M + H]^+$ = 408.0 | 76 | 0.37 |
| A154 | 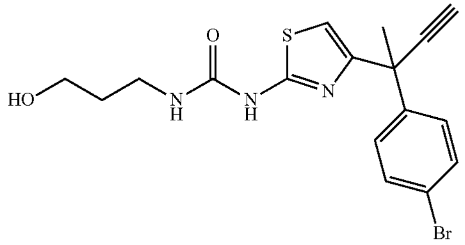 [SMILES: C#CC(C)(c1ccc(Br)cc1)c1csc(NC(=O)NCCCO)n1] | 1-(4-(2-(4-bromophenyl)but-3-yn-2-yl)thiazol-2-yl)-3-(3-hydroxypropyl)urea | $^1$H NMR (400 MHz, CDCl3) δ 7.46 (d, J = 7.6 Hz, 2H), 7.37 (d, J = 8.4 Hz, 2H), 6.76 (s, 1H), 3.64 (t, J = 5.2 Hz, 2H), 3.43 (t, J = 6.0 Hz, 2H), 2.58 (s, 1H), 1.95 (s, 3H), 1.70-1.69 (m, 2H). | $[M + H]^+$ = 408.0 | 21 | 0.38 |

TABLE 4-continued

| Com. ID | Structure | Name | HNMR | LCMS | Kinase assay IC50 nM. | NFkB assay IC50 µM |
|---|---|---|---|---|---|---|
| A155 | 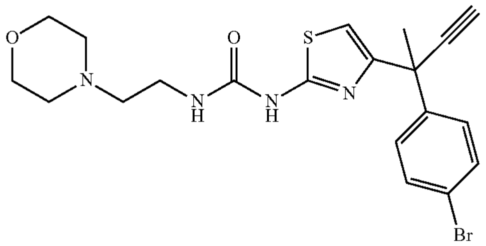 [SMILES: C#CC(C)(c1ccc(Br)cc1)c1csc(NC(=O)NCCN2CCOCC2)n1] | 1-(4-(2-(4-bromophenyl)but-3-yn-2-yl)thiazol-2-yl)-3-(2-morpholinoethyl)urea | $^1$H NMR (400 MHz, CDCl3) δ 7.48-7.42 (m, 4H), 7.00 (s, 1H), 4.11-4.08 (m, 2H), 3.82-3.67 (m, 2H), 3.66-3.63 (m, 4H), 3.35 (s, 2H), 3.33-3.21 (m, 2H), 3.00 (s, 1H), 1.94 (s, 3H). | $[M + H]^+$ = 463.1 | 30 | 0.90 |
| A156 | 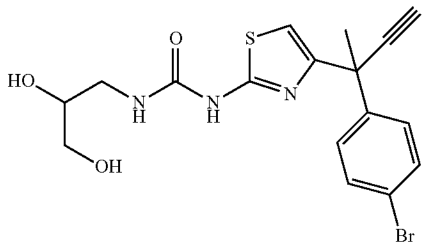 [SMILES: C#CC(C)(c1ccc(Br)cc1)c1csc(NC(=O)NCC(O)CO)n1] | 1-(4-(2-(4-bromophenyl)but-3-yn-2-yl)thiazol-2-yl)-3-(2,3-dihydroxypropyl)urea | $^1$H NMR (400 MHz, METHANOL-d4)7.44 (s, 4H), 6.91 (d, J = 1.0 Hz, 1H), 3.66-3.75 (m, 1H), 3.51 (d, J = 5.3 Hz, 2H), 3.38-3.47 (m, 1H), 3.21 (ddd, J = 13.8, 6.9, 2.6 Hz, 1H), 2.95 (s, 1H), 1.92 ppm (s, 3H) | $[M + H]^+$ = 424.0 | 22 | 0.38 |
| A157 | 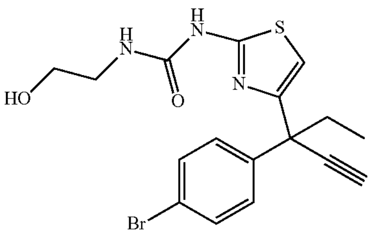 [SMILES: C#CC(CC)(c1ccc(Br)cc1)c1csc(NC(=O)NCCO)n1] | 1-(4-(3-(4-bromophenyl)pent-1-yn-3-yl)thiazol-2-yl)-3-(2-hydroxyethyl)urea | $^1$H NMR R (400 MHz, CDCl3) δ 7.44-7.42 (m, 2H), 7.37-7.35 (m, 2H), 6.81 (s, 1H), 3.53-3.50 (m, 2H), 3.38-3.35 (m, 2H), 2.59 (s, 1H), 2.38-2.29 (m, 1H), 2.21-2.12 (m, 1H), 0.94 (t, J = 7.6 Hz, 3H) | $[M + H]^+$ = 408.0 | 22 | 1.36 |
| A158 | 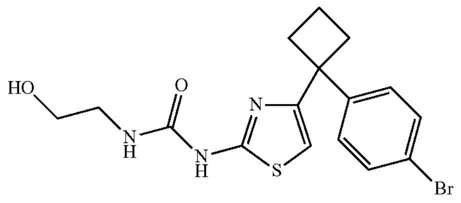 [SMILES: O=C(NCCO)Nc1nc(C2(c3ccc(Br)cc3)CCC2)cs1] | 1-(4-(1-(4-bromophenyl) cyclobutyl)thiazol-2-yl)-3-(2-hydroxyethyl)urea | $^1$H NMR (400 MHz, DMSO-d6) δ 10.50 (s, 1H), 7.47 (br d, J = 8.28 Hz, 2H), 7.19 (br d, J = 8.28 Hz, 2H), 6.66 (s, 1H), 6.47 (br s, 1H), 4.76 (br s, 1H), 3.41 (br d, J = 5.27 Hz, 2H), 3.16 (br d, J = 5.77 Hz, 2H), 2.65 (br d, J = 13.30 Hz, 2H), 2.33 (br s, 2H), 1.91-2.03 (m, 1H), 1.83 (br s, 1H) | $[M + H]^+$ = 398 | 67 | 2.86 |

TABLE 4-continued

| Com. ID | Structure | Name | HNMR | LCMS | Kinase assay IC50 nM. | NFkB assay IC50 μM |
|---|---|---|---|---|---|---|
| A159 | 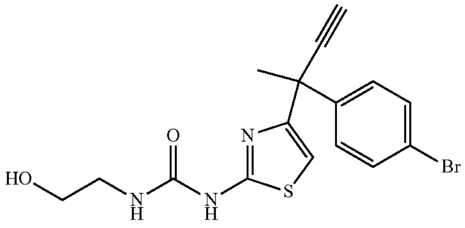 [SMILES: C#CC(C)(c1ccc(Br)cc1)c1csc(NC(=O)NCCO)n1] | 1-(4-(2-(4-bromophenyl)but-3-yn-2-yl)thiazol-2-yl)-3-(2-hydroxyethyl)urea | $^1$H NMR (400 MHz, CHLOROFORM-d)7.46 (d, J = 8.5 Hz, 2H), 7.36 (d, J = 8.5 Hz, 2H), 6.72 (s, 1H), 3.62 (br d, J = 4.3 Hz, 2H), 3.36 (br d, J = 3.9 Hz, 2H), 2.67 (s, 1H), 1.96 ppm (s, 3H) | $[M + H]^+$ 94.0 | 48 | 0.49 |
| A160 | 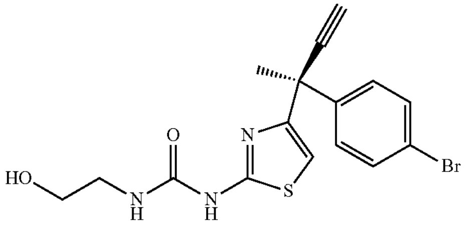 [SMILES: C#C[C@@](C)(c1ccc(Br)cc1)c1csc(NC(=O)NCCO)n1] | (S)-1-(4-(2-(4-bromophenyl)but-3-yn-2-yl)thiazol-2-yl)-3-(2-hydroxyethyl)urea | $^1$H NMR (400 MHz, CDCl3) δ 7.41-7.39 (m, 2H), 7.31-7.29 (m, 2H), 7.24 (s, 1H), 3.45-3.43 (m, 2H), 3.32-3.29 (m, 2H), 2.52 (s, 1H), 1.89 (s, 3H). | $[M + H]^+$ = 394.0 | 10 | 0.17 |
| A161 | 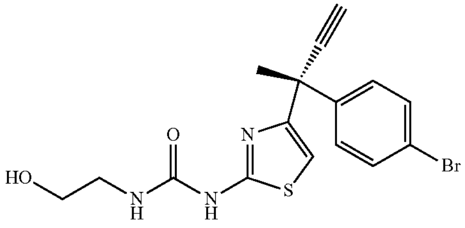 [SMILES: C#C[C@](C)(c1ccc(Br)cc1)c1csc(NC(=O)NCCO)n1] | (R)-1-(4-(2-(4-bromophenyl)but-3-yn-2-yl)thiazol-2-yl)-3-(2-hydroxyethyl)urea | $^1$H NMR (400 MHz, CDCl3) δ 7.37-7.35 (m, 2H), 7.26-7.24 (m, 2H), 7.19 (s, 1H), 6.69 (s, 1H), 3.38-3.37 (m, 2H), 3.25-3.24 (m, 2H), 2.47 (s, 1H), 1.84 (s, 3H). | $[M + H]^+$ = 394.0 | 68 | 0.55 |
| A162 | 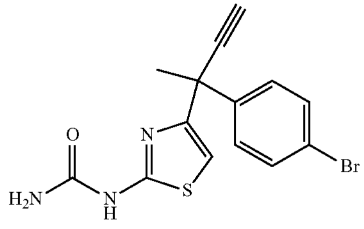 [SMILES: C#CC(C)(c1ccc(Br)cc1)c1csc(NC(N)=O)n1] | 1-(4-(2-(4-bromophenyl)but-3-yn-2-yl)thiazol-2-yl)urea | $^1$H NMR (400 MHz, DMSO) δ 10.60 (s, 1H), 7.53-7.50 (m, 2H), 7.39-7.37 (m, 2H), 6.90 (s, 1H), 3.50 (s, 1H), 1.85 (s, 3H). | $[M + H]^+$ = 352.0 | 38 | 0.18 |

TABLE 4-continued

| Com. ID | Structure | Name | HNMR | LCMS | Kinase assay IC50 nM. | NFkB assay IC50 μM |
|---|---|---|---|---|---|---|
| A163 | 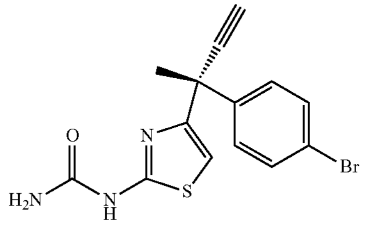 [SMILES: C#C[C@](C)(c1ccc(Br)cc1)c1csc(NC(N)=O)n1] | (S)-1-(4-(2-(4-bromophenyl)but-3-yn-2-yl)thiazol-2-yl)urea | $^1$H NMR (400 MHz, DMSO) δ 10.61 (s, 1H), 7.53-7.51 (m, 2H), 7.39-7.34 (m, 2H), 5.76 (s, 3H), 3.50 (s, 1H), 1.85 (s, 3H). | $[M + H]^+ = 349.9$ | 4 | 0.35 |
| A164 | 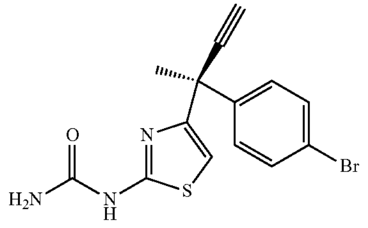 [SMILES: C#C[C@@](C)(c1ccc(Br)cc1)c1csc(NC(N)=O)n1] | (R)-1-(4-(2-(4-bromophenyl)but-3-yn-2-yl)thiazol-2-yl)urea | $^1$H NMR (400 MHz, DMSO) δ 10.64 (s, 1H), 7.53-7.50 (m, 2H), 7.39-7.37 (m, 2H), 6.89 (s, 1H), 3.50 (s, 1H), 1.85 (s, 3H). | $[M + H]^+ = 350.0$ | 17 | 0.59 |
| A165 | 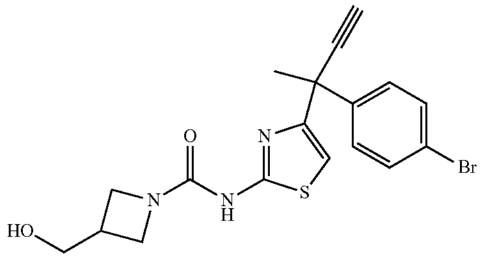 [SMILES: C#CC(C)(c1ccc(Br)cc1)c1csc(NC(=O)N2CC(CO)C2)n1] | N-(4-(2-(4-bromophenyl)but-3-yn-2-yl)thiazol-2-yl)-3-(hydroxymethyl) azetidine-1-carboxamide | $^1$H NMR (400 MHz, CDCl3) δ 7.79 (br, 1H), 7.41-7.39 (m, 2H), 7.31-7.29 (m, 2H), 7.24 (s, 1H), 6.75 (s, 1H), 4.07 (t, J = 8.0 Hz, 2H), 3.83-3.80 (m, 2H), 3.72-3.71 (m, 2H), 2.81-2.77 (m, 1H), 2.54 (s, 1H), 1.89 (s, 3H). | $[M + H]^+ = 420.0$ | 138 | 0.73 |

TABLE 4-continued

| Com. ID | Structure | Name | HNMR | LCMS | Kinase assay IC50 nM. | NFkB assay IC50 μM |
|---|---|---|---|---|---|---|
| A166 | 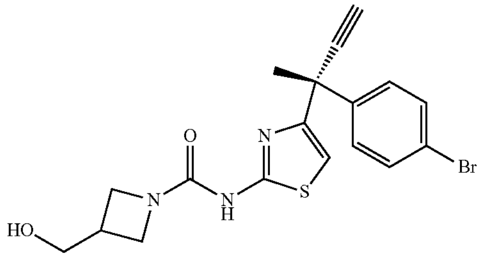 [SMILES: C#C[C@](C)(c1ccc(Br)cc1)c1csc(NC(=O)N2CC(CO)C2)n1] | (R)-N-(4-(2-(4-bromophenyl)but-3-yn-2-yl)thiazol-2-yl)-3-(hydroxymethyl) azetidine-1-carboxamide | $^1$H NMR (400 MHz, CDCl3) δ 7.85 (br, 1H), 7.46-7.43 (m, 2H), 7.36-7.33 (m, 2H), 6.79 (s, 1H), 4.11-4.08 (m, 2H), 3.88-3.85 (m, 2H), 3.76-3.75 (m, 2H), 2.87-2.80 (m, 1H), 2.58 (s, 1H), 1.94 (s, 3H). | $[M + H]^+$ = 420.0 | 25 | 5.71 |
| A167 | 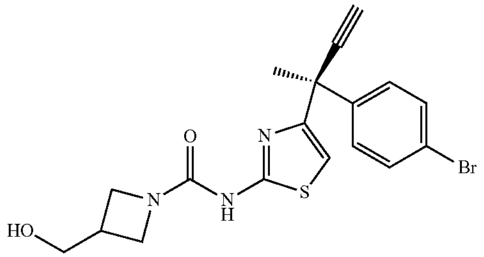 [SMILES: C#C[C@@](C)(c1ccc(Br)cc1)c1csc(NC(=O)N2CC(CO)C2)n1] | (S)-N-(4-(2-(4-bromophenyl)but-3-yn-2-yl)thiazol-2-yl)-3-(hydroxymethyl) azetidine-1-carboxamide | $^1$H NMR (400 MHz, CDCl3) δ 7.85 (br, 1H), 7.45-7.43 (m, 2H), 7.36-7.33 (m, 2H), 6.79 (s, 1H), 4.11-4.09 (m, 2H), 3.87-3.85 (m, 2H), 3.77-3.75 (m, 2H), 2.85-2.81 (m, 1H), 2.58 (s, 1H), 1.93 (s, 3H). | $[M + H]^+$ = 420.0 | 7 | 0.74 |
| A168 | 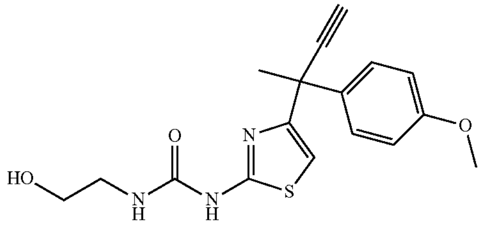 [SMILES: C#CC(C)(c1ccc(OC)cc1)c1csc(NC(=O)NCCO)n1] | 1-(2-hydroxyethyl)-3-(4-(2-(4-methoxyphenyl)but-3-yn-2-yl)thiazol-2-yl)urea | $^1$H NMR (400 MHz, CDCl3) δ 7.38 (d, J = 8.8 Hz. 2H), 6.87-6.84 (m, 2H), 6.73 (s, 1H), 3.80 (s, 3H), 3.45 (s, 2H), 3.35-3.33 (m, 2H), 2.54 (s, 1H), 1.94 (s, 3H). | $[M + H]^+$ = 346.1 | 27 | 0.40 |

TABLE 4-continued

| Com. ID | Structure | Name | HNMR | LCMS | Kinase assay IC50 nM. | NFkB assay IC50 μM |
|---|---|---|---|---|---|---|
| A169 | 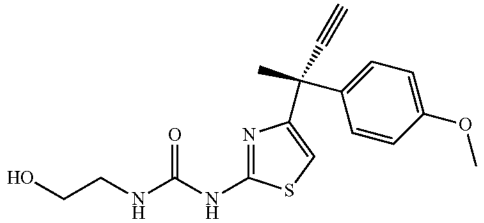 [SMILES: C#C[C@](C)(c1ccc(OC)cc1)c1csc(NC(=O)NCCO)n1] | (R)-1-(2-hydroxyethyl)-3-(4-(2-(4-methoxyphenyl)but-3-yn-2-yl)thiazol-2-yl)urea | $^1$H NMR (400 MHz, CDCl3) δ 7.36 (d, J = 8.8 Hz, 2H), 6.83 (d, J = 8.8 Hz, 2H), 6.70 (s, 1H), 3.78 (s, 3H), 3.46 (br d, J = 4.8 Hz, 2H), 3.32 (br d, J = 4.8 Hz, 2H), 2.52 (s, 1H), 1.92 (s, 3H) | $[M + H]^+$ = 346 | 23 | 1.67 |
| A170 | 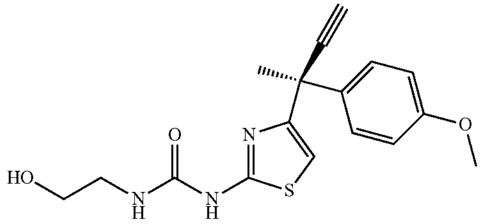 [SMILES: C#C[C@@](C)(c1ccc(OC)cc1)c1csc(NC(=O)NCCO)n1] | (S)-1-(2-hydroxyethyl)-3-(4-(2-(4-methoxyphenyl)but-3-yn-2-yl)thiazol-2-yl)urea | $^1$H NMR (400 MHz, CDCl3) δ 7.37 (d, J = 8.8 Hz, 2H), 6.84 (d, J = 8.8 Hz, 2H), 6.70 (s, 1H), 3.78 (s, 3H), 3.49 (br d, J = 5.3 Hz, 2H), 3.34 (br d, J = 5.3 Hz, 2H), 2.52 (s, 1H), 1.92 (s, 3H) | $[M + H]^+$ = 346 | 8 | 0.46 |
| A171 | 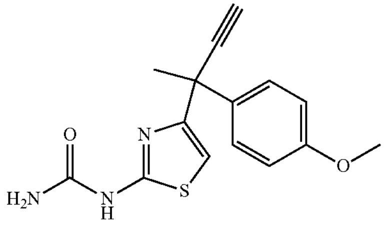 [SMILES: C#CC(C)(c1ccc(OC)cc1)c1csc(NC(N)=O)n1] | 1-(4-(2-(4-methoxyphenyl)but-3-yn-2-yl)thiazol-2-yl)urea | $^1$H NMR (400 MHz, DMSO-d6) δ 10.58 (s, 1H), 7.33 (d, J = 8.8 Hz, 2H), 6.86 (d, J = 8.8 Hz, 2H), 6.81 (s, 1H), 6.22 (br s, 2H), 3.72 (s, 3H), 3.40 (s, 1H), 1.83 (s, 3H) | $[M + H]^+$ = 302 | 16 | 0.73 |
| A172 | 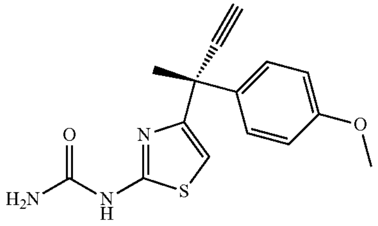 [SMILES: C#C[C@](C)(c1ccc(OC)cc1)c1csc(NC(N)=O)n1] | (R)-1-(4-(2-(4-methoxyphenyl)but-3-yn-2-yl)thiazol-2-yl)urea | $^1$H NMR (400 MHz, DMSO-d6) δ 10.58 (br s, 1H), 7.33 (d, J = 8.8 Hz, 2H), 6.86 (d, J = 8.8 Hz, 2H), 6.81 (s, 1H), 6.24 (br s, 1H), 3.72 (s, 3H), 3.41 (s, 1H), 1.83 (s, 3H) | $[M + H]^+$ = 302 | 36 | 1.28 |

TABLE 4-continued

| Com. ID | Structure | Name | HNMR | LCMS | Kinase assay IC50 nM. | NFkB assay IC50 µM |
|---|---|---|---|---|---|---|
| A173 | 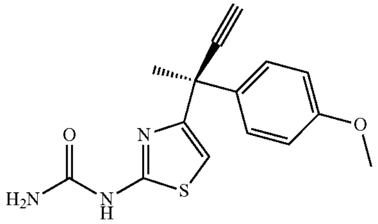 [SMILES: C#C[C@@](C)(c1ccc(OC)cc1)c1csc(NC(N)=O)n1] | (S)-1-(4-(2-(4-methoxyphenyl)but-3-yn-2-yl)thiazol-2-yl)urea | $^1$H NMR (400 MHz, DMSO-d6) δ 10.60 (br s, 1H), 7.33 (d, J = 8.8 Hz, 2H), 6.86 (d, J = 8.8 Hz, 2H), 6.80 (s, 1H), 6.23 (br s, 1H), 3.72 (s, 3H), 3.40 (s, 1H), 1.83 (s, 3H) | $[M + H]^+ = 302$ | 8 | 0.58 |
| A174 | 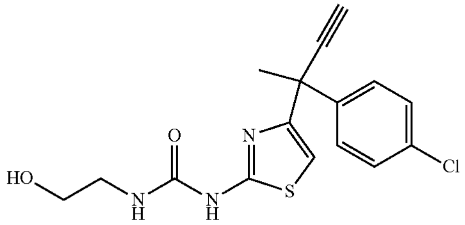 | 1-(4-(2-(4-chlorophenyl)but-3-yn-2-yl)thiazol-2-yl)-3-(2-hydroxyethyl)urea | $^1$H NMR (400 MHz, DMSO-d6) δ 10.64 (s, 1H), 7.33-7.46 (m, 4H), 6.90 (s, 1H), 6.34 (br s, 1H), 4.75 (t, J = 5.14 Hz, 1H), 3.50 (s, 1H), 3.41 (q, J = 5.52 Hz, 2H), 3.16 (q, J = 5.52 Hz, 2H), 1.85 (s, 3H) | $[M + H]^+ = 350$ | 34 | 0.31 |
| A175 | 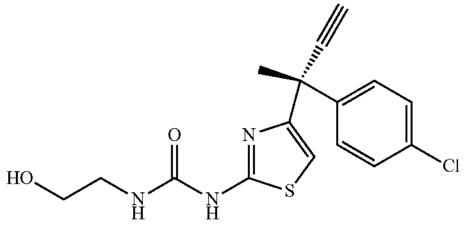 | (R)-1-(4-(2-(4-chlorophenyl)but-3-yn-2-yl)thiazol-2-yl)-3-(2-hydroxyethyl)urea | $^1$H NMR (400 MHz, DMSO-d6) δ 10.63 (br s, 1H), 7.33-7.48 (m, 4H), 6.90 (s, 1H), 6.35 (br s, 1H), 4.75 (t, J = 5.27 Hz, 1H), 3.50 (s, 1H), 3.41 (g, J = 5.35 Hz, 2H), 3.16 (q, J = 5.52 Hz, 2H), 1.85 (s, 3H) | $[M + H]^+ = 350$ | 32 | 1.31 |
| A176 | 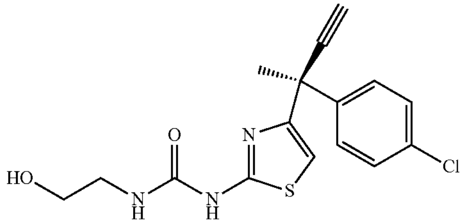 [SMILES: C#C[C@@](C)(c1ccc(Cl)cc1)c1csc(NC(=O)NCCO)n1] | (S)-1-(4-(2-(4-chlorophenyl)but-3-yn-2-yl)thiazol-2-yl)-3-(2-hydroxyethyl)urea | $^1$H NMR (400 MHz, DMSO-d6) δ 10.64 (br s, 1H), 7.34-7.49 (m, 4H), 6.90 (s, 1H), 6.35 (br s, 1H), 4.76 (t, J = 5.14 Hz, 1H), 3.51 (s, 1H), 3.42 (q, J = 5.52 Hz, 2H), 3.16 (q, J = 5.35 Hz, 2H), 1.85 (s, 3H) | $[M + H]^+ = 350$ | 5.4 | 0.28 |

TABLE 4-continued
| Com. ID | Structure | Name | HNMR | LCMS | Kinase assay IC50 nM. | NFkB assay IC50 µM |
|---|---|---|---|---|---|---|
| A177 | 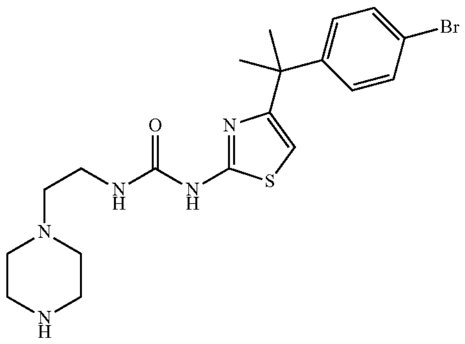 [SMILES: CC(C)(c1ccc(Br)cc1)c1csc(NC(=O)NCCN2CCNCC2)n1] | 1-(4-(2-(4-bromophenyl)propan-2-yl)thiazol-2-yl)-3-(2-(piperazin-1-yl)ethyl)urea | | $[M + H]^+ = 452$ | 249 | 1.66 |
| A178 | 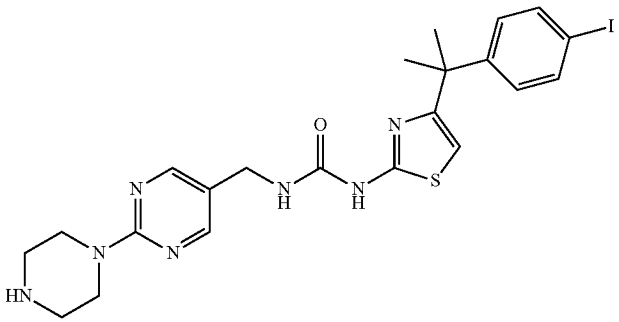 [SMILES: CC(C)(c1ccc(I)cc1)c1csc(NC(=O)NCc2cnc(N3CCNCC3)nc2)n1] | 1-(4-(2-(4-iodophenyl)propan-2-yl)thiazol-2-yl)-3-((2-(piperazin-1-yl)pyrimidin-5-yl)methyl)urea | | $[M + H]^+ = 564$ | 42 | 0.92 |

TABLE 4-continued
| Com. ID | Structure | Name | HNMR | LCMS | Kinase assay IC50 nM. | NFkB assay IC50 µM |
|---|---|---|---|---|---|---|
| A179 | 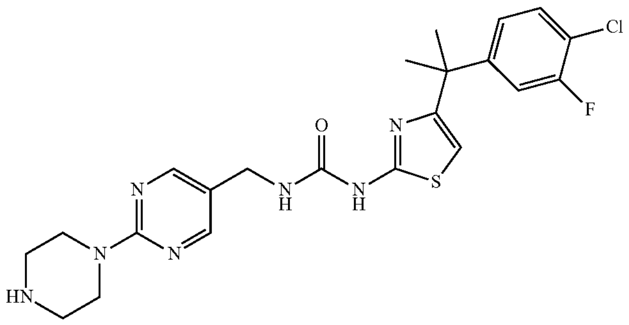 | 1-(4-(2-(4-chloro-3-fluorophenyl)propan-2-yl)thiazol-2-yl)-3-((2-(piperazin-1-yl)pyrimidin-5-yl)methyl)urea | | $[M + H]^+ = 490$ | 95 | 1.36 |
| A180 | 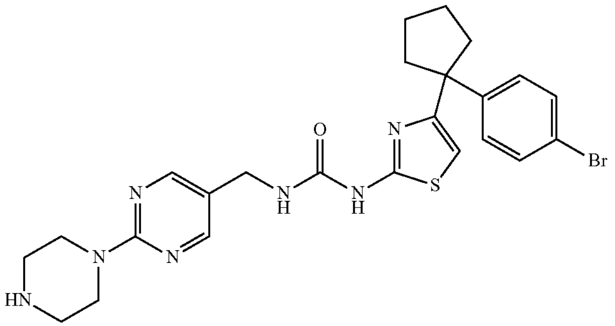 [SMILES: O=C(NCc1cnc(N2CCNCC2)nc1)Nc1nc(C2(c3ccc(Br)cc3)CCCC2)cs1] | 1-(4-(1-(4-bromophenyl)cyclopentyl)thiazol-2-yl)-3-((2-(piperazin-1-yl)pyrimidin-5-yl)methyl)urea | | $[M + H]^+ = 542$ | 45 | |

TABLE 4-continued
| Com. ID | Structure | Name | HNMR | LCMS | Kinase assay IC50 nM. | NFkB assay IC50 μM |
|---|---|---|---|---|---|---|
| A181 | 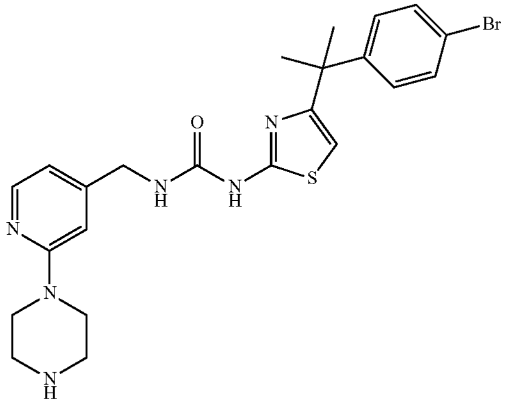 [SMILES: CC(C)(c1ccc(Br)cc1)c1csc(NC(=O)NCc2ccnc(N3CCNCC3)c2)n1] | 1-(4-(2-(4-bromophenyl)propan-2-yl)thiazol-2-yl)-3-((2-(piperazin-1-yl)pyridin-4-yl)methyl)urea | | $[M + H]^+ = 515$ | 131 | 1.52 |
| A182 | 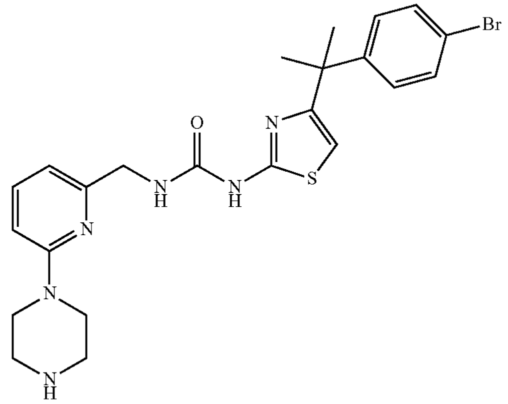 [SMILES: CC(C)(c1ccc(Br)cc1)c1csc(NC(=O)NCc2cccc(N3CCNCC3)n2)n1] | 1-(4-(2-(4-bromophenyl)propan-2-yl)thiazol-2-yl)-3-((6-(piperazin-1-yl)pyridin-2-yl)methyl)urea | | $[M + H]^+ = 515$ | 163 | 4.30 |

TABLE 4-continued
| Com. ID | Structure | Name | HNMR | LCMS | Kinase assay IC50 nM. | NFkB assay IC50 μM |
|---|---|---|---|---|---|---|
| A183 | 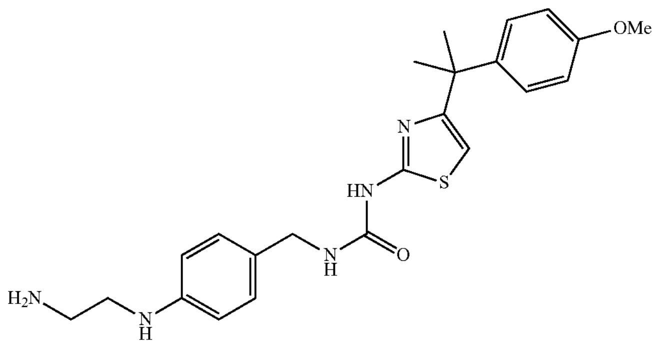 [SMILES: COc1ccc(C(C)(C)c2csc(NC(=O)NCc3ccc(NCCN)cc3)n2)cc1] | 1-(4-((2-aminoethyl)amino)benzyl)-3-(4-(2-(4-methoxyphenyl)propan-2-yl)thiazol-2-yl)urea | | $[M + H]^+ = 440$ | 52 | 2.31 |
| A184 | 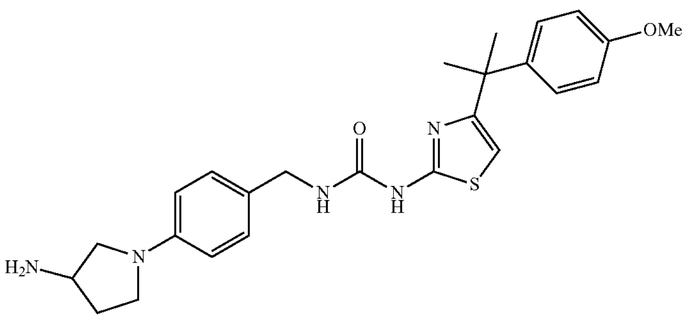 [SMILES: COc1ccc(C(C)(C)c2csc(NC(=O)NCc3ccc(N4CCC(N)C4)cc3)n2)cc1] | 1-(4-(3-aminopyrrolidin-1-yl)benzyl)-3-(4-(2-(4-methoxyphenyl)propan-2-yl)thiazol-2-yl)urea | | $[M + H]^+ = 466$ | 242 | |

TABLE 4-continued
| Com. ID | Structure | Name | HNMR | LCMS | Kinase assay IC50 nM. | NFkB assay IC50 μM |
|---|---|---|---|---|---|---|
| A185 | 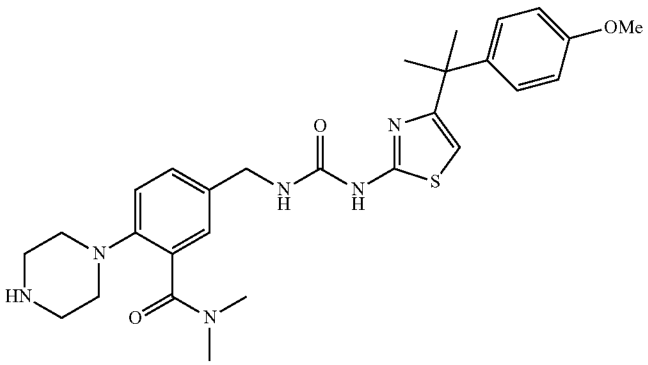 [SMILES: COc1ccc(C(C)(C)c2csc(NC(=O)NCc3ccc(N4CCNCC4)c(C(=O)N(C)C)c3)n2)cc1] | 5-((3-(4-(2-(4-methoxyphenyl) propan-2-yl)thiazol-2-yl)ureido)methyl)-N,N-dimethyl-2-(piperazin-1-yl)benzamide | | $[M + H]^+ = 537$ | 56 | |
| A186 | 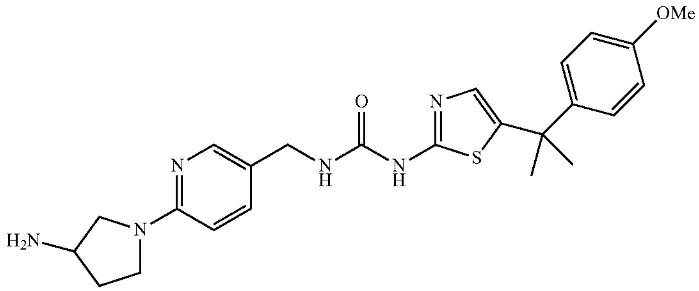 [SMILES: COc1ccc(C(C)(C)c2cnc(NC(=O)NCc3ccc(N4CCC(N)C4)nc3)s2)cc1] | 1-((6-(3-aminopyrrolidin-1-yl)pyridin-3-yl)methyl)-3-(4-(2-(4-methoxyphenyl) propan-2-yl)thiazol-2-yl)urea | | $[M + H]^+ = 467$ | 19 | 1.55 |

TABLE 4-continued
| Com. ID | Structure | Name | HNMR | LCMS | Kinase assay IC50 nM. | NFkB assay IC50 μM |
|---|---|---|---|---|---|---|
| A187 | 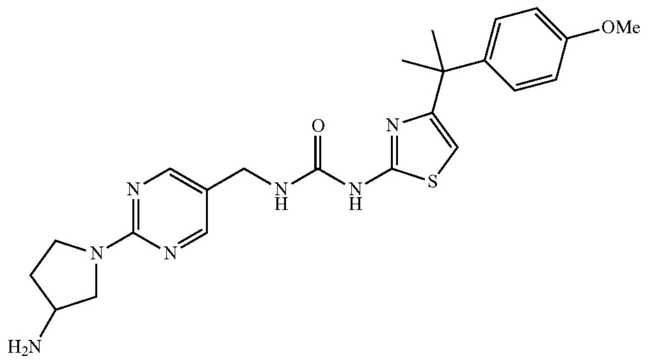 [SMILES: COc1ccc(C(C)(C)c2csc(NC(=O)NCc3cnc(N4CCC(N)C4)nc3)n2)cc1] | 1-((2-(3-aminopyrrolidin-1-yl)pyrimidin-5-yl)methyl)-3-(4-(2-(4-methoxyphenyl)propan-2-yl)thiazol-2-yl)urea | | $[M + H]^+ = 468$ | 7 | 0.7 |
| A188 | 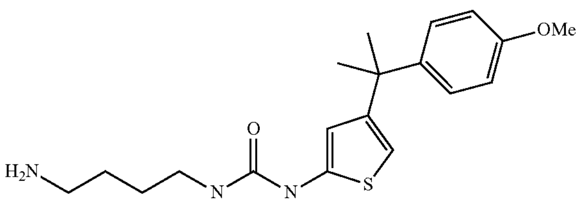 [SMILES: COc1ccc(C(C)(C)c2csc(NC(=O)NCCCCN)c2)cc1] | 1-(4-aminobutyl)-3-(4-(2-(4-methoxyphenyl)propan-2-yl)thiophen-2-yl)urea | | $[M + H]^+ = 362$ | 59 | |
| A189 | 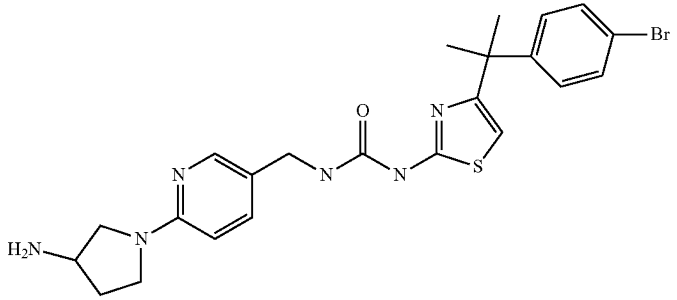 [SMILES: CC(C)(c1ccc(Br)cc1)c1csc(NC(=O)NCc2ccc(N3CCC(N)C3)nc2)n1] | 1-((6-(3-aminopyrrolidin-1-yl)pyridin-3-yl)methyl)-3-(4-(2-(4-bromophenyl)propan-2-yl)thiazol-2-yl)urea | | $[M + H]^+ = 515$ | 41 | 2.31 |

TABLE 4-continued
| Com. ID | Structure | Name | HNMR | LCMS | Kinase assay IC50 nM. | NFkB assay IC50 μM |
|---|---|---|---|---|---|---|
| A190 | 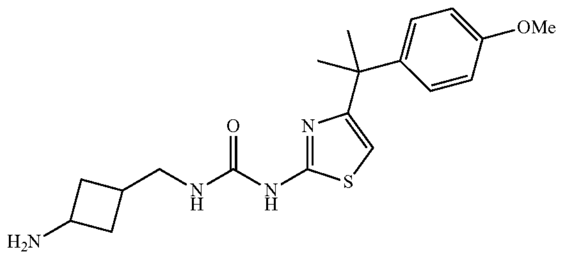 [SMILES: COc1ccc(C(C)(C)c2csc(NC(=O)NCC3CC(N)C3)n2)cc1] | 1-((3-aminocyclobutyl)methyl)-3-(4-(2-(4-methoxyphenyl)propan-2-yl)thiazol-2-yl)urea | | $[M + H]^+ = 375$ | 458 | 3.02 |
| A191 | 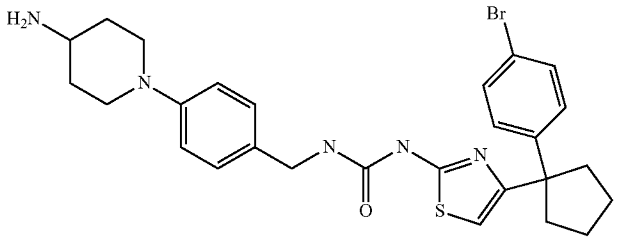 [SMILES: NC1CCN(c2ccc(CNC(=O)Nc3nc(C4(c5ccc(Br)cc5)CCCC4)cs3)cc2)CC1] | 1-(4-(4-aminopiperidin-1-yl)benzyl)-3-(4-(1-(4-bromophenyl)cyclopentyl)thiazol-2-yl)urea | | $[M + H]^+ = 554$ | 80 | 6.91 |
| A192 | 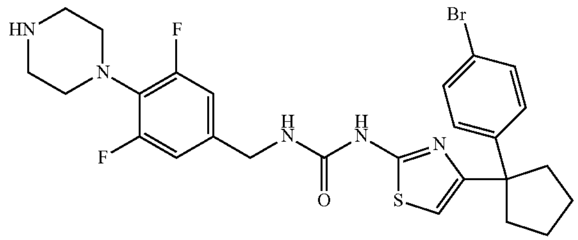 [SMILES: O=C(NCc1cc(F)c(N2CCNCC2)c(F)c1)Nc1nc(C2(c3ccc(Br)cc3)CCCC2)cs1] | 1-(4-(1-(4-bromophenyl)cyclopentyl)thiazol-2-yl)-3-(3,5-difluoro-4-(piperazin-1-yl)benzyl)urea | | $[M + H]^+ = 576$ | 106 | 4.34 |

TABLE 4-continued
| Com. ID | Structure | Name | HNMR | LCMS | Kinase assay IC50 nM. | NFkB assay IC50 μM |
|---|---|---|---|---|---|---|
| A193 | 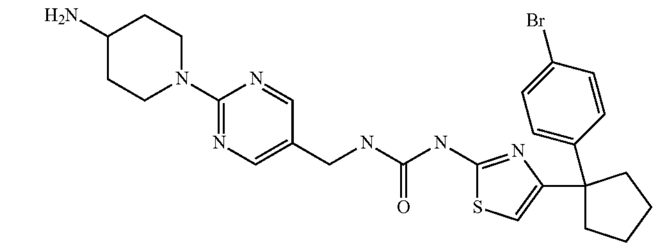 [SMILES: NC1CCN(c2ncc(CNC(=O)Nc3nc(C4(c5ccc(Br)cc5)CCCC4)cs3)cn2)CC1] | 1-(4-(4-aminopiperidin-1-yl)benzyl)-3-(4-(1-(4-bromophenyl)cyclopentyl)thiazol-2-yl)urea | | $[M + H]^+ = 556$ | 15 | 6.93 |
| A194 | 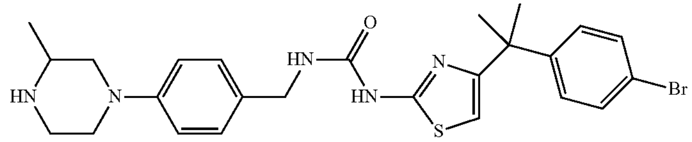 [SMILES: CC1CN(c2ccc(CNC(=O)Nc3nc(C(C)(C)c4ccc(Br)cc4)cs3)cc2)CCN1] | 1-(4-(2-(4-bromophenyl)propan-2-yl)thiazol-2-yl)-3-(4-(3-methylpiperazin-1-yl)benzyl)urea | | $[M + H]^+ = 528$ | 172 | 3.71 |
| A195 | 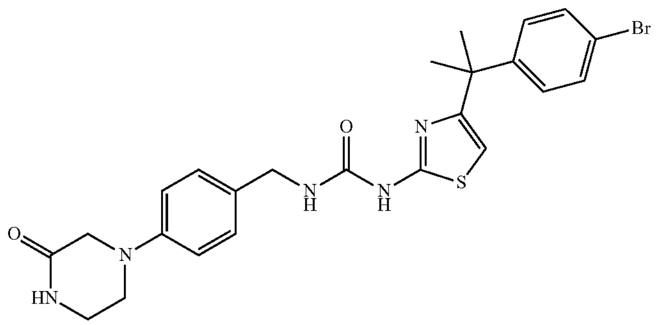 [SMILES: CC(C)(c1ccc(Br)cc1)c1csc(NC(=O)NCc2ccc(N3CCNC(=O)C3)cc2)n1] | 1-(4-(2-(4-bromophenyl)propan-2-yl)thiazol-2-yl)-3-(4-(3-oxopiperazin-1-yl)benzyl)urea | | $[M + H]^+ = 528$ | 132 | 9.94 |

TABLE 4-continued
| Com. ID | Structure | Name | HNMR | LCMS | Kinase assay IC50 nM. | NFkB assay IC50 µM |
|---|---|---|---|---|---|---|
| A196 | 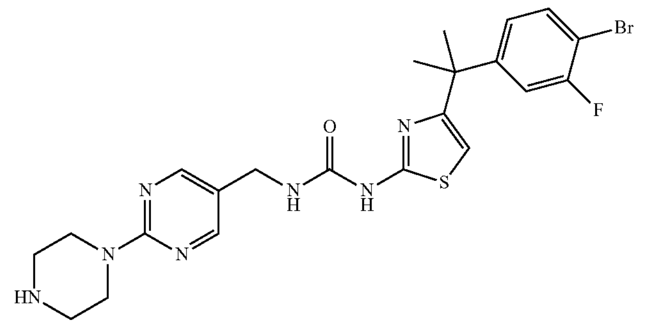 [SMILES: CC(C)(c1ccc(Br)c(F)c1)c1csc(NC(=O)NCc2cnc(N3CCNCC3)nc2)n1] | 1-(4-(2-(4-bromo-3-fluorophenyl)propan-2-yl)thiazol-2-yl)-3-((2-(piperazin-1-yl)pyrimidin-5-yl)methyl)urea | | $[M + H]^+ = 534$ | 76 | 3.34 |
| A197 | 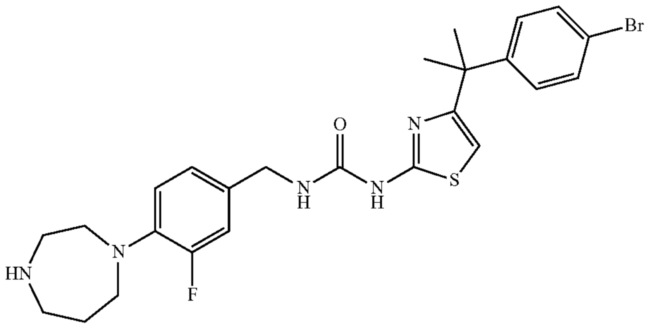 [SMILES: CC(C)(c1ccc(Br)cc1)c1csc(NC(=O)NCc2ccc(N3CCCNCC3)c(F)c2)n1] | 1-(4-(1,4-diazepan-1-yl)-3-fluorobenzyl)-3-(4-(2-(4-bromophenyl)propan-2-yl)thiazol-2-yl)urea | | $[M + H]^+ = 546$ | 67 | |
| A198 | 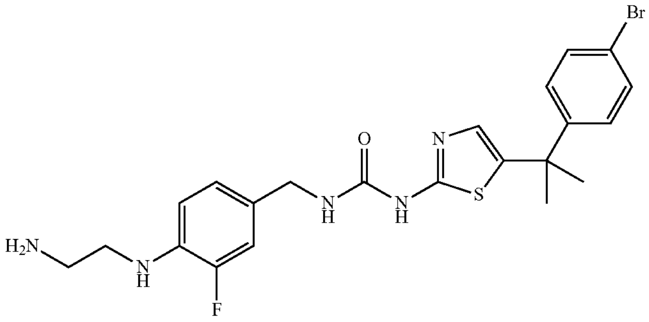 [SMILES: CC(C)(c1ccc(Br)cc1)c1cnc(NC(=O)NCc2ccc(NCCN)c(F)c2)s1] | 1-(4-((2-aminoethyl)amino)-3-fluorobenzyl)-3-(4-(2-(4-bromophenyl)propan-2-yl)thiazol-2-yl)urea | | $[M + H]^+ = 506$ | 18 | 1.32 |

TABLE 4-continued
| Com. ID | Structure | Name | HNMR | LCMS | Kinase assay IC50 nM. | NFkB assay IC50 μM |
|---|---|---|---|---|---|---|
| A199 | 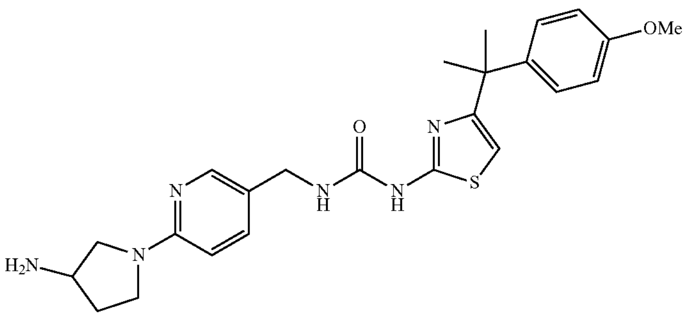 [SMILES: COc1ccc(C(C)(C)c2csc(NC(=O)NCc3ccc(N4CCC(N)C4)nc3)n2)cc1] | 1-((6-(3-aminopyrrolidin-1-yl)pyridin-3-yl)methyl)-3-(4-(2-(4-methoxyphenyl)propan-2-yl)thiazol-2-yl)urea | | $[M + H]^+ = 467$ | 34 | 0.46 |
| A200 | 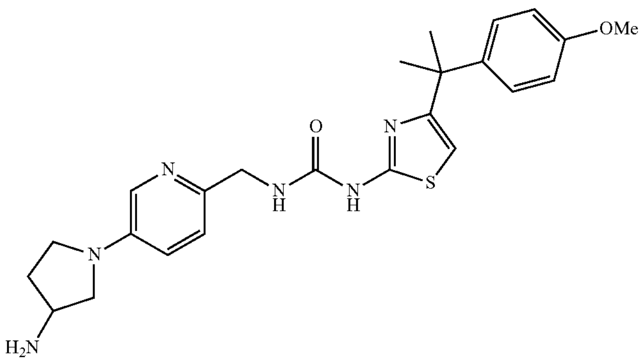 [SMILES: COc1ccc(C(C)(C)c2csc(NC(=O)NCc3ccc(N4CCC(N)C4)cn3)n2)cc1] | 1-((5-(3-aminopyrrolidin-1-yl)pyridin-2-yl)methyl)-3-(4-(2-(4-methoxyphenyl)propan-2-yl)thiazol-2-yl)urea | | $[M + H]^+ = 467$ | 43 | 0.52 |

TABLE 4-continued
| Com. ID | Structure | Name | HNMR | LCMS | Kinase assay IC50 nM. | NFkB assay IC50 μM |
|---|---|---|---|---|---|---|
| A201 | 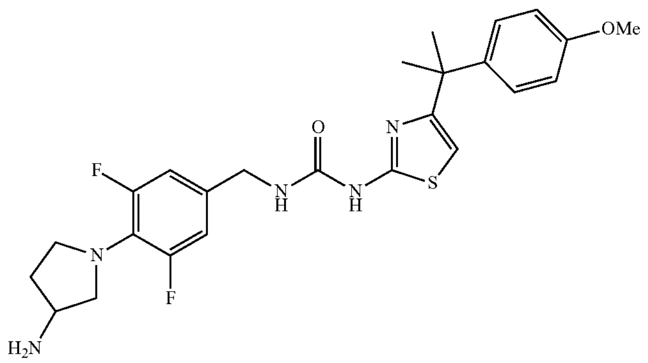 [SMILES: COc1ccc(C(C)(C)c2csc(NC(=O)NCc3cc(F)c(N4CCC(N)C4)c(F)c3)n2)cc1] | 1-(4-(3-aminopyrrolidin-1-yl)-3,5-difluorobenzyl)-3-(4-(2-(4-methoxyphenyl)propan-2-yl)thiazol-2-yl)urea | | $[M + H]^+ = 502$ | 25 | 0.53 |
| A202 | 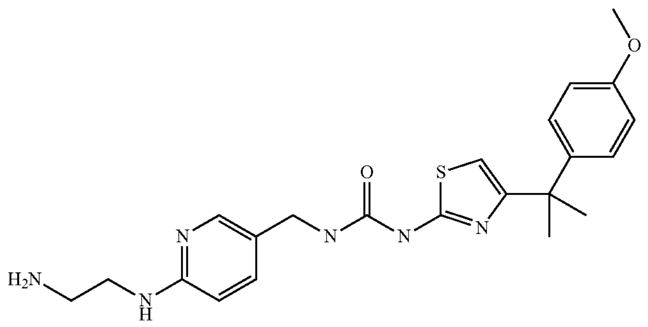 [SMILES: COc1ccc(C(C)(C)c2csc(NC(=O)NCc3ccc(NCCN)nc3)n2)cc1] | 1-((6-((2-aminoethyl)amino)pyridin-3-yl)methyl)-3-(4-(2-(4-methoxyphenyl)propan-2-yl)thiazol-2-yl)urea | | $[M + H]^+ = 441$ | 34 | 5.71 |

TABLE 4-continued
| Com. ID | Structure | Name | HNMR | LCMS | Kinase assay IC50 nM. | NFkB assay IC50 µM |
|---|---|---|---|---|---|---|
| A203 | 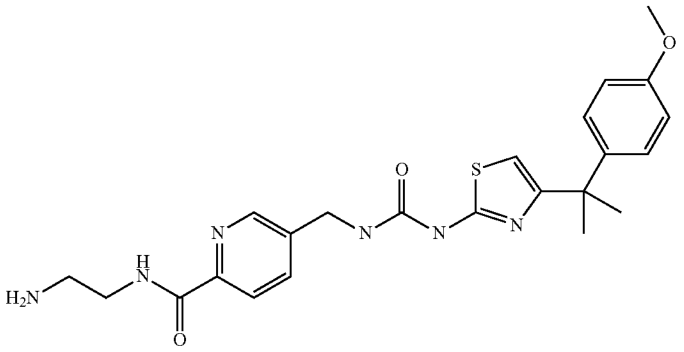 [SMILES: COc1ccc(C(C)(C)c2csc(NC(=O)NCc3ccc(C(=O)NCCN)nc3)n2)cc1] | N-(2-aminoethyl)-5-((3-(4-(2-(4-methoxyphenyl)propan-2-yl)thiazol-2-yl)ureido)methyl)picolinamide | | $[M + H]^+ = 469$ | 94 | 5.70 |
| A204 | 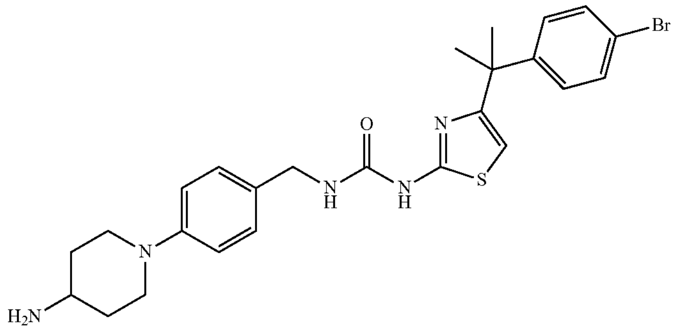 [SMILES: CC(C)(c1ccc(Br)cc1)c1csc(NC(=O)NCc2ccc(N3CCC(N)CC3)cc2)n1] | 1-(4-(4-aminopiperidin-1-yl)benzyl)-3-(4-(2-(4-bromophenyl)propan-2-yl)thiazol-2-yl)urea | | $[M + H]^+ = 528$ | 9 | 1.89 |

TABLE 4-continued
| Com. ID | Structure | Name | HNMR | LCMS | Kinase assay IC50 nM. | NFkB assay IC50 μM |
| --- | --- | --- | --- | --- | --- | --- |
| A205 | 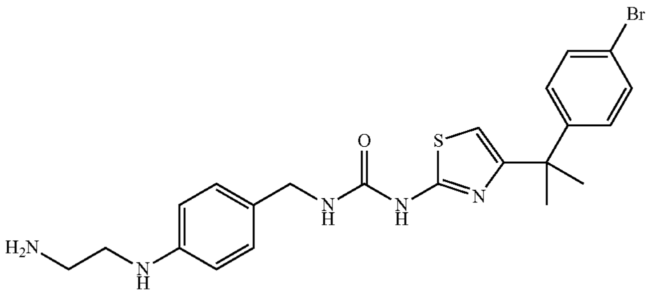 [SMILES: CC(C)(c1ccc(Br)cc1)c1csc(NC(=O)NCc2ccc(NCCN)cc2)n1] | 1-(4-((2-aminoethyl)amino)benzyl)-3-(4-(2-(4-bromophenyl)propan-2-yl)thiazol-2-yl)urea | | $[M + H]^+ = 488$ | 59 | 1.48 |
| A206 | 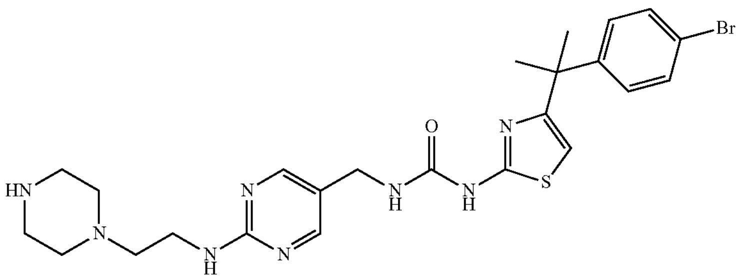 [SMILES: CC(C)(c1ccc(Br)cc1)c1csc(NC(=O)NCc2cnc(NCCN3CCNCC3)nc2)n1] | 1-(4-(2-(4-bromophenyl)propan-2-yl)thiazol-2-yl)-3-((2-((2-(piperazin-1-yl)ethyl)amino)pyrimidin-5-yl)methyl)urea | | $[M + H]^+ = 559$ | 68 | |

TABLE 4-continued
| Com. ID | Structure | Name | HNMR | LCMS | Kinase assay IC50 nM. | NFkB assay IC50 μM |
|---|---|---|---|---|---|---|
| A207 | 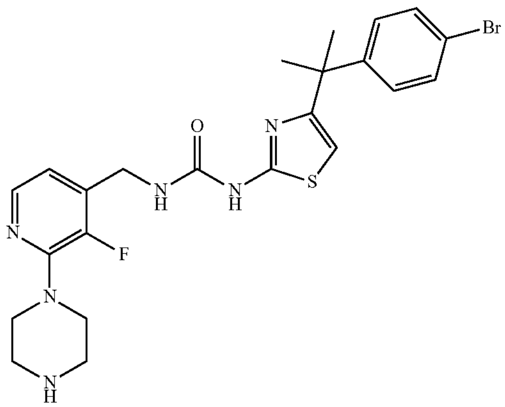 [SMILES: CC(C)(c1ccc(Br)cc1)c1csc(NC(=O)NCc2ccnc(N3CCNCC3)c2F)n1] | 1-(4-(2-(4-bromophenyl)propan-2-yl)thiazol-2-yl)-3-((3-fluoro-2-(piperazin-1-yl)pyridin-4-yl)methyl)urea | | $[M + H]^+ = 533$ | 99 | 2.18 |
| A208 | 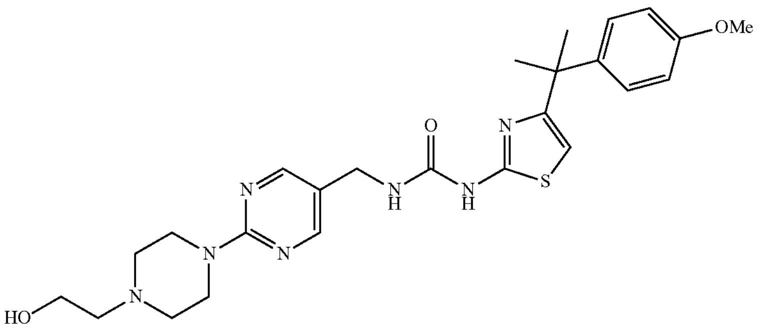 [SMILES: COc1ccc(C(C)(C)c2csc(NC(=O)NCc3cnc(N4CCN(CCO)CC4)nc3)n2)cc1] | 1-((2-(4-(2-hydroxyethyl)piperazin-1-yl)pyrimidin-5-yl)methyl)-3-(4-(2-(4-methoxyphenyl)propan-2-yl)thiazol-2-yl)urea | | $[M + H]^+ = 512$ | 78 | 0.76 |

TABLE 4-continued
| Com. ID | Structure | Name | HNMR | LCMS | Kinase assay IC50 nM. | NFkB assay IC50 μM |
|---|---|---|---|---|---|---|
| A209 | 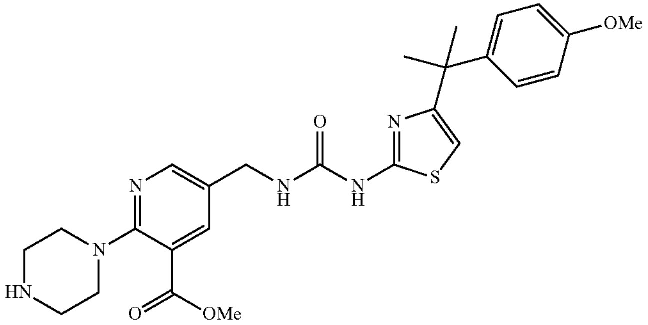 | 5-((3-(4-(2-(4-methoxyphenyl)propan-2-yl)thiazol-2-yl)ureido)methyl)-2-(piperazin-1-yl)nicotinamide | | $[M + H]^+ = 510$ | 43 | |
| A210 | 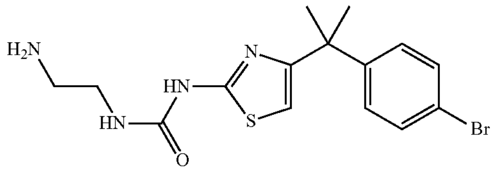 [SMILES: CC(C)(c1ccc(Br)cc1)c1csc(NC(=O)NCCN)n1] | 1-(2-aminoethyl)-3-(4-(2-(4-bromophenyl)propan-2-yl)thiazol-2-yl)urea | | $[M + H]^+ = 383$ | 95 | 4.16 |
| A211 | 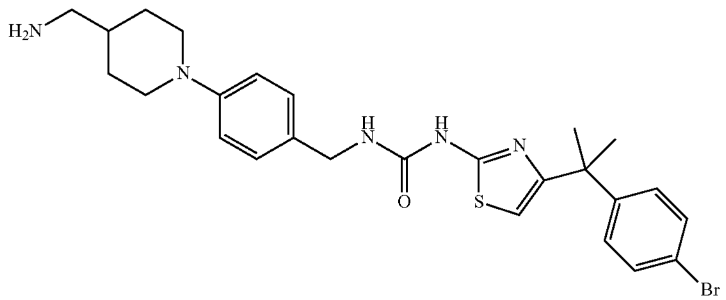 [SMILES: CC(C)(c1ccc(Br)cc1)c1csc(NC(=O)NCc2ccc(N3CCC(CN)CC3)cc2)n1] | 1-(4-(4-(aminomethyl)piperidin-1-yl)benzyl)-3-(4-(2-(4-bromophenyl)propan-2-yl)thiazol-2-yl)urea | | $[M + H]^+ = 542$ | 94 | 2.59 |

TABLE 4-continued
| Com. ID | Structure | Name | HNMR | LCMS | Kinase assay IC50 nM. | NFkB assay IC50 μM |
|---|---|---|---|---|---|---|
| A212 | 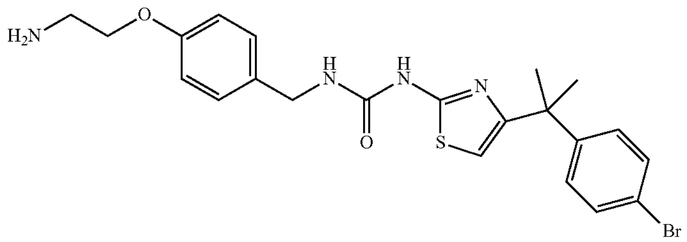 [SMILES: CC(C)(c1ccc(Br)cc1)c1csc(NC(=O)NCc2ccc(OCCN)cc2)n1] | 1-(4-(2-aminoethoxy)benzyl)-3-(4-(2-(4-bromophenyl)propan-2-yl)thiazol-2-yl)urea | | $[M + H]^+ = 489$ | 289 | 2.75 |
| A213 | 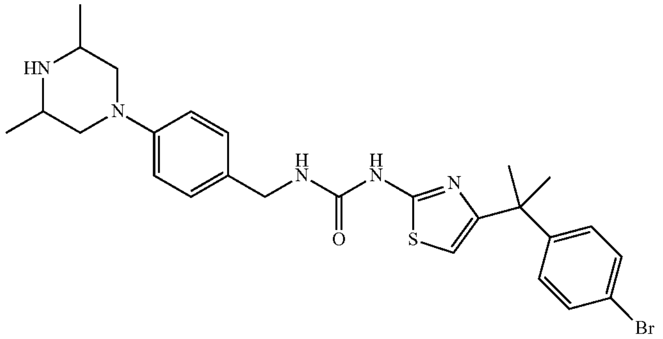 [SMILES: CC1CN(c2ccc(CNC(=O)Nc3nc(C(C)(C)c4ccc(Br)cc4)cs3)cc2)CC(C)N1] | 1-(4-(2-(4-bromophenyl)propan-2-yl)thiazol-2-yl)-3-(4- (3,5-dimethylpiperazin-1-yl)benzyl)urea | | $[M + H]^+ = 542$ | 9 | 6.38 |

TABLE 4-continued
| Com. ID | Structure | Name | HNMR | LCMS | Kinase assay IC50 nM. | NFkB assay IC50 μM |
|---|---|---|---|---|---|---|
| A214 | 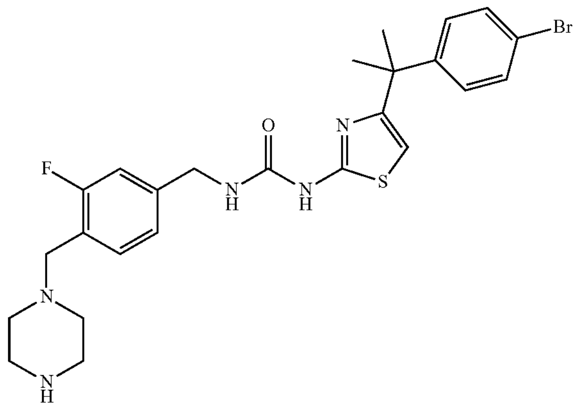 [SMILES: CC(C)(c1ccc(Br)cc1)c1csc(NC(=O)NCc2ccc(CN3CCNCC3)c(F)c2)n1] | 1-(4-(2-(4-bromophenyl)propan-2-yl)thiazol-2-yl)-3-(3-fluoro-4-(piperazin-1-ylmethyl)benzyl)urea | | $[M + H]^+ = 546$ | 40 | 1.56 |
| A215 | 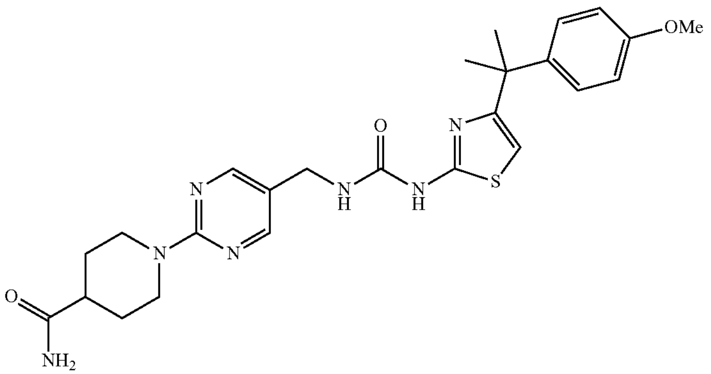 [SMILES: COc1ccc(C(C)(C)c2csc(NC(=O)NCc3cnc(N4CCC(C(N)=O)CC4)nc3)n2)cc1] | 1-(5-((3-(4-(2-(4-methoxyphenyl)propan-2-yl)thiazol-2-yl)ureido)methyl)pyrimidin-2-yl)piperidine-4-carboxamide | | $[M + H]^+ = 510$ | 150 | 2.21 |

TABLE 4-continued

| Com. ID | Structure | Name | HNMR | LCMS | Kinase assay IC50 nM. | NFkB assay IC50 μM |
|---|---|---|---|---|---|---|
| A216 | 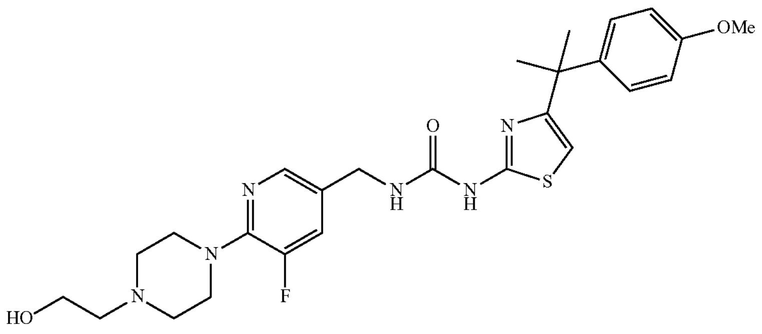 [SMILES: COc1ccc(C(C)(C)c2csc(NC(=O)NCc3cnc(N4CCN(CCO)CC4)c(F)c3)n2)cc1] | 1-((5-fluoro-6-(4-(2-hydroxyethyl) piperazin-1-yl)pyridin-3-yl) methyl)-3-(4-(2-(4-methoxyphenyl) propan-2-yl)thiazol-2-yl)urea | | $[M + H]^+ = 529$ | 61 | 1.43 |
| A217 | 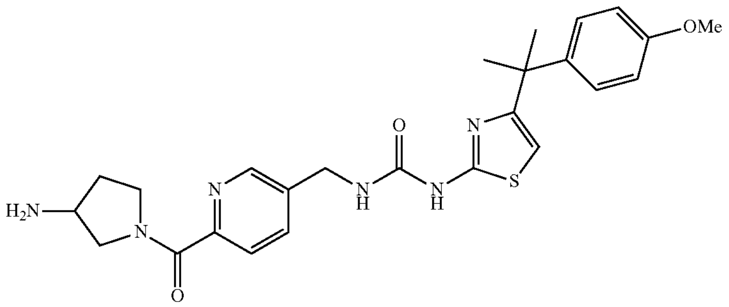 [SMILES: COc1ccc(C(C)(C)c2csc(NC(=O)NCc3ccc(C(=O)N4CCC(N)C4)nc3)n2)cc1] | 1-((6-(3-aminopyrrolidine-1-carbonyl)pyridin-3-yl)methyl)-3-(4-(2-(4-methoxyphenyl) propan-2-yl)thiazol-2-yl)urea | | $[M + H]^+ = 495$ | 56 | 32.58 |
| A218 | 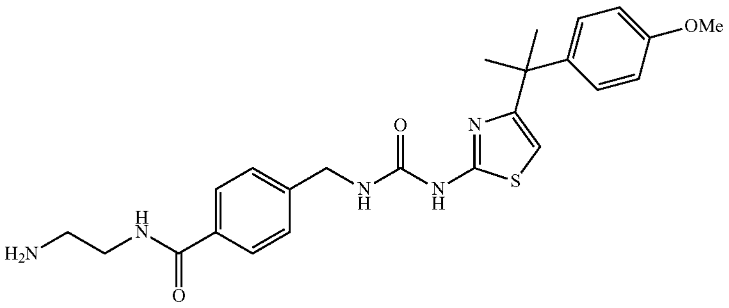 [SMILES: COc1ccc(C(C)(C)c2csc(NC(=O)NCc3ccc(C(=O)NCCN)cc3)n2)cc1] | N-(2-aminoethyl)-4-((3-(4-(2-(4-methoxyphenyl) propan-2-yl)thiazol-2-yl)ureido)methyl) benzamide | | $[M + H]^+ = 468$ | 29 | 6.71 |

TABLE 4-continued

| Com. ID | Structure | Name | HNMR | LCMS | Kinase assay IC50 nM. | NFkB assay IC50 μM |
|---|---|---|---|---|---|---|
| A219 | 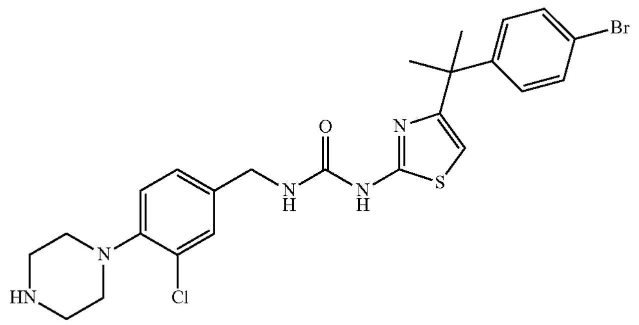 [SMILES: CC(C)(c1ccc(Br)cc1)c1csc(NC(=O)NCc2ccc(N3CCNCC3)c(Cl)c2)n1] | 1-(4-(2-(4-bromophenyl)propan-2-yl)thiazol-2-yl)-3-(3-chloro-4-(piperazin-1-yl)benzyl)urea | $^1$H NMR (400 MHz, DMSO-d6) δ 10.76 (br s, 1H), 9.25 (br s, 2H), 7.43 (d, J = 8.56 Hz, 2H), 7.34 (d, J = 1.96 Hz, 1H), 7.24-7.20 (m, 1H), 7.15 (d, J = 8.56 Hz, 4H), 6.74 (s, 1H), 4.25 (br d, J = 5.62 Hz, 2H), 3.27-3.08 (m, 8H), 1.57 (s, 6H) | $[M + H]^+$ = 550.0 | 46 | 2.73 |
| A220 | 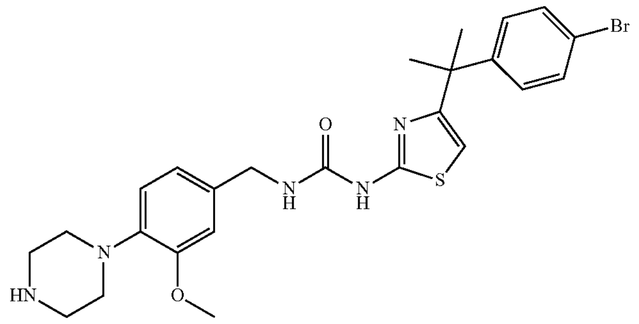 [SMILES: COc1cc(CNC(=O)Nc2nc(C(C)(C)c3ccc(Br)cc3)cs2)ccc1N1CCNCC1] | 1-(4-(2-(4-bromophenyl)propan-2-yl)thiazol-2-yl)-3-(3-methoxy-4-(piperazin-1-yl)benzyl)urea | $^1$H NMR (400 MHz, DMSO-d6) δ 10.67 (br s, 1H) 9.14 (br s, 2H), 7.43 (d, J = 8.56 Hz, 2H), 7.15 (d, J = 8.56 Hz, 2H), 7.12 (br s, 1H), 6.93-6.88 (m, 2H), 6.80 (br d, J = 8.07 Hz, 1H), 6.74 (s, 1H), 4.25 (br d, J = 5.38 Hz, 2H), 3.77 (s, 3H), 3.18 (br d, J = 14.18 Hz, 8H), 1.57 (s, 6H). | $[M + H]^+$ = 544.2 | 44 | 1.32 |

TABLE 4-continued

| Com. ID | Structure | Name | HNMR | LCMS | Kinase assay IC50 nM. | NFkB assay IC50 µM |
|---|---|---|---|---|---|---|
| A221 | 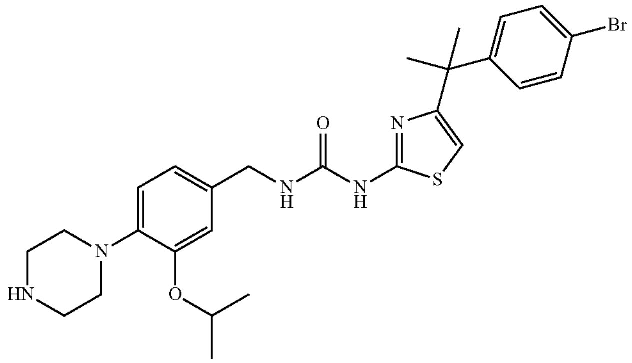 [SMILES: CC(C)Oc1cc(CNC(=O)Nc2nc(C(C)(C)c3ccc(Br)cc3)cs2)ccc1N1CCNCC1] | 1-(4-(2-(4-bromophenyl)propan-2-yl)thiazol-2-yl)-3-(3-isopropoxy-4-(piperazin-1-yl)benzyl)urea | $^1$H NMR (400 MHz, DMSO-d6) δ 10.79 (br s, 1H), 9.48 (br s, 2H), 7.49 (br d, J = 8.80 Hz, 1H), 7.43 (d, J = 8.56 Hz, 2H), 7.15 (d, J = 8.56 Hz, 2H), 7.03 (br d, J = 8.07 Hz, 1H), 6.94 (s, 1H), 6.81 (br d, J = 7.83 Hz, 1H), 6.77 (s, 1H), 6.01 (br s, 8H), 4.61 (dt, J = 11.98, 5.99 Hz, 1H), 4.24 (br d, J = 4.40 Hz, 2H), 1.58 (s, 6H), 1.28 (d, J = 6.11 Hz, 6H). | $[M + H]^+$ = 574.1 | 144 | 2.38 |
| A222 | 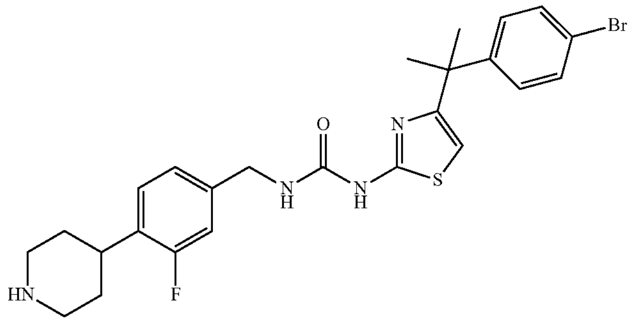 [SMILES: CC(C)(c1ccc(Br)cc1)c1csc(NC(=O)NCc2ccc(C3CCNCC3)c(F)c2)n1] | 1-(4-(2-(4-bromophenyl)propan-2-yl)thiazol-2-yl)-3-(3-fluoro-4-(piperidin-4-yl)benzyl)urea | $^1$H NMR (400 MHz, DMSO-d6) δ 10.76 (br s, 1H), 9.06 (br s, 1H), 8.88 (br d, J = 9.78 Hz, 1H), 7.43 (d, J = 8.56 Hz, 2H), 7.29-7.19 (m, 2H), 7.15 (d, J = 8.56 Hz, 2H), 7.10-7.04 (m, 2H), 6.74 (s, 1H), 4.28 (br d, J = 5.62 Hz, 2H),3.33 (br d, J = 12.47 Hz, 2H), 3.14-2.93 (m, 2H), 1.93-1.81 (m, 3H), 1.57 (s, 6H), 1.23 (br s, 2H). | $[M + H]^+$ = 532.2 | 56 | 0.93 |

TABLE 4-continued

| Com. ID | Structure | Name | HNMR | LCMS | Kinase assay IC50 nM. | NFkB assay IC50 µM |
|---|---|---|---|---|---|---|
| A223 | 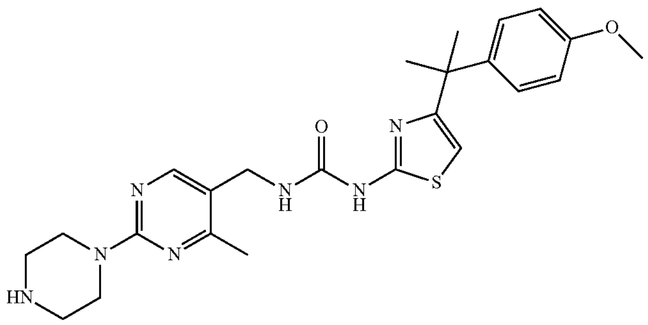 [SMILES: COc1ccc(C(C)(C)c2csc(NC(=O)NCc3cnc(N4CCNCC4)nc3C)n2)cc1] | 1-(4-(2-(4-methoxyphenyl)propan-2-yl)thiazol-2-yl)-3-((4-methyl-2-(piperazin-1-yl)pyrimidin-5-yl)methyl)urea | $^1$H NMR (400 MHz, DMSO-d6) δ 9.50 (br s, 2H), 8.23 (s, 1H), 7.76-7.57 (m, 1H), 7.17-7.06 (m, 2H), 6.86-6.79 (m, 2H), 6.72 (s, 1H), 4.26-4.18 (m, 2H), 4.0-3.92 (m, 4H), 3.70 (s, 3H), 3.13 (s, 4H), 2.40 (s, 3H), 1.57 (s, 6H). | $[M + H]^+$ = 482.4 | 49 | 0.76 |
| A224 | 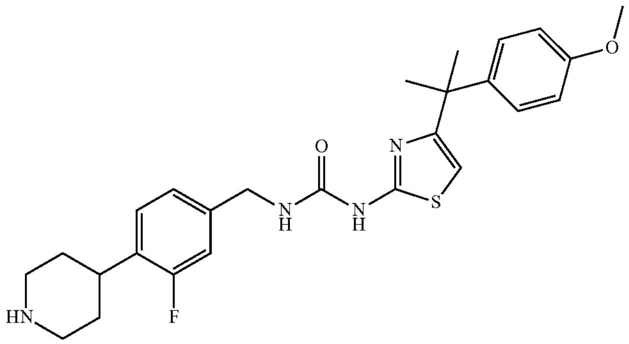 [SMILES: COc1ccc(C(C)(C)c2csc(NC(=O)NCc3ccc(C4CCNCC4)c(F)c3)n2)cc1] | 1-(3-fluoro-4-(piperidin-4-yl)benzyl)-3-(4-(2-(4-methoxyphenyl)propan-2-yl)thiazol-2-yl)urea | $^1$H NMR (400 MHz, DMSO-d6) δ 10.73 (br s, 1H), 8.93 (br s, 1H), 8.72 (br s, 1H), 7.26-7.20 (m, 1H), 7.16-7.02 (m, 5H), 6.81 (d, J = 8.80 Hz, 2H), 6.66 (s, 1H), 4.29 (br d, J = 5.87 Hz, 2H), 3.70 (s, 3H), 3.34 (br d, J = 12.23 Hz, 2H), 3.15-3.07 (m, 1H), 3.07-2.94 (m, 2H), 1.87 (br s, 4H), 1.57 (s, 6H). | $[M + H]^+$ = 483.2 | 21 | 0.73 |

TABLE 4-continued

| Com. ID | Structure | Name | HNMR | LCMS | Kinase assay IC50 nM. | NFkB assay IC50 μM |
|---|---|---|---|---|---|---|
| A225 | 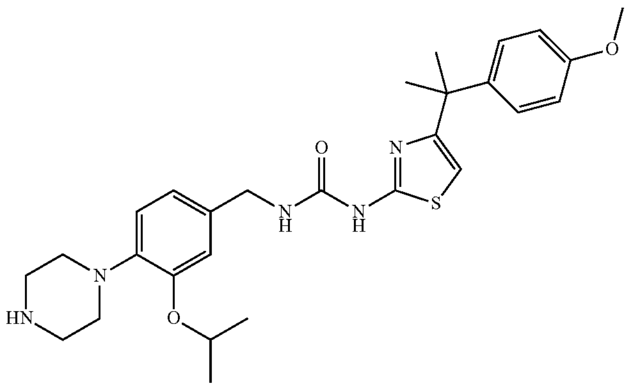 [SMILES: COc1ccc(C(C)(C)c2csc(NC(=O)NCc3ccc(N4CCNCC4)c(OC(C)C)c3)n2)cc1] | 1-(3-isopropoxy-4-(piperazin-1-yl)benzyl)-3-(4-(2-(4-methoxyphenyl)propan-2-yl)thiazol-2-yl)urea | $^1$H NMR (400 MHz, CD3OD) δ 7.23-7.16 (m, 3H), 7.11 (s, 1H), 7.07 (s, 1H), 6.97-6.87 (m, 3H), 4.75 (dt, J = 11.49, 5.75 Hz, 1H), 4.40 (s, 2H), 3.76 (s, 3H), 3.51 (s, 8H), 1.69 (s, 6H), 1.38 (d, J = 5.87 Hz. 6H). | $[M + H]^+ = 524.3$ | 108 | 1.05 |
| A226 | 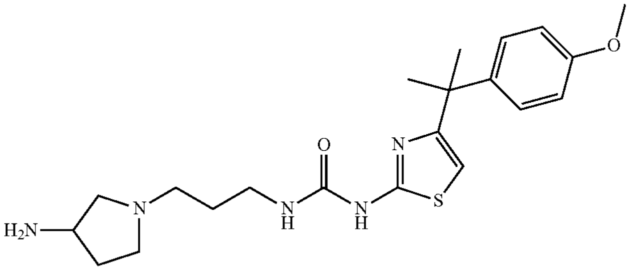 [SMILES: COc1ccc(C(C)(C)c2csc(NC(=O)NCCCN3CCC(N)C3)n2)cc1] | 1-(3-(3-aminopyrrolidin-1-yl)propyl)-3-(4-(2-(4-methoxyphenyl)propan-2-yl)thiazol-2-yl)urea | $^1$H NMR (400 MHz, DMSO-d6) δ 11.30 (s, 1H) 10.94 (s, 1H) 8.64 (s, 1H) 8.55 (s, 1H) 7.09 (d, J = 8.82 Hz, 2H) 6.95 (s, 1H) 6.78 (d, J = 8.82 Hz, 2H) 6.64 (s, 1H) 4.00 (d, J = 13.89 Hz, 1H) 3.67 (s, 3H) 3.37-3.49 (m, 1H) 3.35 (s,2H) 3.01-3.23 (m, 5H) 2.06-2.28 (m, 1H) 1.92-2.06 (m, 1H) 1.75-1.86 (m, 2H) 1.54 (s, 6H) | $[M + H]^+ = 418.3$ | 100 | 4.82 |
| A227 | 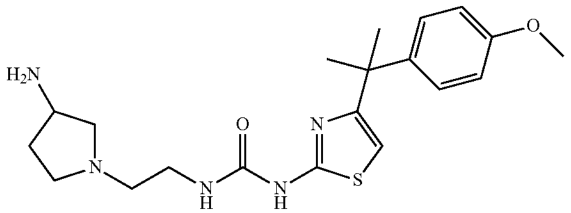 [SMILES: COc1ccc(C(C)(C)c2csc(NC(=O)NCCN3CCC(N)C3)n2)cc1] | 1-(2-(3-aminopyrrolidin-1-yl)ethyl)-3-(4-(2-(4-methoxyphenyl)propan-2-yl)thiazol-2-yl)urea | $^1$H NMR (400 MHz, D2O) δ 7.20-7.13 (m, 2H), 6.95 (s, 1H), 6.89-6.83 (m, 2H), 4.20-3.74 (m, 3H), 3.71 (s, 3H), 3.68-3.47 (m, 4H), 3.46-3.32 (m, 2H), 2.65-2.48 (m, 1H), 2.24-2.07 (m, 1H), 1.56 (s, 6H). | $[M + H]^+ = 404.3$ | 138 | 3.12 |

TABLE 4-continued

| Com. ID | Structure | Name | HNMR | LCMS | Kinase assay IC50 nM. | NFkB assay IC50 μM |
|---|---|---|---|---|---|---|
| A228 | 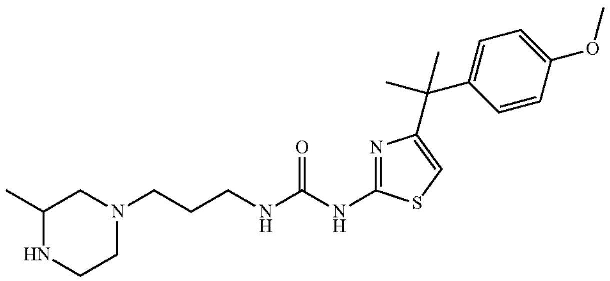 | 1-(4-(2-(4-methoxyphenyl)propan-2-yl)thiazol-2-yl)-3-(3-(3-methylpiperazin-1-yl)propyl)urea | $^1$H NMR (400 MHz, DMSO-$d_6$) δ 11.79 (br s, 1H), 10.68 (br s, 1H), 9.97 (br s, 2H), 7.12 (d, J = 8.6 Hz, 2H), 6.88 (s, 1H), 6.81 (d, J = 8.8 Hz, 2H), 6.67 (s, 1H), 3.75-3.62 (m, 6H), 3.58-3.49 (m, 1H), 3.48-3.36 (m, 1H), 3.29-3.16 (m, 3H), 3.15-2.99 (m, 3H), 1.96-1.82 (m, 2H), 1.57 (s, 6H), 1.30 (d. J = 6.4 Hz, 2H). | $[M + H]^+$ = 432.3 | 100 | 3.86 |
| A229 | 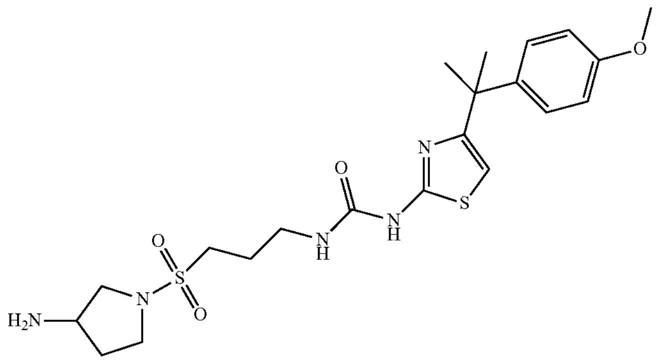 [SMILES: COc1ccc(C(C)(C)c2csc(NC(=O)NCCCS(=O)(=O)N3CCC(N)C3)n2)cc1] | 1-(3-((3-aminopyrrolidin-1-yl)sulfonyl)propyl)-3-(4-(2-(4-methoxyphenyl)propan-2-yl)thiazol-2-yl)urea | $^1$H NMR (400 MHz, DMSO-d6) δ 8.47 (br s, 3H), 7.24 (br s, 1H), 7.12 (d, J = 8.82 Hz, 2H), 6.82 (d, J = 8.60 Hz, 2H), 6.70 (s, 1H), 3.83 (br d, J = 5.07 Hz, 1H), 3.70 (s, 3H), 3.58 (br dd, J = 10.80, 6.62 Hz, 1H), 3.52-3.43 (m, 1H), 3.41-3.28 (m, 3H), 3.26-3.13 (m, 4H), 2.22 (dq, J = 13.70, 6.90 Hz, 1H), 2.05-1.92 (m, 1H), 1.84 (dt, J = 14.55, 7.06 Hz, 2H), 1.57 (s, 6H). | $[M + H]^+$ = 482.2 | 169 | 2.27 |

TABLE 4-continued

| Com. ID | Structure | Name | HNMR | LCMS | Kinase assay IC50 nM. | NFkB assay IC50 μM |
|---|---|---|---|---|---|---|
| A230 | 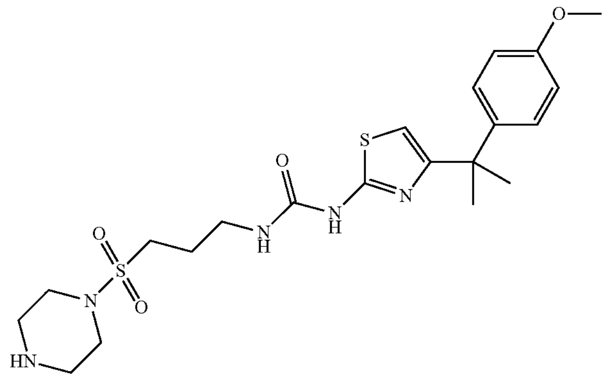 [SMILES: COc1ccc(C(C)(C)c2csc(NC(=O)NCCCS(=O)(=O)N3CCNCC3)n2)cc1] | 1-(4-(2-(4-methoxyphenyl)propan-2-yl)thiazol-2-yl)-3-(3-(piperazin-1-ylsulfonyl)propyl)urea | $^1$H NMR (400 MHz, DMSO-d6) δ 7.10-7.07 (m, 2H), 6.78-6.75 (m, 2H), 6.59 (s, 1H), 3.67 (s, 3H), 3.30-3.15 (m, 2H), 3.02-2.95 (m, 6H), 2.68-2.66 (m, 4H), 1.79-1.72 (m, 2H), 1.52 (s, 6H). | $[M + H]^+$ = 482.2 | 127 | 3.01 |
| A231 | 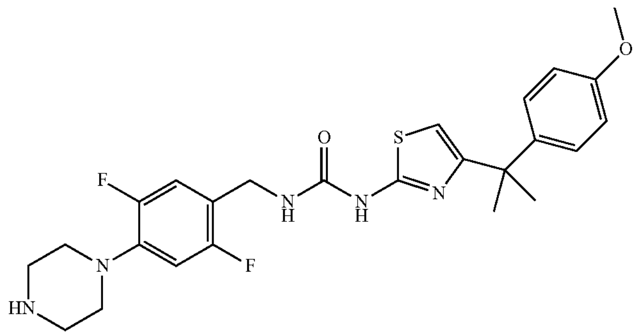 [SMILES: COc1ccc(C(C)(C)c2csc(NC(=O)NCc3cc(F)c(N4CCNCC4)cc3F)n2)cc1] | 1-(2,5-difluoro-4-(piperazin-1-yl)benzyl)-3-(4-(2-(4-methoxyphenyl)propan-2-yl)thiazol-2-yl)urea hydrochloride | $^1$H NMR (400 MHz, DMSO-d6) δ 10.75 (br s, 1H), 9.33 (br s, 2H), 7.39 (br s, 1H), 7.16-7.10 (m, 3H), 6.98 (dd, J = 11.36, 7.39 Hz, 1H), 6.80 (d, J = 8.82 Hz, 2H), 6.68 (s, 1H), 4.27 (br d, J = 5.51 Hz, 2H), 3.70 (s, 3H), 3.23 (br s, 8H), 1.57 (s, 6H), | $[M + H]^+$ = 502.2 | 27 | 3.36 |

TABLE 4-continued

| Com. ID | Structure | Name | HNMR | LCMS | Kinase assay IC50 nM. | NFkB assay IC50 μM |
|---|---|---|---|---|---|---|
| A232 | 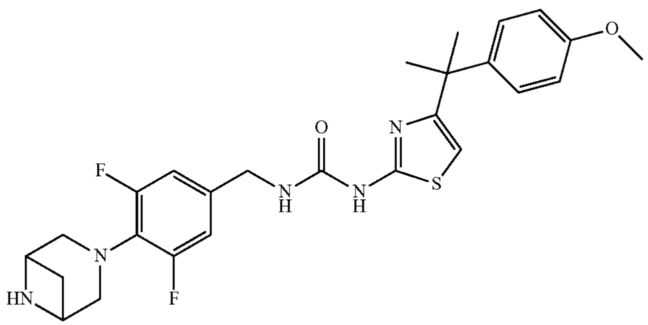 [SMILES: COc1ccc(C(C)(C)c2csc(NC(=O)NCc3cc(F)c(N4CC5CC(C4)N5)c(F)c3)n2)cc1] | 1-(4-(3,6-diazabicyclo[3.1.1]heptan-3-yl)-3,5-difluorobenzyl)-3-(4-(2-(4-methoxyphenyl)propan-2-yl)thiazol-2-yl)urea | $^1$H NMR (400 MHz, DMSO-d6) δ 10.85-10.72 (m, 1H), 9.80-9.68 (m, 1H), 8.16-8.08 (m, 1H), 7.12 (br d, J = 8.8 Hz, 2H), 7.05-6.93 (m, 2H), 6.86-6.76 (m, 2H), 6.71-6.64 (m, 1H), 4.27 (br d, J = 6.1 Hz, 4H), 3.88 (s, 2H), 3.70 (s, 3H), 3.54-3.49 (m, 2H), 2.86-2.76 (m, 1H), 2.14-2.06 (m, 1H), 1.57 (s, 6H). | $[M + H]^+ = 514.3$ | 88 | 0.59 |
| A233 | 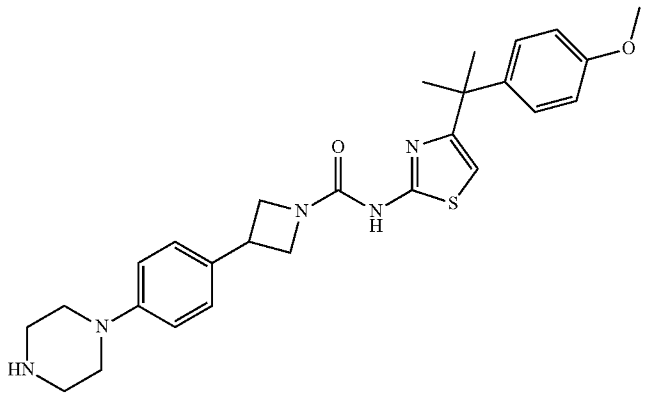 [SMILES: COc1ccc(C(C)(C)c2csc(NC(=O)N3CC(c4ccc(N5CCNCC5)cc4)C3)n2)cc1] | N-(4-(2-(4-methoxyphenyl)propan-2-yl)thiazol-2-yl)-3-(4-(piperazin-1-yl)phenyl)azetidine-1-carboxamide | $^1$H NMR (400 MHz, DMSO-d6) δ 9.25 (br s, 2H), 7.33 (s, 0.4H), 7.25-7.23 (m, 2H), 7.20-7.18 (m, 2H), 7.14-7.12 (m, 0.4H), 6.98-6.96 (m, 2H),6.82-6.80 (m, 2H), 6.66 (s, 1H), 4.38-4.36 (m, 2H), 3.94-3.91 (m, 2H), 3.76-3.72 (m, 1H), 3.72 (s, 3H), 3.39-3.38 (m, 4H), 3.37-3.20 (m, 4H), 1.60 (s, 6H). | $[M + H]^+ = 492.2$ | 43 | 0.33 |
| A234 | 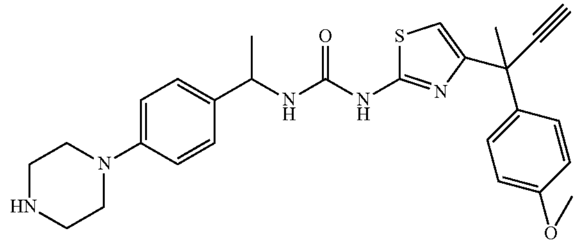 [SMILES: C#CC(C)(c1ccc(OC)cc1)c1csc(NC(=O)NC(C)c2ccc(N3CCNCC3)cc2)n1] | 1-(4-(2-(4-methoxyphenyl)but-3-yn-2-yl)thiazol-2-yl)-3-(1-(4-(piperazin-1-yl)phenyl)ethyl)urea | $^1$H NMR (400 MHz, DMSO-d6) δ 10.50 (br s, 1H), 9.22 (br s, 2H), 7.31 (d, J = 8.8 Hz, 2H), 7.19 (d, J = 8.4 Hz, 3H), 6.95 (d, J = 8.4 Hz, 2H), 6.85 (dd, J = 8.4, 1.2 Hz, 2H), 6.81-6.79 (m, 1H), 4.76-4.73 (m, 1H), 3.71 (s, 3H), 3.39 (s, 1H), 3.35-3.32 (m, 4H) 3.24-3.16 (m, 4H), 1.82 (d, J = 2.4 Hz, 3H), 1.33 (d, J = 6.8 Hz, 3H) | $[M + Na]^+ = 512.3$ | 36 | 2.67 |

TABLE 4-continued

| Com. ID | Structure | Name | HNMR | LCMS | Kinase assay IC50 nM. | NFkB assay IC50 μM |
|---|---|---|---|---|---|---|
| A235 | 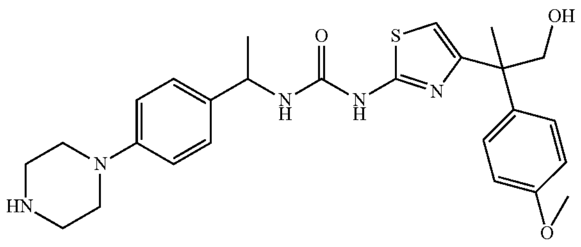 [SMILES: COc1ccc(C(C)(CO)c2csc(NC(=O)NC(C)c3ccc(N4CCNCC4)cc3)n2)cc1] | 1-(4-(1-hydroxy-2-(4-methoxyphenyl)propan-2-yl)thiazol-2-yl)-3-(1-(4-(piperazin-1-yl)phenyl)ethyl)urea | $^1$H NMR (400 MHz, DMSO-d6) δ 10.47 (br s, 1H), 9.11 (br s, 2H), 7.36-7.23 (m, 1H), 7.19 (d, J = 8.8 Hz, 2H), 7.10 (d, J = 8.8 Hz, 2H), 6.95 (d, J = 8.8 Hz, 2H), 6.75 (d, J = 8.0 Hz, 2H), 6.69 (s, 1H), 4.77-4.73 (m, 1H), 3.80-3.76 (m, 1H), 3.70 (s, 3H) 3.34-3.31 (m, 4H), 3.24-3.16 (m, 4H), 2.07 (s, 1H), 1.55 (s, 3H), 1.33 (d, J = 6.8 Hz, 3H) | $[M + H]^+ = 496.2$ | 61 | 27.01 |
| A236 | 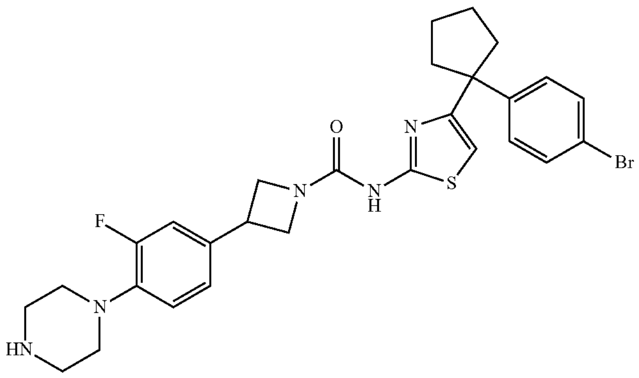 [SMILES: O=C(Nc1nc(C2(c3ccc(Br)cc3)CCCC2)cs1)N1CC(c2ccc(N3CCNCC3)c(F)c2)C1] | N-(4-(1-(4-bromophenyl)cyclopentyl)thiazol-2-yl)-3-(3-fluoro-4-(piperazin-1-yl)phenyl)azetidine-1-carboxamide | $^1$H NMR (400 MHz, MeOD) δ 7.34 (d, J = 8.56 Hz, 2H) 7.21 (d, J = 8.56 Hz, 2H) 7.08-7.00 (m, 3H) 6.68 (s, 1H) 4.59 (br d, J = 16.63 Hz, 1H) 4.40 (t, J = 8.56 Hz, 2H) 3.98 (dd, J = 8.31, 6.11 Hz, 2H) 3.77-3.87 (m, 1H) 3.02 (br d, J = 6.11 Hz, 8H) 2.43-2.53 (m, 2H) 2.01-2.13 (m, 2H) 1.62-1.77 (m, 4H) | $[M + H]^+ = 584.3$ | 13 | 4.50 |

TABLE 4-continued

| Com. ID | Structure | Name | HNMR | LCMS | Kinase assay IC50 nM. | NFkB assay IC50 μM |
|---|---|---|---|---|---|---|
| A237 | 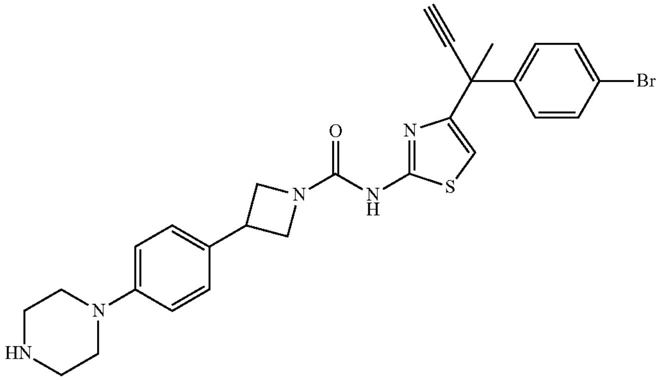 [SMILES: C#CC(C)(c1ccc(Br)cc1)c1csc(NC(=O)N2CC(c3ccc(N4CCNCC4)cc3)C2)n1] | N-(4-(2-(4-bromophenyl)but-3-yn-2-yl)thiazol-2-yl)-3-(4-(piperazin-1-yl)phenyl)azetidine-1-carboxamide | $^1$H NMR (400 MHz, DMSO-d6) δ 10.93 (s, 1H) 9.22 (s, 2H) 7.47 (d, J = 8.4 Hz, 2H) 7.30 (d, J = 8.4 Hz, 2H) 7.21 (d, J = 8.4 Hz, 2H), 6.90-6.98 (m, 3H), 4.30 (br s, 1H), 3.87-3.84 (m, 2H), 3.66-3.74 (m, 1H), 3.46 (s, 1H), 3.31-3.30 (m, 4H), 3.22-3.10 (m, 4H), 1.82 (s, 3H) | $[M + H]^+$ = 550.1 | 7 | 0.61 |
| A238 | 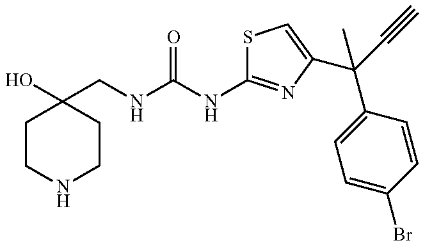 [SMILES: C#CC(C)(c1ccc(Br)cc1)c1csc(NC(=O)NCC2(O)CCNCC2)n1] | 1-(4-(2-(4-bromophenyl)but-3-yn-2-yl)thiazol-2-yl)-3-((4-hydroxypiperidin-4-yl)methyl)urea | $^1$H NMR (400 MHz, MeOD) δ 7.53-7.20 (m, 2H), 7.44-7.42 (m, 2H), 7.14 (s, 1H), 3.33-3.27 (m, 2H), 3.26-3.25 (m, 4H), 3.16 (s, 1H), 1.95 (s, 3H), 1.79-1.77 (m, 4H) | $[M + H]^+$ = 465.1 | 19 | 27.00 |
| A239 | 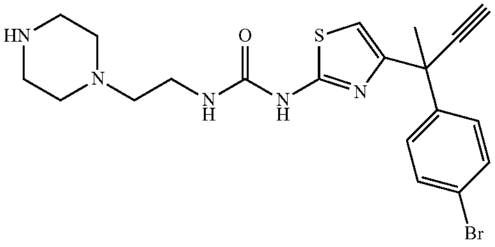 [SMILES: C#CC(C)(c1ccc(Br)cc1)c1csc(NC(=O)NCCN2CCNCC2)n1] | 1-(4-(2-(4-bromophenyl)but-3-yn-2-yl)thiazol-2-yl)-3-(2-(piperazin-1-yl)ethyl)urea | $^1$H NMR (400 MHz,METHANOL-d4) 7.47-7.54 (m, 2H), 7.38-7.46 (m, 2H), 7.14 (s, 1H), 3.62-3.82 (m, 8H), 3.47 (br t, J = 5.6 Hz, 2H), 3.14 (s, 1H), 1.95 ppm (s, 3H) | $[M + H]^+$ = 462.0 | 20 | 0.85 |

TABLE 4-continued
| Com. ID | Structure | Name | HNMR | LCMS | Kinase assay IC50 nM. | NFkB assay IC50 µM |
|---|---|---|---|---|---|---|
| A240 | 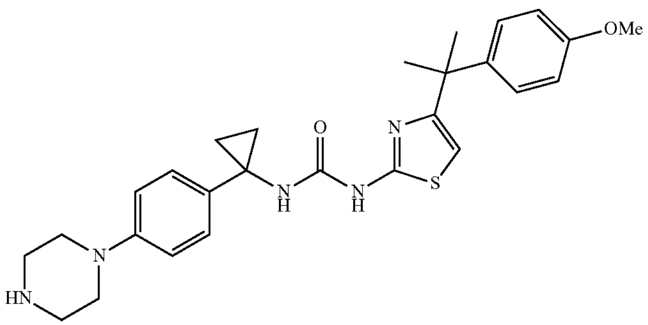 [SMILES: COc1ccc(C(C)(C)c2csc(NC(=O)NC3(c4ccc(N5CCNCC5)cc4)CC3)n2)cc1] | 1-(4-(2-(4-methoxyphenyl)propan-2-yl)thiazol-2-yl)-3-(1-(4-(piperazin-1-yl)phenyl)cyclopropyl)urea | | $[M + H]^+ = 492$ | 97 | 1.88 |
| A241 | 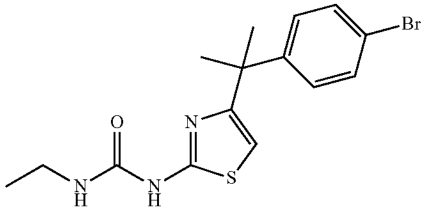 [SMILES: CCNC(=O)Nc1nc(C(C)(C)c2ccc(Br)cc2)cs1] | 1-(4-(2-(4-bromophenyl)propan-2-yl)thiazol-2-yl)-3-ethylurea | | $[M + H]^+ = 368.1$ | 98 | 3.41 |
| A242 | 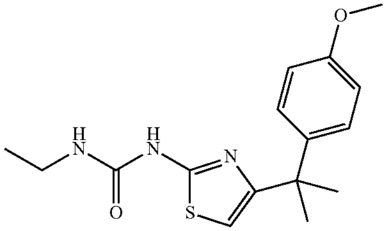 [SMILES: CCNC(=O)Nc1nc(C(C)(C)c2ccc(OC)cc2)cs1] | 1-ethyl-3-(4-(2-(4-methoxyphenyl)propan-2-yl)thiazol-2-yl)urea | | $[M + H]^+ = 320$ | 42 | 0.98 |

TABLE 4-continued

| Com. ID | Structure | Name | HNMR | LCMS | Kinase assay IC50 nM. | NFkB assay IC50 μM |
|---|---|---|---|---|---|---|
| A243 | 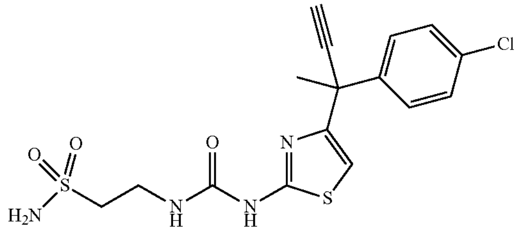 [SMILES: C#CC(C)(c1ccc(Cl)cc1)c1csc(NC(=O)NCCS(N)(=O)=O)n1] | 2-(3-(4-(2-(4-chlorophenyl)but-3-yn-2-yl)thiazol-2-yl)ureido)ethane-1-sulfonamide | $^1$H NMR (400 MHz, CDCl3) δ 7.44-7.26 (m, 4H), 6.75 (s, 2H), 5.82 (s, 2H), 3.80-3.65 (m, 2H), 3.25-3.13 (m, 2H), 2.63 (s, 1H), 1.92 (s, 3H). MS (ESI) m/z (M+H)+ = 413.0 | $[M + H]^+ = 413.1$ | 23 | 0.59 |
| A244 | 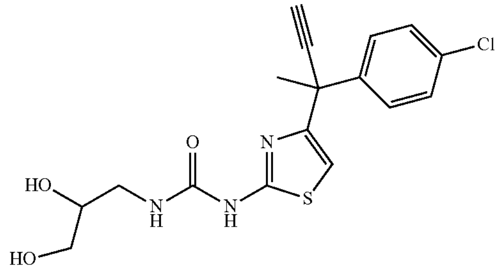 [SMILES: C#CC(C)(c1ccc(Cl)cc1)c1csc(NC(=O)NCC(O)CO)n1] | 1-(4-(2-(4-chlorophenyl)but-3-yn-2-yl)thiazol-2-yl)-3-(2,3-dihydroxypropyl)urea | $^1$H NMR (400 MHz, CDCl3) δ 9.63 (br. s, 1H), 7.39-7.35 (m, 2H), 7.25-7.19 (m, 2H), 6.65 (s, 2H), 3.72-3.62 (m, 1H), 3.52-3.33 (m, 2H), 3.29-3.09 (m, 2H), 2.56 (s, 1H), 1.86 (s, 3H). MS (ESI) m/z $(M + H)^+ = 380.0$ | $[M + H]^+ = 380.1$ | 72 | 1.03 |
| A245 | 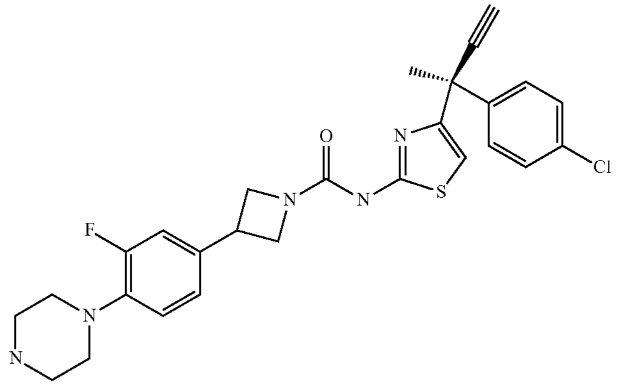 [SMILES: C#C[C@@](C)(c1ccc(Cl)cc1)c1csc(NC(=O)N2CC(c3ccc(N4CCNCC4)c(F)c3)C2)n1] | (S)-N-(4-(2-(4-chlorophenyl)but-3-yn-2-yl)thiazol-2-yl)-3-(3-fluoro-4-(piperazin-1-yl)phenyl)azetidine-1-carboxamide | $^1$H NMR (400 MHz, DMSO-d6) δ 10.95 (s, 1H), 8.97 (br s, 2H), 7.35-7.42 (m, 4H), 7.20-7.30 (m, 1H), 7.11-7.18 (m, 1H), 7.04-7.09 (m, 1H), 6.97 (s, 1H), 4.33 (br t, J = 8.11 Hz, 2H), 3.91 (br t, J = 7.03 Hz, 2H), 3.75-3.81 (m, 1H), 3.48 (s, 1H), 3.21 (br d, J = 8.94 Hz, 8H), 1.85 (s, 3H) | $[M + H]^+ = 524.1$ | 16 | 0.68 |

TABLE 4-continued

| Com. ID | Structure | Name | HNMR | LCMS | Kinase assay IC50 nM. | NFkB assay IC50 μM |
|---|---|---|---|---|---|---|
| A246 | 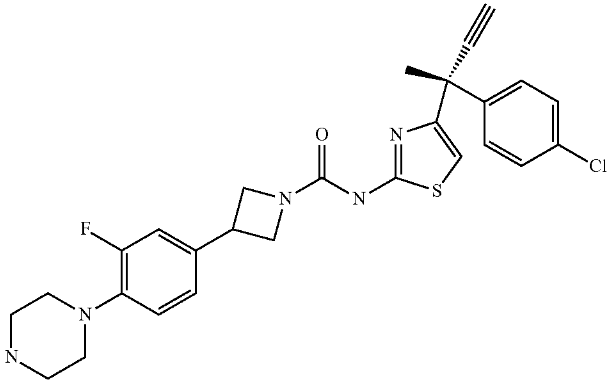 [SMILES: C#C[C@](C)(c1ccc(Cl)cc1)c1csc(NC(=O)N2CC(c3ccc(N4CCNCC4)c(F)c3)C2)n1] | (R)-N-(4-(2-(4-chlorophenyl)but-3-yn-2-yl)thiazol-2-yl)-3-(3-fluoro-4-(piperazin-1-yl)phenyl)azetidine-1-carboxamide | $^1$H NMR (400 MHz, DMSO-d6) δ 10.95 (s, 1H), 8.95 (br s, 2H), 7.35-7.42 (m, 4H), 7.18-7.30 (m, 1H), 7.10-7.17 (m, 1H), 7.02-7.09 (m, 1H), 6.97 (s, 1H), 4.33 (br t. J = 8.17 Hz, 2H), 3.86-3.97 (m, 2H), 3.75-3.81 (m, 1H), 3.48 (s, 1H), 3.23 (br s, 4H), 3.20 (br s, 4H), 1.86 (s, 3H) | $[M + H]^+$ = 524.1 | 29 | 1.59 |
| A247 | 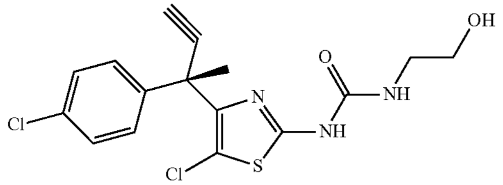 | (S)-1-(5-chloro-4-(2-(4-chlorophenyl)but-3-yn-2-yl)thiazol-2-yl)-3-(2-hydroxyethyl)urea | $^1$H NMR (400 MHz, DMSO-d6) δ 10.92(1, 1H), 7.38-7.36 (m, 4H), 6.49 (s, 1H), 4.80 (s, 1H), 3.58 (s, 1H), 3.45-3.35 (m, 2H), 3.22-3.18 (m, 2H), 1.85 (s, 3H) | $[M + H]^+$ = 429.7 | 408 | 1.85 |
| A248 | 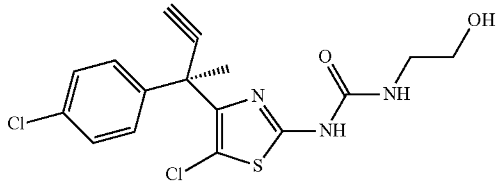 | (R)-1-(5-chloro-4-(2-(4-chlorophenyl)but-3-yn-2-yl)thiazol-2-yl)-3-(2-hydroxyethyl)urea | $^1$H NMR (400 MHz, DMSO-d6) δ 10.92(1, 1H), 7.40-7.30 (m, 4H), 6.50 (s, 1H), 4.77 (s, 1H), 3.55 (s, 1H), 3.43-3.35 (m, 2H), 3.20-3.15 (m, 2H), 1.87 (s, 3H) | $[M + H]^+$ = 429.9 | 1294 | 2.73 |

TABLE 4-continued

| Com. ID | Structure | Name | HNMR | LCMS | Kinase assay IC50 nM. | NFkB assay IC50 μM |
|---|---|---|---|---|---|---|
| A249 | 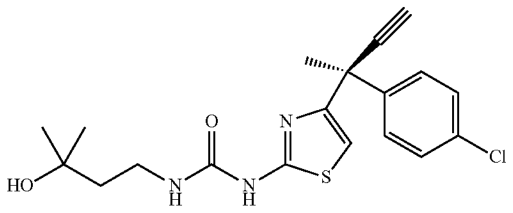 [SMILES: C#C[C@@](C)(c1ccc(Cl)cc1)c1csc(NC(=O)NCCC(C)(C)O)n1] | (S)-1-(4-(2-(4-chlorophenyl)but-3-yn-2-yl)thiazol-2-yl)-3-(3-hydroxy-3-methylbutyl)urea | $^1$H NMR (400 MHz, DMSO-d6) δ 10.66 (s, 1H), 7.40-7.46 (m, 2H), 7.33-7.39 (m, 2H), 6.88 (s, 1H), 6.27 (s, 1H), 4.32 (s, 1H), 3.48 (s, 1H), 3.13-3.23 (m, 2H), 1.85 (s, 3H), 1.45-1.57 (m, 2H), 1.09 ppm (s, 6H) | $[M + H]^+$ = 392.0 | 128 | 0.67 |
| A250 | 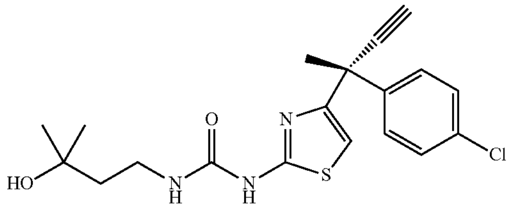 [SMILES: C#C[C@](C)(c1ccc(Cl)cc1)c1csc(NC(=O)NCCC(C)(C)O)n1] | (R)-1-(4-(2-(4-chlorophenyl)but-3-yn-2-yl)thiazol-2-yl)-3-(3-hydroxy-3-methylbutyl)urea | $^1$H NMR (400 MHz, DMSO-d6) δ 10.65 (s, 1H), 7.41-7.46 (m, 2H), 7.34-7.40 (m, 2H), 6.88 (s, 1H), 6.26 (s, 1H), 4.31 (s, 1H), 3.49 (s, 1H), 3.13-3.22 (m, 2H), 1.85 (s, 3H), 1.46-1.56 (m, 2H), 1.09 ppm (s, 6H) | $[M + H]^+$ = 392.0 | 417 | 1.18 |
| A251 | 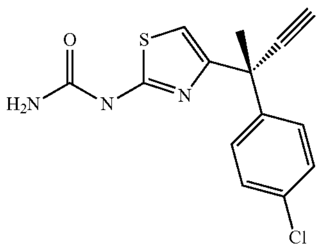 [SMILES: C#C[C@](C)(c1ccc(Cl)cc1)c1csc(NC(N)=O)n1] | (R)-1-(4-(2-(4-chlorophenyl)but-3-yn-2-yl)thiazol-2-yl)urea | $^1$H NMR (400 MHz, DMSO-d6) δ 10.59(1, 1H), 7.44-7.42 (m, 2H), 7.38-7.36 (m, 2H), 6.89 (s, 1H), 6.22 (s, 1H), 3.49 (s, 1H), 1.85 (s, 3H) | $[M + H]^+$ = 305.9 | 81 | 1.67 |
| A252 | 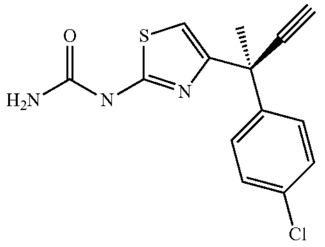 [SMILES: C#C[C@@](C)(c1ccc(Cl)cc1)c1csc(NC(N)=O)n1] | (S)-1-(4-(2-(4-chlorophenyl)but-3-yn-2-yl)thiazol-2-yl)urea | $^1$H NMR (400 MHz, DMSO-d6) δ 10.60(1, 1H), 7.44-7.42 (m, 2H), 7.39-7.36 (m, 2H), 6.90 (s, 1H), 6.22 (s, 1H), 3.49 (s, 1H), 1.85 (s, 3H) | $[M + H]^+$ = 305.9 | 30 | 0.53 |

TABLE 4-continued

| Com. ID | Structure | Name | HNMR | LCMS | Kinase assay IC50 nM. | NFkB assay IC50 µM |
|---|---|---|---|---|---|---|
| A253 | 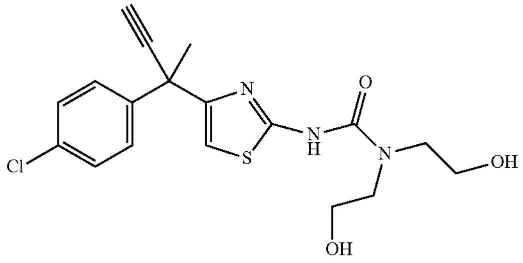 [SMILES: C#CC(C)(c1ccc(Cl)cc1)c1csc(NC(=O)N(CCO)CCO)n1] | 3-(4-(2-(4-chlorophenyl)but-3-yn-2-yl)thiazol-2-yl)-1,1-bis(2-hydroxyethyl)urea | $^1$H NMR (400 MHz, DMSO-d6) d: 7.36 (4H, J = 19.6 Hz, t), 6.91 (1H, s), 3.51 (4H, s), 3.45 (1H, s), 3.40 (4H, s), 1.83 (3H, s) | $[M + H]^+$ = 394.0 | 172 | 3.05 |
| A254 | 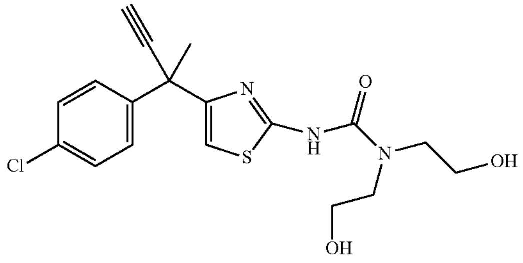 | 3-(4-(2-(4-chlorophenyl)but-3-yn-2-yl)thiazol-2-yl)-1-(2-hydroxyethyl)-1-methylurea | $^1$H NMR (400 MHz, DMSO-d6) d: 7.38-7.33 (4H, m), 6.90 (1H, s), 3.47 (2H, J = 10.4 Hz, t), 3.44 (1H, s), 3.37 (2H, J = 10.4 Hz, t), 2.91 (3H, s), 1.82 (3H, s) | $[M + H]^+$ = 364.0 | 548 | 2.07 |
| A255 | 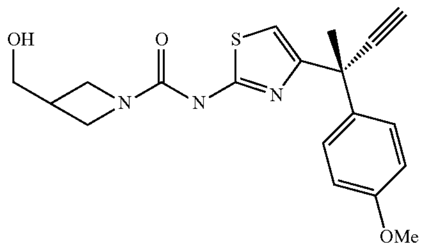 [SMILES: C#C[C@](C)(c1ccc(OC)cc1)c1csc(NC(=O)N2CC(CO)C2)n1] | (R)-3-(hydroxymethyl)-N-(4-(2-(4-methoxyphenyl)but-3-yn-2-yl)thiazol-2-yl)azetidine-1-carboxamide | $^1$H NMR (400 MHz, DMSO-$d_6$) δ 10.83 (s, 1H), 7.29 (d, J = 8.78 Hz, 2H), 6.87 (s, 1H), 6.85 (s, 2H), 4.78 (t, J = 5.27 Hz, 1H), 3.94 (br s, 2H), 3.71 (s, 3H), 3.68 (br s, 2H), 3.48 (t, J = 5.65 Hz, 2H), 3.38 (s, 1H), 2.56-2.70 (m, 1H), 1.83 (s, 3H). | $[M + H]^+$ = 372.0 | 109 | |

TABLE 4-continued

| Com. ID | Structure | Name | HNMR | LCMS | Kinase assay IC50 nM. | NFkB assay IC50 µM |
|---|---|---|---|---|---|---|
| A256 | 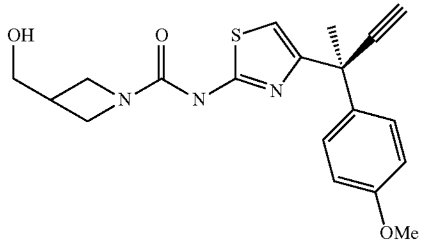 [SMILES: C#C[C@@](C)(c1ccc(OC)cc1)c1csc(NC(=O)N2CC(CO)C2)n1] | (S)-3-(hydroxymethyl)-N-(4-(2-(4-methoxyphenyl)but-3-yn-2-yl)thiazol-2-yl)azetidine-1-carboxamide | $^1$H NMR (400 MHz, DMSO-$d_6$) δ 10.85 (s, 1H), 7.30 (br d, J = 8.78 Hz, 2H), 6.87 (s, 1H), 6.86 (s, 2H), 4.79 (t, J = 5.14 Hz, 1H), 3.86-4.07 (m, 2H), 3.72 (s, 3H), 3.69 (br s, 2H), 3.49 (br t, J = 5.52 Hz, 2H), 3.39 (s, 1H), 2.56-2.72 (m, 1H), 1.84 (s, 3H). | $[M + H]^+$ = 372.1 | 43 | |
| A257 | 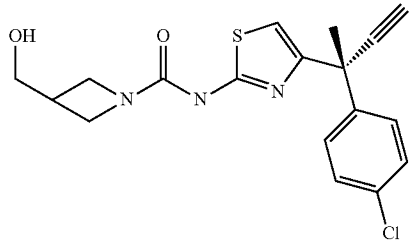 [SMILES: C#C[C@](C)(c1ccc(Cl)cc1)c1csc(NC(=O)N2CC(CO)C2)n1] | (R)-N-(4-(2-(4-chlorophenyl)but-3-yn-2-yl)thiazol-2-yl)-3-(hydroxymethyl) azetidine-1-carboxamide | $^1$H NMR (400 MHz, CDCl3) δ 7.79 (s, 1H), 7.45-7.40 (m, 2H), 7.30-7.20 (m, 2H), 6.78 (s, 1H), 4.20-4.08 (m, 2H), 3.90-3.84 (m, 2H), 3.80-3.75 (m, 2H), 2.88-2.75 (m, 1H), 2.57 (s, 1H), 2.10-2.00 (m, 1H), 1.92 (s, 3H). | $[M + H]^+$ = 376.1 | 246 | |
| A258 | 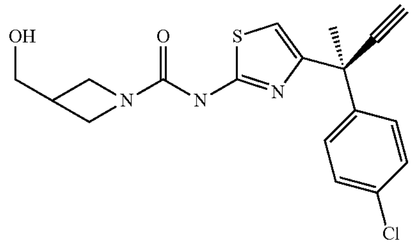 [SMILES: C#C[C@@](C)(c1ccc(Cl)cc1)c1csc(NC(=O)N2CC(CO)C2)n1] | (S)-N-(4-(2-(4-chlorophenyl)but-3-yn-2-yl) thiazol-2-yl)-3-(hydroxymethyl) azetidine-1-carboxamide | $^1$H NMR (400 MHz, CDCl3) δ 7.78 (s, 1H), 7.45-7.36 (m, 2H), 7.30-7.20 (m, 2H), 6.78 (s, 1H), 4.20-4.08 (m, 2H), 3.90-3.84 (m, 2H), 3.80-3.75 (m, 2H), 2.90-2.80 (m, 1H), 2.57 (s, 1H), 2.05-1.95 (m, 1H), 1.93 (s, 3H). | $[M + H]^+$ = 376.1 | 57 | |

TABLE 4-continued

| Com. ID | Structure | Name | HNMR | LCMS | Kinase assay IC50 nM. | NFkB assay IC50 µM |
|---|---|---|---|---|---|---|
| A259 | 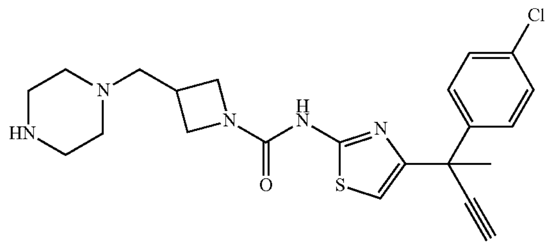 [SMILES: C#CC(C)(c1ccc(Cl)cc1)c1csc(NC(=O)N2CC(CN3CCNCC3)C2)n1] | N-(4-(2-(4-chlorophenyl)but-3-yn-2-yl)thiazol-2-yl)-3-(piperazin-1-ylmethyl)azetidine-1-carboxamide | | 444.2 | 48 | 0.44 |
| A260 | 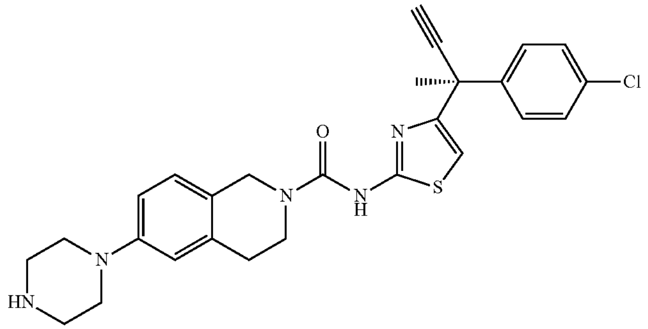 [SMILES: C#C[C@@](C)(c1ccc(Cl)cc1)c1csc(NC(=O)N2CCc3cc(N4CCNCC4)ccc3C2)n1] | (S)-N-(4-(2-(4-chlorophenyl)but-3-yn-2-yl)thiazol-2-yl)-6-(piperazin-1-yl)-3,4-dihydroisoquinoline-2(1H)-carboxamide | $^1$H NMR (400 MHz, DMSO-$d_6$) δ 8.23 (s, 1H), 7.41-7.35 (m, 4H), 6.99-6.91 (m, 2H), 6.75 (d, J = 7.7 Hz, 1H), 6.67 (s, 1H), 4.47 (s, 2H), 3.63 (s, 2H), 3.05 (s, 4H), 2.90 (s, 4H), 2.70 (s, 2H), 1.81 (s, 3H). | 506.2 | 74 | 1.08 |
| A261 | 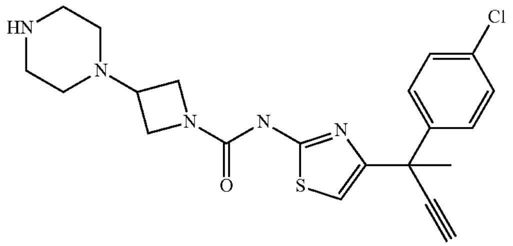 [SMILES: C#CC(C)(c1ccc(Cl)cc1)c1csc(NC(=O)N2CC(N3CCNCC3)C2)n1] | N-(4-(2-(4-chlorophenyl)but-3-yn-2-yl)thiazol-2-yl)-3-(piperazin-1-yl)azetidine-1-carboxamide | | 430.1 | 83 | 0.51 |

TABLE 4-continued
| Com. ID | Structure | Name | HNMR | LCMS | Kinase assay IC50 nM. | NFkB assay IC50 µM |
|---|---|---|---|---|---|---|
| A262 | 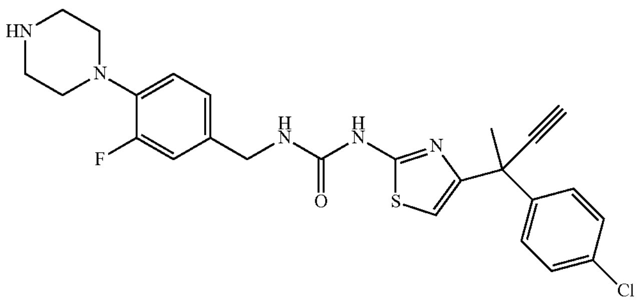 [SMILES: C#CC(C)(c1ccc(Cl)cc1)c1csc(NC(=O)NCc2ccc(N3CCNCC3)c(F)c2)n1] | 1-(4-(2-(4-chlorophenyl)but-3-yn-2-yl)thiazol-2-yl)-3-(3-fluoro-4-(piperazin-1-yl)benzyl)urea | | 498.1 | 13 | 0.67 |
| A263 | 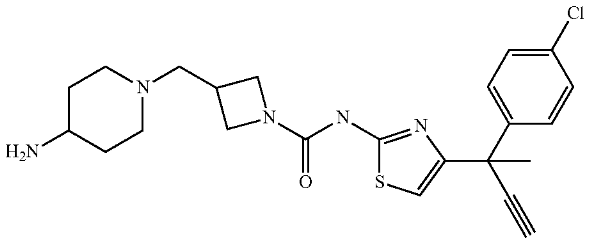 [SMILES: C#CC(C)(c1ccc(Cl)cc1)c1csc(NC(=O)N2CC(CN3CCC(N)CC3)C2)n1] | 3-((4-aminopiperidin-1-yl)methyl)-N-(4-(2-(4-chlorophenyl)but-3-yn-2-yl)thiazol-2-yl)azetidine-1-carboxamide | | 458.1 | 39 | 1.44 |
| A264 | 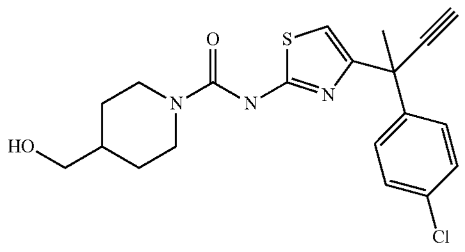 [SMILES: C#CC(C)(c1ccc(Cl)cc1)c1csc(NC(=O)N2CCC(CO)CC2)n1] | N-(4-(2-(4-chlorophenyl)but-3-yn-2-yl)thiazol-2-yl)-4-(hydroxymethyl)piperidine-1-carboxamide | | 404.1 | 1374 | 2.81 |

TABLE 4-continued
| Com. ID | Structure | Name | HNMR | LCMS | Kinase assay IC50 nM. | NFkB assay IC50 μM |
|---|---|---|---|---|---|---|
| A265 | 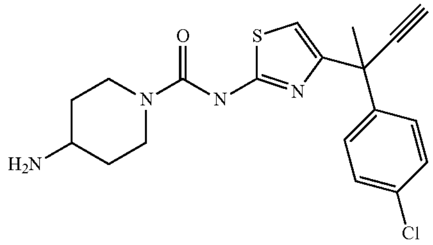 [SMILES: C#CC(C)(c1ccc(Cl)cc1)c1csc(NC(=O)N2CCC(N)CC2)n1] | 4-amino-N-(4-(2-(4-chlorophenyl)but-3-yn-2-yl)thiazol-2-yl)piperidine-1-carboxamide | | 389.1 | 4974 | 2.90 |
| A266 | 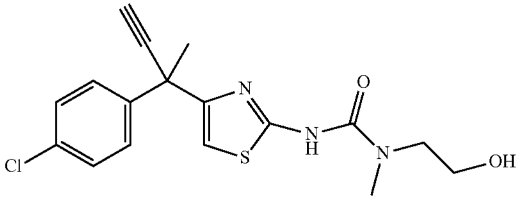 [SMILES: C#CC(C)(c1ccc(Cl)cc1)c1csc(NC(=O)N(C)CCO)n1] | 3-(4-(2-(4-chlorophenyl)but-3-yn-2-yl)thiazol-2-yl)-1-(2-hydroxyethyl)-1-metbylurea | $^1$H NMR (400 MHz, DMSO-$d_6$) δ 7.34 (t, J = 20.0 Hz, 4H), 6.87 (s, 1H), 3.44-3.40 (m, J = 16.0, 5H), 2.88 (s, 3H), 1.79 (s, 3H). | 364.0 | 546 | 2.07 |
| A267 | 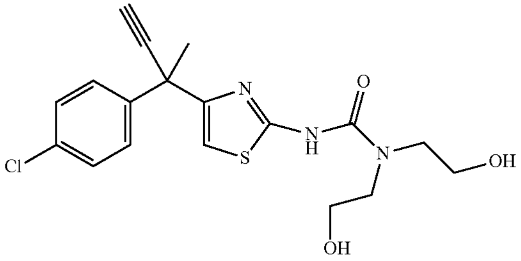 [SMILES: C#CC(C)(c1ccc(Cl)cc1)c1csc(NC(=O)N(CCO)CCO)n1] | 3-(4-(2-(4-chlorophenyl)but-3-yn-2-yl)thiazol-2-yl)-1,1-bis(2-hydroxyethyl)urea | $^1$H NMR (400 MHz, DMSO-$d_6$) δ 7.34 (t, J = 20.0 Hz, 4H), 6.86 (s, 1H), 3.46-3.40 (m, J = 16.0, 9H), 1.78 (s, 3H). | 394.0 | 171 | 3.05 |

TABLE 4-continued

| Com. ID | Structure | Name | HNMR | LCMS | Kinase assay IC50 nM. | NFkB assay IC50 μM |
|---|---|---|---|---|---|---|
| A268 | 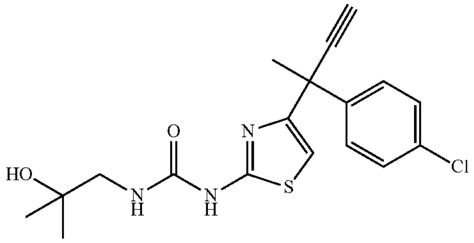 [SMILES: C#CC(C)(c1ccc(Cl)cc1)c1csc(NC(=O)NCC(C)(C)O)n1] | 1-(4-(2-(4-chlorophenyl)but-3-yn-2-yl)thiazol-2-yl)-3-(2-hydroxy-2-methylpropyl)urea | $^1$H NMR (400 MHz, DMSO-$d_6$) δ 7.43-7.34 (dd, J = 27.8, 7.5 Hz, 4H), 6.87 (s, 1H), 6.38 (s, 1H), 4.56 (s, 1H), 3.02 (d, J = 4.0 Hz, 2H), 1.83 (s, 3H), 1.03 (s, 6H) | 378.1 | 218 | 1.31 |
| A269 | 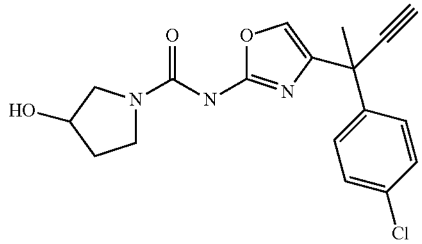 [SMILES: C#CC(C)(c1ccc(Cl)cc1)c1coc(NC(=O)N2CCC(O)C2)n1] | N-(4-(2-(4-chlorophenyl)but-3-yn-2-yl)thiazol-2-yl)-3-hydroxypyrrolidine-1-carboxamide | $^1$H NMR (400 MHz, DMSO-$d_6$) δ 7.36 (s, 4H), 6.90 (s, 1H), 4.93 (s, 1H), 4.22 (s, 1H), 3.44 (s, 4H), 1.83 (s, 3H), 1.74 (s, 2H). | 376.0 | 881 | 1.26 |
| A270 | 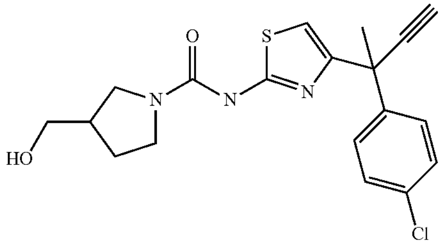 [SMILES: C#CC(C)(c1ccc(Cl)cc1)c1csc(NC(=O)N2CCC(CO)C2)n1] | N-(4-(2-(4-chlorophenyl)but-3-yn-2-yl)thiazol-2-yl)-3-(hydroxymethyl) pyrrolidine-1-carboxamide | $^1$H NMR (400 MHz, DMSO-$d_6$) δ 7.36 (s, 4H), 6.90 (s, 1H), 4.68 (s, 1H), 3.44 (s, 4H), 3.11 (s, 2H), 2.24 (s, 1H), 1.83 (s, 3H), 1.60 (s, 2H). | 390.1 | 904 | 1.97 |

TABLE 4-continued
| Com. ID | Structure | Name | HNMR | LCMS | Kinase assay IC50 nM. | NFkB assay IC50 μM |
|---|---|---|---|---|---|---|
| A271 | 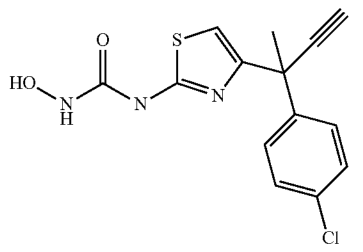 [SMILES: C#CC(C)(c1ccc(Cl)cc1)c1csc(NC(=O)NO)n1] | 1-(4-(2-(4-chlorophenyl)but-3-yn-2-yl)thiazol-2-yl)-3-hydroxyurea | $^1$H NMR (400 MHz, DMSO-$d_6$) δ 7.40-7.36 (m, J = 16.0 Hz, 4H), 6.94 (s, 1H), 3.47 (s, 1H), 1.84 (s, 3H). | 322.0 | 493 | 0.73 |
| A272 | 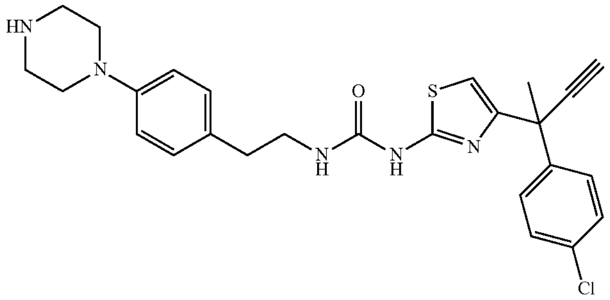 [SMILES: C#CC(C)(c1ccc(Cl)cc1)c1csc(NC(=O)NCCc2ccc(N3CCNCC3)cc2)n1] | 1-(4-(2-(4-chlorophenyl)but-3-yn-2-yl)thiazol-2-yl)-3-(4-(piperazin-1-yl)phenethyl)urea | | 494.1 | 135 | 0.89 |
| A273 | 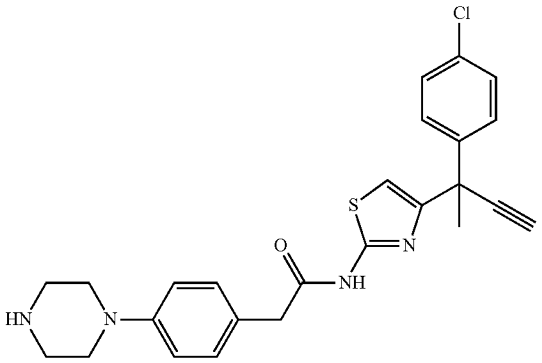 [SMILES: C#CC(C)(c1ccc(Cl)cc1)c1csc(NC(=O)Cc2ccc(N3CCNCC3)cc2)n1] | N-(4-(2-(4-chlorophenyl)but-3-yn-2-yl)thiazol-2-yl)-2-(4-(piperazin-1-yl)phenyl)acetamide | $^1$H NMR (400 MHz, DMSO-$d_6$) δ 7.31 (s, 4H), 7.13-7.09 (m, 4H), 6.83 (d, J = 8.0 Hz, 1H), 3.54 (s, , 2H), 3.50 (m, 4H), 2.78 (s, 4H), 1.84 (s, 3H). | 465.1 | 60 | 2.68 |

TABLE 4-continued
| Com. ID | Structure | Name | HNMR | LCMS | Kinase assay IC50 nM. | NFkB assay IC50 μM |
|---|---|---|---|---|---|---|
| A274 | 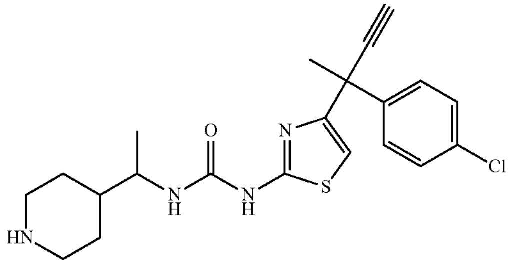 [SMILES: C#CC(C)(c1ccc(Cl)cc1)c1csc(NC(=O)NC(C)C2CCNCC2)n1] | 1-(4-(2-(4-chlorophenyl)but-3-yn-2-yl)thiazol-2-yl)-3-(1-(piperidin-4-yl)ethyl)urea | $^1$H NMR (400 MHz, DMSO-$d_6$) δ 7.41-7.34 (m, 4H), 6.86 (s, 1H), 3.16 (s, 4H), 2.67 (s, 1H), 1.82 (s, 3H), 1.66 (s, 2H), 1.49 (s, 1H), 1.25 (s, 2H), 1.01 (s, 3H). | 417.1 | 467 | 2.55 |
| A275 | 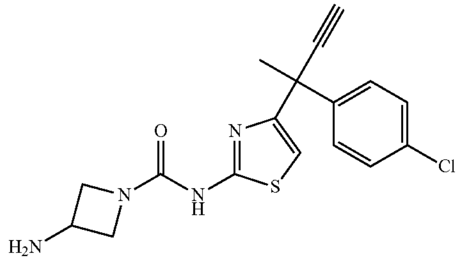 [SMILES: C#CC(C)(c1ccc(Cl)cc1)c1csc(NC(=O)N2CC(N)C2)n1] | 3-amino-N-(4-(2-(4-chlorophenyl)but-3-yn-2-yl)thiazol-2-yl)azetidine-1-carboxamide | | 361.0 | 503 | 1.59 |
| A276 | 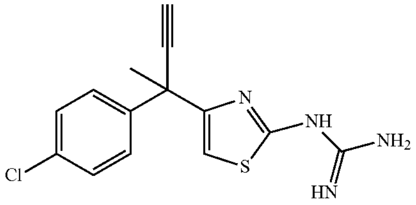 [SMILES: C#CC(C)(c1ccc(Cl)cc1)c1csc(NC(=N)N)n1] | 1-(4-(2-(4-chlorophenyl)but-3-yn-2-yl)thiazol-2-yl)guanidine | | 305.0 | 475 | 1.58 |

TABLE 4-continued

| Com. ID | Structure | Name | HNMR | LCMS | Kinase assay IC50 nM. | NFkB assay IC50 µM |
|---|---|---|---|---|---|---|
| A272 | 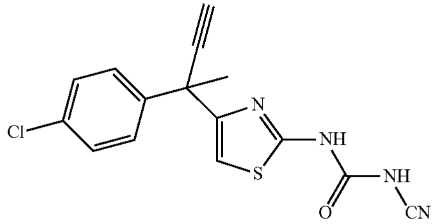 [SMILES: C#CC(C)(c1ccc(Cl)cc1)c1csc(NC(=O)NC#N)n1] | | | $[M + H]^+$ = 331.0 | 666 | NA |
| A273 | 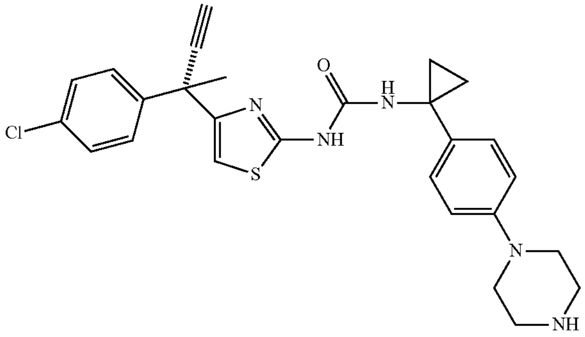 [SMILES: C#C[C@@](C)(c1ccc(Cl)cc1)c1csc(NC(=O)NC2(c3ccc(N4CCNCC4)cc3)CC2)n1] | 1-(4-(2-(4-chlorophenyl)but-3-yn-2-yl)thiazol-2-yl)-3-(1-(4-(piperazin-1-yl)phenyl) cyclopropyl)urea | $^1H$ NMR (400 MHz, DMSO-$d_6$) δ 10.77-11.73 (m, 1H), 8.01 (br s, 1H), 7.39-7.44 (m, 2H), 7.34-7.39 (m, 2H), 7.02 (d, J = 8.70 Hz, 2H), 6.86 (s, 1H), 6.80 (br d, J = 8.82 Hz, 2H), 3.48 (s, 1H), 2.92-2.99 (m, 4H), 2.75-2.83 (m, 4H), 1.84 (s, 3H), 1.06 (br d, J = 9.06 Hz, 4H). | 506.1 | 237 | 3.20 |
| A274 | 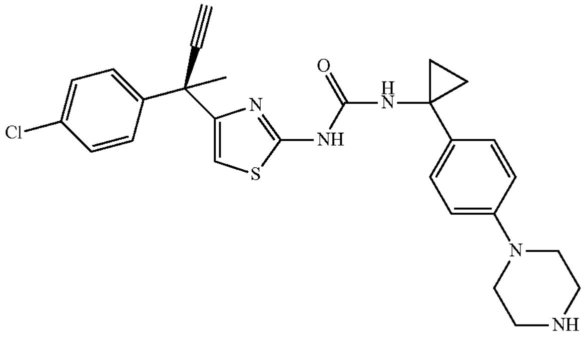 [SMILES: C#C[C@](C)(c1ccc(Cl)cc1)c1csc(NC(=O)NC2(c3ccc(N4CCNCC4)cc3)CC2)n1] | 1-(4-(2-(4-chlorophenyl)but-3-yn-2-yl)thiazol-2-yl)-3-(1-(4-(piperazin-1-yl)phenyl) cyclopropyl)urea | $^1H$ NMR (400 MHz, DMSO-$d_6$) δ 10.50 (br s, 1H), 7.40-7.47 (m, 2H), 7.34-7.40 (m, 2H), 7.02 (br d, J = 8.70 Hz, 3H), 6.91 (s, 1H), 6.82 (br d, J = 8.82 Hz, 2H), 3.50 (s, 1H), 2.92-3.04 (m, 4H), 2.75-2.88 (m, 4H), 1.84 (s, 3H), 1.09 (br d, J = 3.58 Hz, 4H). | 506.1 | 327 | 3.8 |

TABLE 4-continued

| Com. ID | Structure | Name | HNMR | LCMS | Kinase assay IC50 nM. | NFkB assay IC50 µM |
|---|---|---|---|---|---|---|
| A275 | 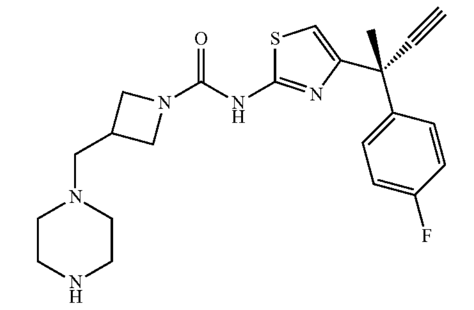 [SMILES: C#C[C@](C)(c1ccc(F)cc1)c1csc(NC(=O)N2CC(CN3CCNCC3)C2)n1] | N-(4-(2-(4-fluorophenyl)but-3-yn-2-yl)thiazol-2-yl)-3-(piperazin-1-ylmethyl)azetidine-1-carboxamide | $^1$H NMR (400 MHz, DMSO-$d_6$) δ 12.00 (br s, 1H), 11.01 (br s, 1H), 9.79 (br s, 2H), 7.40 (dd, J = 8.66, 5.40 Hz, 2H), 7.13 (t, J = 8.66 Hz, 2H), 6.93 (s, 1H), 4.09 (br s, 2H), 3.76-3.85 (m, 2H), 3.57 (br d, J = 4.77 Hz, 2H), 3.39-3.53 (m, 7H), 3.26 (br s, 2H), 3.11 (br d, J = 6.53 Hz, 1H), 1.85 (s, 3H). | 428.0 | 246 | 3.38 |
| A276 | 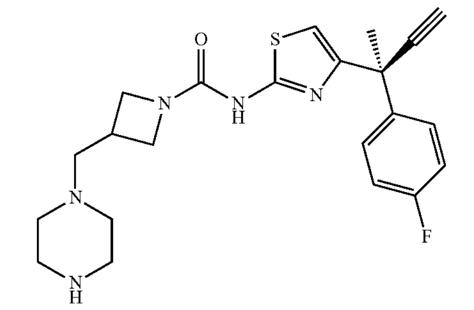 [SMILES: C#C[C@@](C)(c1ccc(F)cc1)c1csc(NC(=O)N2CC(CN3CCNCC3)C2)n1] | N-(4-(2-(4-fluorophenyl)but-3-yn-2-yl)thiazol-2-yl)-3-(piperazin-1-ylmethyl)azetidine-1-carboxamide | $^1$H NMR (400 MHz, DMSO-$d_6$) δ 12.01 (br s, 1H), 11.01 (br s, 1H), 9.79 (br s, 2H), 7.40 (dd, J = 8.41, 5.40 Hz, 2H), 7.13 (t, J = 8.78 Hz, 2H), 6.93 (s, 1H), 4.01-4.12 (m, 2H), 3.75-3.85 (m, 2H), 3.58 (br s, 2H), 3.37-3.52 (m, 7H), 3.27 (br s, 2H), 3.10 (br s, 1H), 1.85 (s, 3H). | 428.1 | 345 | 0.56 |
| A277 | 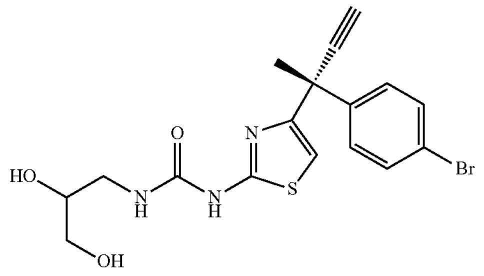 [SMILES: C#C[C@](C)(c1ccc(Br)cc1)c1csc(NC(=O)NCC(O)CO)n1] | 1-(4-(2-(4-bromophenyl)but-3-yn-2-yl)thiazol-2-yl)-3-(2,3-dihydroxypropyl)urea | $^1$H NMR (400 MHz, DMSO-$d_6$) δ 10.60 (br s, 1H), 7.51 (d, J = 8.53 Hz, 2H), 7.37 (d, J = 8.53 Hz, 2H), 6.90 (s, 1H), 6.33 (br s, 1H), 4.86 (br d, J = 4.77 Hz, 1H), 4.59 (t, J = 5.65 Hz, 1H), 3.50 (s, 1H), 3.42-3.49 (m, 1H), 3.34-3.37 (m, 0.5H), 3.20-3.31 (m, 2.5H), 2.90-3.04 (m, 1H), 1.85 (s, 3H). | 424.0 | 2667 | 1.23 |

TABLE 4-continued

| Com. ID | Structure | Name | HNMR | LCMS | Kinase assay IC50 nM. | NFkB assay IC50 μM |
|---|---|---|---|---|---|---|
| A278 | 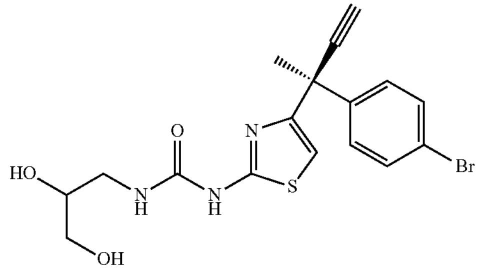 [SMILES: C#C[C@@](C)(c1ccc(Br)cc1)c1csc(NC(=O)NCC(O)CO)n1] | 1-(4-(2-(4-bromophenyl)but-3-yn-2-yl)thiazol-2-yl)-3-(2,3-dihydroxypropyl)urea | $^1$H NMR (400 MHz, DMSO-$d_6$) δ 10.62 (br s, 1H), 7.51 (d, J = 8.53 Hz, 2H), 7.37 (d, J = 8.53 Hz, 2H), 6.89 (s, 1H), 6.34 (br s, 1H), 4.86 (br d, J = 4.52 Hz, 1H), 4.60 (t, J = 5.40 Hz, 1H), 3.50 (s, 1H), 3.47 (br d, J = 4.77 Hz, 1H), 3.35 (br s, 0.5H), 3.20-3.31 (m, 2.5H), 2.90-3.03 (m, 1H), 1.84 (s, 3H). | 424.0 | 624 | 0.52 |
| A279 | 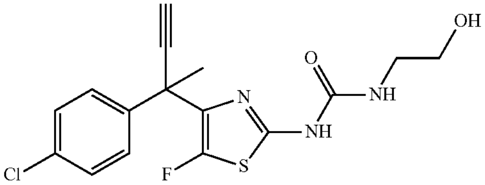 [SMILES: C#CC(C)(c1ccc(Cl)cc1)c1nc(NC(=O)NCCO)sc1F] | 1-(4-(2-(4-chlorophenyl)but-3-yn-2-yl)-5-fluorothiazol-2-yl)-3-(2-hydroxyethyl)urea | $^1$H NMR (400 MHz, DMSO-$d_6$) δ 10.65 (s, 1H), 7.50-7.35 (m, 4H), 6.34 (br. s, 1H), 4.76 (t, J = 4.0 Hz, 1H), 3.53 (s, 1H), 3.41 (q, J = 4.0 Hz, 1H), 3.15 (q, J = 4.0 Hz, 1H), 1.86 (s, 3H). | 368.0 | 222 | 4.23 |
| A280 | 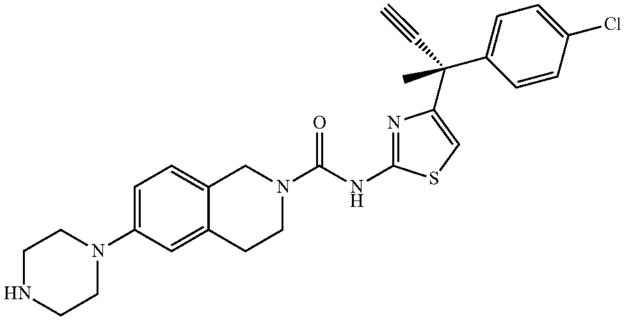 [SMILES: C#C[C@](C)(c1ccc(Cl)cc1)c1csc(NC(=O)N2CCc3cc(N4CCNCC4)ccc3C2)n1] | N-(4-(2-(4-chlorophenyl)but-3-yn-2-yl)thiazol-2-yl)-6-(piperazin-1-yl)-3,4-dihydroisoquinoline-2(1H)-carboxamide | $^1$H NMR (400 MHz, DMSO-$d_6$) δ 7.44-7.35 (m, 4H), 7.01-6.94 (m, 2H), 6.81-6.75 (m, 1H), 6.72-6.68 (m, 1H), 4.53 (s, 2H), 3.66 (t, J = 8 Hz, 2H ), 3.50 (s, 1H), 3.05-2.99 (m, 4H), 2.88-2.82 (m, 4H), 2.75 (t, J = 8 Hz, 2H ), 1.87 (s, 3H). | 506.5 | 21 | 2.18 |

TABLE 4-continued

| Com. ID | Structure | Name | HNMR | LCMS | Kinase assay IC50 nM. | NFkB assay IC50 μM |
|---|---|---|---|---|---|---|
| A281 | 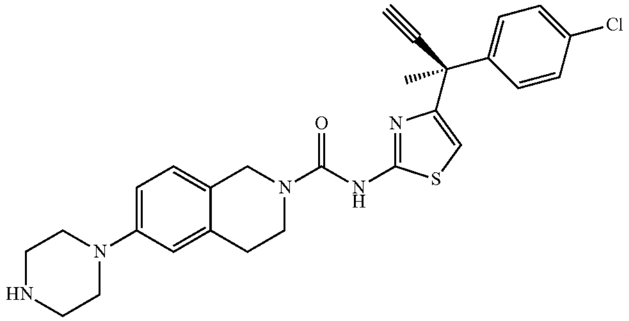 [SMILES: C#C[C@@](C)(c1ccc(Cl)cc1)c1csc(NC(=O)N2CCc3cc(N4CCNCC4)ccc3C2)n1] | N-(4-(2-(4-chlorophenyl)but-3-yn-chlorophenyl)but2-yl)thiazol-2-yl)-6-(piperazin-1-yl)-3,4-dihydroisoquinoline-2(1H)-carboxamide | $^{1}$H NMR (400 MHz, DMSO-$d_6$) δ 7.44-7.36 (m, 4H), 7.01-6.94 (m, 2H), 6.80-6.75 (m, 1H), 6.71-6.68 (m, 1H), 4.53 (s, 2H), 3.66 (t, J = 8 Hz, 2H ), 3.50 (s, 1H), 3.04-2.98 (m, 4H), 2.86-2.80 (m, 4H), 2.75 (t, J = 8 Hz, 2H ), 1.87 (s, 3H). | 506.5 | 38 | 0.86 |
| A282 | 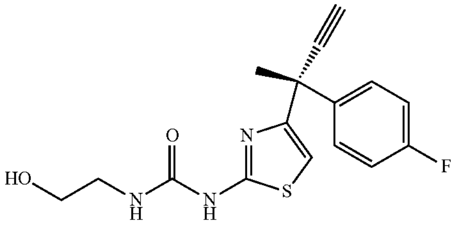 [SMILES: C#C[C@](C)(c1ccc(F)cc1)c1csc(NC(=O)NCCO)n1] | 1-(4-(2-(4-fluorophenyl)but-3-yn-2-yl)thiazol-2-yl)-3-(2-hydroxyethyl)urea | $^{1}$H NMR (400 MHz, DMSO-$d_6$ δ 10.63 (s, 1H), 7.44 (dd, J = 8.78, 5.52 Hz, 2H), 7.13 (t, J = 8.91 Hz, 2H), 6.87 (s, 1H), 6.34 (br s, 1H), 4.75 (t, J = 5.02 Hz, 1H), 3.48 (s, 1H), 3.41 (q, J = 5.52 Hz, 2H), 3.16 (q, J = 5.60 Hz, 2H), 1.85 (s, 3H). | 334.1 | 2153 | 7.72 |
| A283 | 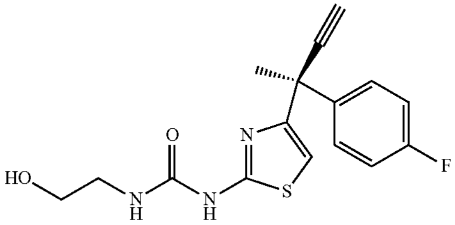 [SMILES: C#C[C@@](C)(c1ccc(F)cc1)c1csc(NC(=O)NCCO)n1] | 1-(4-(2-(4-fluorophenyl)but-3-yn-2-yl)thiazol-2-yl)-3-(2-hydroxyethyl)urea | $^{1}$H NMR (400 MHz, DMSO-$d_6$) δ 10.63 (s, 1H), 7.44 (dd, J = 8.78, 5.52 Hz, 2H), 7.13 (t, J = 8.91 Hz, 2H), 6.88 (s, 1H), 6.33 (br s, 1H), 4.75 (t, J = 5.14 Hz, 1H), 3.48 (s, 1H), 3.41 (q, J = 5.35 Hz, 2H), 3.16 (q, J = 5.52 Hz, 2H), 1.85 (s, 3H). | 334.1 | 550 | 1.70 |

TABLE 4-continued

| Com. ID | Structure | Name | HNMR | LCMS | Kinase assay IC50 nM. | NFkB assay IC50 μM |
|---|---|---|---|---|---|---|
| A284 | 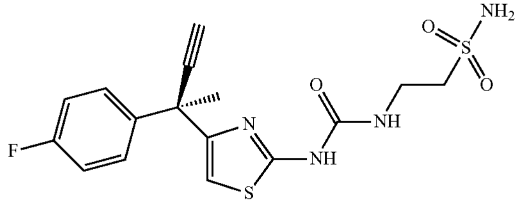 [SMILES: C#C[C@](C)(c1ccc(F)cc1)c1csc(NC(=O)NCCS(N)(=O)=O)n1] | 2-(3-(4-(2-(4-fluorophenyl)but-3-yn-2-yl)thiazol-2-yl)ureido) ethanesulfonamide | $^1$H NMR (400 MHz, DMSO-$d_6$) δ 10.94 (br s, 1H), 7.44 (dd, J = 8.78, 5.52 Hz, 2H), 7.13 (t, J = 8.91 Hz, 2H), 6.92 (s, 2H), 6.90 (s, 1H), 6.48 (br t, J = 5.65 Hz, 1H), 3.49-3.56 (m, 2H), 3.48 (s, 1H), 3.13 (t, J = 6.65 Hz, 2H), 1.85 (s, 3H). | 397.0 | 666 | 2.60 |
| A285 | 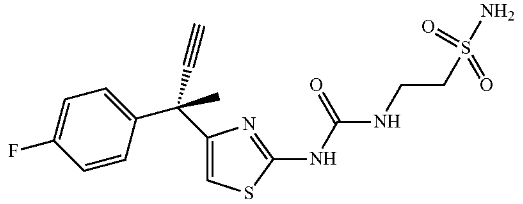 [SMILES: C#C[C@@](C)(c1ccc(F)cc1)c1csc(NC(=O)NCCS(N)(=O)=O)n1] | 2-(3-(4-(2-(4-fluorophenyl)but-3-yn-2-yl)thiazol-2-yl)ureido) ethanesulfonamide | $^1$H NMR (400 MHz, DMSO-$d_6$) δ 10.95 (br s, 1H), 7.37-7.50 (m, 2H), 7.13 (t, J = 8.78 Hz, 2H), 6.92 (s, 2H), 6.90 (s, 1H), 6.48 (br t, J = 5.90 Hz, 1H), 3.49-3.56 (m, 2H), 3.48 (s, 1H), 3.14 (t, J = 6.65 Hz, 2H), 1.85 (s, 3H). | 397.1 | 350 | 1.36 |
| A286 | 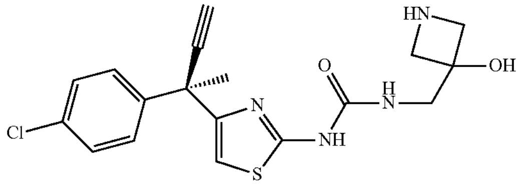 [SMILES: C#C[C@](C)(c1ccc(Cl)cc1)c1csc(NC(=O)NCC2(O)CNC2)n1] | 1-(4-(2-(4-chlorophenyl)but-3-yn-2-yl)thiazol-2-yl)-3-((3-hydroxyazetidin-3-yl)methyl)urea | $^1$H NMR (400 MHz, DMSO-$d_6$) δ 10.75 (br s, 1H), 9.17 (br s, 1H), 8.99 (br s, 1H), 7.46-7.41 (m, 2H), 7.40-7.36 (m, 2H), 6.93 (s, 1H), 6.82 (br s, 1H), 3.75-3.90 (m, 5H), 3.52 (s, 1H), 3.43 (d, J = 6.0 Hz, 2H), 1.85 (s, 3H) | 391.1 | 495 | 15.40 |
| A287 | 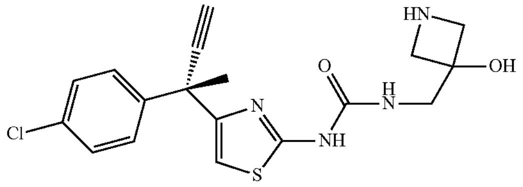 [SMILES: C#C[C@@](C)(c1ccc(Cl)cc1)c1csc(NC(=O)NCC2(O)CNC2)n1] | 1-(4-(2-(4-chlorophenyl)but-3-yn-2-yl)thiazol-2-yl)-3-((3-hydroxyazetidin-3-yl)methyl)urea | $^1$H NMR (400 MHz, DMSO-$d_6$) δ 10.75 (br s, 1H), 9.10 (br s, 1H), 8.95 (br s, 1H), 7.45-7.41 (m, 2H), 7.40-7.35 (m, 2H), 6.93 (s, 1H), 6.77 (br s, 1H), 3.86 (br s, 5H), 3.51 (s, 1H) 3.43 (br d, J = 6.0 Hz, 2H), 1.85 (s, 3H) | 391.1 | 130 | 4.40 |

TABLE 4-continued

| Com. ID | Structure | Name | HNMR | LCMS | Kinase assay IC50 nM. | NFkB assay IC50 µM |
|---|---|---|---|---|---|---|
| A288 | 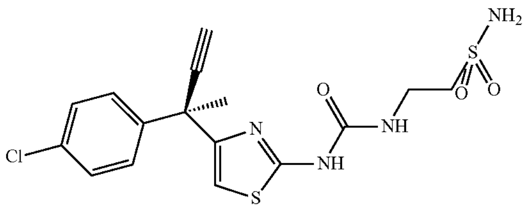 [SMILES: C#C[C@](C)(c1ccc(Cl)cc1)c1csc(NC(=O)NCCS(N)(=O)=O)n1] | 2-(3-(4-(2-(4-chlorophenyl)but-3-yn-2-yl)thiazol-2-yl)ureido) ethanesulfonamide | $^1$H NMR (400 MHz, $CDCl_3$) δ 9.48 (br s, 1H), 7.30 (s, 4H), 6.76 (s, 1H), 6.05 (br s, 3H), 3.75-3.65 (m, 2H), 3.09-2.99 (m, 2H), 2.53 (s, 1H), 1.87 (s, 3H) | 413.1 | 270 | 1.21 |
| A289 | 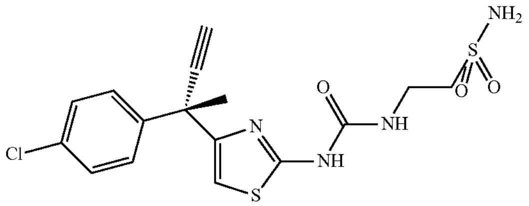 [SMILES: C#C[C@@](C)(c1ccc(Cl)cc1)c1csc(NC(=O)NCCS(N)(=O)=O)n1] | 2-(3-(4-(2-(4-chlorophenyl)but-3-yn-2-yl)thiazol-2-yl)ureido) ethanesulfonamide | $^1$H NMR (400 MHz, $CDCl_3$) δ 9.48 (br s, 1H), 7.30 (s, 4H), 6.76 (s, 1H), 6.06 (br s, 3H), 3.75-3.65 (m, 2H), 3.10-2.98 (m, 2H), 2.53 (s, 1H) 1.87 (s, 3H) | 413.1 | 54 | 0.47 |
| A290 | 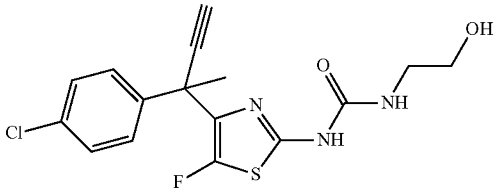 [SMILES: C#CC(C)(c1ccc(Cl)cc1)c1nc(NC(=O)NCCO)sc1F] | 1-(4-(2-(4-chlorophenyl)but-3-yn-2-yl)-5-fluorothiazol-2-yl)-3-(2-hydroxyethyl)urea | $^1$H NMR (400 MHz, DMSO-$d_6$) δ 10.65 (s, 1H), 7.50-7.35 (m, 4H), 6.34 (br. s, 1H), 4.76 (t, J = 4.0 Hz, 1H), 3.53 (s, 1H), 3.41 (q, J = 4.0 Hz, 1H), 3.15 (q, J = 4.0 Hz, 1H), 1.86 (s, 3H). | 368.0 | 222 | 4.23 |

TABLE 4-continued

| Com. ID | Structure | Name | HNMR | LCMS | Kinase assay IC50 nM. | NFkB assay IC50 µM |
|---|---|---|---|---|---|---|
| A291 | 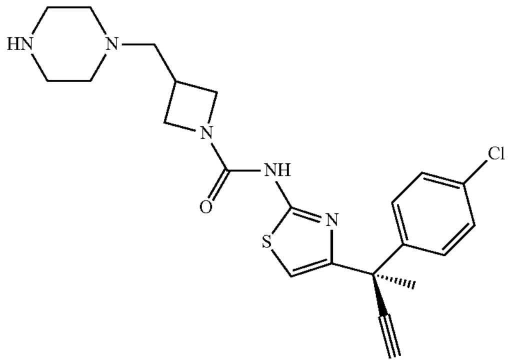 [SMILES: C#C[C@](C)(c1ccc(Cl)cc1)c1csc(NC(=O)N2CC(CN3CCNCC3)C2)n1] | N-(4-(2-(4-chlorophenyl)but-3-yn-2-yl)thiazol-2-yl)-3-(piperazin-1-ylmethyl)azetidine-1-carboxamide | $^1$H NMR (400 MHz, DMSO-$d_6$) δ 7.46-7.34 (m, 4H), 6.94 (s, 1H), 4.10-3.95 (m, 2H), 4.0 (br. s, 2H), 3.58 (br. s, 2H), 3.49 (br. s. 1H), 2.81-2.70 (m, 1H), 2.64 (br. s, 4H), 2.46-2.40 (m, 3H), 2.24 (br. s, 4H), 1.85 (s, 3H). | 444.0 | 109 | 1.65 |
| A292 | 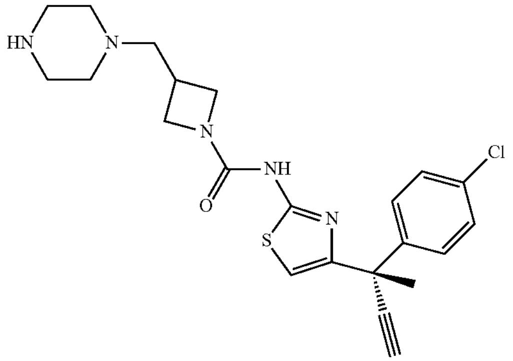 [SMILES: C#C[C@@](C)(c1ccc(Cl)cc1)c1csc(NC(=O)N2CC(CN3CCNCC3)C2)n1] | N-(4-(2-(4-chlorophenyl)but-3-yn-2-yl)thiazol-2-yl)-3-(piperazin-1-ylmethyl)azetidine-1-carboxamide | $^1$H NMR (400 MHz, DMSO-$d_6$) δ 10.91 (br. s, 1H), 8.78 (br. s, 1H), 7.42-7.35 (m, 4H), 6.95 (s, 1H), 4.09-3.96 (m, 2H), 3.65-3.55 (br. s, 2H), 3.50 (br. s, 1H), 3.08-2.99 (m, 4H), 2.87-2.70 (m, 1H), 2.60-2.52 (m, 4H), 1.85 (s, 3H). | 444.1 | 43 | 0.65 |
| A293 | 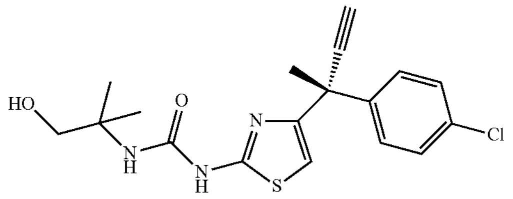 [SMILES: C#C[C@](C)(c1ccc(Cl)cc1)c1csc(NC(=O)NC(C)(C)CO)n1] | 1-(4-(2-(4-chlorophenyl)but-3-yn-2-yl)thiazol-2-yl)-3-(1-hydroxy-2-methylpropan-2-yl)urea | $^1$H NMR (400 MHz, DMSO-$d_6$) δ 10.47 (s, 1H), 7.29-7.49 (m, 4H), 6.88 (s, 1H), 6.15 (br. s, 1H), 4.93 (t, J = 5.40 Hz, 1H), 3.49 (s, 1H), 3.33 (br s, 2H), 1.84 (s, 3H), 1.19 (s, 6H). | 378.1 | 9361 | 8.11 |

TABLE 4-continued

| Com. ID | Structure | Name | HNMR | LCMS | Kinase assay IC50 nM. | NFkB assay IC50 μM |
|---|---|---|---|---|---|---|
| A294 | 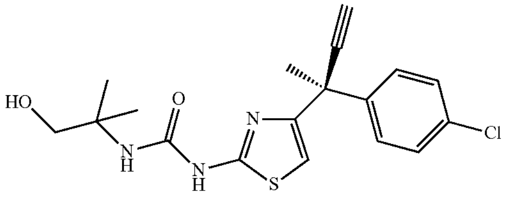 [SMILES: C#C[C@@](C)(c1ccc(Cl)cc1)c1csc(NC(=O)NC(C)(C)CO)n1] | 1-(4-(2-(4-chlorophenyl)but-3-yn-2-yl)thiazol-2-yl)-3-(1-hydroxy-2-methylpropan-2-yl)urea | $^1$H NMR (400 MHz, DMSO-$d_6$) δ 10.47 (s, 1H), 7.31-7.50 (m, 4H), 6.88 (s. 1H), 6.15 (br s, 1H), 4.94 (t. J = 5.52 Hz, 1H), 3.49 (s, 1H), 3.33 (br s, 2H), 1.84 (s, 3H), 1.19 (s, 6H). | 378.1 | 285 | 3.04 |
| A295 | 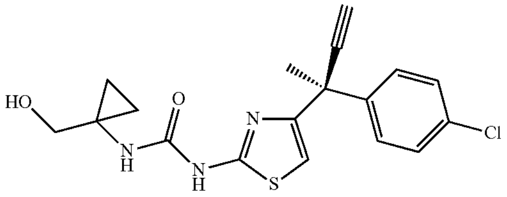 [SMILES: C#C[C@@](C)(c1ccc(Cl)cc1)c1csc(NC(=O)NC2(CO)CC2)n1] | 1-(4-(2-(4-chlorophenyl)but-3-yn-2-yl)thiazol-2-yl)-3-(1-(hydroxymethyl)cyclopropyl)urea | $^1$H NMR (400 MHz, DMSO-$d_6$) δ 10.46 (br s, 1H), 7.33-7.47 (m, 4H), 6.91 (s, 1H), 6.57 (br s, 1H), 4.58-4.99 (m, 1H), 3.49 (s, 1H), 3.37 (br s, 2H), 1.84 (s, 3H), 0.54-0.75 (m, 4H). | 376.1 | 522 | 1.79 |
| A296 | 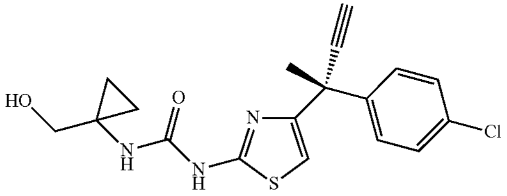 [SMILES: C#C[C@](C)(c1ccc(Cl)cc1)c1csc(NC(=O)NC2(CO)CC2)n1] | 1-(4-(2-(4-chlorophenyl)but-3-yn-2-yl)thiazol-2-yl)-3-(1-(hydroxymethyl)cyclopropyl)urea | $^1$H NMR (400 MHz, DMSO-$d_6$) δ 10.45 (br s, 1H), 7.31-7.45 (m, 4H), 6.92 (s, 1H), 6.55 (br s, 1H), 4.77 (br s, 1H), 3.49 (s, 1H), 3.36-3.37 (m, 2H), 1.84 (s, 3H), 0.53-0.77 (m, 4H) | 376.1 | 114 | 4.79 |
| A297 | 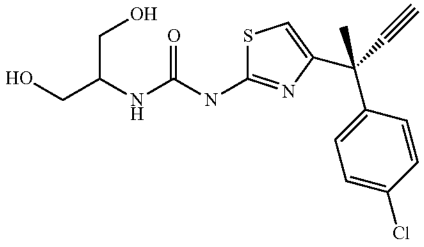 [SMILES: C#C[C@](C)(c1ccc(Cl)cc1)c1csc(NC(=O)NC(CO)CO)n1] | 1-(4-(2-(4-chlorophenyl)but-3-yn-2-yl)thiazol-2-yl)-3-(1,3-dihydroxypropan-2-yl)urea | $^1$H NMR (400 MHz, $CDCl_3$) δ 7.42 (d, J = 8.3 Hz, 2H), 7.31-7.27 (m, 2H), 6.76 (s, 1H), 3.87 (s, 1H), 3.71-3.52 (m, 4H), 2.60 (s, 1H), 1.93 (s, 3H) | 380.1 | 935 | 4.39 |

TABLE 4-continued

| Com. ID | Structure | Name | HNMR | LCMS | Kinase assay IC50 nM. | NFkB assay IC50 μM |
|---|---|---|---|---|---|---|
| A298 | 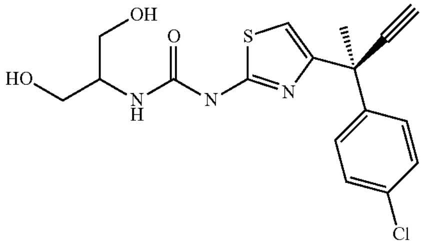 [SMILES: C#C[C@@](C)(c1ccc(Cl)cc1)c1csc(NC(=O)NC(CO)CO)n1] | 1-(4-(2-(4-chlorophenyl)but-3-yn-2-yl)thiazol-2-yl)-3-(1,3-dihydroxypropan-2-yl)urea | $^{1}H$ NMR (400 MHz, $CDCl_3$) δ 7.41 (d, J = 8.3 Hz, 2H), 7.32-7.26 (m, 2H), 6.75 (s, 1H), 3.86 (s, 1H), 3.69-3.52 (m, 4H), 2.60 (s, 1H), 1.92 (s, 3H) | 380.1 | 246 | 1.15 |
| A299 | 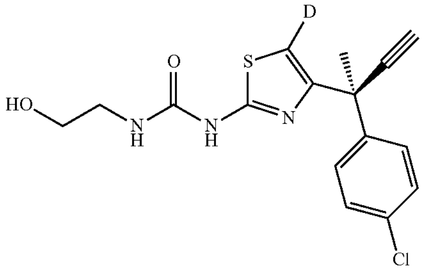 [SMILES: [2H]c1sc(NC(=O)NCCO)nc1[C@@](C)(C#C)c1ccc(Cl)cc1] | 1-(4-(2-(4-chlorophenyl)but-3-yn-2-yl)thiazol-2-yl)-3-(2-hydroxyethyl)urea | $^{1}H$ NMR (400 MHz, $CDCl_3$) δ 7.44-7.36 (m, 2H), 7.31-7.27 (m, 2H), 6.77 (s, 1H), 3.52-3.41 (m, 2H), 3.39-3.27 (m, 2H), 2.56 (s, 1H), 1.93 (s, 3H) | 351.1 | 58 | 0.46 |
| A300 | 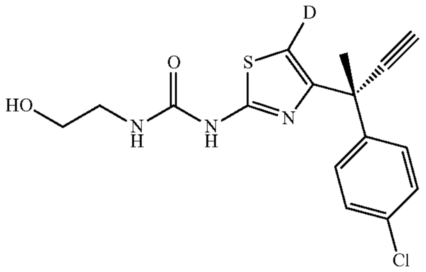 [SMILES: [2H]c1sc(NC(=O)NCCO)nc1[C@](C)(C#C)c1ccc(Cl)cc1] | 1-(4-(2-(4-chlorophenyl)but-3-yn-2-yl)thiazol-2-yl)-3-(2-hydroxyethyl)urea | $^{1}H$ NMR (400 MHz, $CDCl_3$) δ 7.43-7.36 (m, 2H), 7.29 (d, J = 7.3 Hz, 2H), 6.77 (s, 1H), 3.53-3.41 (m, 2H), 3.38-3.27 (m, 2H), 2.56 (s, 1H), 1.93 (s, 3H) | 351.1 | 341 | 3.01 |

TABLE 4-continued

| Com. ID | Structure | Name | HNMR | LCMS | Kinase assay IC50 nM. | NFkB assay IC50 µM |
|---|---|---|---|---|---|---|
| A301 | 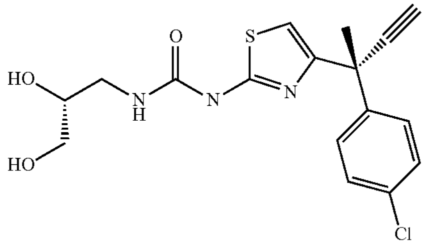 [SMILES: C#C[C@](C)(c1ccc(Cl)cc1)c1csc(NC(=O)NC[C@@H](O)CO)n1] | 1-(4-(2-(4-chlorophenyl)but-3-yn-2-yl)thiazol-2-yl)-3-((R)-2,3-dihydroxypropyl)urea | $^1H$ NMR (400 MHz, DMSO-$d_6$) δ 10.64 (br s, 1H), 7.47-7.40 (m, 2H), 7.40-7.34 (m, 2H), 6.89 (s, 1H), 6.41 (s, 1H), 3.54-3.42 (m, 2H), 3.37-3.20 (m, 3H), 3.04-2.91 (m, 1H), 1.85 (s, 3H) | 380.0 | 354 | 2.22 |
| A302 | 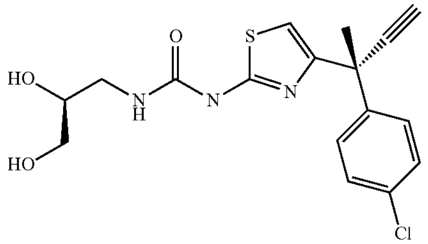 [SMILES: C#C[C@](C)(c1ccc(Cl)cc1)c1csc(NC(=O)NC[C@H](O)CO)n1] | 1-(4-(2-(4-chlorophenyl)but-3-yn-2-yl)thiazol-2-yl)-3-((S)-2,3-dihydroxypropyl)urea | $^1H$ NMR (400 MHz, DMSO-$d_6$) δ 10.64 (br s, 1H), 7.46-7.40 (m, 2H), 7.40-7.34 (m, 2H), 6.89 (s, 1H), 6.43 (s, 1H), 3.54-3.43 (m, 2H), 3.37-3.20 (m, 3H), 3.03-2.91 (m, 1H), 1.85 (s, 3H) | 379.9 | 417 | 2.04 |
| A303 | 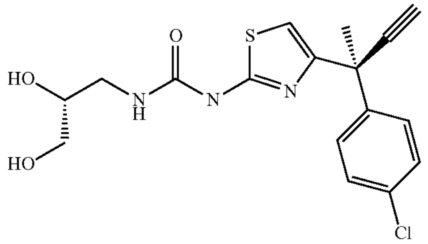 [SMILES: C#C[C@@](C)(c1ccc(Cl)cc1)c1csc(NC(=O)NC[C@@H](O)CO)n1] | 1-(4-(2-(4-chlorophenyl)but-3-yn-2-yl)thiazol-2-yl)-3-((R)-2,3-dihydroxypropyl)urea | $^1H$ NMR (400 MHz, DMSO-$d_6$) δ 10.64 (br s, 1H), 7.48-7.40 (m, 2H), 7.40-7.33 (m, 2H), 6.89 (s, 1H), 6.43 (s, 1H), 3.56-3.41 (m, 2H), 3.37-3.19 (m, 3H), 3.04-2.88 (m, 1H), 1.85 (s, 3H) | 380.0 | 101 | 0.66 |

TABLE 4-continued

| Com. ID | Structure | Name | HNMR | LCMS | Kinase assay IC50 nM. | NFkB assay IC50 μM |
|---|---|---|---|---|---|---|
| A304 | 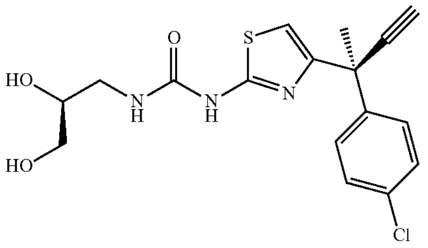 [SMILES: C#C[C@@](C)(c1ccc(Cl)cc1)c1csc(NC(=O)NC[C@H](O)CO)n1] | 1-(4-(2-(4-chlorophenyl)but-3-yn-2-yl)thiazol-2-yl)-3-((S)-2,3-dihydroxypropyl)urea | $^1H$ NMR (400 MHz, DMSO-$d_6$) δ 10.67 (br s, 1H), 7.48-7.40 (m, 2H), 7.33 (m, 2H), 6.90 (s, 1H), 6.54 (s, 1H), 3.57-3.42 (m, 2H), 3.38-3.20 (m, 3H), 3.07-2.90 (m, 1H), 1.85 (s, 3H) | 380.0 | 90 | 0.52 |
| A305 | 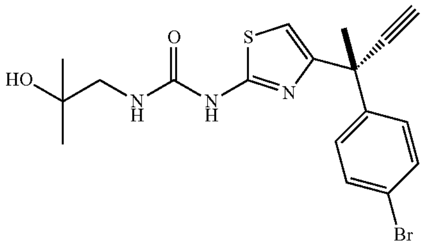 [SMILES: C#C[C@](C)(c1ccc(Br)cc1)c1csc(NC(=O)NCC(C)(C)O)n1] | 1-[4-[1-(4-bromophenyl)-1-methyl-prop-2-ynyl]thiazol-2-yl]-3-(2-hydroxy-2-methyl-propyl)urea | $^1H$ NMR (400 MHz, DMSO-$d_6$) δ 10.57 (br. s, 1H), 7.51 (d, J = 8.5 Hz, 2H), 7.38 (d, J = 8.6 Hz, 2H), 6.89 (s. 1H), 6.37 (br. s, 1H), 4.54 (s, 1H), 3.50 (s, 1H), 3.04 (d, J = 5.7 Hz, 2H), 1.85 (s, 3H), 1.05 (s, 6H). | 422.0 | 167 | 2.69 |
| A306 | 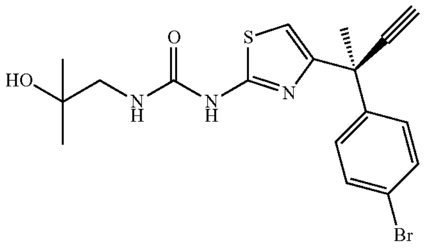 [SMILES: C#C[C@@](C)(c1ccc(Br)cc1)c1csc(NC(=O)NCC(C)(C)O)n1] | 1-[4-[1-(4-bromophenyl)-1-methyl-prop-2-ynyl]thiazol-2-yl]-3-(2-hydroxy-2-methyl-propyl)urea | $^1H$ NMR (400 MHz, DMSO-$d_6$) δ 10.57 (br. s, 1H), 7.51 (d, J = 8.6 Hz, 2H), 7.38 (d, J = 8.6 Hz, 2H), 6.89 (s, 1H), 6.37 (br. s, 1H), 4.54 (s, 1H), 3.50 (s, 1H), 3.04 (d, J = 5.7 Hz, 2H), 1.85 (s, 3H), 1.05 (s, 6H). | 422.1 | 56 | 0.83 |

TABLE 4-continued
| Com. ID | Structure | Name | HNMR | LCMS | Kinase assay IC50 nM. | NFkB assay IC50 μM |
|---|---|---|---|---|---|---|
| A307 | 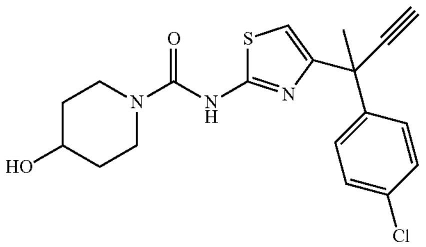 [SMILES: C#CC(C)(c1ccc(Cl)cc1)c1csc(NC(=O)N2CCC(O)CC2)n1] | N-(4-(2-(4-chlorophenyl)but-3-yn-2-yl)thiazol-2-yl)-4-hydroxypiperidine-1-carboxamide | | 390.1 | 2058 | 3.15 |
| A308 | 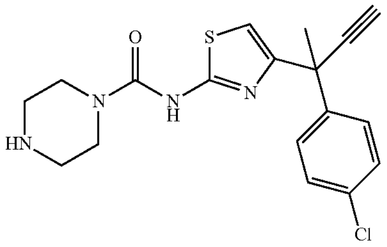 [SMILES: C#CC(C)(c1ccc(Cl)cc1)c1csc(NC(=O)N2CCNCC2)n1] | N-(4-(2-(4-chlorophenyl)but-3-yn-2-yl)thiazol-2-yl)piperazine-1-carboxamide | | 375.1 | 1535 | 5.33 |
| A309 | 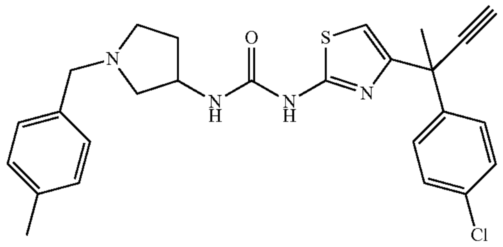 [SMILES: C#CC(C)(c1ccc(Cl)cc1)c1csc(NC(=O)NC2CCN(Cc3ccc(C)cc3)C2)n1] | 1-(4-(2-(4-chlorophenyl)but-3-yn-2-yl)thiazol-2-yl)-3-(1-(4-methylbenzyl)pyrrolidin-3-yl)urea | $^1$H NMR (400 MHz, DMSO-$d_6$ δ 10.44 (br s, 1H), 7.48-7.33 (m, 4H), 7.23-7.06 (m, 4H), 6.90 (s, 1H), 6.51 (br s, 1H), 4.10 (br s, 1H), 3.60-3.43 (m, 3H), 2.74-2.59 (m, 1H), 2.56-2.51 (m, 1H), 2.38-2.21 (m, 5H), 2.20-2.08 (m, 1H), 1.84 (s, 3H), 1.54-1.40 (m, 1H). | 479.1 | 1414 | 4.12 |

TABLE 4-continued

| Com. ID | Structure | Name | HNMR | LCMS | Kinase assay IC50 nM. | NFkB assay IC50 μM |
|---|---|---|---|---|---|---|
| A310 | 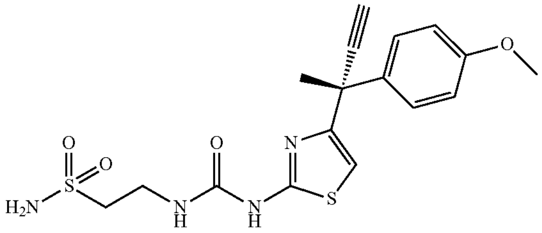 [SMILES: C#C[C@](C)(c1ccc(OC)cc1)c1csc(NC(=O)NCCS(N)(=O)=O)n1] | 2-(3-(4-(2-(4-methoxyphenyl)but-3-yn-2-yl)thiazol-2-yl)ureido) ethanesulfonamide | $^1$H NMR (400 MHz, $CDCl_3$) δ 7.32-7.27 (m, 2H), 6.89-6.79 (m, 2H), 6.74 (s, 1H), 6.02 (br s, 3H), 3.80 (s, 3H), 3.74-3.59 (m, 2H), 3.15-2.95 (m, 2H), 2.54 (s, 1H), 1.87 (s, 3H). | 409.0 | 223 | 0.98 |
| A311 | 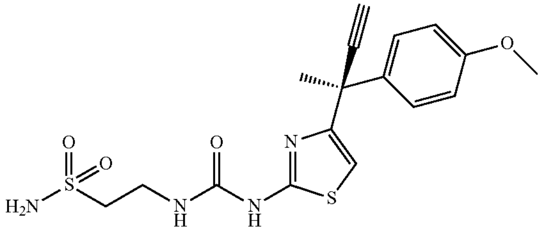 [SMILES: C#C[C@@](C)(c1ccc(OC)cc1)c1csc(NC(=O)NCCS(N)(=O)=O)n1] | 2-(3-(4-(2-(4-methoxyphenyl)but-3-yn-2-yl)thiazol-2-yl)ureido) ethanesulfonamide | $^1$H NMR (400 MHz, $CDCl_3$) δ 7.27-7.23 (m, 2H), 6.88-6.80 (m, 2H), 6.75 (s, 1H), 6.07 (br s, 3H), 3.80 (s, 3H), 3.74-3.62 (m, 2H), 3.10-2.93 (m, 2H), 2.51 (s, 1H), 1.86 (s, 3H). | 409.0 | 95 | 0.66 |
| A312 | 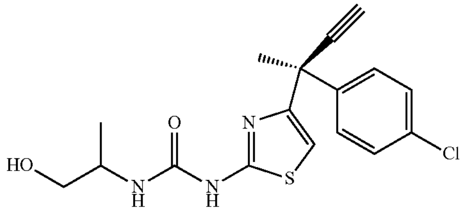 [SMILES: C#C[C@@](C)(c1ccc(Cl)cc1)c1csc(NC(=O)NC(C)CO)n1] | 1-(4-(2-(4-chlorophenyl)but-3-yn-2-yl)thiazol-2-yl)-3-(1-hydroxypropan-2-yl)urea | $^1$H NMR (400 MHz, $CD_3OD$) δ 7.54-7.46 (m, 2H), 7.32-7.25 (m, 2H), 6.91 (s, 1H), 3.93-3.76 (m, 1H), 3.60-3.41 (m, 2H), 2.96 (s, 1H), 1.92 (s, 3H), 1.16 (d, J = 6.4 Hz, 3H). | 365.6 | 545 | 2.12 |
| A313 | 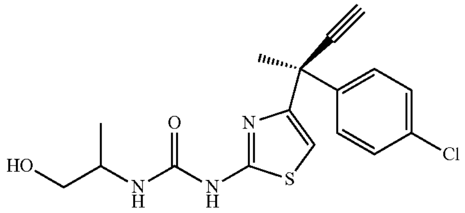 [SMILES: C#C[C@@](C)(c1ccc(Cl)cc1)c1csc(NC(=O)NC(C)CO)n1] | 1-(4-(2-(4-chlorophenyl)but-3-yn-2-yl)thiazol-2-yl)-3-(1-hydroxypropan-2-yl)urea | $^1$H NMR (400 MHz, $CD_3OD$) δ 7.55-7.43 (m, 2H), 7.37-7.24 (m, 2H), 6.90 (s, 1H), 3.91-3.76 (m, 1H), 3.56-3.44 (m, 2H), 2.96 (s, 1H), 1.92 (s, 3H), 1.16 (d, J = 6.4 Hz, 3H). | 365.5 | 614 | 2.82 |

TABLE 4-continued

| Com. ID | Structure | Name | HNMR | LCMS | Kinase assay IC50 nM. | NFkB assay IC50 μM |
|---|---|---|---|---|---|---|
| A314 | 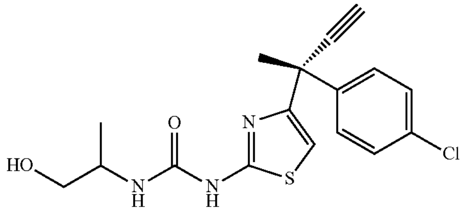 [SMILES: C#C[C@](C)(c1ccc(Cl)cc1)c1csc(NC(=O)NC(C)CO)n1] | 1-(4-(2-(4-chlorophenyl)but-3-yn-2-yl)thiazol-2-yl)-3-(1-hydroxypropan-2-yl)urea | $^1H$ NMR (400 MHz, $CD_3OD$) δ 7.58-7.39 (m, 2H), 7.36-7.18 (m, 2H), 6.90 (s, 1H), 3.97-3.75 (m, 1H), 3.62-3.37 (m, 2H), 2.96 (s, 1H), 1.92 (s, 3H), 1.16 (d, J = 6.4 Hz, 3H). | 365.5 | 261 | 0.80 |
| A315 | 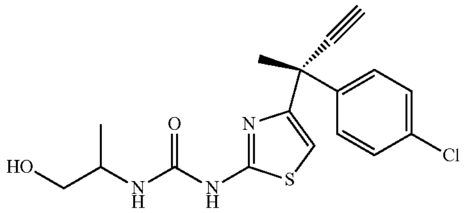 [SMILES: C#C[C@](C)(c1ccc(Cl)cc1)c1csc(NC(=O)NC(C)CO)n1] | 1-(4-(2-(4-chlorophenyl)but-3-yn-2-yl)thiazol-2-yl)-3-(1-hydroxypropan-2-yl)urea | $^1H$ NMR (400 MHz, $CD_3OD$) δ 7.57-7.46 (m, 2H), 7.35-7.21 (m, 2H), 6.91 (s, 1H), 4.00-3.73 (m, 1H), 3.56-3.41 (m, 2H), 2.96 (m, 1H), 1.92 (s, 3H), 1.16 (d, J = 6.4 Hz. 3H). | 365.6 | 81 | 0.65 |
| A316 | 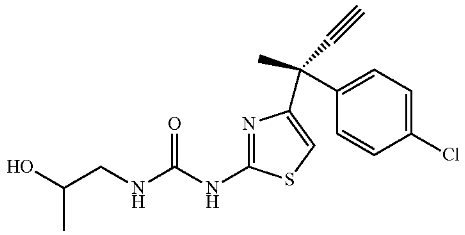 [SMILES: C#C[C@](C)(c1ccc(Cl)cc1)c1csc(NC(=O)NCC(C)O)n1] | 1-(4-(2-(4-chlorophenyl)but-3-yn-2-yl)thiazol-2-yl)-3-(2-hydroxypropyl)urea | $^1H$ NMR (400 MHz, $CD_3OD$) δ 7.54-7.44 (m, 2H), 7.32-7.25 (m, 2H), 6.91 (s, 1H), 3.90-3.76 (m, 1H), 3.28 (s, 1H), 3.16-3.04 (m, 1H), 2.95 (s, 1H), 1.92 (s, 3H), 1.15 (d, J = 6.4 Hz, 3H). | 365.6 | 421 | 1.81 |
| A317 | 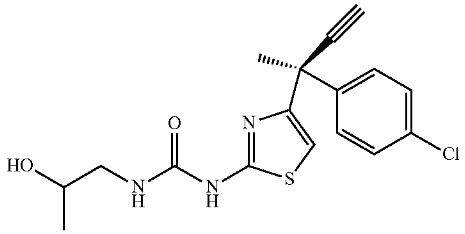 [SMILES: C#C[C@@](C)(c1ccc(Cl)cc1)c1csc(NC(=O)NCC(C)O)n1] | 1-(4-(2-(4-chlorophenyl)but-3-yn-2-yl)thiazol-2-yl)-3-(2-hydroxypropyl)urea | $^1H$ NMR (400 MHz, $CD_3OD$) δ 7.52-7.44 (m, 2H), 7.32-7.26 (m, 2H), 6.91 (s, 1H), 3.89-3.78 (m, 1H), 3.30-3.25 (m, 1H), 3.15-3.06 (m, 1H), 2.95 (s, 1H), 1.92 (s, 3H), 1.15 (d. J = 6.4 Hz, 3H). | 365.6 | 85 | 0.97 |

TABLE 4-continued

| Com. ID | Structure | Name | HNMR | LCMS | Kinase assay IC50 nM. | NFkB assay IC50 µM |
|---|---|---|---|---|---|---|
| A318 | 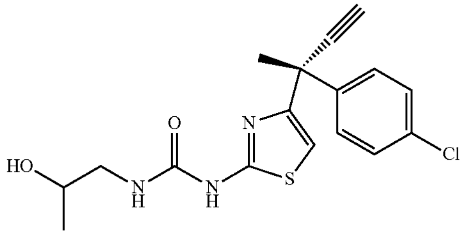 [SMILES: C#C[C@](C)(c1ccc(Cl)cc1)c1csc(NC(=O)NCC(C)O)n1] | 1-(4-(2-(4-chlorophenyl)but-3-yn-2-yl)thiazol-2-yl)-3-(2-hydroxypropyl)urea | $^1$H NMR (400 MHz, $CD_3OD$) δ 7.56-7.43 (m, 2H), 7.34-7.22 (m, 2H), 6.91 (s, 1H), 3.92-3.70 (m, 1H), 3.30-3.25 (m, 1H), 3.15-3.06 (m, 1H), 2.95 (s, 1H), 1.92 (s, 3H), 1.15 (d, J = 6.4 Hz, 3H). | 365.6 | 534 | 2.24 |
| A319 | 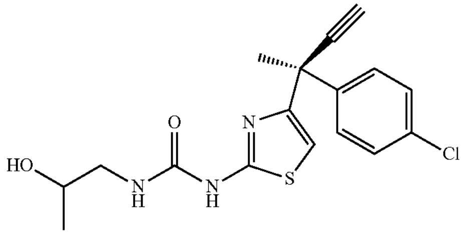 [SMILES: C#C[C@@](C)(c1ccc(Cl)cc1)c1csc(NC(=O)NCC(C)O)n1] | 1-(4-(2-(4-chlorophenyl)but-3-yn-2-yl)thiazol-2-yl)-3-(2-hydroxypropyl)urea | $^1$H NMR (400 MHz, $CD_3OD$) δ 7.59-7.43 (m, 2H), 7.35-7.14 (m, 2H), 6.91 (s, 1H), 3.89-3.75 (m, 1H), 3.30-3.24 (m, 1H), 3.14-3.05 (m, 1H), 2.95 (s, 1H), 1.92 (s, 3H), 1.15 (d. J = 6.4 Hz, 3H). | 365.6 | 156 | 0.67 |
| A320 | 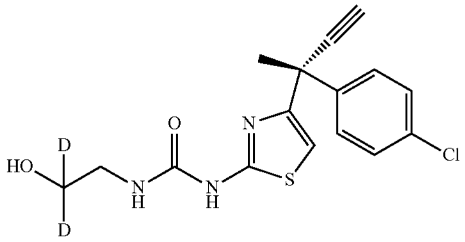 [SMILES: [2H]C([2H])(O)CNC(=O)Nc1nc([C@](C)(C#C)c2ccc(Cl)cc2)cs1] | 1-14-[1-(4-chlorophenyl)-1-methyl-prop-2-ynyl]thiazol-2-yl]-3-(2,2-dideuterio-2-hydroxy-ethyl)urea | $^1$H NMR (400 MHz, $CDCl_3$) δ 7.34-7.28 (m, 2H), 7.22-7.19 (m, 2H), 6.69 (s, 1H), 3.23 (d, J = 5.5 Hz, 2H), 2.48 (s, 1H), 1.84 (s, 3H) | 352.1 | 44 | |

TABLE 4-continued
| Com. ID | Structure | Name | HNMR | LCMS | Kinase assay IC50 nM. | NFkB assay IC50 µM |
|---|---|---|---|---|---|---|
| A321 | 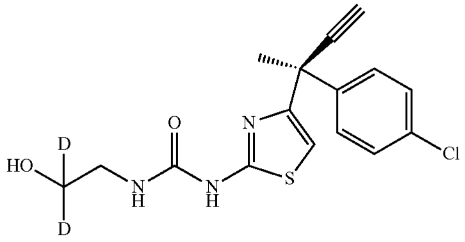 [SMILES: [2H]C([2H])(O)CNC(=O)Nc1nc([C@@](C)(C#C)c2ccc(Cl)cc2)cs1] | 1-14-11-(4-chlorophenyl)-1-methyl-prop-2-ynyl]thiazol-2-yl]-3-(2,2-dideuterio-2-hydroxy-ethyl)urea | $^1H$ NMR (400 MHz, $CDCl_3$) δ 7.43-7.35 (m, 2H), 7.31-7.27 (m, 2H), 6.76 (s, 1H), 3.31 (d, J = 5.5 Hz, 2H), 2.55 (s, 1H), 1.92 (s, 3H) | 352.1 | 28 | 0.30 |

Example 10

Preparation of tert-butyl 4-(4-((3(4-(1-(4-bromo phenyl)ethyl)thiazol-2-yl)ureido)methyl)phenyl) piperazine-1-carboxylate

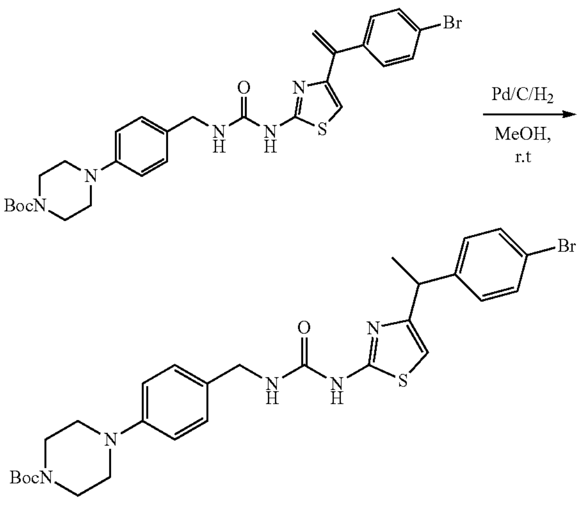

To a solution of tert-butyl 4-(4-((3-(4-(1-(4-bromophenyl) vinyl)thiazol-2-yl)ureido)methyl)phenyl)piperazine-1-carboxylate (120 mg) in MeOH (5 mL) was added Pd/C (12 mg), the mixture was stirred overnight at RT under hydrogen pressure. After filtration and evaporation, the obtained residue was purified by column chromatography on a silica gel to afford tert-butyl 4-(4-((3-(4-(1-(4-bromophenyl)ethyl)thiazol-2-yl)ureido)methyl)phenyl)piperazine-1-carboxylate (73 mg).

Example 11

Preparation of tert-butyl 4-(5-((3-(4-(2-(4-bromophenyl)propan-2-yl)thiazol-2-yl)ureido methyl-3-fluoropyridin-2-yl)piperazine-1-carboxylate

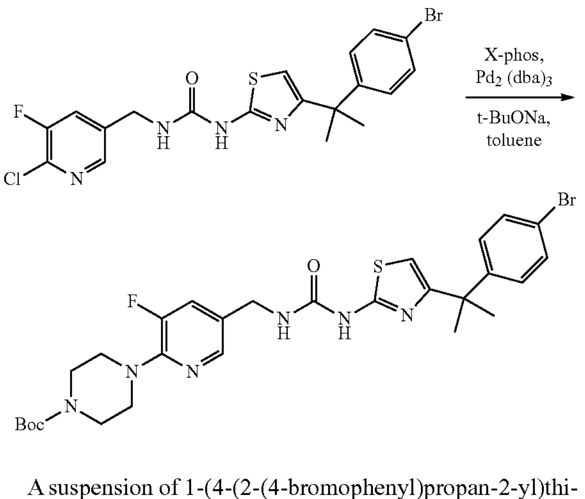

A suspension of 1-(4-(2-(4-bromophenyl)propan-2-yl)thiazol-2-yl)-3-((6-chloro-5-fluoropyridin-3-yl)methyl)urea (174 mg 0.4 mmol), tert-butyl piperazine-1-carboxylate (82 mg, 0.44 mmol), X-phos (39 mg, 0.08 mmol), $Pd_2$ (dba)$_3$ (36.6 mg, 0.04 mmol) and t-BuONa (46.1 mg, 0.48 mmol) in toluene (5 ml) was stirred at 90° C. under $N_2$ atmosphere overnight. The reaction mixture was cooled to RT and filtered off the solid, the residue was dissolved in ethyl acetate (100 mL) and washed with brine. The organic phase was dried over $MgSO_4$, filtered, concentrated in vacuum to give the crude product, which was purified by flashed column to give the desired product (67 mg, 0.1 mmol, yield 25%).

Example 12

Preparation of 5-((3-(4-(2-(4-methoxyphenyl)propan-2-yl)thiazol-2-yl ureido methyl)-2-(3-methylpiperazin-1-yl)benzamide

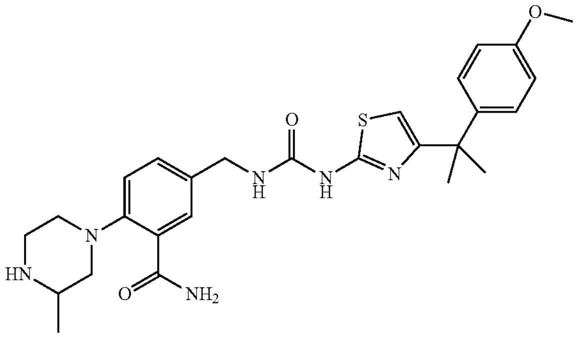 [SMILES: COc1ccc(C(C)(C)c2csc(NC(=O)NCc3ccc(N4CCNC(C)C4)c(C(N)=O)c3)n2)cc1]

Step 1 Preparation of 2-(4-(tert-butoxycarbonyl)-3-methylpiperazin-1-yl)-5-((3-(4-(2-(4-methoxyphenyl)propan-2-yl)thiazol-2-yl)ureido)methyl)benzoic acid

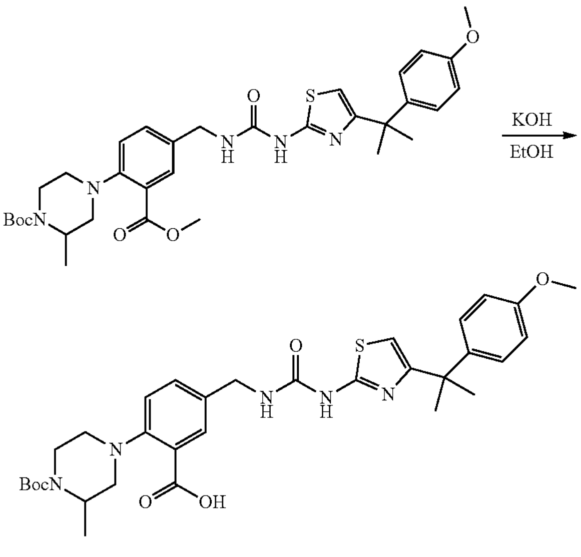

A mixture of tert-butyl 4-(2-(methoxycarbonyl)-4-((3-(4-(2-(4-methoxyphenyl)propan-2-yl)thiazol-2-yl)ureido) methyl)phenyl)-2-methylpiperazine-1-carboxylate (270 mg, 0.42 mmol, 1 eq) and KOH (23.5 mg, 0.42 mmol, 1 eq), was heated to reflux for 0.5 h. After cooling, the reaction was quenched with sat. $NH_4Cl$ (aq), extracted with EA, washed with brine, dried over $Na_2SO_4$, filtered and evaporated to dryness. The resulting residue was purified by Prep-TLC to give the desired compound (215 mg).

Step 2: Preparation of tert-butyl 4-(2-carbamoyl-4-((3-(4-(2-(4-methoxyphenyl)propan-2-yl)thiazol-2-yl)ureido)methyl)phenyl)-2-methylpiperazine-1-carboxylate

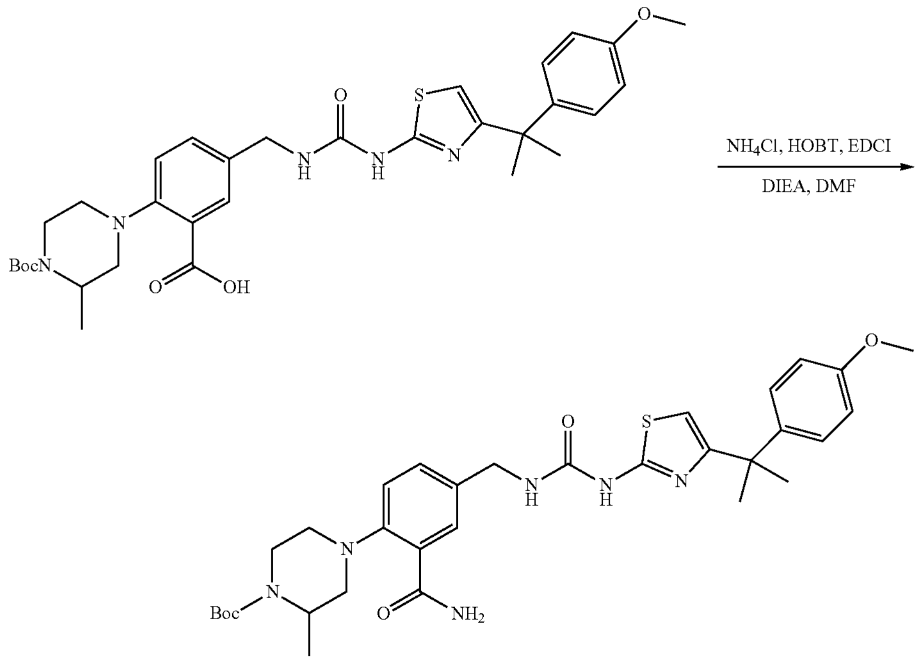

A mixture of 2-(4-(tert-butoxycarbonyl)-3-methylpiperazin-1-yl)-5-((3-(4-(2-(4-methoxyphenyl)propan-2-yl)thiazol-2-yl)ureido)methyl)benzoic acid (215 mg, 0.34 mmol, 1 eq), EDCI (132 mg, 0.69 mmol, 2 eq), HOBt (93 mg, 0.69 mmol, 2 eq) and DIEA (133 mg, 1.03 mmol, 3 eq) were dissolved in THF (0.1 M) and stirred for 15 min at RT. $NH_4C_1$ (36.9 mg, 0.69 mmol, 2 eq) was then added in one portion and the reaction was stirred at RT. Once judged complete by TLC analysis, the resulting suspension was diluted with EtOAc and washed with brine and then dried ($Na_2SO_4$), filtered and evaporated to dryness. The resulting residue was purified by trituration or Prep-TLC to give the desired product (201 mg).

Example 13

Preparation of 1-((6-((2-hydroxyethyl)amino)pyridin-3-yl)methyl)-3-(4-(2-(4-methoxyphenyl)propan-2-yl)thiazol-2-yl)urea

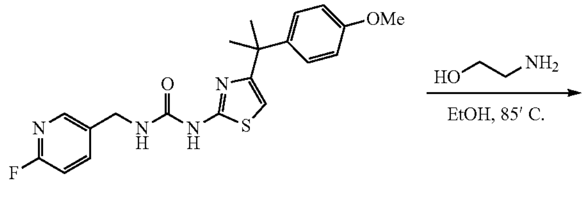

-continued

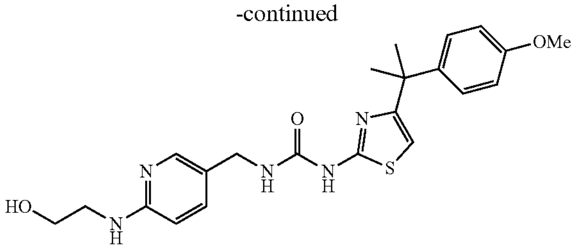

A mixture of 1-((6-fluoropyridin-3-yl)methyl)-3-(4-(2-(4-methoxyphenyl)propan-2-yl)thiazol-2-yl)urea (50 g, 0.13 mmol, 1.0 eq) and 2-aminoethanol (11.9 mg, 0.19 mmol, 1.5 eq) in EtOH was heated to 90° C. for 14 h. After the reaction was cooled down to RT, concentrated to give a residue, which was purified by column chromatography on a silica gel to afford 1-((6-((2-hydroxyethyl)amino)pyridin-3-yl)methyl)-3-(4-(2-(4-methoxyphenyl)propan-2-yl)thiazol-2-yl)urea (21 mg).

Example 14

Preparation of 1-(4-(2-(4-methoxyphenyl)but-3-yn-2-yl)thiazol-2-yl)-3-(1-(4-(piperazin-1-yl)phenyl)ethyl)urea

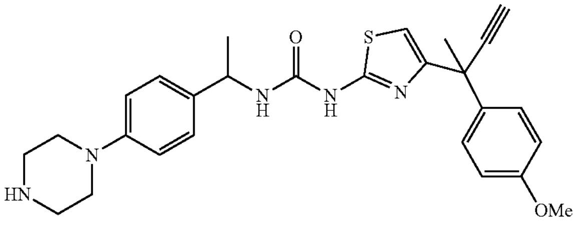 [SMILES: C#CC(C)(c1ccc(OC)cc1)c1csc(NC(=O)NC(C)c2ccc(N3CCNCC3)cc2)n1]

Step 1. Preparation of methyl 2-(4-methoxyphenyl)acetate

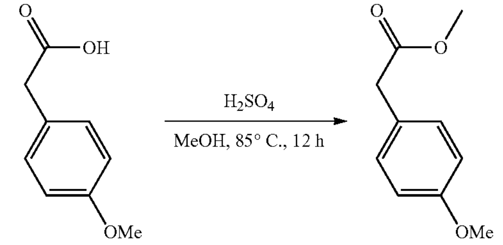

A mixture of 2-(4-methoxyphenyl)acetic acid (20.0 g, 120.4 mmol) in MeOH (100 mL) was added $H_2SO_4$ (1.2 g, 12.0 mmol, 642 μL) at 15° C. The mixture was stirred for 12 h at 85° C. The mixture was diluted with EA (400 mL), washed with sat. $NaHCO_3$ aq (100 mL), brine (10 mL), dried over anhydrous $Na_2SO_4$, filtered and concentrated in vacuum to give a residue. The residue was purified by silica column (ethyl acetate in petroleum ether=0-15%). The desired product (21.6 g, yield: 99.7%) was obtained as yellow oil.

$^1$H NMR (400 MHz, $CDCl_3$) δ 7.21 (d, J 8.8 Hz, 2H) 6.87 (d, J=8.8 Hz, 2H), 3.80 (s, 3H), 3.69 (s, 3H), 3.58 (s, 2H)

Step 2. Preparation of compound methyl 2-(4-methoxyphenyl)-3-oxobutanoate

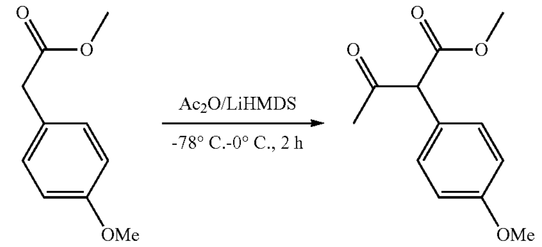 [SMILES: COC(=O)Cc1ccc(OC)cc1 ; "Ac2O/LiHMDS" ; COC(=O)C(C(C)=O)c1ccc(OC)cc1]

To a solution of compound obtained from step 1 above (23.8 g, 132.2 mmol) in THF (200 mL) was added LiHMDS (1 M, 159 mL) at −78° C. The mixture was stirred for 20 min at −78° C. Acetyl acetate (13.5 g, 132.2 mmol) was added to the solution. Then the mixture was warmed to 0° C. and stirred for 2 h at 0° C. The mixture was quenched with sat $NH_4C_1$ aq. (50 mL) and extracted with EA (3×50 mL). The combined organic layers were washed with brine (10 mL), dried over anhydrous $Na_2SO_4$, filtered and concentrated in vacuum. The residue was purified on silica gel chromatography (ethyl acetate in petroleum ether=0-15%) to give the desired compound (14.23 g, yield: 48.4%) as a yellow oil.

$^1$H NMR (400 MHz, $CDCl_3$-d) δ=12.97 (s, 1H), 7.25-7.23 (m, 1.5H), 7.07-7.03 (m, 2H), 6.87-6.85 (m, 2H), 4.63 (s, 0.5H), 3.80 (s, 3H), 3.78 (s, 1.5H), 3.73 (s, 1.5H), 3.67 (s, 3H), 2.15 (s, 1.5H), 1.83 (s, 3H). MS (ESI) m/z $(M+H)^+$=223.1

Step 3. Preparation of compound methyl 2-(4-methoxyphenyl)-2-methyl-3-oxobutanoate

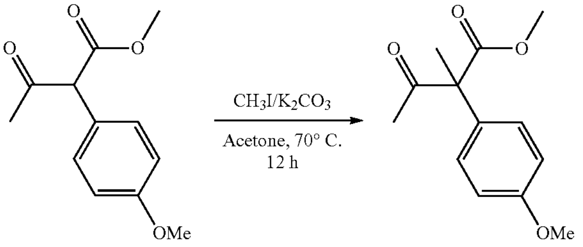 [SMILES: COC(=O)C(C(C)=O)c1ccc(OC)cc1 ; "CH3I/K2CO3" ; COC(=O)C(C)(C(C)=O)c1ccc(OC)cc1]

To a mixture of compound obtained from step 2 above (14.5 g, 65.4 mmol) and $K_2CO_3$ (45.2 g, 326.9 mmol) in ACETONE (100 mL) was added $CH_3$ (26.0 g, 183.3 mmol) at 15° C. The mixture was stirred at 70° C. for 12 h. The mixture was filtered and the filtrate was concentrated in vacuum to give a residue. The residue was purified by silica column (ethyl acetate in petroleum ether=0-15%). The desired compound (9.76 g, yield: 63.2%) was obtained as a colorless oil.

$^1$H NMR (400 MHz, $CDCl_3$) δ 7.25-7.19 (m, 2H), 6.95-6.86 (m, 2H), 3.82 (s, 3H), 3.79 (s, 3H), 2.10 (s, 3H), 1.77 (s, 3H)

Step 4. Preparation of compound methyl 4-bromo-2-(4-methoxyphenyl)-2-methyl-3-oxobutanoate

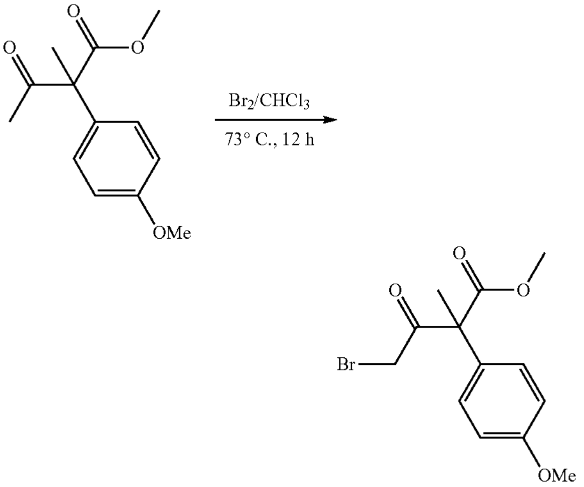

To a solution of compound obtained from step 3 above (1 g, 4.2 mmol) in $CHCl_3$ (20 mL) was added $Br_2$ (676 mg, 4.2 mmol) at 15° C. The mixture was stirred at 73° C. for 12 h. The mixture was washed with $H_220$ (20 mL), brine (10 mL), dried over anhydrous $Na_2SO_4$, filtered and concentrated in vacuum to give a residue. The desired product (1.03 g, crude) was obtained as a colorless oil. The crude product was directly used for the next step without further purification.

MS (ESI) m/z $(M+H)^+$=315.1

Step 5. Preparation of compound methyl 2-(2-aminothiazol-4-yl)-2-(4-methoxyphenyl)propanoate

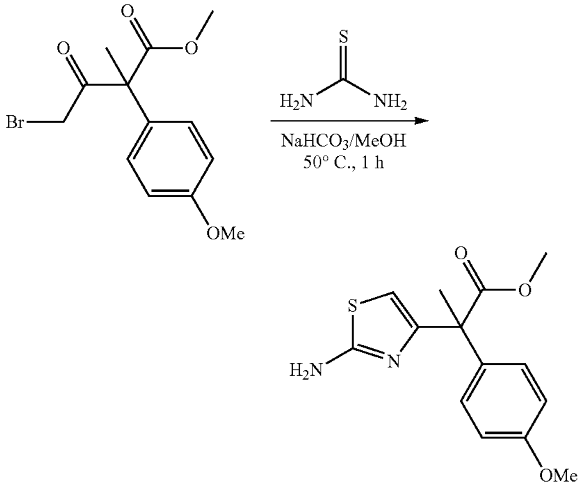

A mixture of compound obtained from step 4 above (1.03 g, 3.3 mmol), THIOUREA (299 mg, 3.9 mmol) and $NaHCO_3$ (329 mg, 3.9 mmol) in MeOH (15 m L) was stirred at 50° C. for 1 h. The mixture was concentrated in vacuum directly. The residue was triturated with $H_2O$ (20 mL) at 15° C. for 10 min., filtered and the cake was concentrated in vacuum to give a residue. The desired product (0.79 g, yield: 82.68%) was obtained as a yellow solid $^1H$ NMR (400 MHz, $CDCl_3$) δ 7.20-7.18 (m, 2H), 6.97-6.92 (m, 2H), 6.88-6.86 (m, 2H), 5.95 (s, 1H), 3.73 (s, 3H), 3.61 (s, 3H), 1.77 (s, 3H).

Step 6. Preparation of compound methyl 2-(4-methoxyphenyl)-2-(2-((phenoxycarbonyl)amino)thiazol-4-yl)propanoate

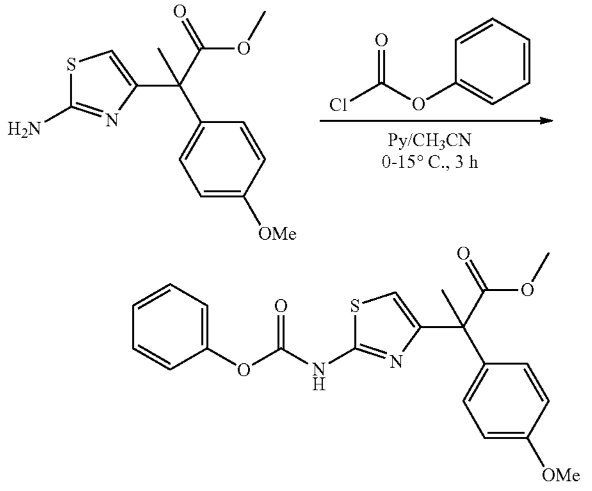

To a mixture of compound obtained from step 5 above 00 mg, 1.03 mmoL) and PYRIDINE (97.4 mg, 1.23 mmol) in $CH_3CN$ (3 mL) was added phenyl carbonochloridate (169 mg, 1.08 mmol) at 0° C. The mixture was stirred at 15° C. for 3 h. The mixture was concentrated in vacuum directly. The residue was purified by silica column (ethyl acetate in petroleum ether=0-30%) to give the desired compound (330 mg, yield: 77.97%) which was obtained as a yellow oil.

MS (ESI) m/z $(M+H)^+$413.0

Step 7. Preparation of compound tert-butyl 4-(4-(1-(3-(4-(1-methoxy-2-(4-methoxyphenyl)-1-oxopropan-2-yl)thiazol-2-yl)ureido)ethyl)phenyl)piperazine-1-carboxylate

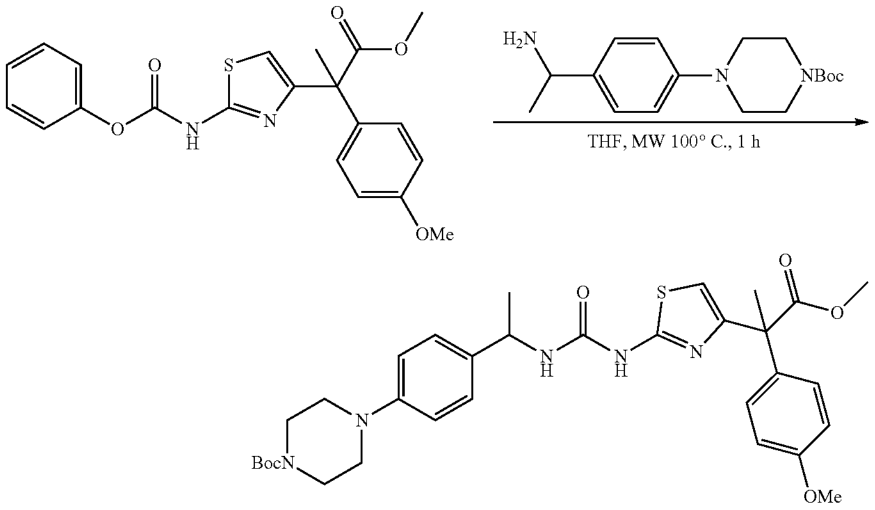

To a mixture of compound obtained from step 6 above (330 mg, 800 μmol) and tert-butyl 4-14-(1-aminoethyl) phenyl]piperazine-1-carboxylate (269 mg, 880 mol) in THF (2 mL) was stirred at 100° C. for I h under Microwave The mixture was directly concentrated in vacuum to give a residue. The residue was purified by silica column (ethyl acetate in petroleum ether=0-80%). The desired compound (441 mg, yield: 88.37%) was obtained as a yellow oil.

MS (ESI) m/z $(M+H)^{+}$=646.2

Step 8. Preparation of compound tert-butyl 4-(4-(1-(3-(4-(1-hydroxy-2-(4-methoxyphenyl)propan-2-yl) thiazol-2-yl)ureido)ethyl)phenyl)piperazine-1-carboxylate

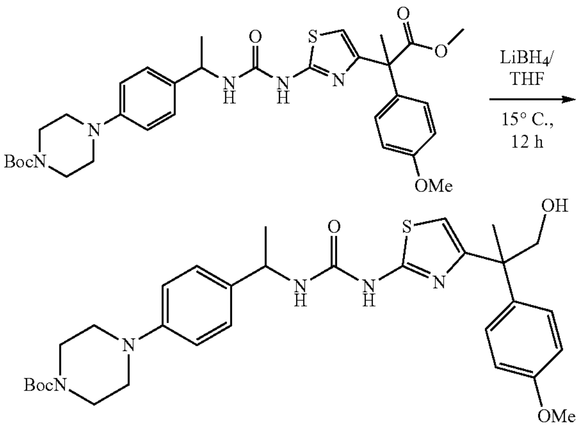

To a solution of compound obtained from step 7 above (370 mg, 593 μmol) in THF (10 mL) was added $LiBH_4$ (26 mg, 1.2 mmol) at 15° C. The mixture was stirred for 12 h at 15° C. The mixture was diluted with sat.$NH_4Cl$ (15 mL) and extracted with EA (3×15 mL). The organic layers were washed with brine (10 mL), dried over anhydrous $Na_2SO_4$, filtered and concentrated in vacuum. The residue was purified by silica column (ethyl acetate in petroleum ether=0-100%) to give the desired compound (307 mg, yield: 87.0%) which was obtained as a yellow solid.

$^{1}$H NMR (400 MHz, $CDCl_3$) δ 7.17 (d, J=8.4 Hz, 2H), 7.09-7.06 (m, 2H), 6.86-6.80 (m, 4H), 6.45 (s, 1H), 4.94-4.91 (m, 1H), 4.05-4.00 (m, 1H), 3.81-3.77 (m, 4 H), 3.56-3.54 (m, 4H) 3.09-3.07 (m, 4H), 1.56 (d, J=1.6 Hz, 3H), 1.49 (s, 9H), 1.46 (d, J=6.8 Hz, 3H).

Step 9. Preparation of compound 1-(4-(1-hydroxy-2-(4-methoxyphenyl)propan-2-yl)thiazol-2-yl)-3-(1-(4-(piperazin-1-yl)phenyl)ethyl)urea hydrochloride

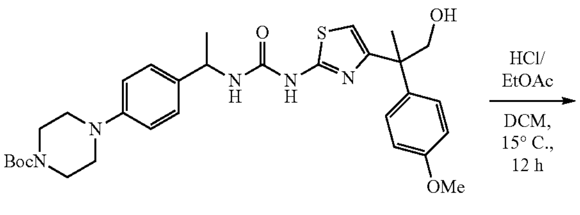

-continued

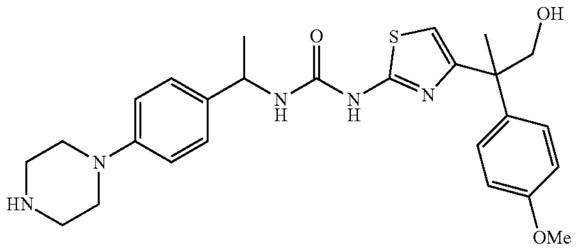

To a solution of compound obtained from step 8 above (50 mg, 83.93 μmol) in DCM (2 mL) was added HCl/EtOAc (4 M, 2 mL) at 15° C. The mixture was stirred for 12 h at 15° C. The mixture was concentrated in vacuum to give the desired compound (34 mg, yield: 76.1%) was obtained as a yellow solid.

$^{1}$H NMR (400 MHz, DMSO) δ 10.47 (br s, 1H), 9.11 (br s, 2H), 7.36-7.23 (m, 1H), 7.19 (d, J=8.8 Hz, 2H), 7.10 (d, J=8.8 Hz, 2H), 6.95 (d, J=8.8 Hz, 2H), 6.75 (d, J=8.0 Hz, 2H), 6.69 (s, I H), 4.77-4.73 (m, 1H), 3.80-3.76 (m, 1H), 3.70 (s, 3H) 3.34-3.31 (m, 4H), 3.24-3.16 (m, 4H), 2.07 (s, 1H), 1.55 (s, 3H), 1.33 (d, J=6.8 Hz, 3 H). MS (EST) m/z $(M+H)^{+}$=496.2

Step 10. Preparation of compound tert-butyl 4-(4-(1-(3-(4-(2-(4-methoxyphenyl)-1-oxopropan-2-yl) thiazol-2-yl)ureido)ethyl)phenyl)piperazine-1-carboxylate

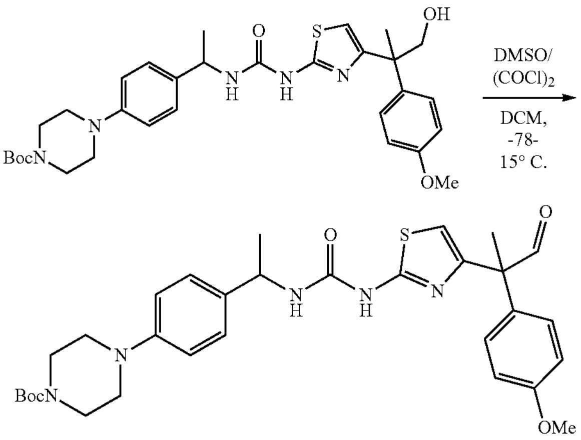

To a solution of oxalyl dichloride (68.2 mg, 537.14 μmo) in DCM (2 mL) was added DMSO (66 mg, 839 μmol) at −78° C. After 10 min, compound obtained from step 9 above (100 mg, 168 μmol) in DCM (2 mL) was added and stirred for 1 h at −78° C. $Et_3N$ (170 mg, 1.68 mmol) was added and stirred for 10 more min then warmed to 15° C. and stirred for another 1 h. The mixture was diluted with $H_2O$ (20 mL), extracted with DCM (3×20 μL). The organic layers were washed with brine (10 mL), dried over anhydrous $Na_2SO_4$, filtered and concentrated in vacuum to give a residue. The desired product (120 mg, crude) was obtained as a yellow oil. The crude product was directly used for the next step without further purification.

Step 11. Preparation of compound tert-butyl 4-(4-(1-(3-(4-(2-(4-methoxyphenyl)but-3-yn-2-yl)thiazol-2-yl)ureido)ethyl)phenyl)piperazine-1-carboxylate

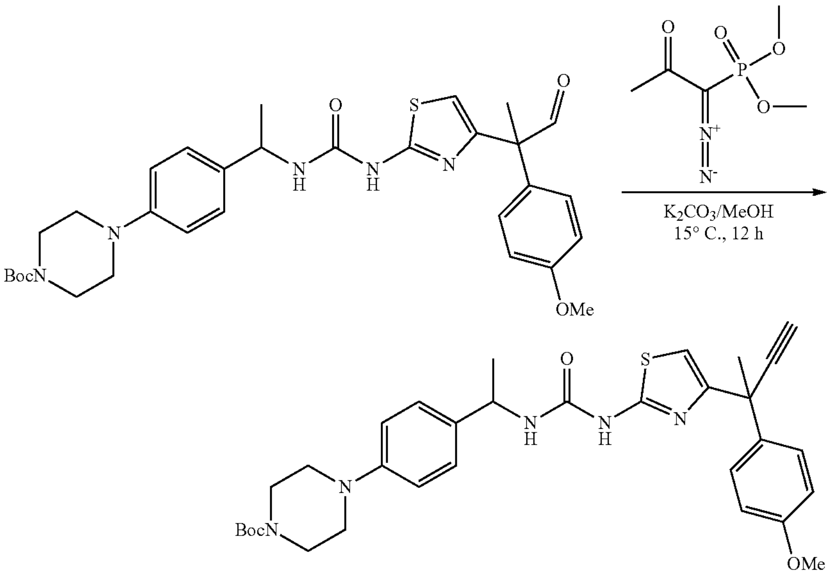

A mixture of compound obtained from step 10 above (100 mg, 168 μmol), dimethyl (1-diazo-2-oxopropyl)phosphonate (49 mg, 252.6 μmol) and $K_2CO_3$ (47 mg 337 μmol in MeOH (5 mL) was stirred for 1 h at 15° C. The reaction was directly concentrated in vacuum. The residue was purified by prep. HPLC (column: Venusil ASB Phenyl 150*30 mm*5 um; mobile phase: [water(0.05% HCl)-ACN];B %:65%-95%,10 min) to give the desired compound (50 mg, yield: 50.34%) was obtained as a yellow oil.

MS (ESI) m/z $(M+H)^+$=590.3

Step 12. Preparation of compound 1-(4-(2-(4-methoxyphenyl)but-3-yn-2-yl)thiazol-2-yl)-3-(1-(4-(piperazin-1-yl)phenyl)ethyl)urea

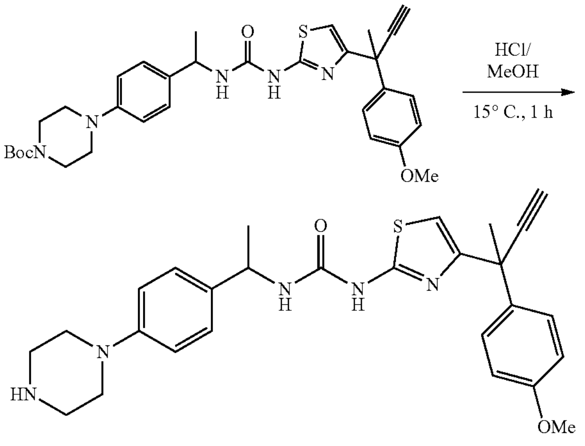

The desired compound (39 mg, yield: 87.4%) was obtained as a yellow solid using De-BOC method.

$^1H$ NMR (400 MHz, DMSO-$d_6$) δ 10.50 (br s, 1H), 9.22 (br s, 2H), 7.31 (d, J=8.8 Hz, 2H), 7.19 (d, J=8.4 Hz, 3H), 6.95 (d, J=8.4 Hz, 2H), 6.85 (dd, J=8.4, 1.2 Hz, 2H), 6.81-6.79 (m, 1H), 4.76-4.73 (m, 1H), 3.71 (s, 3H), 3.39 (s, 1H), 3.35-3.32 (m, 4H) 3.24-3.16 (m, 4H), 1.82 (d, J=2.4 Hz, 3H), 1.33 (d, J=6.8 Hz, 3H).

MS (ESI) m/z $(M+Na)^+$=512.3

Example 15

Preparation of 1-(4-(2-4-cyclopropyphenyl)propan-2-yl)thiazol-2-yl)-3-4-(piperazin-1-yl)benzyl)urea

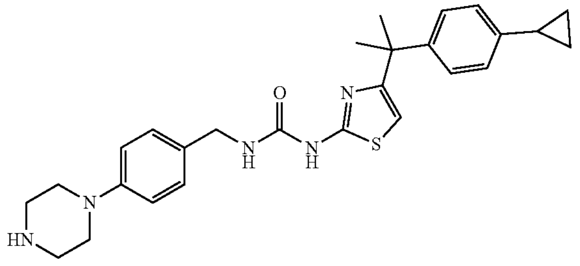 [SMILES: CC(C)(c1ccc(C2CC2)cc1)c1csc(NC(=O)NCc2ccc(N3CCNCC3)cc2)n1]

Step 1: Preparation of tert-butyl 4-(4-((3-(4-(2-(4-cyclopropylphenyl)propan-2-yl)thiazol-2-yl)ureido)methyl)phenyl)piperazine-1-carboxylate

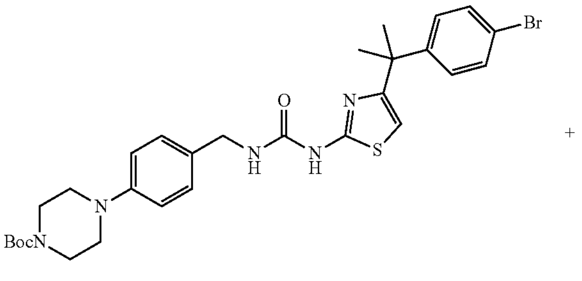

-continued

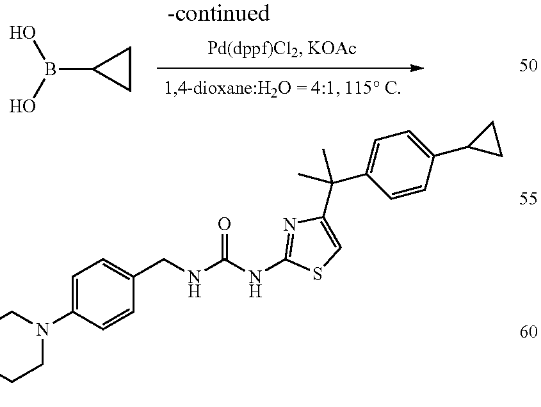

To a solution of compound obtained from step I above (81 mg, 0.13 mmol) in 1,4-dioxane (4 mL) and $H_2O$ (1 mL) was added cyclopropylboronic acid (14 mg, 0.16 mmol), $Pd(dppf)Cl_2$ (10 mg, 0.013 mmol), KOAc (25 mg, 0.26 mmol). The reaction mixture was stirred at 115° C. overnight under $N_2$ atmosphere. The reaction progress was monitored by TLC. After the completion of the reaction, the mixture was filtered through a pad of celite, washed with EA. The filtrate was removed under reduced pressure and the residue was purified by column chromatography on silica gel (PE/EA=2:1) to give the desired compound (45 mg, yield: 60. %) as a white solid.

Step 2.Preparation of compound 1-(4-(2-(4-cyclopropylphenyl)propan-2-yl)thiazol-2-yl)-3-(4-(piperazin-1-yl)benzyl)urea

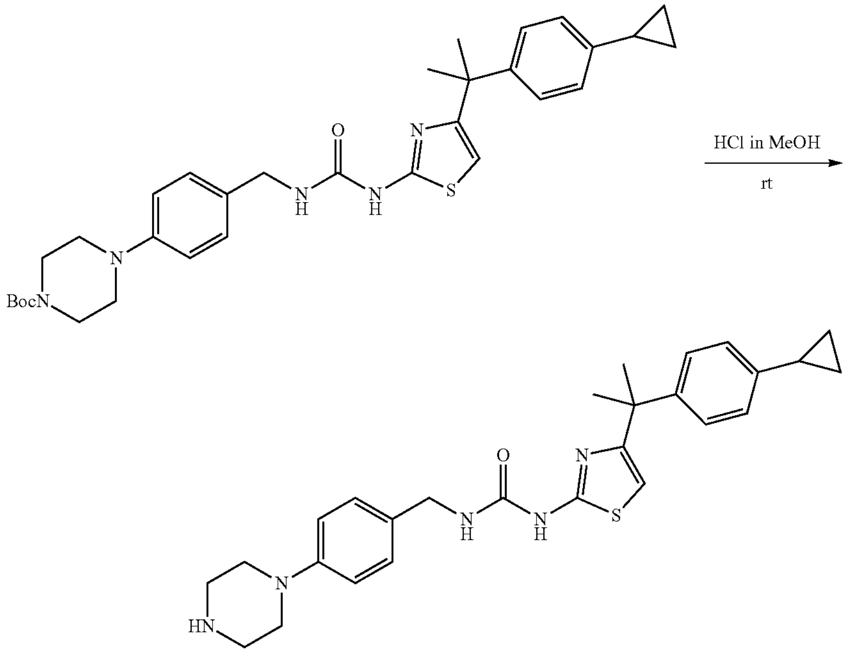

The desired compound was obtained as a white solid (40 mg, HCl salt, yield: 100%) with the procedure described in example 9. MS (ESI) m/z $(M+H)^+$=476.2.

General Method A

Carboxylic acids (1 equiv), EDCI (2-2.5 equiv), with or without HOBt (2 equiv) and DIEA (3 equiv)/pyridine/DMAP were dissolved in T-IF/DMF and stirred for 15-30 min at RT. Amine (1 equiv) was then added in one portion and the reaction was stirred at RT to 70° C. for 2-16 hours. Once the reaction was completed, the resulting suspension was diluted with organic solvent and washed with brine and then dried. After filtration and evaporation, the resulting residue was purified by trituration/Prep-TLC/chromatography/Prep-HPLC to give the product.

Example 16

Preparation of compound 4-((2-hydroxyethyl)amino)-N-(4-2-(4-methoxyphenyl)propan-2-yl)thiazol-2-yl)benzamide

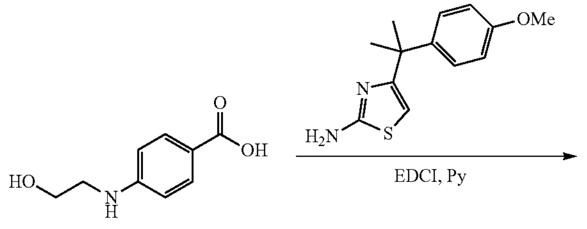

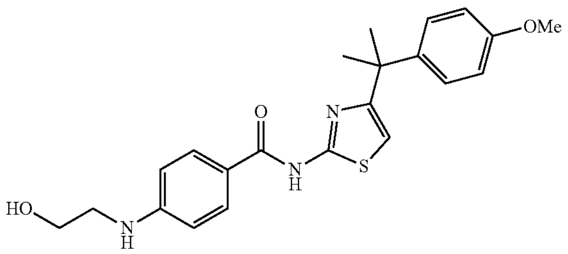

To a solution of 4-((2-hydroxyethyl)amino)benzoic acid (200 mg, 1.10 mmol) and 4-[1-(4-methoxyphenyl)-1-methyl-ethyl]thiazol-2-amine (261.98 mg, 919.85 umol, HCl) in Py (8 mL) was added EDCI (440.84 mg, 2.30 mmol). The mixture was stirred at 70° C. for 16 hr. The reaction mixture was concentrated to give a residue. The residue was purified by prep-HPLC (column: Agela ASB 150x25 mmx5 um; mobile phase: [water (0.05% HCl)-ACN]; B %:48%-78%, 10 min). The desired compound (52 mg, yield: 13.57%) was obtained as a pale yellow solid.

$^1$H NMR (400?MHz, DMSO-$d_6$) δ 12.06 (br s, 1H), 7.87 (d, J=8.8 Hz, 2H), 7.12 (d, J=8.8 Hz,

2H), 6.86 (s, 1H), 6.82 (d, J=8.8 Hz, 2H), 6.62 (d, J=8.8 Hz, 2H), 3.70 (s, 3H), 3.54 (t, J:=5.9

Hz, 2H), 3.16 (t, J=5.9 Hz, 2H), 1.62 (s, 6H). MS (ESI) m/z $(M+H)^+$=412.5.

General Method B

The acid chloride was obtained by using $SOCl_2$ in appropriate solvent like DCM. To the acid chloride solution TEA or pyridine (3 equiv) a and mine (1 equiv) in DCM were added slowly at 0° C.: under $N_2$, and further stirred for 0.5-2 h at RT. Once the reaction was completed, it was quenched with H0, extracted by EA and washed with brine then dried ($Na_2SO_4$), filtered and evaporated to dryness. The resulting residue was purified by trituration/Prep-TLC/chromatography/Prep-HPLC to give the product.

Example 17

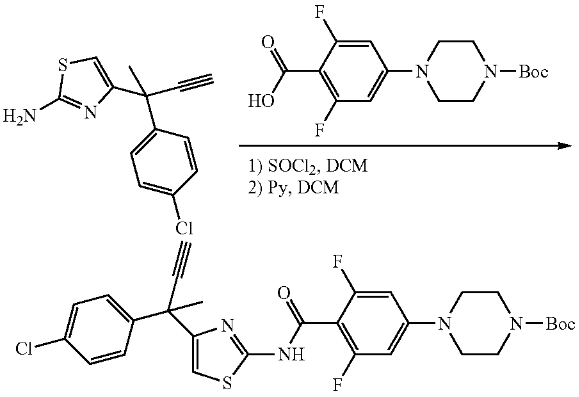

To a solution of 4-(4-tert-butoxycarbonylpiperazin-1-yl)-2,6-difluoro-benzoic acid (150 mg 438.16 umol) in DCM (6 mL) was added $SOCl_2$ (31.8 uL, 438.16 umol). The mixture was stirred at 25° C. for 1 hr. The Py (176.74 uL, 2.19 mmol) was added and the reaction was stirred at 25° C. for 5 min, then 4-[1-(4-chlorophenyl)-1-methyl-prop-2-ynyl]thiazol-2-amine (115.07 mg, 437.94 umol) was added and the mixture was stirred at 25° C. for 16 hr. The reaction mixture was concentrated to give a residue. The residue was purified by flash silica gel chromatography (PE:EA=1:0 to 1:1). The desired compound (152 mg, yield: 54.4%) was obtained as a colorless oil.

MS (ESI) m/z $(M+H)^+$=587.1.

General Method C

Carboxylic acids (1 equiv), HATU (1.2 equiv) or HBTU or PyBOP, and TEA or DIEA (3 equiv.) were dissolved in appropriate organic solvent, like THF or DMF and stirred for 15-30 min at RT. Amine (1-1.5 equiv.) was then added in one portion and the reaction was stirred at RT-100° C. for 4-16 hours. Once the reaction was completed, the resulting suspension was diluted with organic solvent and washed with brine and then dried. After filtration and evaporation, the resulting residue was purified by trituration/Prep-TLC/chromatography/Prep-HPLC to give the product.

Example 18

Preparation of compound methyl N-(4-(2-(4-bromophenyl)but-3-yn-2-yl)thiazol-2-y)-3-tert-butyldiphenylsilyl)oxy)cyclobutane-1-carboxamide

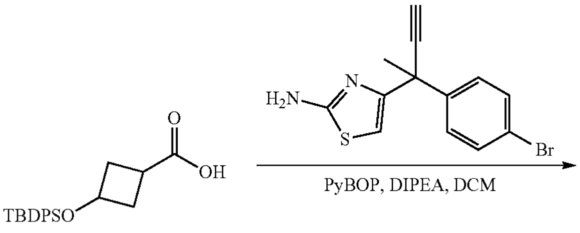

-continued

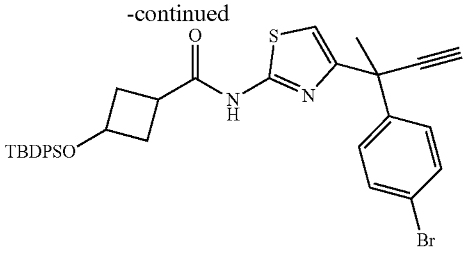

To a solution of 3-[tert-butyl(diphenyl)silyl]oxycyclobutanecarboxylic acid (1.36 g, 3.84 mmol), in DC M (10 mL) was added PyBOP (2.00 g, 3.84 mmol) at 25° C., After stirred for 10 min, methyl 2-(2-aminothiazol-4-yl)-2-(4-bromophenyl)propanoate (523.61 mg, 1.53 mmol) and DIPEA (594.97 mg, 4.60 mmol) was added at 25° C. and the mixture was stirred for 12 h at 25° C. The mixture was diluted with DCM (30 mL), washed with 1-20 (10 mL), brine (10 ml), dried over anhydrous $Na_2SO_4$, filtered and concentrated in vacuum. The obtained residue was purified by silica column (ethyl acetate in petroleum ether=0-25%). The desired compound (1.4 g, crude) was obtained as yellow oil MS (ESI) m/z $(M+H)^+$=643.1

The following examples were synthesized analogous to the procedure of example 16, 17 and 18 using the appropriate intermediates and the corresponding fragments:

TABLE 5

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B001 | 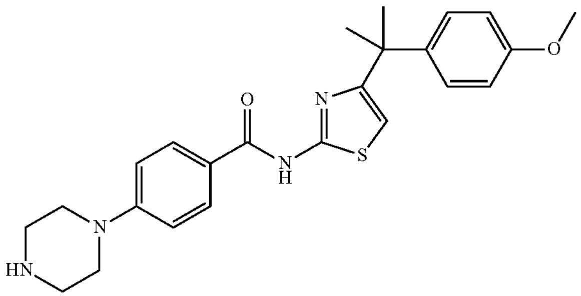 [SMILES: COc1ccc(C(C)(C)c2csc(NC(=O)c3ccc(N4CCNCC4)cc3)n2)cc1] | N-(4-(2-(4-methoxyphenyl)propan-2-yl)thiazol-2-yl)-4-(piperazin-1-yl)benzamide | $^1$H NMR (400 MHz, MeOD) δ 8.75-8.74 (m, 1 H), 8.43-8.40 (m, 1 H), 7.44-7.42 (m, 2 H), 7.33-7.31 (m, 1 H), 7.22-7.20 (m, 2 H), 6.98 (s, 1 H), 4.08-4.06 (m, 4 H), 3.44-3.42 (m, 4 H), 1.72 (s, 6 H). | $[M + H]^+$ = 437 | 123 | 0.75 |
| B002 | 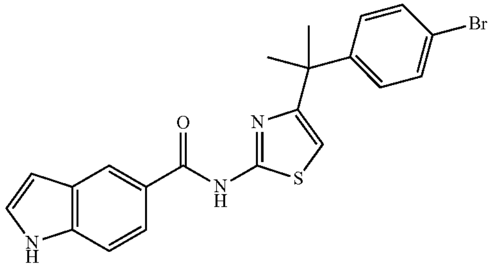 [SMILES: CC(C)(c1ccc(Br)cc1)c1csc(NC(=O)c2ccc3[nH]ccc3c2)n1] | N-(4-(2-(4-bromophenyl)propan-2-yl)thiazol-2-yl)-1H-indole-5-carboxamide | $^1$H NMR (400 MHz, cdcl3) δ 8.42 (s, 1H), 8.25 (s, 1H), 7.75 (dd, J = 8.6, 1.8 Hz, 1H), 7.44 (d, J = 8.6 Hz, 1H), 7.41-7.36 (m, 2H), 7.31-7.27 (m, 1H), 7.15-7.11 (m, 2H), 6.68 (s, 1H), 6.65 (s, 1H), 1.67 (d, J = 6.9 Hz, 6H). | $[M + H]^+$ = 442 | 206 | 2.33 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B003 | 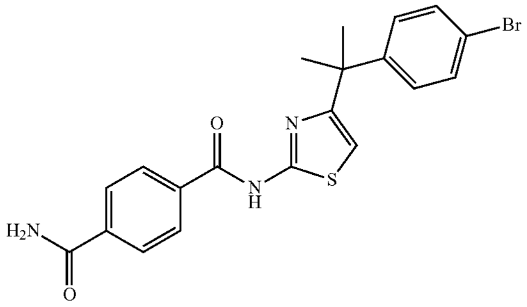 [SMILES: CC(C)(c1ccc(Br)cc1)c1csc(NC(=O)c2ccc(C(N)=O)cc2)n1] | N-(4-(2-(4-bromophenyl)propan-2-yl)thiazol-2-yl)terephthalamide | | $[M + H]^+$ = 444 | 192 | |
| B004 | 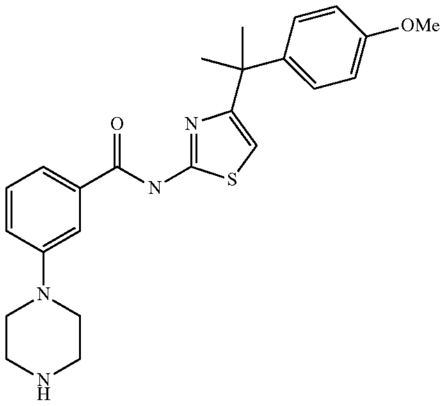 [SMILES: COc1ccc(C(C)(C)c2csc(NC(=O)c3cccc(N4CCNCC4)c3)n2)cc1] | N-(4-(2-(4-methoxyphenyl)propan-2-yl)thiazol-2-yl)-3-(piperazin-1-yl)benzamide | | $[M + H]^+$ = 437 | 211 | 2.84 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B005 | 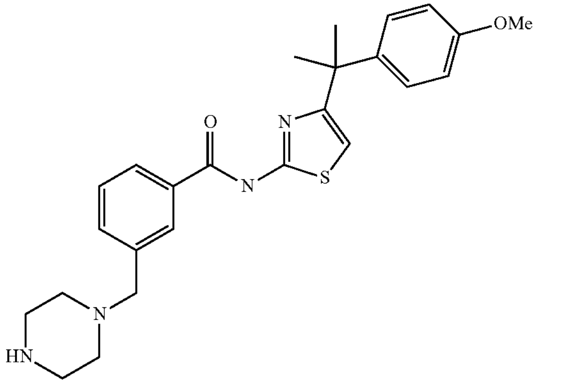 [SMILES: COc1ccc(C(C)(C)c2csc(NC(=O)c3cccc(CN4CCNCC4)c3)n2)cc1] | N-(4-(2-(4-methoxyphenyl)propan-2-yl)thiazol-2-yl)-3-(piperazin-1-ylmethyl)benzamide | | $[M+H]^+$ = 451 | 215 | 1.61 |
| B006 | 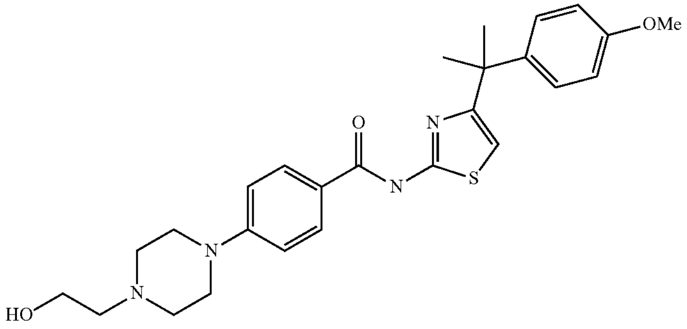 [SMILES: COc1ccc(C(C)(C)c2csc(NC(=O)c3ccc(N4CCN(CCO)CC4)cc3)n2)cc1] | 4-(4-(2-hydroxyethyl)piperazin-1-yl)-N-(4-(2-(4-methoxyphenyl)propan-2-yl)thiazol-2-yl)benzamide | | $[M+H]^+$ = 481 | 595 | 2.71 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B007 | 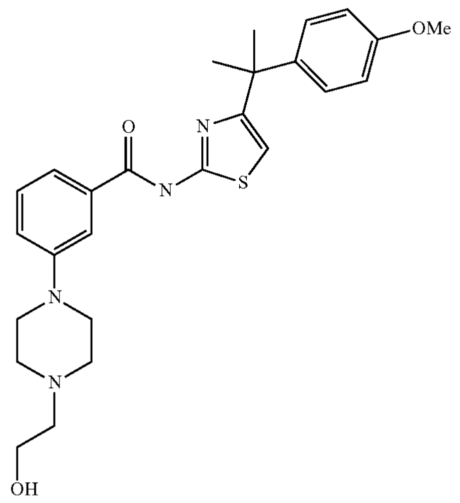 [SMILES: COc1ccc(C(C)(C)c2csc(NC(=O)c3cccc(N4CCN(CCO)CC4)c3)n2)cc1] | 3-(4-(2-hydroxyethyl)piperazin-1-yl)-N-(4-(2-(4-methoxyphenyl)propan-2-yl)thiazol-2-yl)benzamide | | $[M + H]^+$ = 481 | 230 | 1.17 |
| B008 | 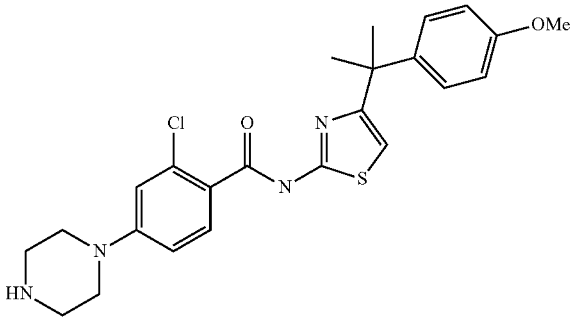 [SMILES: COc1ccc(C(C)(C)c2csc(NC(=O)c3ccc(N4CCNCC4)cc3Cl)n2)cc1] | 2-chloro-N-(4-(2-(4-methoxyphenyl)propan-2-yl)thiazol-2-yl)-4-(piperazin-1-yl)benzamide | | $[M + H]^+$ = | 37 | 0.37 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B009 | 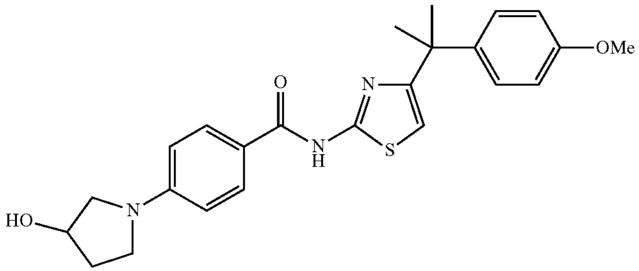 [SMILES: COc1ccc(C(C)(C)c2csc(NC(=O)c3ccc(N4CCC(O)C4)cc3)n2)cc1] | 4-(3-hydroxypyrrolidin-1-yl)-N-(4-(2-(4-methoxyphenyl)propan-2-yl)thiazol-2-yl)benzamide | | $[M + H]^+$ = 438 | 951 | 0.78 |
| B010 | 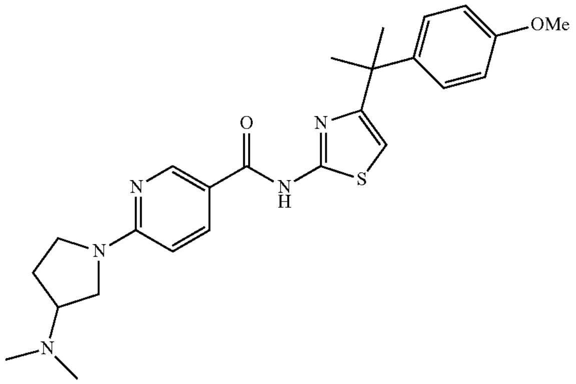 [SMILES: COc1ccc(C(C)(C)c2csc(NC(=O)c3ccc(N4CCC(N(C)C)C4)nc3)n2)cc1] | 6-(3-(dimethylamino)pyrrolidin-1-yl)-N-(4-(2-(4-methoxyphenyl)propan-2-yl)thiazol-2-yl)nicotinamide | | $[M + H]^+$ = 466 | 187 | 0.84 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B011 | 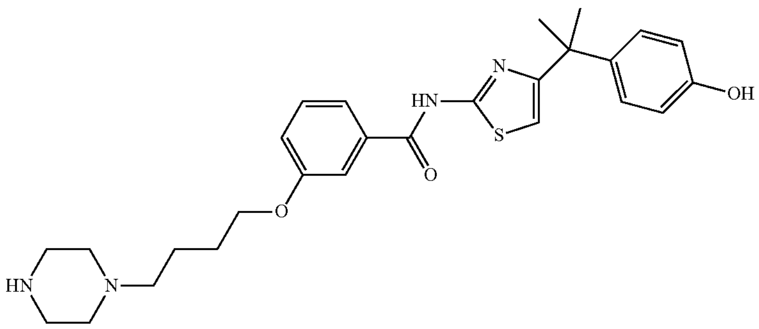 | N-(4-(2-(4-methoxyphenyl)propan-2-yl)thiazol-2-yl)-3-(4-(piperazin-1-yl)butoxy)benzamide | | $[M+H]^+$ = 509 | 230 | 1.64 |
| B012 | 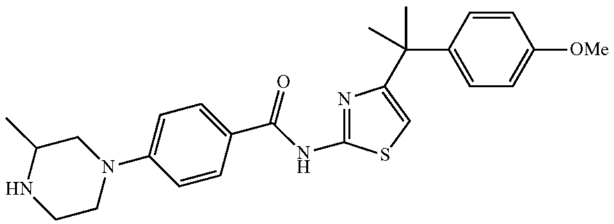 [SMILES: COc1ccc(C(C)(C)c2csc(NC(=O)c3ccc(N4CCNC(C)C4)cc3)n2)cc1] | N-(4-(2-(4-methoxyphenyl)propan-2-yl)thiazol-2-yl)-4-(3-methylpiperazin-1-yl)benzamide | | $[M+H]^+$ = 451 | 118 | 0.76 |
| B013 | 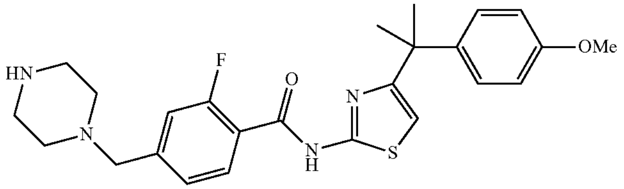 [SMILES: COc1ccc(C(C)(C)c2csc(NC(=O)c3ccc(CN4CCNCC4)cc3F)n2)cc1] | 2-fluoro-N-(4-(2-(4-methoxyphenyl)propan-2-yl)thiazol-2-yl)-4-(piperazin-1-ylmethyl)benzamide | | $[M+H]^+$ = 469 | 111 | 1.02 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B014 | 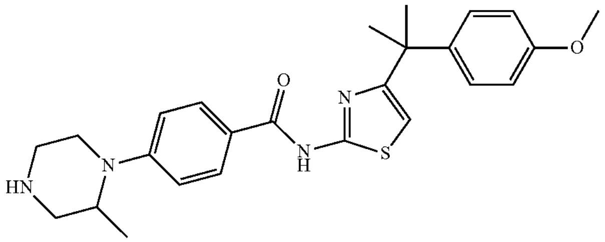 [SMILES: COc1ccc(C(C)(C)c2csc(NC(=O)c3ccc(N4CCNCC4C)cc3)n2)cc1] | tert-butyl 4-(4-((4-(2-(4-methoxyphenyl)propan-2-yl)thiazol-2-yl)carbamoyl)phenyl)-3-methylpiperazine-1-carboxylate | | $[M + H]^+$ = 451 | 300 | 1.17 |
| B015 | 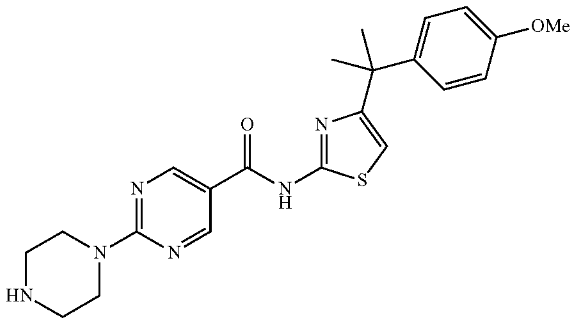 [SMILES: COc1ccc(C(C)(C)c2csc(NC(=O)c3cnc(N4CCNCC4)nc3)n2)cc1] | N-(4-(2-(4-methoxyphenyl)propan-2-yl)thiazol-2-yl)-2-(piperazin-1-yl)pyrimidine-5-carboxamide | | $[M + H]^+$ = 439 | 161 | 4.67 |
| B016 | 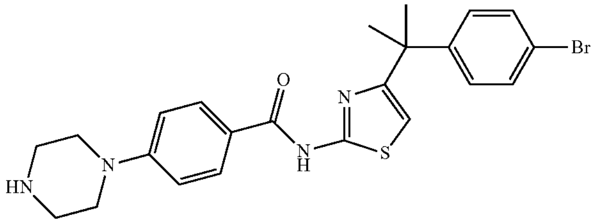 [SMILES: CC(C)(c1ccc(Br)cc1)c1csc(NC(=O)c2ccc(N3CCNCC3)cc2)n1] | N-(4-(2-(4-bromophenyl)propan-2-yl)thiazol-2-yl)-4-(piperazin-1-yl)benzamide | | $[M + H]^+$ = 485 | 60 | |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B017 | 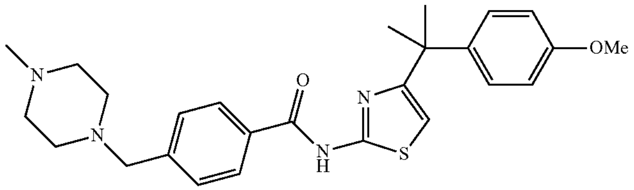 [SMILES: COc1ccc(C(C)(C)c2csc(NC(=O)c3ccc(CN4CCN(C)CC4)cc3)n2)cc1] | N-(4-(2-(4-methoxyphenyl)propan-2-yl)thiazol-2-yl)-4-((4-methylpiperazin-1-yl)methyl)benzamide | | $[M+H]^+$ = 465 | 148 | 3.76 |
| B018 | 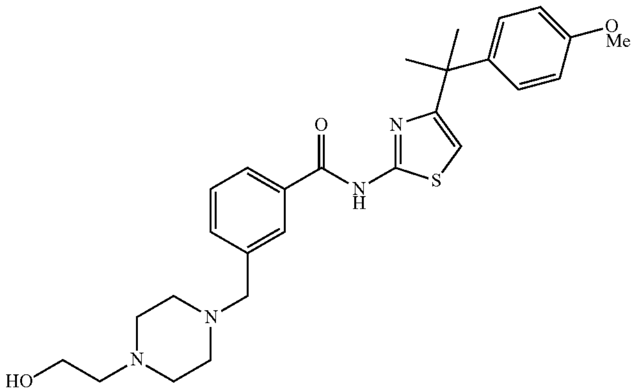 [SMILES: COc1ccc(C(C)(C)c2csc(NC(=O)c3cccc(CN4CCN(CCO)CC4)c3)n2)cc1] | 3-((4-(2-hydroxyethyl)piperazin-1-yl)methyl)-N-(4-(2-(4-methoxyphenyl)propan-2-yl)thiazol-2-yl)benzamide | | $[M+H]^+$ = 495 | 187 | 1.64 |
| B019 | 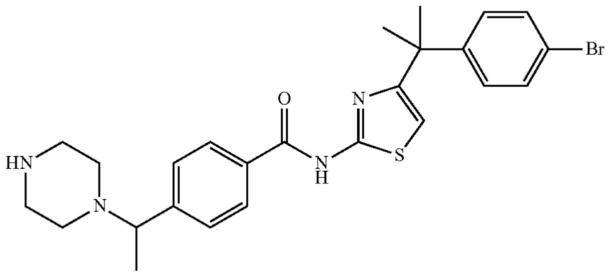 [SMILES: CC(c1ccc(C(=O)Nc2nc(C(C)(C)c3ccc(Br)cc3)cs2)cc1)N1CCNCC1] | N-(4-(2-(4-bromophenyl)propan-2-yl)thiazol-2-yl)-4-(1-(piperazin-1-yl)ethyl)benzamide | | $[M+H]^+$ = 513 | 98 | 1.27 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B020 | 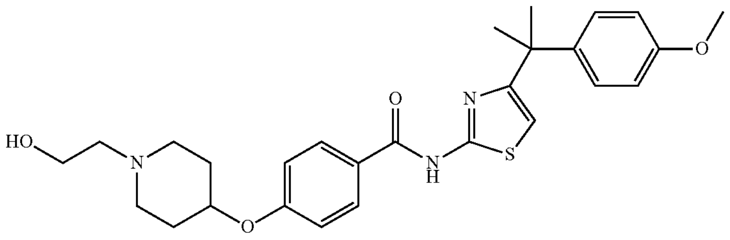 [SMILES: COc1ccc(C(C)(C)c2csc(NC(=O)c3ccc(OC4CCN(CCO)CC4)cc3)n2)cc1] | 4-((1-(2-hydroxyethyl)piperidin-4-yl)oxy)-N-(4-(2-(4-methoxyphenyl)propan-2-yl)thiazol-2-yl)benzamide | | $[M + H]^+$ = 496 | 170 | |
| B021 | 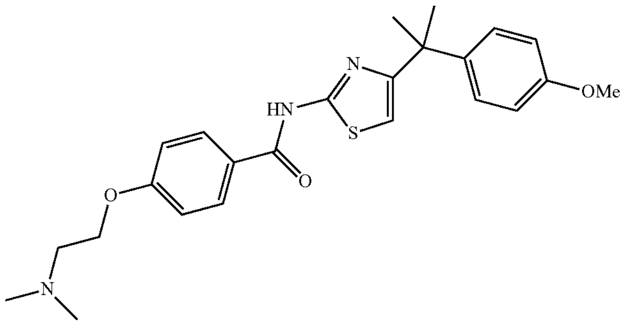 [SMILES: COc1ccc(C(C)(C)c2csc(NC(=O)c3ccc(OCCN(C)C)cc3)n2)cc1] | 4-(2-(dimethylamino)ethoxy)-N-(4-(2-(4-methoxyphenyl)propan-2-yl)thiazol-2-yl)benzamide | | $[M + H]^+$ = 440 | 83 | 1.48 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B022 | 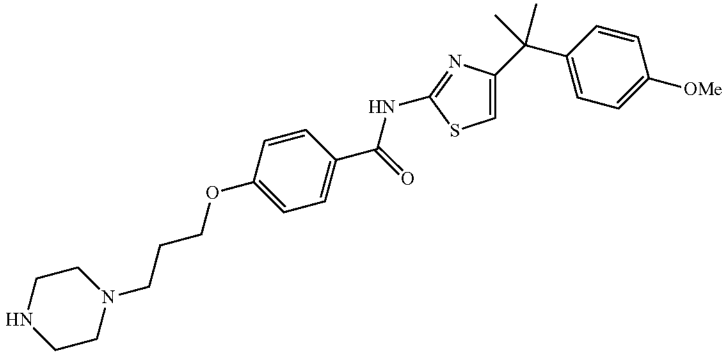 [SMILES: COc1ccc(C(C)(C)c2csc(NC(=O)c3ccc(OCCCN4CCNCC4)cc3)n2)cc1] | N-(4-(2-(4-methoxyphenyl)propan-2-yl)thiazol-2-yl)-4-(3-(piperazin-1-yl)propoxy)benzamide | | $[M + H]^+$ = 495 | 294 | 0.55 |
| B023 | 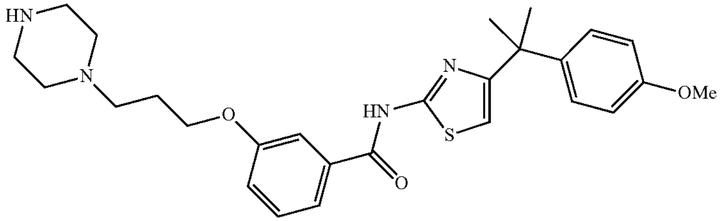 [SMILES: COc1ccc(C(C)(C)c2csc(NC(=O)c3cccc(OCCCN4CCNCC4)c3)n2)cc1] | N-(4-(2-(4-methoxyphenyl)propan-2-yl)thiazol-2-yl)-3-(3-(piperazin-1-yl)propoxy)benzamide | | $[M + H]^+$ = 495 | 150 | 6.15 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B024 | 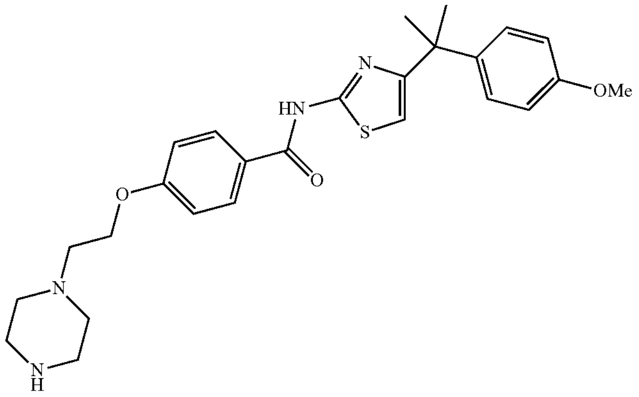 [SMILES: COc1ccc(C(C)(C)c2csc(NC(=O)c3ccc(OCCN4CCNCC4)cc3)n2)cc1] | N-(4-(2-(4-methoxyphenyl)propan-2-yl)thiazol-2-yl)-4-(2-(piperazin-1-yl)ethoxy)benzamide | | $[M + H]^+$ = 481 | 116 | 4.29 |
| B025 | 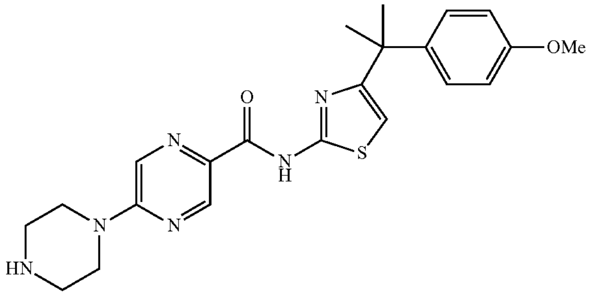 [SMILES: COc1ccc(C(C)(C)c2csc(NC(=O)c3cnc(N4CCNCC4)cn3)n2)cc1] | N-(4-(2-(4-methoxyphenyl)propan-2-yl)thiazol-2-yl)-5-(piperazin-1-yl)pyrazine-2-carboxamide | | $[M + H]^+$ = 439 | 298 | 3.59 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B026 | 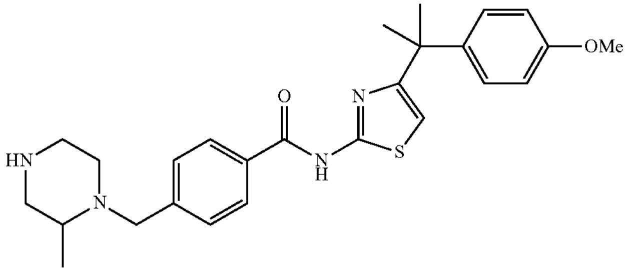 [SMILES: COc1ccc(C(C)(C)c2csc(NC(=O)c3ccc(CN4CCNCC4C)cc3)n2)cc1] | N-(4-(2-(4-methoxyphenyl)propan-2-yl)thiazol-2-yl)-4-((2-methylpiperazin-1-yl)methyl)benzamide | | $[M+H]^+$ = 465 | 127 | 0.61 |
| B027 | 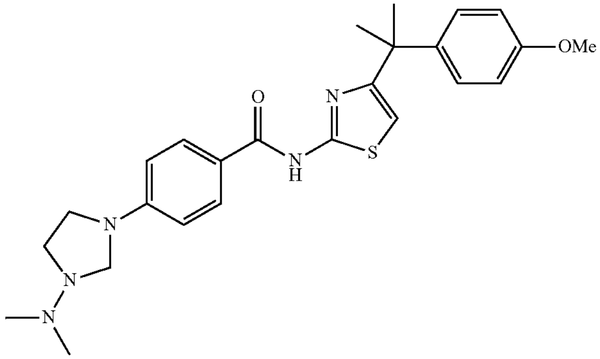 [SMILES: COc1ccc(C(C)(C)c2csc(NC(=O)c3ccc(N4CCN(N(C)C)C4)cc3)n2)cc1] | 4-(3-(dimethylamino)pyrrolidin-1-yl)-N-(4-(2-(4-methoxyphenyl)propan-2-yl)thiazol-2-yl)benzamide | | $[M+H]^+$ = 465 | 219 | 3.38 |
| B028 | 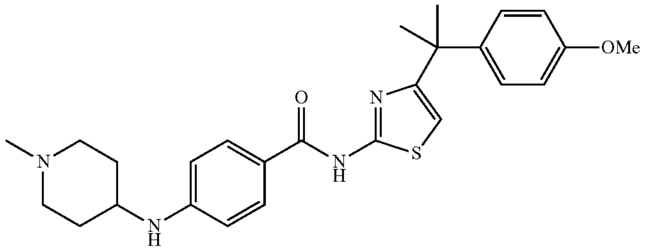 [SMILES: COc1ccc(C(C)(C)c2csc(NC(=O)c3ccc(NC4CCN(C)CC4)cc3)n2)cc1] | N-(4-(2-(4-methoxyphenyl)propan-2-yl)thiazol-2-yl)-4-((1-methylpiperidin-4-yl)amino)benzamide | | $[M+H]^+$ = 465 | 271 | 2.36 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B029 | 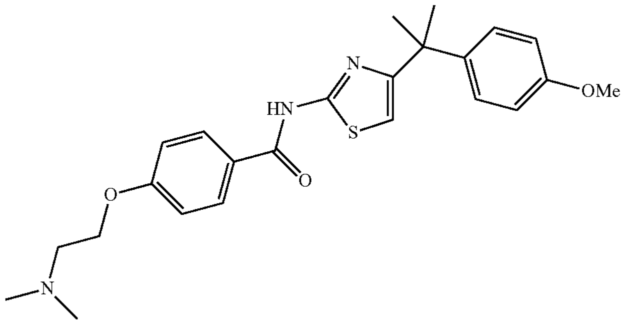 [SMILES: COc1ccc(C(C)(C)c2csc(NC(=O)c3ccc(OCCN(C)C)cc3)n2)cc1] | 4-(2-(dimethylamino)ethoxy)-N-(4-(2-(4-methoxyphenyl)propan-2-yl)thiazol-2-yl)benzamide | | $[M + H]^+$ = 440 | 83 | 1.48 |
| B030 | 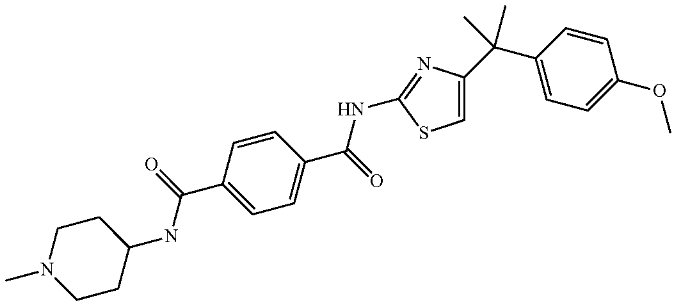 | N1-(4-(2-(4-methoxyphenyl)propan-2-yl)thiazol-2-yl)-N4-(1-methylpiperidin-4-yl)terephthalamide | | $[M + H]^+$ = 493 | 155 | 1.98 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B031 | 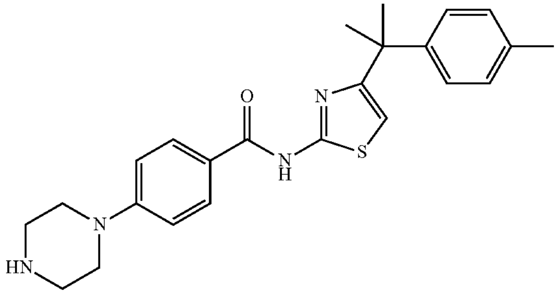 [SMILES: Cc1ccc(C(C)(C)c2csc(NC(=O)c3ccc(N4CCNCC4)cc3)n2)cc1] | 4-(piperazin-1-yl)-N-(4-(2-(p-tolyl)propan-2-yl)thiazol-2-yl)benzamide | | $[M + H]^+$ = 421 | 37 | 0.51 |
| B032 | 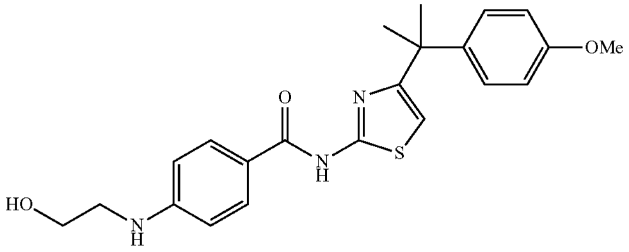 [SMILES: COc1ccc(C(C)(C)c2csc(NC(=O)c3ccc(NCCO)cc3)n2)cc1] | 4-((2-hydroxyethyl)amino)-N-(4-(2-(4-methoxyphenyl)propan-2-yl)thiazol-2-yl)benzamide | | $[M + H]^+$ = 412 | 280 | 3.81 |
| B033 | 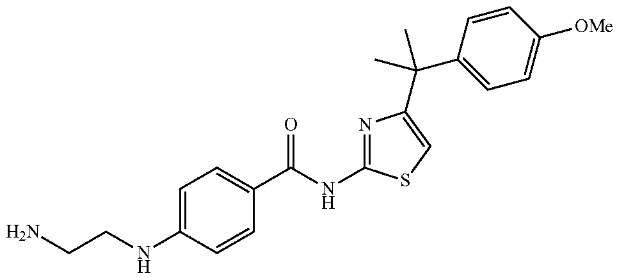 [SMILES: COc1ccc(C(C)(C)c2csc(NC(=O)c3ccc(NCCN)cc3)n2)cc1] | 4-((2-aminoethyl)amino)-N-(4-(2-(4-methoxyphenyl)propan-2-yl)thiazol-2-yl)benzamide | | $[M + H]^+$ = 411 | 247 | 6.45 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B034 | 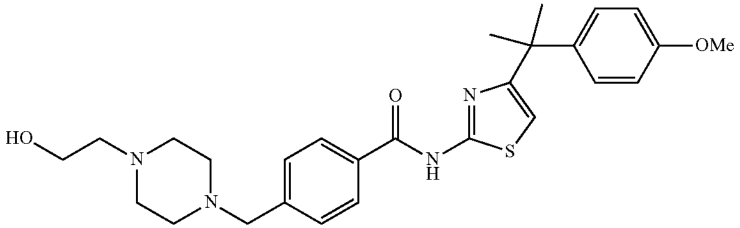 [SMILES: COc1ccc(C(C)(C)c2csc(NC(=O)c3ccc(CN4CCN(CCO)CC4)cc3)n2)cc1] | 4-((4-(2-hydroxyethyl)piperazin-1-yl)methyl)-N-(4-(2-(4-methoxyphenyl)propan-2-yl)thiazol-2-yl)benzamide | | $[M + H]^+$ = 495 | 44 | 0.95 |
| B035 | 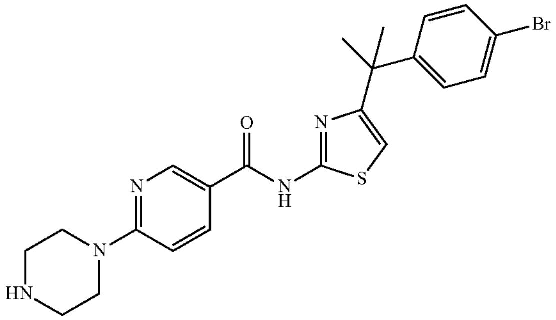 [SMILES: CC(C)(c1ccc(Br)cc1)c1csc(NC(=O)c2ccc(N3CCNCC3)nc2)n1] | N-(4-(2-(4-bromophenyl)propan-2-yl)thiazol-2-yl)-6-(piperazin-1-yl)nicotinamide | $^1$H NMR (400 MHz, DMSO-d6) δ 12.29 (br s, 1 H), 9.42 (br s, 2 H), 8.02-8.00 (m, 2 H), 7.13-7.11 (m, 1 H), 7.05-7.03 (m, 2 H), 6.90 (s, 1 H), 6.83-6.80 (m, 2 H), 3.69 (s, 3 H), 3.58-3.56 (m, 4 H), 3.17-3.16 (m, 4 H), 1.63 (s, 6 H). | $[M + H]^+$ = 486.2 | 75 | 2.76 |
| B036 | 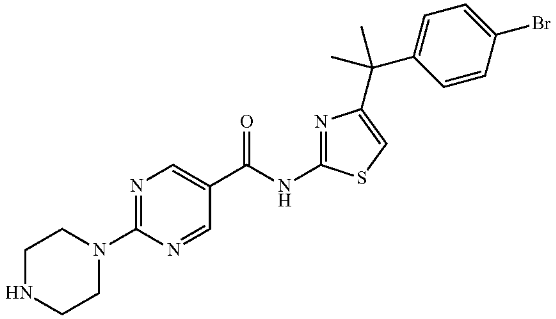 [SMILES: CC(C)(c1ccc(Br)cc1)c1csc(NC(=O)c2cnc(N3CCNCC3)nc2)n1] | N-(4-(2-(4-bromophenyl)propan-2-yl)thiazol-2-yl)-2-(piperazin-1-yl)pyrimidine-5-carboxamide | $^1$H NMR (400 MHz, DMSO-$d_6$) δ 12.51 (br s, 1H), 9.28 (br s, 2H), 9.00 (s, 2H), 7.49-7.41 (m, 2H), 7.19-7.12 (m, 2H). 7.04 (s, 1H), 4.13-3.99 (m, 4H), 3.21-3.15 (m, 4H), 1.64 (s, 6H). | $[M + H]^+$ = 487.1 | 110 | 4.79 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B037 | 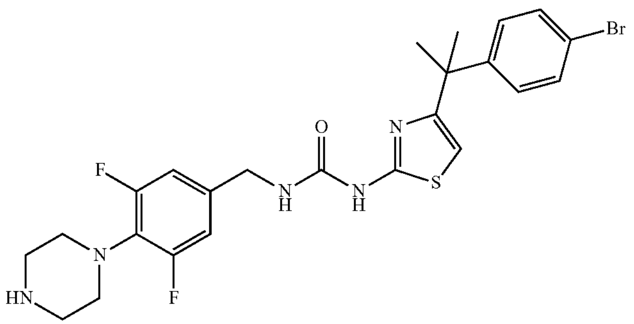 [SMILES: CC(C)(c1ccc(Br)cc1)c1csc(NC(=O)NCc2cc(F)c(N3CCNCC3)c(F)c2)n1] | 1-(4-(2-(4-bromophenyl)propan-2-yl)thiazol-2-yl)-3-(3,5-difluoro-4-(piperazin-1-yl)benzyl)urea | $^1$H NMR (400 MHz, MeOD) δ 7.54-7.46 (m, 2H), 7.21 (d, J = 8.8 Hz, 2H), 7.12 (s, 1H), 6.97 (d, J = 9.8 Hz, 2H), 4.39 (s, 2H), 3.43-3.37 (m, 4H), 3.36-3.32 (m, 4H), 1.71 (s, 6H). | $[M + Na]^+$ = 574.1 | 23 | 1.68 |
| B038 | 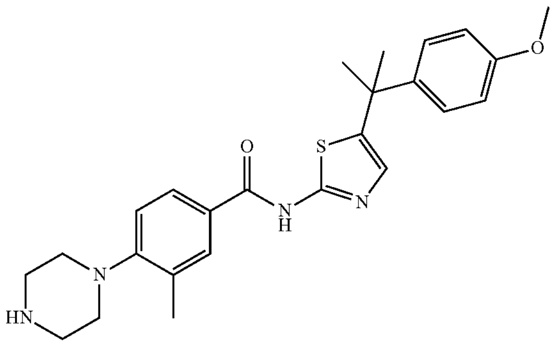 | 3-fluoro-N-(5-(2-(4-methoxyphenyl)propan-2-yl)thiazol-2-yl)-4-(piperazin-1-yl)benzamide | $^1$H NMR (400 MHz, MeOD) δ 7.86 (br d, J = 8.56 Hz, 1 H), 7.78 (dd, J = 13.57, 1.83 Hz, 1 H), 7.25-7.17 (m, 3 H), 7.07 (s, 1 H), 6.87 (d, J = 8.80 Hz, 2 H), 3.76 (s, 3 H), 3.49 (br d, J = 5.14 Hz, 4 H), 3.41 (br d, J = 5.14 Hz, 4 H), 1.73 (s, 6 H). | $[M + H]^+$ = 455.2 | 216 | 4.65 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B039 | 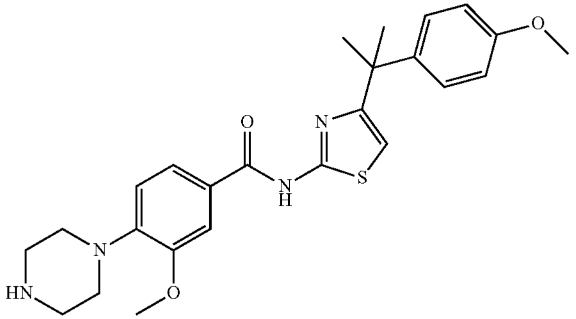 [SMILES: COc1ccc(C(C)(C)c2csc(NC(=O)c3ccc(N4CCNCC4)c(OC)c3)n2)cc1] | 3-methoxy-N-(4-(2-(4-methoxyphenyl)propan-2-yl)thiazol-2-yl)-4-(piperazin-1-yl)benzamide | $^1$H NMR (400 MHz, DMSO-d6) δ 7.65 (s, 2H), 7.12 (br d, J = 8.8 Hz, 2H), 6.93-6.87 (m, 2H), 6.82 (d, J = 8.8 Hz, 2H), 3.85 (s, 3H), 3.70 (s, 3H), 2.98 (br s, 4H), 2.82 (br s, 4H), 1.63 (s, 6H). | $[M + H]^+$ = 467.1 | 123 | 2.97 |
| B040 | 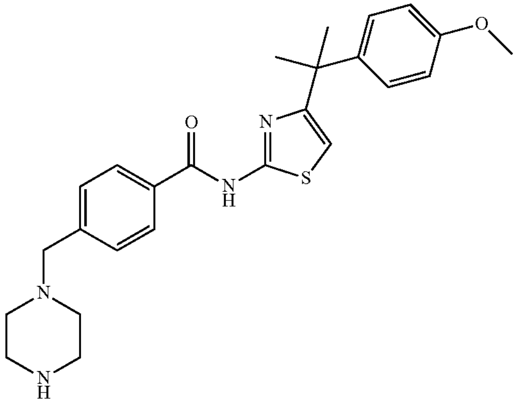 [SMILES: COc1ccc(C(C)(C)c2csc(NC(=O)c3ccc(CN4CCNCC4)cc3)n2)cc1] | N-(4-(2-(4-methoxyphenyl)propan-2-yl)thiazol-2-yl)-4-(piperazin-1-ylmethyl)benzamide | $^1$H NMR (400MHz, DMSO-d6) δ = 12.67 (br s, 1H), 9.61 (br s, 1H), 8.59 (br d, J = 7.9 Hz, 1H), 8.13 (d, J = 8.2 Hz, 2H), 7.78 (br d, J = 8.2 Hz, 2H), 7.13 (d, J = 8.6 Hz, 2H), 6.98 (s, 1H), 6.82 (d, J = 8.6 Hz, 2H), 4.59-4.34 (m, 2H), 3.95 (br s, 8H), 3.70 (s, 3H), 3.49-3.43 (m, 2H), 1.64 (s, 6H) | $[M + H]^+$ = 451.2 | 93 | 0.71 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B041 | 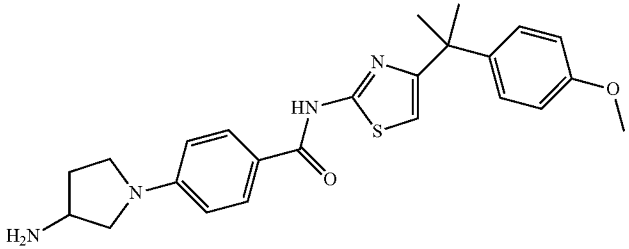 [SMILES: COc1ccc(C(C)(C)c2csc(NC(=O)c3ccc(N4CCC(N)C4)cc3)n2)cc1] | 4-(3-aminopyrrolidin-1-yl)-N-(4-(2-(4-methoxyphenyl)propan-2-yl)thiazol-2-yl)benzamide | $^1$H NMR (400 MHz, DMSO-$d_6$) δ 11.79 (br s, 1H), 8.26 (br s, 3H), 8.01 (d, J = 9.0 Hz, 2H), 7.20-7.13 (m, 2H), 6.85-6.80 (m, 2H), 6.79 (s, 1H), 6.62 (d, J = 8.8 Hz, 2H), 4.05-3.90 (m, 1H), 3.73 (s, 3H), 3.62-3.54 (m, 2H), 3.48-3.38 (m, 2H), 2.42-2.35 (m, 1H), 2.20-2.13 (m, 1H), 1.66 (s, 6H). | $[M + H]^+$ = 437.1 | 80 | 3.96 |
| B042 | 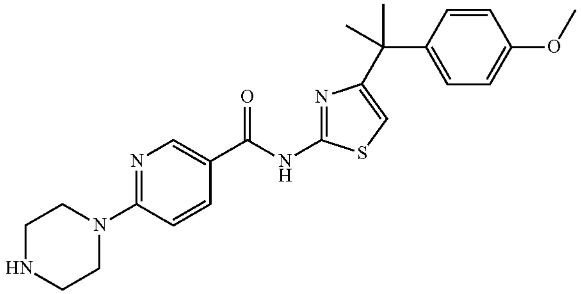 [SMILES: COc1ccc(C(C)(C)c2csc(NC(=O)c3ccc(N4CCNCC4)nc3)n2)cc1] | N-(4-(2-(4-methoxyphenyl)propan-2-yl)thiazol-2-yl)-6-(piperazin-1-yl)nicotinamide | $^1$H NMR (400 MHz, MeOD) δ 8.78 (d, J = 1.71 Hz, 1 H), 8.43 (br d, J = 7.82 Hz, 1 H), 7.34 (br d, J = 9.29 Hz, 1 H), 7.22 (d, J = 8.80 Hz, 2 H), 7.06 (s, 1 H), 6.87 (d, J = 8.80 Hz, 2 H), 4.09 (br s, 4 H), 3.76 (s, 3 H), 3.43 (br s, 4 H), 1.73 (s, 6 H). | $[M + H]^+$ = 438.2 | 86 | 0.663 |
| B043 | 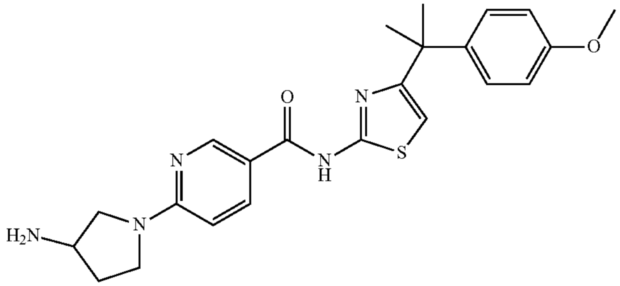 [SMILES: COc1ccc(C(C)(C)c2csc(NC(=O)c3ccc(N4CCC(N)C4)nc3)n2)cc1] | 6-(3-aminopyrrolidin-1-yl)-N-(4-(2-(4-methoxyphenyl)propan-2-yl)thiazol-2-yl)nicotinamide | $^1$H NMR (400 MHz, DMSO-$d_6$) δ 12.66 (br s, 1H), 8.75 (s, 1H), 8.63 (br s, 3H), 8.40 (d, J = 10.3 Hz, 1H), 7.16-7.06 (m, 3H), 6.96 (s, 1H), 6.82 (d, J = 8.8 Hz, 2H), 4.08-3.98 (m, 1H), 3.92-3.80 (m, 3H), 3.70 (s, 4H), 2.41-2.19 (m, 2H), 1.63 (s, 6H) | $[M + H]^+$ = 438.1 | 140 | 1.49 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B044 | 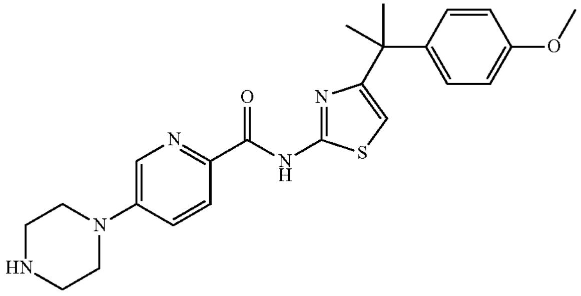 [SMILES: COc1ccc(C(C)(C)c2csc(NC(=O)c3ccc(N4CCNCC4)cn3)n2)cc1] | N-(4-(2-(4-methoxyphenyl)propan-2-yl)thiazol-2-yl)-5-(piperazin-1-yl)picolinamide | $^1$H NMR (400 MHz, DMSO-$d_6$) δ 11.64 (br s, 1H), 9.39 (br s, 2H), 8.44-8.37 (m, 1H), 8.03 (d, J = 8.8 Hz, 1H), 7.56 (d, J = 8.6 Hz, 1H), 7.16 (d, J = 8.8 Hz, 2H), 6.94 (s, 1H), 6.83 (d, J = 8.8 Hz, 2H), 3.70 (s, 3H), 3.69-3.63 (m, 4H), 3.28-3.16 (m, 4H), 1.63 (s, 6H). | $[M + H]^+$ = 438.1 | 213 | 1.86 |
| B045 | 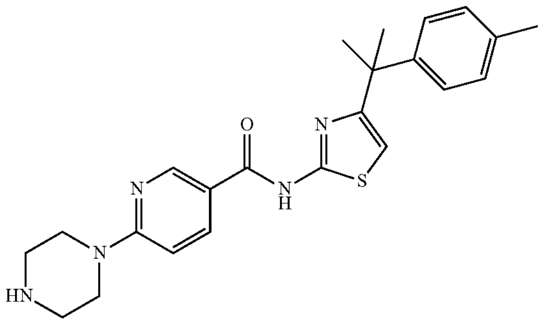 [SMILES: Cc1ccc(C(C)(C)c2csc(NC(=O)c3ccc(N4CCNCC4)nc3)n2)cc1] | 6-(piperazin-1-yl)-N-(4-(2-(p-tolyl)propan-2-yl)thiazol-2-yl)nicotinamide | $^1$H NMR (400 MHz, DMSO-d6) δ 12.37 (br s, 1 H), 9.28 (br s, 2 H), 8.83 (d, J = 1.54 Hz, 1 H), 8.23 (br d, J = 9.26 Hz, 1 H), 7.11-7.04 (m, 4 H), 6.99 (d, J = 9.04 Hz, 1 H), 6.94 (s, 1 H), 3.89 (br s, 4 H), 3.16 (br s, 4 H), 2.23 (s, 3 H), 1.63 (s, 6 H). | $[M + H]^+$ = 422.2 | 30 | 0.23 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B046 | 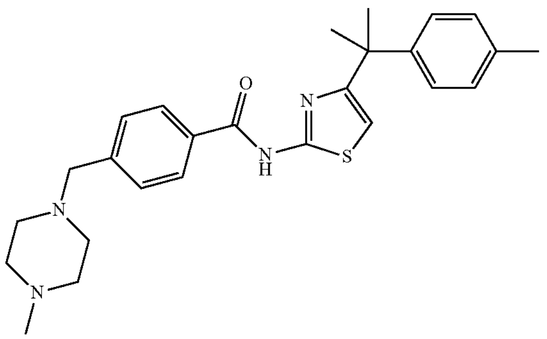 [SMILES: Cc1ccc(C(C)(C)c2csc(NC(=O)c3ccc(CN4CCN(C)CC4)cc3)n2)cc1] | 4-((4-methylpiperazin-1-yl)methyl)-N-(4-(2-(p-tolyl)propan-2-yl)thiazol-2-yl)benzamide | $^1$H NMR (400 MHz MeOD) δ 8.12 (d, J = 8.07 Hz, 2 H), 7.83 (d, J = 8.31 Hz, 2 H), 7.20-7.16 (m, 2 H), 7.14-7.10 (m, 2 H), 7.08 (s, 1 H), 4.57 (s, 2 H), 3.64 (br s, 8 H), 3.01 (s, 3 H), 2.29 (s, 3 H), 1.73 (s, 6 H). | $[M + H]^+$ = 449.3 | 28 | 0.21 |
| B047 | 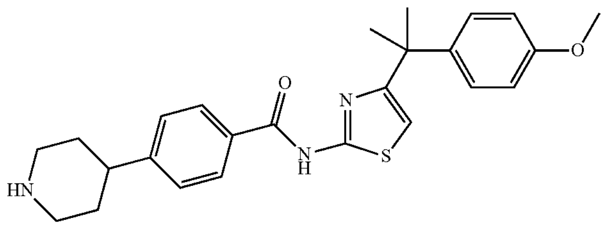 [SMILES: COc1ccc(C(C)(C)c2csc(NC(=O)c3ccc(C4CCNCC4)cc3)n2)cc1] | N-(4-(2-(4-methoxyphenyl)propan-2-yl)thiazol-2-yl)-4-(piperidin-4-yl)benzamide hydrochloride | $^1$H NMR (400 MHz, MeOD) δ 8.08-7.96 (m, 2 H), 7.48 (br d, J = 6.61 Hz, 2 H), 7.26-7.16 (m, 2 H), 7.13-7.03 (m, 1 H), 6.86 (br d, J = 6.84 Hz, 2 H), 3.75 (s, 3 H), 3.56-3.45 (m, 2 H), 3.23-3.09 (m, 2 H), 3.03 (br t, J = 12.13 Hz, 1 H), 2.15-2.03 (m, 2 H), 1.94 (q, J = 13.38 Hz, 2 H), 1.72 (s, 6 H). | $[M + H]^+$ = 436.2 | 128 | 0.54 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B048 | 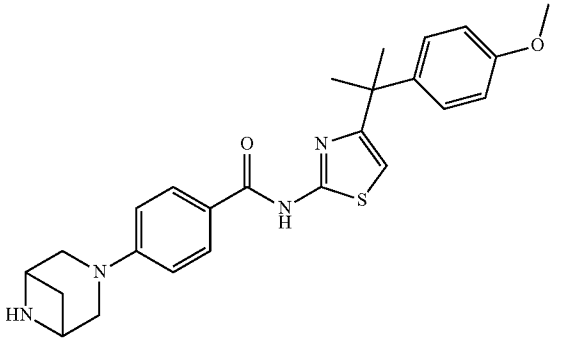 [SMILES: COc1ccc(C(C)(C)c2csc(NC(=O)c3ccc(N4CC5CC(C4)N5)cc3)n2)cc1] | 4-(3,6-diazabicyclo[3.1.1]heptan-3-yl)-N-(4-(2-(4-methoxyphenyl)propan-2-yl)thiazol-2-yl)benzamide | $^1$H NMR (400 MHz, DMSO-d6) δ 12.18 (br s, 1H), 9.99 (br s, 1H), 8.39 (br s, 1H), 8.04 (d, J = 8.8 Hz, 2H), 7.15-7.07 (m, 2H), 6.87 (s, 1H), 6.80 (dd, J = 1.9, 8.9 Hz, 4H), 4.46 (br s, 2H), 3.89-3.72 (m, 4H), 3,68 (s, 3H), 2.95-2.82 (m, 1H), 1.83 (br dd, J = 5.8, 10.0 Hz, 1H), 1.61 (s, 6H) | $[M + H]^+$ = 450 | 73 | 0.77 |
| B049 | 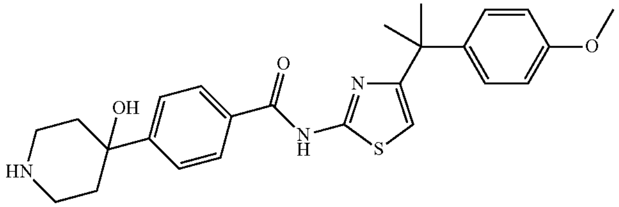 [SMILES: COc1ccc(C(C)(C)c2csc(NC(=O)c3ccc(C4(O)CCNCC4)cc3)n2)cc1] | 4-(4-hydroxypiperidin-4-yl)-N-(4-(2-(4-methoxyphenyl)propan-2-yl)thiazol-2-yl)benzamide hydrochloride | $^1$H NMR (400 MHz, MeOD) δ 8.06 (br d, J = 8.38 Hz, 2 H), 7.73 (d, J = 8.60 Hz, 2 H), 7.23 (d, J = 8.82 Hz, 2 H), 7.15-7.05 (m, 1 H), 6.88 (d, J = 8.82 Hz, 2 H), 3.76 (s, 3 H), 3.51-3.42 (m, 2 H), 3.40-3.33 (m, 2 H), 2.36-2.23 (m, 2 H), 1.93 (br d, J = 13.89 Hz, 2 H), 1.74 (s, 6 H). | $[M + H]^+$ = 452.2 | 459 | 0.37 |
| B050 | 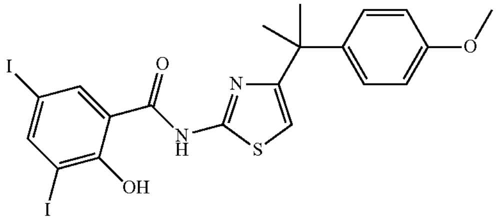 [SMILES: COc1ccc(C(C)(C)c2csc(NC(=O)c3cc(I)cc(I)c3O)n2)cc1] | 2-hydroxy-3,5-diiodo-N-(4-(2-(4-methoxyphenyl)propan-2-yl)thiazol-2-yl)benzamide | $^1$H NMR (400 MHz, CDCl3) δ ppm 8.28 (br s, 1 H) 8.13-8.18 (m, 1 H) 7.21 (d, J = 8.80 Hz, 2 H) 6.90 (d, J = 8.80 Hz, 2 H) 6.66 (s, 1 H) 3.82 (s, 3 H) 1.74 (s, 6 H) | $[M + H]^+$ = 620.9 | 77 | 0.71 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B051 | 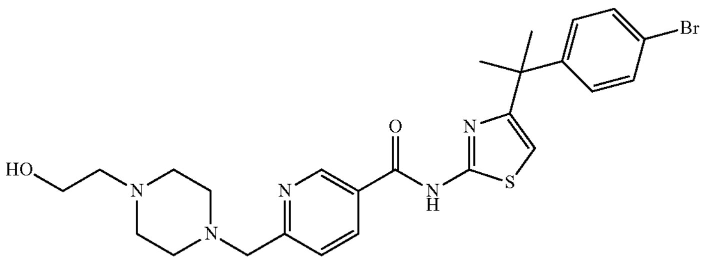 [SMILES: CC(C)(c1ccc(Br)cc1)c1csc(NC(=O)c2ccc(CN3CCN(CCO)CC3)nc2)n1] | N-(4-(2-(4-bromophenyl)propan-2-yl)thiazol-2-yl)-6-((4-(2-hydroxyethyl)piperazin-1-yl)methyl)nicotinamide | $^1$H NMR (400 MHz, MeOD) δ 9.05 (d, J = 1.76 Hz, 1 H), 9.08-9.00 (m, 1 H), 8.33 (dd, J = 8.16, 2.43 Hz, 1 H), 7.65 (d, J = 8.16 Hz, 1 H), 7.39 (d, J = 8.82 Hz, 2 H), 7.19 (d, J = 8.60 Hz, 2 H), 6.88 (s, 1 H), 3.73 (s, 2 H), 3.67 (t, J = 6.06 Hz, 2 H), 2.49-2.67 (m, 10 H), 1.69 (s, 6 H). | $[M + H]^+$ = 546.2 | 61 | 0.54 |
| B052 | 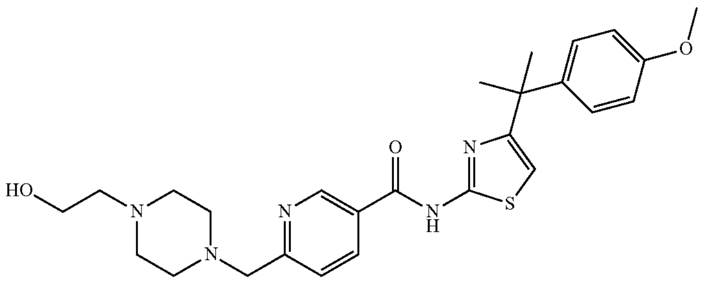 [SMILES: COc1ccc(C(C)(C)c2csc(NC(=O)c3ccc(CN4CCN(CCO)CC4)nc3)n2)cc1] | 6-((4-(2-hydroxyethyl)piperazin-1-yl)methyl)-N-(4-(2-(4-methoxyphenyl)propan-2-yl)thiazol-2-yl)nicotinamide | $^1$H NMR (400 MHz, $CD_3Cl$) δ 11.35 (br s, 1H), 8.69-8.56 (m, 1H), 8.16 (d, J = 8.1 Hz, 1H), 7.72-7.62 (m, 1H), 7.30-7.25 (m, 2H), 7.23-7.18 (m, 2H), 6.88 (d, J = 8.8 Hz, 2H), 6.61 (s, 1H), 3.79 (s, 3H), 1.80 (s, 6H). | $[M + H]^+$ = 496.2 | 111 | 1.73 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B053 | 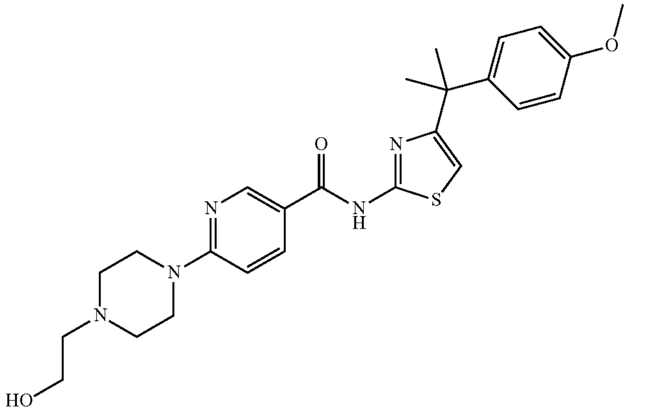 [SMILES: COc1ccc(C(C)(C)c2csc(NC(=O)c3ccc(N4CCN(CCO)CC4)nc3)n2)cc1] | 6-(4-(2-hydroxyethyl)piperazin-1-yl)-N-(4-(2-(4-methoxyphenyl)propan-2-yl)thiazol-2-yl)nicotinamide | $^1$H NMR (400 MHz, MeOD) δ 8.71 (d, J = 2.45 Hz, 1 H), 8.04 (dd, J = 9.17, 2.57 Hz, 1 H), 7.17 (d, J = 8.80 Hz, 2 H), 6.85-6.78 (m, 3 H), 6.74 (s, 1 H), 3.74 (s, 3 H), 3.73-3.69 (m, 6 H), 2.63-2.59 (m, 4 H), 2.57 (t, J = 5.87 Hz, 2 H), 1.67 (s, 6 H). | $[M + H]^+$ = 482.2 | 104 | 1.97 |
| B054 | 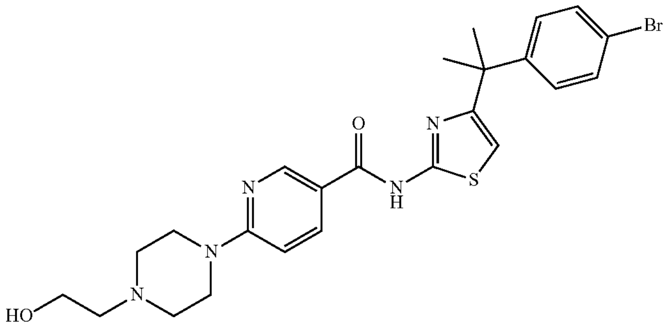 [SMILES: CC(C)(c1ccc(Br)cc1)c1csc(NC(=O)c2ccc(N3CCN(CCO)CC3)nc2)n1] | N-(4-(2-(4-bromophenyl)propan-2-yl)thiazol-2-yl)-6-(4-(2-hydroxyethyl)piperazin-1-yl)nicotinamide | $^1$H NMR (400 MHz, DMSO-$d_6$) δ 12.31-12.23 (m, 1H), 8.79 (br s, 1H), 8.21-8.05 (m. 2H), 7.45 (br d, J = 8.4 Hz, 2H), 7.16 (br d, J = 7.9 Hz, 2H), 6.98 (br s, 1H), 6.89-6.83 (m, 1H), 4.54-4.38 (m, 2H), 3.62 (br s, 5H), 3.57-3.47 (m, 3H), 2.44-2.39 (m, 2H), 1.63 (br s, 6H) | $[M + H]^+$ = 532.1 | 269 | 1.02 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B055 | 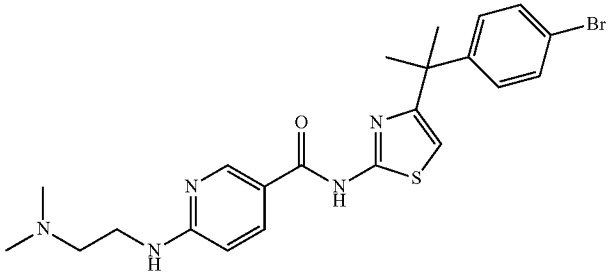 [SMILES: CN(C)CCNc1ccc(C(=O)Nc2nc(C(C)(C)c3ccc(Br)cc3)cs2)cn1] | N-(4-(2-(4-bromophenyl)propan-2-yl)thiazol-2-yl)-6-((2-(dimethylamino)ethyl)amino) nicotinamide | $^1$H NMR (400 MHz, DMSO-$d_6$) δ 12.66 (br s, 1H), 8.75 (s, 1H), 8.63 (br s, 3H), 8.40 (d, J = 10.3 Hz, 1H), 7.16-7.06 (m, 3H), 6.96 (s, 1H), 6.82 (d, J = 8.8 Hz, 2H), 4.08-3.98 (m, 1H), 3.92-3.80 (m, 3H), 3.70 (s, 4H), 2.41-2.19 (m, 2H), 1.63 (s, 6H) | $[M + H]^+$ = 490.2 | 125 | 3.06 |
| B056 | 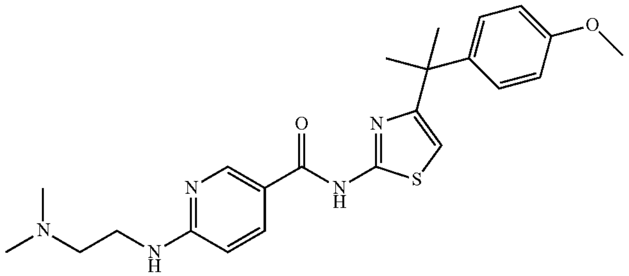 | 6-((2-(dimethylamino)ethyl)amino)-N-(4-(2-(4-methoxyphenyl)propan-2-yl)thiazol-2-yl)nicotinamide | $^1$H NMR (400 MHz, $CD_3Cl$) δ 11.35 (br s, 1H), 8.69-8.56 (m, 1H), 8,16 (d, J = 8.1 Hz, IH), 7.72-7.62 (m, 1H), 7.30-7.25 (m, 2H), 7.23-7.18 (m, 2H), 6.88 (d, J = 8.8 Hz, 2H), 6.61 (s, 1H), 3.79 (s, 3H), 1.80 (s, 6H) | $[M + H]^+$ = 440.2 | 120 | 0.70 |
| B057 | 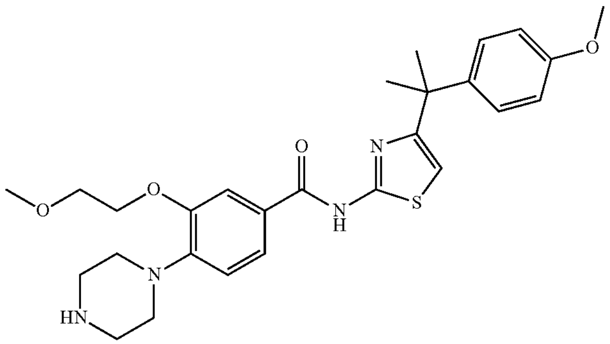 | 3-(2-methoxyethoxy)-N-(4-(2-(4-methoxyphenyl)propan-2-yl)thiazol-2-yl)-4-(piperazin-1-yl)benzamide hydrochloride | $^1$H NMR (400 MHz, DMSO-d6) δ 12.43 (br s, 1 H), 9.42 (br s, 2 H), 7.79-7.52 (m, 2 H), 7.12 (br d, J = 8.56 Hz, 2 H), 7.00 (br d, J = 8.31 Hz, 1 H), 6.92 (s, 1 H), 6.82 (br d, J = 8.56 Hz, 2 H), 4.20 (br s, 1 H), 3.74-3.68 (m, 5 H), 3.33 (s, 7 H), 3.19 (br s, 4 H), 1.63 (s, 6 H). | $[M + H]^+$ = 511.2 | 103 | 0.91 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B058 | 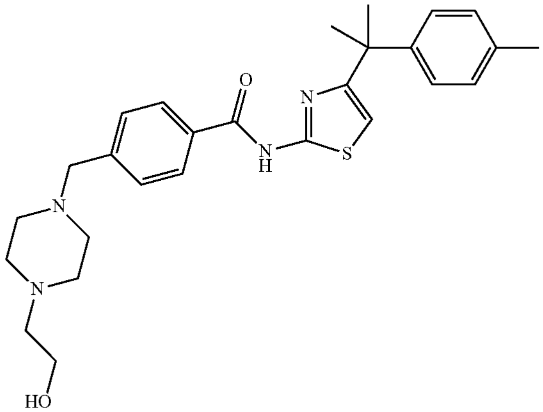 [SMILES: Cc1ccc(C(C)(C)c2csc(NC(=O)c3ccc(CN4CCN(CCO)CC4)cc3)n2)cc1] | 4-((4-(2-hydroxyethyl)piperazin-1-yl)methyl)-N-(4-(2-(p-tolyl)propan-2-yl)thiazol-2-yl)benzamide | $^1$H NMR (400 MHz, DMSO-$d_6$) δ 8.14-8.12 (m, 2H), 7.85-7.83 (m, 2H), 7.20-7.18 (m, 2H), 7.14-7.12 (m, 2H), 7.08 (s, 1H), 4.59 (s, 2H), 3.85-3.55 (m, 8H), 3.50-3.43 (m, 2H), 2.30 (s, 3H), 1.74 (s, 6H). | $[M + H]^+$ = 479.6 | 68 | 0.61 |
| B059 | 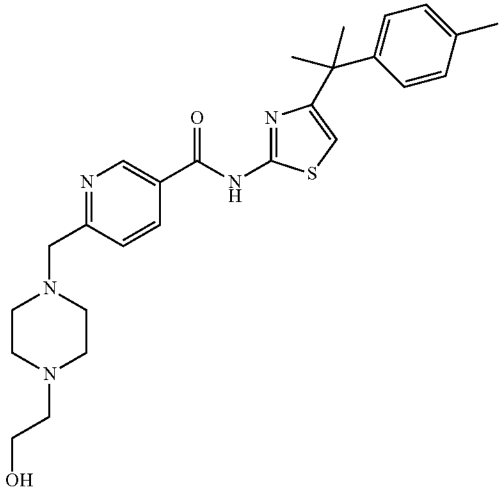 [SMILES: Cc1ccc(C(C)(C)c2csc(NC(=O)c3ccc(CN4CCN(CCO)CC4)nc3)n2)cc1] | 6-((4-(2-hydroxyethyl)piperazin-1-yl)methyl)-N-(4-(2-(p-tolyl)propan-2-yl)thiazol-2-yl)nicotinamide | $^1$H NMR (400 MHz, $CDCl_3$-d) δ 9.09-9.05 (m, 1H), 8.33-8.28 (m, 1H), 7.75 (br d, J = 8.8 Hz, 3H), 7.45-7.41 (m, 1H), 7.13-7.08 (m, 3H), 7.06-7,02 (m, 1H), 6.61-6.57 (m, 1H), 3.83-3.77 (m, 3H), 3.64-3.55 (m, 1H), 2.45-2.38 (m, 8H), 2.26-2.18 (m, 1H), 1.63-1.58 (m, 3H), 1.19 (s, 6H). | $[M + H]^+$ = 480.3 | 159 | 1.18 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B060 | 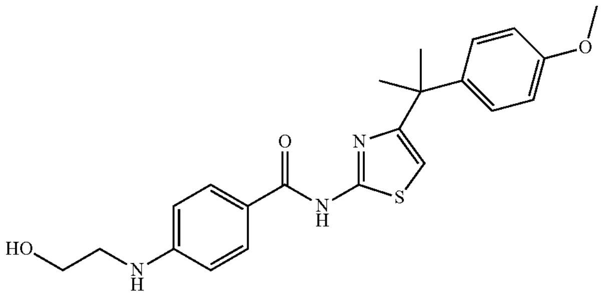 [SMILES: COc1ccc(C(C)(C)c2csc(NC(=O)c3ccc(NCCO)cc3)n2)cc1] | 4-((2-hydroxyethyl)amino)-N-(4-(2-(4-methoxyphenyl)propan-2-yl)thiazol-2-yl)benzamide | $^1$H NMR (400 MHz, DMSO-d6) δ 12.06 (br s, 1H), 7.87 (d, J = 8.8 Hz, 2H), 7.12 (d, J = 8.8 Hz, 2H), 6.86 (s, 1H), 6.82 (d, J = 8.8 Hz, 2H), 6.62 (d, J = 8.8 Hz, 2H), 3.70 (s, 3H), 3.54 (t, J = 5.9 Hz, 2H), 3,16 (t, J = 5.9 Hz, 2H), 1.62 (s, 6H) | $[M + H]^+$ = 412.2 | 280 | 1.23 |
| B061 | 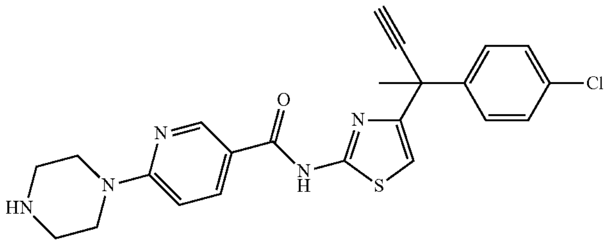 [SMILES: C#CC(C)(c1ccc(Cl)cc1)c1csc(NC(=O)c2ccc(N3CCNCC3)nc2)n1] | N-(4-(2-(4-chlorophenyl)but-3-yn-2-yl)thiazol-2-yl)-6-(piperazin-1-yl)nicotinamide | $^1$H NMR (400 MHz DMSO-d6) δ 12.56 (br s, 1 H), 9.61 (br s, 2 H), 8.83 (d, J = 2.8 Hz, 1 H), 8.28 (dd, J = 9.2, 2.4 Hz, 1 H), 7.45-7.38 (m, 4 H), 7.18 (s, 1 H), 7.09 (d, J = 8.8 Hz, 1 H), 3.99-3.93 (m, 4 H), 3.55 (s, 1 H), 3.18 (br s, 4 H), 1.91 (s, 3 H) | $[M + H]^+$ = 452.1 | 167 | 0.78 |
| B062 | 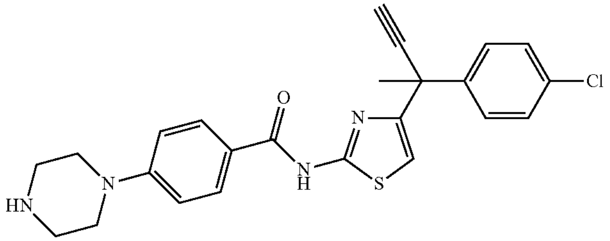 [SMILES: C#CC(C)(c1ccc(Cl)cc1)c1csc(NC(=O)c2ccc(N3CCNCC3)cc2)n1] | N-(4-(2-(4-chlorophenyl)but-3-yn-2-yl)thiazol-2-yl)-4-(piperazin-1-yl)benzamide | $^1$H NMR (400 MHz, DMSO-d6) δ = 12.36 (s, 1H), 9.25 (br s, 2H), 8.01 (d, J = 8.9 Hz, 2H), 7.45-7.37 (m, 4H), 7.14 (s, 1H), 7.04 (d, J = 9.1 Hz, 2H), 3.58-3.55 (m, 4H), 3.18 (br s, 4H), 1.91 (s, 3H) | $[M + H]^+$ = 451.1 | 12 | 1.01 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B063 | 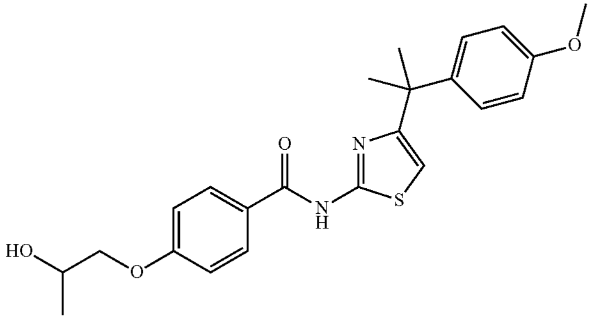 [SMILES: COc1ccc(C(C)(C)c2csc(NC(=O)c3ccc(OCC(C)O)cc3)n2)cc1] | 4-(2-hydroxypropoxy)-N-(4-(2-(4-methoxyphenyl)propan-2-yl)thiazol-2-yl)benzamide | (400 MHz, DMSO-d6) δ 12.36 (br s, 1H), 8.05 (d, J = 9.0 Hz, 2H), 7.12 (d, J = 8.8 Hz, 2H), 7.02 (d, J = 9.0 Hz, 2H), 6.91 (s, 1H), 6.82 (d, J = 8.8 Hz, 2H), 3.99-3.93 (m, 1H), 3.88 (d, J = 4.0 Hz, 2H), 3.70 (s, 3H), 1.63 (s, 6H), 1,14 (d, J = 6.3 Hz, 3H) | $[M + H]^+$ = 427.1 | 245 | 2.10 |
| B064 | 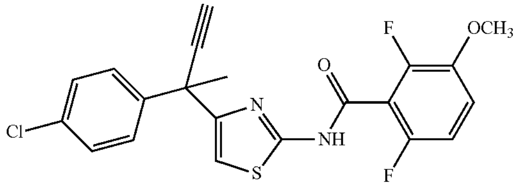 [SMILES: C#CC(C)(c1ccc(Cl)cc1)c1csc(NC(=O)c2c(F)ccc(OC)c2F)n1] | N-(4-(2-(4-chlorophenyl)but-3-yn-2-yl)thiazol-2-yl)-2,6-difluoro-3-methoxybenzamide | | | 54 | 3.37 |
| B065 | 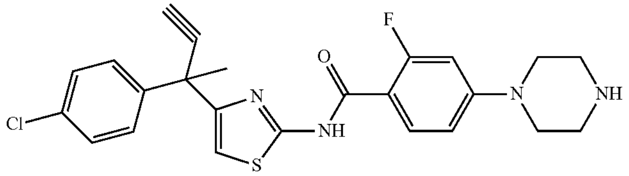 [SMILES: C#CC(C)(c1ccc(Cl)cc1)c1csc(NC(=O)c2ccc(N3CCNCC3)cc2F)n1] | N-(4-(2-(4-chlorophenyl)but-3-yn-2-yl)thiazol-2-yl)-2-fluoro-4-(piperazin-1-yl)benzamide | | $[M + H]^+$ = 469.1 | 34 | |
| B066 | 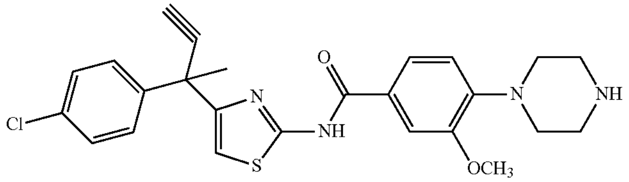 | N-(4-(2-(4-chlorophenyl)but-3-yn-2-yl)thiazol-2-yl)-3-methoxy-4-(piperazin-1-yl)benzamide | $^1$H NMR (400 MHz, DMSO-d6) d: 7.66 (1H, J = 8.8 Hz, d), 7.41-7.35 (5H, m), 7.16 (1H, s), 6.91 (1H, J = 7.2 Hz, d), 3.83 (3H, s), 3.51 (1H, s), 3.01 (4H, s), 2.87 (4H, s), 1.88 (3H, s) | $[M + H]^+$ = 481.1 | 29 | |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B067 | 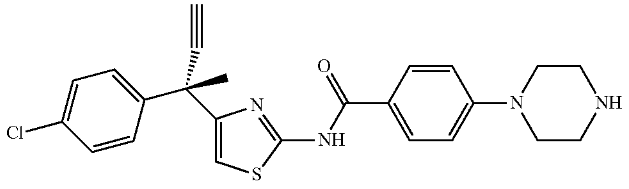 [SMILES: C#C[C@@](C)(c1ccc(Cl)cc1)c1csc(NC(=O)c2ccc(N3CCNCC3)cc2)n1] | N-(4-(2-(4-chlorophenyl)but-3-yn-2-yl)thiazol-2-yl)-4-(piperazin-1-yl)benzamide | $^1$H NMR (400 MHz, DMSO-d6) δ 12.36 (br s, 1 H), 9.31 (br s, 2 H), 8.02 (d, J = 8.78 Hz, 2 H), 7.35-7.47 (m, 4 H), 7.14 (s, 1 H), 7.04 (d, J = 8.78 Hz, 2 H), 3.49-3.65 (m, 5 H), 3.19 (br d, J = 4.77 Hz, 4 H), 1.91 (s, 3 H). | 451.0 | 90 | 1.43 |
| B068 | 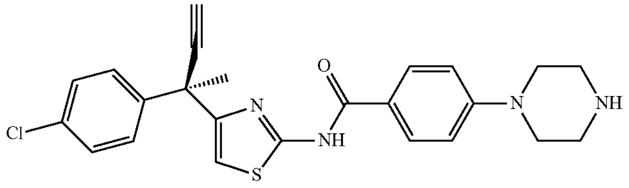 [SMILES: C#C[C@](C)(c1ccc(Cl)cc1)c1csc(NC(=O)c2ccc(N3CCNCC3)cc2)n1] | N-(4-(2-(4-chlorophenyl)but-3-yn-2-yl)thiazol-2-yl)-4-(piperazin-1-yl)benzamide | $^1$H NMR (400 MHz, DMSO-$d_6$) δ 12.36 (s, 1 H), 9.19 (br s, 2 H), 8.02 (d, J = 8.78 Hz, 2 H), 7.36-7.46 (m, 4 H), 7.15 (s, 1 H), 7.04 (d, J = 8.78 Hz, 2 H), 3.53-3.60 (m, 5 H), 3.19 (br s, 4 H), 1.91 (s, 3 H). | 451.0 | 530 | 4.16 |
| B069 | 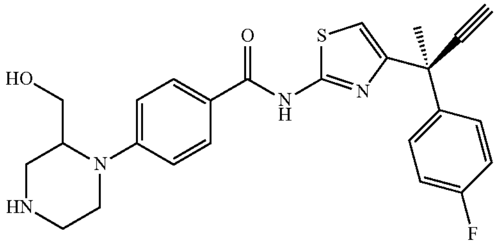 [SMILES: C#C[C@@](C)(c1ccc(F)cc1)c1csc(NC(=O)c2ccc(N3CCNCC3CO)cc2)n1] | N-[4-[1-(4-fluorophenyl)-1-methyl-prop-2-ynyl]thiazol-2-yl]-4-[2-(hydroxymethyl)piperazin-1-yl]benzamide | $^1$H NMR (400 MHz, $CDCl_3$) δ 9.26 (br s, 1H), 7.78 (d, J = 8.9 Hz, 2H), 7.45 (dd, J = 5.2, 8.8 Hz, 2H), 6.99 (t, J = 8.7 Hz, 2H), 6.89-6.85 (m, 3H), 4.04-3.98 (m, 1H), 3.98-3.89 (m, 2H), 3.66-3.54 (m, 1H), 3.53-3.46 (m, 1H), 3.43 (br d, J = 11.7 Hz, 1H), 3.20 (br d, J = 11.3 Hz, 1H), 3.14 (br d, J = 11.9 Hz, 1H), 3.16-3.08 (m, 1H), 2.96 (dt, J = 4.2, 11.7 Hz, 1H), 2.59 (s, 1H), 1.97 (s, 3H), 2.02-1.93 (m, 1H). | 465.0 | 20 | 0.96 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B070 | 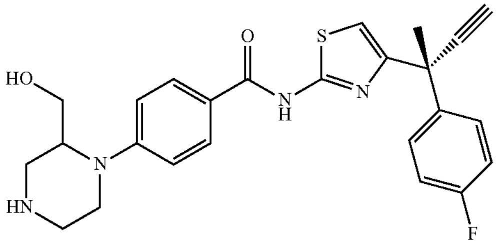 [SMILES: C#C[C@](C)(c1ccc(F)cc1)c1csc(NC(=O)c2ccc(N3CCNCC3CO)cc2)n1] | N-[4-[1-(4-fluorophenyl)-1-methyl-prop-2-ynyl]thiazol-2-yl]-4-[2-(hydroxymethyl)piperazin-1-yl]benzamide | $^1$H NMR (400 MHz, $CDCl_3$) δ 9.23 (br s, 1H), 7.74 (d, J = 8.9 Hz, 2H), 7.43-7.39 (m, 2H), 6.95 (t, J = 8.6 Hz, 2H), 6.86-6.80 (m, 3H), 4.00-3.94 (m, 1H), 3.94-3.85 (m, 2H), 3.56-3.49 (m, 1H), 3.49-3.42 (m, 1H), 3.39 (br d, J = 12.2 Hz, 1H), 3.16 (br d, J = 9.5 Hz, 1H), 3.09 (br d, J = 12.0 Hz, 1H), 2.91 (dt, J = 4.4, 11.7 Hz, 1H), 2.54 (s, 1H), 1.93 (s, 3H). | 465.0 | 169 | 2.07 |
| B071 | 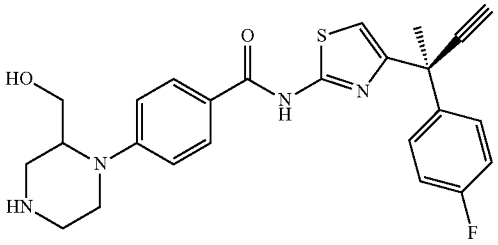 [SMILES: C#C[C@@](C)(c1ccc(F)cc1)c1csc(NC(=O)c2ccc(N3CCNCC3CO)cc2)n1] | N-[4-[1-(4-fluorophenyl)-1-methyl-prop-2-ynyl]thiazol-2-yl]-4-[2-(hydroxymethyl)piperazin-1-yl]benzamide | $^1$H NMR (400 MHz, $CDCl_3$) δ 9.62 (br s, 1H), 7.30 (br s, 2H), 7.07 (br s, 2H), 6.64-6.58 (m, 2H), 6.50-6.34 (m, 1H), 6.50-6.31 (m, 3H), 4.62 (br s, 1H), 3.78 (br s, 1H), 3.64 (br s, 1H), 3.50 (br s, 1H), 3.36 (br s, 1H), 3.23 (br s, 3H), 3.00-2.56 (m, 2H), 2.27 (br s, 1H), 1.70 (br s, 3H). | 465.0 | 60 | 1.30 |
| B072 | 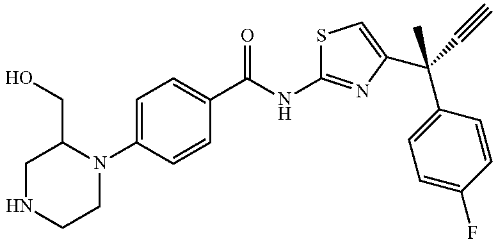 [SMILES: C#C[C@](C)(c1ccc(F)cc1)c1csc(NC(=O)c2ccc(N3CCNCC3CO)cc2)n1] | N-[4-[1-(4-fluorophenyl)-1-methyl-prop-2-ynyl]thiazol-2-yl]-4-[2-(hydroxymethyl)piperazin-1-yl]benzamide | $^1$H NMR (400 MHz, $CDCl_3$) δ 9.26 (br s, 1H), 7.76 (d, J = 8.9 Hz, 2H), 7.45-7.40 (m, 2H), 6.97 (t, J = 8.8 Hz, 2H), 6.90-6.82 (m, 3H), 4.02-3.96 (m, 1H), 3.96-3.85 (m, 2H), 3.57-3.51 (m, 1H), 3.44-3.43 (m, 1H), 3.50-3.43 (m, 1H), 3.40 (br d, J = 11.8 Hz, 1H), 3.17 (br d, J = 11.4 Hz, 1H), 3.10 (br d, J = 11.8 Hz, 1H), 2.93 (dt, J = 4.3, 11.7 Hz, 1H), 2.56 (s, 1H), 1.95 (s, 3H). | 465.0 | 260 | 4.13 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B073 | 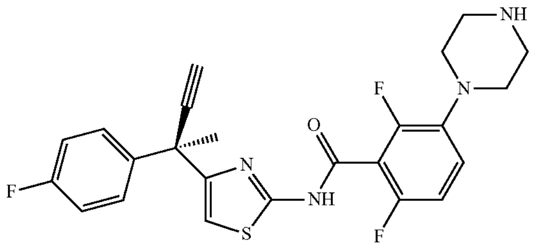 [SMILES: C#C[C@](C)(c1ccc(F)cc1)c1csc(NC(=O)c2c(F)ccc(N3CCNCC3)c2F)n1] | 2,6-difluoro-N-(4-(2-(4-fluorophenyl)but-3-yn-2-yl)thiazol-2-yl)-3-(piperazin-1-yl)benzamide | $^{1}$H NMR (400 MHz, DMSO-$d_6$) δ 13.06 (s, 1 H), 9.12 (br s, 2 H), 7.49-7.43 (m, 2 H), 7.32-7.24 (m, 2 H), 7.16 (t, J = 8.8 Hz, 3 H), 3.55 (s, 1 H) 3.22, (br s, 8 H), 1.92 (s, 3 H) | 471.1 | 851 | 2.39 |
| B074 | 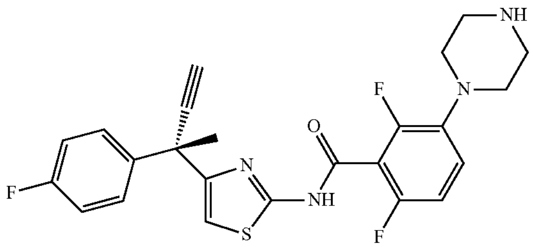 [SMILES: C#C[C@@](C)(c1ccc(F)cc1)c1csc(NC(=O)c2c(F)ccc(N3CCNCC3)c2F)n1] | 2,6-difluoro-N-(4-(2-(4-fluorophenyl)but-3-yn-2-yl)thiazol-2-yl)-3-(piperazin-1-yl)benzamide | $^{1}$H NMR (400 MHz, DMSO-$d_6$) δ 13.07 (s, 1 H), 9.23 (br s, 2 H), 7.49-7.42 (m, 2 H), 7.31-7.24 (m, 2 H), 7.14 (t, J = 8.8 Hz, 3 H), 3.55 (s, 1 H), 3.22 (s, 8 H), 1.92 (s, 3 H) | 471.1 | 96 | 0.36 |
| B075 | 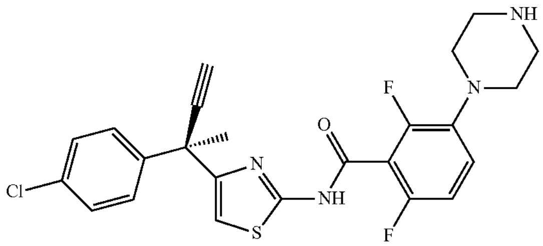 [SMILES: C#C[C@](C)(c1ccc(Cl)cc1)c1csc(NC(=O)c2c(F)ccc(N3CCNCC3)c2F)n1] | N-(4-(2-(4-chlorophenyl)but-3-yn-2-yl)thiazol-2-yl)-2,6-difluoro-3-(piperazin-1-yl)benzamide | $^{1}$H NMR (400 MHz, DMSO-$d_6$) δ 13.05 (s, 1 H), 9.36 (br s, 2 H), 7.48-7.37 (m, 4 H), 7.31-7.23 (m, 2 H), 7.18-7.15 (t, J = 8.8 Hz, 3 H), 3.56 (s, 1 H), 3.22 (s, 8 H), 1.90 (s, 3 H) | 487.1 | 308 | 2.13 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B076 | 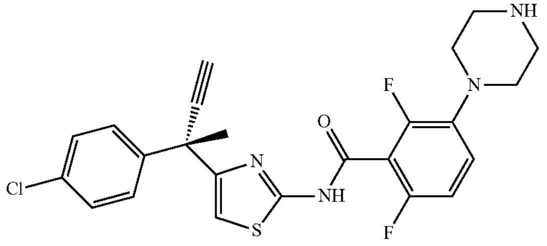 [SMILES: C#C[C@@](C)(c1ccc(Cl)cc1)c1csc(NC(=O)c2c(F)ccc(N3CCNCC3)c2F)n1] | N-(4-(2-(4-chlorophenyl)but-3-yn-2-yl)thiazol-2-yl)-2,6-difluoro-3-(piperazin-1-yl)benzamide | $^1$H NMR (400 MHz, DMSO-$d_6$) δ 13.05 (s, 1 H), 9.33 (br s, 2 H), 7.46-7.37 (m, 4 H), 7.32-7.23 (m, 2 H), 7.12-7.18 (m, 1 H), 3.56 (s, 1 H), 3.22 (s, 8 H), 1.90 (s, 3 H) | 487.1 | 85 | 0.64 |
| B077 | 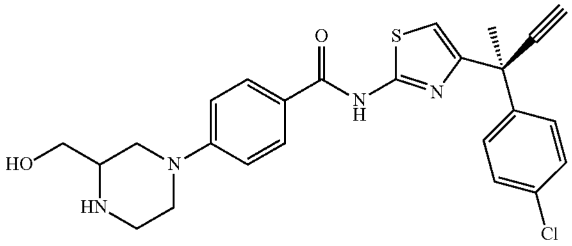 [SMILES: C#C[C@@](C)(c1ccc(F)cc1)c1csc(NC(=O)c2ccc(N3CCNC(CO)C3)cc2)n1] | N-(4-(2-(4-chlorophenyl)but-3-yn-2-yl)thiazol-2-yl)-4-(3-(hydroxymethyl)piperazin-1-yl)benzamide | $^1$H NMR (400 MHz, DMSO-$d_6$) δ 7.97 (d, J = 8.9 Hz, 2H), 7.45-7.37 (m, 4H), 7.12 (s, 1H), 6.94 (d, J = 9.2 Hz, 2H), 4,70 (br s, 1H), 3.85-3.70 (m, 2H), 3.53 (s, 1H), 3.41-3.36 (m, 1H), 3.01-2.95 (m, 1H), 2.76-2.67 (m, 3H), 2.47-2.38 (m, 1H), 1.91 (s, 3H) | 481.1 | 90 | 1.35 |
| B078 | 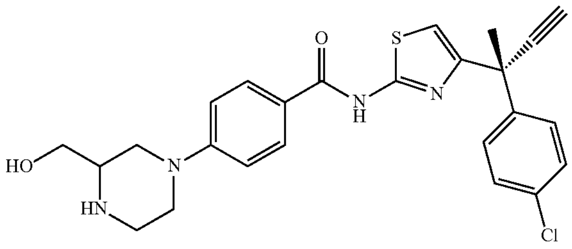 | N-(4-(2-(4-chlorophenyl)but-3-yn-2-yl)thiazol-2-yl)-4-(3-(hydroxymethyl)piperazin-1-yl)benzamide | $^1$H NMR (400 MHz, DMSO-$d_6$) δ 7.97 (d, J = 8.9 Hz, 2H), 7.45-7.37 (m, 4H), 7.11 (s, 1H), 6.93 (d, J = 8.9 Hz, 2H), 4.69 (br s, 1H), 3.79 (d, J = 11,2 Hz, 1H), 3,72 (d, J = 8.2 Hz, 1H), 3.52 (s, 1H), 3.40-3.36 (m, 2H), 3.01-2.95 (m, 1H), 2.76-2.67 (m, 3H), 2.41 (t, J = 11.0 Hz, 1H), 1.91 (s, 3H) | 481.1 | 169 | 2.13 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B079 | 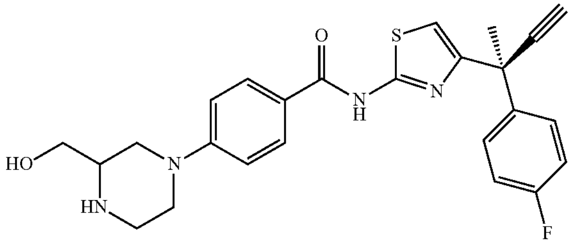 | N-(4-(2-(4-chlorophenyl)but-3-yn-2-yl)thiazol-2-yl)-4-(3-(hydroxymethyl)piperazin-1-yl)benzamide | $^1$H NMR (400 MHz, DMSO-$d_6$) δ 7.97 (d, J = 8.8 Hz, 2H), 7.51-7.40 (m, 2H), 7.15 (t, J = 8.9 Hz, 2H), 7.05-6.88 (m, 3H), 4.70 (br s, 1H), 3.82-3.65 (m, 2H), 3.49 (s, 1H), 3.41-3.37 (m, 2H), 3.04-2.93 (m, 1H), 2.80-2.63 (m, 3H), 2.44-2.32 (m, 1H), 1.91 (s, 3H) $^{19}$F NMR (376 MHz, DMSO-$d_6$) δ −116.67 (s, 1F) | 465.2 | 174 | 2.99 |
| B080 | 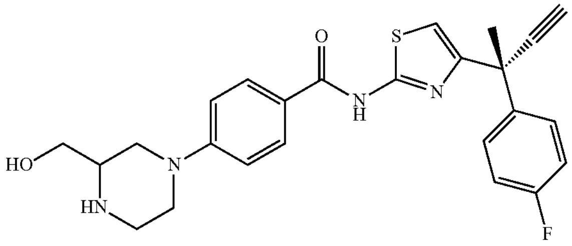 [SMILES: C#C[C@](C)(c1ccc(F)cc1)c1csc(NC(=O)c2ccc(N3CCNC(CO)C3)cc2)n1] | N-(4-(2-(4-chlorophenyl)but-3-yn-2-yl)thiazol-2-yl)-4-(3-(hydroxymethyl)piperazin-1-yl)benzamide | $^1$H NMR (400 MHz, DMSO-$d_6$) δ 7.98 (d, J = 8.8 Hz, 2H), 7.49-7.36 (m, 2H), 7.15 (t, J = 8.8 Hz, 2H), 7.10 (s, 1H), 6.95 (d, J = 9.0 Hz, 2H), 4.83 (br s, 1H), 3.84-3.74 (m, 2H), 3.51 (s, 1H), 3.44-3.41 (m, 2H), 3.05-2.99 (m, 1H), 2.82-2.73 (m, 3H), 2.49-2.48 (m, 1H), 1.91 (s, 3H) $^{19}$F NMR (376 MHz, DMSO-$d_6$) δ −116.51 (s, 1F) | 465.2 | 286 | 3.30 |
| B081 | 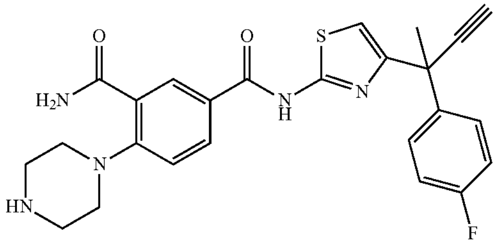 [SMILES: C#CC(C)(c1ccc(F)cc1)c1csc(NC(=O)c2ccc(N3CCNCC3)c(C(N)=O)c2)n1] | N1-(4-(2-(4-fluorophenyl)but-3-yn-2-yl)thiazol-2-yl)-4-(piperazin-1-yl)isophthalamide | $^1$H NMR (400 MHz, DMSO-$d_6$) δ 12.59 (br s, 1H), 9.42 (br s, 2H), 8.22 (d, J = 2.0 Hz, 1H), 8.15-8.07 (m, 1H), 7.88 (s, 1H), 7.61 (s, 1H), 7.50-7.42 (m, 2H), 7.20-7.13 (m, 4H), 3.53 (s, 1H), 3.29 (s, 4H), 3.23 (s, 4H), 1.92 (s, 3H) $^{19}$F NMR (376 MHz, DMSO-$d_6$) δ −116.46 (s, 1F) | 478.2 | 102 | 0.96 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B082 | 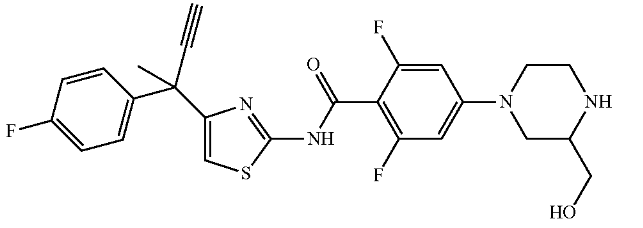 [SMILES: C#CC(C)(c1ccc(F)cc1)c1csc(NC(=O)c2c(F)cc(N3CCNC(CO)C3)cc2F)n1] | 2,6-difluoro-N-(4-(2-(4-fluorophenyl)but-3-yn-2-yl)thiazol-2-yl)-4-(3-(hydroxymethyl)piperazin-1-yl)benzamide | $^1$H NMR (400 MHz, DMSO-$d_6$) δ 12.77 (s, 1H), 9.81-9.64 (m, 1H), 9.61-9.41 (m, 1H), 7.48-7.41 (m, 2H), 7.19-7.17 (m, 1H), 7.15-7.12 (m, 1H), 6.87 (s, 1H), 6.79 (d, J = 12.0 Hz, 2H), 3.98 (t, J = 15.7 Hz, 2H), 3.77-3.63 (m, 2H), 3.54 (s, 1H), 3.30-3.20 (m, 3H), 3.16-2.97 (m, 2H), 1.90 (s, 3H) $^{19}$F NMR (376 MHz, DMSO-$d_6$) δ −111.73-111.77 (m, 2F), −116.39 (s, 1F) | 501.1 | 25 | 0.43 |
| B083 | 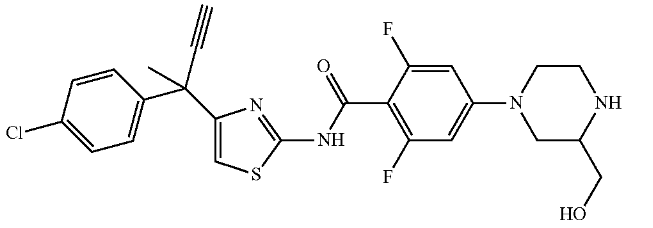 [SMILES: C#CC(C)(c1ccc(Cl)cc1)c1csc(NC(=O)c2c(F)cc(N3CCNC(CO)C3)cc2F)n1] | N-(4-(2-(4-chlorophenyl)but-3-yn-2-yl)thiazol-2-yl)-2,6-difluoro-4-(3-(hydroxymethyl)piperazin-1-yl)benzamide | $^1$H NMR (400 MHz, DMSO-$d_6$) δ 7.52-7.36 (m, 4H), 7.16 (s, 1H), 6.63 (d, J = 12.6 Hz, 2H), 4.68 (t, J = 5.2 Hz, 1H), 3.77-3.63 (m, 2H), 3.54 (s, 1H), 3.00-2.93 (m, 1H), 2.80-2.63 (m, 3H), 2.47-2.29 (m, 3H), 1.90 (s, 3H) $^{19}$F NMR (376 MHz, DMSO-$d_6$) δ −112.15 (s, 2F) | 517.1 | 78 | 1.27 |
| B084 | 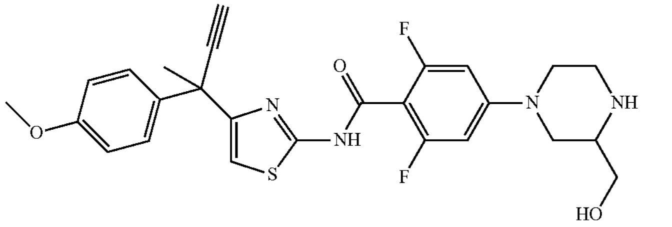 [SMILES: C#CC(C)(c1ccc(OC)cc1)c1csc(NC(=O)c2c(F)cc(N3CCNC(CO)C3)cc2F)n1] | 2,6-difluoro-4-(3-(hydroxymethyl)piperazin-1-yl)-N-(4-(2-(4-methoxyphenyl)but-3-yn-2-yl)thiazol-2-yl)benzamide | $^1$H NMR (400 MHz, DMSO-$d_6$) δ 12.74 (br s, 1H), 9.65-9.47 (m, 1H), 9.41-9.21 (m, J = 10.0 Hz, 1H), 7.34-7.30 (m, 2H), 7.12 (s, 1H), 6.87 (d, J = 8.8 Hz, 2H), 6.79 (d, J = 12.0 Hz, 2H), 3.97 (t, J = 15.1 Hz, 2H), 3.75-3.70 (m, 4H), 3.68-3.62 (m, 1H), 3.46 (s, 1H), 3.32-3.17 (m, 3H), 3.14-2.99 (m, 2H), 1.88 (s, 3H) $^{19}$F NMR (376 MHz, DMSO-$d_6$) δ −111.79 (s, 2F) | 513.2 | 28 | 0.39 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B085 | 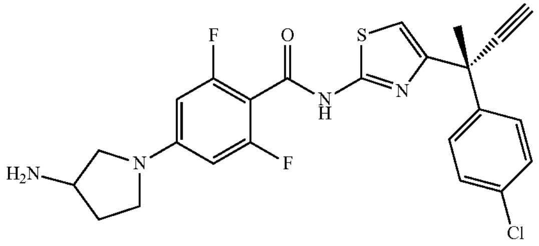 [SMILES: C#C[C@](C)(c1ccc(Cl)cc1)c1csc(NC(=O)c2c(F)cc(N3CCC(N)C3)cc2F)n1] | 4-(3-aminopyrrolidin-1-yl)-N-(4-(2-(4-chlorophenyl)but-3-yn-2-yl)thiazol-2-yl)-2,6-difluorobenzamide | $^{1}$H NMR (400 MHz, DMSO-$d_6$) δ 12.65 (s, 1H), 8.29 (br. s, 3H), 7.46-7.37 (m, 4 H), 7.19 (s, 1H), 6.37-6.29 (m, 2 H), 3.97 (br. s, 1H), 3.62-3.55 (m, 1 H), 3.55 (s, 1H), 3.52-3.47 (m, 1 H), 3.38-3.32 (m, 2 H), 2.37-2.26 (m, 1H), 2.16-2.05 (m, 1H), 1.90 (s, 3H). | 487.4 | 395 | 2.58 |
| B086 | 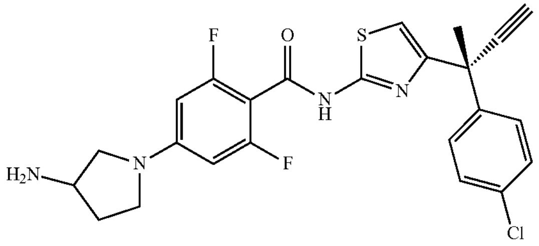 [SMILES: C#C[C@](C)(c1ccc(Cl)cc1)c1csc(NC(=O)c2c(F)cc(N3CCC(N)C3)cc2F)n1] | 4-(3-aminopyrrolidin-1-yl)-N-(4-(2-(4-chlorophenyl)but-3-yn-2-yl)thiazol-2-yl)-2,6-difluorobenzamide | $^{1}$H NMR (400 MHz, DMSO-$d_6$) δ 12.65 (s, 1H), 8.29 (br. s, 3H), 7.46-7.37 (m, 4 H), 7.19 (s, 1H), 6.35-6.31 (m, 2 H), 3.96 (br. s, 1H), 3.62-3.55 (m, 1 H), 3.55 (s, 1H), 3.52-3.47 (m, 1 H), 3.38-3.32 (m, 2 H), 2.37-2.26 (m, 1H), 2.16-2.05 (m, 1H), 1.90 (s. 3H). | 487.1 | 286 | 2.57 |
| B087 | 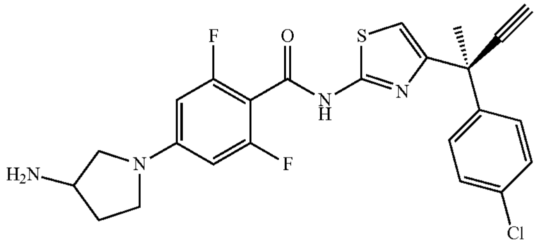 [SMILES: C#C[C@@](C)(c1ccc(Cl)cc1)c1csc(NC(=O)c2c(F)cc(N3CCC(N)C3)cc2F)n1] | 4-(3-aminopyrrolidin-1-yl)-N-(4-(2-(4-chlorophenyl)but-3-yn-2-yl)thiazol-2-yl)-2,6-difluorobenzamide | $^{1}$H NMR (400 MHz, DMSO-$d_6$) δ 12.64 (s, 1H), 8.28 (br. s, 3H), 7.46-7.37 (m, 4 H), 7.19 (s, 1H), 6.35-6.31 (m, 2 H), 3.97 (br. s, 1H), 3.62-3.55 (m, 1 H), 3.55 (s, 1H), 3.52-3.47 (m, 1 H), 3.38-3.32 (m, 2 H), 2.37-2.26 (m, 1H), 2.16-2.05 (m, 1H), 1.90 (s, 3H). | 487.4 | 38 | 1.18 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B088 | 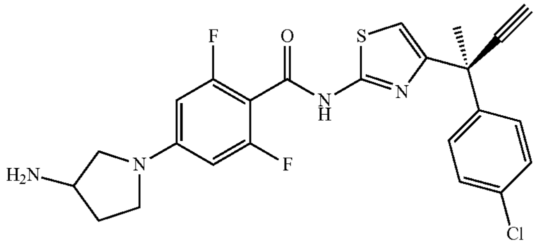 [SMILES: C#C[C@@](C)(c1ccc(Cl)cc1)c1csc(NC(=O)c2c(F)cc(N3CCC(N)C3)cc2F)n1] | 4-(3-aminopyrrolidin-1-yl)-N-(4-(2-(4-chlorophenyl)but-3-yn-2-yl)thiazol-2-yl)-2,6-difluorobenzamide | $^1$H NMR (400 MHz, DMSO-$d_6$) δ 12.65 (s, 1H), 8.26 (br. s, 3H), 7.46-7.37 (m, 4 H), 7.19 (s, 1H), 6.35-6.31 (m, 2 H), 3.96 (br. s, 1H), 3.62-3.55 (m, 1 H), 3.55 (s, 1H), 3.52-3.47 (m, 1 H), 3.38-3.32 (m, 2 H), 2.37-2.26 (m, 1H), 2.16-2.05 (m, 1H), 1.90 (s, 3H). | 487.0 | 42 | 0.92 |
| B089 | 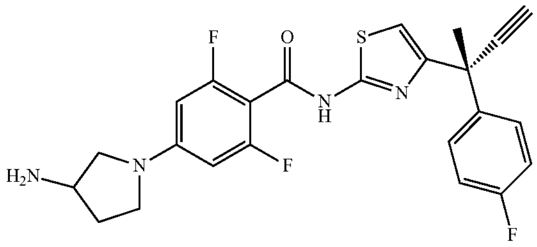 [SMILES: C#C[C@](C)(c1ccc(F)cc1)c1csc(NC(=O)c2c(F)cc(N3CCC(N)C3)cc2F)n1] | 4-(3-aminopyrrolidin-1-yl)-2,6-difluoro-N-(4-(2-(4-fluorophenyl)but-3-yn-2-yl)thiazol-2-yl)benzamide | $^1$H NMR (400 MHz, DMSO-$d_6$) δ 12.66 (s, 1H), 8.28 (br. s, 3H), 7.50-7.40 (m, 2 H), 7.20-7.10 (m, 3H), 6.40-6.30 (m, 2 H), 3.96 (br. s, 1H), 3.61-3.55 (m, 1 H), 3.53 (s, 1H), 3.51-3.45 (m, 1 H), 3.41-3.33 (m, 2 H), 2.35-2.27 (m, 1H), 2.15-2.07 (m, 1H), 1.91 (s. 3H) | [M + Na$^+$] = 493.0 | 681 | 2.77 |
| B090 | 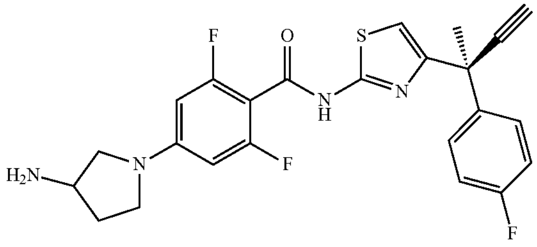 [SMILES: C#C[C@@](C)(c1ccc(F)cc1)c1csc(NC(=O)c2c(F)cc(N3CCC(N)C3)cc2F)n1] | 4-(3-aminopyrrolidin-1-yl)-2,6-difluoro-N-(4-(2-(4-fluorophenyl)but-3-yn-2-yl)thiazol-2-yl)benzamide | $^1$H NMR (400 MHz, DMSO-$d_6$) δ 12.65 (s, 1H), 8.29 (br. s, 3H), 7.50-7.40 (m, 2 H), 7.20-7.10 (m, 3H), 6.40-6.30 (m, 2 H), 3.96 (br. s, 1H), 3.61-3.55 (m, 1 H), 3.54 (s, 1H), 3.51-3.45 (m, 1 H), 3.41-3.33 (m, 2 H), 2.39-2.26 (m, 1H), 2.16-2.07 (m, 1H), 1.91 (s, 3H). | 471.0 | 107 | 1.52 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B091 | 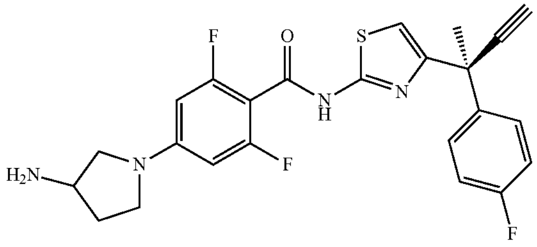 [SMILES: C#C[C@@](C)(c1ccc(F)cc1)c1csc(NC(=O)c2c(F)cc(N3CCC(N)C3)cc2F)n1] | 4-(3-aminopyrrolidin-1-yl)-2,6-difluoro-N-(4-(2-(4-fluorophenyl)but-3-yn-2-yl)thiazol-2-yl)benzamide | $^1$H NMR (400 MHz, DMSO-$d_6$) δ 12.66 (s, 1H), 8.25 (br. s, 3H), 7.50-7.40 (m, 2 H), 7.20-7.10 (m, 3H), 6.40-6.30 (m, 2 H), 3.96 (br. s, 1H), 3.61-3.55 (m, 1 H), 3.53 (s, 1H), 3.51-3.45 (m, 1 H), 3.39-3.31 (m, 2 H), 2.35-2.26 (m, 1H), 2.24-2.05 (m, 1H), 1.91 (s, 3H). | 471.0 | 65 | 1.05 |
| B092 | 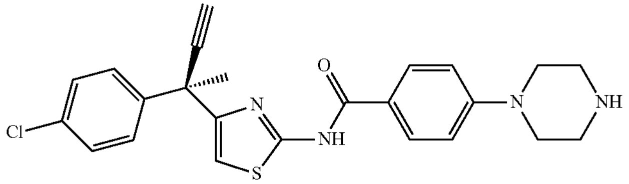 [SMILES: C#C[C@](C)(c1ccc(Cl)cc1)c1csc(NC(=O)c2ccc(N3CCNCC3)cc2)n1] | N-(4-(2-(4-chlorophenyl)but-3-yn-2-yl)thiazol-2-yl)-4-(piperazin-1-yl)benzamide | $^1$H NMR (400 MHz, DMSO-$d_6$) δ 10.57 (br s, 1H), 7.50 (d, J = 8.6 Hz, 2H), 7.36 (d, J = 8.6 Hz, 2H), 6.90 (s, 1H), 6.28 (br s, 1H), 4.75 (t, J = 5.1 Hz, 2H), 3.60 (br. dd, J = 4.8, 8.1 Hz, 1H), 3.50 (s, 1H), 3.42-3.35 (m, 4H), 1.84 (s, 3H). | 424.1 | 219 | 3.44 |
| B093 | 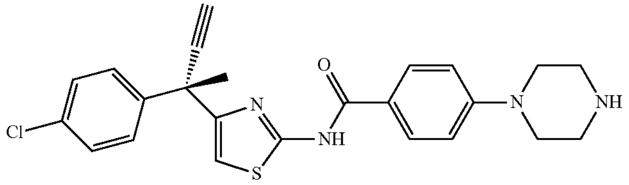 [SMILES: C#C[C@@](C)(c1ccc(Cl)cc1)c1csc(NC(=O)c2ccc(N3CCNCC3)cc2)n1] | N-(4-(2-(4-chlorophenyl)but-3-yn-2-yl)thiazol-2-yl)-4-(piperazin-1-yl)benzamide | $^1$H NMR (400 MHz, DMSO-$d_6$) δ 10.56 (br s, 1H), 7.50 (d, J = 8.6 Hz, 2H), 7.36 (d, J = 8.6 Hz, 2H), 6.90 (s, 1H), 6.28 (br s, 1H), 4.75 (t, J = 5.1 Hz, 2H), 3.63-3.57 (m, 1H), 3.50 (s. 1H), 3.42-3.35 (m, 4H), 1.84 (s, 3H). | 424.0 | 43 | 0.58 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B094 | 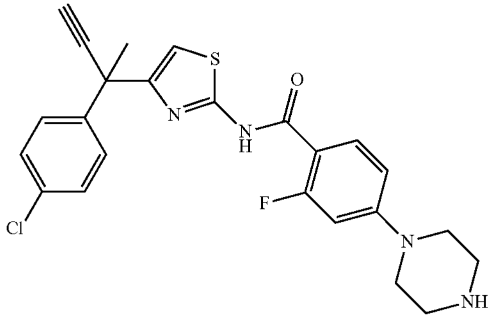 [SMILES: C#CC(C)(c1ccc(Cl)cc1)c1csc(NC(=O)c2ccc(N3CCNCC3)cc2F)n1] | N-(4-(2-(4-chlorophenyl)but-3-yn-2-yl)thiazol-2-yl)-2-fluoro-4-(piperazin-1-yl)benzamide | | 469.1 | 151 | 2.46 |
| B095 | 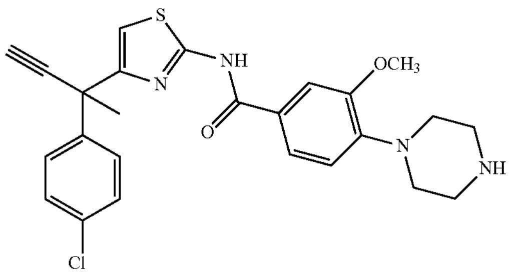 [SMILES: C#CC(C)(c1ccc(Cl)cc1)c1csc(NC(=O)c2ccc(N3CCNCC3)c(OC)c2)n1] | N-(4-(2-(4-chlorophenyl)but-3-yn-2-yl)thiazol-2-yl)-3-methoxy-4-(piperazin-1-yl)benzamide | $^1$H NMR (400 MHz, DMSO-$d_6$) δ 7.66 (d, J = 8.8 Hz, 2H), 7.41-7.36 (m, J = 20.0 Hz, 4H), 7.15 (s, 1H), 6.92 (d, J = 8.0 Hz, 1H), 3.83 (s, 3H), 3.51 (s, 4H), 3.02 (s, 1H), 2.87 (s, 4H), 1.88 (s, 3H). | 481.1 | 184 | 1.20 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B096 | 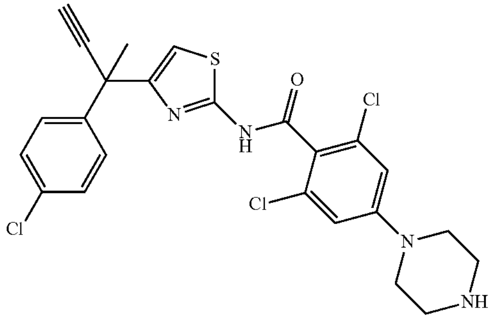 [SMILES: C#CC(C)(c1ccc(Cl)cc1)c1csc(NC(=O)c2c(Cl)cc(N3CCNCC3)cc2Cl)n1] | 2,6-dichloro-N-(4-(2-(4-chlorophenyl)but-3-yn-2-yl)thiazol-2-yl)-4-(piperazin-1-yl)benzamide | | 519.0 | 312 | |
| B097 | 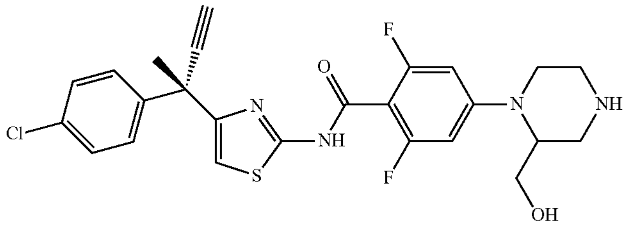 [SMILES: C#C[C@@](C)(c1ccc(Cl)cc1)c1csc(NC(=O)c2c(F)cc(N3CCNCC3CO)cc2F)n1] | N-[4-[1-(4-chlorophenyl)-1-methyl-prop-2-ynyl]thiazol-2-yl]-2,6-difluoro-4-[2-(hydroxymethyl)piperazin-1-yl]benzamide | $^1$H NMR (400 MHz, DMSO-$d_6$) δ 12.72 (s, 1H), 9.37 (br s, 1H), 8.72 (br s, 1H), 7.44-7.37 (m, 4H), 7.20 (s, 1H), 6.71 (d, J = 12.5 Hz, 2H), 4.13 (br s, 1H), 3.75 (br s, 1H), 3.60 (br s, 1H), 3.58 (br s, 1H), 3.57 (br s, 1H), 3.49 (br s, 1H), 3.46 (br s, 1H), 3.33-3.23 (m, 2H), 3.15 (br d, J = 8.8 Hz. 1H), 3.03 (brd, J = 12.5 Hz, 1H), 1.90 (s, 3H). | 517.0 | 119 | 1.14 |
| B098 | 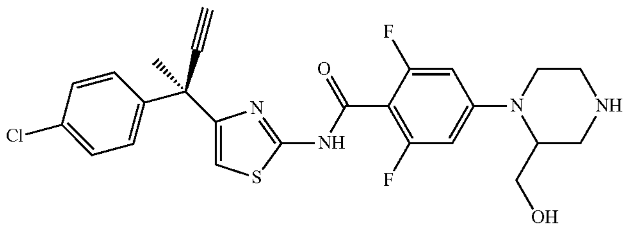 [SMILES: C#C[C@](C)(c1ccc(Cl)cc1)c1csc(NC(=O)c2c(F)cc(N3CCNCC3CO)cc2F)n1] | N-[4-[1-(4-chlorophenyl)-1-methyl-prop-2-ynyl]thiazol-2-yl]-2,6-difluoro-4-[2-(hydroxymethyl)piperazin-1-yl]benzamide | $^1$H NMR (400 MHz, DMSO-$d_6$) δ 12.72 (s, 1H), 9.51 (br s, 1H), 8.85 (br s, 1H), 7.50-7.33 (m, 4H), 7.20 (s, 1H), 6.71 (br d, J = 12.5 Hz, 2H), 4.13 (br s, 1H), 3.83 (br d, J = 14.3 Hz, 2H), 3.74 (br dd, J = 7.8, 11.3 Hz, 1H), 3.62-3.56 (m, 1H), 3.55 (s, 1H), 3.47 (br d, J = 13.0 Hz, 1H), 3.34-3.22 (m, 2H), 3.20-3.08 (m, 1H), 3.02 (br d, J = 10.3 Hz, 1H), 1.90 (s, 3H). | 517.0 | 20 | 0.26 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B099 | 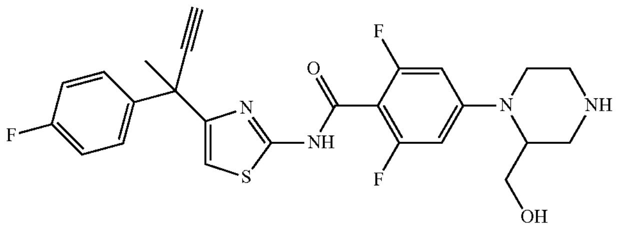 [SMILES: C#CC(C)(c1ccc(F)cc1)c1csc(NC(=O)c2c(F)cc(N3CCNCC3CO)cc2F)n1] | 2,6-difluoro-N-[4-[1-(4-fluorophenyl)-1-methyl-prop-2-ynyl]thiazol-2-yl]-4-[2-(hydroxymethyl)piperazin-1-yl]benzamide | $^1$H NMR (400 MHz, DMSO-$d_6$) δ 7.48-7.41 (m, 1H), 7.44 (dd, J = 5.5, 8.8 Hz, 2H), 7.20-7.10 (m, 3H), 6.57 (br d, J = 13.1 Hz, 2H), 4.71 (br s, 1H), 3.76-3.65 (m, 2H), 3.52 (s, 1H), 3.48 (br d, J = 10.4 Hz, 1H), 3.12 (br d, J = 12.3 Hz, 1H), 2.96-2.90 (m, 1H), 2.89-2.81 (m, 1H), 2.68 (br d, J = 3.2 Hz, 1H), 2.66-2.61 (m, 1H), 2.61-2.54 (m, 1H), 1.90 (s, 3H). | 501.0 | 30 | 0.64 |
| B100 | 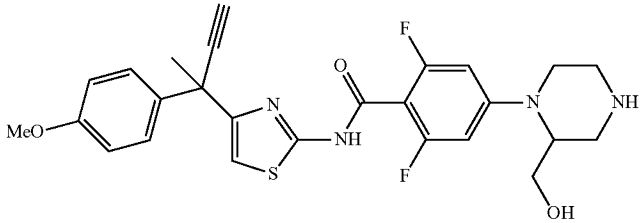 [SMILES: C#CC(C)(c1ccc(OC)cc1)c1csc(NC(=O)c2c(F)cc(N3CCNCC3CO)cc2F)n1] | 2,6-difluoro-4-[2-(hydroxymethyl)piperazin-1-yl]-N-[4-[1-(4-methoxyphenyl)-1-methyl-prop-2-ynyl]thiazol-2-yl]benzamide | $^1$H NMR (400 MHz, DMSO-$d_6$) δ 12.71 (s, 1H), 9.53 (br s, 1H), 8.87 (br s, 1H), 7.35-7.30 (m, 2H), 7.11 (s, 1H), 6.90-6.85 (m, 2H), 6.71 (br d, J = 12.4 Hz, 2H), 3.72 (s, 4H), 3.61-3.56 (m, 1H), 3.49-3.41 (m, 2H), 3.32-3.23 (m, 2H), 3.13 (br s, 1H), 3.01 (br d, J = 10.1 Hz, 1H), 1.88 (s, 3H). | 513.0 | 21 | 0.38 |
| B101 | 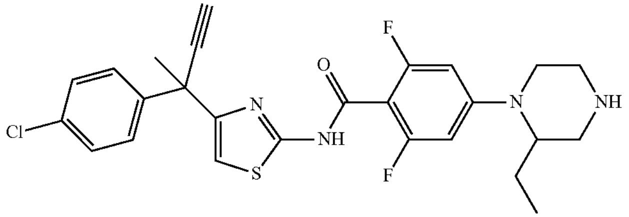 [SMILES: C#CC(C)(c1ccc(Cl)cc1)c1csc(NC(=O)c2c(F)cc(N3CCNCC3CC)cc2F)n1] | N-(4-(2-(4-chlorophenyl)but-3-yn-2-yl)thiazol-2-yl)-4-(2-ethylpiperazin-1-yl)-2,6-difluorobenzamide | | 515.1 | 70 | 2.47 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B102 | 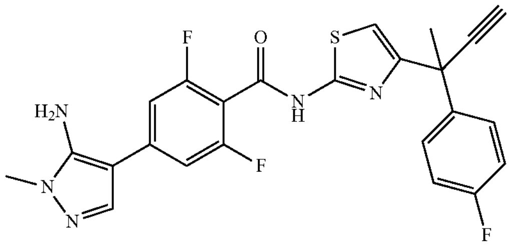 [SMILES: C#CC(C)(c1ccc(F)cc1)c1csc(NC(=O)c2c(F)cc(-c3cnn(C)c3N)cc2F)n1] | 4-(5-amino-1-methyl-1H-pyrazol-4-yl)-2,6-difluoro-N-(4-(2-(4-fluorophenyl)but-3-yn-2-yl)thiazol-2-yl)benzamide | $^1$H NMR (400 MHz, DMSO-$d_6$) δ 12.98 (br s, 1H), 7.67 (s, 1H), 7.51-7.40 (m, 2H), 7.33-7.09 (m, 5H), 5.80 (s, 2H), 3.59 (s, 3H), 3.54 (s, 1H), 1.92 (s, 3H). | 482.1 | 1269 | 2.25 |
| B103 | 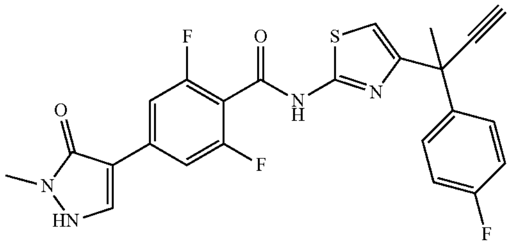 [SMILES: C#CC(C)(c1ccc(F)cc1)c1csc(NC(=O)c2c(F)cc(-c3c[nH]n(C)c3=O)cc2F)n1] | 2,6-difluoro-N-(4-(2-(4-fluorophenyl)but-3-yn-2-yl)thiazol-2-yl)-4-(2-methyl-3-oxo-2,3-dihydro-1H-pyrazol-4-yl)benzamide | $^1$H NMR (400 MHz, $CD_3OD$): δ 7.97 (br s, 1H), 7.60-7.51 (m, 4H), 7.11 (s, 1H), 7.01 (br t, J = 8.6 Hz, 2H), 3.53 (s, 3H), 2.97 (s, 1H), 1.97 (s, 3H) | 483.0 | 5139 | 5.21 |
| B104 | 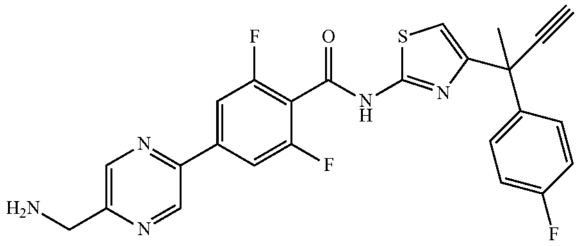 [SMILES: C#CC(C)(c1ccc(F)cc1)c1csc(NC(=O)c2c(F)cc(-c3cnc(CN)cn3)cc2F)n1] | 4-(5-(aminomethyl)pyrazin-2-yl)-2,6-difluoro-N-(4-(2-(4-fluorophenyl)but-3-yn-2-yl)thiazol-2-yl)benzamide | $^1$H NMR (400 MHz, $CD_3OD$) δ 9.28 (s, 1H), 8.81 (s, 1H), 7.94 (d, J = 8.8 Hz, 2H), 7.64-7.48 (m, 2H), 7.16 (s, 1H), 7.06-6.95 (m, 2H), 4.45 (s, 2H), 2.99 (s, 1H), 2.04-1.92 (m, 3H). | 494.0 | 1474 | 2.98 |

TABLE 5-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| B105 | 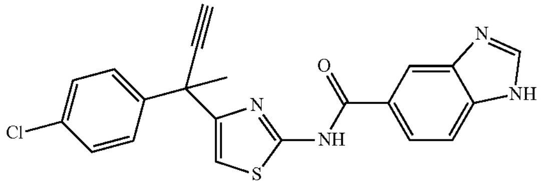 HCl | N-[4-[1-(4-chloropheny])-1-methyl-prop-2-ynyl]thiazol-2-yl]-1H-benzimidazole-5-carboxamide | $^1H$ NMR (400 MHz, DMSO-$d_6$) δ 12.61 (br s, 2H), 8.50-8.30 (m, 2H), 7.94 (br s, 1H), 7.62 (br s, 1H), 7.47-7.44 (m, 2H), 7.42-7.38 (m, 2H), 7.17 (s, 1H), 3.55 (s, 1H), 1.92 (s, 3H) | 407.2 | | |
| B106 | 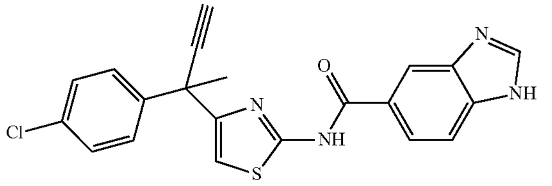 [SMILES: C#CC(C)(c1ccc(Cl)cc1)c1csc(NC(=O)c2ccc3[nH]cnc3c2)n1] | N-[4-[1-(4-chlorophenyl)-1-methyl-prop-2-ynyl]thiazol-2-yl]-1H-benzimidazole-5-carboxamide | $^1H$ NMR (400 MHz, DMSO-$d_6$) δ 12.90-12.70 (m, 1H), 12.62 (br d, J = 9.3 Hz, 1H), 8.49-8.39 (m, 1H), 8.37-8.31 (m, 1H), 7.94 (ddd, J = 1.4, 8.5, 14.6 Hz, 1H), 7.74-7.59 (m, 1H), 7.47-7.44 (m, 2H), 7.42-7.38 (m, 2H), 7.18 (d, J = 2.0 Hz, 1H), 3.55 (s, 1H), 1.93 (s, 3H) | 407.2 | | |

TABLE 6

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| C001 | 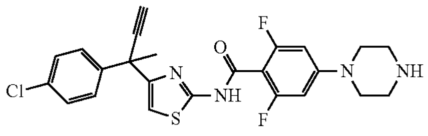 [SMILES: C#CC(C)(c1ccc(Cl)cc1)c1csc(NC(=O)c2c(F)cc(N3CCNCC3)cc2F)n1] | N-(4-(2-(4-chlorophenyl)but-3-yn-2-yl)thiazol-2-yl)-2.6-difluoro-4-(piperazin-1-yl)benzamide | $^{1}$H NMR (400 MHz, DMSO-d6) δ 12.77 (s, 1 H), 9.25 (br s, 2 H), 7.33-7.49 (m, 4 H), 7.21 (s, 1 H), 6.78 (br d, J = 12.05 Hz, 2 H), 3.52-3.58 (m, 5 H), 3.16 (br s, 4 H), 1.90 (s, 3 H) | [M + H]$^+$ = 487 | 3.7 | 0.59 |
| C002 | 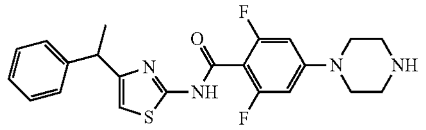 [SMILES: CC(c1ccccc1)c1csc(NC(=O)c2c(F)cc(N3CCNCC3)cc2F)n1] | 2,6-difluoro-N-(4-(1-phenylethyl)thiazol-2-yl)-4-(piperazin-1-yl)benzamide | $^{1}$H NMR (400 MHz, DMSO-d6) δ =12.62 (br s, 1H), 9.37 (br s, 2H), 7.35-7.11 (m, 5H), 6.95 (s, 1H), 6.79 (d, J = 12.0 Hz, 2H), 4.16 (br s, 4H), 3.62-3.52 (m, 4H), 1.56 (d, J = 7.3 Hz, 3H) | [M + H]$^+$ = 429.1 | 47 | 0.83 |
| C003 | 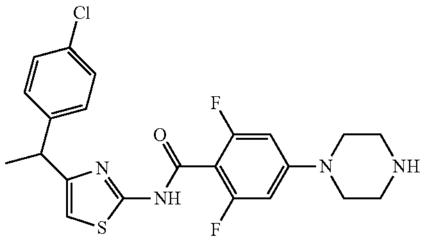 [SMILES: CC(c1ccc(Cl)cc1)c1csc(NC(=O)c2c(F)cc(N3CCNCC3)cc2F)n1] | N-(4-(1-(4-chlorophenyl)ethyl) thiazol-2-yl)-2,6-difluoro-4-(piperazin-1-yl)benzamide | $^{1}$H NMR (400 MHz, DMSO-d6) δ 12.62 (br s, 1 H), 9.43 (br s, 2 H), 7.37-7.31 (m, 2 H), 7.29-7.22 (m, 2 H), 6.97 (s, 1 H), 6.79 (br d, J = 12.0 Hz, 2 H), 4.19 (q, J = 7.2 Hz, 1 H), 3.64-3.54 (m, 4 H), 3.16 (br s, 4 H), 1.55 (d, J = 7.2 Hz, 3 H) | [M + H]$^+$ = 463.1 | 11 | 1.34 |
| C004 | 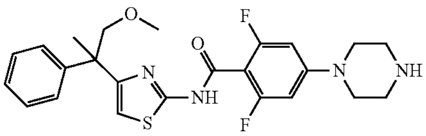 [SMILES: COCC(C)(c1ccccc1)c1csc(NC(=O)c2c(F)cc(N3CCNCC3)cc2F)n1] | 2,6-difluoro-N-(4-(1-methoxy-2-phenylpropan-2-yl)thiazol-2-yl)-4-(piperazin-1-yl)benzamide | | [M + H]$^+$ = | 22 | 0.66 |
| C005 | 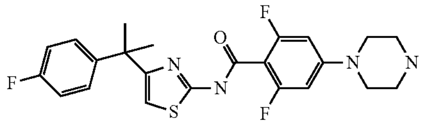 [SMILES: CC(C)(c1ccc(F)cc1)c1csc(NC(=O)c2c(F)cc(N3CCNCC3)cc2F)n1] | 2,6-difluoro-N-(4-(2-(4-fluorophenyl)propan-2-yl)thiazol-2-yl)-4-(piperazin-1-yl)benzamide | $^{1}$H NMR (400 MHz, DMSO-d6) fluoro (s, 1 H), 9.01 (s, 2 H), 7.21 (d, 2 H), 7.05 (d, 2 H), 7.00 (s, 1 H), 6.76 (d, 2 H), 3.53 (t, 4 H), 3.15 (t, 4 H), 1.62 (s, 6H) | [M + H]$^+$ = 461.2 | 6 | 0.68 |
| C006 | 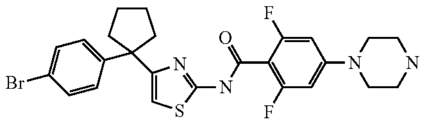 [SMILES: O=C(Nc1nc(C2(c3ccc(Br)cc3)CCCC2)cs1)c1c(F)cc(N2CCNCC2)cc1F] | N-(4-(1-(4-bromophenyl) cyclopentyl)thiazol-2-yl)-2,6-difluoro-4-(piperazin-1-yl)benzamide | $^{1}$H NMR (400 MHz, DMSO-d6) δ7.42 (d, 2 H), 7.22 (d, 2 H), 7.04 (s, 1 H), 6.62 (s, 2 H), 3.18 (t, 4 H), 2.76 (t, 4 H), 2.45 (t, 4 H), 2.02 (t, 2 H), 1.62 (t, 2 H) | [M + H]$^+$ = 547.1 | 43 | 2.53 |
| C007 | 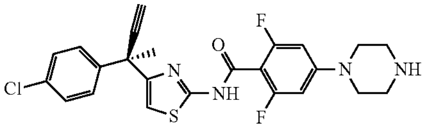 [SMILES: C#C[C@](C)(c1ccc(Cl)cc1)c1csc(NC(=O)c2c(F)cc(N3CCNCC3)cc2F)n1] | (R)-N-(4-(2-(4-chlorophenyl)but-3-yn-2-yl)thiazol-2-yl)-2,6-difluoro-4-(piperazin-1-yl)benzamide | $^{1}$H NMR (400 MHz, DMSO-d6) δ 12.75 (s, 1 H), 9.42 (br. s, 2 H), 7.45-7.35 (m, 4 H), 7.20 (s, 1 H), 6.79 (s, 1 H), 6.76 (s, 1 H), 3.60-3.55 (m, 4 H), 3.54 (s, 1 H), 2.51-2.49 (m, 4H), 1.90 (s, 3 H) | [M + H]$^+$ = 487.1 | 10 | 2.40 |
| C008 | 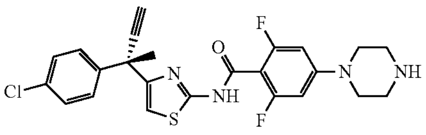 [SMILES: C#C[C@@](C)(c1ccc(Cl)cc1)c1csc(NC(=O)c2c(F)cc(N3CCNCC3)cc2F)n1] | (S)-N-(4-(2-(4-chlorophenyl)but-3-yn-2-yl)thiazol-2-yl)-2,6-difluoro-4-(piperazin-1-yl)benzamide | $^{1}$H NMR (400 MHz, DMSO-d6) δ 12.75 (s, 1 H), 9.47 (br. s, 2 H), 7.46-7.36 (m, 4 H), 7.20 (s, 1 H), 6.79 (s, 1 H), 6.76 (s, 1 H), 3.61-3.55 (m, 4 H), 3.54 (s, 1 H), 3.19-3.11 (m, 4H), 1.89 (s, 3 H) | [M + H]$^+$ = 487.1 | 5 | 0.32 |

TABLE 6-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| C009 | 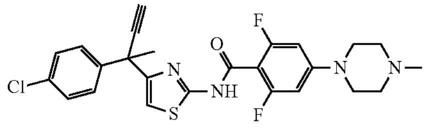 [SMILES: C#CC(C)(c1ccc(Cl)cc1)c1csc(NC(=O)c2c(F)cc(N3CCN(C)CC3)cc2F)n1] | N-(4-(2-(4-chlorophenyl)but-3-yn-2-yl)thiazol-2-yl)-2,6-difluoro-4-(4-methylpiperazin-1-yl)benzamide | $^1$H NMR (400 MHz, DMSO-d6) δ 2.76 (s, 1H), 7.34-7.47 (m, 4H), 7.20 (s, 1H), 6.75 (br d, J = 12.2 Hz, 2H), 3.56-3.66 (m, 2H), 3.54 (s, 1H), 3.42-3.52 (m, 2H), 2.99-3.16 (m, 4H), 2.74 (s, 3H), 1.90 (s, 3H). | $[M + H]^+$ = 501.1 | 7 | 0.70 |
| C010 | 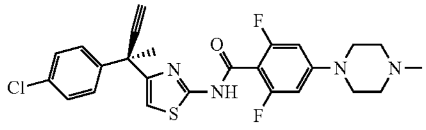 [SMILES: C#C[C@](C)(c1ccc(Cl)cc1)c1csc(NC(=O)c2c(F)cc(N3CCN(C)CC3)cc2F)n1] | (R)-N-(4-(2-(4-chlorophenyl)but-3-yn-2-yl)thiazol-2-yl)-2,6-difluoro-4-(4-methylpiperazin-1-yl)benzamide | $^1$H NMR (400 MHz, DMSO-d6) δ 12.79 (s, 1 H), 10.96 (br. s, 1 H), 7.45-7.35 (m, 4 H), 7.21 (s, 1 H), 6.82 (s, 1 H), 6.79 (s, 1 H), 4.09-4.00 (m, 2 H), 3.58 (s, 1 H), 3.49-3.40 (m, 2 H), 3.30-3.20 (m, 2 H), 3.13-3.01 (m, 2H), 2.82-2.76 (m, 3 H), 1.90 (s, 3 H) | $[M + H]^+$ = 501.1 | 56 | 1.49 |
| C011 | 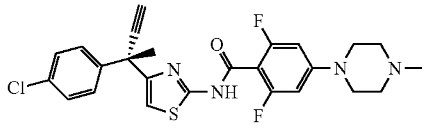 [SMILES: C#C[C@@](C)(c1ccc(Cl)cc1)c1csc(NC(=O)c2c(F)cc(N3CCN(C)CC3)cc2F)n1] | (S)-N-(4-(2-(4-chlorophenyl)but-3-yn-2-yl)thiazol-2-yl)-2,6-difluoro-4-(4-methylpiperazin-1-yl)benzamide | $^1$H NMR (400 MHz, DMSO-d6) δ 12.79 (s, 1 H), 11.02 (br. s, 1 H), 7.47-7.35 (m, 4 H), 7.21 (s, 1 H), 6.82 (s, 1 H), 6.79 (s, 1 H), 4.09-4.00 (m, 2 H), 3.56 (s, 1 H), 3.49-3.40 (m, 2 H), 3.32-3.20 (m, 2 H), 3.13-3.01 (m, 2H), 2.82-2.76 (m, 3 H), 1.90 (s, 3 H) | $[M + H]^+$ = 501.1 | 18 | 0.44 |
| C012 | 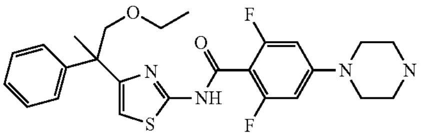 [SMILES: CCOCC(C)(c1ccccc1)c1csc(NC(=O)c2c(F)cc(N3CCNCC3)cc2F)n1] | N-(4-(1-ethoxy-2-phenylpropan-2-yl)thiazol-2-yl)-2,6-difluoro-4-(piperazin-1-yl)benzamide | $^1$H NMR (400 MHz, DMSO-d6) d: 7.22-7.18 (5H, m), 6.89 (1H,s), 6.61 (2H, J = 12 Hz, d), 3.83 (2H, s), 3.42-3.40 (2H, m), 3.14 (4H, t), 2.73 (4H, t), 1.64 (3H, s), 1.01 (3H, s) | $[M + H]^+$ = 487.1 | 78 | 1.45 |
| C013 | 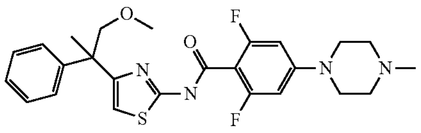 [SMILES: COCC(C)(c1ccccc1)c1csc(NC(=O)c2c(F)cc(N3CCN(C)CC3)cc2F)n1] | N-(4-(1-ethoxy-2-phenylpropan-2-yl)thiazol-2-yl)-2,6-difluoro-4-(4-methylpiperazin-1-yl)benzamide | $^1$H NMR (400 MHz, DMSO-d6) d: 7.24-7.15 (5H, m), 6.89 (1H,s), 6.66 (2H, J = 12 Hz, d), 3.80 (2H, s), 3.25 (4H, s), 3.22 (3H, s), 2.35 (4H, s), 2.17 (3H, s), 1.63 (3H, s). | $[M + H]^+$ = 487.1 | 91 | 1.05 |
| C014 | 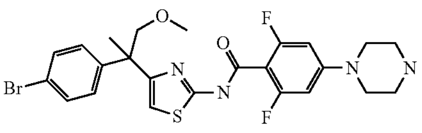 [SMILES: COCC(C)(c1ccc(Br)cc1)c1csc(NC(=O)c2c(F)cc(N3CCNCC3)cc2F)n1] | N-(4-(2-(4-bromophenyl)-1-methoxypropan-2-yl)thiazol-2-yl)-2,6-difluoro-4-(piperazin-1-yl)benzamide | $^1$H NMR (400 MHz, DMSO-d6) δ 12.80 (s, 1 H), 7.81 (d, 2 H), 7.07 (d, 2 H), 7.03 (s, 2 H), 6.74 (s, 1 H), 3.81 (s, 2 H), 3.23 (s, 3 H), 3.18 (t, 4 H), 2.76 (t, 4 H), 1.72 (s, 3 H) | $[M + H]^+$ = 551.1 | 13 | 1.19 |
| C015 | 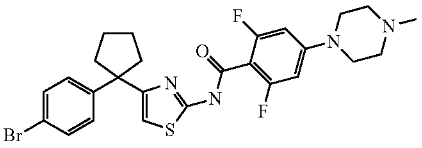 [SMILES: CN1CCN(c2cc(F)c(C(=O)Nc3nc(C4(c5ccc(Br)cc5)CCCC4)cs3)c(F)c2)CC1] | N-(4-(1-(4-bromophenyl) cyclopentyl)thiazol-2-yl)-2,6-difluoro-4-(4-methylpiperazin-1-yl)benzamide | $^1$H NMR (400 MHz, DMSO-d6) d: 7.42 (2H, J = 8 Hz, d), 7.20 (2H, J = 4 Hz, d), 7.03 (1H, s), 6.65 (2H, J = 12 Hz, d), 3.38 (4H, s), 2.35 (4H, s), 2.17 (3H, s) 2.01 (4H, s), 1.62 (4H, J = 8 Hz, d). | $[M + H]^+$ = 561.1 | 266 | 17.01 |

TABLE 6-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| C016 | 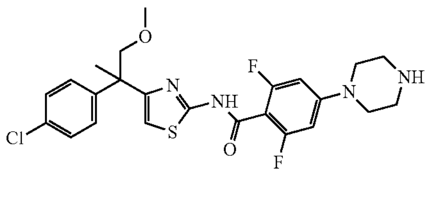 [SMILES: COCC(C)(c1ccc(Cl)cc1)c1csc(NC(=O)c2c(F)cc(N3CCNCC3)cc2F)n1] | N-(4-(2-(4-chlorophenyl)-1-methoxypropan-2-yl)thiazol-2-yl)-2,6-difluoro-4-(piperazin-1-yl)benzamide | $^1$H NMR (400 MHz, DMSO-$d_6$) δ12.64 (s, 1 H), 9.39 (s, 2 H), 7.34-7.29 (m, 2 H) 7.22-7.19 (m, 2 H), 6.99 (s, 1 H), 6.78 (d, J =12.0 Hz, 2 H), 3.80-3.77 (m, 2 H), 3.60-3.55 (m, 4 H) 3.1 (s, 3 H) 3.18-3.12 (m, 4 H), 1.65 (s, 3 H) | $[M + H]^+$ = 507.1 | 16 | 1.11 |
| C017 | 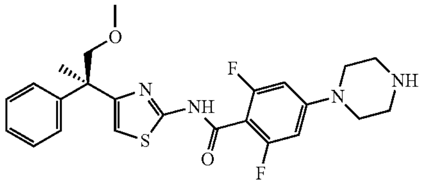 [SMILES: COC[C@](C)(c1ccccc1)c1csc(NC(=O)c2c(F)cc(N3CCNCC3)cc2F)n1] | (R)-2,6-difluoro-N-(4-(1-methoxy-2-phenylpropan-2-yl)thiazol-2-yl)-4-(piperazin-1-yl)benzamide | $^1$H NMR (400 MHz, DMSO-d6) δ 7.30-7.20 (m, 5H), 6.96 (s, 1H), 6.70-6.60 (m, 2H), 3.84 (s, 2H), 3.27 (s, 3H), 3.25-3.17 (m, 3H), 2.83-2.75 (m, 3H), 1.67 (s, 3H | $[M + H]^+$ = 473.1 | 67 | 1.38 |
| C018 | 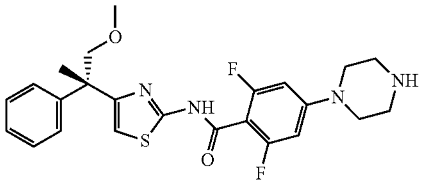 [SMILES: COC[C@@](C)(c1ccccc1)c1csc(NC(=O)c2c(F)cc(N3CCNCC3)cc2F)n1] | (S)-2,6-difluoro-N-(4-(1-methoxy-2-phenylpropan-2-yl)thiazol-2-yl)-4-(piperazin-1-yl)benzamide | $^1$H NMR (400 MHz, DMSO-d6) δ 7.29-7.23 (m, 2H), 7.21-7.13 (m, 3H), 6.98 (s, 1H), 6.79-6.72 (m, 2H), 3.84 (s, 2H), 3,50-3.44 (m, 4H), 3.26 (s, 3H), 3.12-3.06 (m, 4H), 1.67 (s, 3H) | $[M + H]^+$ = 473.1 | 36 | 0.97 |
| C019 | 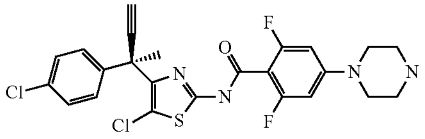 [SMILES: C#C[C@](C)(c1ccc(Cl)cc1)c1nc(NC(=O)c2c(F)cc(N3CCNCC3)cc2F)sc1Cl] | (R)-N-(5-chloro-4-(2-(4-chlorophenyl)but-3-yn-2-yl)thiazol-2-yl)-2,6-difluoro-4-(piperazin-1-yl)benzamide | $^1$H NMR (400 MHz, DMSO-d6) δ 13.07 (s, 1 H), 9.16 (s, 2 H), 7.41 (s, 4 H), 6.83 (d. J = 12.4 Hz, 2 H), 3.63 (s, 1 H), 3.62-3.57 (m, 4 H), 3.19 (br s, 4 H), 1.94 (s, 3 H). | $[M + H]^+$ = 521.0 | | |
| C020 | 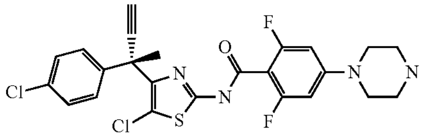 [SMILES: C#C[C@@](C)(c1ccc(Cl)cc1)c1nc(NC(=O)c2c(F)cc(N3CCNCC3)cc2F)sc1Cl] | (S)-N-(5-chloro-4-(2-(4-chlorophenyl)but-3-yn-2-yl)thiazol-2-yl)-2,6-difluoro-4-(piperazin-1-yl)benzamide | $^1$H NMR (400 MHz, DMSO-d6) δ 13.07 (s, 1 H), 9.23 (s, 2 H), 7.41 (s, 4 H), 6.83 (d, J =12.4 Hz, 2 H), 3.63 (s, 1 H), 3.62-3.57 (m, 4 H), 3.19 (br s, 4 H), 1.94 (s, 3 H) | $[M + H]^+$ = 521.0 | 88 | |
| C021 | 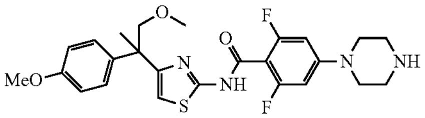 [SMILES: COCC(C)(c1ccc(OC)cc1)c1csc(NC(=O)c2c(F)cc(N3CCNCC3)cc2F)n1] | 2,6-difluoro-N-(4-(1-methoxy-2-(4-methoxyphenyl) propan-2-yl)thiazol-2-yl)-4-(piperazin-1-yl)benzamide | | | 44 | 0.95 |
| C022 | 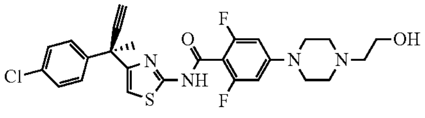 [SMILES: C#C[C@](C)(c1ccc(Cl)cc1)c1csc(NC(=O)c2c(F)cc(N3CCN(CCO)CC3)cc2F)n1] | (R)-N-(4-(2-(4-chlorophenyl)but-3-yn-2-yl)thiazol-2-yl)-2,6-difluoro-4-(4-(2-hydroxyethyl)piperazin-1-yl)benzamide | $^1$H NMR (400 MHz, DMSO-$d_6$) δ 12.68 (br., s, 1H), 7.42-7.39 (m, 4 H), 7.18 (s, 1 H), 6.67-6.65 (m, 2 H), 4.51-4.48 (m, 1 H), 3.53 (s, 1 H), 3.30-3.22 (m, 2 H), 2.44-2.39 (m, 2 H), 1.89 (s, 3 H). | $[M + H]^+$ = 531.0 | 188 | |

TABLE 6-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| C023 | 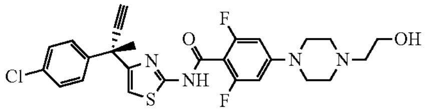 [SMILES: C#C[C@@](C)(c1ccc(Cl)cc1)c1csc(NC(=O)c2c(F)cc(N3CCN(CCO)CC3)cc2F)n1] | (S)-N-(4-(2-(4-chlorophenyl)but-3-yn-2-yl)thiazol-2-yl)-2,6-difluoro-4-(4-(2-hydroxyethyl)piperazin-1-yl)benzamide | $^1$H NMR (400 MHz, DMSO-$d_6$) δ 12.68 (br., s, IH), 7.50-7.40 (m, 4 H), 7.19 (s, 1 H), 6.73-6.62 (m, 2 H), 4.60 (br., s, 1H), 3.53 (s, 1 H), 3.35-3.25 (m, 4 H), 2.73-2.50 (m, 6 H), 1.90 (s, 3 H). | $[M + H]^+$ = 531.0 | 60 | |
| C024 | 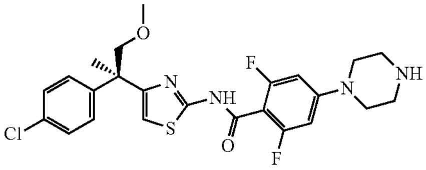 [SMILES: COC[C@](C)(c1ccc(Cl)cc1)c1csc(NC(=O)c2c(F)cc(N3CCNCC3)cc2F)n1] | (R)-N-(4-(2-(4-chlorophenyl)-1-methoxypropan-2-yl)thiazol-2-yl)-2,6-difluoro-4-(piperazin-1-yl)benzamide | 1H NMR (400 MHz, DMSO-d6) 12.64 (s, 1 H), 9.41 (s, 2 H), 7.32 (d, J = 8.4 Hz, 2 H) 7.22 (d, J = 8.8 Hz, 2 H), 6.99 (s, 1 H), 6.78 (d, J = 12.0 Hz, 2 H), 3.87-3.78 (m, 2 H) 3.62-3.55 (m, 4 H), 3.26 (s, 3 H), 3.20-3.13 (m, 4 H), 1.66 (s, 3H) | $[M + H]^+$ = 507.1 | 130 | |
| C025 | 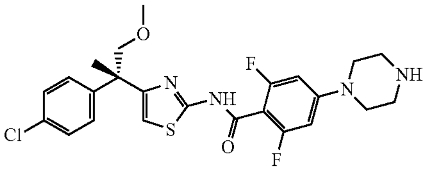 [SMILES: COC[C@@](C)(c1ccc(Cl)cc1)c1csc(NC(=O)c2c(F)cc(N3CCNCC3)cc2F)n1] | (S)-N-(4-(2-(4-chlorophenyl)-1-methoxypropan-2-yl)thiazol-2-yl)-2,6-difluoro-4-(piperazin-1-yl)benzamide | $^1$H NMR (400 MHz, DMSO-d6) 12.64 (s, 1 H), 9.42 (s, 2 H), 7.32 (d, J = 8.4 Hz, 2 H) 7.21 (d, J = 8.8 Hz, 2 H), 6.99 (s, 1 H), 6.78 (d, J = 12.0 Hz, 2 H), 3.87-3.76 (m, 2 H) 3.58-3.56 (m, 4 H), 3.26 (s, 3 H) 3.20-3.13 (m, 4 H), 1.65 (s, 3 H) | $[M + H]^+$ = 507.1 | 8 | |
| C026 | 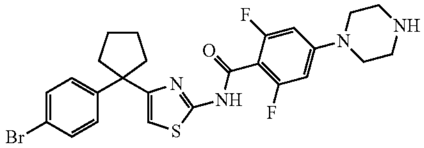 [SMILES: O=C(Nc1nc(C2(c3ccc(Br)cc3)CCCC2)cs1)c1c(F)cc(N2CCNCC2)cc1F] | N-(4-(1-(4-bromophenyl)cyclopentyl)thiazol-2-yl)-2,6-difluoro-4-(piperazin-1-yl)benzamide | $^1$H NMR (400 MHz, DMSO-$d_6$) δ 7.42 (m, 2 H), 7.22 (m, 2 H), 7.04 (s, 1 H), 6.62 (d, J = 8.9 Hz, 2 H), 3.18 (m, 4 H), 2.76 (m, 4 H), 2.45 (s, 1 H), 2.02 (m, 2 H), 2.01 (s, 1 H), 1.62 (m, 4 H) | 547.2 | 437 | 2.53 |
| C027 | 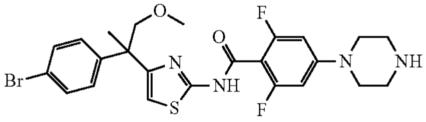 [SMILES: COCC(C)(c1ccc(Br)cc1)c1csc(NC(=O)c2c(F)cc(N3CCNCC3)cc2F)n1] | N-(4-(2-(4-bromophenyl)-1-methoxypropan-2-yl)thiazol-2-yl)-2,6-difluoro-4-(piperazin-1-yl)benzamide | $^1$H NMR (400 MHz, DMSO-$d_6$) δ 7.44 (d, J = 8.5 Hz, 2 H), 7.14 (d, J = 8.5 Hz, 2 H), 6.98 (s, 1 H), 6.74 (d, 2 H), 3.85-3.77 (m, 2 H), 3.51 (s, 4 H), 3.26 (s, 3 H), 3.11 (s, 4 H), 1.65 (s, 3 H) | 551.3 | 100 | 1.19 |
| C028 | 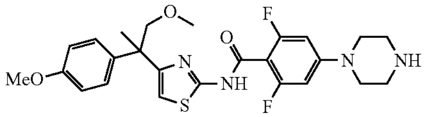 [SMILES: COCC(C)(c1ccc(OC)cc1)c1csc(NC(=O)c2c(F)cc(N3CCNCC3)cc2F)n1] | 2,6-difluoro-N-(4-(1-methoxy-2-(4-methoxyphenyl)propan-2-yl)thiazol-2-yl)-4-(piperazin-1-yl)benzamide | | 503.3 | 288 | 0.95 |
| C029 | 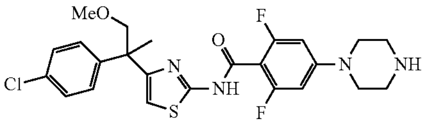 [SMILES: COCC(C)(c1ccc(Cl)cc1)c1csc(NC(=O)c2c(F)cc(N3CCNCC3)cc2F)n1] | N-(4-(2-(4-chlorophenyl)-1-methoxypropan-2-yl)thiazol-2-yl)-2,6-difluoro-4-(piperazin-1-yl)benzamide | | 507.2 | 128 | 5.05 |

TABLE 6-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| C030 | 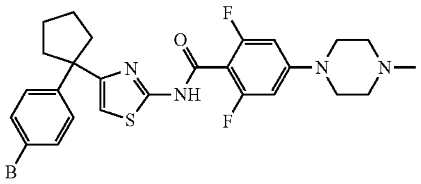 | N-(4-(1-(4-bromophenyl) cyclopentyl)thiazol-2-yl)-2,6-difluoro-4-(4-methylpiperazin-1-yl)benzamide | $^1$H NMR (400 MHz, DMSO-$d_6$) δ 7.42 (d, J = 8.0 Hz, 2H), 7.22 (d, ) = 8.0 Hz, 2H), 7.03 (s, 1H), 6.66 (d, J = 12.0 Hz, 2H), 3.26 (s, 4H), 2.36 (s, 4H), 2.17 (s, 3H), 2.02 (s, 4H), 1.61 (s, 4H). | 561.1 | 1770 | 17.00 |
| C031 | 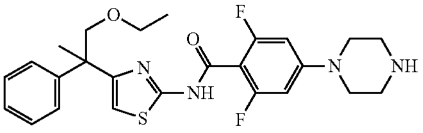 [SMILES: CCOCC(C)(c1ccccc1)c1csc(NC(=O)c2c(F)cc(N3CCNCC3)cc2F)n1] | N-(4-(1-ethoxy-2-phenylpropan-2-yl)thiazol-2-yl)-2,6-difluoro-4-(piperazin-1-yl)benzamide | $^1$H NMR (400 MHz, DMSO-$d_6$) δ 7.24-7.12 (m, J = 48.0 Hz, 5H), 6.93 (s, 1H), 6.62 (d, J = 12.0 Hz, 2H), 3.84 (s, 2H), 3.42 (q, J = 16.0 Hz, 2H), 3.17 (s, 4H), 2.75 (s, 4H), 1.64 (s, 3H), 1.05 (t, J = 12.0 Hz, 3H). | 487.2 | 642 | 3.66 |
| C032 | 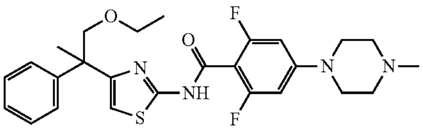 [SMILES: CCOCC(C)(c1ccccc1)c1csc(NC(=O)c2c(F)cc(N3CCN(C)CC3)cc2F)n1] | 2,6-difluoro-N-(4-(1-methoxy-2-phenylpropan-2-yl)thiazol-2-yl)-4-(4-methylpiperazin-1-yl)benzamide | $^1$H NMR (400 MHz, DMSO-$d_6$) δ 7.27-7.13 (m, J = 56.0 Hz, 5H), 6.89 (s, 1H), 6.66 (d, J = 12.0 Hz, 2H), 3.81 (s, 2H), 3.28 (s, 4H), 3.26 (s, 3H), 2.40-2.37 (m, 4H), 2.17 (s, 3H), 1.64 (s, 3H). | 487.2 | 593 | 1.05 |
| C033 | 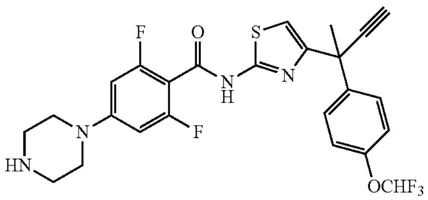 | N-(4-(2-(4-(difluoromethoxy) phenyl)but-3-yn-2-yl)thiazol-2-yl)-2,6-difluoro-4-(piperazin-1-yl)benzamide | | 519.1 | 73 | 3.13 |
| C034 | 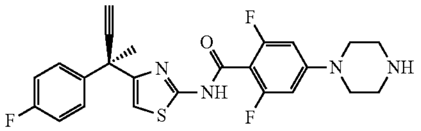 [SMILES: C#C[C@](C)(c1ccc(F)cc1)c1csc(NC(=O)c2c(F)cc(N3CCNCC3)cc2F)n1] | 2,6-difluoro-N-(4-(2-(4-fluorophenyl)but-3-yn-2-yl)thiazol-2-yl)-4-(piperazin-1-yl)benzamide | $^1$H NMR (400 MHz, DMSO-$d_6$) δ 12.76 (s, 1 H), 9.28 (br s, 2 H), 7.44 (dd, J = 8.91, 5.40 Hz, 2 H), 7.09-7.20 (m, 3 H), 6.78 (br d, J = 12.05 Hz, 2 H), 3.54-3.62 (m, 4 H), 3.53 (s, 1 H), 3.16 (br s, 4 H), 1.90 (s, 3 H). | 471.1 | 40 | 2.27 |
| C035 | 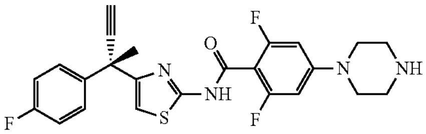 [SMILES: C#C[C@@](C)(c1ccc(F)cc1)c1csc(NC(=O)c2c(F)cc(N3CCNCC3)cc2F)n1] | 2,6-difluoro-N-(4-(2-(4-fluorophenyl)but-3-yn-2-yl)thiazol-2-yl)-4-(piperazin-1-yl)benzamide | $^1$H NMR (400 MHz, DMSO-$d_6$) δ 12.76 (s, 1 H), 9.57 (br s, 2 H), 7.39-7.49 (m, 2 H), 7.09-7.20 (m, 3 H), 6.77 (br d, J = 12.30 Hz, 2 H), 3.54-3.65 (m, 4 H), 3.53 (s, 1 H), 3.15 (br s, 4 H), 1.90 (s, 3 H). | 471.1 | 19 | 0.39 |
| C036 | 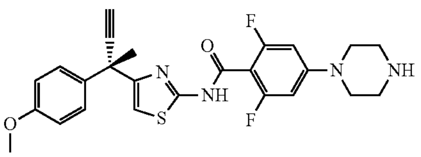 [SMILES: C#C[C@@](C)(c1ccc(OC)cc1)c1csc(NC(=O)c2c(F)cc(N3CCNCC3)cc2F)n1] | 2,6-difluoro-N-[4-[1-(4-methoxyphenyl)-1-methyl-prop-2-ynyl]thiazol-2-yl]-4-piperazin-1-yl-benzamide | $^1$H NMR (400 MHz, DMSO-$d_6$) δ 12.76 (s, 1H), 8.89 (br s, 2H), 7.32 (d, J = 8.8 Hz, 2H), 7.12 (s, 1H), 6.87 (d, J = 9.0 Hz, 2H), 6.79 (d, J = 12.1 Hz, 2H), 3.72 (s, 3H), 3.56-3.52 (m, 4H), 3.47 (s, 1H), 3.18 (br s, 4H), 1.88 (s, 3H) | 483.0 | 67 | 2.18 |

TABLE 6-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| C037 | 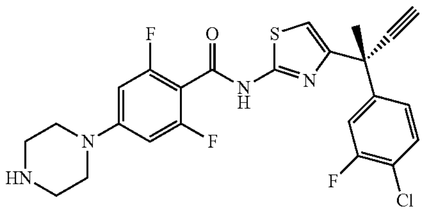 [SMILES: C#C[C@](C)(c1ccc(Cl)c(F)c1)c1csc(NC(=O)c2c(F)cc(N3CCNCC3)cc2F)n1] | N-(4-(2-(4-chloro-3-fluorophenyl)but-3-yn-2-yl)thiazol-2-yl)-2,6-difluoro-4-(piperazin-1-yl)benzamide | $^1$H NMR (400 MHz, DMSO-$d_6$) δ 12.77 (s. 1 H), 9.25 (br s, 2 H), 7.56 (t, J = 8.17 Hz, 1 H), 7.42 (dd, J = 10.85, 2.15 Hz, 1 H), 7.28 (dd, J = 8.46, 1.91 Hz, 1 H), 7.23 (s, 1 H), 6.79 (br d, J = 12.16 Hz, 2 H), 3.62 (s, 1 H), 3.50-3.60 (m, 4 H), 3.17 (br s, 4 H), 1.91 (s, 3 H). | 505.0 | 151 | 2.30 |
| C038 | 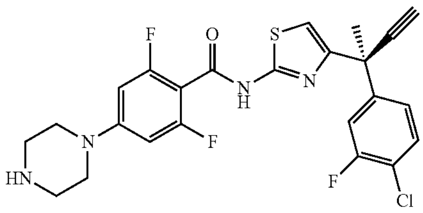 [SMILES: C#C[C@@](C)(c1ccc(Cl)c(F)c1)c1csc(NC(=O)c2c(F)cc(N3CCNCC3)cc2F)n1] | N-(4-(2-(4-chloro-3-fluorophenyl)but-3-yn-2-yl)thiazol-2-yl)-2,6-difluoro-4-(piperazin-1-yl)benzamide | $^1$H NMR (400 MHz, DMSO-$d_6$) δ 12.76 (s, 1 H), 9.12 (br s, 2 H), 7.56 (t, J = 8.16 Hz, 1 H), 7.42 (dd, J = 10.79, 2.01 Hz, 1 H), 7.28 (br d, J = 8.78 Hz, 1 H), 7.23 (s, 1 H), 6.79 (br d. J = 12.05 Hz, 2 H), 3.61 (s, 1 H), 3.53 - 3.59 (m, 4 H), 3.17 (br s, 4 H), 1.92 (s, 3H). | 505.0 | 17 | 0.72 |
| C039 | 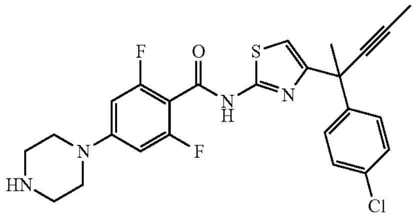 [SMILES: CC#CC(C)(c1ccc(Cl)cc1)c1csc(NC(=O)c2c(F)cc(N3CCNCC3)cc2F)n1] | N-(4-(2-(4-chlorophenyl)pent-3-yn-2-yl)thiazol-2-yl)-2,6-difluoro-4-(piperazin-1-yl)benzamide | $^1$H NMR (400MHz, DMSO-$d_6$) δ 12.76 (br s, 1H), 9.42 (br s, 2H), 7,45-7.40 (m, 2H), 7.40-7.35 (m, 2H), 7.17 (s, 1H), 6.78 (d, J-12.3 Hz, 2H), 3.65-3.52 (m, 4H), 3.23-3.10 (m, 4H), 1.89 (s, 3H), 1.87 (s, 3H) | 501.2 | 36 | 2.28 |
| C040 | 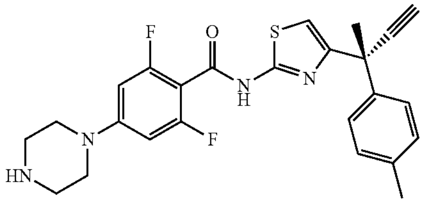 [SMILES: C#C[C@](C)(c1ccc(C)cc1)c1csc(NC(=O)c2c(F)cc(N3CCNCC3)cc2F)n1] | 2,6-difluoro-N-[4-[1-methyl-1-(p-tolyl)prop-2-ynyl]thiazol-2-yl]-4-piperazin-1-yl-benzamide | $^1$H NMR (400MHz, DMSO-$d_6$) δ 7.30 (d, J = 8.1 Hz, 2H), 7.16-7.07 (m, 3H), 6.71 (br d, J = 12.4 Hz, 2H), 3.47 (s, 1H), 3.39-3.34 (m, 4H), 3,00-2.89 (m, 4H), 2.25 (s, 3H), 1.88 (s, 3H). | 467.0 | 29 | 1.27 |
| C041 | 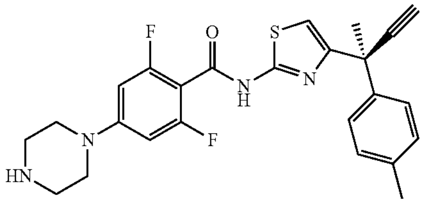 [SMILES: C#C[C@@](C)(c1ccc(C)cc1)c1csc(NC(=O)c2c(F)cc(N3CCNCC3)cc2F)n1] | 2,6-difluoro-N-[4-[1-methyl-1-(p-tolyl)prop-2-ynyl]thiazol-2-yl]-4-piperazin-1-yl-benzamide | $^1$H NMR (400 MHz, DMSO-$d_6$) δ 7.30 (d, J = 8.1 Hz, 2H), 7.13-7.10 (m, 3H), 6.64 (d, J = 12.6 Hz, 2H), 3.45 (s, 1H), 3.24-3.13 (m, 6H), 2.78-2.75 (m, 4H), 2.26 (s, 3H), 1.88 (s, 3H). | 467.0 | 7 | 0.60 |
| C042 | 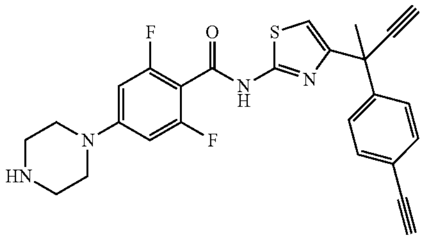 [SMILES: C#Cc1ccc(C(C)(C#C)c2csc(NC(=O)c3c(F)cc(N4CCNCC4)cc3F)n2)cc1] | N-[4-[1-(4-ethynylphenyl)-1-methyl-prop-2-ynyl]thiazol-2-yl]-2,6-difluoro-4-piperazin-1-yl-benzamide | $^1$H NMR (400 MHz, DMSO-$d_6$) δ 12.76 (br s, 1H), 9.52 (br s, 2H), 7.47-7.41 (m, 4H), 7.21 (s, 1H), 6.77 (br d, J = 12.1 Hz, 2H), 4.16 (s, 1H), 3.58 (br s, 4H), 3.15 (br s, 4H), 1.90 (s, 3H). | 477.1 | 101 | 0.61 |

TABLE 6-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| C043 | 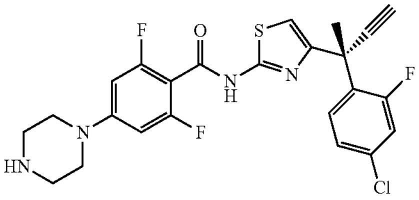 [SMILES: C#C[C@@](C)(c1csc(NC(=O)c2c(F)cc(N3CCNCC3)cc2F)n1)c1ccc(Cl)cc1F] | N-(4-(2-(4-chloro-2-fluorophenyl)but-3-yn-2-yl)thiazol-2-yl)-2,6-difluoro-4-(piperazin-1-yl)benzamide | $^1$H NMR (400 MHz, DMSO-$d_6$) δ 12.75 (s, 1 H), 9.18 (br s, 2 H), 7.67 (t, J = 8.8 Hz, 1 H), 7.39-7.29 (m, 2 H), 7.19 (s, 1 H), 6.78 (br d, J = 12.0 Hz, 2 H), 3.59 (s, 1 H), 3.58-3.55 (m, 4 H), 3.17 (br s, 4 H), 1.94 (s, 3 H) | 505.1 | 285 | 3.47 |
| C044 | 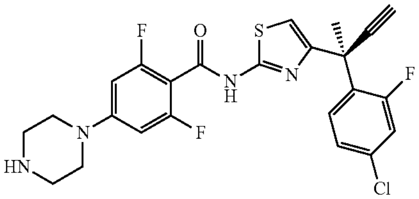 [SMILES: C#C[C@](C)(c1csc(NC(=O)c2c(F)cc(N3CCNCC3)cc2F)n1)c1ccc(Cl)cc1F] | N-(4-(2-(4-chloro-2-fluorophenyl)but-3-yn-2-yl)thiazol-2-yl)-2,6-difluoro-4-(piperazin-1-yl)benzamide | $^1$H NMR (400 MHz, DMSO-$d_6$) δ 12.76 (s, 1 H), 9.14 (br s, 2 H), 7.67 (t, J = 8.8 Hz, 1 H), 7.38-7.31 (m, 2 H), 7.20 (s, 1 H), 6.78 (d, J =12.4 Hz, 2 H), 3.60 (s, 1 H) 3.58-3.53 (m, 4 H), 3.18 (br s, 4 H), 1.95 (s, 3 H) | 505.1 | 25 | 1.45 |
| C045 | 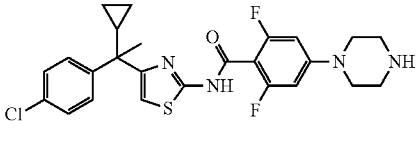 [SMILES: CC(c1ccc(Cl)cc1)(c1csc(NC(=O)c2c(F)cc(N3CCNCC3)cc2F)n1)C1CC1] | N-(4-(1-(4-chlorophenyl)-1-cyclopropylethyl) thiazol-2-yl)-2,6-difluoro-4-(piperazin-1-yl)benzamide | $^1$H NMR (400 MHz, DMSO-$d_6$) δ 12.61 (s, 1 H), 9.26 (br s, 2 H), 7.34-7.29 (m, 2 H), 7.20 (d, J = 8.8 Hz, 2 H), 7.14 (s, 1 H), 6.77 (d, J = 12.4 Hz, 2 H), 3.62-3.49 (m, 4 H), 3.16 (br s, 4 H), 1.53-1.46 (m, 1 H), 1.42 (s, 3 H) 0.58-0.51 (m, 1 H), 0.49-0.42 (m, 1 H), 0.29-0.22 (m, 1 H), 0.21-0.14 (m, 1 H) | 503.1 | 25 | 1.63 |
| C046 | 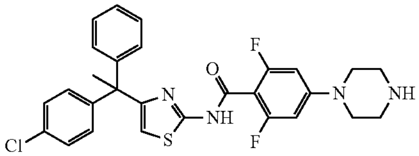 [SMILES: CC(c1ccccc1)(c1ccc(Cl)cc1)c1csc(NC(=O)c2c(F)cc(N3CCNCC3)cc2F)n1] | N-(4-(1-(4-chlorophenyl)-1-phenylethyl)thiazol-2-yl)-2,6-difluoro-4-(piperazin-1-yl)benzamide | $^1$H NMR (400 MHz, DMSO-$d_6$) δ 12.70 (s, 1 H), 9.21 (br s, 2 H), 7.37-7,28 (m, 4 H), 7.25-7.20 (m, 1 H), 7.15-7.08 (m, 4 H), 6.79 (d, J, =12.0 Hz, 2 H), 6.60 (s, 1 H) 3.60-3.56 (m, 4 H), 3.17 (br s, 4 H) 2.07 (s, 3 H) | 539.2 | 377 | 5.5 |
| C047 | 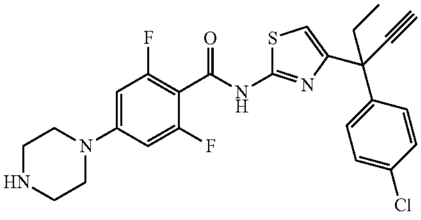 [SMILES: C#CC(CC)(c1ccc(Cl)cc1)c1csc(NC(=O)c2c(F)cc(N3CCNCC3)cc2F)n1] | N-(4-(3-(4-chlorophenyl)pent-1-yn-3-yl)thiazol-2-yl)-2,6-difluoro-4-(piperazin-1-yl)benzamide | $^1$H NMR (400 MHz, DMSO-$d_6$) δ 12.75 (s, 1H), 9.23 (br s, 2H), 7.49-7.43 (m, 2H), 7.41-7.36 (m, 2H), 7.21 (s, 1H), 6.78 (d, J = 12.0 Hz, 2H), 3.61 (s, 1H), 3.59-3.53 (m, 4H), 3.17 (s, 4H), 2.40-2.30 (m, 1H), 2.23-2.14 (m, 1H), 0.88-0.81 (m, 3H). $^{19}$F NMR (376 MHz, DMSO-$d_6$) δ −111.77 (s, 2F) | 501.1 | 131 | 2.65 |
| C048 | 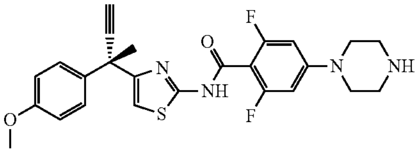 [SMILES: C#C[C@@](C)(c1ccc(OC)cc1)c1csc(NC(=O)c2c(F)cc(N3CCNCC3)cc2F)n1] | 2,6-difluoro-N-(4-(2-(4-methoxyphenyl)but-3-yn-2-yl)thiazol-2-yl)-4-(piperazin-1-yl)benzamide | $^1$H NMR (400 MHz, DMSO-$d_6$) δ 12.75 (s, 1H), 9.55 (br s, 2H), 7.32-7.27 (m, 2H), 7.11 (s, 1H), 6.87-6.82 (m, 2H), 6.79-6.71 (m, 2H), 3.71 (s, 3H), 3.60-3.52 (m, 4H), 3.46 (s, 1H), 3.16-3.07 (br s, 4H), 1.88 (s, 3H). | 483.1 | 16 | 0.41 |

TABLE 6-continued

The following examples were synthesized analogous to the procedure of example 16, 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| C049 | 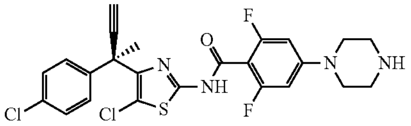 [SMILES: C#C[C@](C)(c1ccc(Cl)cc1)c1nc(NC(=O)c2c(F)cc(N3CCNCC3)cc2F)sc1Cl] | N-(5-chloro-4-(2-(4-chlorophenyl)but-3-yn-2-yl)thiazol-2-yl)-2,6-difluoro-4-(piperazin-1-yl)benzamide | $^1$H NMR (400 MHz, DMSO-$d_6$) δ 13.07 (s, 1 H), 9.16 (br s, 2 H), 7.41 (s, 4 H), 6.83 (d, J = 12.4 Hz, 2 H), 3.63 (s, 1 H), 3.62-3.57 (m, 4 H), 3.19 (br s, 4 H), 1.94 (s, 3 H) | 521.1 | 4524 | |
| C050 | 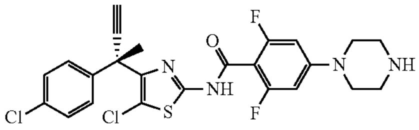 [SMILES: C#C[C@@](C)(c1ccc(Cl)cc1)c1nc(NC(=O)c2c(F)cc(N3CCNCC3)cc2F)sc1Cl] | N-(5-chloro-4-(2-(4-chlorophenyl)but-3-yn-2-yl)thiazol-2-yl)-2,6-difluoro-4-(piperazin-1-yl)benzamide | $^1$H NMR (400 MHz, DMSO-$d_6$) δ 13.07 (br s, 1 H), 9.23 (br s, 2 H), J = 12.4 Hz, 2 H), 3.63 (s, 7.41 (s, 4 H), 6.83 (br d, 1 H) 3.62-3.57 (m, 4 H), 3.19 (br s, 4 H), 1.94 (s, 3 H) | 521.1 | 923 | |

TABLE 7

The following examples were synthesized analogous to the procedure of example 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| D001 | 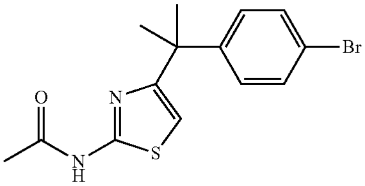 [SMILES: CC(=O)Nc1nc(C(C)(C)c2ccc(Br)cc2)cs1] | N-(4-(2-(4-bromophenyl)propan-2-yl)thiazol-2-yl)acetamide | $^1$H NMR (400 MHz, dmso) δ 12.00 (s, 1H), 7.40 (d, J = 8.6 Hz, 2H), 7.11 (d, J = 8.5 Hz, 2H), 6.87 (s, 1H), 2.02 (s, 3H), 1.57 (s, 6H). | $[M + H]^+$ = 339 | 100 | 2.01 |
| D002 | 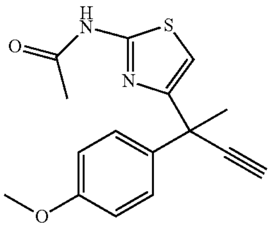 [SMILES: C#CC(C)(c1ccc(OC)cc1)c1csc(NC(C)=O)n1] | N-(4-(2-(4-methoxyphenyl)but-3-yn-2-yl)thiazol-2-yl)acetamide | $^1$H NMR (400 MHz, DMSO-d6) δ 12.15 (s, 1 H), 7.30 (d, J = 8.8 Hz, 2 H), 6.99 (s, 1 H), 6.86 (d, J = 8.8 Hz, 2 H), 3.71 (s, 3 H), 3.42 (s, 1 H), 2.06 (s, 3 H), 1.85 (s, 3 H). | $[M + H]^+$ = 301.1 | 196 | 1.14 |
| D003 | 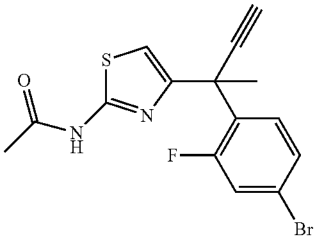 [SMILES: C#CC(C)(c1csc(NC(C)=O)n1)c1ccc(Br)cc1F] | N-(4-(2-(4-bromo-2-fluorophenyl)but-3-yn-2-yl)thiazol-2-yl)acctamide | $^1$H NMR (400 MHz, DMSO-d6) δ 12.14 (s, 1H), 7.59 (t. J = 8.4 Hz, 1H), 7.45 (d, J = 9.5 Hz, 2H), 7.09-7.06 (m, 1H), 3.58-3.54 (m, 1H), 2.07 (s, 3H), 1,92 (s, 3H | $[M + H]^+$ = 367.0 | 183 | 1.72 |

TABLE 7-continued

The following examples were synthesized analogous to the procedure of example 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| D004 | 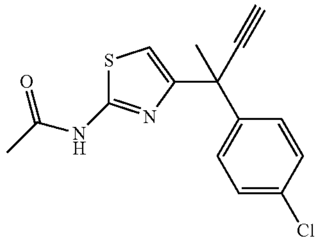 [SMILES: C#CC(C)(c1ccc(Cl)cc1)c1csc(NC(C)=O)n1] | N-(4-(2-(4-chlorophenyl)but-3-yn-2-yl)thiazol-2-yl)acetamide | $^1$H NMR (400 MHz, CDCl3) δ 9.98 (br s, 1H), 7.45 (d, J = 8.5 Hz, 2H), 7.30 (d, J = 8.5 Hz, 2H), 6.88 (s, 1H), 2.63 (s, 1H), 2.25 (s, 3H), 1.99 (s, 3H) | [M + H]$^+$ = 305 | 18 | 0.75 |
| D005 | 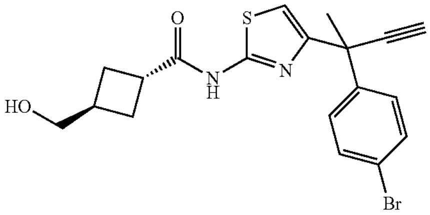 [SMILES: C#CC(C)(c1ccc(Br)cc1)c1csc(NC(=O)[C@H]2C[C@H](CO)C2)n1] | rac-(1r,3r)-N-(4-(2-(4-bromophenyl)but-3-yn-2-yl)thiazol-2-yl)-3-(hydroxymethyl) cyclobutanecarboxamide | $^1$H NMR (400 MHz, CDCl3) δ 8.67 (br s, 1 H), 7.42-7.45 (m, 2 H), 7.34-7.38 (m, 2 H), 6.90 (s, 1 H), 3.70 (br d, J = 3.6 Hz, 2 H), 3.11-3.20 (m, 1 H), 2.56-2.64 (m, 2 H) 2.45-2.53 (m, 2 H), 2.09-2.17 (m, 2 H), 1.95 (s, 3 H), 1.43 (br s, 1 H) | [M + H]$^+$ = 419.0 | 98 | 0.63 |
| D006 | 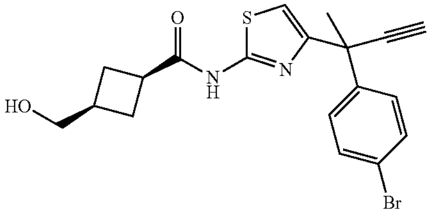 [SMILES: C#CC(C)(c1ccc(Br)cc1)c1csc(NC(=O)[C@H]2C[C@@H](CO)C2)n1] | rac-(1s,3s)-N-(4-(2-(4-bromophenyl)but-3-yn-2-yl)thiazol-2-yl)-3-(hydroxymethyl) cyclobutanecarboxamide | $^1$H NMR (400 MHz, CDCl3) δ 13.28 (s, 1 H), 7.48-7.56 (m, 4 H), 6.91 (s, 1 H), 3.65 (d, J = 4.4 Hz, 2 H), 3.32 (t, J = 7.6 Hz, 1 H), 2.78 (s, 1 H), 2.65-2.55 (m, 1 H), 2.43-2.52 (m, 2 H), 2.34-2.32 (m, 2 H), 2.15 (s, 3 H), | [M + H]$^+$ = 419.0 | 40 | 0.82 |
| D007 | 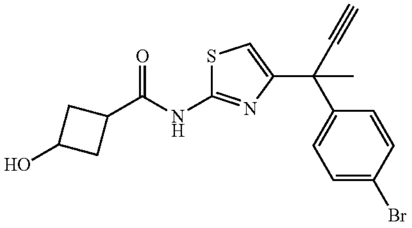 [SMILES: C#CC(C)(c1ccc(Br)cc1)c1csc(NC(=O)C2CC(O)C2)n1] | N-(4-(2-(4-bromophenyl)but-3-yn-2-yl)thiazol-2-yl)-3-hydroxycyclo-butanecarboxamide | $^1$H NMR (400 MHz, DMSO-d6) δ 12.10 (s, 1 H) 7.48-7.54 (m, 2 H) 7.34 (d, J = 8.53 Hz, 2 H) 7.09 (s, 1 H) 5.19 (d, J = 7.03 Hz, 1 H) 3.90-4.01 (m, 1 H) 3.51 (s, 1 H) 3.33 (s, 3 H) 2.63-2.71 (m, 1 H) 2.29-2.37 (m, 2 H) 1.94-2.04 (m, 2 H) 1.86 (s, 3 H) | [M + H]$^+$ = 405.0 | 55 | 0.97 |
| D008 | 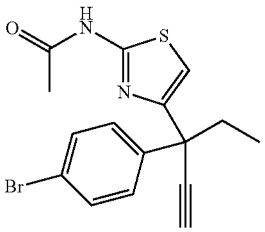 [SMILES: C#CC(CC)(c1ccc(Br)cc1)c1csc(NC(C)=O)n1] | N-(4-(3-(4-bromophenyl)pent-1-yn-3-yl)thiazol-2-yl)acetamide | $^1$H NMR (400 MHz, CHLOROFORM-d) δ 8.77 (s, 1 H), 7.45-7.38, (m, 4 H), 6.95 (s, 1 H), 2.63 (s, 1 H), 2.43-2.34 (m, 1 H), 2.24-2.14 (m, 4 H), 0.93 (t, J = 7.2 Hz, 3 H) | [M + H]$^+$ = 363.0 | 143 | 2.11 |

TABLE 7-continued

The following examples were synthesized analogous to the procedure of example 17 and 18 using the appropriate intermediates and the corresponding fragment

| Com. ID | Structure | Name | HNMR | LCMS | Kinase assay IC50 nM | NFkB assay IC50 nM |
|---|---|---|---|---|---|---|
| D009 | 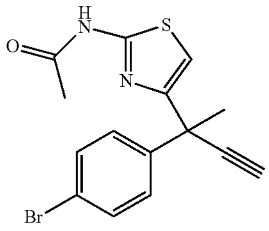 [SMILES: C#CC(C)(c1ccc(Br)cc1)c1csc(NC(C)=O)n1] | N-(4-(2-(4-bromophenyl)but-3-yn-2-yl)thiazol-2-yl)acetamide | $^1$H NMR (400 MHz, CDCl3) δ 8.79 (br s, 1H), 7.46-7.39 (m, 2H), 7.39-7.31 (m, 2H), 6.90 (s, 1H), 2.58 (s, 1H), 2.20 (s, 3H), 1.95 (s, 3H) | $[M + H]^+$ = 350.9 | 16 | 0.96 |
| D010 | 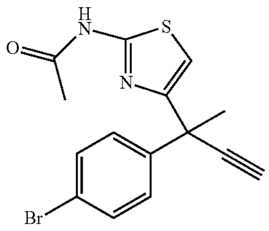 [SMILES: C#CC(C)(c1ccc(Br)cc1)c1csc(NC(C)=O)n1] | (R)-N-(4-(2-(4-bromophenyl)but-3-yn-2-yl)thiazol-2-yl)acetamide | $^1$H NMR (400 MHz, CDCl3) δ 8.74 (br s, 1H), 7.51-7.40 (m, 2H), 7.40-7.31 (m, 2H), 6.90 (s, 1H), 2.58 (s, 1H), 2.21 (s, 3H), 1.95 (s, 3H) | $[M + H]^+$ = 350.9 | 102 | 6.38 |
| D011 | 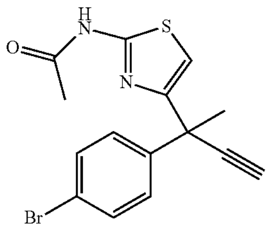 [SMILES: C#CC(C)(c1ccc(Br)cc1)c1csc(NC(C)=O)n1] | (S)-N-(4-(2-(4-bromophenyl)but-3-yn-2-yl)thiazol-2-yl)acetamide | $^1$H NMR (400 MHz, CDCl3) δ 8.78 (br s, 1H), 7.48-7.40 (m, 2H), 7.39-7.30 (m, 2H), 6.90 (s, 1H), 2.58 (s, 1H), 2.21 (s, 3H), 1.95 (s, 3H) | $[M + H]^+$ = 350.8 | 14 | 0.39 |

Example 20

6-((2-(dimethylamino)ethyl)amino-(N-(4-(2-(4-methoxyphenyl)propan-2-yl)thiazol-2-yl)nicotinamide

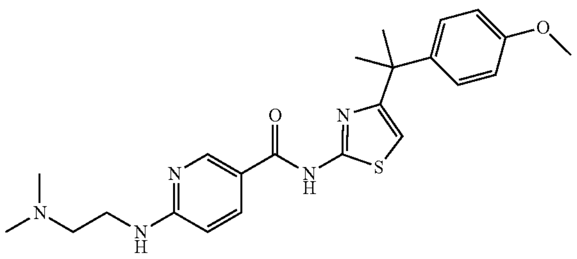

Step 1. Preparation of compound 6-chloro-N-(4-(2-(4-methoxyphenyl)propan-2-yl)thiazol-2-yl)nicotinamide

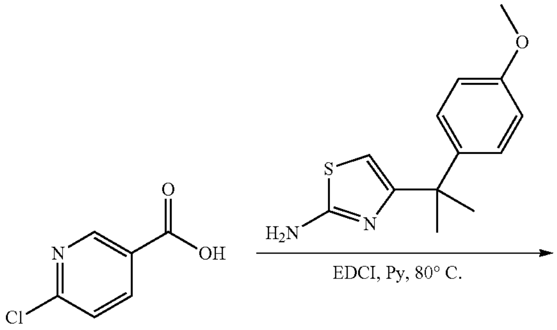

-continued

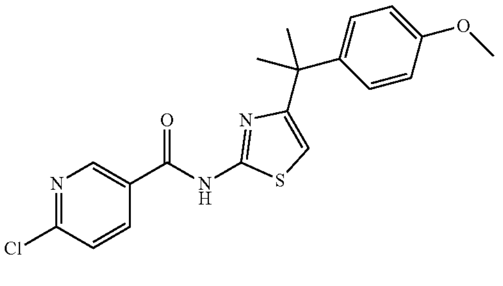

A mixture of compound 4-(2-(4-methoxyphenyl)propan-2-yl)thiazol-2-amine (100 mg, 0.35 mmol, HCl salt), compound 6-chloronicotinic acid (83.0 mg, 0.53 mmol) and EDCI (135 mg, 0.70 mmol) in pyridine (3 mL) was stirred at 80° C. for 2 h. The reaction mixture was concentrated. The residue was purified by silica gel chromatography (PE: EA=2:1). Desired compound (63 mg, 46.26% yield) was obtained as yellow oil.

MS (ESI) m/z $(M+H)^+$=388.0

Step 2. Preparation of compound 6-((2-(dimethylamino)ethyl)amino)-N-(4-(2-(4-methoxyphenyl)propan-2-yl)thiazol-2-yl)nicotinamide

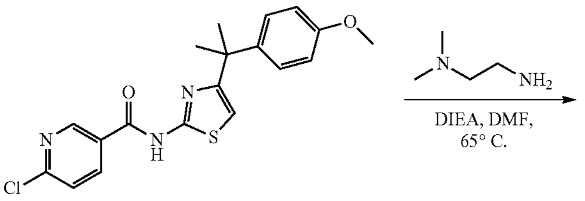

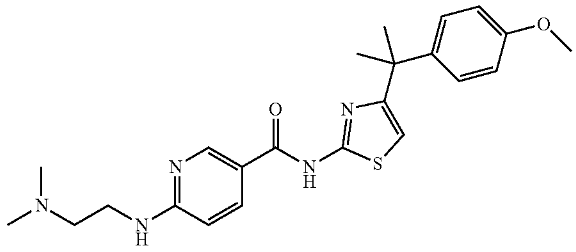

A mixture of compound obtained from step 1 above (63 mg, 0.16 mmol), N,N-dimethylethane-1,2-diamine (43.0 mg, 0.49 mmol) and DIEA (84.0 mg, 0.65 mmol) in DMF (5 mL) was stirred at 65° C. for 16 h. The reaction mixture was concentrated. The residue was purified prep-HPLC (water (0.05% HCl)-ACN]). The desired compound (25.01 mg, 35.0% yield) was obtained as a yellow solid.

1H NMR (400 MHz, MeOD) δ 8.43-8.32 (m, 1H), 8.18-8.11 (m, 1H), 7.35 (s, 1H), 7.23-7.14 (m, 3H), 6.83 (d, J:=8.8 Hz, 2H), 6.79 (s, 1H), 3.76 (m, 4H), 1.70 (s, 6H).

MS (ESI) m/z $(M+H)^+$=440.2

Example 21

Preparation of compound 6-((4-(2-hydroxyethyl)piperazin-1-yl)methyl)-N-(4-(2-(p-tolyl)roan-2-yl)thiazol-2-yl)nicotinamide

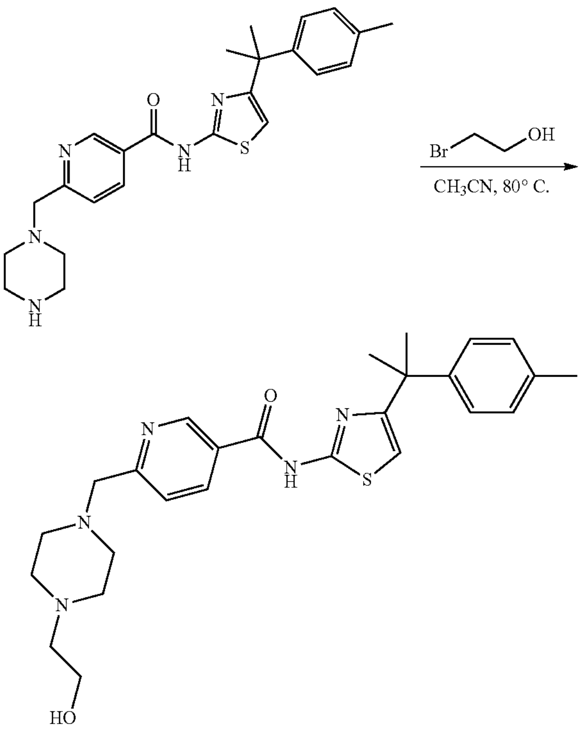

To a solution of compound 6-(piperazin-1-ylmethyl)-N-(4-(2-(p-tolyl)propan-2-yl)thiazol-2-yl)nicotinamide (0.03 g, 69 μmol, 1 eq) in $CH_3CN$ (10 mL) was added 2-bromoethanol (9.47 mg, 76 μmol, 5 μL, 1.1 eq) and $K_2CO_1$ (19 mg, 137.8 μmol, 2 eq). Then the reaction mixture was stirred at 80° C. for 16 hr. The reaction was concentrated under reduced pressure to afford a residue. The residue was purified by prep-HPLC (water (0.225% FA)-ACN]; B %:15%-45%, 7.5 min). Compound (2.3 mg, yield: 6.9%) was obtained as a white solid.

$^1H$ NMR (400 MHz, $CDC_3$) δ 9.09-9.05 (m, 1H), 8.33-8.28 (m, 1H), 7.75 (br d, J=8.8 Hz, 3H), 7.45-7.41 (m, 1H), 7.13-7.08 (m, 3H), 7.06-7.02 (m, 1H), 6.61-6.57 (m, 1H), 3.83-3.77 (m, 3H), 3.64-3.55 (m, 1H), 2.45-2.38 (m, 81H) 2.26-2.18 (m, 1H), 1.63-1.58 (m, 3H), 1.19 (s, 6H). MS (ESI) m/z $(M1+H)^+$=480.3.

Example 22

(1r,3r)-N-(4-(2-(4-bromophenyl)but-3-yn-2-yl)thiazol-2-yl)-3-(hydroxymethyl)cyclobutane-1-carboxamide

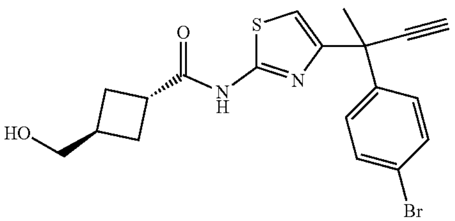 [SMILES: C#CC(C)(c1ccc(Br)cc1)c1csc(NC(=O)[C@H]2C[C@H](CO)C2)n1]

Step 1. Preparation of compound methyl 3-(((tert-butyldiphenylsilyl)oxy)methyl) cyclobutanecarboxylate

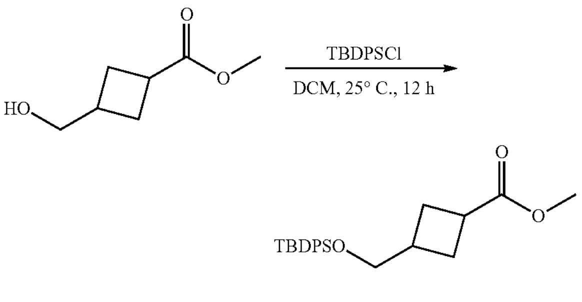

To a solution of methyl 3-(hydroxymethyl)cyclobutanecarboxylate (200 mg, 1.39 mmol) and imidazole (189 mg, 2.77 mmol) in DCM (5 mL) was added TBDPSCl (458 mg, 1.66 mmol, 427 p L) at 25° C. The solution was stirred for 12 h at 25° C. The mixture was diluted with DCM (30 mL), washed with $H_2O$ (3×10 mL), brine (10 mL), dried over anhydrous $Na_3SO$, filtered and concentrated in vacuum to give a residue. The residue was purified by silica column (ethyl acetate in petroleum ether=0-20%). The desired compound (420 mg, yield: 79.1%) was obtained as a yellow oil.

MS (ESI) m/z $(M+H)^+$=383.1

Step 2. Preparation of compound 3-(((tert-butyldiphenylsilyl)oxy)methyl) cyclobutanecarboxylic acid

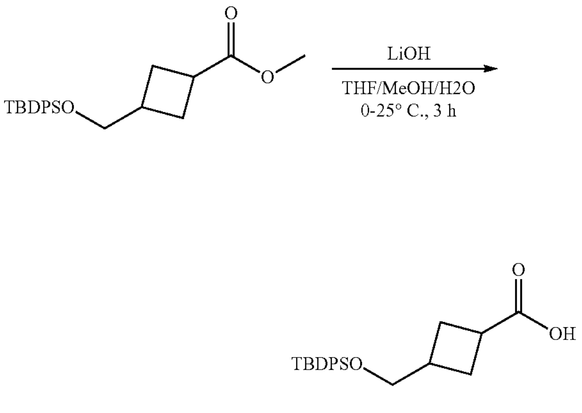

To mixture of compound obtained from step 1 above (412 mg, 1.08 mmol) in THF (1.5 mL)/MeOH (0.5 mL)/$H_2O$ (0.5 mL) was added LiOH·$H_2O$ (90.6 mg, 2.16 mmol) at 0° C. The mixture was stirred for 3 h at 25° C. The mixture was diluted with $H_2O$ (15 mL), adjusted pH=6-7, extracted with EA (15 mL×3). The combined organic layers were washed with brine (10 mL), dried over anhydrous $Na_2SO_4$, filtered and concentrated in vacuum to give a residue. The desired compound (413 mg, crude) was obtained as a yellow solid. The crude product was directly used for next step without further purification MS (ESI) m/z $(M+Na)^+$=391.1

Step 3. Preparation of compound methyl 2-(4-bromophenyl)-2-(2-((1R, 3R)-3-(((tert-butyldiphenylsilyl)oxy)methyl)cyclobutanecarboxamido)thiazol-4-yl)propanoate

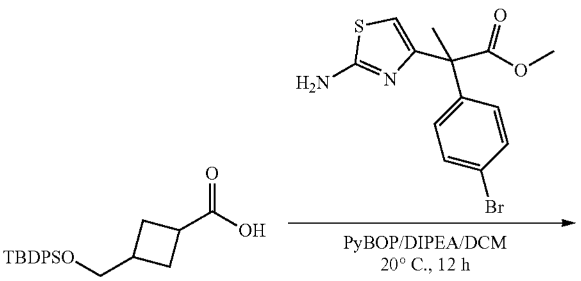

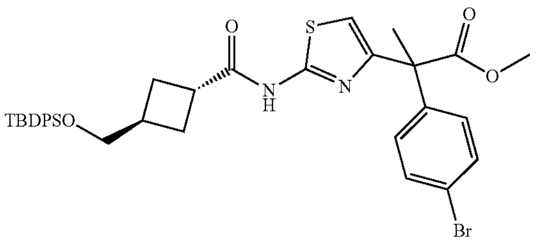

+

A

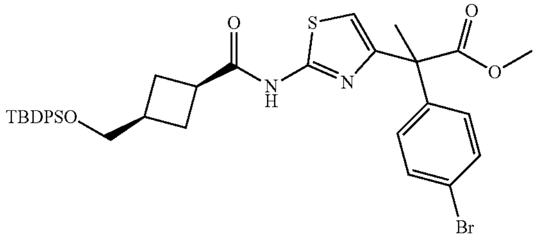

B

To solution of compound obtained from step 2 above (410 mg, 1.11 mmol) and DIPEA (173 mg, 1.34 mmol, 233 μL) in DCM (5 mL) was stirred for 10 min at 20° C. Methyl 2-(2-aminothiazol-4-vi)-2-(4-bromophenyl)propanoate (152 mg, 446 μmol) and PyBOP (580 mg, 1.11 mmol) was added at 20° C. The mixture was stirred for 12 h at 20° C. The mixture was diluted with DCM (30 mL), washed with 120 (10 mL), brine (10 mL), dried over anhydrous $Na_2SO_4$, filtered and concentrated in vacuum to give a residue. The residue was purified by silica column (ethyl acetate in petroleum ether-O-20%). The desired compound A (194 mg, crude) was obtained as a yellow oil. The other desired compound B (186 mg, crude) obtained as a yellow oil. The crude product was directly used for next step without further purification. The chiral of the products were confirmed in the final step.

Step 4. Preparation of compound (1R,3R)—N-(4-(2-(4-bromophenyl)-1-hydroxypropan-2-yl)thiazol-2-yl)-3-(((tert-butyldiphenylsilyl)oxy)methyl)cyclobutanecarboxamide

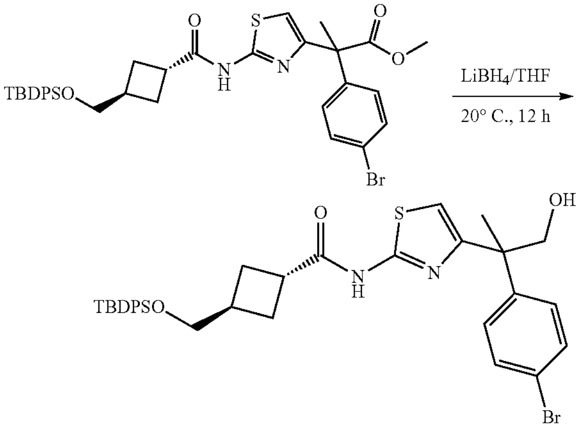

To a solution of compound obtained from step 3 above (194 mg, 280.4 μmol) in THF (5 mL) was added $LiBH_4$ (31 mg, 10.40 mmol) at 20° C. The mixture was stirred at 20° C. for 12 h. The mixture was quenched with sat. $NH_4Cl$ aq (10 mL), diluted with $H_2O$ (20 mL) and extracted with EA (20 mL×3). The organic layer was washed with brine (10 mL), dried over anhydrous $Na_2SO_4$, filtered and concentrated in vacuum to give a residue. The residue was purified by silica column (ethyl acetate in petroleum ether=0-30%). The desired compound (77 mg, yield: 41.4%) was obtained as a yellow oil.

MS (ESI) m/z $(M+H)^+$=663.1

Step 5. Preparation of compound (1R,3R)—N-(4-(2-(4-bromophenyl)-1-oxopropan-2-yl)thiazol-2-yl)-3-(((tert-butyldiphenylsilyl)oxy)methyl)cyclobutanecarboxamide

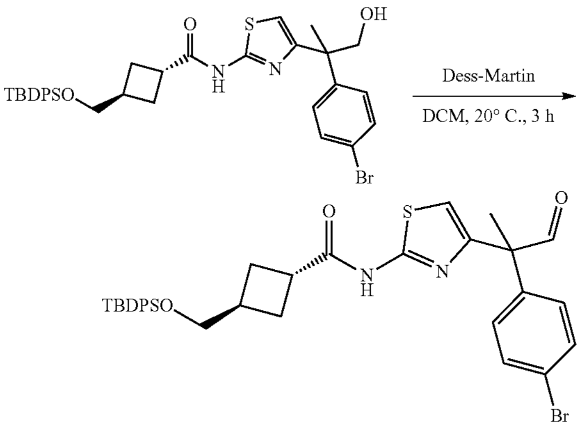

To a mixture of Dess-Martin (73 mg, 171.2 μmol, 53 μL) in DCM (2 mL) was added the solution of compound obtained from step 4 above (77 mg, 132 μmol) in DCM (2 mL) at 20° C. The mixture was stirred for 3 h at 20° C. The mixture was quenched with sat. $NaHCO_3$ (10 mL)/sat $Na_2S_2O_4$ (10 mL), extracted with DCM (15 mL×3). The combined organic layers were washed with brine (10 mL), dried over anhydrous $Na_2SO_4$, filtered and concentrated in vacuum to give a residue. The desired compound (77 mg, crude) was obtained as a yellow solid. The crude product was directly used for next step without further purification.

Step 6. Preparation of compound (JR, 3R)—N-(4-(2-(4-bromophenyl)but-3-yn-2-yl)thiazol-2-yl)-3-(((tert-butyldiphenylsilyl)oxy)methyl)cyclobutanecarboxamide

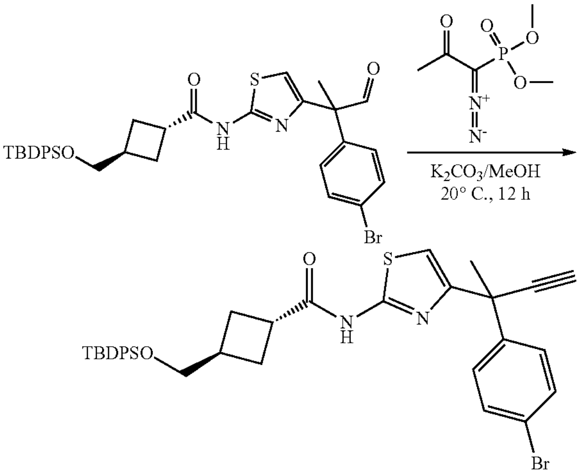

To a solution of compound obtained from step 5 above (77 mg, 116 μmol), 1-diazo-1-dimethoxyphosphoryl-propan-2-one (34 mg, 174.5 μmol) and $K_2CO_3$ (32 mg, 232.7 μmol) in MeOH (2 mL) was stirred for 12 h at 20° C. The mixture was concentrated in vacuum to give a residue. The residue was purified by silica column (ethyl acetate in petroleum ether=0-15%). The desired compound (37 mg, yield: 48.3%) was obtained as a yellow oil.

MS (ESI) m/z $(M+H)^+$=657.1

Step 7. Preparation of compound (1R,3R)—N-(4-(2-(4-bromophenyl)but-3-yn-2-yl)thiazol-2-yl)-3-(hydroxymethyl)cyclobutanecarboxamide

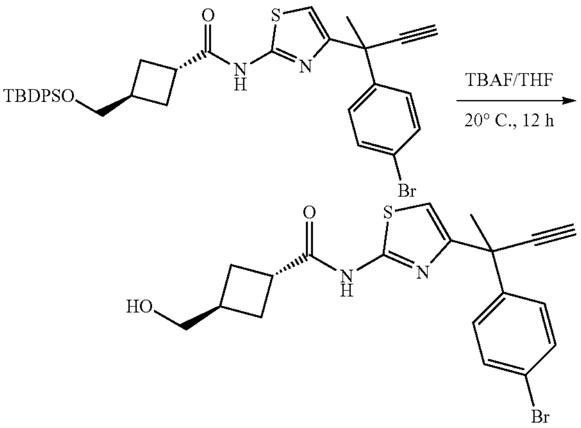

To a solution of compound obtained from step 6 above (37 mg, 56.3 μmol) in THF (2 mL) was added TBAF (1 M, 0.1 mL) at 20° C. The mixture was stirred for 12 h at 20° C. The mixture was diluted with EA (50 mL),washed with $H_2O$ (10 mL×3), brine (10 mL), dried over anhydrous $Na_2SO_4$, filtered and concentrated in vacuum to give a residue The residue was purified by silica column (ethyl acetate in petroleum ether=0-15%). The desired compound (12.61 mg, yield: 53.5%) was obtained as a yellow solid.

$^1H$ NMR (400 MHz, $CDCl_3$-d) δ=13.28 (br s, 1H), 7.56-7.48 (m, 4H), 6.91 (s, 1H), 3.65 (d, J=4.4 Hz, 2H), 3.34-3.30 (m, 1H), 2.77 (s, I H), 2.63-2.61 (m, 1H), 2.52-243 (m, 2H), 2.34-2.32 (m, 2H), 2.15 (s, 3H). MS (ESI) m/z $(M+H)^+$=419.0.

The other isomer was synthesized using the similar procedure above.

Example 23

4-((4-(2-hydroxyethyl)piperazine-1-yl)methyl)-N-(4-(2-(4-methoxyphenyl)propan-2-yl)triazol-2-yl)benzamide

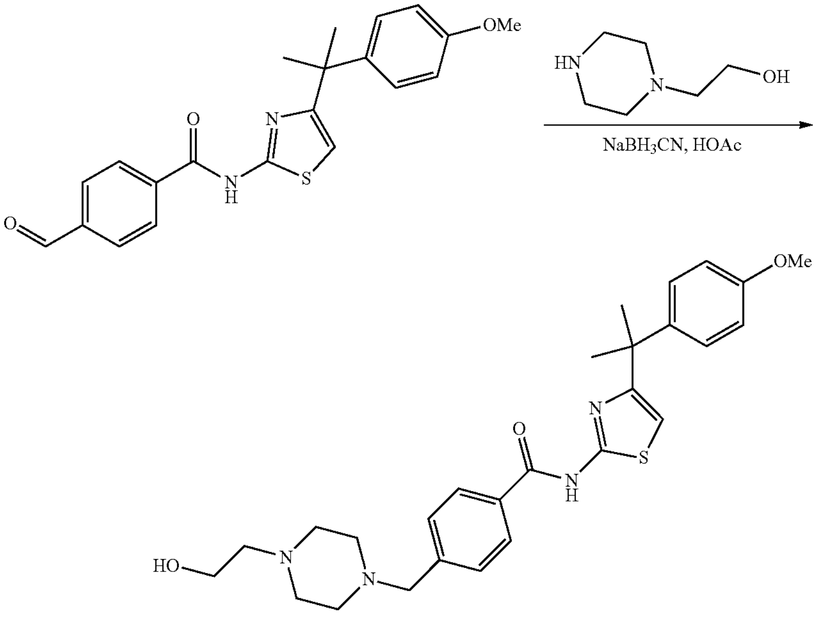

To a solution of compound 4-formyl-N-(4-(2-(4-methoxyphenyl)propan-2-yl)thiazol-2-yl)benzamide (120 mg, 0.32 mmol) and 2-(piperazin-1-yl)ethan-1-ol (42 mg, 0.32 mmol) in DCM (5 mL) was added $NaBH_3CN$ (59 mg, 0.95 mmol) and HOAc (2 drops). The mixture was stirred at r.t overnight. The reaction mixture was concentrated to give a residue. The residue was purified by flash silica gel chromatography (DCM:MeOH=1:0 to 10:1). The desired compound (80 mg, yield: 51.4%) was obtained as a white solid.

MS (EST) m/z $(M+H)^+$=495.2

Methods of Use

ALPK1 is an intracytoplasmic serine threonine protein kinase that plays an important role in activating the innate immune response. ALPK1 binds to the bacterial pathogen-associated molecular pattern metabolite (PAMP), ADP-D-glycero-beta-D-manno-heptose (ADP-heptose). ALPK1-ADP-heptose binding occurs through direct interaction at the ALPK1 N-terminal domain. This interaction stimulates the kinase activity of ALPK1 and its phosphorylation and activation of TRAF-interacting protein with forkhead-associated domain (TIFA). In turn, TIFA activation triggers proinflammatory NFkB signaling, including proinflammatory cytokine and chemokine expression and/or secretion. Accordingly, the compounds disclosed herein are generally useful as inhibitors of ALPK1 kinase activity and downstream activation of NFkB proinflammatory signaling.

The disclosure provides for the use of a compound of Formula 1, or a subembodiment thereof as described herein, for inhibiting ALPK1 kinase activity and reducing inflammation in a target tissue. The methods also encompass the use of a compound of Formula L or a subembodiment thereof as described herein, for treating a disease, disorder, or condition characterized by excessive or inappropriate ALPK1-dependent proinflammatory signaling. In embodiments, the disease is Kawasaki disease.

In embodiments, the disclosure provides methods for inhibiting ALPK1 kinase activity in a mammalian cell or target tissue by contacting the cell or target tissue with a compound of Formula T, or a subembodiment described herein. In embodiments, the methods comprise administering a pharmaceutical composition comprising a compound of Formula I, or a subembodiment described herein, to a subject in an amount effective to inhibit ALPK1 kinase activity in a target cell or tissue of the subject. In embodiments, the methods comprise reducing inflammation in a target tissue of a subject in need of such therapy by administering to the subject a compound of Formula I, or a subembodiment described herein, or a pharmaceutical composition comprising same.

In embodiments, the disclosure provides methods of treating a subject having a disease or disorder characterized by excessive or inappropriate activation of ALPK1 kinase activity, the methods comprising administering to the subject a compound of Formula I, or a subembodiment described herein. In embodiments, the disease is Kawasaki disease. In embodiments, the disclosure further provides methods of identifying a disease, disorder, or condition for treatment with a compound of Formula I, or a subembodiment described herein, the methods comprising assaying a biological sample from a subject diagnosed with the disease, disorder, or condition for one or more of an activating mutation in ALPK1, and overexpression of ALPK1 mRNA or protein in cells or tissues involved in the disease, disorder, or condition, as compared to cells or tissues of a reference not involved in the disease, disorder, or condition. In embodiments, the activating mutation in ALPK1 is 2770T>C, p. (S924P)

In the context of the methods described here, the term "treating" may refer to the amelioration or stabilization of one or more symptoms associated with the disease, disorder or condition being treated. The term "treating" may also encompass the management of disease, disorder or condition, referring to the beneficial effects that a subject derives from a therapy but which does not result in a cure of the underlying disease, disorder, or condition.

In embodiments where a therapeutically effective amount of a compound described herein is administered to a subject, the therapeutically effective amount is the amount sufficient to achieve a desired therapeutic outcome, for example the amelioration or stabilization of one or more symptoms of the disease, disorder or condition being treated.

In embodiments, a therapeutically effective amount is the amount required to achieve at least an equivalent therapeutic effect compared to a standard therapy. An example of a standard therapy is an FDA-approved drug indicated for treating the same disease, disorder or condition.

In the context of any of the methods described here, the subject is preferably a human but may be a non-human mammal, preferably a non-human primate. In other embodiments, the non-human mammal may be, for example, a dog, cat, a rodent (e.g., a mouse, a rat, a rabbit), a horse, a cow, a sheep, a goat, or any other non-human mammal.

In embodiments, the human subject is selected from an adult human, a pediatric human, or a geriatric human, as those terms are understood by the medical practitioner, for example as defined by the U.S. Food and Drug Administration.

The disclosure provides methods of treating Kawasaki disease, the methods comprising administering a pharmaceutical composition comprising a compound of Formula I, or a subembodiment described herein, to a subject in need of such treatment.

In embodiments, the methods described here may include monotherapy with a compound of Formula (I), or a subembodiment described herein, or combination therapy, for example a therapeutic regimen comprising a compound of Formula (I), or a subembodiment described herein, in combination with one or more additional therapies or active agents. In embodiments, the administration of a compound of Formula (I), or a subembodiment described herein, or a therapeutic regimen comprising same, leads to the reduction or elimination of at least one symptom of a disease or disorder characterized by excessive or inappropriate activation of ALPK1 kinase activity (e.g., Kawasaki disease) being treated or improvement in at least one marker of disease progression or disease severity. In embodiments, the methods reduce autoantibody production and resulting autoimmune sequelae and pathologies as measured by the appropriate disease related scale.

In embodiments directed to methods of treating Kawasaki disease, the administration of a compound of Formula (I), or a subembodiment described herein, or a therapeutic regimen comprising a compound of Formula (1), or a subembodiment described herein, and at least one additional therapy or therapeutic agent, leads to the reduction or elimination of at least one symptom of Kawasaki disease. In embodiments, the at least one symptom of Kawasaki disease is selected from a fever, red eyes, rash, red and swollen tongue or lips, swollen and red skin, swollen lymph nodes, bilateral conjunctival injection, oral mucosal changes, irritability, peeling of skin, joint pain, diarrhea, vomiting, and abdominal pain.

In embodiments directed to methods of treating Kawasaki disease, the administration of a compound of Formula (I), or a subembodiment described herein, or a therapeutic regimen comprising a compound of Formula (I), or a subembodiment described herein, and at least one additional therapy or therapeutic agent, leads to the reduction or elimination of at least one marker of disease progression or disease severity. Such markers may include, but not limited to, inflammatory biomarkers selected from erythrocyte sedimentation rate (ESR), total leucocyte count(TLC), platelet count, mean platelet volume (MPV), platelet distribution width (PDW), C-Reactive protein (CRP), procalcitonin, and peripheral blood eosinophilia (PBE); immunological biomarkers selected from CD8 T cells, Th1 cells, Th2 cells, CD14+ monocytes, CD69+CD8T cells, effector memory T-cells (Tem), regulatory T cells (Treg), central memory T-cells (Tem), myeloid and plasmocytoid dendritic cells (DC), Th17 proportions, IFN-Y and IL-2, IL-4, IL-10, IL-6, IL-17A/F, ROR-gt, TGF-b, TNFa, CXCL10 (IP-10), and CCL-2; and proteomic biomarkers selected from NT-pro BNP, suppression of tumorigenicity 2(sST2), cardiac troponin I (cTnI)r, periostin, gamma-glutamyl transferase(GGT) and alanine transferase (ALT), clusterin, thrombospondin (TSP-I and TSP-2), fibrinogen beta and gamma chains, CD5 antigen-like precursor (CD5L), nitric oxide synthases (iNOS), periostin, lipopolysaccharide-binding protein (LBP), leucine-rich alpha-2-glycoprotein (LRG1), angiotensinogen (AGT), tenacin-C, and urine protein markers (e.g., filamin, talin, complement regulator CSMD3, immune pattern recognition receptor muclin, and immune cytokine protease meprin A) (Chaudhary, et. al. *Front Pediatr.* 2019; 7:242).

Kawasaki Disease

Kawasaki disease (KD) ("Kawasaki syndrome" or "mucocutaneous lymph node syndrome") is a disease that causes inflammation in arteries, veins, and capillaries in children, generally children younger than 5 years of age. Clinical manifestations include fever, rash, swelling of the hands and feet, irritation and redness of the whites of the eyes, swollen lymph glands in the neck, and irritation and inflammation of the mouth, lips, and throat. Kawasaki disease may also cause heart disease in childhood.

The cause of Kawasaki disease is unknown, but it is believed to result from an excessive immune response to an infection in children who are genetically predisposed (McCrindle, et al. *Circulation.* 135 (17): e927-e999). Genetic factors are also thought to influence pathology and response to treatment, in particular the development of coronary artery aneurysms, but the exact nature of the genetic contribution remains unknown (Lo et al. *Clinical Immology* 2020 214: 108385). A majority of association studies have implicated genes with immune regulatory functions (Dietz, et al. *European Journal of Pediatrics.* 176 (8): 995-1009, 2017). For example, SNPs in FCGR2A, CASP3, BLK, ITPKC, CD40 and ORAI1 may be linked to susceptibility, prognosis, and risk of developing coronary artery aneurysms (Elakabawi, et al. *Cardiology Research.* 11 (1): 9-14, 2020).

Children with Kawasaki disease are typically treated with intravenous immunoglobulin (IVIG) and/or salicylate therapy administered in high doses of aspirin, which gives improvement usually within 24 hours (Baumer, et al. *The Cochrane Database of Systematic Reviews*, October 2006). Alternatively, only salicylate therapy (e.g., aspirin) is started at high doses until the fever subsides, and then is continued at a low dose usually for two months to prevent blood clots from forming. Corticosteroids have also been used, especially when other treatments fail or symptoms recur (Sundel, et al. *The Journal of Pediatrics.* 142 (6): 611-16, 2003).

"Periodic Fever, Aphthous Stomatitis, Pharyngitis, and Adenitis" ("PFAPA") syndrome is characterized as a "periodic disease" because it presents as short episodes of illness alternating with healthy periods, typically recurring about monthly or from 21-28 days. The illness presents with a high fever lasting several days and accompanied by some or all of the symptoms identified in its name (mouth sores or "aphthous stomatitis", sore throat or "pharyngitis", and enlarged lymph nodes of "cervical adenitis"). While both PFAPA and Kawasaki disease are rare diseases, patients with Kawasaki disease are predisposed to developing PFAPA compared to the general population. In addition, there is at least one reported case of a PFAPA patient developing Kawasaki disease. The intersection of these patient cohorts may represent a shared genetic predisposition to dysregulated innate immune responses. Since genetic mutations in ALPK1 have been found to cause PFAPA, ALPK1 mutations in PFAPA pateints may also predispose those patients to develop Kawasaki disease (Broderick, et al, *Pediatrics.* 2011 February; 127(2):e489-93; Ninomiya, et ad. *Pediatr Int.* 2013 December; 55(6):801-2).

Kawasaki patients may also develop vasculitis and cardiac disorders. Kawasaki patients who do not respond the IVIG treatment may experience an inflammatory cascade that produces endothelial dysfunction and vascular wall damage. This cascade also results in aneurysmal dilation in some Kawasaki patients. Therefore, some severe Kawasaki patients experience coronary artery diseases and myocardial infarction. In a study comprised of 5,771 community-dwelling individuals recruited in Japan, two ALPK1 single nucleotide polymorphisms, SNPs rs2074380 and rs2074381, contributed to genetic susceptibility to myocardial infarction. (Fujimaki, et al. *Biomedical Reports,* 2013 2:127-131). In another study by Yamada, these same two ALPK1 polymorphisms were significantly associated with the prevalence of chronic artery disease. (Yamada, et al. *Biomedical Reports,* 2015 3:413-419). Further linking ALPK1 to cardiovascular complications is the finding that oxidative stress, oxidized low density lipoprotein (LDL), atheroprone flow and hyperlidemia activate the TIFA-NLRP3 pathway in human umbilical vein endothelial cells (HUVECs). ALPK1 is also likely activated by these stimuli, since ALPK1 phosphorylates TIFA for downstream NLRP3 activation in endothelial cells (Lin et al, *PNAS,* 113, 52, 15078-15083). Accordingly, in embodiments of the methods described here, the subject in need of therapy is a human subject diagnosed with Kawasaki disease carrying one or both of the ALPK1 SNPs defined by rs2074380 and rs2074381.

Combination Therapy

The present disclosure also provides methods comprising combination therapy. As used herein, "combination therapy" or "co-therapy" includes the administration of a therapeutically effective amount of a compound of Formula (I), or a pharmaceutically acceptable salt thereof, with at least one additional therapy or active agent, also referred to herein as an "active pharmaceutical ingredient" ("API"), as part of a treatment regimen intended to provide a beneficial effect from the co-action of the compound of Formula (I), or a pharmaceutically acceptable salt thereof, and the additional active agent. In accordance with the embodiments described below, "the additional API" is understood to refer to the at least one additional therapeutic agent administered in a combination therapy regimen with a compound of Formula (1), or a pharmaceutically acceptable salt thereof. The additional API may be administered in the same or a separate dosage form from the compound of Formula (I), or a pharmaceutically acceptable salt thereof; and the additional API may be administered by the same or a separate route of administration than the compound of Formula (I), or a pharmaceutically acceptable salt thereof. In addition, it is understood that more than one of the additional APIs described below may be utilized in the combination therapy regimen. The terms "combination therapy" or "combination therapy regimen" are not intended to encompass the administration of two or more therapeutic compounds as part of separate monotherapy regimens that incidentally and arbitrarily result in a beneficial effect that was not intended or predicted.

Preferably, the administration of a composition comprising a compound of Formula (I), or a pharmaceutically acceptable salt thereof, in combination with one or more additional APIs as discussed herein provides a synergistic response in the subject being treated. In this context, the term "synergistic" refers to the efficacy of the combination being more than the additive effects of either single therapy alone.

The synergistic effect of a combination therapy according to the disclosure can permit the use of lower dosages and/or less frequent administration of at least one agent in the combination compared to its dose and/or frequency outside of the combination. Additional beneficial effects of the combination can be manifested in the avoidance or reduction of adverse or unwanted side effects associated with the use of either therapy in the combination alone (also referred to as monotherapy).

In the context of combination therapy, administration of a composition including the compound of Formula (I), or a pharmaceutically acceptable salt thereof may be simultaneous with or sequential to the administration of the one or more additional active agents or APIs. In another embodiment, administration of the different components of a combination therapy may be at different frequencies.

In embodiments, the additional API may be formulated for co-administration with a composition including the compound of Formula (I), or a pharmaceutically acceptable salt thereof in a single dosage form. The additional API(s) may also be administered separately from the dosage form that comprises the compound of Formula (I), or a pharmaceutically acceptable salt thereof. When the additional active agent is administered separately from the compound of Formula (I), or a pharmaceutically acceptable salt thereof, it can be by the same or a different route of administration, and/or at the same or different time.

In embodiments directed to methods of combination therapy for treating a disease or disorder characterized by excessive or inappropriate activation of ALPK1 kinase activity (e.g., Kawasaki disease), the methods may comprise administering a compound of Formula (I), or a subembodiment thereof as described herein, and at least one additional therapeutic agent selected from IVIG therapy, salicylate therapy, and corticosteroid therapy. In further embodiments, the additional therapeutic agent is an inhibitor of an inflammatory cytokine such as IL-1, TNFalpha, IL-17, IL-23 and cholesterol-lowering drugs including atorvastatin.

Pharmaceutical Compositions

In embodiments, the disclosure provides pharmaceutical compositions comprising a compound of Formula I, or a subembodiment thereof, as described herein, and one or more carriers or excipients, preferably pharmaceutically acceptable carriers or excipients. As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Excipients for preparing a pharmaceutical composition are generally those that are known to be safe and non-toxic when administered to a human or animal body. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, and suitable mixtures of any of the foregoing. The particular excipients utilized in a composition will depend upon various factors, including chemical stability and solubility of the compound being formulated and the intended route of administration.

A pharmaceutical composition can be provided in bulk or unit dosage form. It is especially advantageous to formulate pharmaceutical compositions in unit dosage form for ease of administration and uniformity of dosage. The term "unit dosage form" refers to physically discrete units suited as unitary dosages for the subject to be treated; each unit containing a predetermined quantity of an active compound calculated to produce the desired therapeutic effect in association with the required pharmaceutical carrier. A unit dosage form can be an ampoule, a vial, a suppository, a dragee, a tablet, a capsule, an IV bag, or a single pump on an aerosol inhaler.

In therapeutic applications, dose may vary depending on the chemical and physical properties of the active compound as well as clinical characteristics of the subject, including e.g., age, weight, and co-morbidities. Generally, the dose should be a therapeutically effective amount. An effective amount of a pharmaceutical composition is that which provides an objectively identifiable improvement as noted by the clinician or other qualified observer. For example, alleviating a symptom of a disorder, disease or condition.

A pharmaceutical composition as described herein may take any suitable form (e.g. liquids, aerosols, solutions, inhalants, mists, sprays; or solids, powders, ointments, pastes, creams, lotions, gels, patches and the like) for administration by any desired route (e.g. pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). In embodiments, the pharmaceutical composition is in the form of an orally acceptable dosage form including, but not limited to, capsules, tablets, buccal forms, troches, lozenges, and oral liquids in the form of emulsions, aqueous suspensions, dispersions or solutions. Capsules may contain excipients such as inert fillers and/or diluents including starches (e.g., corn, potato or tapioca starch), sugars, artificial sweetening agents, powdered celluloses, such as crystalline and microcrystalline celluloses, flours, gelatins, gums, etc. In the case of tablets for oral use, carriers which are commonly used include lactose and corn starch. Lubricating agents, such as magnesium stearate, can also be added.

In embodiments, the pharmaceutical composition is in the form of a tablet. The tablet can comprise a unit dose of a compound described here together with an inert diluent or carrier such as a sugar or sugar alcohol, for example lactose, sucrose, sorbitol or mannitol. The tablet can further comprise a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. The tablet can further comprise binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. butylated hydroxytoluene), buffering agents (e.g. phosphate or citrate buffers), and effervescent agents such as citrate/bicarbonate mixtures. The tablet may be a coated tablet. The coating can be a protective film coating (e.g. a wax or varnish) or a coating designed to control the release of the active compound, for example a delayed release (release of the active after a predetermined lag time following ingestion) or release at a particular location in the gastrointestinal tract. The latter can be achieved, for example, using enteric film coatings such as those sold under the brand name Eudragit®.

Tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, tale, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecyl sulfate, magnesium aluminum silicate, and triethanolamine.

In embodiments, the pharmaceutical composition is in the form of a hard or soft gelatin capsule. In accordance with this formulation, the compound of the present invention may be in a solid, semi-solid, or liquid form.

In embodiments, the pharmaceutical composition is in the form of a sterile aqueous solution or dispersion suitable for parenteral administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

In embodiments, the pharmaceutical composition is in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions can be prepared in water with the aid of co-solvent or a surfactant. Examples of suitable surfactants include polyethylene glycol (PEG)-fatty acids and PEG-fatty acid mono and diesters, PEG glycerol esters, alcohol-oil transesterification products, polyglyceryl fatty acids, propylene glycol fatty acid esters, sterol and sterol derivatives, polyethylene glycol sorbitan fatty acid esters, polyethylene glycol alkyl ethers, sugar and its derivatives, polyethylene glycol alkyl phenols, polyoxyethylene-polyoxypropylene (POE-POP) block copolymers, sorbitan fatty acid esters, ionic surfactants, fat-soluble vitamins and their salts, water-soluble vitamins and their amphiphilic derivatives, amino acids and their salts, and organic acids and their esters and anhydrides. Dispersions can also be prepared, for example, in glycerol, liquid polyethylene glycols and mixtures of the same in oils.

The present disclosure also provides packaging and kits comprising pharmaceutical compositions for use in the methods described here. The kit can comprise one or more containers selected from the group consisting of a bottle, a vial, an ampoule, a blister pack, and a syringe. The kit can further include one or more of instructions for use, one or more syringes, one or more applicators, or a sterile solution suitable for reconstituting a compound or composition described here.

All percentages and ratios used herein, unless otherwise indicated, are by weight.

The invention is further described and exemplified by the following non-limiting examples.

EXAMPLES

In embodiments, a compound of Formula I, or a subembodiment described herein, is an inhibitor of ALPK1 as measured, for example, in an in vitro kinase assay, or an assay designed to measure the activation of downstream targets of ALPK1 pathway activation, for example NFkB transcriptional activation and the secretion of proinflammatory cytokines and chemokines, such as IL-8, which is also referred to as CXCL-8. In another example, ALPK1 inhibitory activity is measured in an assay utilizing THP-1-derived macrophage cells. In this assay, the ALPK1-TIFA-IL1β pathway is activated by an ALPK1 agonist, D-glycero-D-manno-6-fluoro-heptose-1β-S-ADP. Inhibitory activity is measured as suppression of IL1β in the presence of a compound of Formula I, or a subembodiment described herein. In another example, ALPK1 inhibitory activity is measured in an in vivo gene expression study using a panel of genes involved in innate immunity whose expression is induced upon ALPK1 activation in coronary artery, aorta and heart muscle. In another example, ALPK1 inhibitory activity is measured in an in vivo gene expression study using a panel of genes involved in innate immunity whose expression is induced upon ALPK1 activation in PBMC cells. In general, the computer program XL fit was used for data analysis, including non-linear regression analysis. The half maximal inhibitory concentration (IC50) was used as the measure of a compound's effectiveness in the assays. IC50 values were determined using the following logistic equation Y=min+(max−min)/(1+(X/IC50^−hillslope), where Y is the value at the compound concentration, X. The concentration response curve fitting was conducted using GraphPad Prism version 6.00 software.

ALPK1 in vitro Kinase Assay

ALPK1 kinase activity was measured in an in vitro assay using ADP-Heptose as the ALPK1 ligand and activator of its kinase activity and TIFA protein as the ALPK1 phosphorylation substrate. Since phosphorylated TIFA proteins oligomerize, Homogeneous Time-Resolved Fluorescence (HTRF) was used to measure protein:protein interaction between HA-tagged TIFA proteins as an indicator of TIFA phosphorylation.

In brief, dose-response studies were performed with HEK293 cells cultured in Dulbecco's Modified Eagle Medium (DMEM) supplemented 10% fetal bovine serum (FBS, Hyclone™) containing antibiotics (pen/strep, G418) in 384-well assay plates. Each well contained 0.1 mg TIFA, ALPK1 (2 nM final concentration in reaction mixture) and kinase buffer (100 mM of HEPES pH 7.4, 4 mM DTT, 40 mM $MgCl_2$, 20 mM of β-Glycerol phosphate disodium salt, 0.4 mM of $Na_3VO_4$, 0.16 mg/mL). Titrations of the test compounds were prepared in dimethylsulphoxide (DMSO). The reaction was initiated by addition of ATP and ADP-Heptose.

For HTRF, samples were incubated with a Tb cryptate-labeled anti-HA antibody for capturing HA-tagged proteins according to the manufacturer's instructions (PerkinElmer™, CisBio™) and the fluorescence signal was quantified (Tecan Infinite F NANO+). HTRF signals were calculated as the HTRF ratio (ratio of fluorescence measured at 665 nm and 620 nm)×104 (thereby using the signal at 620 nm as an internal standard).

All compounds exhibited a dose-dependent decrease in TIFA phosphorylation in this assay. IC50 values were determined using 3- or 4-parameter logistic equation using GraphPad Prism version 6.00. The reference compound, A027, was used as a positive control for each plate. This compound has an IC50 of ~50 nanomolar (nM) in this assay. IC50 values for the test compounds ranged from I to 1000 nM and are shown in Tables 4-7.

NFκB Gene Reporter Alkaline Phosphatase Assay

An alkaline phosphatase reporter assay system was used to measure inhibition of ALPK1-dependent NFκB reporter gene activation. Briefly, HEK293 cells stably expressing an NF-kB reporter (referred to herein as "G9 cells") were maintained in DMEM as described above. For the assay, cells were seeded into 96-well plates at a density of 10,000 cells/well in Freestyle-M 293 Expression Medium (ThermoFisher), and allowed to attach overnight. Cells were pretreated with serially diluted compounds for 30 min and then stimulated with D-glycero-D-manno-6-fluoro-heptose-1β-S-ADP. This compound is an analog of ADP-heptose that shows increased stability in vitro along with a similar ability to activate ALPK1 kinase activity. NFkB gene activation was detected using the chromogenic substrate, para-nitrophenyl phosphate (pNPP) according to the manufacturer's protocols (pNPP Phosphatase Assay, Beyotine Biotechnology). All compounds exhibited a dose-dependent decrease in NFkB promoter-driven gene expression in this assay. IC50 values ranged from 1-10 micromolar (uM) and are shown in Tables 4-7.

PMA-Differentiated THP-1 Cell Based Assay

Peripheral blood mononuclear cells (PBMCs) from Kawasaki patients show activation of ALPK1-TIFA-IL1β pathway. We evaluated the ability of ALPK1 inhibitors to suppress IL1β levels following ALPK1 activation in THP-1-derived macrophage cells in which the ALPK1-TIFA-IL1β pathway is activated by an ALPK1 agonist, D-glycero-D-manno-6-fluoro-heptose-1β-S-ADP.

THP-1 cells were cultured in RPMI 1640 containing 10% heat inactivated FBS, penicillin (100 units/ml) and streptomycin (100 g/ml), and maintained in a humidified incubator with 95% atmospheric air and 5% CO2. Prior to the experiment, THP-1 cells were seeded into 24-well flat-bottom plate at a cell density of 50,0000 cells/ml. Phorbol myristate acetate (PMA; 50 ng/mil) was used to treat THP-i cells for 48 h, and then THP-1-derived macrophages were obtained. Following treatment THP-1 cells were pretreated with serially diluted compounds for 2 hours and then stimulated with D-glycero-D-manno-6-fluoro-heptose-13-S-ADP for 4 h. Total RNA was extracted using the TRIzol method and reverse-transcribed. The mRNA expression levels IL1β were detected by SYBR green gene expression assays. Expression levels of mRNA were normalized to GAPDH. Relative expression was calculated by comparing to vehicle control and the values were plotted as fold induction. All activity results were expressed as the mean of triplicate determinations. IC50 was determined from dose response curve using Prism Software, version 6.00 from GraphPad Software.

Figure 2A:
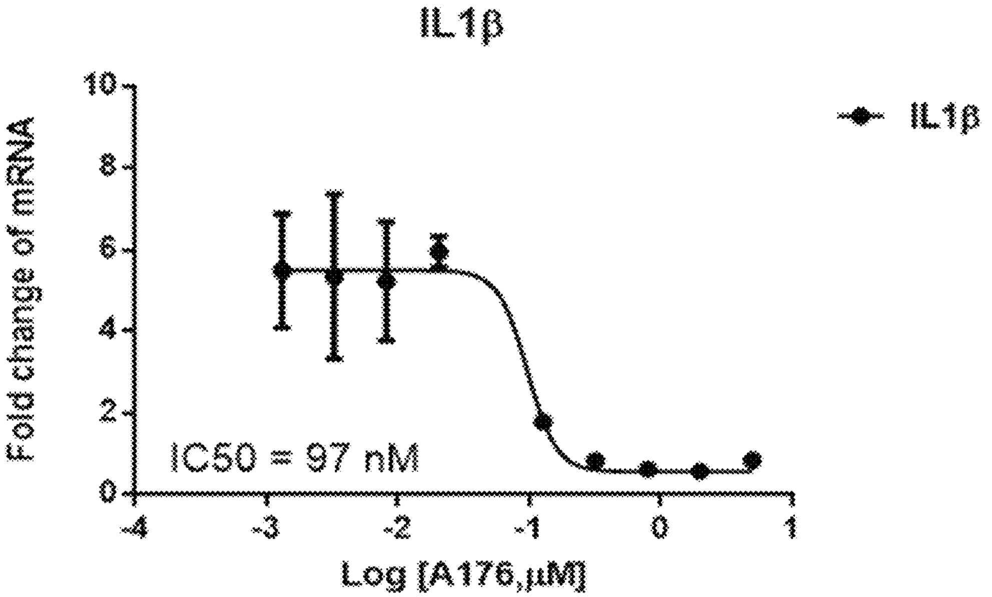
FIG. 2A-2B: Line graphs showing fold-change in IL-10 mRNA versus log concentration for A176 (A) IC50=97 nM; and C008 (B) IC50=15 nM; in PMA-differentiated THP-1 cells stimulated with the ALPK1 agonist, D-glycero-D-manno-6-fluoro-heptose-1β-S-ADP.
Figure 2B:
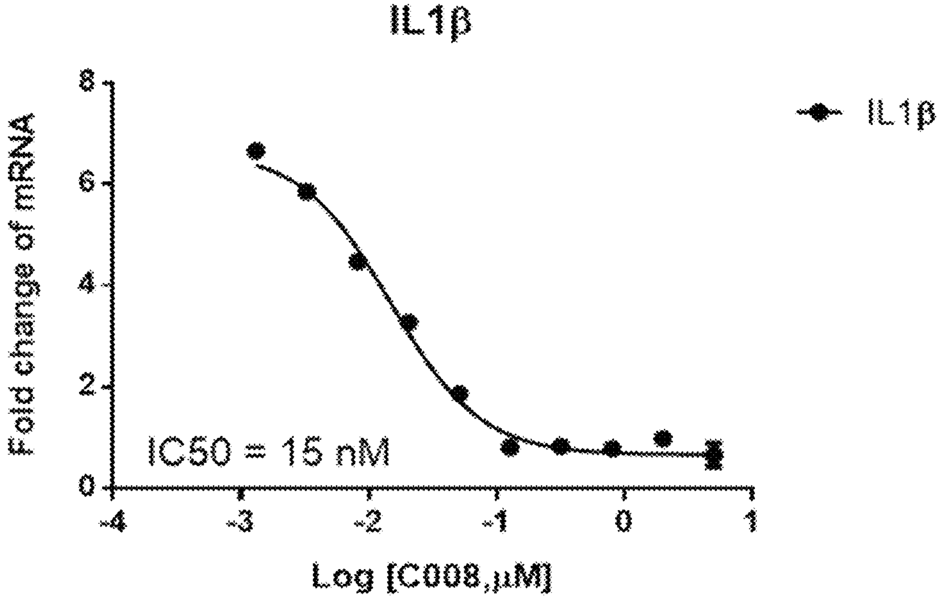

As shown in FIG. 2A-B, the ALPK1 inhibitors A176 and $C_{008}$ showed potent inhibition of IL1β mRNA induced by ALPK1 activation in this assay, with IC50 values of 97 nM and 15 nM, respectively.

Inhibition of Activated ALPK1

Activating mutations in ALPK1 are associated with certain diseases and disorders including PFAPA syndrome. We conducted further experiments to evaluate the ability of representative compounds to inhibit ALPK1 in the context of two activating mutations, T237M and V1092A. In preliminary experiments we determined that IL-8 protein secretion was elevated in cells transiently transfected with human ALPK1 expression vectors containing each of these activating mutations. Accordingly, we used IL-8 secretion as an indicator of activated ALPK1 inhibition in cells expressing these mutations.

First, in preliminary experiments, we established that IL-8 secretion was significantly increased in cells transiently expressing either of the two activating mutations, T237M or V1092A. HEK293 cells were cultured as described above prior to transient transfection with either empty vector or an expression vector encoding (i) human ALPK1 (hALPK1), (ii) hALPK1 with the T237M activating mutation (hALPK1-T237M) (iii) hALPK1 with the V1092A activating mutation (hALPK1-V1092A), or (iv) a kinase dead ALPK1 mutant (hALPK1-T237M-D1194S). Transfection was performed according to manufacturer's protocols (Lipofectamine™ 3000, Thermofisher). Transfected cells were selected, seeded onto 96-well plates and treated with serial dilutions of the test compounds for 6.5 hr. Following treatment, cell viability was determined using a luminescent cell viability assay (Cell Counting-Lite Assay or "CCL Assay" from Vazyme Biotech Co., Ltd.) and cell free supernatants were collected and analyzed for IL-8 protein by IL-8 ELISA as described above. FIG. 1 shows IL-8 secretion for each of the test groups. As shown in the figure, very little IL-8 was detectable in cells transfected with any of the empty vector, hALPK1, or the kinase dead hALPK1 mutant. In contrast, both of the activating mutations in hALPK1 induced significant IL-8 secretion.

Next, we tested a representative set of compounds for inhibition of IL-8 secretion in cells expressing each of the activating ALPK1 mutants, T237M and V1092A. Table 8 shows inhibition of IL-8 secretion in cells transfected with the T237M and Table 9 shows inhibition of IL-8 secretion in cells transfected with the V1092A mutant. For the T237M mutant study, we produced an HEK293 cell line ("A2") stably expressing the T237M hALPK1 mutant. A2 cells were cultured in the presence of test compound (6 uM) for 40 hours total. Fresh medium and compound were added at 24 hours. Cell viability and IL-8 secretion were determined 16 hours after the second addition of compound, using the CCL assay and IL-8 ELISA as described above. Table 8 shows percent inhibition of IL-8 secretion in A2 cells, relative to IL-8 secretion from wild-type HEK293 cells, such that knockdown to the level of IL-8 from wild-type cells was considered to be 100% inhibition.

TABLE 8

Percent inhibition of IL-8 secretion in cells expressing T237M mutant:

| Compd. ID | % Inhibition @ 6 uM |
|---|---|
| C018 | 87 |
| B061 | 75 |
| B062 | 76 |
| A251 | 54 |
| A252 | 71 |
| A160 | 56 |
| A245 | 95 |
| A163 | 83 |
| A173 | 68 |
| C006 | 72 |
| A156 | 75 |
| C009 | 88 |
| C008 | 90 |
| A176 | 84 |

For the V1092A mutant study shown in Table 9, HEK293 cells were transiently transfected with hALPK1-V1092A or hALPK1 (wildtype) expression vectors and then treated with test compounds for 24 hours. Fresh medium and compound were added at 18 hours. Cell viability and IL-8 secretion were determined 6 hours after the second addition of compound, using the CCL assay and IL-8 ELISA as described above. As above, 6 uM test concentration was selected and the table shows percent inhibition of IL-8 secretion relative to wild-type HEK293 cells.

TABLE 9

Percent inhibition of IL-8 secretion in cells expressing V1092A mutant

| Compd. ID | Inhibition @ 6 uM |
|---|---|
| C017 | 68 |
| C018 | 86 |
| B061 | 65 |
| B062 | 98 |
| C016 | 97 |
| A160 | 68 |
| A245 | 100 |
| A167 | 99 |
| A173 | 73 |
| C006 | 57 |
| A156 | 94 |
| A243 | 92 |
| C008 | 90 |
| C009 | 91 |
| A176 | 98 |

Inhibition of ALPK1 in Coronary Artery, Aorta, and Heart Muscle

Kawasaki patients exhibit an abnormal activation of genes involved in innate immunity in coronary artery, aorta, and heart muscles. To examine if the ALPK1 inhibitor can suppress innate immunity genes activated upon ALPK1 activation, SD rats were orally administered compound COOS and gene expression of innate immunity genes was activated by intraperitoneal administration of the ALPK1 agonist, D-glycero-D-manno-6-fluoro-heptose-1β-S-ADP. The coronary artery, aorta and heart muscle tissues were examined for inhibition of ALPK1 inhibitors on innate immunity gene expression.

Twenty male Sprague-Dawley (SD) rats were randomly divided into four groups. A first control group ("normal") was administered vehicle (0.5% MC) orally, followed 2 hours later with PBS administered by intraperitoneal injection (ip). A second control group ("vehicle") was administered vehicle (0.5% MC) orally, followed 2 hours later by ip administration of the ALPK1 agonist, D-glycero-D-manno-6-fluoro-heptose-1 f-S-ADP (50 μpk). Treatment groups were administered ALPK1 inhibitors (40mpk) orally, followed 2 hours later by ip administration of the ALPK1 agonist. The coronary artery, cardiac muscle and aorta from each group were collected 3 hours after administration of the ALPK1 agonist. RNA was isolated and samples were analyzed by RT-PCR for expression of MCP-1 (CCL-2), CCL-7, CXCL-I, CXCL-11, CXCL-10, IL-1β, CCL-5, TNF-a, and IL-6 mRNA. Briefly, total RNA was extracted following the protocol of the Rneasy Mini Kit (QIAGEN, Germany). Messenger RNA was reverse transcribed to cDNA using HiScript Q RT SuperMix for qPCR Kit (Vazyme, Nanjing, China). Quantitative PCR was conducted using AceQ qPCR SYBR Green Master Mix Kit (Vazyme, Nanjing, China) on the QuantStudio 5 applied biosystems (Thermo scientific, USA). Relative mRNA levels were calculated using the 2-ΔΔCT method, and HPRT was used as a reference for gene expression normalization. Data were presented as the gene fold change against their respective expression in the control arm.

Figure 3A:
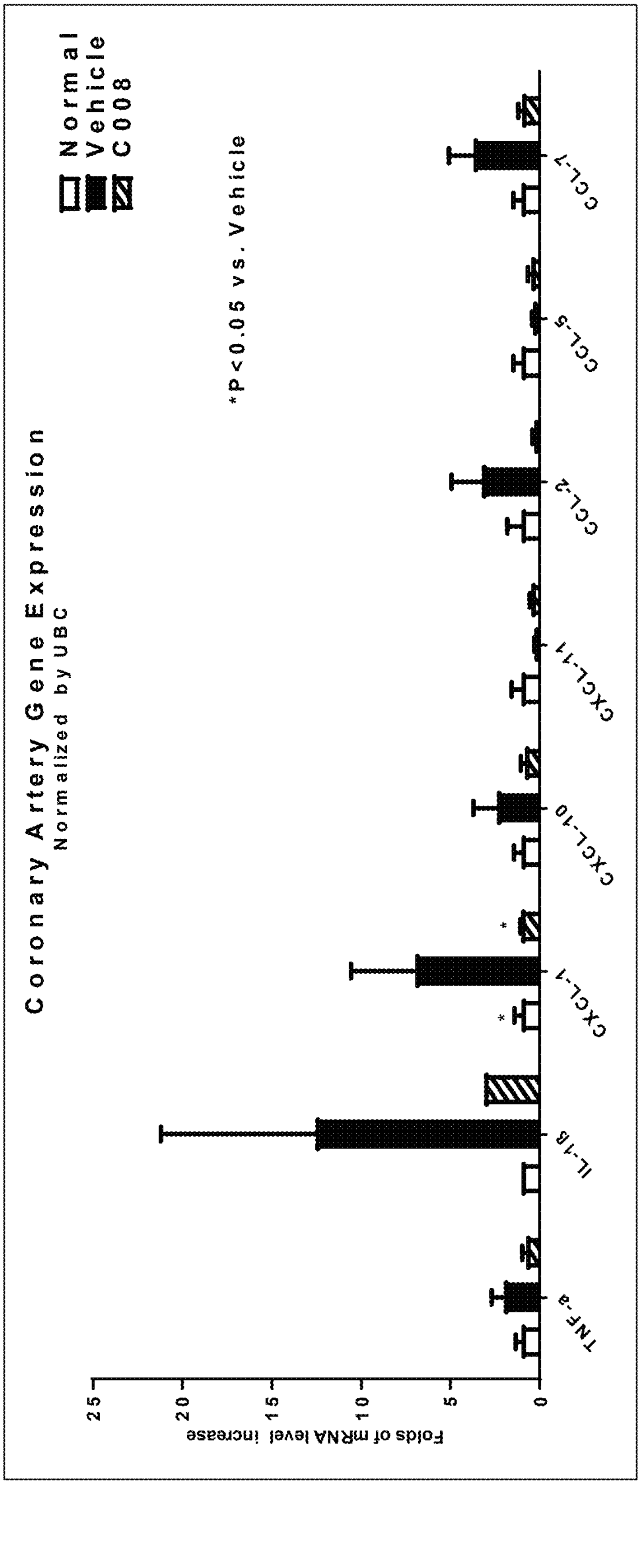
FIG. 3A-3C: Bar graphs showing fold increase in mRNA expression of genes involved in innate immunity in mice treated with vehicle only (normal), vehicle and the ALPK1 agonist, D-glycero-D-manno-6-fluoro-heptose-1β-S-ADP (vehicle), or the ALPK1 agonist and the ALPK1 inhibitor C008 (C008) in coronary artery (A), aorta (B), and heart muscle (C).
Figure 3B:
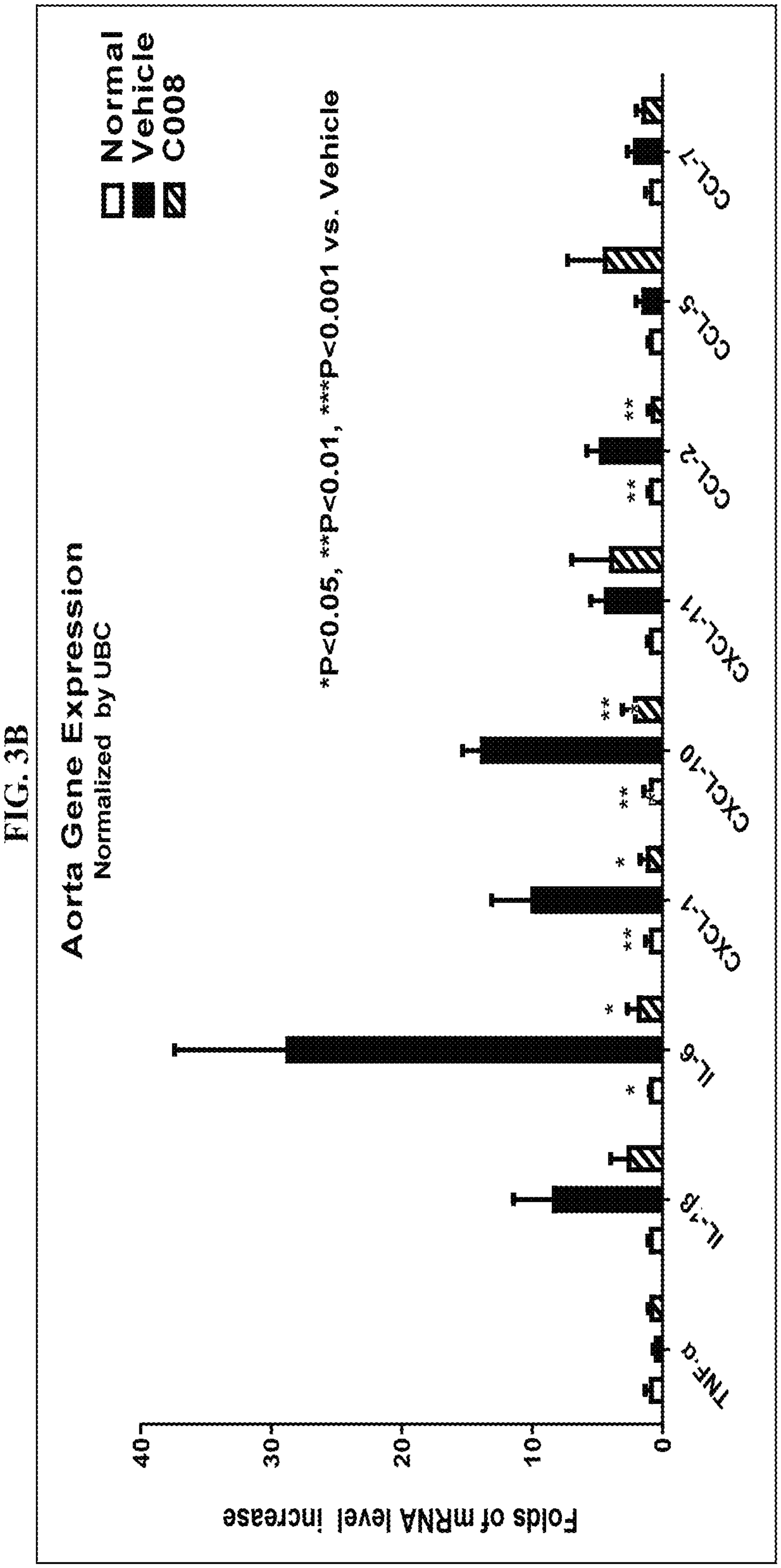
Figure 3C:
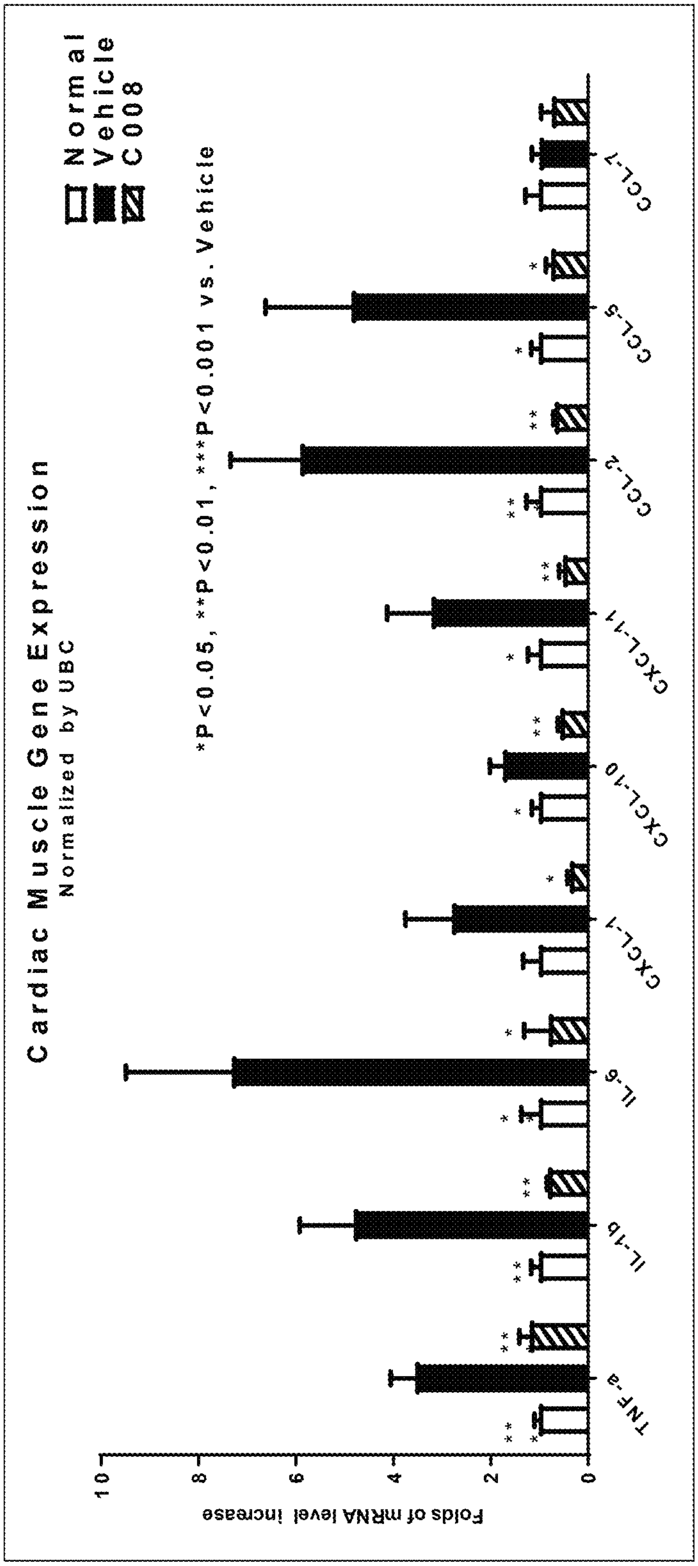

As shown in FIG. 3A-C, compared with the vehicle group, the mRNA expression of coronary artery TNF-α, CXCL-1, CCL-2 and CCL-7, cardiac muscle TNF-a, TL-1b, TL-6, CXCL-1, CXCL-10, CXCL-11, CCL-2 and CCL-5, and aorta IL-6, CXCL-1, CXCL-10, CCL-2 in the $C_{008}$ group were significantly decreased.

Inhibition of ALPK1 in PBMC Cells

The peripheral blood mononuclear cells (PBMC) of Kawasaki patients exhibit an abnormal activation of genes involved in innate immunity. We examined whether ALPK1 inhibitors can suppress ALPK1-dependent activation of a set of such genes in rats. Animals were orally administered compounds C008 and A176 and ALPK1-dependent gene expression was induced by intraperitoneal administration of the ALPK1 agonist, D-glycero-D-manno-6-fluoro-heptose-1β-S-ADP. PBMCs were collected and gene expression analyzed, as described in more detail below.

Thirty-six male Sprague-Dawley (SD) rats were randomly divided into six groups. A first control group ("normal") was administered vehicle (0.5% MC) orally, followed 2 hours later with PBS administered by intraperitoneal injection (ip). A second control group ("vehicle") was administered vehicle (0.5% MC) orally, followed 2 hours later by ip administration of the ALPK1 agonist. D-glycero-D-manno-6-fluoro-heptose-1β-S-ADP (50 pk). Treatment groups were administered ALPK1 inhibitors (10 mpk) orally, followed 2 hours later by ip administration of the ALPK1 agonist. After 3 hours administration of the ALPK1 agonist, the blood was collected from heart, and PBMC were extracted from each group. RNA was isolated and samples were analyzed by RT-PCR for expression of MCP-1 (CCL-2), CCL-7, CXCL-1, CXCL-11, CXCL-10, IL-1β, CCL-5, TNF-a, and IL-6 mRNA. Briefly, total RNA was extracted following the protocol of the Rneasy Mini Kit (QIAGEN, Germany). Messenger RNA was reverse transcribed to cDNA using HiScript Q RT SuperMix for qPCR Kit (Vazyme, Nanjing, China). Quantitative PCR was conducted using AceQ qPCR SYBR Green Master Mix Kit (Vazyme, Nanjing, China) on the QuantStudio 5 applied biosystems (Thermo scientific, USA). Relative mRNA levels were calculated using the 2-ΔΔCT method, and HPRT was used as a reference for gene expression normalization. Data were presented as the gene fold change against their respective expression in the control arm.

Figure 4A:
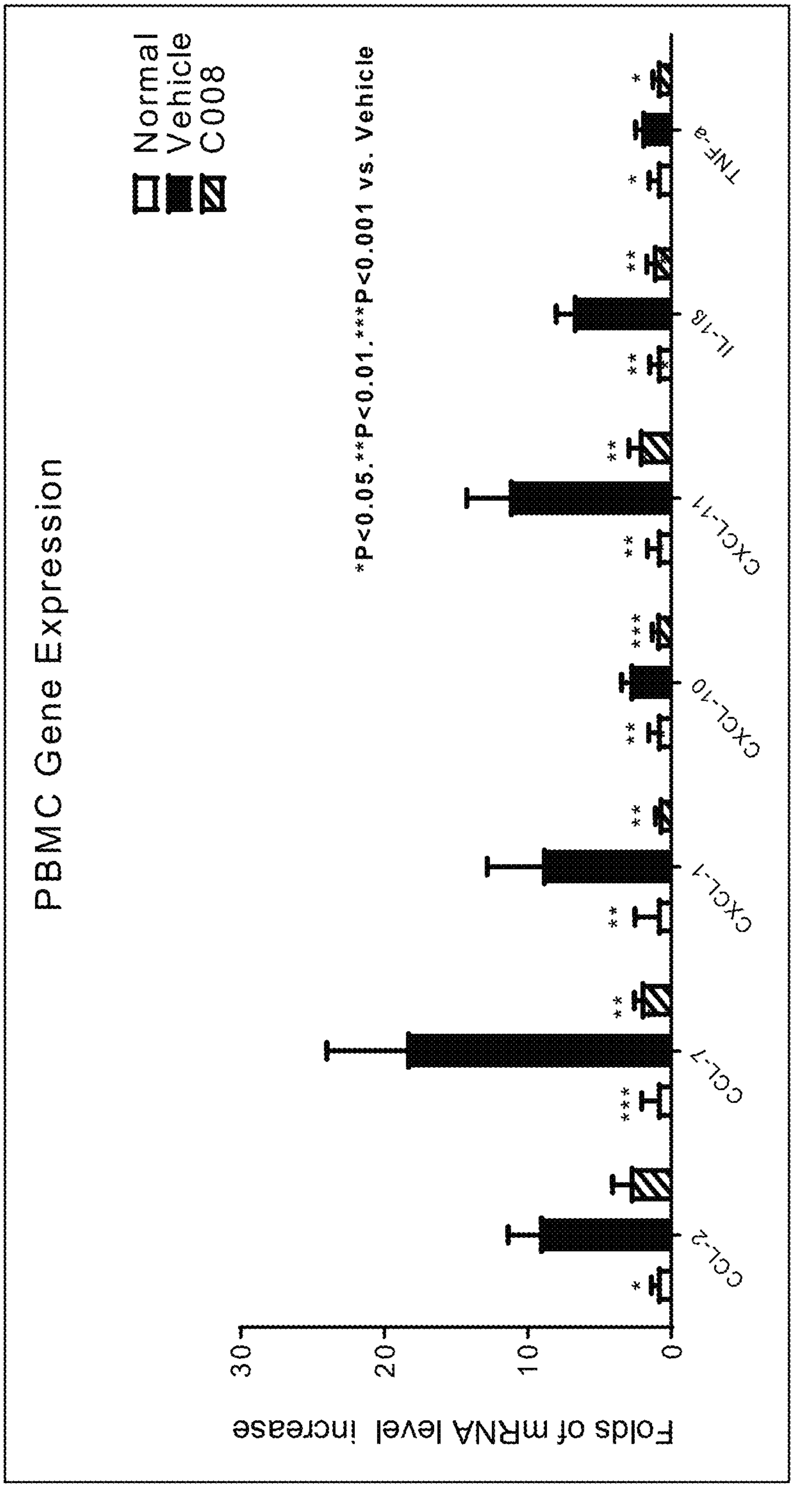
FIG. 4A-4B: Bar graphs showing fold increase in mRNA expression of genes involved in innate immunity, CCL-7, CXCL-1, CXCL-10, CXCL-11, IL-1β, TNF-α and IL-6, in SD rats treated with vehicle only (normal), vehicle and the ALPK1 agonist, D-glycero-D-manno-6-fluoro-heptose-IP-S-ADP (vehicle), or the ALPK1 agonist and the ALPK1 inhibitor C008 (A) or A176 (B) in peripheral blood mononuclear cells (PBMC).
Figure 4B:
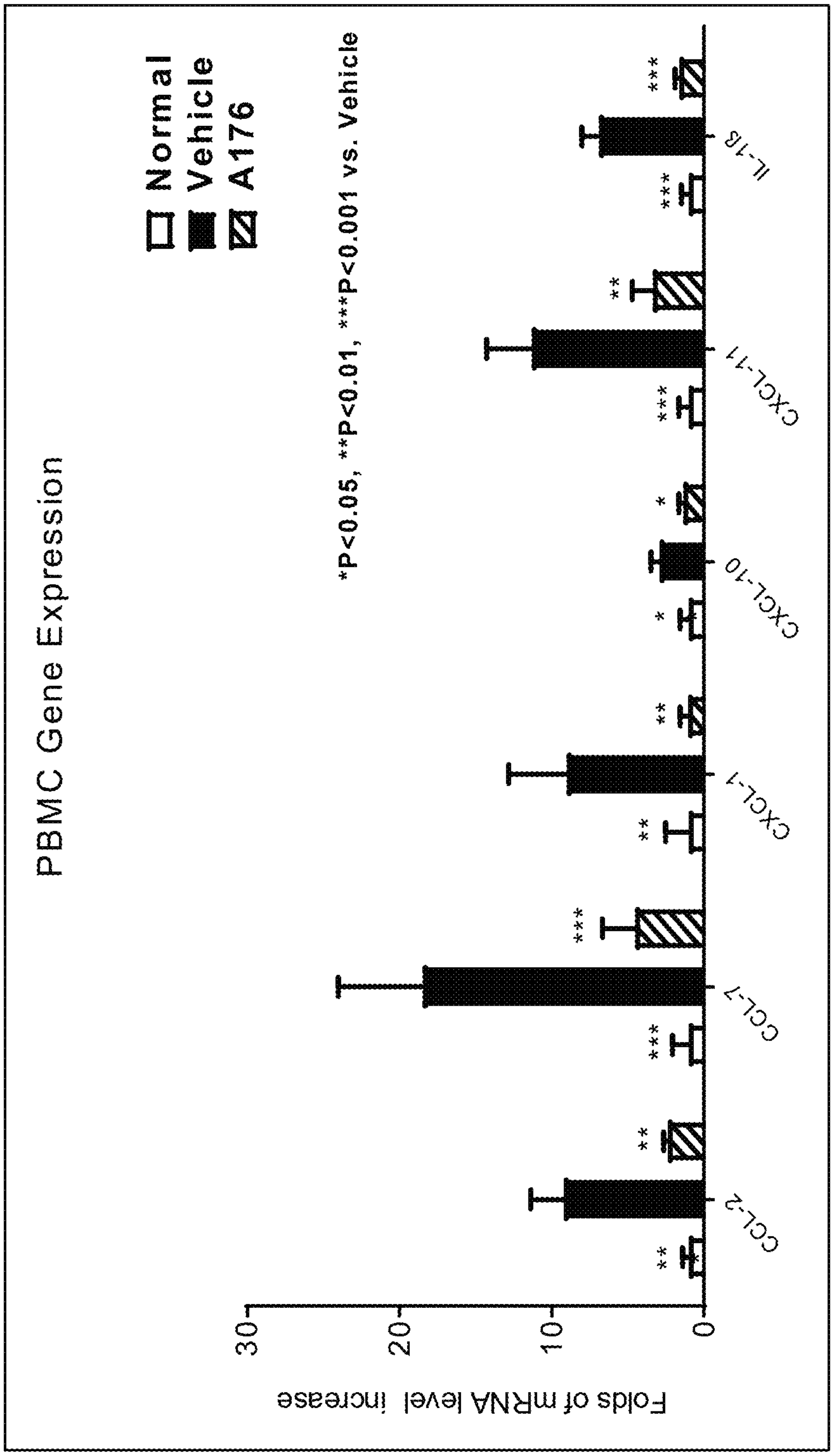

As shown in FIG. 4A-B, compared with the vehicle group, the mRNA expressions of PBMC CCL-7, CXCL-1, CXCL-10, CXCL-11, IL-1β, TNF-α and IL-6 in the $C_{008}$ group were significantly decreased. The mRNA expressions of PBMC CCL-2, CCL-7, CXCL-1, CXCL-10 CXCL-1 I and IL-1i in A176 group were significantly decreased.

Identification of ALPK1 as a Therapeutic Target for Kawasaki Disease

Rahmati et al. used bioinformatics analyses of existing datasets to identify gene and miRNA expression patterns in Kawasaki Disease ("KD") patients. Rahmati et al., *Informatics in Medicine Unlocked* 20 (2020) 100423. The Rahmati study examined eight transcriptome microarray datasets and one miRNA array dataset of KD patients obtained from the Gene Expression Omnibus (GEO) repository, see Barrett T, et al. NCBI GEO: archive for functional genomics data sets-update. *Nucleic Acids Res* 2013; 41:D991-5. Database issue. Rahmati identified 28 genes and 14 miRNAs whose expression was increased in patient samples compared to controls and whose expression also decreased in patients following treatment, relative to before treatment. The expression of selected genes and miRNAs was further analyzed in a cohort of KD patients and healthy individuals using real-time PCR analysis. Based on this analysis, Rahmati concluded that MyD88, KREMEN1, TLR5, ALPK1, IRAK4, PFKFB3, HK3, CREB, CR1, SLC2A14, FPR1, hsa-miR-575, hsamiR-483-5p, hsa-miR-4271, and hsa-miR-4327 are involved in KD pathogenesis and suggested these genes and miRNAs as the subject of further research to establish a KD biosignature and KD biomarkers, which Rahamti proposes could be further studied as a therapeutic target.

We investigated whether ALPK1 signaling in particular was implicated as a key driver in the pathogenesis of KD by conducting a further analysis of the non-normalized microarray transcriptome data described in Hoang et al. *Genome Med* 2014; 6(11):541 and obtained from the NCBI GEO database under the accession number GSE63881. We collected the patient identification (ID), phase, aneurysm condition and response to IVIG treatment from the sample tables and followed the published identification of patients as responsive or resistant to standard intravenous immunoglobulin therapy ("IVIG"), i.e., IVIG-responder or IVIG-resistant. We also followed the published classification of patients into normal coronary arteries (normal CA), aneurysmal coronary arteries (CAA) and dilated coronary arteries (dilated CA).

Hoang et al. investigated whole blood transcriptional profiles of two groups of KD patients, acute and convalescent. These two groups were created from the same 171 KD patients treated with IVIG, and thus represent paired data points from the same 171 KD patients at different times, i.e., during acute and convalescent phases of IVIG therapy. The statistical methods used by Hoang treated the two groups of 171 acute phase samples and 171 convalescent phase samples as independent. This is a common practice in biomedical statistics because with this type of data, variation from the individual base line levels increases the total variance, and can be even larger than the differences between treatment groups, thereby becoming a significant source of false positive results.

In our analysis, we included only patients having transcriptome profiles of both acute and convalescent phases and treated the data statistically as having a paired structure, since the IVIG treatment was applied to the same patient and generated two conditions (acute and convalescent phases). This type of paired structure in the data represents a kind of randomized block experiment whose resulting values are not statistically independent. Therefore, when analyzing data of an experiment with paired structure, methods assuming and requiring independent data may miss the true variation and lead to false positives. Accordingly, we utilized specialized methods considering blocking structures as discussed below.

Based on the response to IVIG and the coronary arteries of each patient, we ended up with six patient groups: IVIG-responder with normal CA, IVIG-responder with dilated CA, IVIG-responder with aneurysmal CA, IVIG-resistant with normal CA, IVIG-resistant with dilated CA, and IVIG-resistant with aneurysmal CA. Probes detected in less than three samples in any group were removed from the dataset.

Quantile normalization was used for our analysis instead of z-score normalization, because it is a global adjustment method that assumes the empirical distribution of each sample to be the same. This assumption is justified in many biomedical gene expression applications in which only a minority of genes are expected to be differentially expressed (Bolstad et al., *Bioinformatics* 2003 19:185-193). Quantile normalization is a widely used pre-processing technique designed to remove noise in microarray data and has been applied to data from Illumina BeadChip arrays such as those used in the datasets we analyzed (See e.g., Du P et al., *Bioinformatics* 2008 24: 1547-1548; Schmidt et al., *BMC Genomics* 2010 11:349-10; Dunning et al., Bioinformatics 2007 23:2183-2184). Quantile normalization was performed on all detected probes among multiple samples using within-array normalization by the limma package in R followed by log 2 transformation.

Next, we processed pair-wise differential expression analysis of the same patients between two phases, also using limma package in R. We moderated paired t-test allowing for phase information effects in the linear model. We processed Benjamini-Hochschule adjustment for multiple test correction, and only genes with adjusted p-value less than 0.05 were considered pair-wise differentially expressed. We calculated fold change of the acute phase against the convalescent phase of each patient, and processed log 2 transformation of the fold change values. We then calculated the mean value of the log 2 transformed fold change values of patients in each of the six groups to generate a heatmap with unsupervised clustering.

We also analyzed the data as in the original study, ignoring the paired block structure and treating the data as independent, i.e., as two groups: (i) 171 acute phase samples against (ii) 171 convalescent phase samples. The comparison was carried out with limma package in R.

Results

Using methods that considered the paired structure of the data, we observed a total of 7,873 genes having significantly differentiated expression levels. When the paired structure was ignored, we observed 8,966 differentially expressed genes. About 13% (1,093) of these were false positives due to individual base line expression level diversity, rather than dysregulation of gene expression in KD patients. Due to the high level of false positives obtained when the paired structure of the data was ignored, we only used the results obtained from the paired comparison for further downstream analysis.

We focused our analysis on a selected set of genes consisting of genes from the following three groups. (1) Genes of the IL1 signaling pathway described by Hoang et al., namely IL1b, IL1R1, IL1R2, IL1RAP, and IL1RN; (2) Genes found to be key responders of ALPK1 signaling based on our previous unpublished work, namely CCL2, CCL3, CCL7, CXCL1, CXCL9, CXCL10, IFNb, IL1b, and TNFa; and (3) the 28 KD related genes described by Rahamati et al., namely ADM, ALPK1, BCL6, CDK5RAP2, CR1, CREB5, CYP1B1, F5, FPR1, HK3, HPSE, IRAK4, KCNJ15, KIF1B, KREMEN1, LIMK2, LRG1, MGAM, MyD88, NFIL3, PFKFB3, PGS1, SIPA1L2, SLC2A14, TLR5, TRIM25, UPP1, ZNF438.

Figure 5:
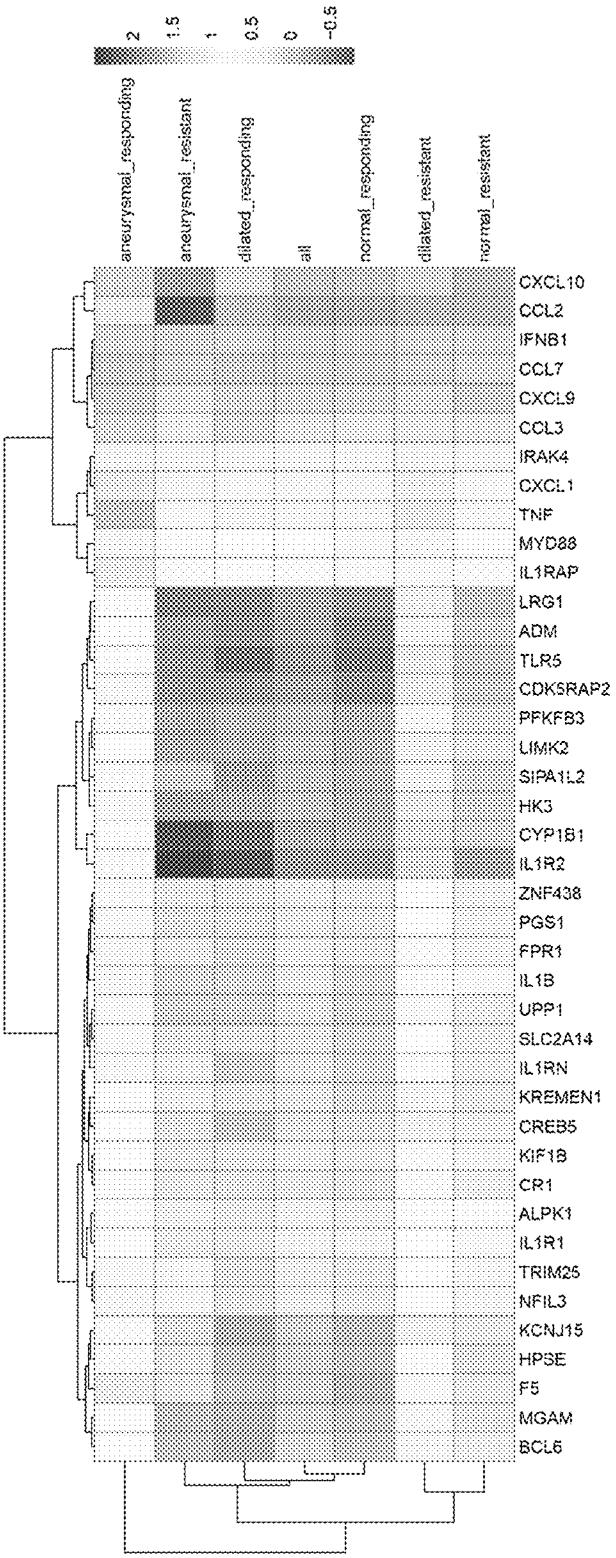
FIG. 5: Heatmap representing color-coded expression levels of Kawasaki disease related genes (log 2 transformed fold change of acute phase against convalescent phase) in all patients and in six patient groups.

All genes but CCL7, CXCL9, CXCL10 and IFNb were significantly differentially expressed between acute and convalescent phases in at least three patient groups. By unsupervised two-dimensional clustering, we observed from the heatmap (FIG. 5) that ALPK1 is clustered with IL1R1, IL1RN, and IL1b, suggesting a co-regulation of gene expressions in Kawasaki disease. This suggests that ALPK1 is involved in IL-1 signaling in Kawasaki disease. We observed ALPK1 with significantly increased expression level considering all the Kawasaki disease patients, as well as in all the six groups of Kawasaki disease patients (see method part for detailed grouping information), especially all the three groups of patients resistant to IVIG treatment with different coronary arteries conditions. These data indicate that ALPK1 is a target for Kawasaki disease, including IVIG resistant patients.

EQUIVALENTS

Those skilled in the art will recognize or be able to ascertain using no more than routine experimentation, many equivalents to the specific embodiments of the invention as described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A method for treating Kawasaki disease in a subject in need of such treatment, the method comprising administering to the subject a compound having a structure of:

Formula I

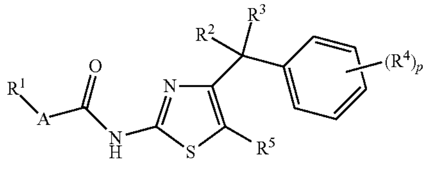

or a pharmaceutically acceptable salt thereof, wherein

A is selected from a bond, azetidinyl, —O—, —N($R^6$)—, —$CH_2$—N($R^6$)—, —$CHR^9$—N($R^6$)—, wherein $R^6$ is selected from H, —OH, optionally substituted $C_1$-$C_6$ alkyl, optionally substituted $C_1$-$C_6$ haloalkyl, optionally substituted $C_1$-$C_6$ alkenyl, optionally substituted $C_1$-$C_6$ hydroxyalkyl, optionally substituted $C_1$-$C_6$ aminoalkyl, optionally substituted $C_1$-$C_6$ alkoxyl, optionally substituted saturated or unsaturated $C_3$-$C_6$ cycloalkyl, and optionally substituted saturated or unsaturated $C_3$-$C_6$ cycloalkoxyl, wherein the optionally substituted $R^6$ moieties comprise 0-3 substituents independently selected from halo, —OH, —COOH, —$NH_2$, ═O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, and $C_1$-$C_6$ alkoxyl;

$R^9$ is selected from optionally substituted $C_1$-$C_6$ alkyl, $C_1$-$C_6$ haloalkyl, optionally substituted saturated or unsaturated $C_3$-$C_6$ cycloalkyl, optionally substituted saturated or unsaturated $C_3$-$C_6$ cycloalkoxyl, wherein optionally substituted $R^9$ moieties comprise 0-2 substituents independently selected from halo, —OH, —COOH, —$NH_2$, —O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, $C_1$-$C_6$ haloalkoxyl, saturated or unsaturated $C_3$-$C_6$ cycloalkyl, saturated or unsaturated $C_3$-$C_6$ cycloalkoxyl, —$CHR^{7f}R^{8f}$, —$OR^{7f}$, —OC(O)($R^{7f}$), —C(O)($R^{7f}$), —C(O)N($R^{7f}R^{8f}$), —C(O)O($R^{7f}$), —$S(O)_2$($R^{7f}$), —S(O)ON($R^{7f}R^{8f}$) and —N($R^{7f}R^{8f}$) wherein each $R^{7f}$ and $R^{8f}$ are independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, $C_1$-$C_6$ haloalkoxyl, saturated or unsaturated $C_3$-$C_6$ cycloalkyl, and saturated or unsaturated $C_3$-$C_6$ cycloalkoxy;

$R^1$ is selected from H, optionally substituted $C_1$-$C_6$ alkyl, optionally substituted $C_1$-$C_6$ alkenyl, optionally substituted $C_1$-$C_6$ hydroxyalkyl, optionally substituted $C_1$-$C_6$ haloalkyl, optionally substituted $C_1$-$C_6$ haloalkoxyl, optionally substituted $C_1$-$C_6$ aminoalkyl, optionally substituted $C_1$-$C_6$ alkoxyl, optionally substituted saturated or unsaturated $C_3$-$C_6$ cycloalkyl, optionally substituted saturated or unsaturated $C_3$-$C_6$ cycloalkoxyl, optionally substituted mono or bicyclic aryl, optionally substituted 5-10 membered heteroaryl containing 1-4 heteroatom ring vertices selected from N, O, and S; optionally substituted saturated or unsaturated 3-7 membered heterocyclyl containing 1-2 heteroatom ring vertices selected from N, O, and S; optionally substituted saturated or unsaturated 7-8 membered bridged heterocyclyl containing 1-2 heteroatom ring vertices selected from N, O, and S; optionally substituted saturated or unsaturated 7-11 membered spiroheterocyclyl containing 1-2 heteroatom ring vertices selected from N, O, and S; and optionally substituted saturated or unsaturated 6-11 membered bicyclic heterocyclyl containing 1-2 heteroatom ring vertices selected from N, O, and S;

wherein optionally substituted $R^1$ moieties comprise 0-4 substituents independently selected from halo, —OH, —COOH, —$NH_2$, ═O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, $C_1$-$C_6$ haloalkoxyl, —$R^{7a}$, —$X^1$—$R^{7a}$, $CHR^{7a}$ $R^{8a}$, —$OR^{7a}$, —O—$X^1$—$R^{7a}$, —$X^1$—O—$X^1$—$R^{7a}$, —OC(O)($R^{7a}$), —O—$X^1$—C(O)($R^{7a}$), —C(O)($R^{7a}$), —C(O)N($R^{7a}R^{8a}$), —$NR^{7a}$ (CO) $R^{8a}$, —C(O)O($R^{7a}$), $S(O)_2R^{7a}$, —$S(O)_2$N($R^{7a}R^{8a}$), —N($R^{7a}R^{8a}$), saturated or unsaturated $C_3$-$C_6$ cycloalkyl, saturated or unsaturated $C_3$-$C_6$ cycloalkoxyl, saturated or unsaturated 3-7 membered heterocyclyl containing 1-2 heteroatom ring vertices selected from N, O, and S, mono or bicyclic aryl, 5-10 membered heteroaryl containing 1-4 heteroatom ring vertices selected from N, O, and S, saturated or unsaturated 7-8 membered bridged heterocyclyl containing 1-2 heteroatom ring vertices selected from N, O, and S, saturated or unsaturated 7-11 membered spiroheterocyclyl containing 1-2 heteroatom ring vertices selected from N, O, and S, and 6-11 membered bicyclic heterocyclyl containing 1-2 heteroatom ring vertices selected from N, O, and S; wherein each $X^1$ is independently $C_1$-6 alkylene;

each $R^{7a}$ and $R^{8a}$ are independently selected from H, $C_1$-$C_6$ alkyl, saturated or unsaturated $C_3$-$C_6$ cycloalkyl, saturated or unsaturated $C_3$-$C_6$ cycloalkoxyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, $C_1$-$C_6$ haloalkoxyl, saturated or unsaturated $C_3$-$C_6$ cycloalkyl, saturated or unsaturated $C_3$-$C_6$ cycloalkoxyl, aryl, saturated or unsaturated $C_3$-$C_6$ cycloalkyl, saturated or unsaturated $C_3$-$C_6$ cycloalkoxyl, saturated or unsaturated 3-7 membered heterocyclyl containing 1-2 heteroatom ring vertices selected from N, O, and S, wherein the aryl and 3-7 membered heterocyclyl groups are substituted with 0-3 substituents selected from halo, —OH, —COOH, —$NH_2$, ═O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl; and the $C_3$-$C_6$ cycloalkyl, $C_3$-$C_6$ cycloalkoxyl, 3-7 membered heterocyclyl, the mono or bicyclic aryl, the 5-10 membered heteroaryl, the saturated or unsaturated 7-8 membered bridged heterocyclyl, the saturated or unsaturated 7-11 membered spiroheterocycly, and the 6-11 membered bicyclic heterocyclyl are each independently substituted with 0 to 3 moieties selected from halo, —OH, —COOH, —$NH_2$, ═O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, saturated or unsaturated $C_3$-$C_6$ cycloalkoxyl, —$CHR^{70}R^{8b}$, —$OR^{76}$, —OC(O)($R^{7b}$), —C(O)($R^{7b}$), —C(O)N($R^{7b}R^{8b}$), —$NR^{7b}$ (CO) $R^{8b}$, —C(O)O($R^{7b}$), —$S(O)_2$ N($R^{7b}R^{8b}$) and —N($R^{7b}R^{8b}$), wherein each $R^{7b}$ and $R^{8b}$ are independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl; or $R^1$ and $R^6$ combine to form a 3-6 membered heterocycloalkyl substituted with 0-3 moieties independently selected from the group consisting of halo, —OH, —COOH, —$NH_2$, ═O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, and $C_1$-$C_6$ alkoxyl;

$R^5$ is selected from H, deuterium, halo, $C_1$-$C_6$ alkyl, $C_1$-$C_6$ deuteroalkyl, and $C_1$-$C_6$ haloalkyl;

$R^2$ and $R^3$ are each independently selected from H, OH, $C_1$-$C_6$ alkyl and $C_2$-$C_6$ alkynyl, wherein $C_1$-$C_6$ alkyl and $C_2$-$C_6$ alkynyl are each substituted with 0-3 moieties independently selected from halo, —OH, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, saturated or unsaturated $C_3$-$C_6$ cycloalkoxyl, —OC(O)($R^{7c}$), —C(O)($R^{7c}$), C(O)O($R^{7c}$), $S(O)_2N(R^{7c}R^{8c})$, and $N(R^{7c}R^{8c})$, wherein each $R^{7c}$ and $R^{8c}$ are independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, $C_1$-$C_6$ haloalkoxy, saturated or unsaturated $C_3$-$C_6$ cycloalkyl, and saturated or unsaturated $C_3$-$C_6$ cycloalkoxyl;

provided that $R^2$ and $R^3$ are not both H; or $R^2$ and $R^3$ combine to form a $C_3$-$C_6$ cycloalkyl ring or a 3-7 membered heterocyclyl containing 1-2 heteroatom ring vertices independently selected from N, O, and S, wherein the ring formed can be optionally substituted with 1-2 substituents independently selected from $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, halo, —OH, =O, —CN, OC(O)($R^{7d}$), —C(O)($R^{7d}$), C(O)O($R^{7d}$), $S(O)_2N(R^{7d}R^{8d})$ and $N(R^{7d}R^{8d})$, wherein each $R^{7d}$ and $R^{8d}$ are independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl;

each $R^4$ is independently selected from halo, —OH, —$NH_2$, CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, saturated or unsaturated $C_3$-$C_6$ cycloalkoxyl, $CHR^{7e}R^{8e}$, $OR^{7e}$, OC(O)($R^{7e}$), C(O)($R^{7e}$), C(O)N($R^{7e}R^{8e}$), C(O)O($R^{7e}$), $S(O)_2N(R^{7e}R^{8e})$ and $N(R^{7e}R^{8e})$ wherein each $R^{7e}$ and $R^{8e}$ are independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, saturated or unsaturated $C_3$-$C_6$ cycloalkoxyl, and the subscript p is 0,1, 2 or 3.

2. The method of claim 1, wherein the compound of Formula I is also a compound of Formula IA:

Formula IA

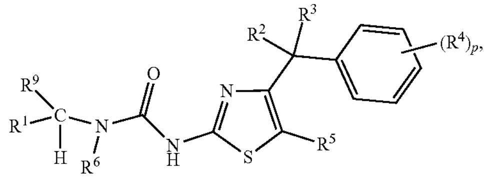

or a pharmaceutically acceptable salt thereof.

3. The method of claim 2, wherein the subject in need of such therapy is a subject carrying one or more genetic mutations in ALPK1.

4. The method of claim 1, wherein the compound of Formula I is also a compound of Formula IA-I:

Formula IA-I

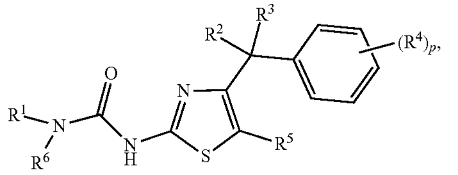

or a pharmaceutically acceptable salt thereof.

5. The method of claim 1, wherein $R^1$ is selected from H and optionally substituted $C_1$-$C_6$ alkyl, wherein optionally substituted $C_1$-$C_6$ alkyl comprises 0-4 substituents independently selected from halo, —OH, —COOH, —$NH_2$, =O, —CN, $C_1$-$C_6$ alkenyl, $C_1$-$C_6$ hydroxyalkyl, $C_1$-$C_6$ alkoxyl, $C_1$-$C_6$ haloalkoxyl, saturated or unsaturated $C_3$-$C_6$ cycloalkyl, saturated or unsaturated $C_3$-$C_6$ cycloalkoxyl, —$CHR^{7a}R^{8a}$, —$OR^{7a}$, —OC(O)($R^{7a}$), —C(O)($R^{7a}$), —C(O)N($R^{7a}R^{8a}$), —C(O)O($R^{7a}$), —$S(O)_2R^{7a}$, —$S(O)_2N(R^{7a}R^{8a})$ and —$N(R^{7a}R^{8a})$, wherein each $R^{7a}$ and $R^{8a}$ are independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, $C_1$-$C_6$ haloalkoxyl, saturated or unsaturated $C_3$-$C_6$ cycloalkyl, and saturated or unsaturated $C_3$-$C_6$ cycloalkoxyl.

6. The method of claim 1, wherein $R^1$ is $C_1$-$C_6$ alkyl substituted with 0-4 substituents independently selected from —OH, $C_1$-$C_6$ hydroxyalkyl, $C_1$-$C_6$ alkoxyl, —OC(O)($R^{7a}$), —$S(O)_2N(R^{7a}R^{8a})$ and —$N(R^{7a}R^{8a})$, wherein each $R^{7a}$ and $R^{8a}$ are independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl.

7. The method of claim 1, wherein $R^1$ is a 5-10 membered heteroaryl containing 1-4 heteroatom ring vertices selected from N, O, and S, the 5-10 membered heteroaryl is substituted with 0 to 3 moieties selected from halo, —OH, —COOH, —$NH_2$, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, 3-7 membered heterocyclyl containing 1-2 heteroatom ring vertices selected from N, O, and S, saturated or unsaturated $C_3$-$C_6$ cycloalkyl, saturated or unsaturated $C_3$-$C_6$ cycloalkoxyl, —$CHR^{7b}R^{8b}$, —$OR^{7b}$, —OC(O)($R^{7b}$), —C(O)($R^{7b}$), —C(O)N($R^{7b}R^{8b}$), —C(O)O($R^{7b}$), —$S(O)_2N(R^{7b}R^{8b})$ and —$N(R^{7b}R^{8b})$, wherein each $R^{7b}$ and $R^{8b}$ are independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl.

8. The method of claim 1, wherein $R^1$ is aryl substituted with 0-3 substituents selected from halo, a 3-7 membered heterocyclyl containing 1-2 heteroatom ring vertices selected from N, O, and S; a 7-8 membered bridged heterocyclyl containing 1-2 heteroatom ring vertices selected from N, O, and S; and a saturated or unsaturated 7-11 membered spiroheterocyclyl containing 1-2 heteroatom ring vertices selected from N, O, and S, wherein the 3-7 membered heterocyclyl, the 7-8 membered bridged heterocyclyl, and the 7-11 membered spiroheterocyclyl are substituted with from 0 to 3 moieties selected from halo, —OH, —COOH, —$NH_2$, —O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, saturated or unsaturated $C_3$-$C_6$ cycloalkoxyl, —$CHR^{7b}R^{8b}$, —$OR^{76}$, —OC(O)($R^{7b}$), —C(O)($R^{7b}$), —C(O)N($R^{76}R^{8b}$), —C(O)O($R^{7b}$), —$S(O)_2R^{7b}$, —$S(O)_2$N($R^{7b}R^{8b}$) and —N($R^{7b}R^{8b}$), wherein each $R^{7b}$ and $R^{8b}$ are independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl.

9. The method of claim 1, wherein the compound of Formula I is also a compound of Formula IB:

Formula IB

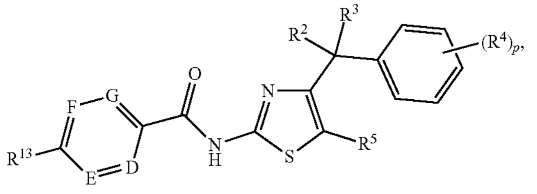

or a pharmaceutically acceptable salt thereof, wherein

D is CR10 or N;

E is CR14 or N;

F is CR12 or N;

G is CR11 or N;

provided that no more than three of D, E, F, and G are N;

$R^{10}$, $R^{11}$, $R^{12}$, $R^{13}$ and $R^{14}$, when present, are each independently selected from H, halo, —OH, —COOH, —$NH_2$, =O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, $C_1$-$C_6$ haloalkoxyl, —$R^{7a}$, —$X^1$—$R^{7a}$, $X^1$—O—$X^1$—$R^{7a}$, —$CHR^{7a}R^{8a}$, —$OR^{7a}$, —O—$X^1$—$R^{7a}$, —OC(O)($R^{7a}$), —O—$X^1$—C(O)($R^{7a}$), —C(O)($R^{7a}$), —C(O)N($R^{7a}R^{8a}$), —C(O)O($R^{7a}$), $S(O)_2R^{7a}$, —$S(O)_2$N($R^{7a}R^{8a}$), —N($R^{7a}R^{8a}$), saturated or unsaturated $C_3$-$C_6$ cycloalkyl, saturated or unsaturated $C_3$-$C_6$ cycloalkoxyl, saturated or unsaturated 3-7 membered heterocyclyl containing 1-2 heteroatom ring vertices selected from N, O, and S; mono or bicyclic aryl, a 9-10 membered bicyclic heteroaryl containing 1-4 heteroatom ring vertices selected from N, O, and S; saturated or unsaturated 7-8 membered bridged heterocyclyl containing 1-2 heteroatom ring vertices selected from N, O, and S; and saturated or unsaturated 7-11 membered spiroheterocyclyl containing 1-2 heteroatom ring vertices selected from N, O, and S; 6-11 membered bicyclic heterocyclyl containing 1-2 heteroatom ring vertices selected from N, O, and S; wherein each $X^1$ is independently $C_1$-6 alkylene;

each $R^{7a}$ and $R^{8a}$ are independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl; and the 3-7 membered heterocyclyl, the mono or bicyclic aryl, the 9-10 membered bicyclic heteroaryl, the 7-8 membered bridged heterocyclyl, the 7-11 membered spiroheterocycly, and the 6-11 membered bicyclic heterocyclyl are each independently substituted with 0 to 2 moieties selected from halo, —OH, —COOH, —$NH_2$, =O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, saturated or unsaturated $C_3$-$C_6$ cycloalkoxyl, —$CHR^{7g}R^{8g}$, —$OR^{7g}$, —OC(O)($R^{7g}$), —C(O)($R^{7g}$), —C(O)N($R^{7g}R^{8g}$), —$NR^{7g}$(CO) $R^{8g}$, —C(O)O($R^{7g}$), —$S(O)_2$N($R^{7g}R^{8g}$) and —N($R^{7g}R^{8g}$), wherein each $R^{7g}$ and $R^{8g}$ are each independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl.

10. The method of claim 9, wherein D, E, F and G are $CR^{10}$, $CR^{14}$, $CR^{12}$, and $CR^{11}$, respectively.

11. The method of claim 9, wherein $R^{12}$ and $R^{14}$ are H;

$R^{10}$ and $R^{11}$ are each independently selected from halo, —OH, —COOH, —$NH_2$, =O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, saturated or unsaturated $C_3$-$C_6$ cycloalkoxyl, —$CHR^{70}R^{8b}$, —$OR^{7b}$, —OC(O)($R^{7b}$), —C(O)($R^{7b}$), —C(O)N($R^{76}R^{8b}$), —C(O)O($R^{7b}$), —$S(O)_2$N($R^{7b}R^{8b}$) and —N($R^{7b}R^{8b}$), wherein $R^{7b}$ and $R^{8b}$ are each independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl; and $R^{13}$ is selected from 3-7 membered heterocyclyl containing 1-2 heteroatom ring vertices selected from N, O, and S, saturated or unsaturated 7-8 membered bridged heterocyclyl containing 1-2 heteroatom ring vertices selected from N, O, and S, and saturated or unsaturated 7-11 membered spiroheterocyclyl containing 1-2 heteroatom ring vertices selected from N, O, and S, wherein the 3-7 membered heterocyclyl, the 7-8 membered bridged heterocyclyl, and the 7-11 membered spiroheterocyclyl are optionally substituted with 0-2 moieties independently selected from halo, —OH, —COOH, —$NH_2$, =O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl.

12. The method of claim 9, wherein $R^{10}$, $R^{11}$, $R^{12}$ and $R^{14}$, when present, are each H; and $R^{13}$ is selected from saturated or unsaturated $C_3$-$C_6$ cycloalkyl, 3-7 membered heterocyclyl containing 1-2 heteroatom ring vertices selected from N, O, and S, saturated or unsaturated 7-8 membered bridged heterocyclyl containing 1-2 heteroatom ring vertices selected from N, O, and S, saturated or unsaturated 7-11 membered spiroheterocyclyl containing 1-2 heteroatom ring vertices selected from N, O, and S, wherein the 3-7 membered heterocyclyl, the 7-8 membered bridged heterocyclyl, and the 7-11 membered spiroheterocyclyl are optionally substituted with 0-2 moieties independently selected from halo, —OH, —COOH, —$NH_2$, —O, —CN, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl.

13. The method of claim 9, wherein the subject in need of such therapy is a subject carrying one or more genetic mutations in ALPK1.

14. The method of claim 9, wherein the compound of Formula IB is also a compound of Formula IB-1 or Formula IB-2:

Formula IB-1

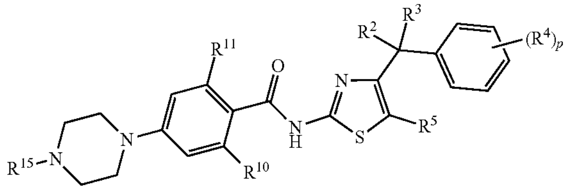

Formula IB-2

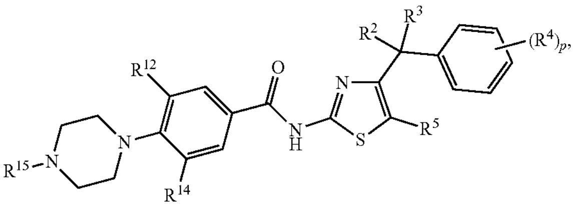

or a pharmaceutically acceptable salt thereof, wherein $R^{15}$ is selected from —OH, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, $C_1$-$C_6$ haloalkoxyl, saturated or unsaturated $C_3$-$C_6$ cycloalkyl, saturated or unsaturated $C_3$-$C_6$ cycloalkoxyl, —$CHR^{70}R^{8b}$, —$C(O)(R^{7b})$, —$C(O)N(R^{70}R^{8b})$, —$C(O)O(R^{7b})$, —$S(O)_2$ $R^{7b}$ and —$S(O)_2$ $N(R^{7b}R^{8b})$, wherein each $R^{7b}$ and $R^{8b}$ are independently selected from H, $C_1$-$C_6$ alkyl, $C_1$-$C_6$ alkenyl, $C_1$-$C_6$ hydroxyalkyl, $C_1$-$C_6$ haloalkyl, $C_1$-$C_6$ aminoalkyl, $C_1$-$C_6$ alkoxyl, saturated or unsaturated $C_3$-$C_6$ cycloalkyl, and saturated or unsaturated $C_3$-$C_6$ cycloalkoxyl.

15. The method of claim 14, wherein $R^{10}$, $R^{11}$, $R^{12}$ and $R^{14}$ are each independently selected from halo and $C_1$-$C_6$ alkyl.

16. The method of claim 14, wherein the compound of Formula IB-1 is also a compound of Formula 1B-1-c, or the compound of Formula IB-2 is also a compound of Formula 1B-2-c:

(1B-1-c)

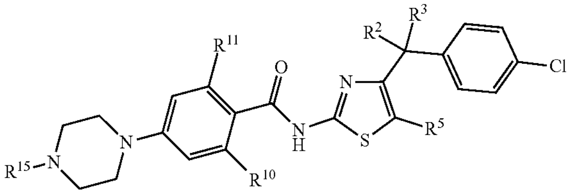

-continued (1B-2-c)

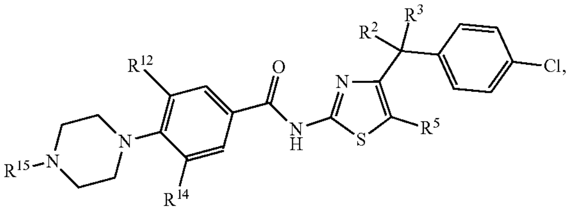

or a pharmaceutically acceptable salt thereof.

17. The method of claim 1, wherein the carbon atom attached to $R^2$ and $R^3$ is the S isomer.

18. The method of claim 1, wherein the compound of Formula I is selected from

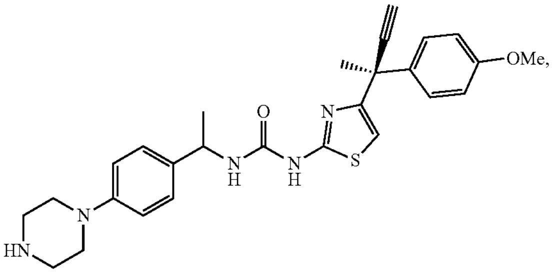

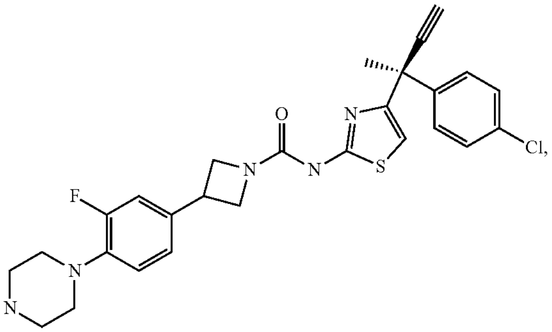

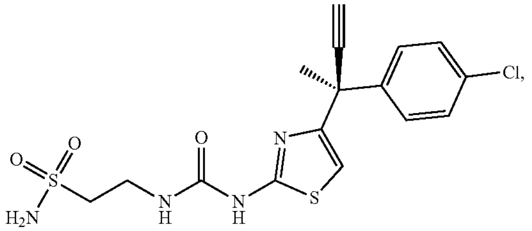

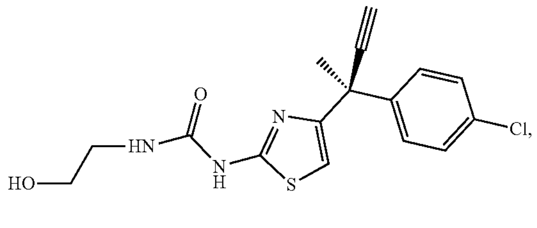

-continued
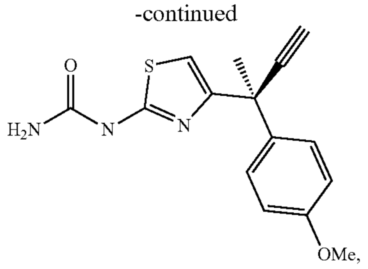,
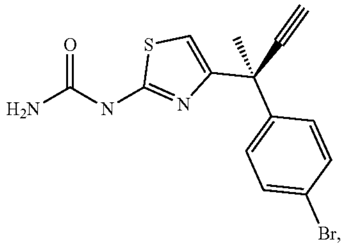,
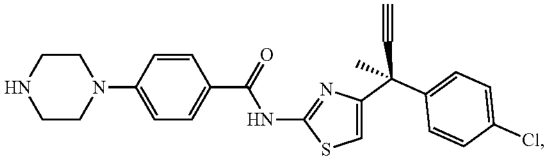,
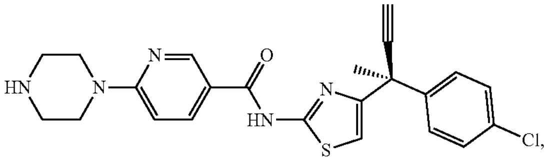,
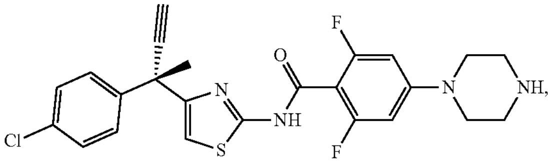,
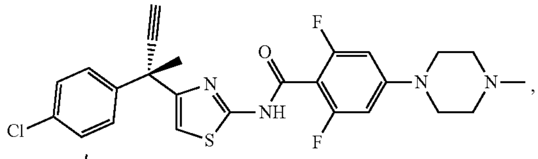,
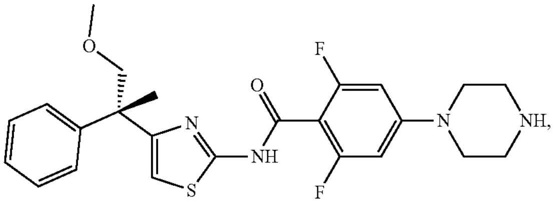,
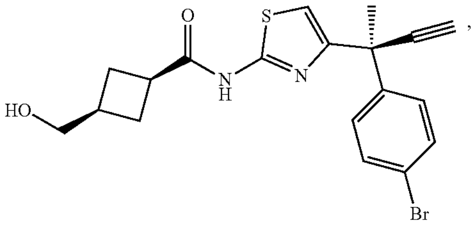,
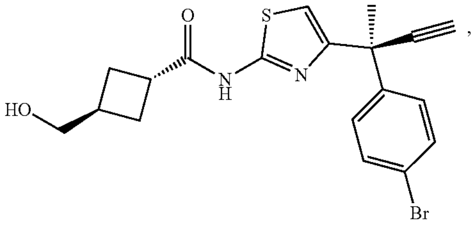,
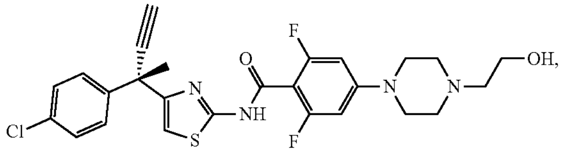,
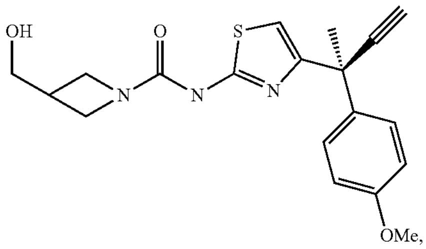, and
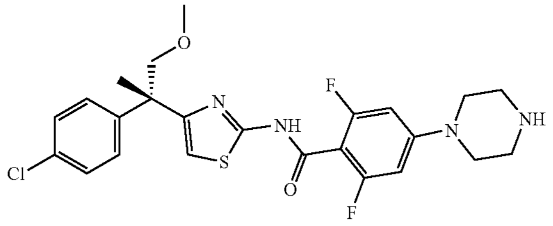
19. The method of claim 1, wherein the subject in need of such treatment is a subject carrying one or more genetic mutations in ALPK1.
20. The method of claim 1, wherein the subject in need of such treatment is a subject diagnosed with Periodic Fever, Aphthous Stomatitis, Pharyngitis, and Adenitis" ("PFAPA").
* * * * *